(12) United States Patent
Cardozo et al.

(10) Patent No.: US 9,873,661 B2
(45) Date of Patent: Jan. 23, 2018

(54) SMALL MOLECULE MALARIAL ALDOLASE-TRAP ENHANCERS AND GLIDEOSOME INHIBITORS

(71) Applicants: NEW YORK UNIVERSITY, New York, NY (US); THE JOHNS HOPKINS UNIVERSITY, Baltimore, MD (US)

(72) Inventors: Timothy J. Cardozo, New York, NY (US); Jürgen Bosch, Pikesville, MD (US); Sondra Maureen Nemetski, New York, NY (US)

(73) Assignees: New York University, New York, NY (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/353,438

(22) PCT Filed: Oct. 25, 2012

(86) PCT No.: PCT/US2012/061875
§ 371 (c)(1),
(2) Date: Apr. 22, 2014

(87) PCT Pub. No.: WO2013/063243
PCT Pub. Date: May 2, 2013

(65) Prior Publication Data
US 2014/0275088 A1 Sep. 18, 2014

Related U.S. Application Data

(60) Provisional application No. 61/551,269, filed on Oct. 25, 2011.

(51) Int. Cl.
*A61K 31/535* (2006.01)
*C07C 249/16* (2006.01)
*C12Q 1/527* (2006.01)
*C07D 239/54* (2006.01)
*C07D 277/34* (2006.01)
*C07C 235/78* (2006.01)
*C07C 243/18* (2006.01)
*C07D 207/337* (2006.01)
*C07D 215/14* (2006.01)
*C07D 239/46* (2006.01)
*C07D 239/47* (2006.01)
*C07D 271/12* (2006.01)
*C07D 333/24* (2006.01)
(Continued)

(52) U.S. Cl.
CPC .......... *C07C 249/16* (2013.01); *C07C 235/78* (2013.01); *C07C 243/18* (2013.01); *C07D 207/337* (2013.01); *C07D 215/14* (2013.01); *C07D 239/46* (2013.01); *C07D 239/47* (2013.01); *C07D 239/54* (2013.01); *C07D 271/12* (2013.01); *C07D 277/34* (2013.01); *C07D 333/24* (2013.01); *C07D 487/04* (2013.01); *C12Q 1/527* (2013.01); *G06F 19/12* (2013.01); *G06F 19/16* (2013.01); *G01N 2333/44* (2013.01); *G01N 2333/445* (2013.01); *G01N 2500/04* (2013.01)

(58) Field of Classification Search
None
See application file for complete search history.

(56) References Cited

U.S. PATENT DOCUMENTS

| 2002/0068838 A1 | 6/2002 | Demassey et al. |
| 2010/0130450 A1 | 5/2010 | Lewis et al. |

FOREIGN PATENT DOCUMENTS

| WO | 2008143876 A2 | 11/2008 |
| WO | 2011087837 A2 | 7/2011 |

OTHER PUBLICATIONS

Buscaglia et al. (Molecular Biology of the Cell, 2003, 14, 4947-4957).*

(Continued)

*Primary Examiner* — Dennis Heyer
*Assistant Examiner* — Daniel M Podgorski
(74) *Attorney, Agent, or Firm* — LeClairRyan, a Professional Corporation

(57) ABSTRACT

In one aspect, the present invention relates to a method of identifying compounds useful in modifying the activity of Aldolase. The method includes providing a first model comprising Aldolase or residues of the amino acid sequence corresponding to SEQ ID NO: 1 said residues being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347, providing one or more candidate compounds, evaluating contact between the candidate compounds and the first model to determine which of the one or more candidate compounds have an ability to bind to and/or fit in the first model, and identifying compounds which, based on said evaluating, have the ability to bind to and/or fit in the first model as compounds potentially useful for modifying the activity of Aldolase. The present invention also discloses compounds and compositions which modify the activity of Aldolase, or a complex between Aldolase and TRAP. Methods of treating or preventing malaria, or an infection by apicomplexan organisms are also disclosed.

2 Claims, 137 Drawing Sheets

(51) Int. Cl.
C07D 487/04 (2006.01)
G06F 19/12 (2011.01)
G06F 19/16 (2011.01)

(56) References Cited

OTHER PUBLICATIONS

Nemetski, "Visualization & Drug Discovery Targeting the Plasmodium falciparum Motor Complex," New York University, Thesis (publication date was in Apr. 2011).

Buscaglia et al. "Modeling the Interaction Between Aldolase and the Thrombospondin-Related Anonymous Protein, a Key Connection of the Malaria Parasite Invasion Machinery," Proteins: Structure, Function, and Bioinformatics 66(3):528-537 (2007).

PCT International Search Report and Written Opinion corresponding to PCT/US2012061875, filed Oct. 25, 2012 (dated Mar. 26, 2013).

Srivastava et.al., "Specificity and Inhibitory Activity of Antibodies to Plasmodium Falciparum Aldolase," J. Immun. 144:1497-1503 (1990).

"Frontiers in Drug Design and Discovery," Caldwell et al., Eds., Bentham Science Publishers Ltd.: Hilversum, The Netherlands (2007).

Bosch et al., "Aldolase Provides an Unusual Binding Site for Thrombospondin-Related Anonymous Protein in the Invasion Machinery of the Malaria Parasite," PNAS 104(17):7015-7020 (2007).

"Apicomplexan Parasites: Molecular Approaches toward Targeted Drug Development," Becker, K., Ed., Wiley-Blackwell, vol. 2, pp. 81-82 (2011).

International Preliminary Report on Patentability for International Patent Application No. PCT/US2012/061875 (dated Apr. 29 2014).

Jewett et al., "Aldolase Forms a Bridge Between Cell Surface Adhesins and the Actin Cytoskeleton in Apicomplexan Parasites," Mol. Cell 11:885-894 (2003).

Buscaglia et al., "Sites of Interaction Between Aldolase and Thrombospondin-Related Anonymous Protein in Plasmodium," Mol. Biol. Cell 14:4947-4957 (2003).

Sultan et al., "TRAP is Necessary for Gliding Motility and Infectivity of Plasmodium Sporozoites," Cell 90:511-522 (1997).

Danley D., "Crystallization to Obtain Protein-Ligand Complexes for Structure-Aided Drug Design," Acta Cryst. D62: 569-575 (2006).

* cited by examiner

| Procedure | Goal | Alternatives | Pitfalls |
|---|---|---|---|
| 1 Receptor modeling | Correct receptor pocket model(s). | Sources: X-ray, NMR, or homology modeling. Apo-form or liganded-form. Alternative conformations predicted by simulations. | Receptor model does not reflect the induced fit. Alternative conformations are missed. |
| 2 Library generation | Sufficiently large and diverse set of relevant compounds. | In-house collection, HTS hits, commercially available compounds, virtual libraries computed from accessible scaffolds and sidechains. | The library is too restricted, molecules are not chemically feasible or not drug-like. |

*FIG. 3*

| Procedure | Goal | Alternatives | Pitfalls |
|---|---|---|---|
| 3 Flexible docking | Correct prediction of the binding geometry. | MC or GA, stochastic global optimization with gradient minimization, incremental construction, grid or explicit receptor representations, etc. | Inaccurate energy function, poor optimization algorithm. Wrong receptor model, inadequate ligand flexibility. |
| 4 Ligand scoring | Maximal separation between binders and non-binders. | Weighted interaction terms, statistical potentials, combination of binding score with QSAR if binders are known. | Poorly predicted binding geometries, score over-training to a particular case/family, large number of false positives. |
| 5 Hit list post-processing | The best task for the chemist, screener or compound vendor. | Clustering, diversity, selection of scaffolds and/or side-chains for a small combinatorial library or parallel synthesis. | Domination of one chemical family, lack of chemical availability, or ADME-tox and patent considerations. |

FIG. 3 (cont.)

FIGURE 16
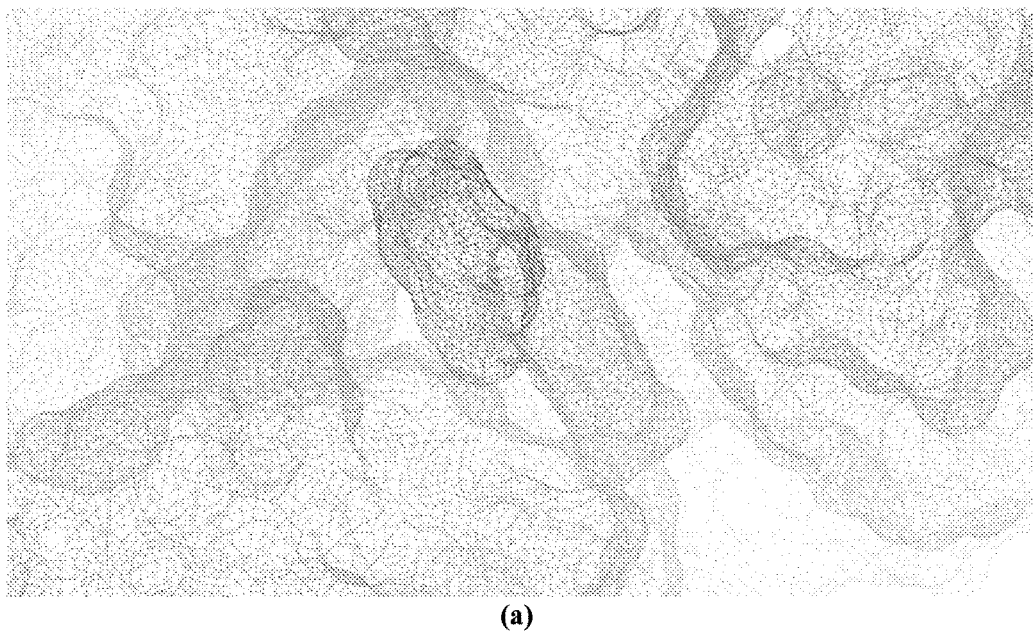
(a)
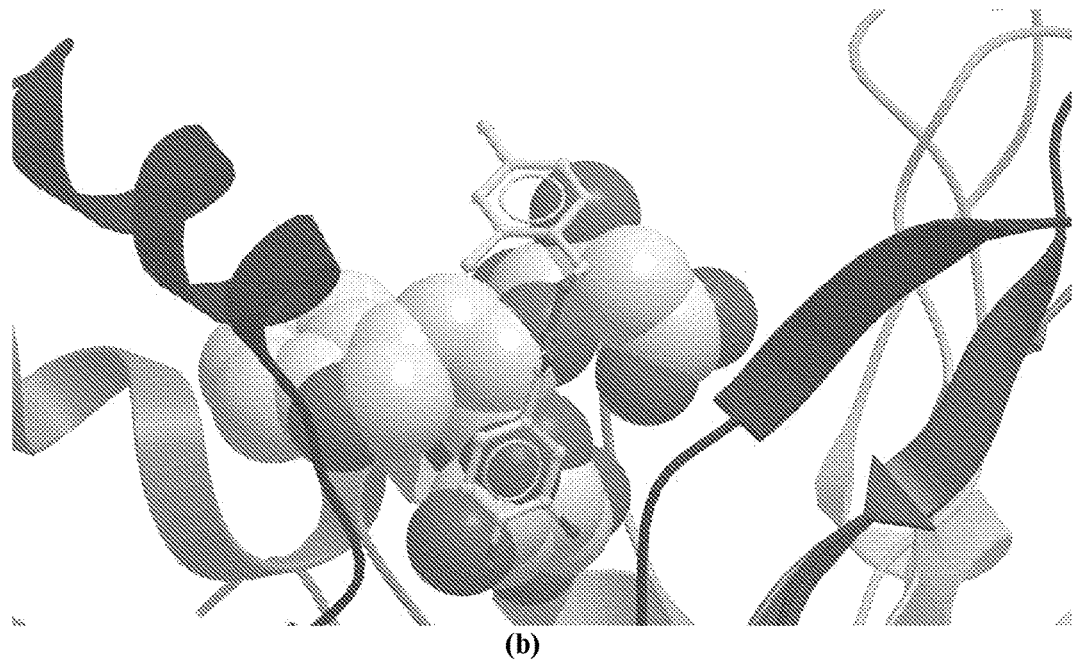
(b)

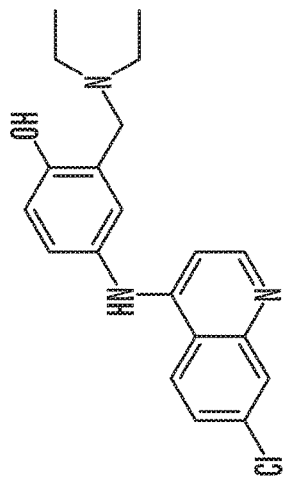
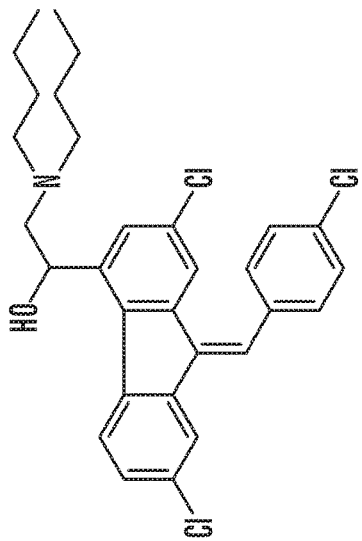
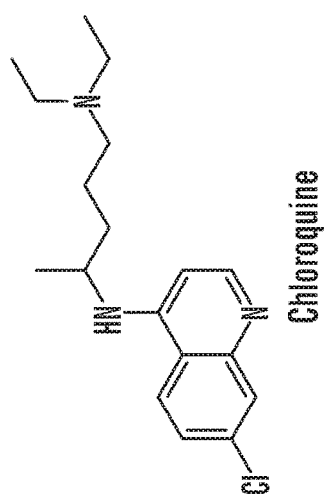
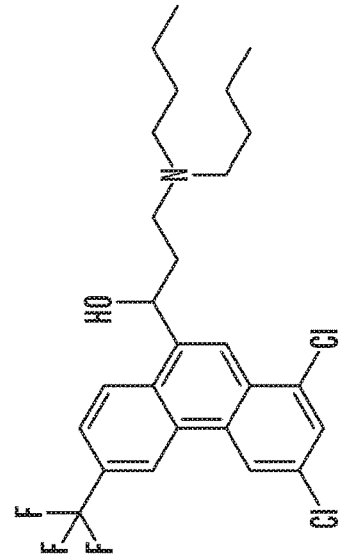
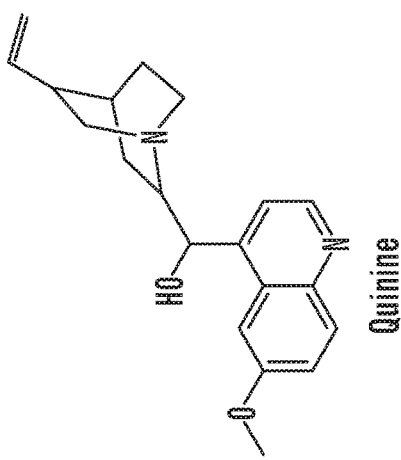
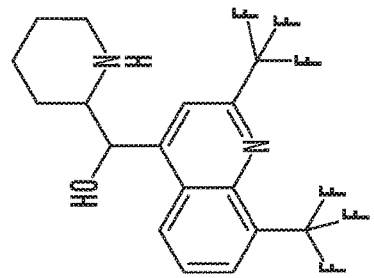
FIG. 22

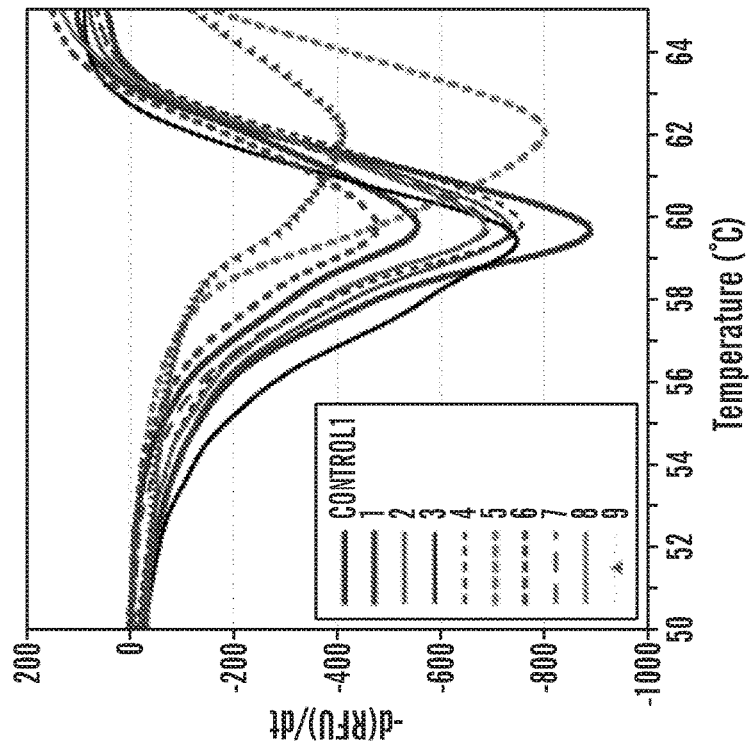
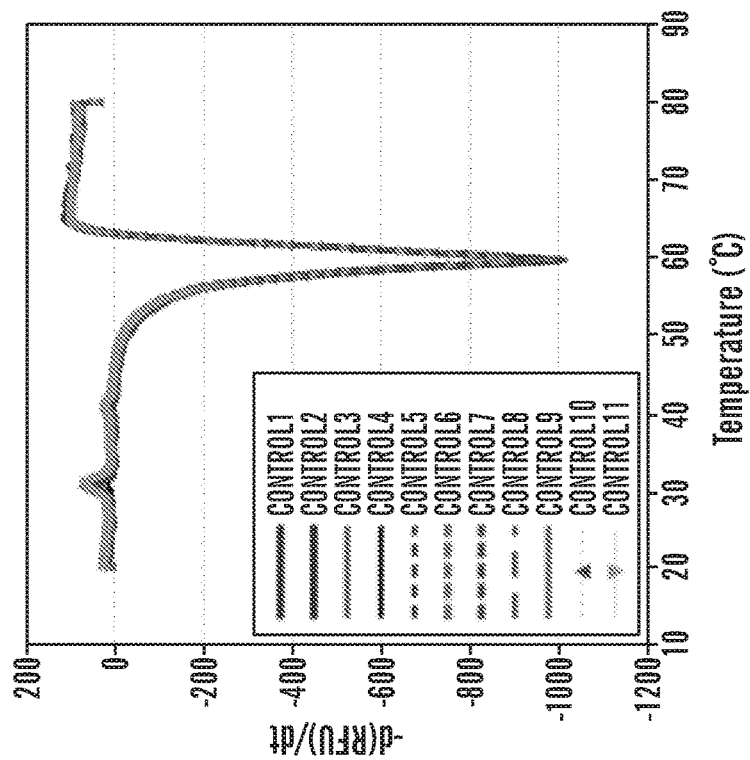
*FIG. 24A*
*FIG. 24B*

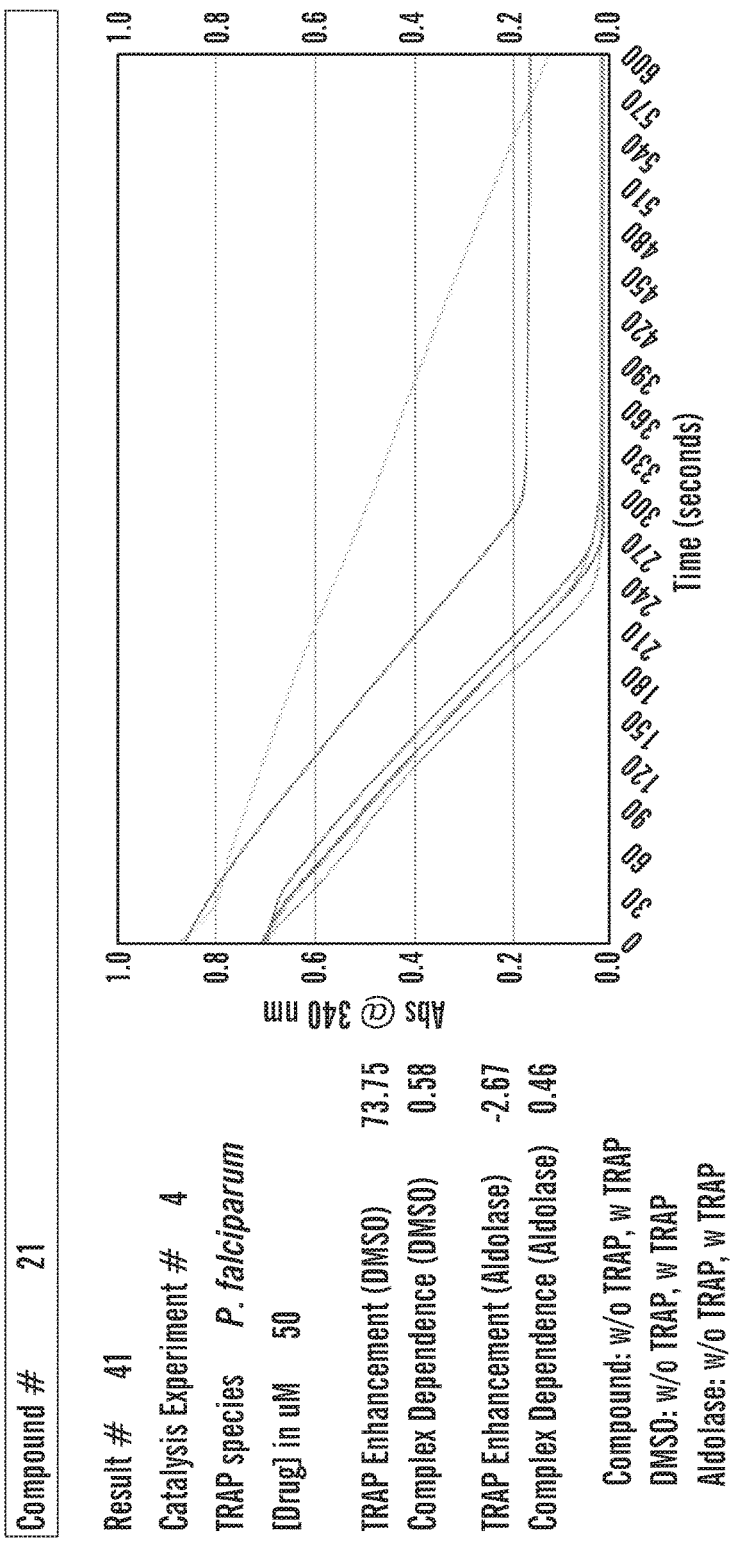
FIG. 2500

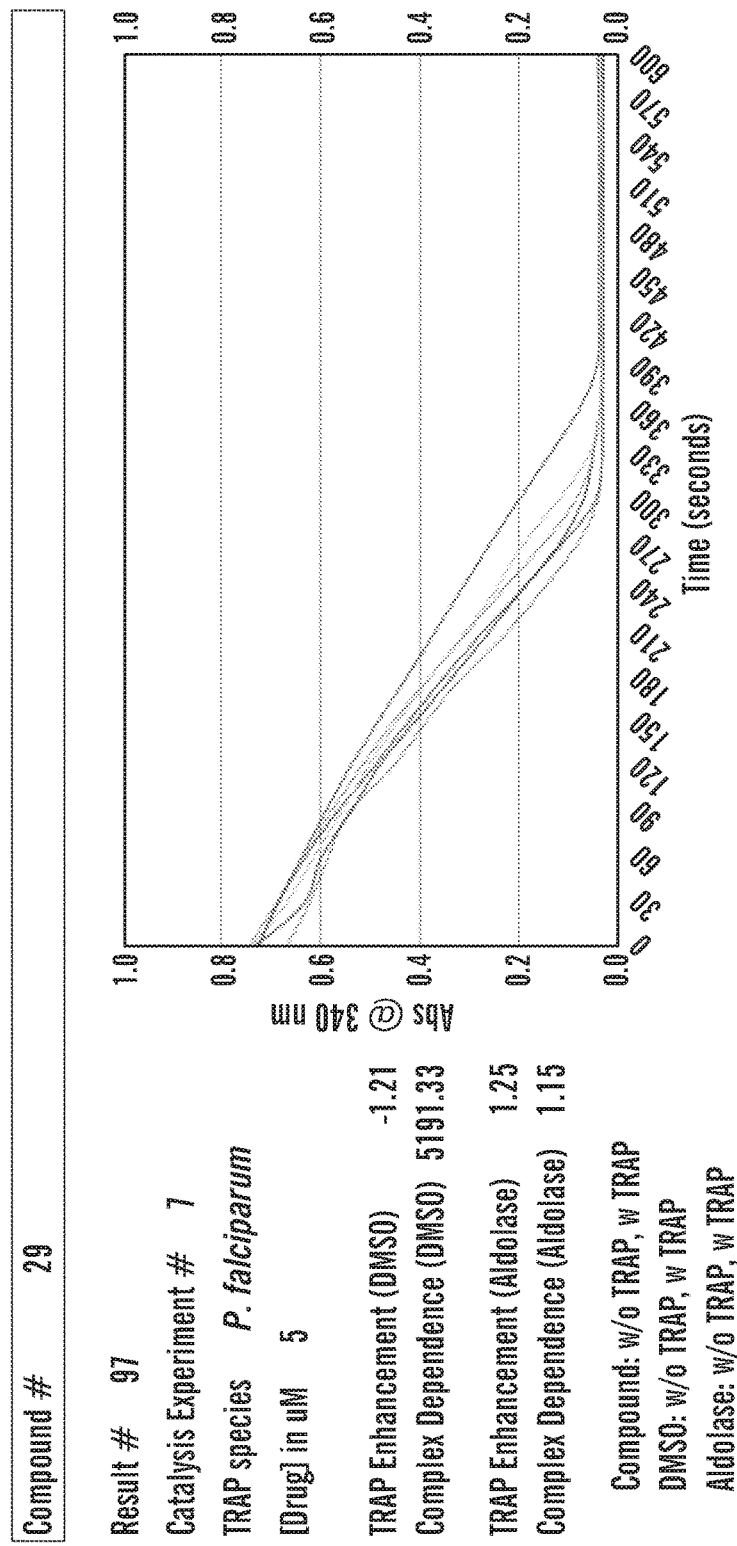
FIG. 25AAA

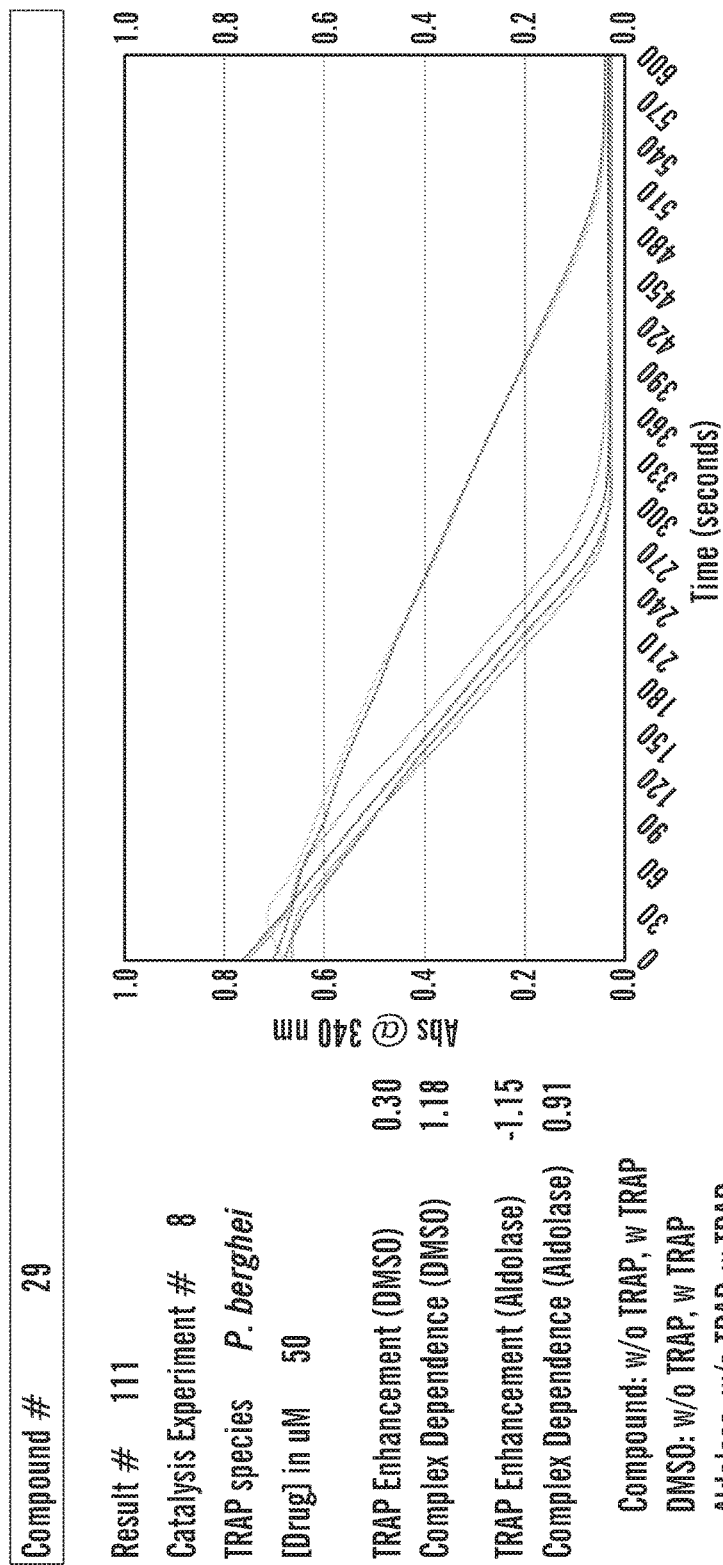
FIG. 25BBB

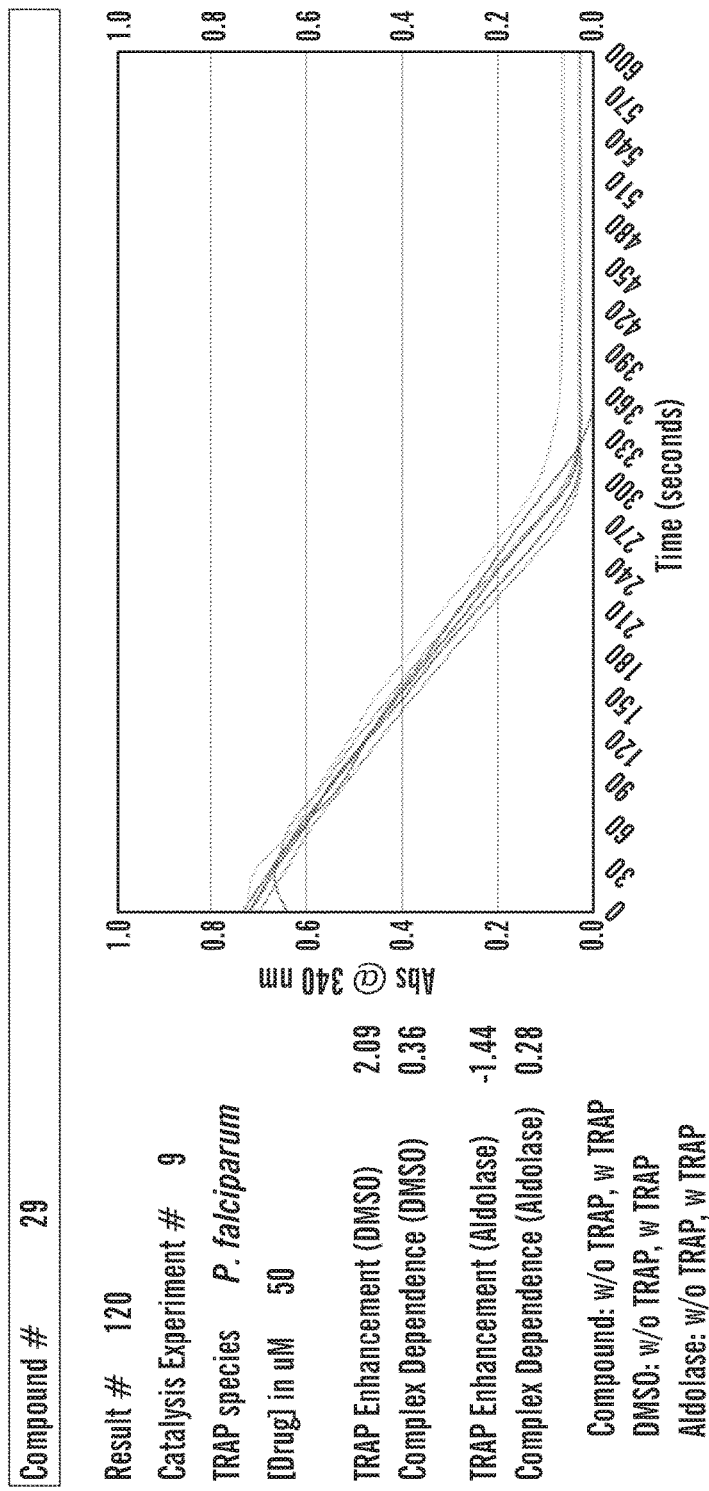
FIG. 25CCC

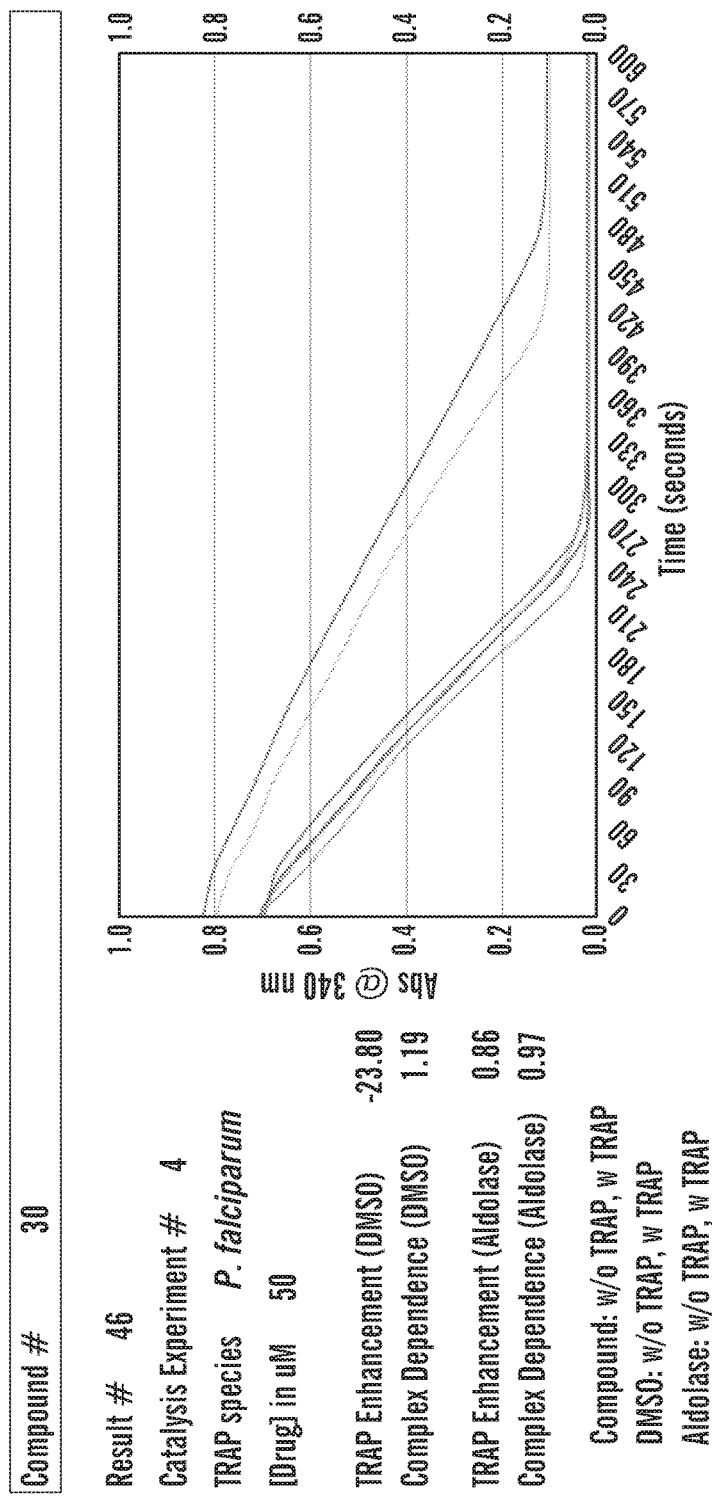
FIG. 25DDD

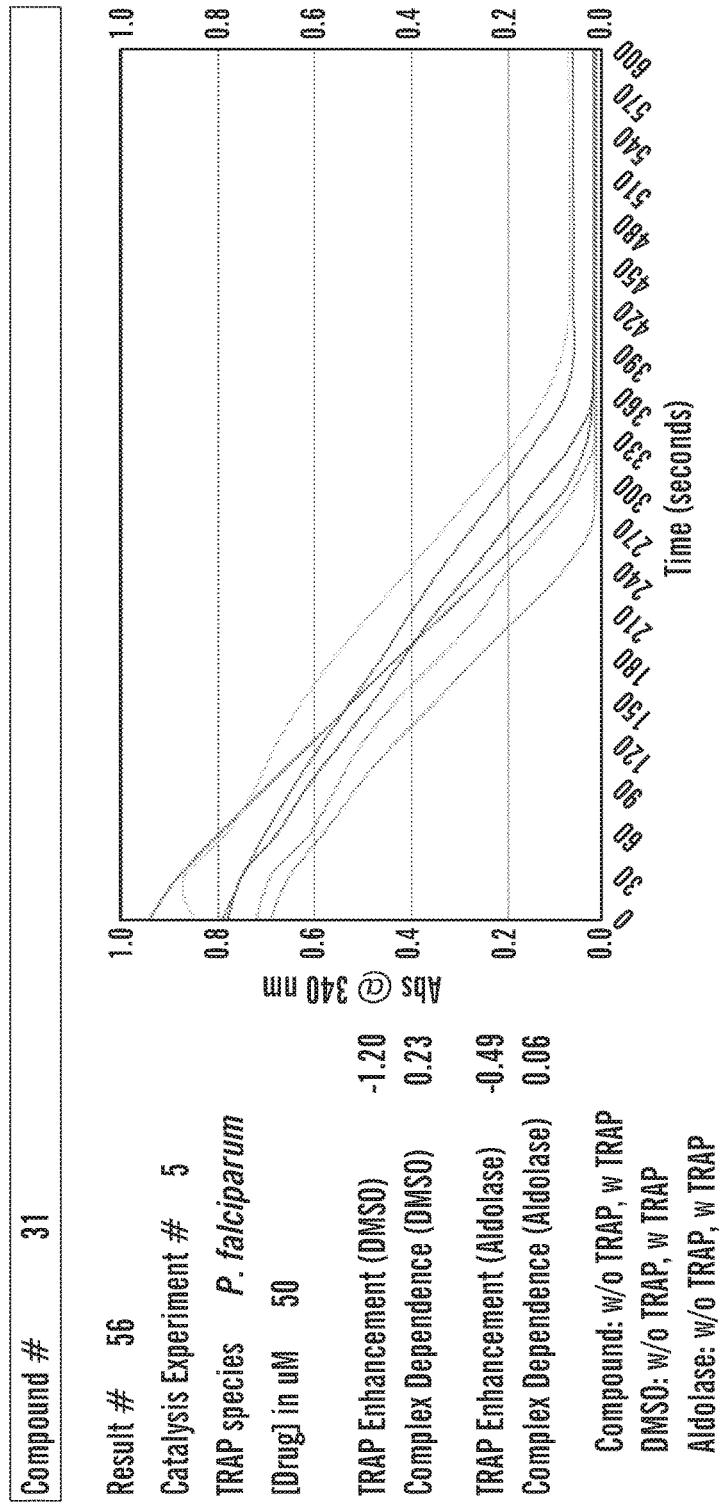
FIG. 25EEE

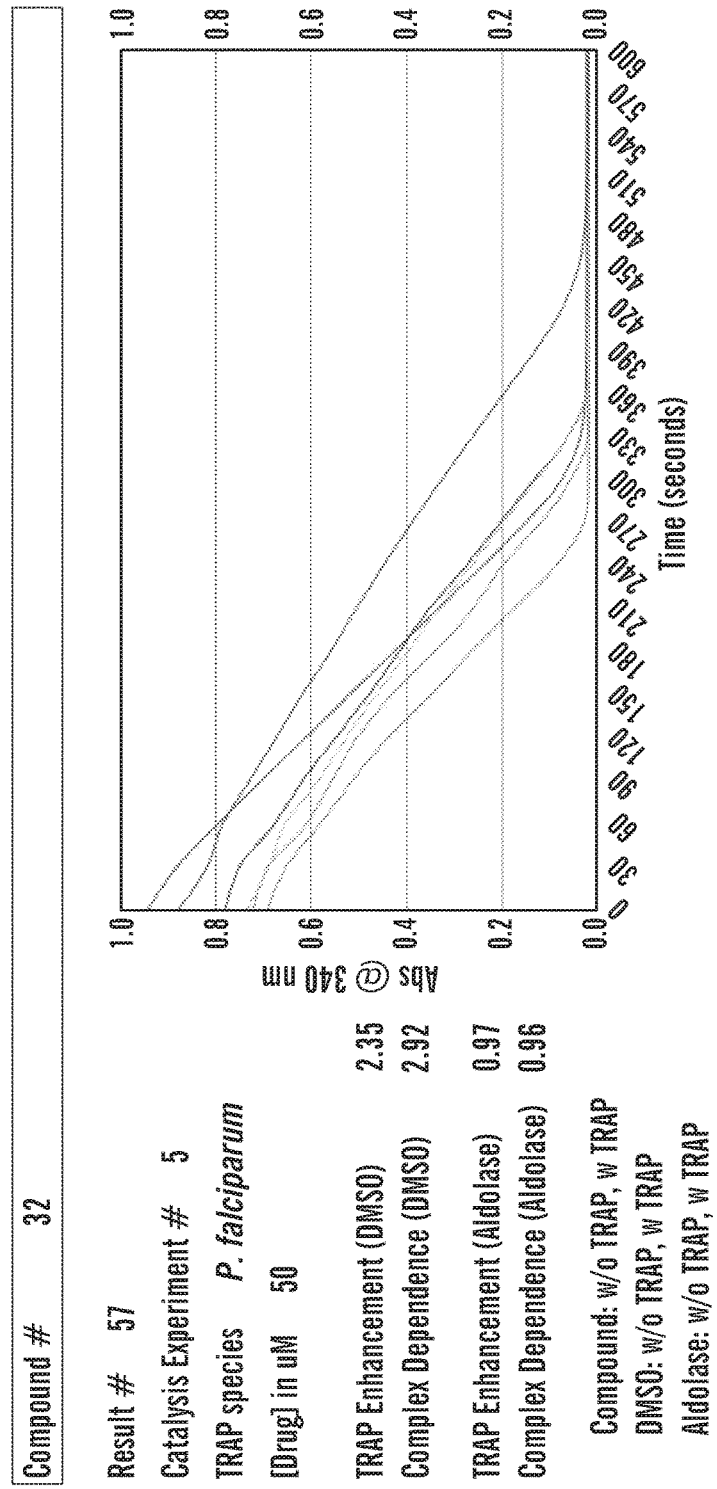
FIG. 25HHH

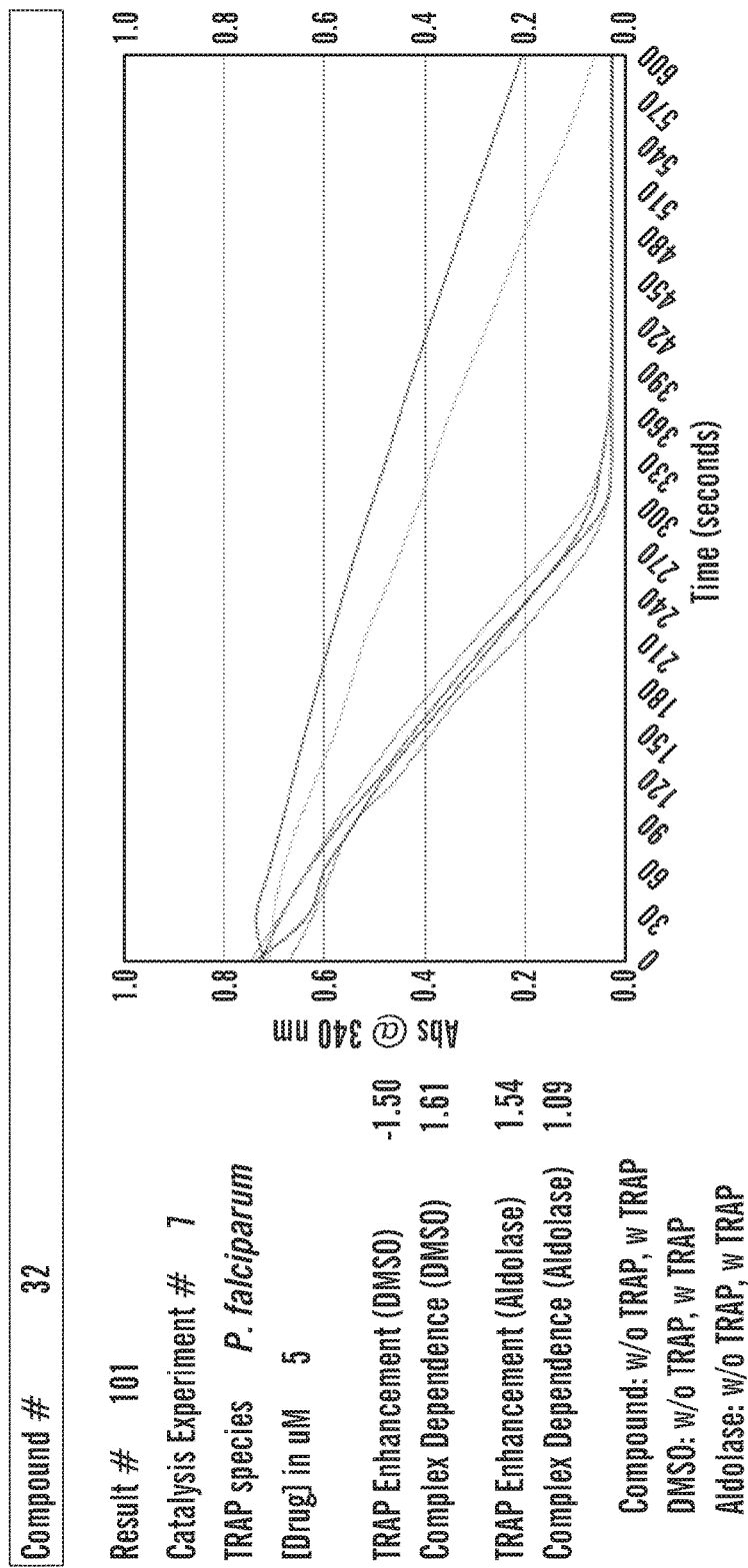
FIG. 25GGG

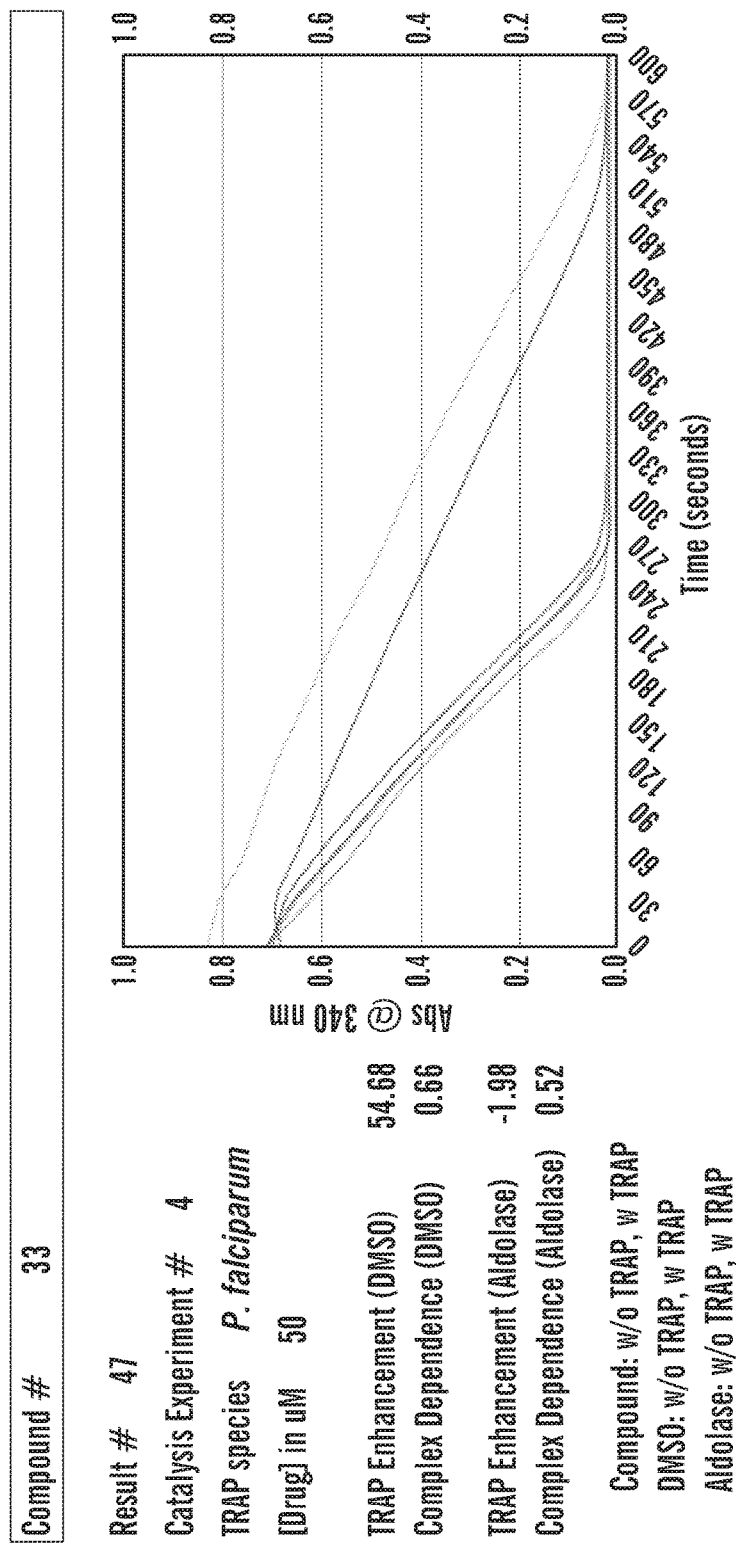
FIG. 25HHH

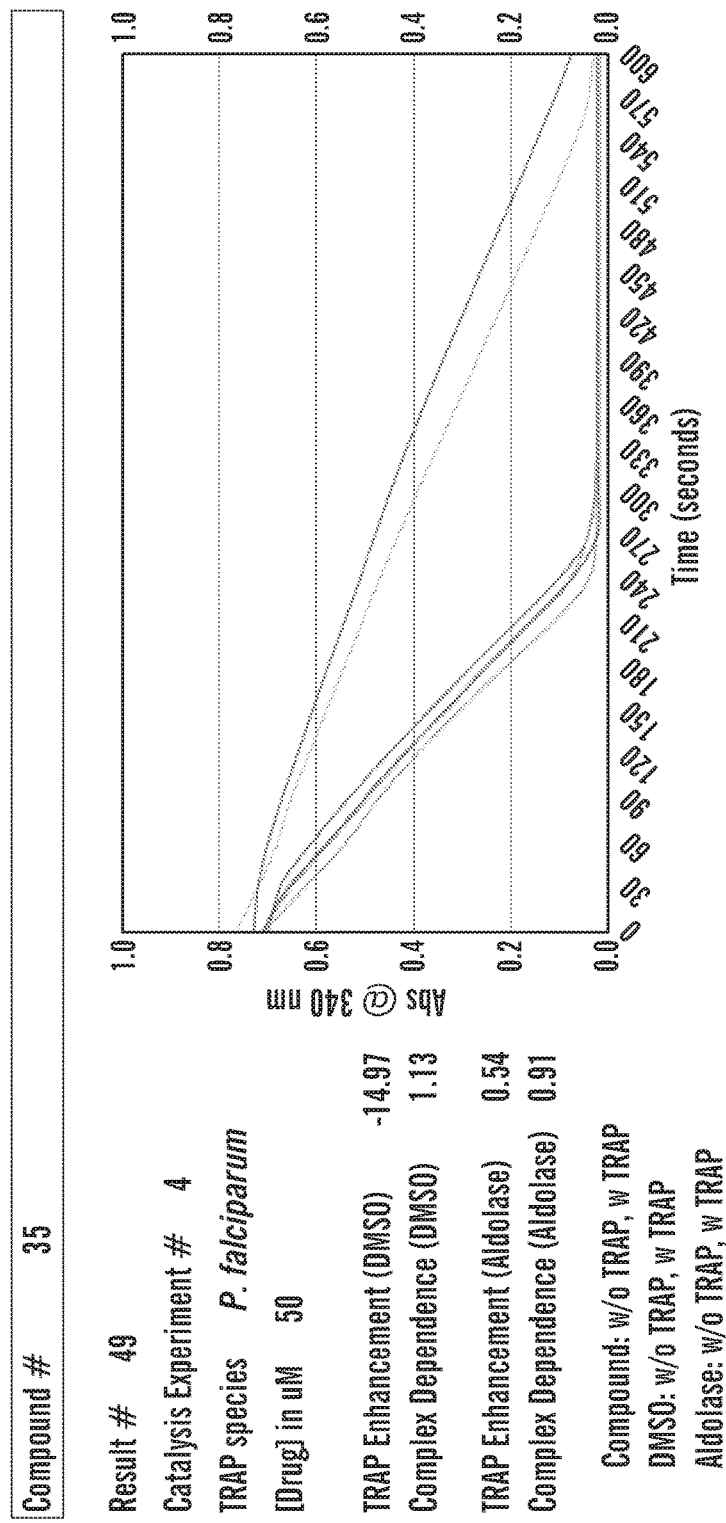
FIG. 25III

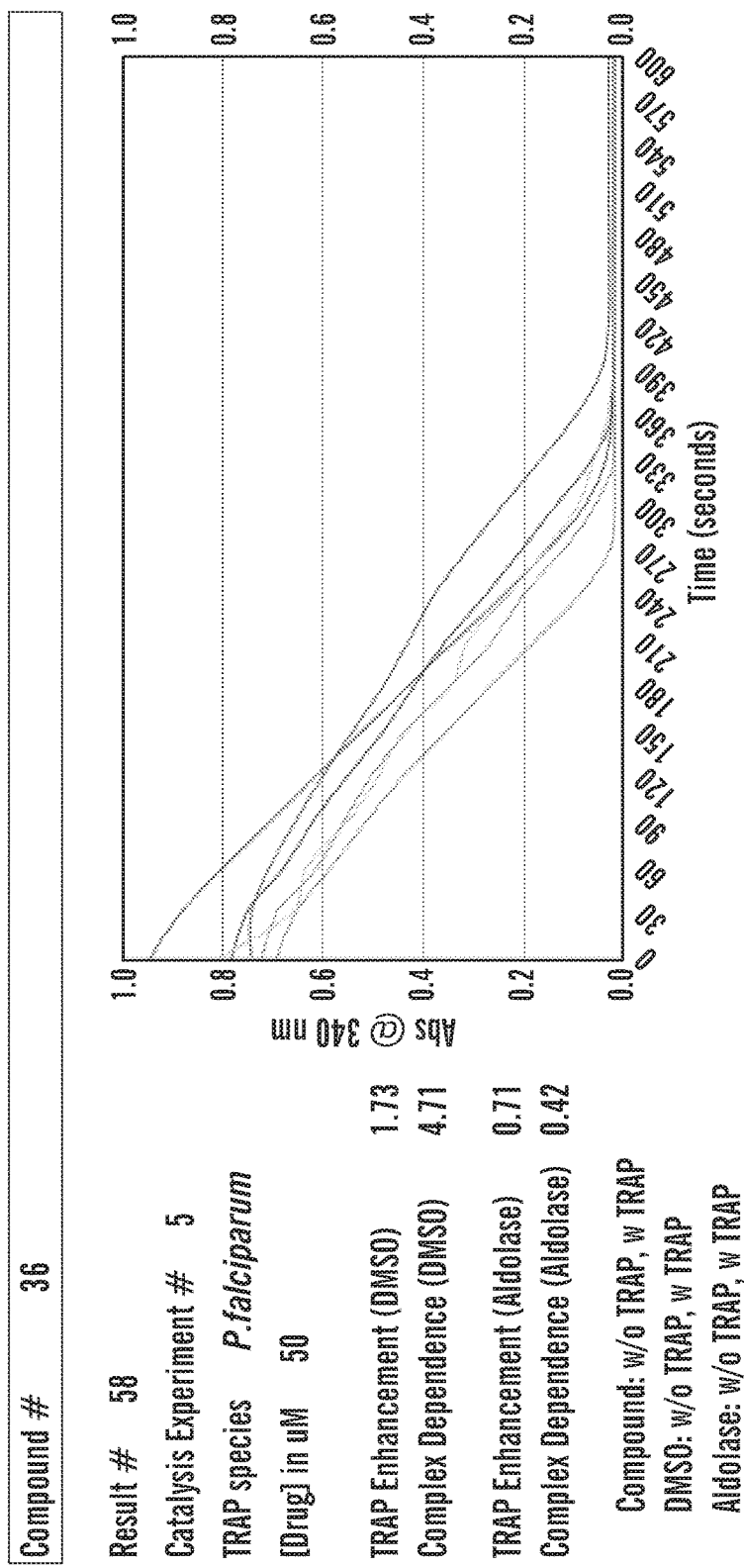
FIG. 25JJJ

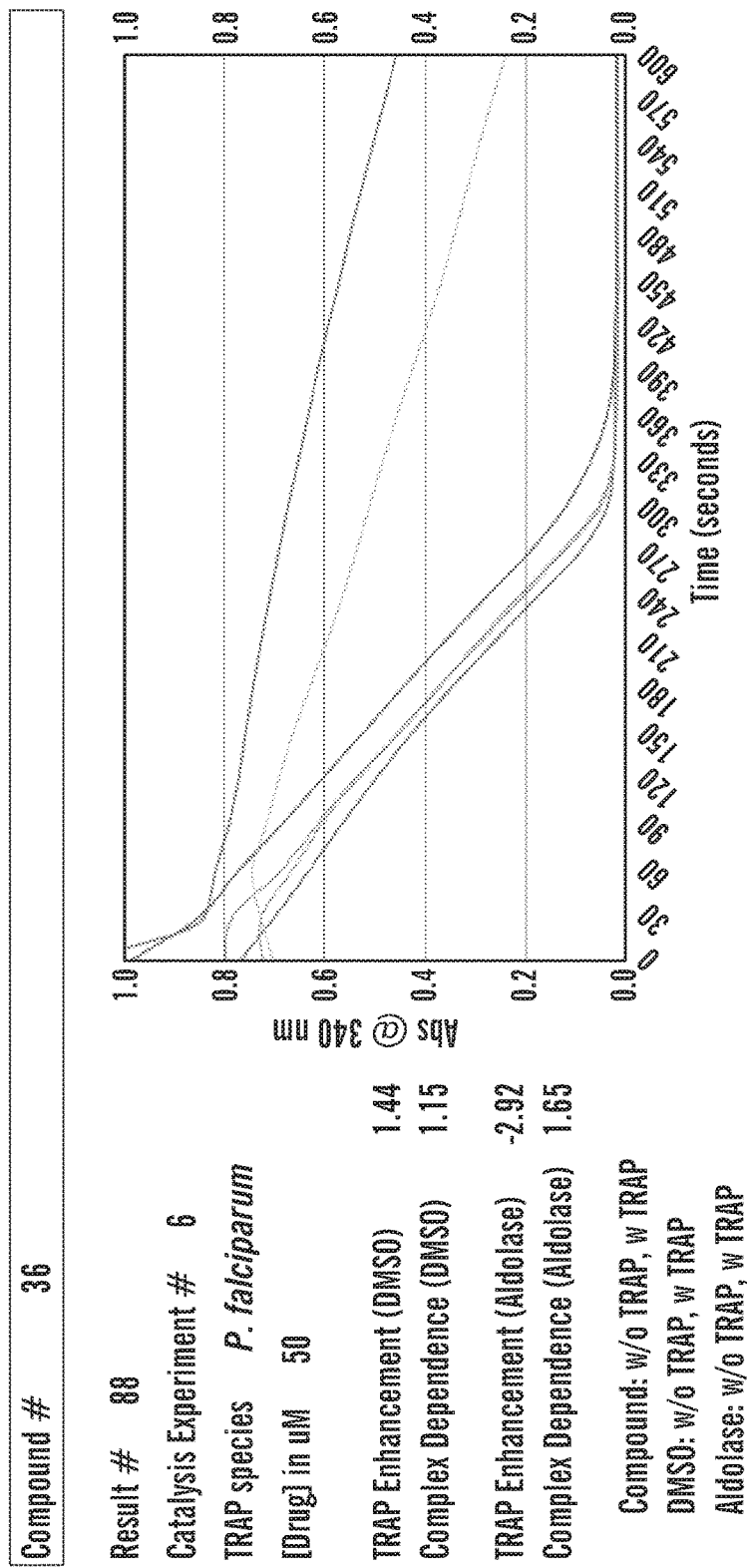
FIG. 25KKK

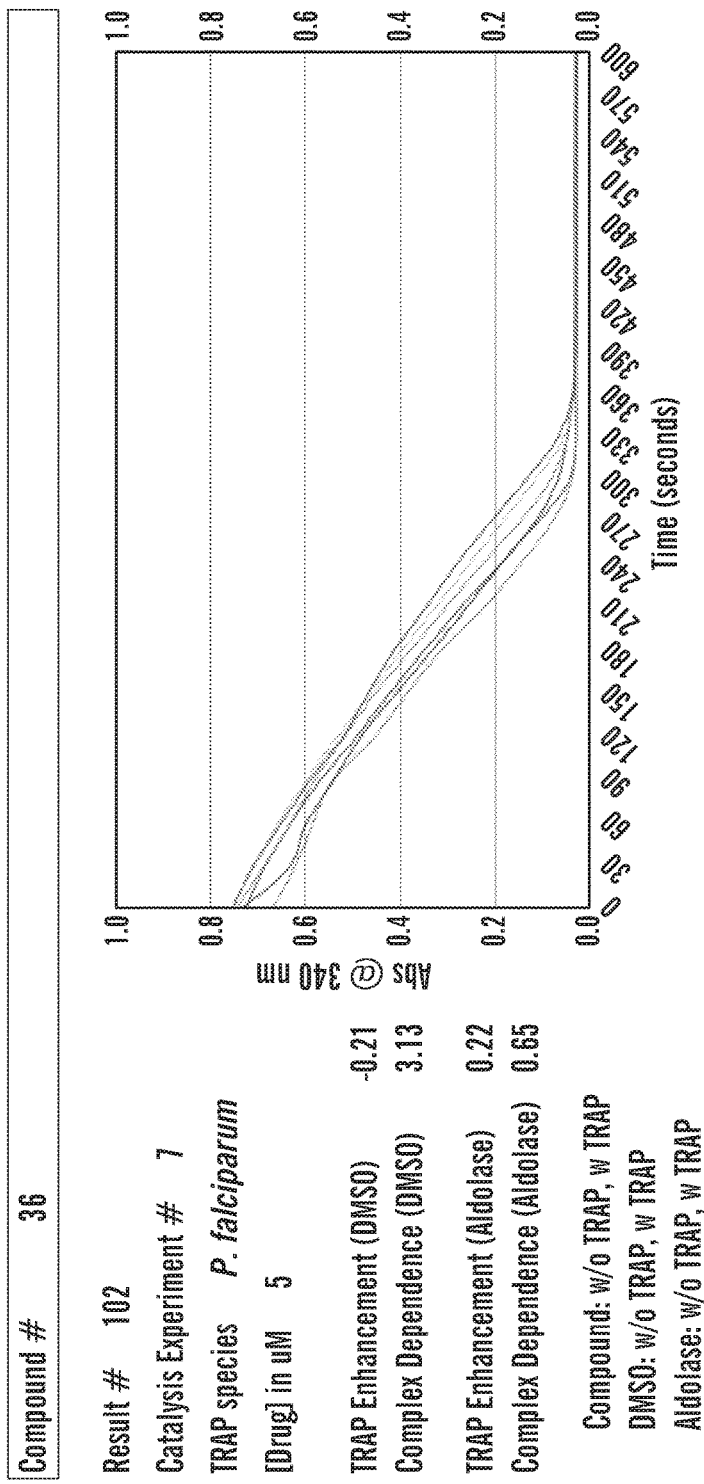
FIG. 25LLL

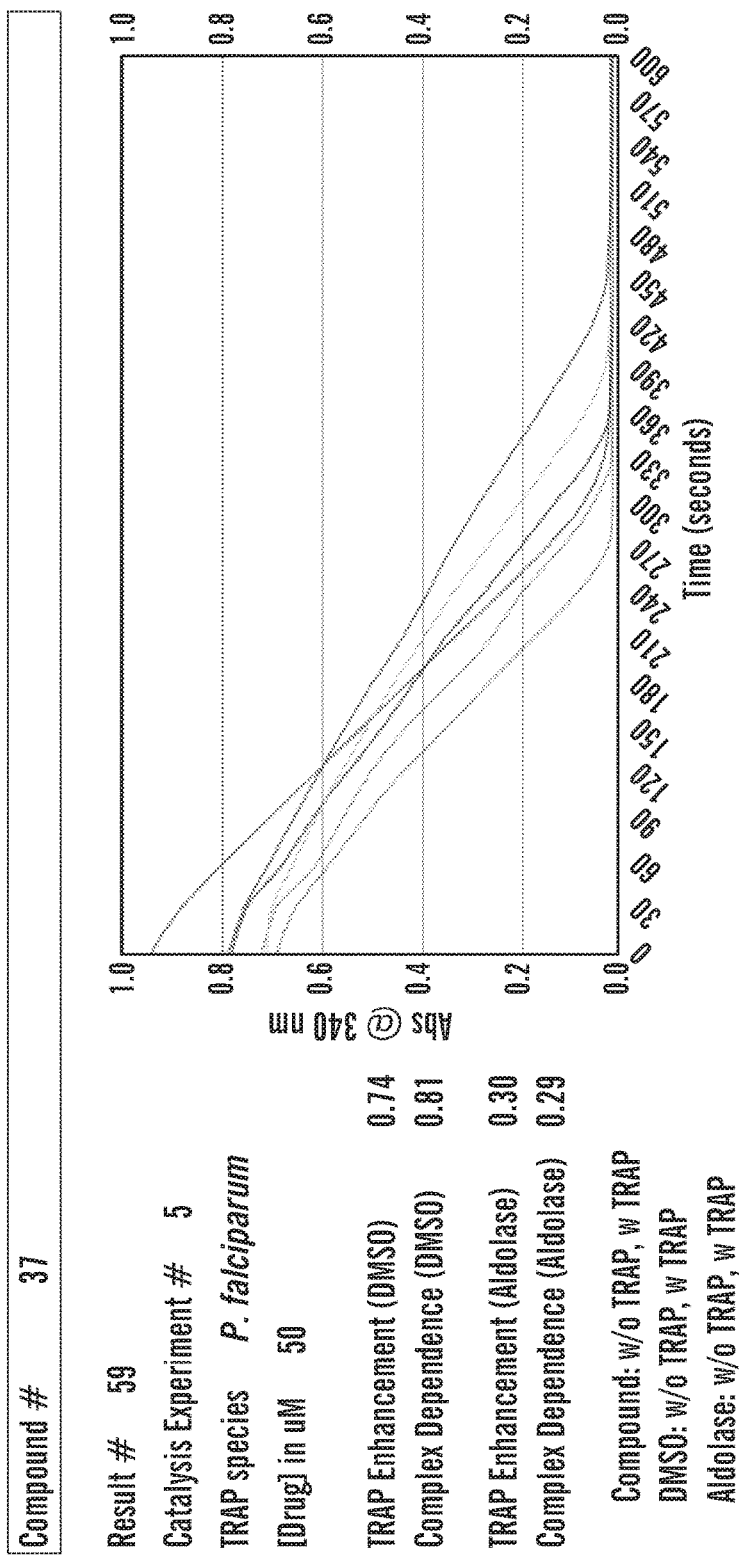
FIG. 25MMM

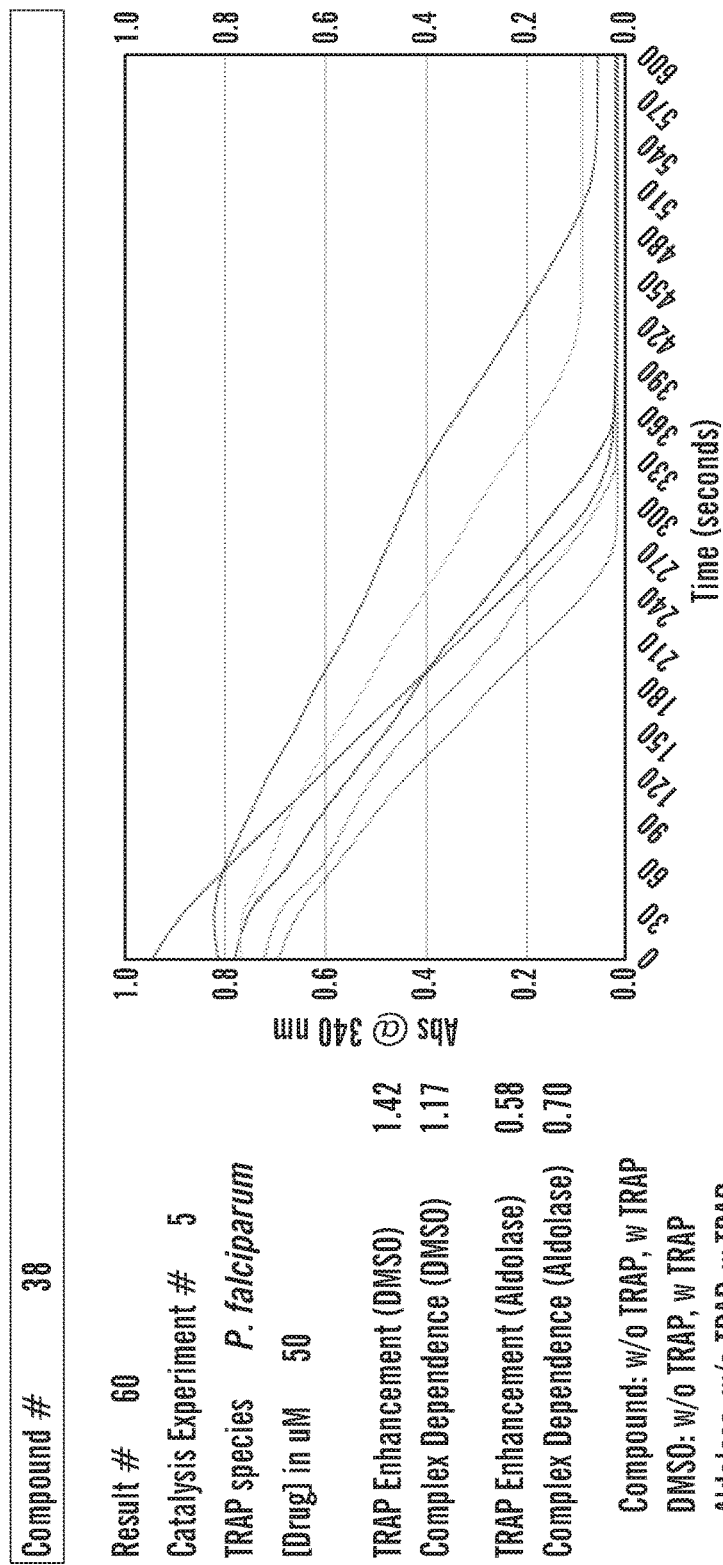
FIG. 25NNN

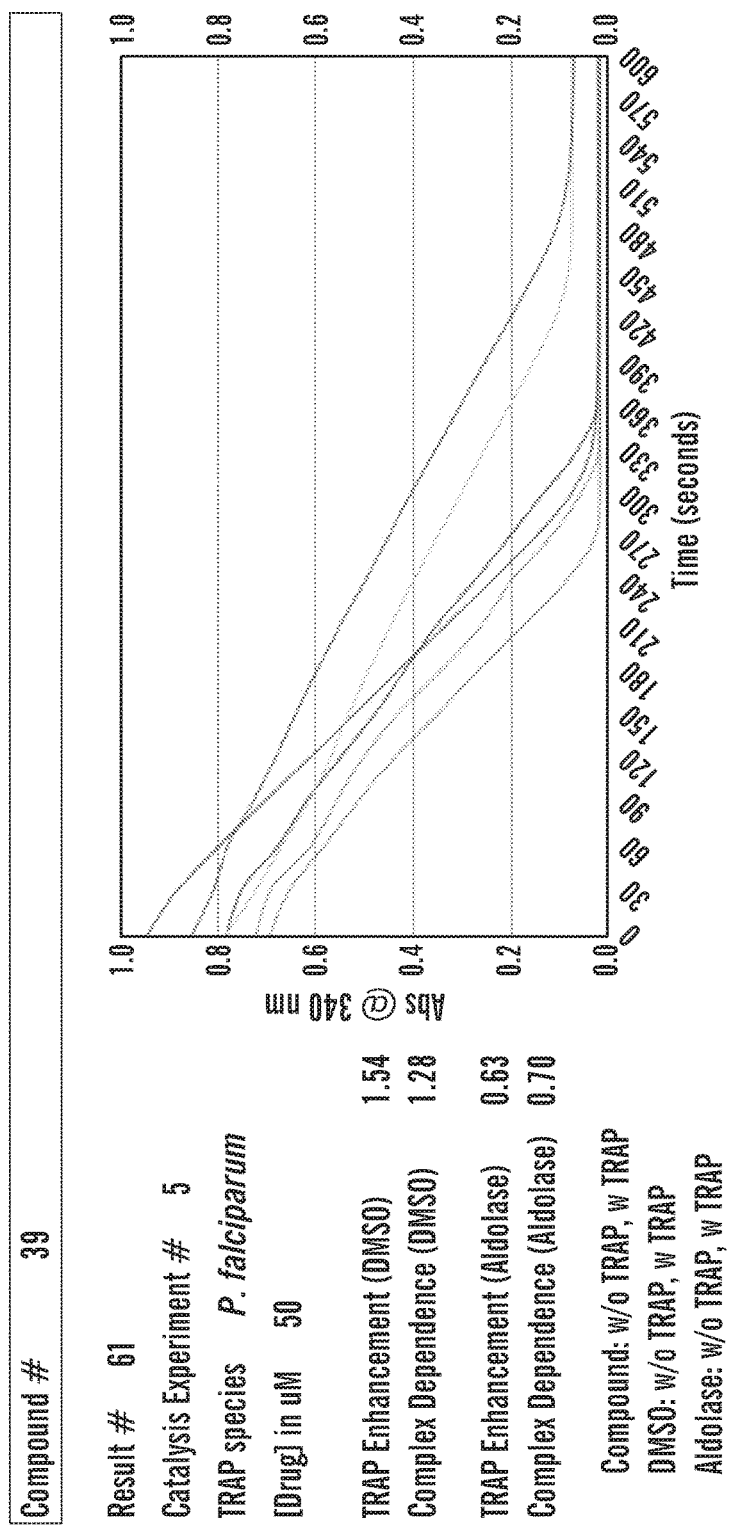
FIG. 25000

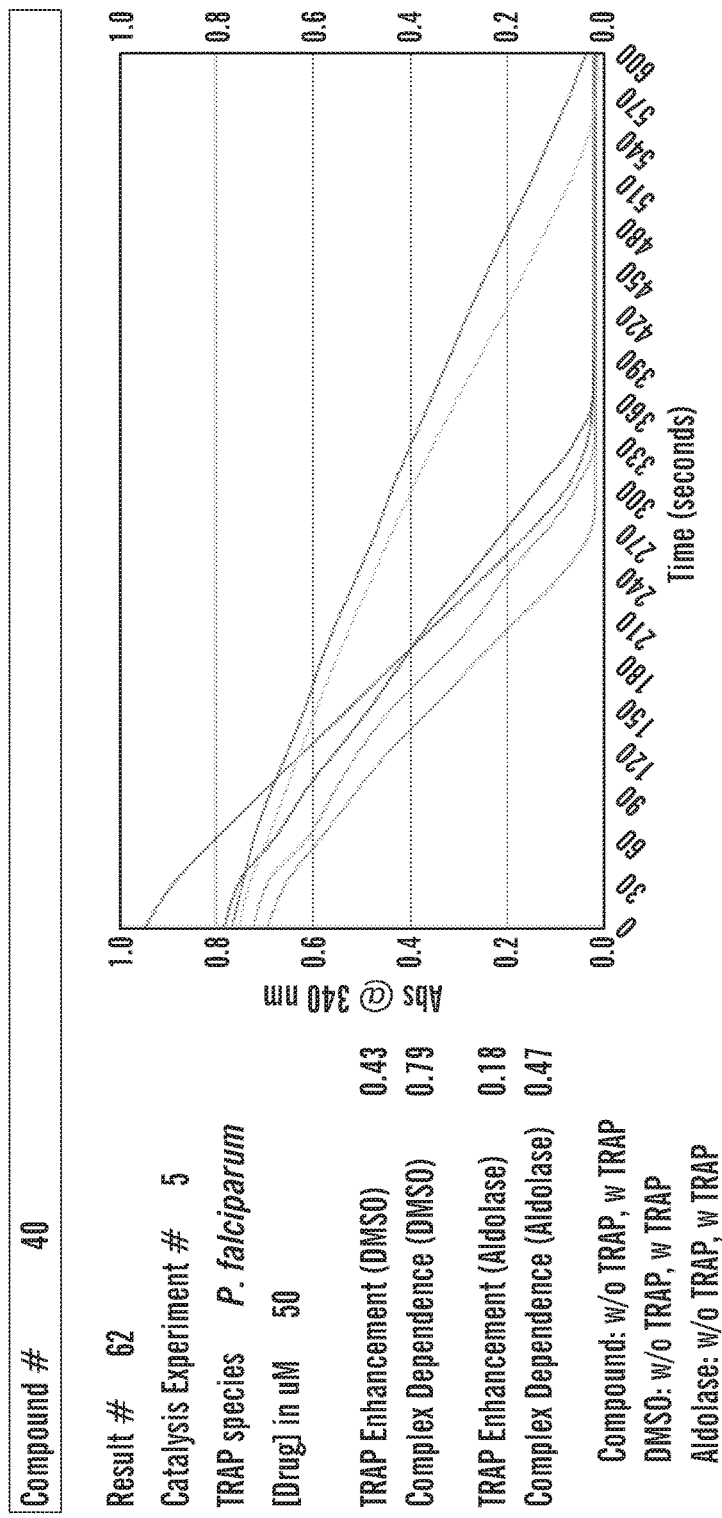
FIG. 25PPP

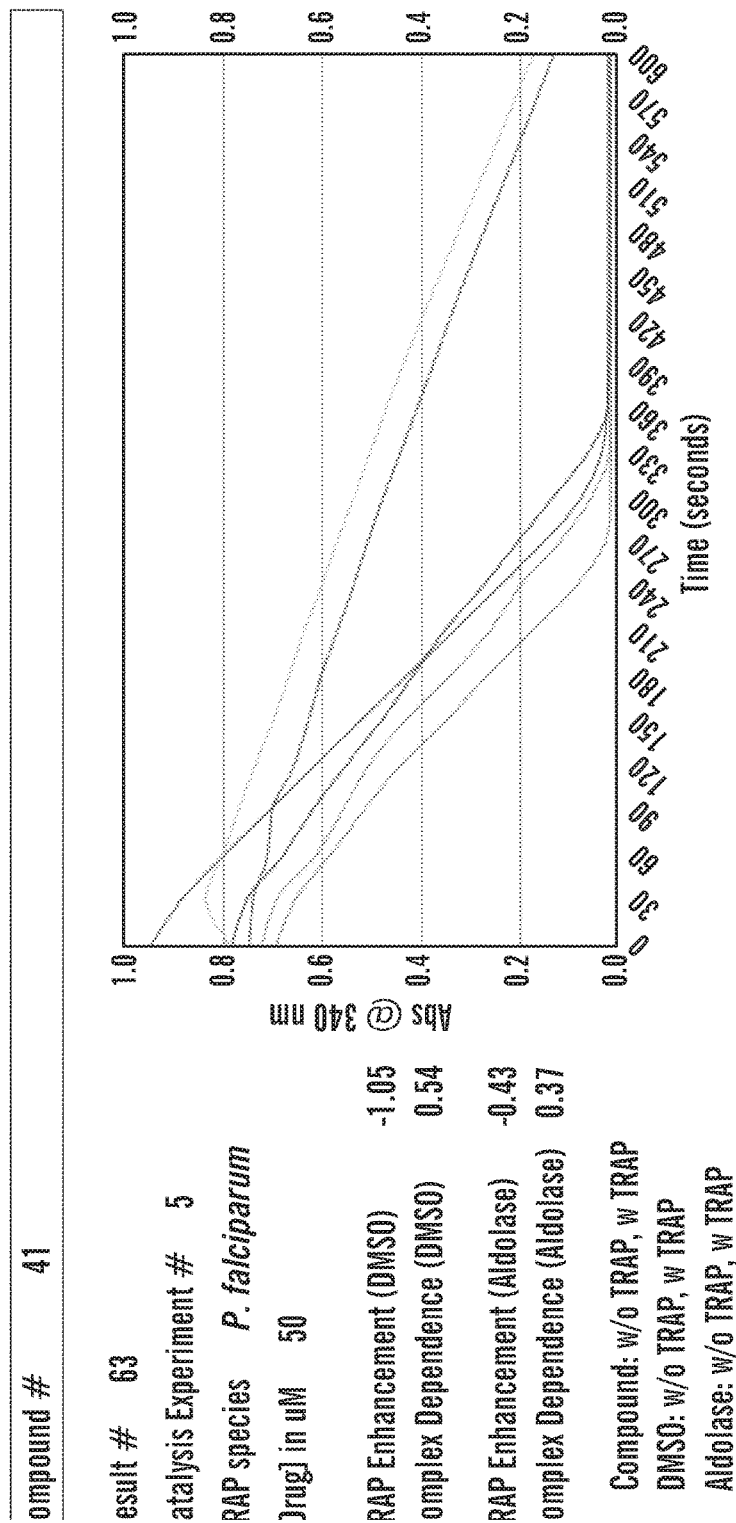
FIG. 25QQQ

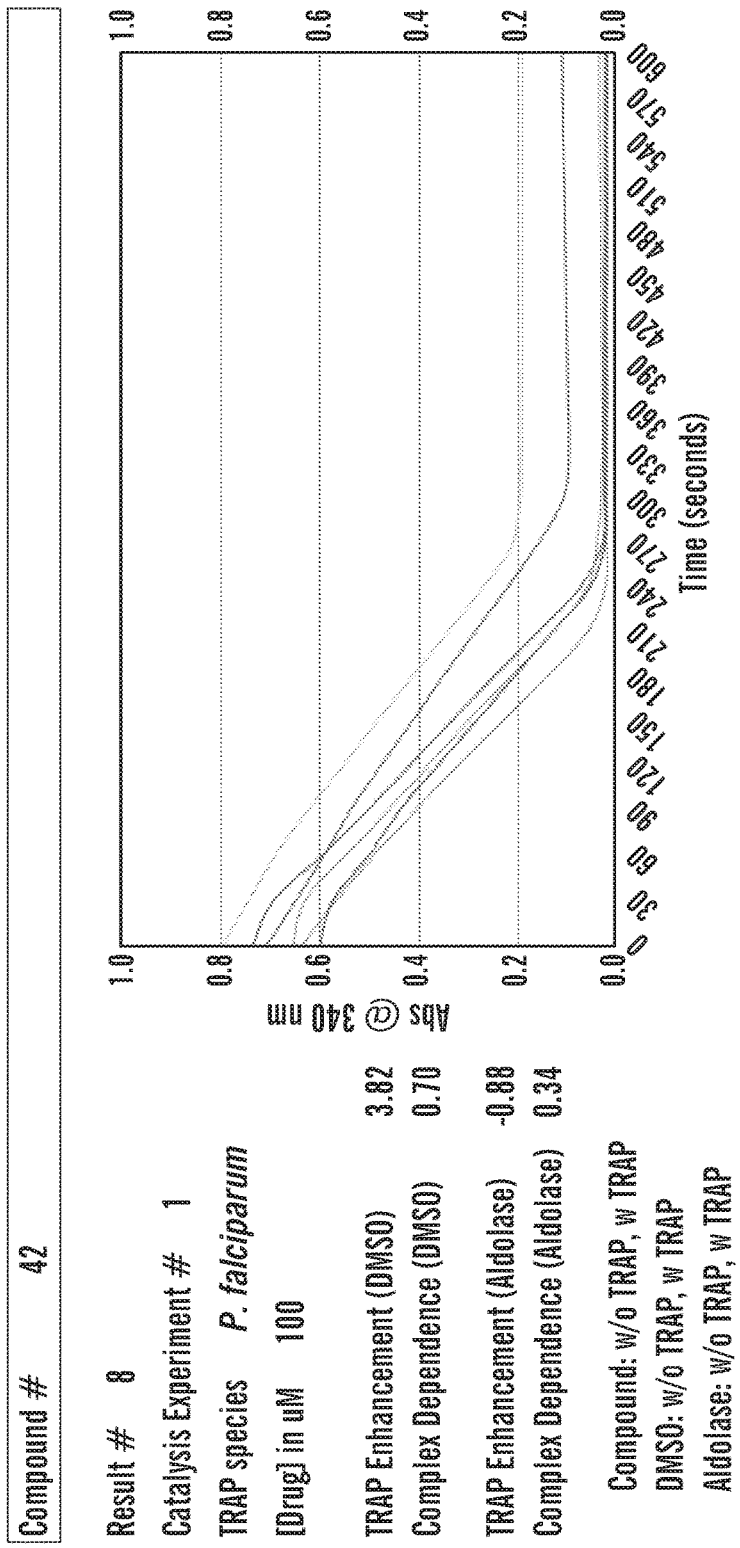
FIG. 25RRR

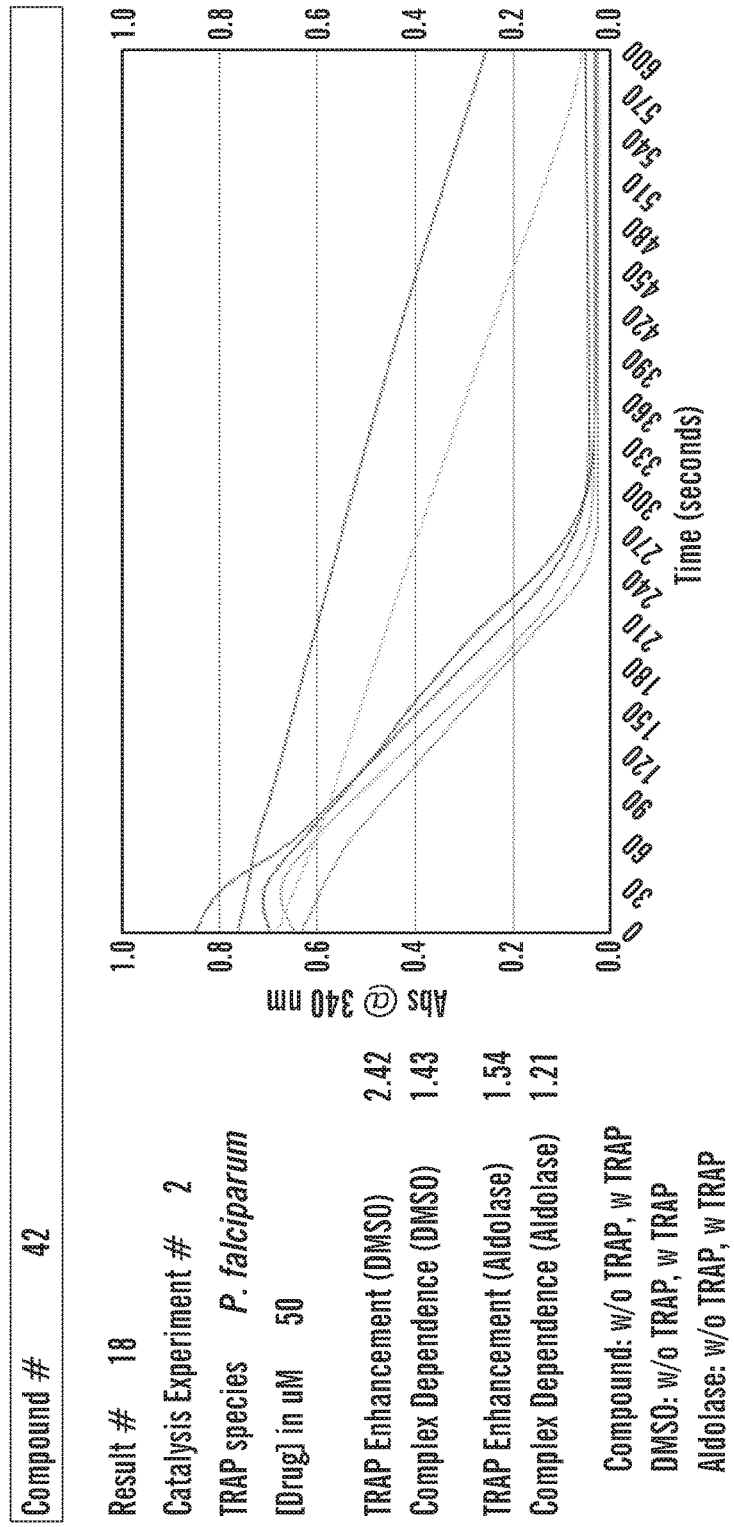
FIG. 25SSS

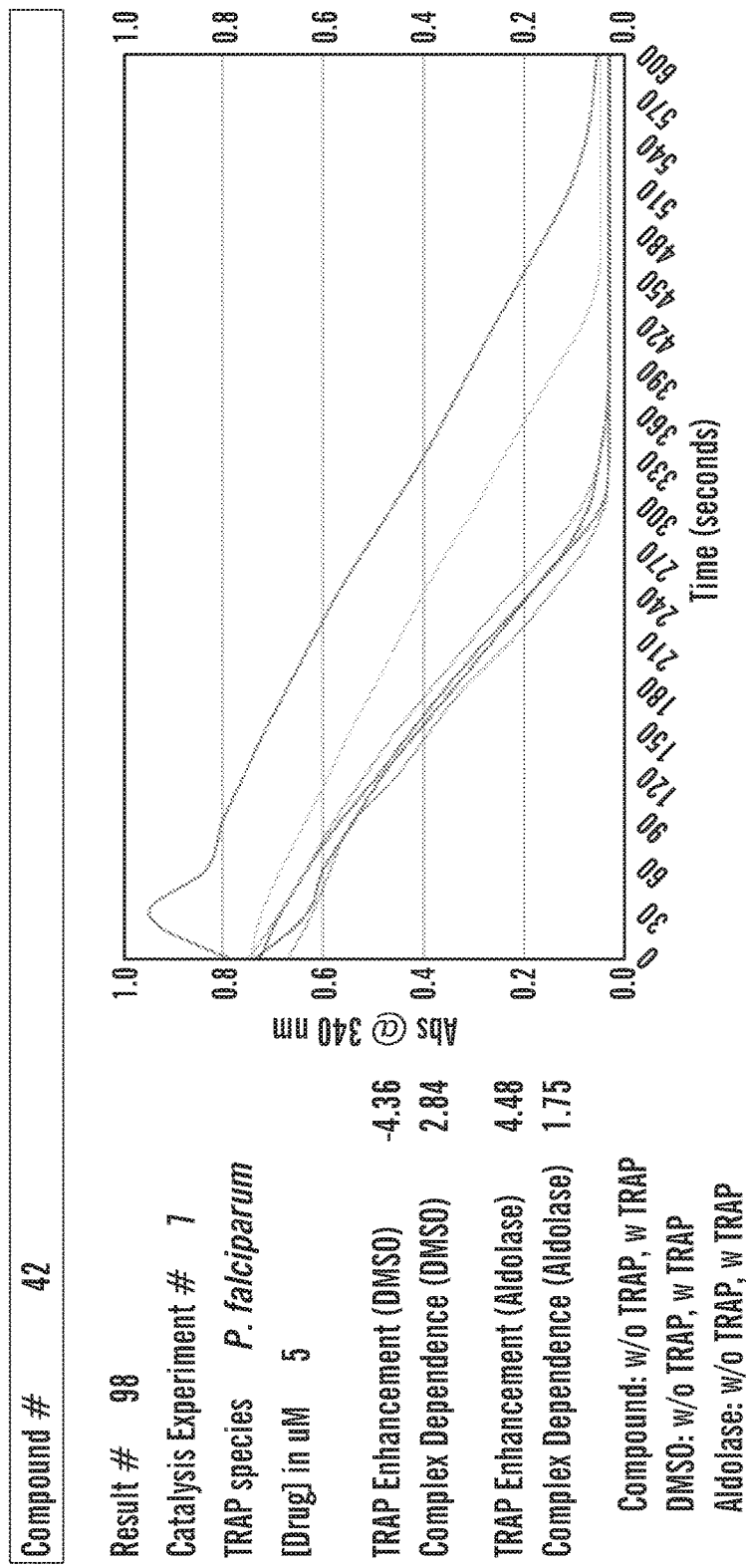
FIG. 25TTT

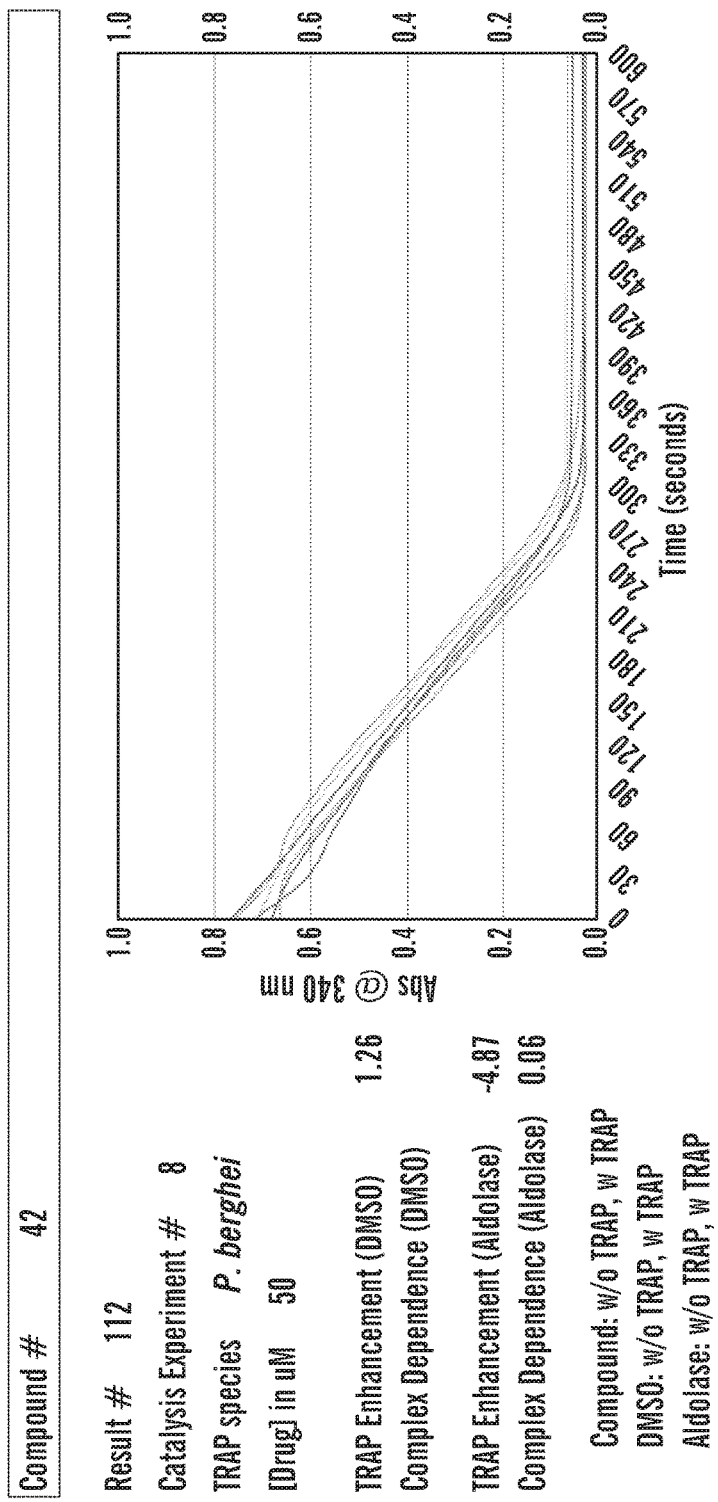
FIG. 25UUU

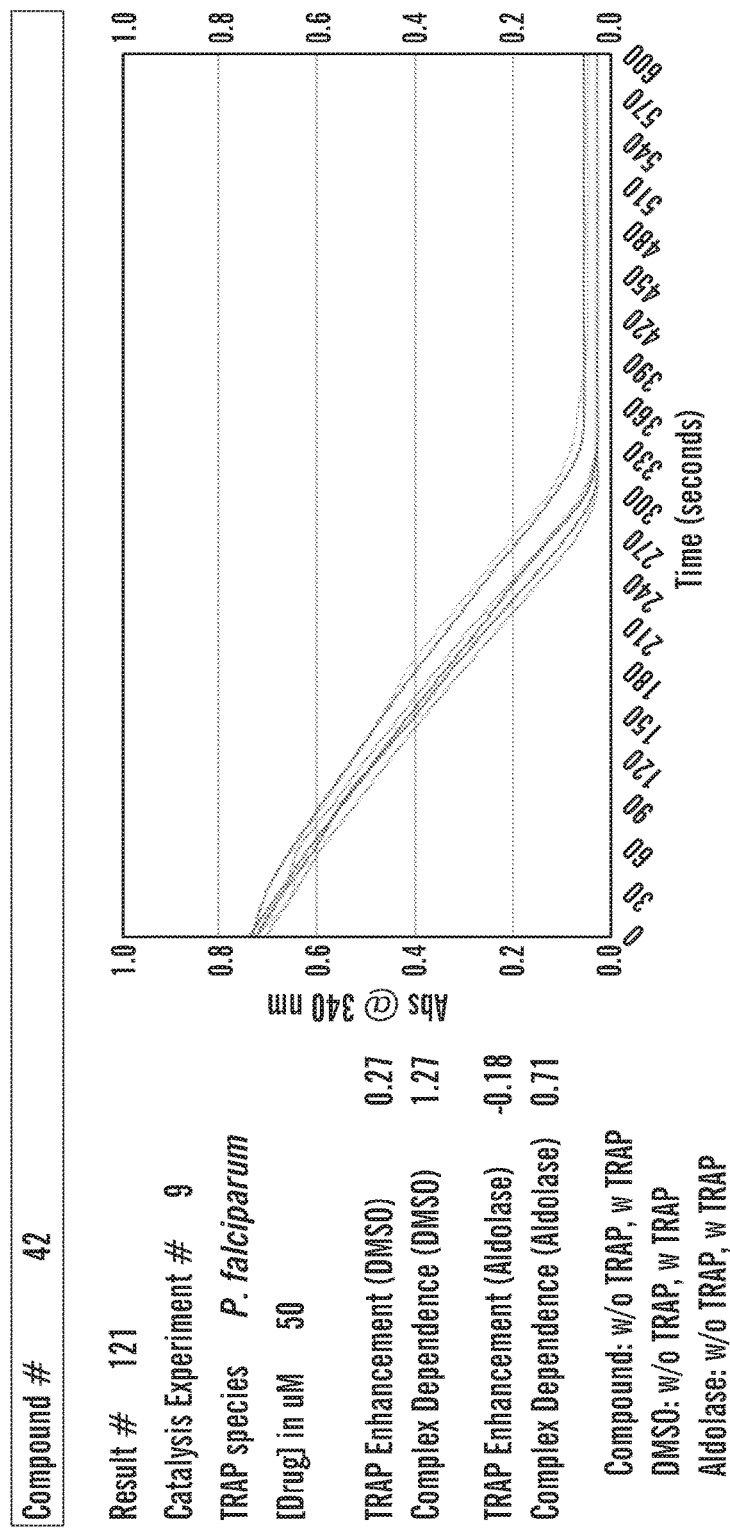
FIG. 25VVV

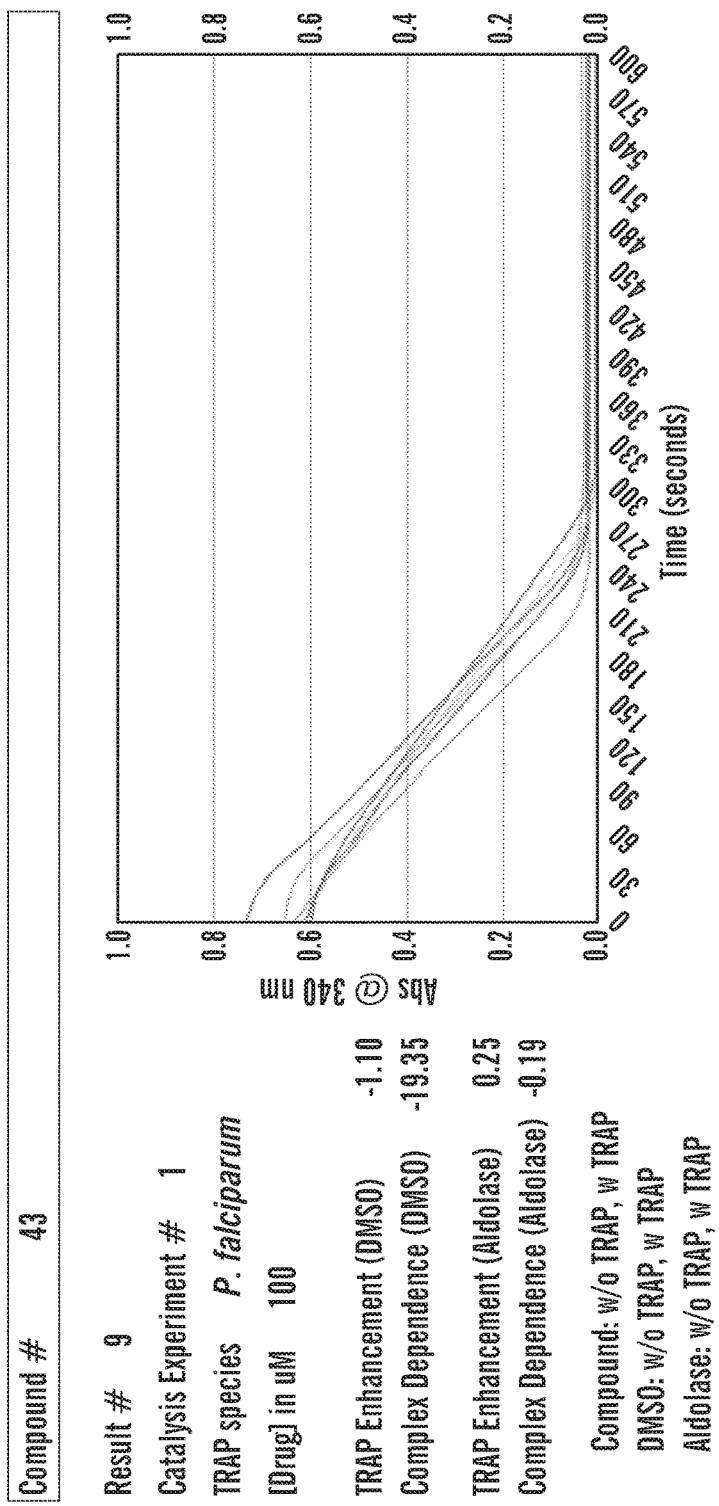
FIG. 25WWW

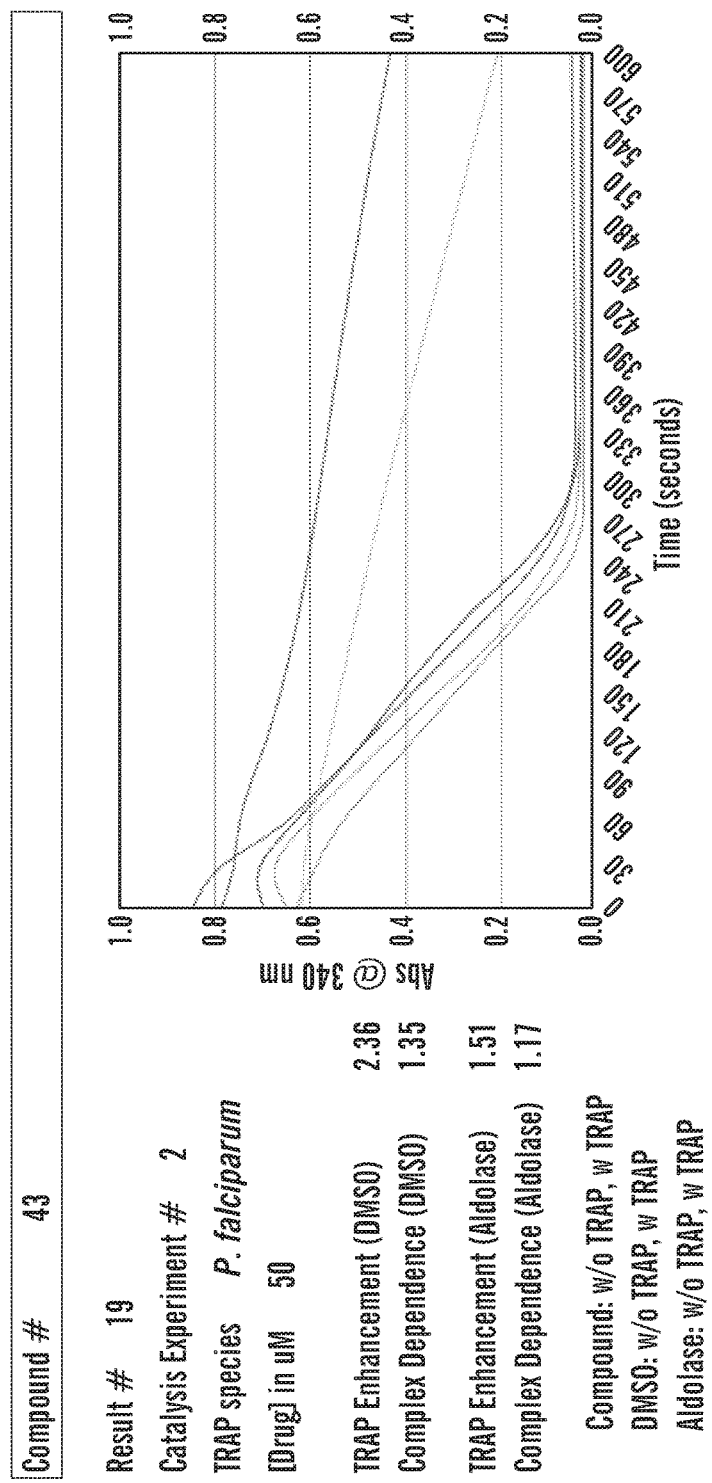
FIG. 25XXX

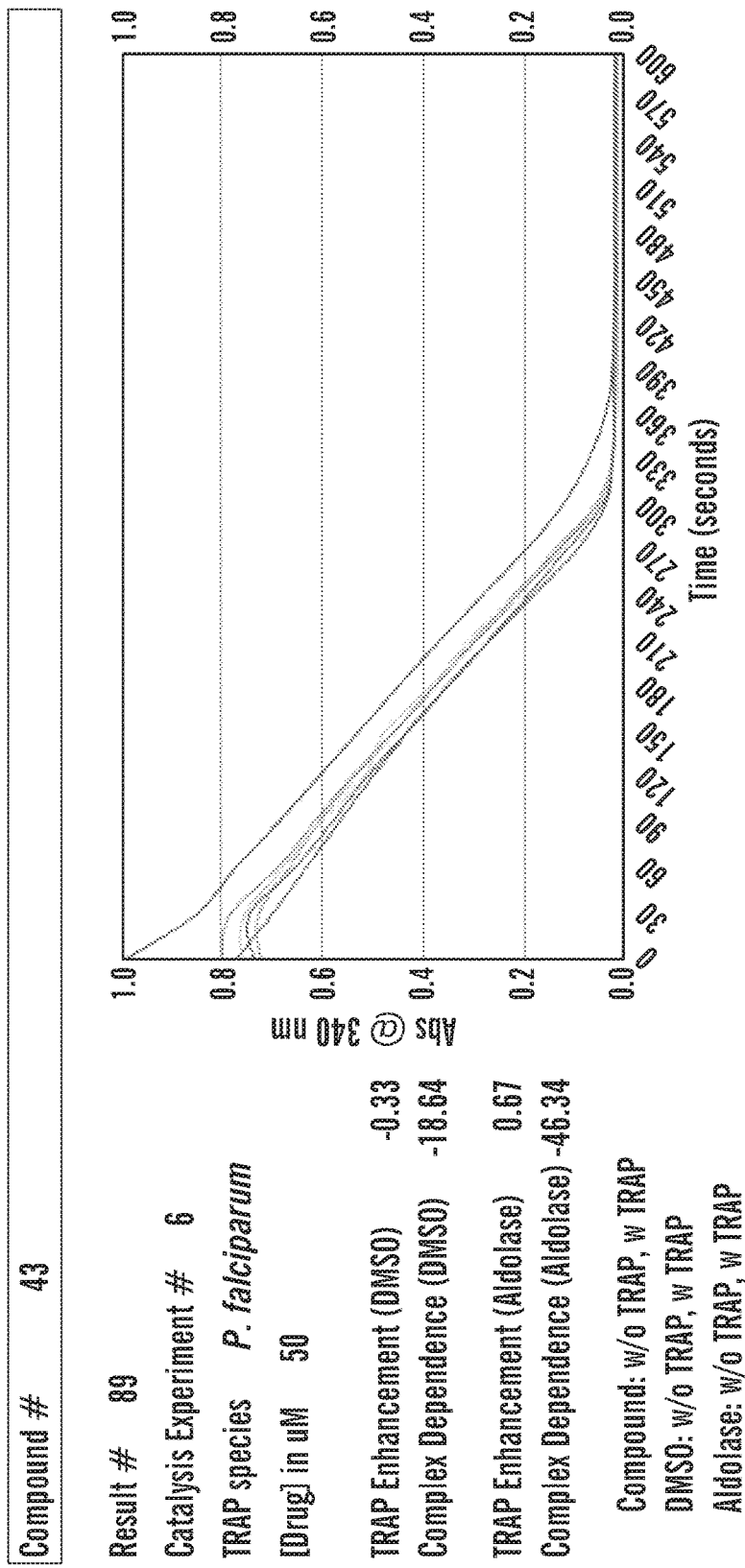
FIG. 25YYY

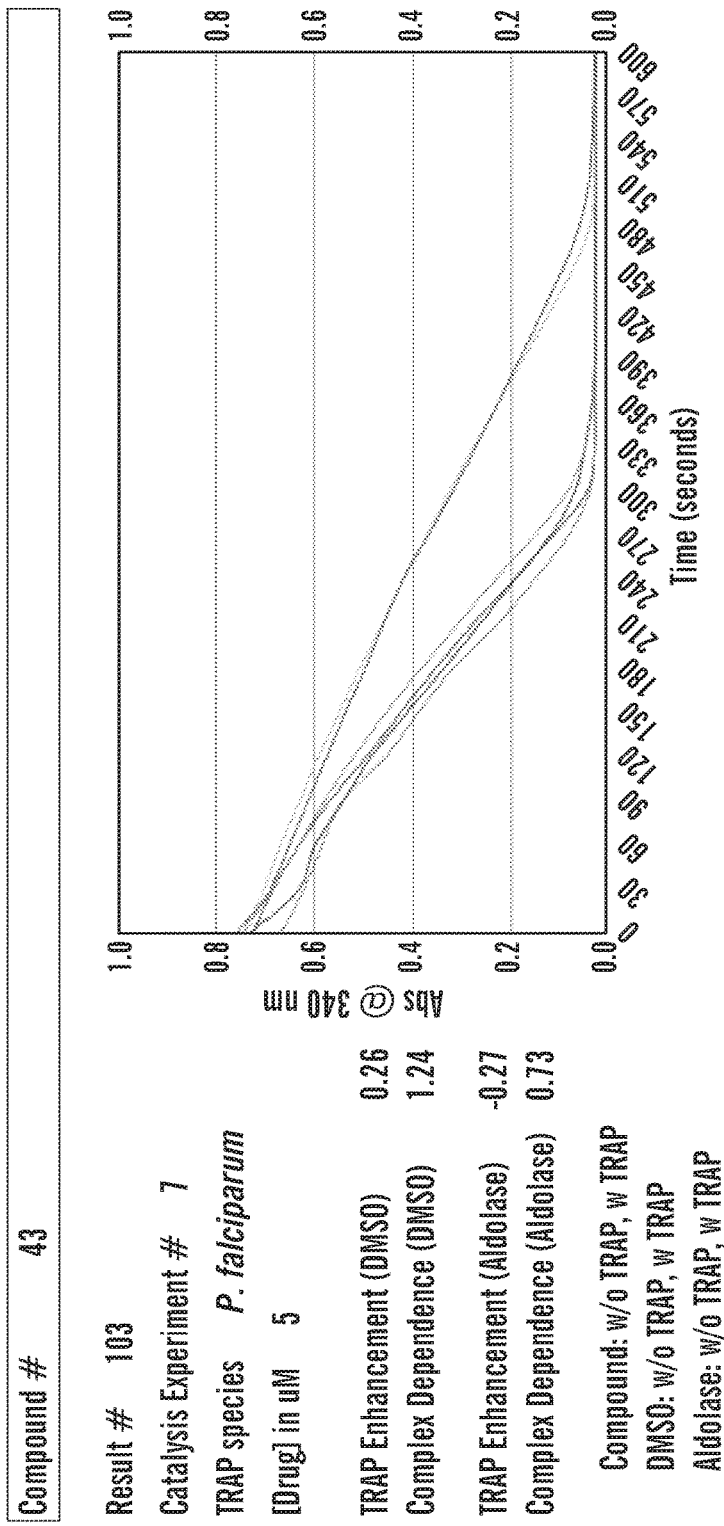
FIG. 25ZZZ

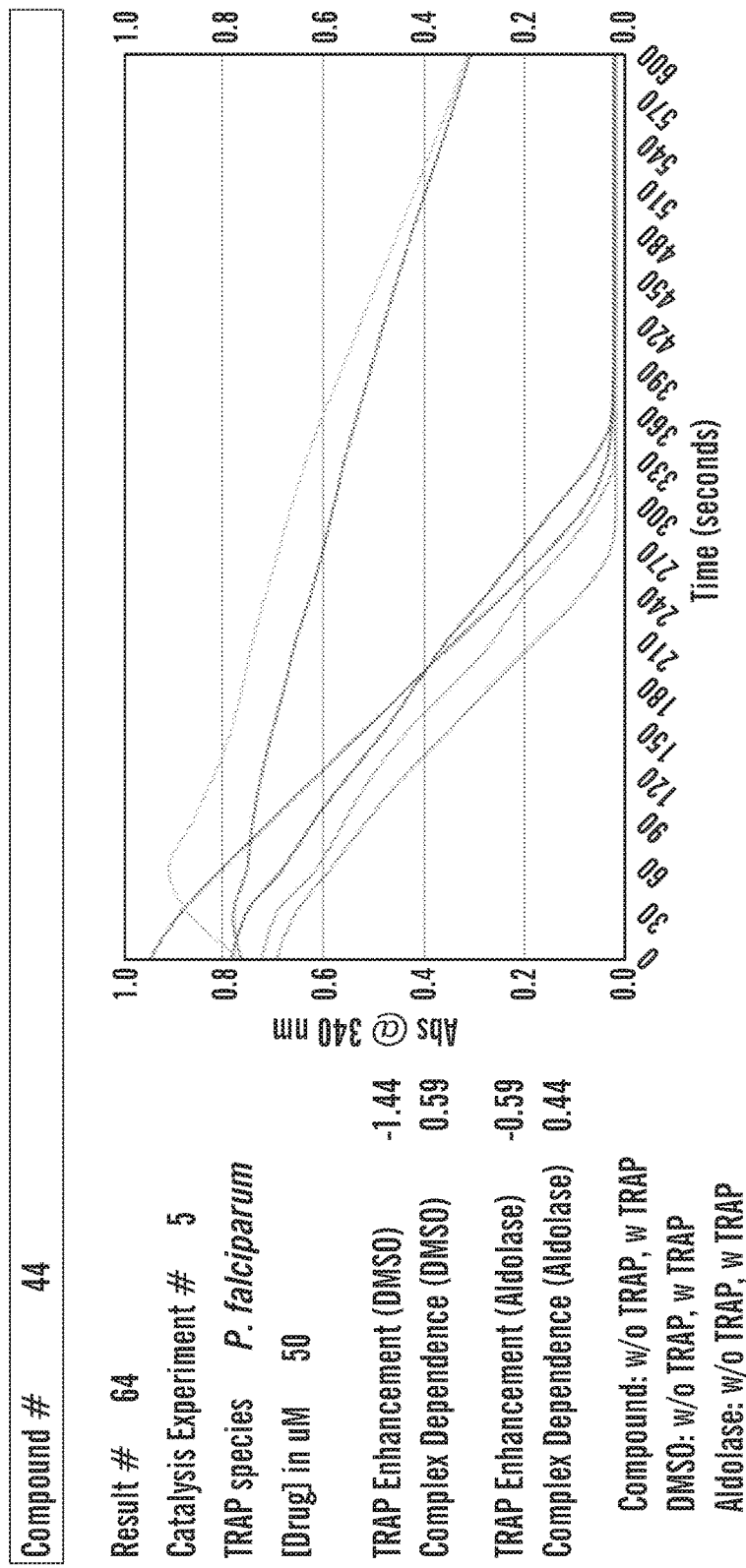
FIG. 25AAAA

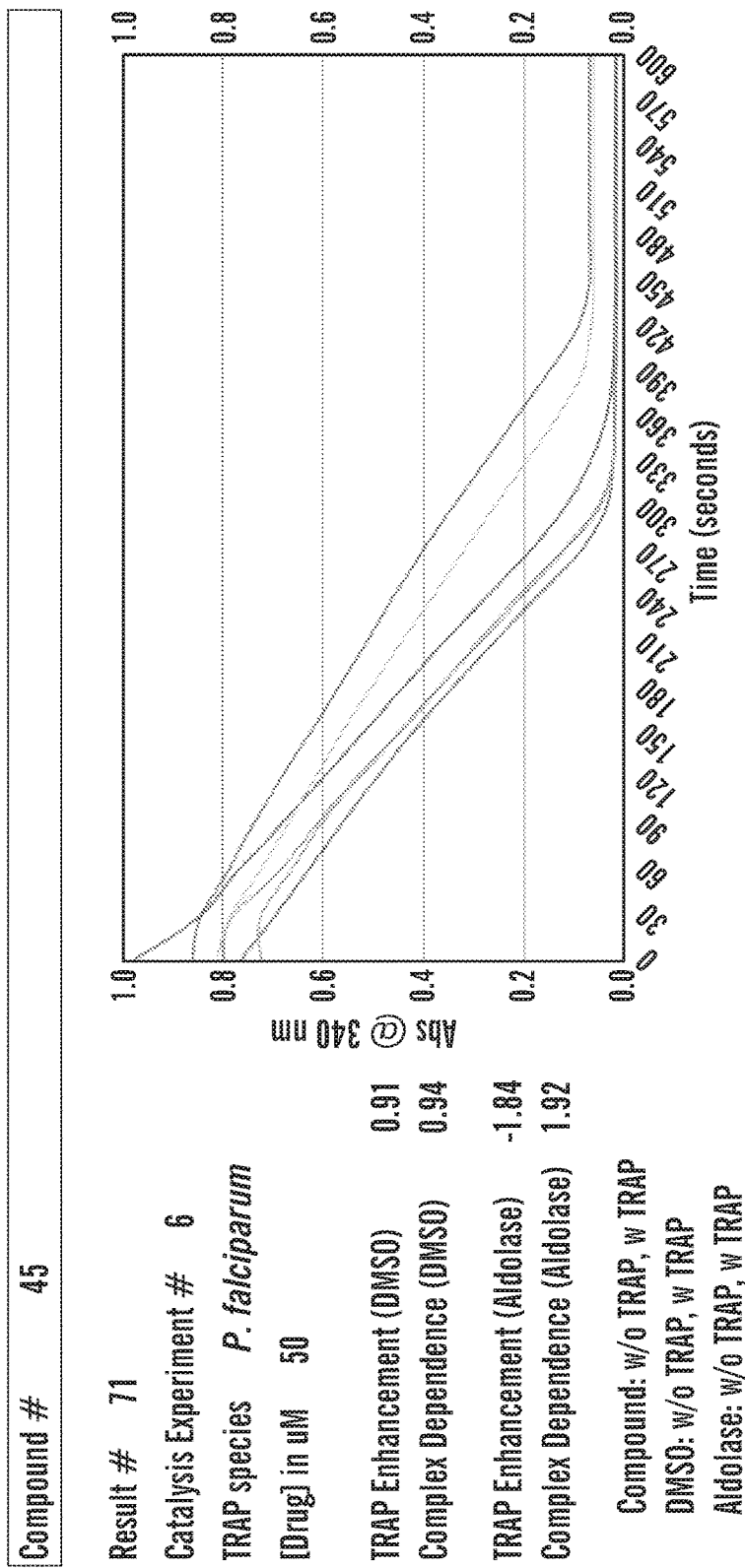
FIG. 25BBBB

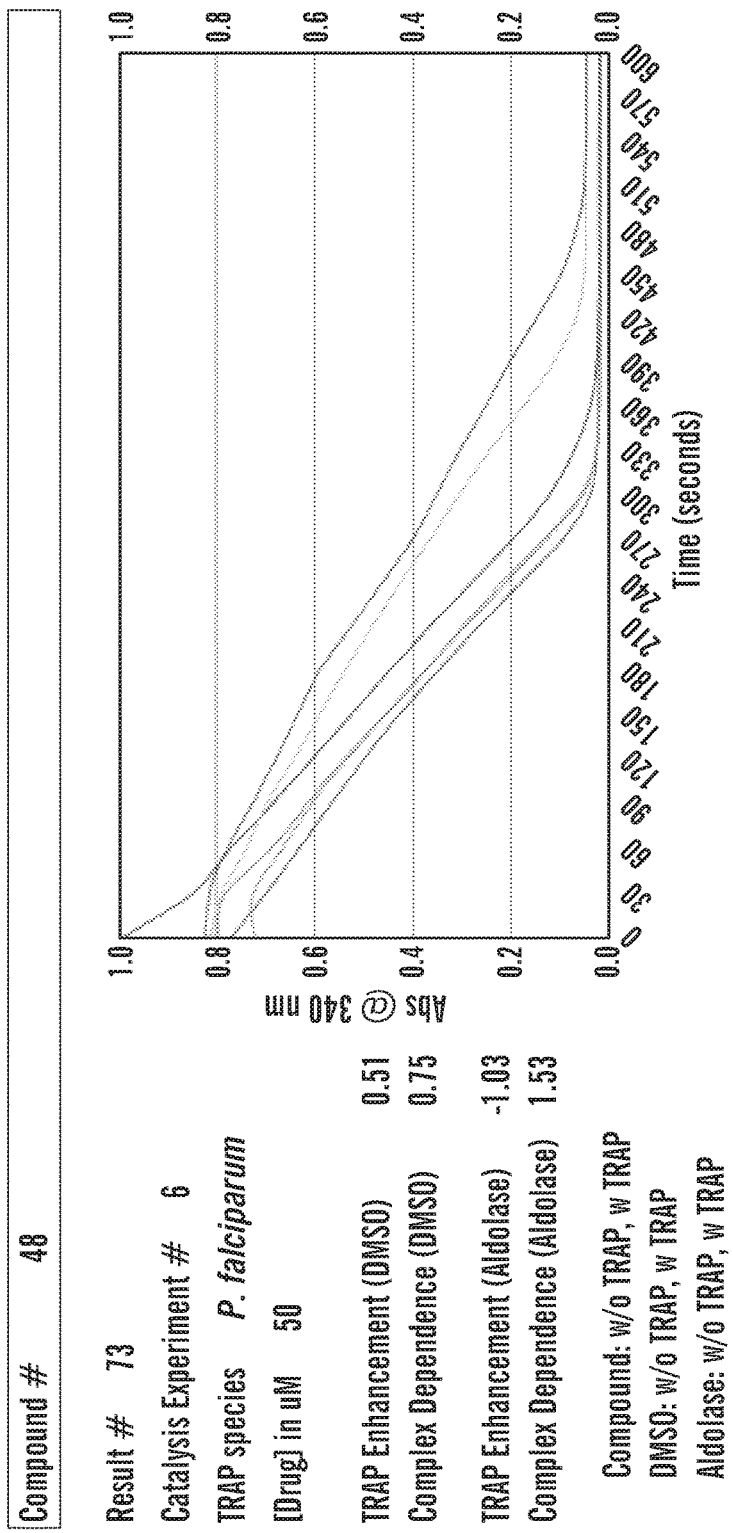
FIG. 25CCCC

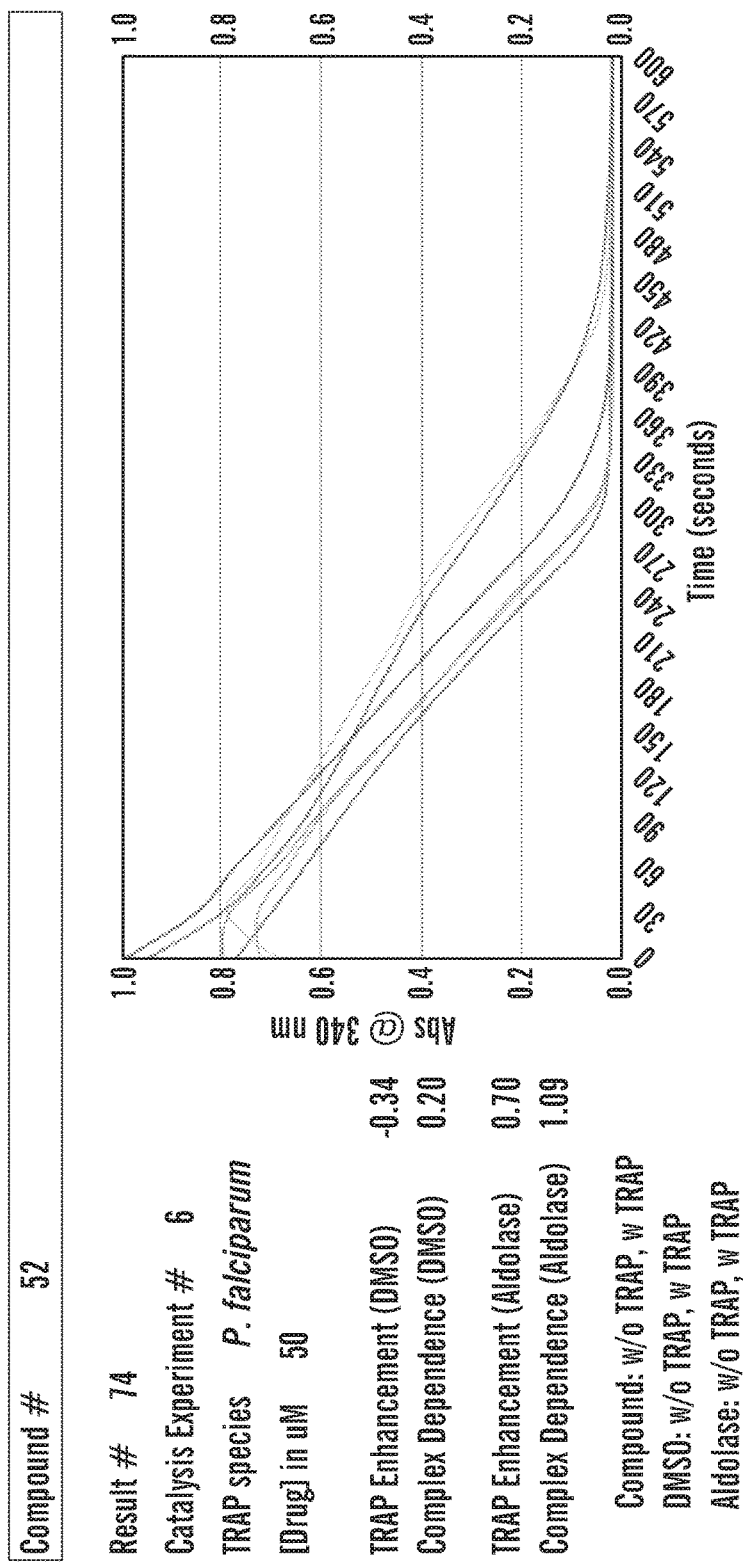
FIG. 25DDDD

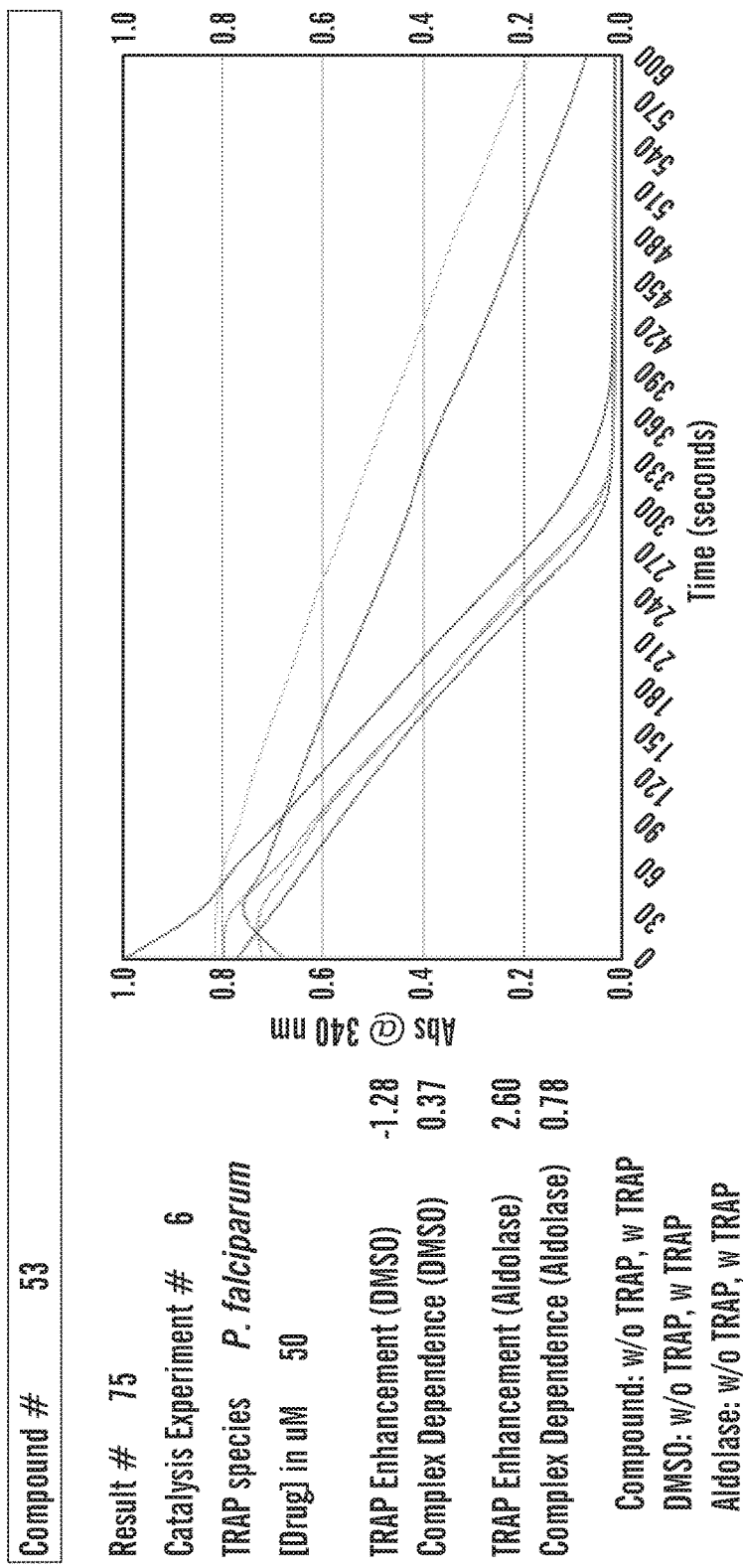
FIG. 25EEEE

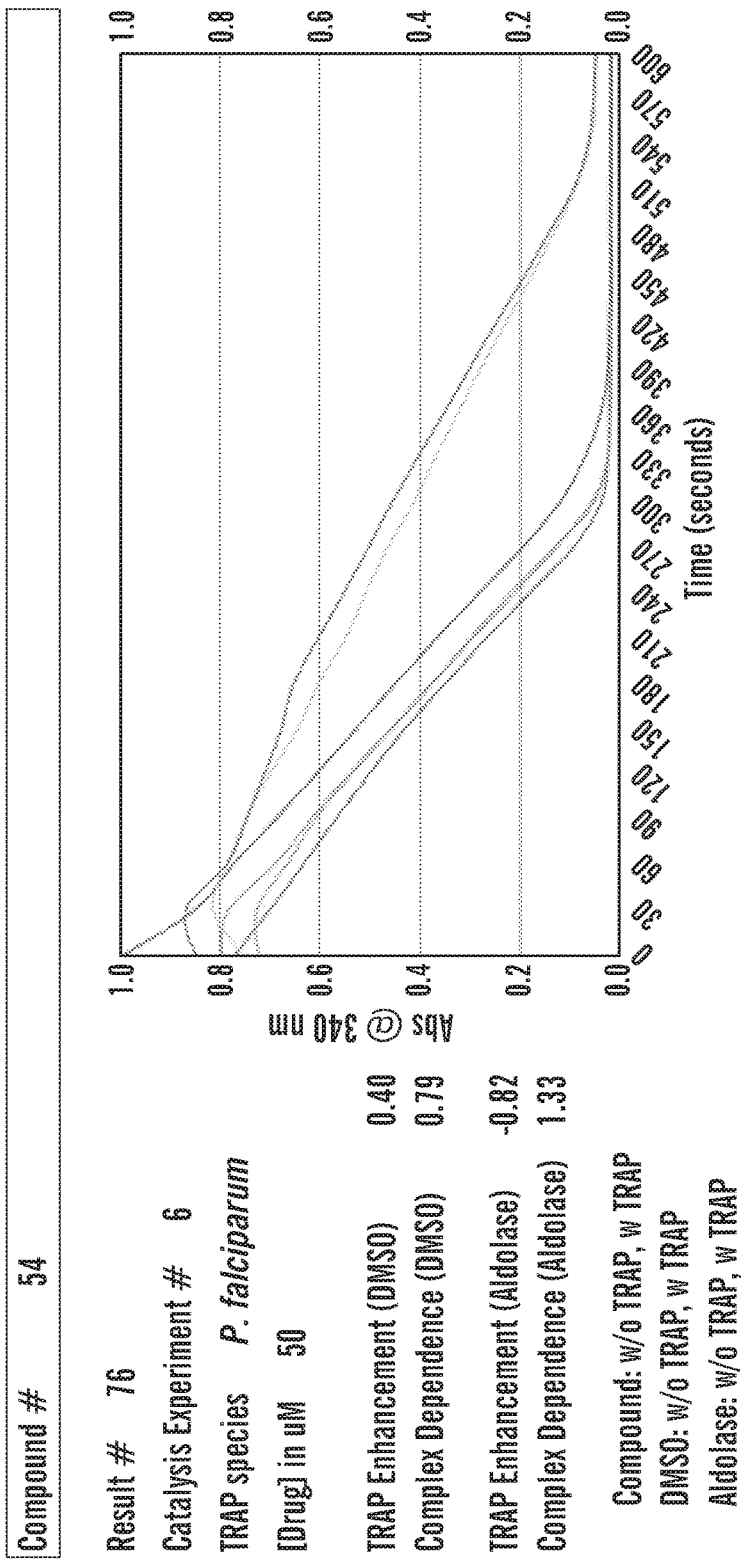
FIG. 25FFFF

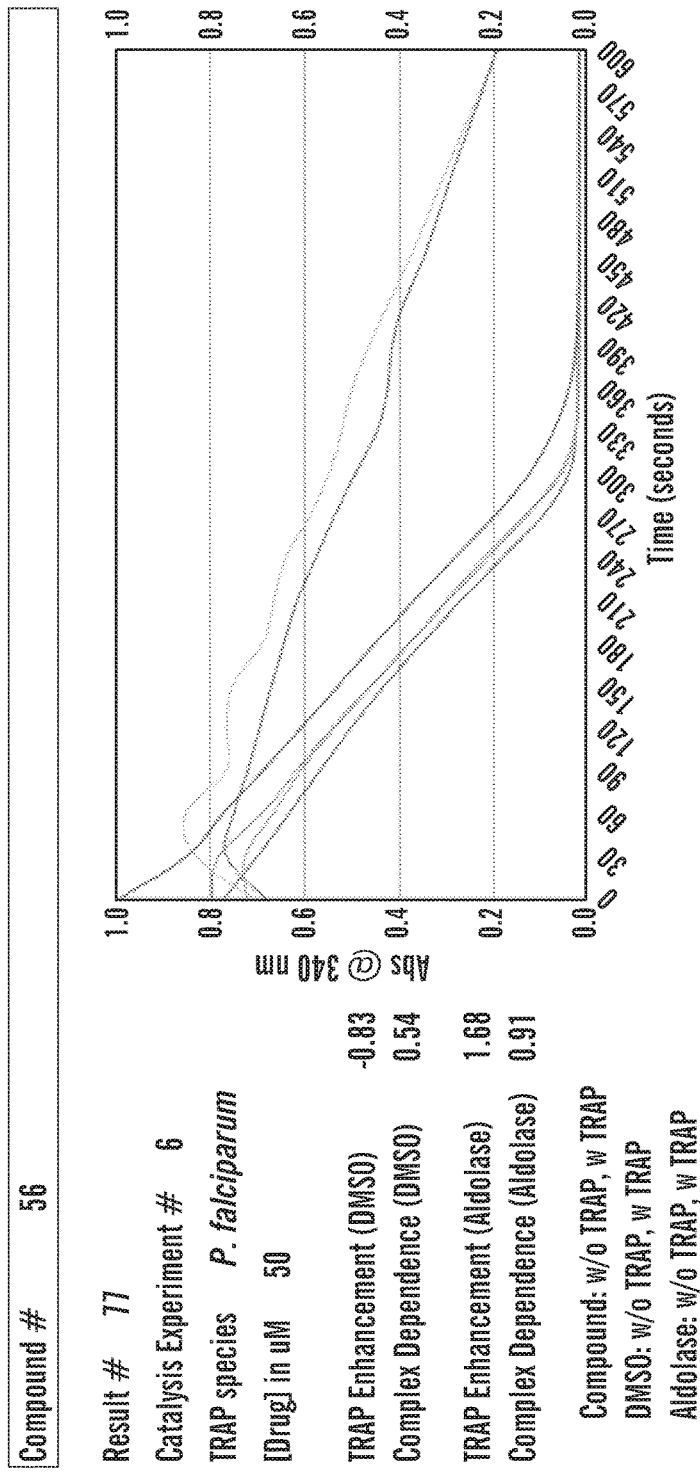
FIG. 25GGGG

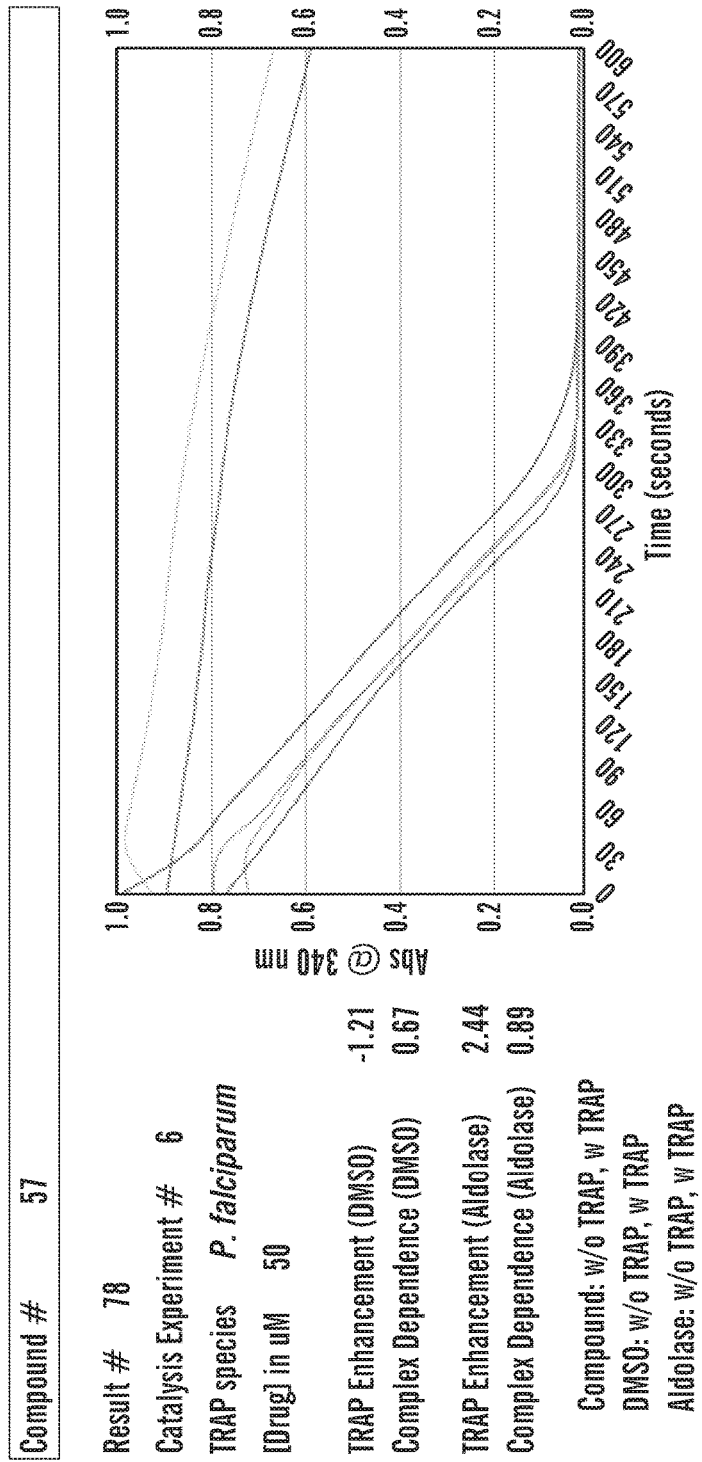
FIG. 25HHHH

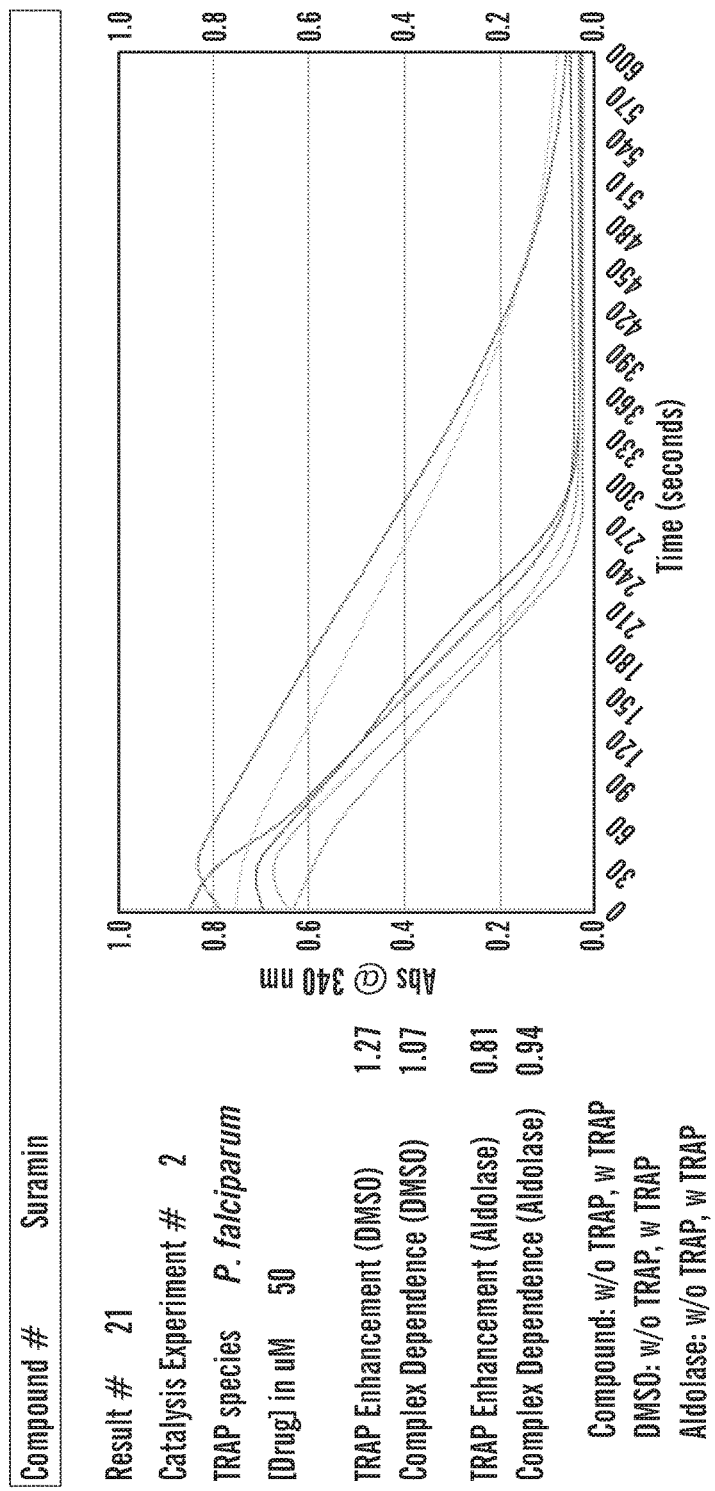
FIG. 25IIII

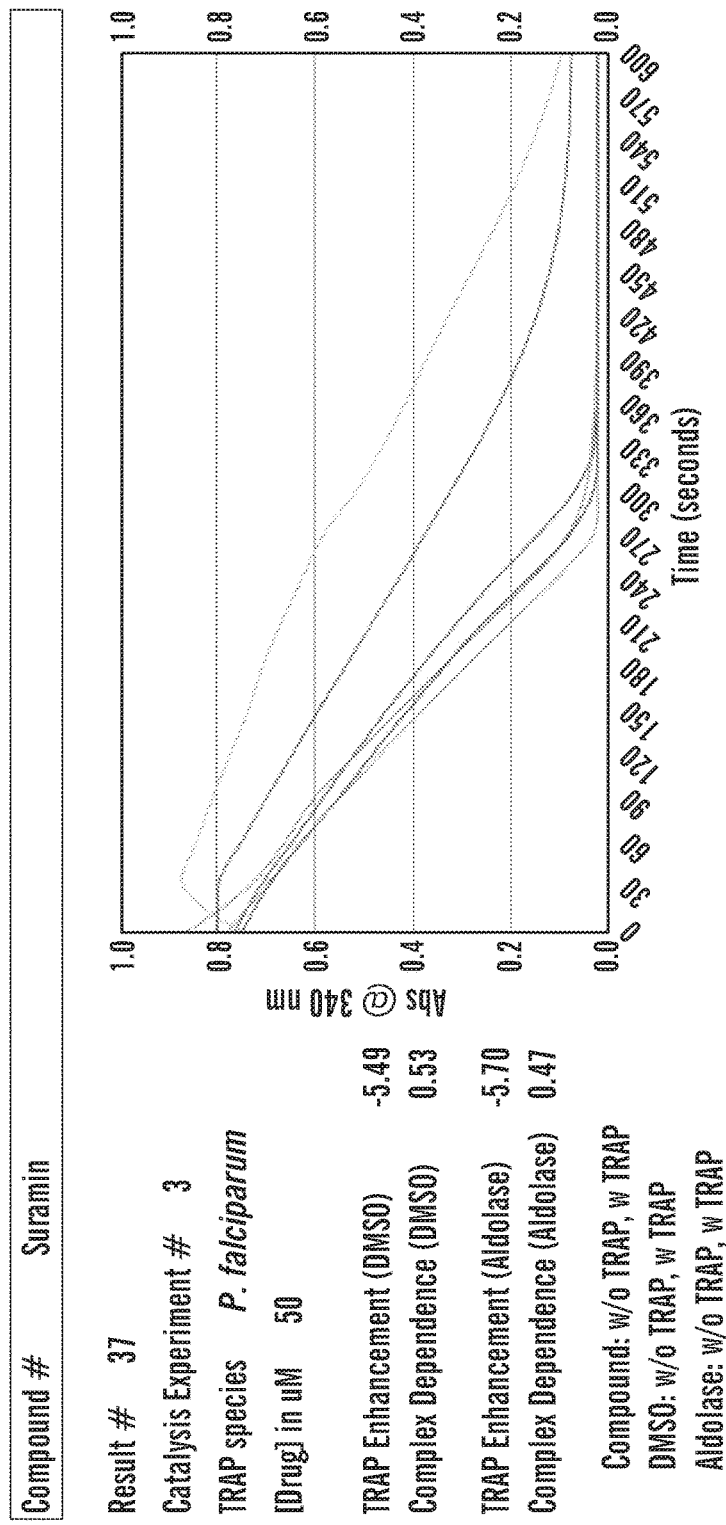
FIG. 25JJJJ

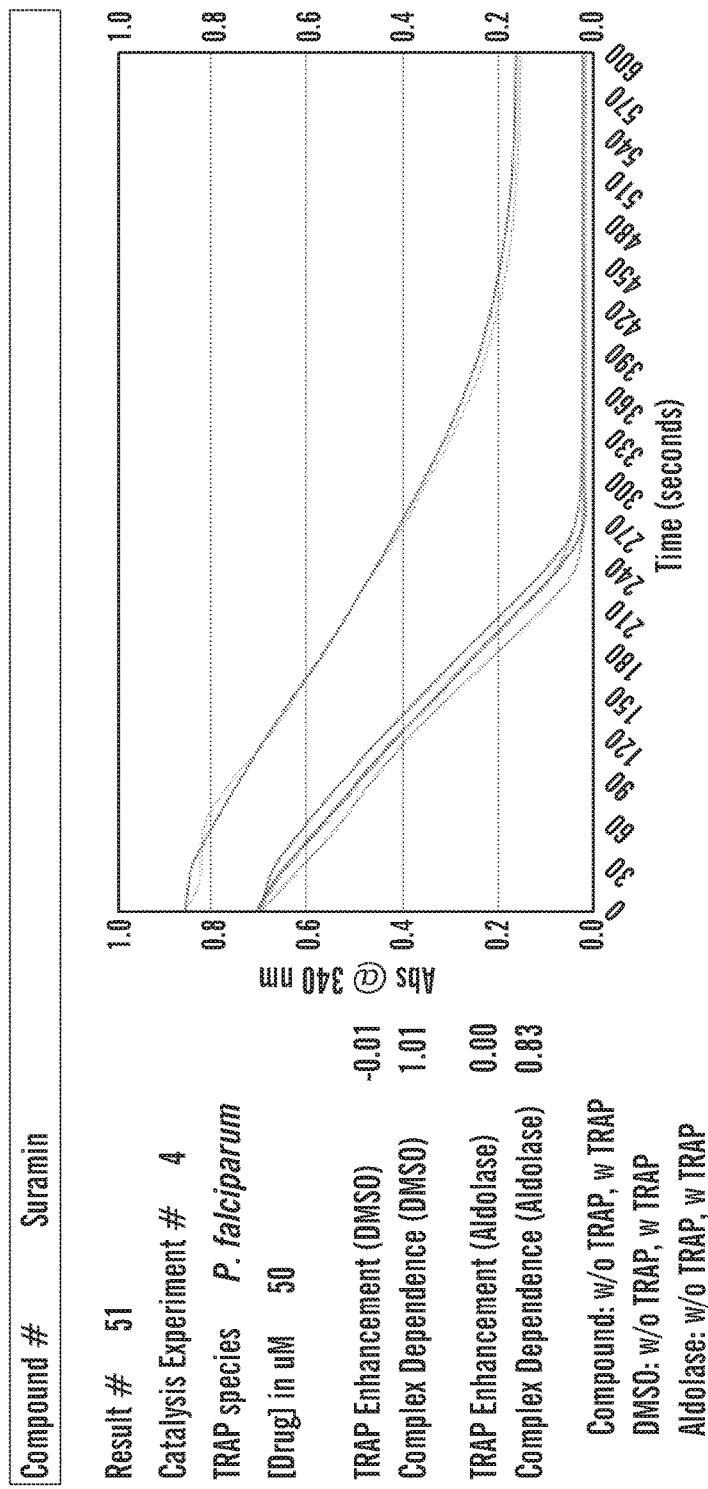
FIG. 25KKKK

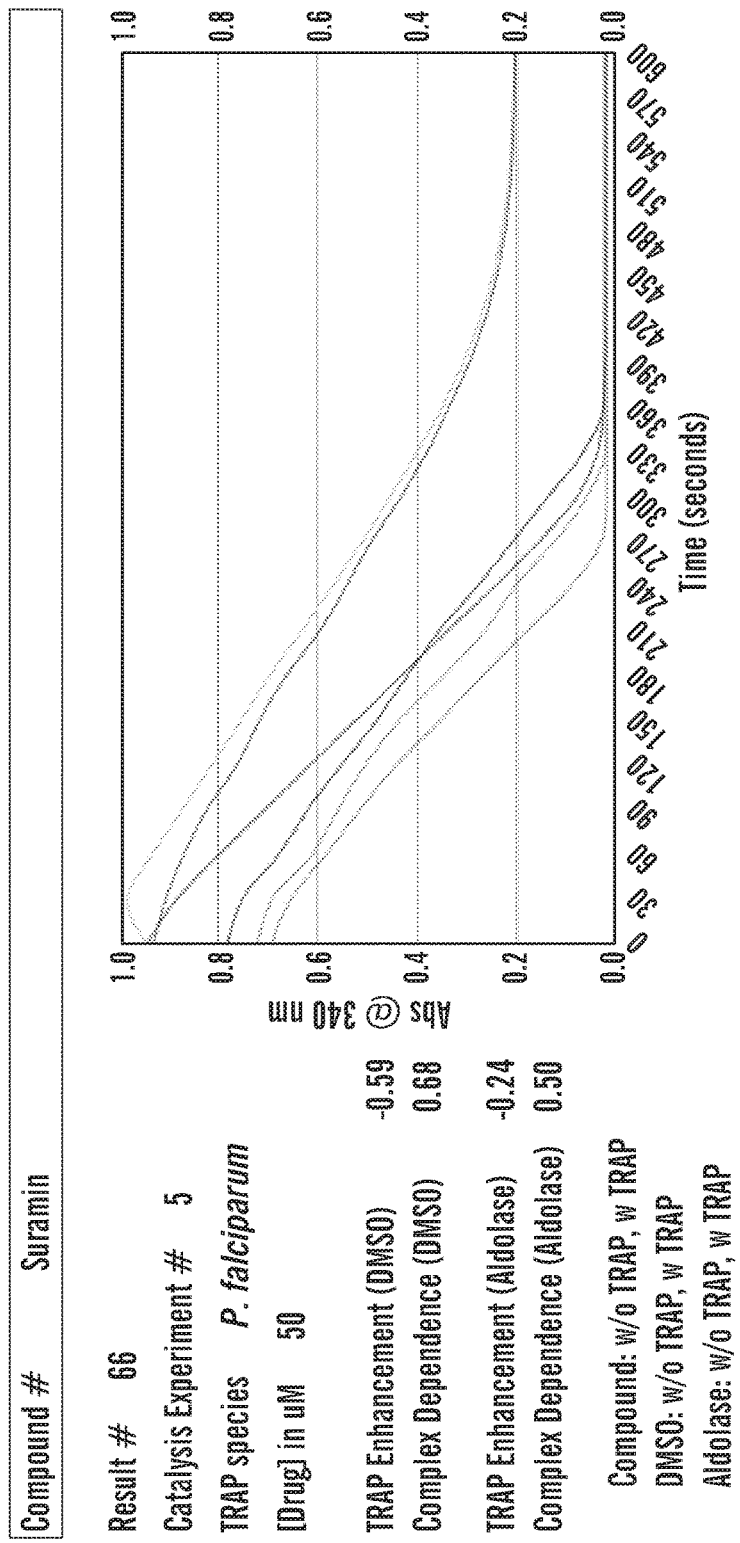
FIG. 25LLLL

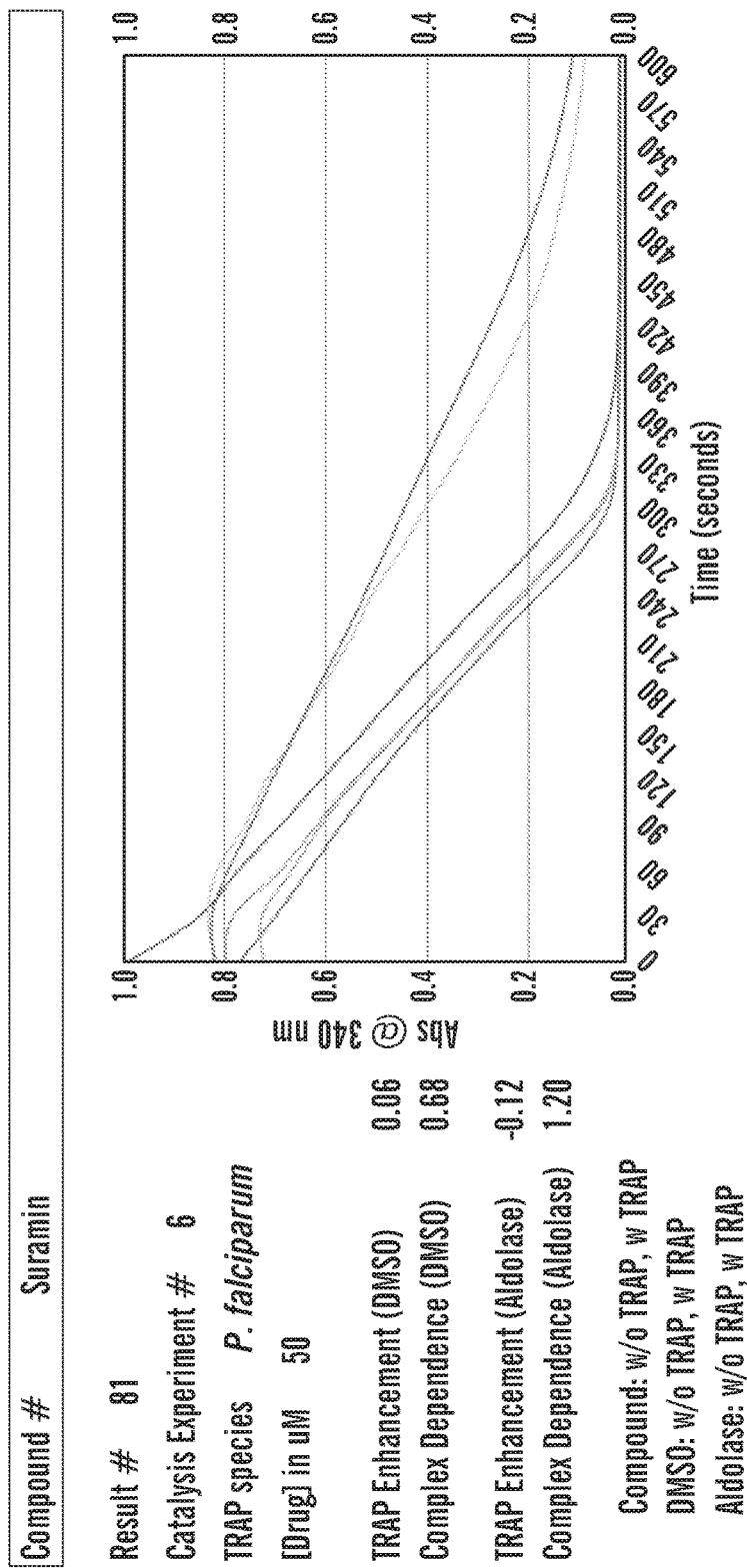
FIG. 25MMMM

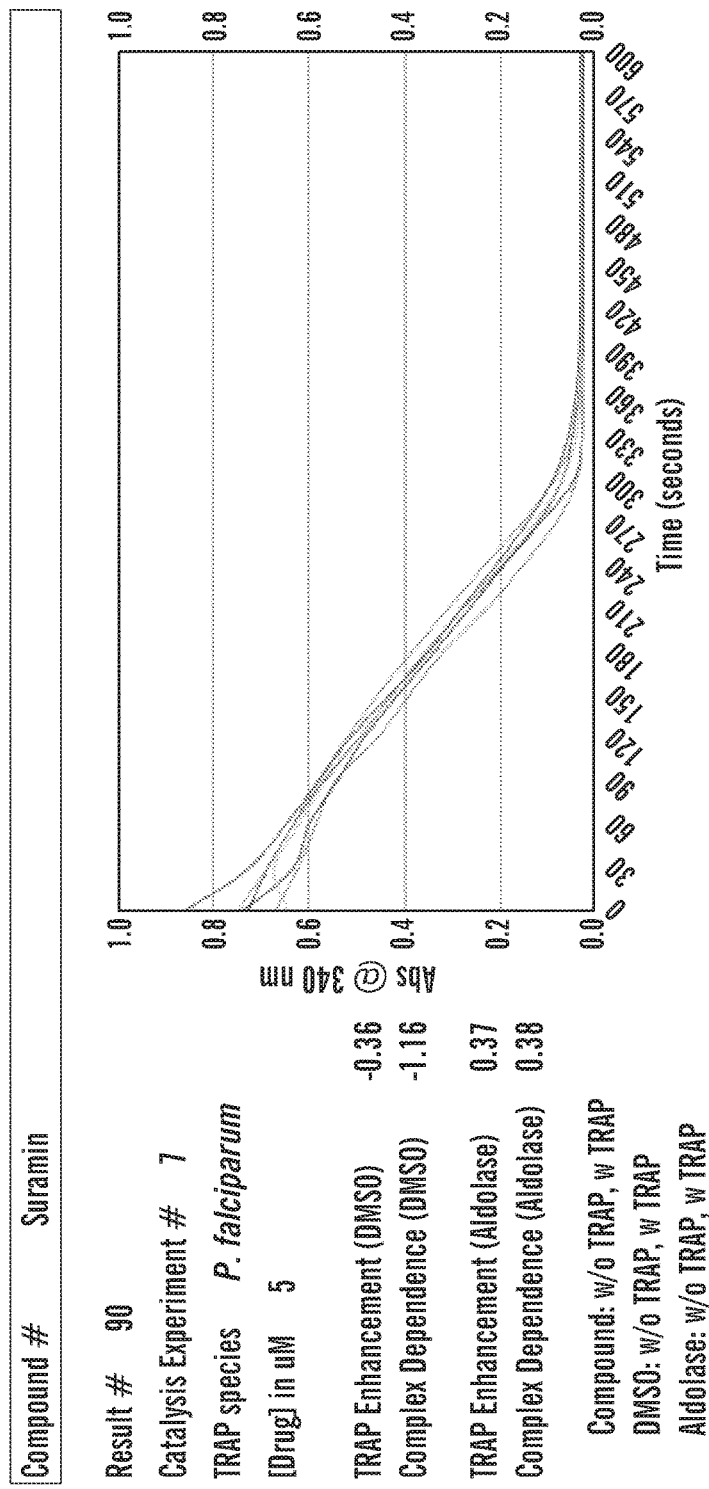
FIG. 25NNNN

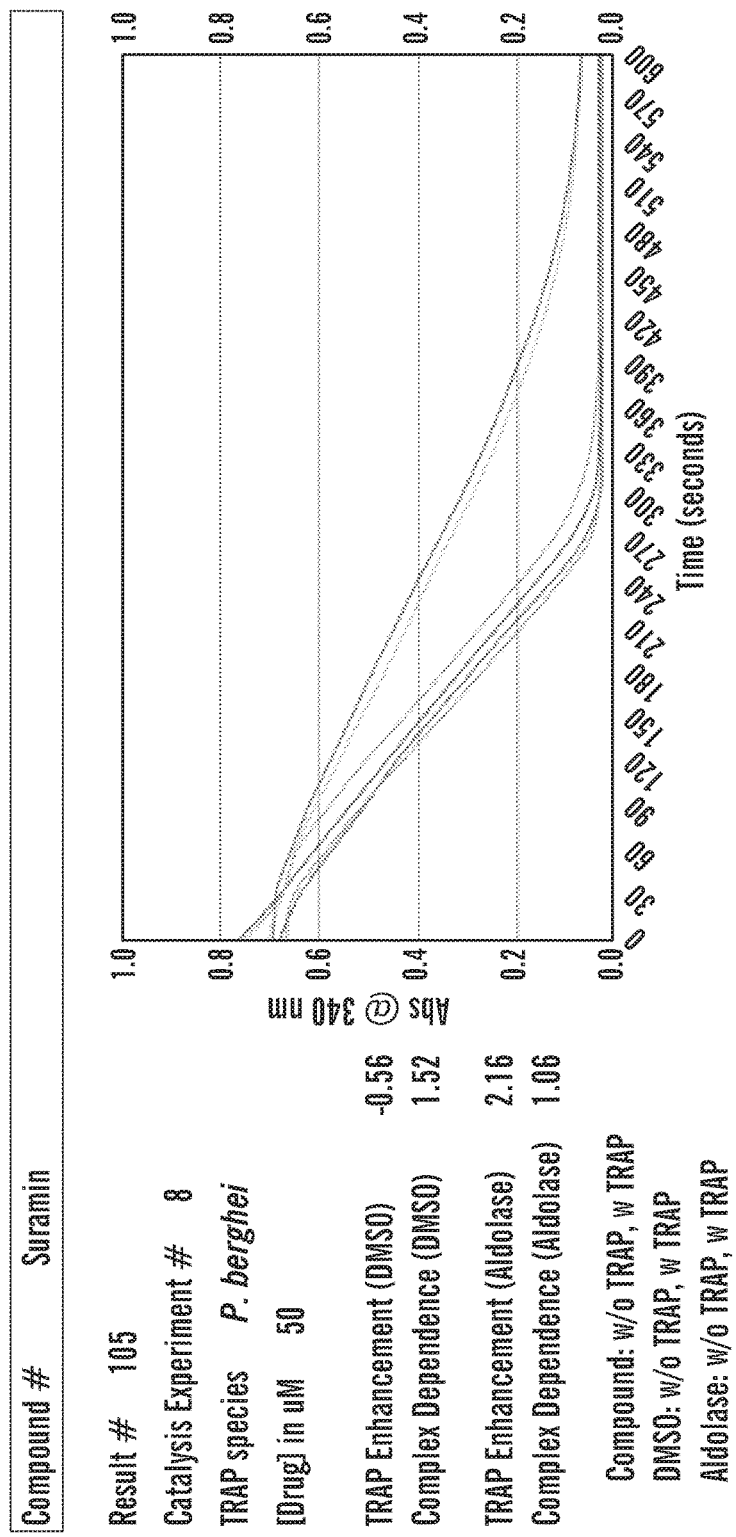
FIG. 250000

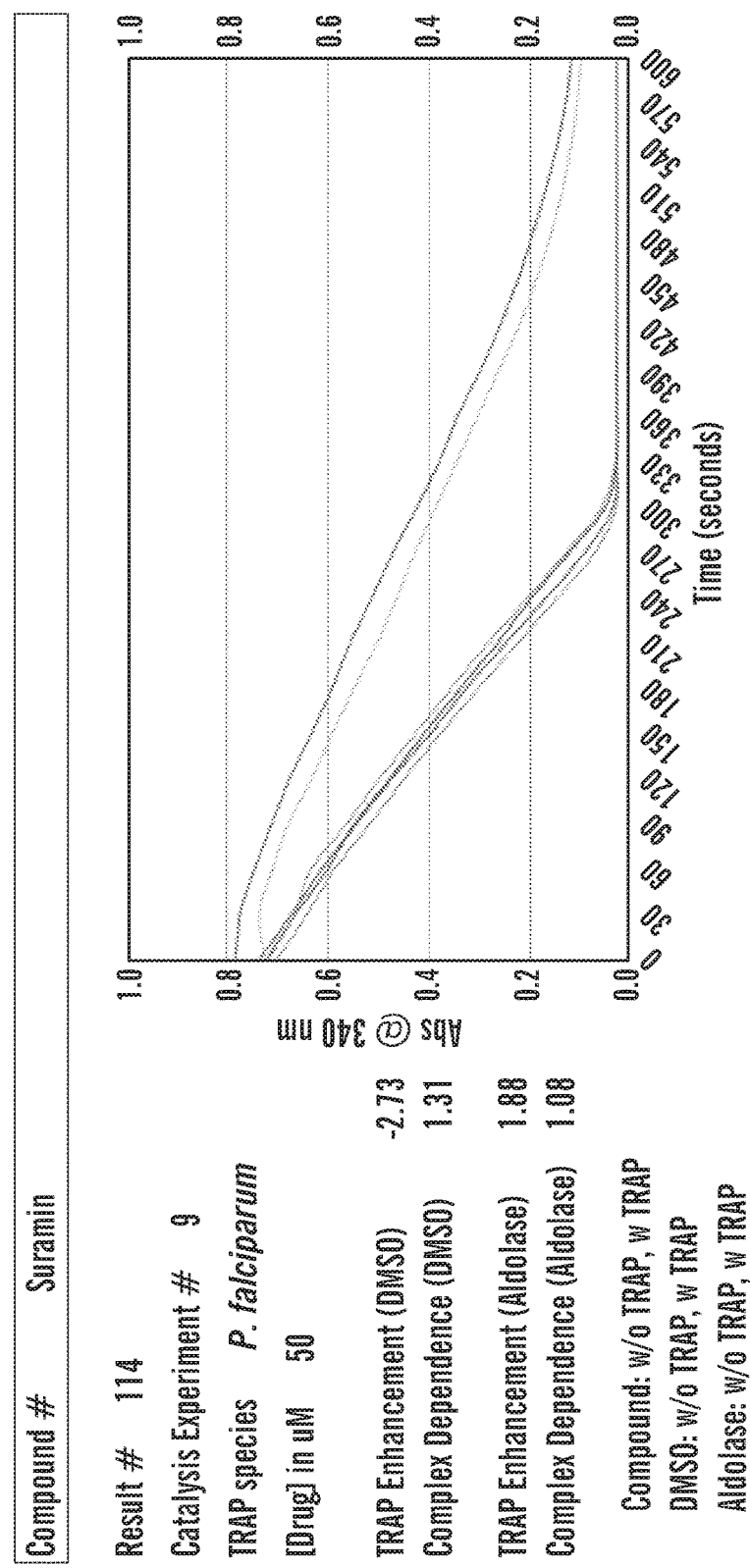
FIG. 25PPPP

| | | |
|---|---|---|
| tr\|B3L9W9\|B3L9W9_PLAKH/1-389 | 1 | . . . . . . . . . . . . . . . . . . . . . . . . |
| tr\|Q968V9\|Q968V9_PLAVI/1-369 | 1 | . . . . . . . . . . . . . . . . . . . . . . . . |
| sp\|P14223\|ALF_PLAFA/1-369 | 1 | . . . . . . . . . . . . . . . . . . . . . . . . |
| tr\|Q4YV79\|Q4YV79_PLABA/1-365 | 1 | . . . . . . . . . . . . . . . . . . . . . . . . |
| tr\|Q7RIB6\|Q7RIB6_PLAYO/1-409 | 1 | M Y R T C S L N E S K C D D K I Y |
| tr\|Q4XW14\|Q4XW14_PLACH/1-366 | 1 | . . . . . . . . . . . . . . . . . . . . . . . . |
| tr\|Q968W1\|Q968W1_PLAVN/1-351 | 1 | . . . . . . . . . . . . . . . . . . . . . . . . |
| Consensus/1-369 | 1 | |
| tr\|B3L9W9\|B3L9W9_PLAKH/1-389 | 55 | G I L A A D E S T Q T I K K R F D |
| tr\|Q968V9\|Q968V9_PLAVI/1-369 | 35 | G I L A A D E S T Q T I K K R F D |
| sp\|P14223\|ALF_PLAFA/1-369 | 35 | G I L A A D E S T Q T I K K R F D |
| tr\|Q4YV79\|Q4YV79_PLABA/1-365 | 32 | G I L A A D E S T Q T I K K R F D |
| tr\|Q7RIB6\|Q7RIB6_PLAYO/1-409 | 75 | G I L A A D E S T Q T I K K R F D |
| tr\|Q4XW14\|Q4XW14_PLACH/1-366 | 32 | G I L A A D E S T Q T I K K R F D |
| tr\|Q968W1\|Q968W1_PLAVN/1-351 | 24 | G I L A A D E S T Q T I K K R F D |
| Consensus/1-369 | 35 | G I L A A D E S T Q T I K K R F D |

FIG. 26

| | | | | | | | | | | | | | | | | | | | | |
|---|---|---|---|---|---|---|---|---|---|---|---|---|---|---|---|---|---|---|---|---|
| Y | K | N | A | P | L | K | L | P | A | D | V | A | E | E | I | A | T | K | L | V | Q | A | G | K | 54 |
| Y | K | N | A | P | L | K | L | P | A | E | V | A | E | E | I | A | T | K | L | V | E | A | G | K | 34 |
| Y | M | N | A | P | K | K | L | P | A | D | V | A | E | L | A | T | A | Q | K | L | V | Q | A | G | K | 34 |
| Y | K | N | A | P | M | K | L | P | K | E | V | A | Q | E | L | A | E | T | A | K | K | L | V | A | A | G | K | 31 |
| Y | K | N | A | P | M | K | L | P | K | E | V | A | Q | E | L | A | E | T | A | K | K | L | V | A | A | G | K | 74 |
| Y | K | N | A | P | M | K | L | P | K | E | V | A | H | E | L | A | D | T | A | K | K | L | V | A | P | G | K | 31 |
| | | | | | M | K | L | P | K | E | V | A | Q | E | L | A | D | T | A | K | L | V | A | P | G | K | 23 |
| X | X | X | X | X | X | K | L | P | X | X | V | A | X | E | X | A | X | T | A | X | K | L | V | X | X | G | K | 34 |
| G | A | I | L | F | E | E | T | L | F | Q | K | N | E | A | G | V | P | L | V | N | L | L | H | D | E | G | I | 128 |
| G | A | I | L | F | E | E | T | L | F | Q | K | N | E | A | G | V | P | L | V | N | L | L | H | D | E | G | I | 108 |
| G | A | I | L | F | E | E | T | L | F | Q | K | N | E | A | G | V | P | M | V | N | L | L | H | N | E | N | I | 108 |
| G | A | I | L | F | E | E | T | L | F | Q | K | N | E | A | G | V | P | L | V | N | L | L | H | D | E | G | I | 105 |
| G | A | I | L | F | E | E | T | L | F | Q | K | N | E | A | G | V | P | L | V | N | L | L | H | D | E | G | I | 148 |
| G | A | I | L | F | E | E | T | L | F | Q | K | N | E | A | G | V | P | L | V | N | L | L | H | D | D | G | I | 105 |
| G | A | I | L | F | E | E | T | L | F | Q | K | N | E | A | G | V | P | L | V | N | L | L | H | D | Q | N | I | 97 |
| G | A | I | L | F | E | E | T | L | F | Q | K | N | E | A | G | V | P | X | V | N | L | L | H | X | X | X | I | 108 |

FIG. 26 (cont.)

| | | | |
|---|---|---|---|
| tr\|B3L9W9\|B3L9W9_PLAKH/1-389 | 129 | I P G I K V D K G L V T | I P C T D |
| tr\|Q968V9\|Q968V9_PLAVI/1-369 | 109 | I P G I K V D K G L V T | I P C T D |
| sp\|P14223\|ALF_PLAFA/1-369 | 109 | I P G I K V D K G L V N | I P C T D |
| tr\|Q4YV79\|Q4YV79_PLABA/1-365 | 106 | I P G I K V D K G L V S | I P C T D |
| tr\|Q7RIB6\|Q7RIB6_PLAYO/1-409 | 149 | I P G I K V D K G L V S | I P C T D |
| tr\|Q4XW14\|Q4XW14_PLACH/1-366 | 106 | I P G I K V D K G L V A | I P C T D |
| tr\|Q968W1\|Q968W1_PLAVN/1-351 | 98 | I P G I K V D K G L V X | I P C T D |
| Consensus/1-369 | 109 | I P G I K V D K G L V X | L P C T D |
| | | | |
| tr\|B3L9W9\|B3L9W9_PLAKH/1-389 | 203 | S I C Q Q N K L V P I V E P E I L |
| tr\|Q968V9\|Q968V9_PLAVI/1-369 | 183 | S I C Q Q N K L V P I V E P E I L |
| sp\|P14223\|ALF_PLAFA/1-369 | 183 | S I C Q Q N K L V P I V E P E I L |
| tr\|Q4YV79\|Q4YV79_PLABA/1-365 | 180 | S I C Q Q N R L V P I V E P E I L |
| tr\|Q7RIB6\|Q7RIB6_PLAYO/1-409 | 223 | S I C Q Q N K L V P I V E P E I L |
| tr\|Q4XW14\|Q4XW14_PLACH/1-366 | 180 | A I C Q Q N K L V P I V E P E I L |
| tr\|Q968W1\|Q968W1_PLAVN/1-351 | 172 | A I C Q Q N K L V P I V E P E I L |
| Consensus/1-369 | 183 | X I C Q Q N X L V P I V E P E I L |

| A | V | L | V | I | D | P | V | K | G | K | P | T | D | L | S | I | Q | E | T | A | W | G | L | A | R | Y | A | 202 |
|---|---|---|---|---|---|---|---|---|---|---|---|---|---|---|---|---|---|---|---|---|---|---|---|---|---|---|---|---|
| A | V | L | V | I | D | P | V | K | G | K | P | T | D | L | S | I | Q | E | T | A | W | G | L | A | R | Y | A | 182 |
| T | V | L | V | I | D | T | A | K | G | K | P | T | D | L | S | I | H | E | T | A | W | G | L | A | R | Y | A | 182 |
| A | V | L | V | I | D | P | A | K | G | K | P | T | D | L | S | I | Q | E | V | S | W | G | L | A | R | Y | A | 179 |
| A | V | L | V | I | D | P | A | K | G | K | P | T | D | L | S | I | Q | E | V | S | W | G | L | A | R | Y | A | 222 |
| A | V | L | V | I | D | P | V | K | G | K | P | T | D | L | S | I | H | E | V | S | W | G | L | A | R | Y | A | 179 |
| A | V | L | V | I | D | P | A | K | G | K | P | T | D | L | S | I | Q | E | V | S | W | G | L | A | R | Y | A | 171 |
| X | X | L | V | I | D | X | X | K | G | K | P | T | D | L | S | I | X | E | X | X | W | G | L | A | R | Y | A | 182 |
| I | L | L | E | G | A | L | L | K | P | N | M | V | T | A | G | Y | D | C | T | V | K | T | K | T | Q | D | I | 276 |
| V | L | L | E | G | A | L | L | K | P | N | M | V | T | A | G | Y | D | C | A | V | K | T | N | T | Q | D | I | 256 |
| V | L | L | E | G | A | L | L | K | P | N | M | V | T | A | G | Y | E | C | T | A | K | T | T | T | Q | D | V | 256 |
| V | L | L | E | G | A | L | L | K | P | N | M | V | T | A | G | Y | D | C | T | E | K | T | K | T | D | D | I | 253 |
| V | L | L | E | G | A | L | L | K | P | N | M | V | T | A | G | Y | D | C | T | E | K | T | K | T | D | D | I | 296 |
| V | L | L | E | G | A | L | L | K | P | N | M | V | T | A | G | Y | D | C | T | E | K | T | K | T | D | D | I | 253 |
| V | L | L | E | G | A | L | L | K | P | N | M | V | T | A | G | Y | D | C | P | E | K | T | K | T | E | D | I | 245 |
| X | L | L | E | G | A | L | L | K | P | N | M | V | T | A | G | Y | X | C | X | X | K | T | X | T | X | D | X | 256 |

FIG. 26 (cont.)

| | | |
|---|---|---|
| tr\|B3L9W9\|B3L9W9_PLAKH/1-389 | 277 | G F L T V R T L S R T V P P A L P |
| tr\|Q968V9\|Q968V9_PLAVI/1-369 | 257 | G F L T V R T L S R T V P P S L P |
| sp\|P14223\|ALF_PLAFA/1-369 | 257 | G F L T V R T L R R T V P P A L P |
| tr\|Q4YV79\|Q4YV79_PLABA/1-365 | 254 | G F T V R T L R R T V P P A L P |
| tr\|Q7RIB6\|Q7RIB6_PLAYO/1-409 | 297 | G F T V R T L R R T V P P A L P |
| tr\|Q4XW14\|Q4XW14_PLACH/1-366 | 254 | G F T V R T L R R T V P P A L P |
| tr\|Q968W1\|Q968W1_PLAVN/1-351 | 246 | G F T V R T L S R T V P P A L P |
| Consensus/1-369 | 257 | G F T V R T L X R T V P P X L P |
| tr\|B3L9W9\|B3L9W9_PLAKH/1-389 | 351 | R E V L L K R A E A N S L A T Y G |
| tr\|Q968V9\|Q968V9_PLAVI/1-369 | 331 | R E V L L K R A E A N S L A T Y G |
| sp\|P14223\|ALF_PLAFA/1-369 | 331 | R E V L L Q R A E A N S L A T Y G |
| tr\|Q4YV79\|Q4YV79_PLABA/1-365 | 328 | R A V L L Q R A E A N S L A T Y G |
| tr\|Q7RIB6\|Q7RIB6_PLAYO/1-409 | 371 | R E V L L Q R A E A N S L A T Y G |
| tr\|Q4XW14\|Q4XW14_PLACH/1-366 | 328 | R E V L L Q R A E A N S L A T Y G |
| tr\|Q968W1\|Q968W1_PLAVN/1-351 | 320 | Q E V L L Q R A E A N S L A T Y G |
| Consensus/1-369 | 331 | X X V L L X R A E A N S L A T Y G |

FIG. 26 (cont.)

| | | |
|---|---|---|
| ALTFSYGRALQASVLNTWKGKKENVAKA | 350 |
| ALTFSYGRALQASVLNTWKGKKENVEKA | 330 |
| ALTFSYGRALQASVLNTWQGKKENVAKA | 330 |
| ALTFSYGRALQASVLNTWQGKKENVAKA | 327 |
| ALTFSYGRALQASVLNTWQGKKENVAKA | 370 |
| ALTFSYGRALQASVLNTWQGKKENVAKA | 327 |
| ALTFSYGRALQASVLSTWQGKKENAAKA | 319 |
| ALTFSYGRALQASVLXTWXGKKENXXKA | 330 |
| | 389 |
| | 369 |
| | 369 |
| | 365 |
| | 409 |
| | 366 |
| | 351 |
| | 369 |

*FIG. 26 (cont.)* tr|B3L9W9|B3L9W9_PLAKH *Plasmodium knowlesi* (strain H) (SEQ ID NO: 5)
tr|Q968V9|Q968V9_PLAVI *Plasmodium vivax* (SEQ ID NO: 7)
sp|P14223|ALF_PLAFA *Plasmodium falciparum* (SEQ ID NO: 4)
tr|Q4YV79|Q4YV79_PLABA *Plasmodium berghei* (strain Anka) (SEQ ID NO: 2)
tr|Q7RIB6|Q7RIB6_PLAYO *Plasmodium yoelii yoelii* (SEQ ID NO: 8)
tr|Q4XW14|Q4XW14_PLACH *Plasmodium chabaudi* (SEQ ID NO: 3)
tr|Q968W1|Q968W1_PLAVN *Plasmodium vinckei* (SEQ ID NO: 6)

| | | | |
|---|---|---|---|
| *P. falciparum* | TRAP | PEQFRLPEENEIN | (SEQ ID NO: 29) |
| *P. vivax* | TRAP | ADQFKLPEDNDIN | (SEQ ID NO: 30) |
| *P. falciparum* | MTRAP | KDNKAMDEEEFIAI | (SEQ ID NO: 31) |
| *P. vivax* | MTRAP | ENSKSMYEDEFIAI | (SEQ ID NO: 32) |
| *P. falciparum* | CTRP | DFEVVDADDPMIN | (SEQ ID NO: 33) |
| *P. vivax* | CTRP | DFEVIDANDPMIN | (SEQ ID NO: 34) |
| *P. falciparum* | TLP | EQNIEIMNDTQIK | (SEQ ID NO: 35) |
| *P. vivax* | TLP | QNIEVKPDETSIQ | (SEQ ID NO: 36) |

All these sequences are incorporated by reference in their entirety.

FIGURE 29A

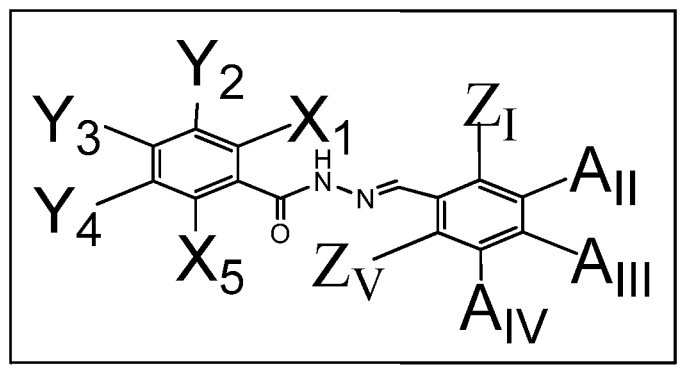

FIGURE 29B

| Substituent Combinations: | |
|---|---|
| a. $Y_2, Y_3$ - $A_{III}, A_{IV}$ + $Z_I$ or $Z_V$ | g. $A_{II}, A_{III}$ - $Y_3, Y_4$ + $X_1$ or $X_5$ |
| b. $Y_2, Y_3$ - $A_{II}, A_{III}$ + $Z_I$ or $Z_V$ | h. $A_{II}, A_{III}$ - $Y_2, Y_3$ + $X_1$ or $X_5$ |
| c. $Y_2, Y_4$ - $A_{III}, A_{IV}$ + $Z_I$ or $Z_V$ | i. $A_{II}, A_{IV}$ - $Y_3, Y_4$ + $X_1$ or $X_5$ |
| d. $Y_2, Y_4$ - $A_{II}, A_{III}$ + $Z_I$ or $Z_V$ | j. $A_{II}, A_{IV}$ - $Y_2, Y_3$ + $X_1$ or $X_5$ |
| e. $Y_4, X_1$ - $A_{III}, A_{IV}$ + $Z_I$ or $Z_V$ | k. $A_I, A_{IV}$ - $Y_2, Y_3$ + $X_1$ or $X_5$ |
| f. $Y_4, X_1$ - $A_{II}, A_{III}$ + $Z_I$ or $Z_V$ | l. $A_I, A_{IV}$ - $Y_3, Y_4$ + $X_1$ or $X_5$ |

SMALL MOLECULE MALARIAL ALDOLASE-TRAP ENHANCERS AND GLIDEOSOME INHIBITORS

This application is a national stage application under 35 U.S.C. §371 from PCT Application No. PCT/US2012/061875, filed Oct. 25, 2012, which claims the benefit of U.S. Provisional Patent Application Ser. No. 61/551,269, filed Oct. 25, 2011, both of which are hereby incorporated by reference in their entirety.

This invention was made with government support under grant number DP2 OD004631 and F30HL094052 awarded by National Institutes of Health (NIH) and National Heart, Lung, and Blood Institute (NHLBI), respectively. The government has certain rights in this invention.

FIELD OF THE INVENTION

The present invention is related to small molecule malarial Aldolase-TRAP enhancers and glideosome inhibitors.

BACKGROUND OF THE INVENTION

Malaria is a serious illness that affects hundreds of millions of people worldwide and kills 700,000-2.7 million people each year. Malaria is caused by protozoan parasites that are transmitted from person to person via the *Anopheles* mosquito (United States Center for Disease Control, Malaria Website; World Health Organization, Global Malaria Programme), or in some cases in endemic areas, by allogeneic blood transfusion from an infected donor (Marcucci et al., "Allogeneic Blood Transfusions Benefit, Risks and Clinical Indications in Countries With a Low or High Human Development Index," *Br. Med. Bull.* 70:15-28 (2004)). Five species of apicomplexan protozoa can infect and cause malaria in humans: *Plasmodium falciparum, P. vivax, P. ovale, P. malaria,* and *P. knowlesi*. The disease is characterized by cyclical episodes of high fever, chills, severe pain, and nausea. In severe cases, caused by *P. falciparum* infection, patients present with brain ischemia ("cerebral malaria") and other end-organ damage. Children and pregnant women are highly susceptible to this form of malaria, which, without immediate and aggressive treatment, is often fatal.

*Plasmodium* species have a very complex lifecycle, involving sexual reproduction (gamete fusion), asexual replication (oocysts and schizonts), invasive stages (sporozoites and merozoites), and two different hosts (mosquito and mammal). *Plasmodium* ookinetes differentiate into oocysts within the *Anopheles* mosquito midgut. Sporozoites develop within and bud off of the oocysts. They are then carried by the mosquito's hemolymph to the salivary glands, where they invade the cells of the salivary ducts. When the infected mosquito bites a human, the sporozoites are injected into his or her skin, through which they migrate until they are able to penetrate a blood vessel and enter the bloodstream. The sporozoites travel to the liver where they invade hepatocytes and develop into merozoites—the invasive form of the *Plasmodium* blood stages (Kappe et al., "*Plasmodium* Sporozoite Molecular Cell Biology," *Annu. Rev. Cell Dev. Biol.* 20:29-59 (2004)).

When the infected hepatocytes rupture, thousands of merozoites are released into the blood and invade erythrocytes, where they proceed through a "ring" form and a trophozoite stage. During these stages, the parasite feeds off of the surrounding red blood cell, ingesting its hemoglobin along with portions of the erythrocyte's cytosol. Parasite proteins released into the host cell induce marked changes to the structure and adhesive properties of the infected red blood cell membrane, causing other cells to clump around them. These erythrocyte "rosettes" adhere to the walls of deep visceral blood vessels, preventing their destruction by the liver and spleen (Bannister and Mitchell, "The Ins, Outs and Roundabouts of Malaria," *Trends Parasitol.* 19:209-213 (2003); Bannister et al., "A Brief Illustrated Guide to the Ultrastructure of *Plasmodium falciparum* Asexual Blood Stages," *Parasitol. Today* 16:427-433 (2000)). After 36, 48, or 72 hours—depending on the *Plasmodium* species—within the red blood cell, the parasite undergoes schizogony (asexual replication). The schizont-infected cells eventually rupture, releasing many new merozoites that can either re-invade other erythrocytes or develop into gametes—the parasite's sexual stage—which can be ingested by another mosquito during a blood meal. Within the mosquito, the gametes fuse and differentiate into ookinetes, and the cycle of infection repeats (Kappe et al., "*Plasmodium* Sporozoite Molecular Cell Biology," *Annu. Rev. Cell Dev. Biol.* 20:29-59 (2004)).

The parasite's blood stages are primarily responsible for the mortality of the disease—the mass rupture of red blood cells causes the painful symptoms of malaria and subsequent anemia. The complications of cerebral malaria ensue when ruptured cells occlude blood vessels supplying the brain or other organs, and the obstruction of placental vasculature contributes to the high mortality rate among pregnant patients (Kappe et al., "*Plasmodium* Sporozoite Molecular Cell Biology," *Annu. Rev. Cell Dev. Biol.* 20:29-59 (2004); Bannister & Mitchell, "The Ins, Outs and Roundabouts of Malaria," *Trends Parasitol.* 19:209-213 (2003); Bannister et al., "A Brief Illustrated Guide to the Ultrastructure of *Plasmodium falciparum* Asexual Blood Stages," *Parasitol. Today* 16:427-433 (2000)).

Two *Plasmodium* species, *P. vivax* and *P. ovale*, also exhibit a hynozoite stage which can remain dormant in the liver for long periods of time, resulting in a relapse of the illness weeks or even years after the initial infection.

*Plasmodium* sporozoites are characterized by an outer pellicle composed of a double-layer inner membrane complex (IMC) surrounded by a plasma membrane (PM) and supported by a microtubule network. An actin-myosin motor lies between the IMC and PM, and is attached to transmembrane adhesive proteins that connect the interior of the parasite cell to receptors, proteoglycans, glycosaminoglycans, and glycoproteins on the host cell's surface. These adhesins are secreted through specialized structures called micronemes on the apical end of the organism. The force transduced by the actin-myosin motor results in the backward redistribution of the adhesive proteins on the parasite's surface. This movement propels sporozoites forward with a spiral-shaped trajectory. When the adhesive proteins reach the posterior end of the cell, they are shed from the zoite membrane, which—at least for sporozoites—allows the parasite's path to be visualized with fluorescently-tagged antibodies to this "protein trail" (Kappe et al., "Apicomplexan Gliding Motility and Host Cell Invasion: Overhauling the Motor Model," *Trends Parasitol.* 20:13-16 (2004)).

While merozoites have not been observed to glide along a surface in the same way sporozoites do, they appear to utilize the same motor machinery to propel themselves into red blood cells (Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006); Pinder et al., "Motile Systems in Malaria Merozoites: How is the Red Blood Cell Invaded?" *Parasitol. Today* 16:240-245 (2000); Pinder et al., "Actomyosin Motor in the Merozoite of the Malaria Parasite, *Plasmodium falciparum*: Implications for Red Cell Invasion," *J. Cell. Sci.* 111:1831-1839 (1998)). When *Plasmodium* merozoites invade host cells, their surface adhesive proteins engage host membrane receptors and form a moving junction between the host cell membrane and the parasite, characterized by a thickened ring within the host cell membrane. The parasite then enters the cell, at which point its surface proteins are cleaved, allowing it to separate from the host cell membrane at its posterior end. The subsequent resealing of the cell membrane generates a specialized "parasitophorous" vacuole within the host cell where parasite differentiation and multiplication occur (Kappe et al., "*Plasmodium* Sporozoite Molecular Cell Biology," *Annu. Rev. Cell Dev. Biol.* 20:29-59 (2004); Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006); Pinder et al., "Motile Systems in Malaria Merozoites: How is the Red Blood Cell Invaded?" *Parasitol. Today* 16:240-245 (2000); Pinder et al., "Actomyosin Motor in the Merozoite of the Malaria Parasite, *Plasmodium falciparum*: Implications for Red Cell Invasion," *J. Cell. Sci.* 111:1831-1839 (1998); Menard, "The Journey of the Malaria Sporozoite Through Its Hosts: Two Parasite Proteins Lead the Way," *Microbes Infect.* 2:633-642 (2000)).

Many of the proteins involved in this form of movement and invasion have been elucidated (Kappe et al., "*Plasmodium* Sporozoite Molecular Cell Biology," *Annu. Rev. Cell Dev. Biol.* 20:29-59 (2004); Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006); Buscaglia et al., "Sites of Interaction Between Aldolase and Thrombospondin-Related Anonymous Protein in *Plasmodium*," *Mol. Biol. Cell.* 14:4947-4957 (2003); Kappe et al., "Apicomplexan Gliding Motility and Host Cell Invasion: Overhauling the Motor Model," *Trends Parasitol.* 20:13-16 (2004); Matuschewski et al., "*Plasmodium* Sporozoite Invasion Into Insect and Mammalian Cells is Directed by the Same Dual Binding System," *Embo J.* 21:1597-1606 (2002); Menard, "The Journey of the Malaria Sporozoite Through Its Hosts: Two Parasite Proteins Lead the Way," *Microbes Infect.* 2:633-642 (2000); Mota & Rodriguez, "Invasion of Mammalian Host Cells by *Plasmodium* Sporozoites," *Bioessays* 24:149-156 (2002); Muller et al., "Thrombospondin Related Anonymous Protein (TRAP) of *Plasmodium falciparum* in Parasite-Host Cell Interactions," *Parassitologia* 35 Suppl:69-72 (1993); Sultan, "Molecular Mechanisms of Malaria Sporozoite Motility and Invasion of Host Cells," *Int. Microbiol.* 2:155-160 (1999); Sultan et al., "TRAP is Necessary for Gliding Motility and Infectivity of *Plasmodium* Sporozoites," *Cell* 90:511-522 (1997); Kappe et al., "Conservation of a Gliding Motility and Cell Invasion Machinery in Apicomplexan Parasites," *J. Cell. Biol.* 147: 937-944 (1999); Green et al., "The MTIP-Myosin A Complex in Blood Stage Malaria Parasites," *J. Mol. Biol.* 355: 933-941 (2006); Jewett & Sibley, "Aldolase Forms a Bridge Between Cell Surface Adhesins and the Actin Cytoskeleton in Apicomplexan Parasites," *Mol. Cell.* 11:885-894 (2003); Yuda et al., "Structure and Expression of an Adhesive Protein-Like Molecule of Mosquito Invasive-Stage Malarial Parasite," *J. Exp. Med.* 189:1947-1952 (1999)). While features of the motor complex were originally resolved in *Plasmodium* sporozoites, and in tachyzoites of the related apicomplexan parasite, *Toxoplasma gondii*, most of its primary components have since been characterized in *Plasmodium* merozoites as well. In the currently prevailing model, the actual motor consists of F-actin (Dobrowolski and Sibley, "*Toxoplasma* Invasion of Mammalian Cells is Powered by the Actin Cytoskeleton of the Parasite," *Cell* 84:933-939 (1996)) and myosin A (MyoA) (Bannister and Mitchell, "The Ins, Outs and Roundabouts of Malaria," *Trends Parasitol.* 19:209-213 (2003); Dobrowolski et al., "Participation of Myosin in Gliding Motility and Host Cell Invasion by *Toxoplasma gondii*," *Mol. Microbiol.* 26:163-173. (1997); Hettmann et al., "A Dibasic Motif in the Tail of a Class XIV Apicomplexan Myosin is an Essential Determinant of Plasma Membrane Localization," *Mol. Biol. Cell* 11:1385-1400 (2000); Heintzelman & Schwartzman, "A Novel Class of Unconventional Myosins From *Toxoplasma gondii*," *J. Mol. Biol.* 271:139-146 (1997)), and is anchored to the IMC via MyoA tail-interacting protein (MTIP) (Bannister. & Mitchell, "The Ins, Outs and Roundabouts of Malaria," *Trends Parasitol.* 19:209-213 (2003); Bergman et al., "Myosin A Tail Domain Interacting Protein (MTIP) Localizes to the Inner Membrane Complex of *Plasmodium* Sporozoites," *J. Cell. Sci.* 116:39-49 (2003)), glideosome associated protein 45 (GAP45), and the integral membrane glycoprotein, GAP50 (Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006); Gaskins et al., "Identification of the Membrane Receptor of a Class XIV Myosin in *Toxoplasma gondii*," *J. Cell. Biol.* 165:383-393 (2004)). Aldolase tetramers link F-actin to the transmembrane adhesin, thrombospondin-related anonymous protein (TRAP), in sporozoites (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007); Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007)), or to its homolog, MTRAP, in merozoites (Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006)). Aldolase is therefore a critical linking molecule in the molecular motor that powers the gliding motility capability of the parasite. As *Plasmodium* Aldolase is highly similar to human Aldolase, and as specificity for *Plasmodium* Aldolase over human Aldolase is required for any potential drug targeting this site, drug development targeted at the Aldolase component of the glideosome is considered challenging to the point of non-obviousness to a reasonable practitioner of the art.

Several effective treatments for malaria exist, including chloroquine, primaquine, sulfadoxine-pyrimethamine, doxycycline, artesunate, and others (Rosenthal, "Antiprotozoal Drugs. in *Basic & Clinical Pharmacology* (ed. Katzung, B. G.) Lange Medical Books/McGraw Hill:New York, pp. 864-885 (2004)). However, many of these drugs have potentially serious side affects and/or are prohibitively expensive. Quinine and quinidine commonly illicit cinchonism, which in some cases can be severe (Katzung, *Basic and Clinical Pharmacology*, Appleton & Lange:Norwalk, Conn., (2004)). Many anti-malarials can produce hemolysis in patients with glucose 6-phosphate dehydrogenase deficiencies (Katzung, *Basic and Clinical Pharmacology*, Appleton & Lange:Norwalk, Conn., (2004)), which due to its conference of some degree of malaria resistance, is commonly found in malaria endemic regions (Kwiatkowski, "How Malaria Has Affected the Human Genome and What Human Genetics Can Teach Us About Malaria," *Am. J. Hum. Genet.* 77:171-192 (2005)). Some anti-malarial agents have also been associated with rare cases of neuropsychiatric toxicities (Katzung, *Basic and Clinical Pharmacology*, Appleton & Lange: Norwalk, Conn., (2004)). Additionally, parasite resistance to these drugs is growing rapidly, especially in areas lacking adequate medical infrastructures and support networks (United States Center for Disease Control Malaria Website; World Health Organization Global Malaria Programme). On the other hand, artemisinin-based combination therapies (ACTs), while still highly effective in most regions, are cumbersome to produce and are often too expensive for patients in endemic areas (Enserink, "Combating Malaria. Malaria Treatment: ACT Two," *Science* 318:560-563 (2007)). Reports of parasite resistance to ACTs—the current gold-standard for malaria treatment—have begun to emerge as well (Noedl et al., "Evidence of Artemisinin-Resistant Malaria in Western Cambodia," *N. Engl. J. Med.* 359:2619-2620 (2008)). This is especially alarming as there are very few other drugs in the malaria pipeline. There is clearly a critical need for the discovery of novel drug targets and reagents to combat this disease.

Most anti-malarials in clinical use target the parasite's haem (quinilones: chloroquine, quinine, amodiaquine, mefloquine, and halofantrine) or folate (antifolates: sulphadoxine-pyrimethine) metabolism pathways, while others interfere with mitochondrial electron-transport via cytochrome C inhibition (atavaquone, proguanil). Additionally, some common antibiotics are effective against malaria by inhibiting prokaryote-like protein synthesis within the malarial apicoplast (tetracycline, doxycycline, and clindamycin). Newer artemisin derivatives (artemether, arteether, artesunate) are believed to rapidly kill merozoites and gametocytes via free-radical generation (Ridley, "Medical Need, Scientific Opportunity and the Drive for Antimalarial Drugs," *Nature* 415:686-693 (2002); Wells et al., "New Medicines to Improve Control and Contribute to the Eradication of Malaria," *Nat. Rev. Drug Discov.* 8:879-891 (2009)).

Considering the global impact of malarial disease, and the years of research and billions of dollars poured into attempts to eradicate it, the above list of treatments and therapeutic targets is alarmingly short. There are clearly many more pathways, mechanisms, and biological features of *Plasmodium* that have yet to be targeted for anti-malarial drug design. The glideosome is thus established as a promising target, and a drug inhibiting the glideosome would be new and useful. Moreover, cross species conservation of the glidoesome might have the potential to be valuable for economical reasons preventing livestock diseases in cattle (*Babesia*) or chicken (*Eimeria*).

Importantly, there are precious few drugs in clinical use that are effective against the exo-erythrocytic stages of the parasite, making the prevention of transmission and disease relapse due to dormant liver-stage hypnozoites especially difficult. Without the ability to effectively prevent initial infections by malaria sporozoites through vaccination or prophylactic drug therapy, it is unlikely to achieve complete global eradication of this deadly disease (Mazier et al., "A Pre-Emptive Strike Against Malaria's Stealthy Hepatic Forms," *Nat. Rev. Drug Discov.* 8:854-864 (2009)).

The present invention is directed to overcoming these and other deficiencies in the art.

SUMMARY OF THE INVENTION

In one aspect, the present invention relates to a method of identifying compounds useful in modifying the activity of Aldolase. The method includes providing a first model comprising Aldolase or residues of the amino acid sequence corresponding to SEQ ID NO: 1 said residues being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347, and providing one or more candidate compounds. Contact between the candidate compounds and the first model is evaluated to determine which of the one or more candidate compounds have an ability to bind to and/or fit in the first model. Compounds which, based on said evaluating, have the ability to bind to and/or fit in the first model are identified as compounds potentially useful for modifying the activity of Aldolase.

A second aspect of the present invention relates to a method of identifying compounds useful in stabilizing a complex between Aldolase and thrombospondin-related anonymous protein (TRAP) or a portion thereof. The method includes providing a complex of first model comprising Aldolase or residues of the amino acid sequence corresponding to SEQ ID NO: 1, said residues being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347; and a second model comprising TRAP or residues of the amino acid sequence corresponding to SEQ ID NO: 38, said residues being at amino acid positions selected from the group consisting of 554, 555, 556, 557, 558, and 559. The method further includes providing one or more candidate compounds and examining contact between the candidate compounds and the complex between the first and the second model to determine which of the one or more candidate compounds have an ability to bind to and/or fit in the complex between the first and the second model, Compounds which, based on said examining, have the ability to bind to and/or fit in the complex between the first and the second model are identified as compounds potentially useful for stabilizing the complex.

A third aspect of the present invention is directed to a pharmaceutical composition which includes a pharmaceutical carrier and a compound selected from the group consisting of:

(1) a compound of formula (I)

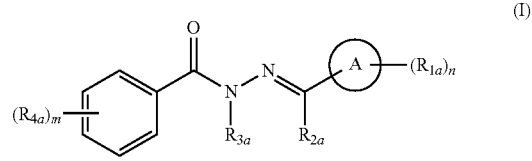

wherein:
n is an integer from 0 to 4;
m is an integer from 0 to 4;
$R_{1a}$ is independently at each occurrence H, halogen, $CF_3$, $CHF_2$, $CH_2F$, OH, $NH_2$, CN, $NO_2$, —$C(O)R_{5a}$, —$SR_{5a}$, —$S(O)R_{5a}$, —$S(O)_2R_{5a}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur; or
two adjacent $R_{1a}$ groups may combine to form a 3- to 7-membered heterocyclic ring containing from 1 to 5 heteroatoms selected from the group consisting of oxygen, nitrogen, and sulfur;
$R_{2a}$ is independently H, halogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;
$R_{3a}$ is independently H, —$SR_{5a}$, —$S(O)R_{5a}$, —$S(O)_2R_{5a}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;
$R_{4a}$ is independently at each occurrence H, halogen, $CF_3$, $CHF_2$, $CH_2F$, OH, $OR_{5a}$, $O(CH_2)_2OR_{5a}$, —$C(O)R_{5a}$, —$OC(O)R_{5a}$, —$NHC(O)R_{5a}$, —$NHC(O)OR_{5a}$—$C(O)OR_{5a}$, —$C(O)NR_{5a}R_{6a}$, —$NHR_{5a}$, —$NR_{5a}R_{6a}$, —$SR_{5a}$, —$S(O)R_{5a}$, —$S(O)_2R_{5a}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl;
two adjacent $R_{4a}$ groups may combine to form a 3- to 7-membered heterocyclic ring containing from 1 to 5 heteroatoms selected from the group consisting of oxygen, nitrogen, sulfur, and bismuth, wherein heterocycyclic ring can be unsaturated or saturated and optionally substituted with from 1-2 substituents independently selected at each occurrence thereof from OH, F and $C_1$-$C_6$ alkyl;
$R_{5a}$ and $R_{6a}$ are independently H, $CHF_2$, $CH_2Ph$, $CH_2C(O)NH_2$, $CH_2CH_2NHSO_2Me$, $C_1$-$C_{16}$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur; and wherein $CH_2Ph$ is optionally substituted with from 1-3 substituents independently selected at each occurrence thereof from F, Cl, OMe; and
A is a substituted or unsubstituted mono or polycyclic aryl or substituted or unsubstituted mono or polycyclic heteroaryl containing from 1 to 5 heteroatoms selected from the group consisting of oxygen, nitrogen, and sulfur;
(2) a compound of formula (II)

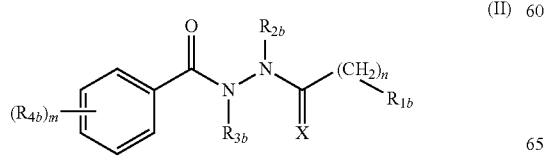

wherein:
X is O, S, or NH;
n is an integer from 0 to 3;
m is an integer from 0 to 3;
$R_{1b}$ is independently H, halogen, $CF_3$, $CHF_2$, $CH_2F$, OH, $NH_2$, CN, $NO_2$, $OR_{5b}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;
$R_{2b}$ and $R_{3b}$ is independently H, —$SR_{5b}$, —$S(O)R_{5b}$, —$S(O)_2R_{5b}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;
$R_{4b}$ is independently at each occurrence H, halogen, $CF_3$, $CHF_2$, $CH_2F$, OH, $OR_{5b}$, —$C(O)R_{5b}$, —$C(O)OR_{5b}$, —$C(O)NR_{5b}R_{6b}$, —$NHR_{5b}$, —$NR_{5b}R_{6b}$, —$SR_{5b}$, —$S(O)R_{5b}$, —$S(O)_2R_{5b}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and
$R_{5b}$ and $R_{6b}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each monocyclic aryl or monocyclic heteroaryl optionally substituted from 1 to 4 times with substituents selected from the group consisting of H, halogen, $CF_3$, $CHF_2$, $CH_2F$, OH, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl;
(3) a compound of formula (III):

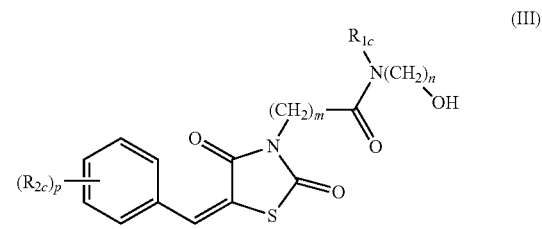

wherein:
m, n, and p are independently integers from 0 to 3;
$R_{1c}$ is H, —$SR_{3c}$, —$S(O)R_{3c}$, —$S(O)_2R_{3c}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;
$R_{2c}$ is independently at each occurrence H, halogen, $CF_3$, $CHF_2$, $CH_2F$, OH, $OR_{3c}$, —$C(O)R_{3c}$, —$C(O)OR_{3c}$, —$C(O)NR_{3c}R_{4c}$, —$NHR_{3c}$, —$NR_{3c}R_{4c}$, —$SR_{3c}$, —$S(O)R_{3c}$, —$S(O)_2R_{3c}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and
$R_{3c}$ and $R_{4c}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur;

(4) a compound of formula (IV):

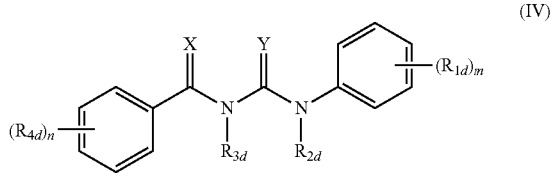

wherein:

m and n are integers from 0 to 3;

X and Y are independently O or S;

$R_{1d}$ and $R_{4d}$ are independently at each occurrence H, halogen, $CF_3$, $CHF_2$, $CH_2F$, OH, $OR_{5d}$, $-C(O)R_{5d}$, $-C(O)OR_{5d}$, $-C(O)NR_{5d}R_{6d}$, $-NHR_{5d}$, $-NR_{5d}R_{6d}$, $-SR_{5d}$, $-S(O)R_{5d}$, $-S(O)_2R_{5d}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl;

$R_{2d}$ and $R_{3d}$ are independently H, $-SR_{5d}$, $-S(O)R_{5d}$, $-S(O)_2R_{5d}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur; and $R_{5d}$ and $R_{6d}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur;

(5) a compound of formula V:

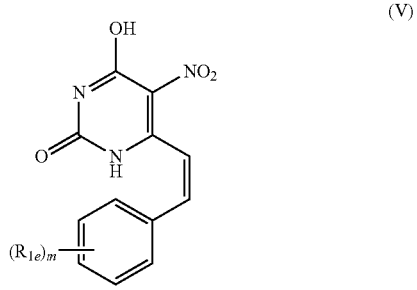

wherein:

m is an integer from 0 to 3 and $R_{1e}$ is independently at each occurrence H, halogen, $CF_3$, $CHF_2$, $CH_2F$, OH, $OR_{5e}$, $-C(O)OR_{5e}$, $-C(O)NR_{5e}R_{6e}$, $-NHR_{5e}$, $-NR_{5e}R_{6e}$, $-SR_{5e}$, $-S(O)R_{5e}$, $-S(O)_2R_{5e}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl or mono or polycyclic heterocycle containing from 1-5 heteroatoms selected from the group consisting of nitrogen, oxygen, and sulfur.

A fourth aspect of the present invention is related to a method of modifying the activity of Aldolase in an apicomplexan organism. The method includes providing an apicomplexan organism, providing the pharmaceutical composition of the present invention, and contacting the pharmaceutical composition with the apicomplexan organism. The contacting modifies the activity of Aldolase in the apicomplexan organism.

A fifth aspect of the present invention is related to a method of stabilizing a complex between Aldolase or portions thereof and thrombospondin-related anonymous protein (TRAP) or portions thereof. The method includes providing an apicomplexan organism, providing the pharmaceutical composition of the present invention, and contacting the pharmaceutical composition with the apicomplexan organism under conditions effective to stabilize the complex between Aldolase or portions thereof and thrombospondin-related anonymous protein (TRAP) or portions thereof.

A sixth aspect of the present invention is related to a method of inhibiting dissociation of cytoplasmic TRAP tail from glideosome in an apicomplexan organism including providing an apicomplexan organism and providing a pharmaceutical composition according to the third aspect of the present invention. The pharmaceutical composition is contacted with the apicomplexan organism under conditions effective to inhibit the dissociation of cytoplasmic TRAP tail from the glideosome.

A seventh aspect of the present invention is related to a method of inhibiting activity and/or survival of an apicomplexan organism. The method includes selecting apicomplexan organism and administering to the selected apicomplexan organism the pharmaceutical composition of the present invention under conditions effective to inhibit the activity and/or survival of the apicomplexan organism.

An eighth aspect of the present invention is related to a method of treating or preventing infection caused by an apicomplexan organism in a subject. The method includes selecting a subject having or susceptible to an infection caused by an apicomplexan organism and administering to the selected subject the pharmaceutical composition of the present invention under conditions effective to prevent or treat the infection caused by an apicomplexan organism.

A ninth aspect of the present invention is related to a method of treating or preventing malarial infection in a subject. The method includes selecting a subject susceptible to or having the malarial infection. A compound is provided which binds to and/or fits in:

a) a first model comprising Aldolase or residues of the amino acid sequence corresponding to SEQ ID NO: 1 being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347; and/or b) a complex between said first model and a second model comprising a thrombospondin-related anonymous protein (TRAP) or residues of the amino acid sequence corresponding to SEQ ID NO: 38 said residues being at amino acid positions selected from the group consisting of 554, 555, 556, 557, 558, and 559.

The compound is administered to the selected subject under conditions effective to treat the malarial infection in the subject.

A growing body of evidence suggests that the apicomplexan glideosome is amenable to anti-parasite drug design, and presents a point of vulnerability in both blood-stage merozoites and pre-erythrocytic sporozoites. Gene-targeting studies have shown that parasites lacking functional TRAP have impaired gliding motility and are unable to infect mosquito salivary glands or rat liver cells (Sultan et al., "TRAP is Necessary for Gliding Motility and Infectivity of *Plasmodium* Sporozoites," *Cell* 90:511-522 (1997); Kappe et al., "Conservation of a Gliding Motility and Cell Invasion Machinery in Apicomplexan Parasites," *J. Cell. Biol.* 147:937-944 (1999), which are hereby incorporated by reference in their entirety). Additionally, *P. berghei* mutants expressing TRAP that is not properly sorted to the apical micronemes or parasite surface are significantly impaired in their ability to glide on glass slides, invade cultured hepatocytes, or infect mice (Bhanot et al., "Defective Sorting of the Thrombospondin-Related Anonymous Protein (TRAP) Inhibits *Plasmodium* Infectivity," *Mol. Biochem. Parasitol.* 126:263-273 (2003), which is hereby incorporated by reference in its entirety). The functional interaction between TRAP and Aldolase appears crucial for these processes as well (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007), which are hereby incorporated by reference in their entirety).

Recent attempts to develop small-molecule anti-malarial agents that inhibit the gliding and invasion machinery also lend support to its validity as a drug target. A high-throughput screening protocol in *Toxoplasma gondii* yielded several small molecules that blocked cellular invasion by interfering with parasite motility, though the precise molecular targets of the drugs were not determined (Carey et al., "A Small-Molecule Approach to Studying Invasive Mechanisms of *Toxoplasma gondii*," *Proc. Nat'l. Acad. Sci. USA* 101:7433-7438 (2004), which is hereby incorporated by reference in its entirety). Panchal and Bhanot demonstrated that a tri-substitued pyrrole previously known to impair apicomplexan growth by inhibiting a cGMP-dependent kinase present in erythrocytic parasites could also protect rodents against malarial infection by blocking sporozoite invasion of hepatocytes, and to some extent, sporozoite motility (Panchal & Bhanot, "Activity of a Trisubstituted Pyrrole in Inhibiting Sporozoite Invasion and Blocking Malaria Infection," *Antimicrob. Agents Chemother.* 54:4269-4274 (2010), which is hereby incorporated by reference in its entirety). Allicin, a compound found in garlic extracts, has also been shown to protect mice challenged with *Plasmodium* sporozoites by disrupting the processing of CS protein (Coppi et al., "Antimalarial Activity of Allicin, a Biologically Active Compound From Garlic Cloves," *Antimicrob. Agents Chemother.* 50:1731-1737 (2006), which is hereby incorporated by reference in its entirety). Recently, computational tools could not be used to identify a set of pyrazole-urea compounds that prevented *P. falciparum* growth and sporozoite motility, likely by inhibiting the interaction between MTIP and MyoA (Kortagere et al., "Structure-Based Design of Novel Small-Molecule Inhibitors of *Plasmodium falciparum*," *J. Chem. Inf. Model* 50:840-849 (2010), which is hereby incorporated by reference in its entirety). These results strongly suggest that the specific intermolecular interactions within the *Plasmodium falciparum* motor complex represent a promising target for drug discovery.

Importantly, the gliding machinery is essential in all stages of the parasite lifecycle, as it is necessary for the invasion of mosquito salivary glands and for the traversal along and through Kupffer cells in the human liver by sporozoites, as well as for the active invasion of erythrocytes by merozoites. Furthermore, many of the proteins in the glideosome are also critical to other homeostatic functions within the parasite, as described for Aldolase above. The critical nature of the glideosome proteins, along with their unambiguous cellular phenotype, make them very attractive targets for rational drug design—disrupting this complex would almost certainly hinder parasite infectivity, while mutations that confer drug resistance would be slow to emerge as they would also interfere with necessary protein functions.

BRIEF DESCRIPTION OF THE DRAWINGS

FIG. 3 shows a flow chart of the VLS procedure used in the present invention. (Abbreviations: ADME-TOX, adsorption, distribution, metabolism, excretion and toxicity; GA, genetic algorithm; MC, Monte Carlo.) Reproduced with permission from Abagyan and Totrov, *Curr Opin Chem Biol*, 2001 (Abagyan & Totrov, "High-Throughput Docking for Lead Generation," *Curr. Opin. Chem. Biol.* 5:375-382 (2001), which is hereby incorporated by reference in its entirety).

FIG. 4A shows the *Plasmodium* TRAP-Aldolase co-crystal structure (Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety) (PDB ID: 2pc4, 2.4 Å) superimposed on *Plasmodium* apo-Aldolase (Kim et al., "Crystal Structure of Fructose-1,6-Bisphosphate Aldolase From the Human Malaria Parasite *Plasmodium falciparum*," *Biochemistry* 37:4388-4396 (1998), which is hereby incorporated by reference in its entirety) (PDB ID: 1a5c, 3.0 Å, white ribbon). The TRAP-bound Aldolase backbone is shown as a green ribbon, with the helix-loop-helix that shifts to accommodate TRAP shown in purple. The C-terminal TRAP peptide is shown in orange ball-and-stick representation. FIG. 4B shows TRAP-bound Aldolase. The Aldolase is colored by sequence conservation to its human homologue (green=identical residues; yellow=residues with similar properties in terms of size, charge, shape, or hydrophobicity; white=completely unconserved). Most of the residues in the enzyme active site, including all of the catalytic residues (cyan ball-and-stick) are conserved between *Plasmodium* and human. However, there are several residues bordering this site, in close proximity to TRAP, that are not conserved in human Aldolase, and that were targeted for drug design work described here.

FIG. 5A shows four pockets found in the crystal structure of unliganded Aldolase (PDB ID: 1a5c, Kim et al., "Crystal Structure of Fructose-1,6-Bisphosphate Aldolase From the Human Malaria Parasite *Plasmodium falciparum*," *Biochemistry* 37:4388-4396 (1998), which is hereby incorporated by reference in its entirety). Aldolase is shown as a backbone ribbon colored blue at it's N-terminus to red at its C-terminus. Active site residues K47, R48, K112, K151, E194, K236, and R309 are shown in green ball-and-stick representation as markers for the TRAP-binding site. Pockets 1 through 4 are shown as space-filling graphical objects, colored blue, red, yellow, and purple, respectively. FIG. 5B shows a plot of the surface area ($Å^2$) vs. volume ($Å^3$) for the 4 pockets. The hatched rectangle denotes the region of the plot containing the area-to-volume ratio within which most known drugs fall (100-500 $Å^{2/3}$ Area/Volume (Cardozo and Abagyan, "Druggability of SCF Ubiquitin Ligase-Protein Interfaces," *Ubiquitin and Protein Degradation, Part B*, Vol. 399 (ed. Deshaies, R. J.) Elsevier Academic Press:San Diego, pp. 634-653 (2005), which is hereby incorporated by reference in its entirety). FIG. 5C shows that pocket 4 and a segment of pocket 1, that falls within the TRAP-binding area, are contacted by non-conserved residues. These non-conserved residues are as follows: □43, N51, E85, L117, A199, and Y244 (green balls-and-sticks). Aldolase and pockets are colored as described in FIG. 5A.

FIG. 6A shows six pockets that were found in the co-crystal structure of Aldolase bound to TRAP (PDB ID: 2pc4, Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety) when the TRAP peptide was removed from the structure. The Aldolase backbone and active site residues are shown as in FIG. 6A. Pockets 1 through 6 are shown as space-filling graphical objects colored blue, red, yellow, green, orange, and purple, respectively. FIG. 6B shows a plot of the surface area ($Å^2$) vs. volume ($Å^3$) for the 6 pockets. FIG. 6C shows that pocket 1 contacts the TRAP-binding region, and is bordered by the non-conserved Aldolase residues, N51, E85, and L117 (green balls-and-sticks). Aldolase and pocket 1 are colored as described in FIG. 6A.

FIG. 7A shows eight pockets that were found in the cocrystal structure of Aldolase bound to TRAP (PDB ID: 2pc4, Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety). Aldolase is shown as a ribbon colored blue at its N-terminus to red at its C-terminus. TRAP is shown as a green ball-and-stick model. Pockets 1 through 8 are shown as space-filling graphical objects, colored blue, red, yellow, green, orange, purple, aquamarine, and peach, respectively. FIG. 7B shows a plot of the surface area ($Å^2$) vs. volume ($Å^3$) for the 8 pockets. Pockets 1, 2, and 3 fall within the 100-500 $Å^{2/3}$ Area/Volume range. FIG. 7C shows pockets 3, 6, and 8 which were targeted by VLS, and are contacted by three non-conserved residues within Aldolase—N51, E85, L117 (green balls-and-sticks)—as well as by the TRAP peptide. Aldolase, TRAP, and pockets are colored as in FIG. 7A.

FIGS. 8A-B show superposition of the docked complex and a co-crystal structure of rabbit muscle Aldolase bound to F16P (PDB ID: 1zai, resolution 1.76 Å (St-Jean et al., "High Resolution Reaction Intermediates of Rabbit Muscle Fructose-1,6-Bisphosphate Aldolase: Substrate Cleavage and Induced Fit," *J. Biol. Chem.* 280:27262-27270 (2005), which is hereby incorporated by reference in its entirety)). Aldolase is displayed as a ribbon with the catalytic residues shown as wires (blue =*P. falciparum*, green=rabbit). The docked F16P is colored orange, while the co-crystallized F16P is colored purple. The superposition of the two structures is very close, especially that of one of the phosphate groups, which are colored red. FIG. 8B shows a close-up view of FIG. 8A. FIG. 8C-D show superposition of the docked complex and a co-crystal structure of human muscle Aldolase bound to F16P (PDB ID: 4ald, resolution 2.8 Å, Dalby et al., "Crystal Structure of Human Muscle Aldolase Complexed With Fructose 1,6-Bisphosphate: Mechanistic Implications," Protein Sci. 8:291-297 (1999), which is hereby incorporated by reference in its entirety). Molecules are colored as in FIGS. 8B and 8C. FIG. 8D shows a close-up of FIG. 8C.

FIGS. 9A-B shows superposition of the docked complex and a co-crystal structure of rabbit muscle Aldolase bound to DHAP (PDB ID: 1j4e, resolution 2.65 Å (Choi et al., "Snapshots of Catalysis: The Structure of Fructose-1,6-(bis)phosphate Aldolase Covalently Bound to the Substrate Dihydroxyacetone Phosphate," Biochemistry 40:13868-13875 (2001), which is hereby incorporated by reference in its entirety)). The superposition of the two structures is very close, especially that of the phosphate groups. FIG. 9B shows a close-up of FIG. 9A. FIGS. 9C-D show superposition of the docked complex and a second co-crystal structure of rabbit muscle Aldolase bound to DHAP (PDB ID: lado, resolution 1.9 Å (Blom and Sygusch, "Product Binding and Role of the C-Terminal Region in Class I D-Fructose 1,6-Bisphosphate Aldolase," Nat. Struct. Biol. 4:36-39 (1997), which is hereby incorporated by reference in its entirety)). DHAP is bound in a different orientation in this co-crystal structure; however, the phosphate group is still positioned in equivalent locations between the docked and co-crystallized structures. FIG. 9D shows a close-up view of FIG. 9C. Molecules are colored as in FIG. 8.

FIG. 10A shows Aldolase colored blue to red by increasing b-factor. The lowest energy docked conformation is likely an artifact due to the unusually high b-factor in this region of the co-crystal structure. TRAP in its position in the co-crystal structure is shown as a green ball-and-stick model, and the docked TRAP is shown in purple. FIGS. 10B-D show Aldolase colored in a gradient from blue at its N-terminus to red at its C-terminus. The lowest energy docked conformation when the area of high b-factor is ignored demonstrates a close correlation between the co-crystal structure and the docking results. TRAP peptides are colored as in FIG. 10A. FIGS. 10B-C show two views of the complex. FIG. 10D shows a close-up of the view in FIG. 10B.

FIG. 11A shows the "2pc4 model" receptor. The green graphical object depicts the pocket around which the VLS boxes were initially built. FIG. 11B shows the "falciparum model" receptor. FIG. 11C shows the "gapped-pocket model" receptor.

FIGS. 16 A-B show the crystallographic resolution of compound 14 in complex with TRAP and aldolase. Compounds that demonstrated a stabilizing effect on the Aldolase-TRAP interaction in vitro were either soaked into existing Plasmodium Aldolase-TRAP crystals or co-crystallized with TRAP and Aldolase. FIG. 16 A shows electron density seen for compound 24 in complex with TRAP and Aldolase depicted as mesh surfaces for each molecule. Compound density can be found near the enzyme's active site in close proximity to TRAP. FIG. 16 B shows the relative atomic locations: the backbone of aldolase is shown in ribbon depiction; the TRAP peptide is showed as space filling spheres; compound 24 is shown in stick depiction. Notably, clear density was seen for both TRAP and compound 24 in all 4 subunits of the Aldolase tetramer, only one of which is shown here.

FIG. 19A shows that similar numbers of viable cells were recovered from both the control and treated samples (approximately 54% of the cells analyzed in each case). The recovered cells were analyzed for the expression of both apoptotic markers. This was indicated by the FL2-H (Fluorescence-height, indicates fluorescence intensity) vs. FSC-H (Forward Scatter-Height, proportional to cell size) plots. FIG. 19B shows that at a concentration of 100 µM none of the compounds induced heightened expression of either apoptotic marker (FL2=Propidium Iodide; FL4=Annexin-APC). Note that for compound 24, the fluorescence peaks for Annexin-APC are shifted slightly to the right, indicating that at higher concentrations, some cytotoxicity would likely be observed. However, the compound dosage used here—100 µM—is already much higher than would typically be observed under physiological conditions.

FIGS. 24A-H show the effects of the VLS hits on the stability of the Aldolase-TRAP complex when measured using a thermal shift assay. The figures display the first derivative plots of the fluorescence curves obtained during the assay. The minimum of each curve represents the sample's melting point ($T_m$). The first figure shows curves obtained for multiple preparations of recombinant *P. falciparum* Aldolase complexed with a peptide derived from the C-terminal 6 residues of *P. berghei* TRAP (PbTRAP6). For these controls, DMSO was added at the same concentration as was used for the compound assays. In all of these cases, the $T_m$ for the Aldolase-TRAP complex is approximately 59.5±1° C., indicating the high robustness and reproducibility of this assay. Only control 1 (lower blue lines) was used for the remaining experiments in which the VLS compounds (numbered in the figures) were added to the complex.

FIG. 27 shows an alignment of TRAP like proteins in *P. falciparum* and *P. vivax* (SEQ ID NOS: 29 to 36). The C-terminal residues of TRAP, MTRAP, CTRP, and TLP are known to interact with Aldolase. Characteristic for the C-terminal tails of these paralogs are the surrounding acidic residues. The compounds identified in the present invention are directly suitable against Aldolase-CTRP interface as they recognize the WN motif in CTRP.

FIG. 28 A shows the results of the SRB cell Proliferation Assay: Fixed cells were stained with Sulforthadaminde B and absorbance was measured at 570 nm. FIG. 28 B shows the results of the PrestoBlue Cell Viability Assay: Live-cells were incubated in drug solution for 72 hrs, the drug solution was then stained and fluorescence at 570 nm was measured throughout time to determine cell viability.

FIG. 29 A-B show analysis of the scaffold. FIG. 29 A shows "identical" and "different" positions for functional groups. Same letter indicates "identical" substituent positions. FIG. 29 B shows substituent combinations derived from the analysis of the scaffold and in-silico docking.

DETAILED DESCRIPTION OF THE INVENTION

Figure 1:
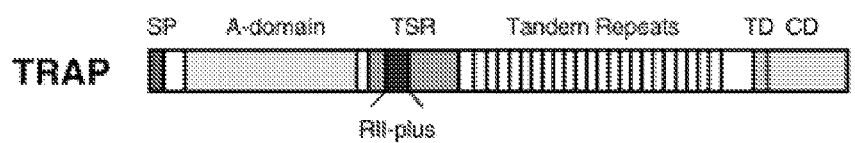
FIG. 1 shows a schematic of Thrombospondin-Related Anonymous Protein, or TRAP, which is a Type I transmembrane protein. The protein's extracellular domain contains a signal peptide (SP), a series of species-specific 18-residue repeats (Tandem Repeats), and 2 adhesive domains that bind host receptors, namely, an integrin-like A-domain which contains a $Mg^{2+}$-dependent adhesion side (MIDAS, metal ion-dependent adhesion site) thought to bind bivalent cations and play a role in receptor recognition (Wengelnik et al., "The A-Domain and the Thrombospondin-Related Motif of *Plasmodium falciparum* TRAP are Implicated in the Invasion Process of Mosquito Salivary Glands," *Embo J.* 18:5195-5204 (1999); Akhouri et al., "Structural and Functional Dissection of the Adhesive Domains of *Plasmodium falciparum* Thrombospondin-Related Anonymous Protein (TRAP)," *Biochem. J.* 379:815-822 (2004), which are hereby incorporated by reference in their entirety), and a thrombospondin repeat (TSR), which folds into a 3-stranded domain with a positively charged groove that may bind sulfate groups of HSPGs on target cells (Kappe et al., "*Plasmodium* Sporozoite Molecular Cell Biology," *Annu. Rev. Cell Dev. Biol.* 20:29-59 (2004); Matuschewski et al., "*Plasmodium* Sporozoite Invasion Into Insect and Mammalian Cells is Directed by the Same Dual Binding System," *Embo J.* 21:1597-1606 (2002); Wengelnik et al., "The A-Domain and the Thrombospondin-Related Motif of *Plasmodium falciparum* TRAP are Implicated in the Invasion Process of Mosquito Salivary Glands," *Embo J.* 18:5195-5204 (1999), which are hereby incorporated by reference in their entirety). The Region II-plus (RII-plus) domain in the related CS protein is involved in oocyst exist within the mosquito midgut (Wang et al., "Exit of *Plasmodium* Sporozoites from Oocysts is an Active Process that Involves the Circumsporozoite Protein," *PLoS Pathog.* 1:e9 (2005), which is hereby incorporated by reference in its entirety), and may play a similar role in TRAP. The cytoplasmic domain binds Aldolase, connecting the motor to the gliding substrate or host cell. When the motor complex reaches the posterior end of the cell, TRAP is cleaved within its transmembrane domain (TD) by rhomboid proteases, leaving its extracellular domain bound to the host cell (Baker et al., "Two *Plasmodium* Rhomboid Proteases Preferentially Cleave Different Adhesins Implicated in all Invasive Stages of Malaria," *PLoS Pathog.* 2:e113 (2006); Sinnis, "The Malaria Sporozoite's Journey Into the Liver," *Infect. Agents Dis.* 5:182-189 (1996), which are hereby incorporated by reference in their entirety). The image is reproduced, with permission, from Kappe et al., *Annu Rev Cell Dev Biol*, 2004 (Kappe et al., "*Plasmodium* Sporozoite Molecular Cell Biology," *Annu. Rev. Cell Dev. Biol.* 20:29-59 (2004), which is hereby incorporated by reference in its entirety.)

In one aspect, the present invention relates to a method of identifying compounds useful in modifying the activity of Aldolase. The method includes providing a first model comprising Aldolase or residues of the amino acid sequence corresponding to SEQ ID NO: 1 said residues being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347, and providing one or more candidate compounds. Contact between the candidate compounds and the first model is evaluated to determine which of the one or more candidate compounds have an ability to bind to and/or fit in the first model. Compounds which, based on said evaluating, have the ability to bind to and/or fit in the first model are identified as compounds potentially useful for modifying the activity of Aldolase.

In one embodiment the method further includes screening the identified compounds in vitro for their ability to kill and/or inhibit growth of an apicomplexan organism and designating the screened compounds which kill and/or inhibit an apicomplexan organism as a therapeutics targeting apicomplexan organisms.

Aldolase

In *Plasmodium*, and other apicomplexa, tetrameric Aldolase is crucial for both motility and cellular ATP generation (Buscaglia et al., "Sites of Interaction Between Aldolase and Thrombospondin-Related Anonymous Protein in *Plasmodium*," *Mol. Biol. Cell.* 14:4947-4957 (2003); Kappe et al., "Apicomplexan Gliding Motility and Host Cell Invasion: Overhauling the Motor Model," *Trends Parasitol.* 20:13-16 (2004); Starnes et al., "Aldolase is Essential for Energy Production and Bridging Adhesin-Actin Cytoskeletal Interactions During Parasite Invasion of Host Cells," *Cell Host Microbe* 5:353-364 (2009), which are hereby incorporated by reference in their entirety). In addition to bridging the motor complex and transmembrane adhesins, Aldolase's other major role in malaria parasites is as an important enzyme in the glycolytic pathway. Aldolase catalyzes the cleavage of fructose-1,6-bisphosphate (F16P) to dihydroxyacetone phosphate (DHAP) and glyceraldehyde 3-phosphate (G3P), which are then further processed by other glycolytic enzymes to eventually yield pyruvate, NADH, water, and ATP.

This pathway is conserved in nearly all organisms, including humans (Horecker et al., "Aldolases," in *The Enzymes*, Vol. 7 (ed. Boyer, P. D.) Academic Press:New York pp. 213-258 (1972), which is hereby incorporated by reference in its entirety). *P. falciparum* parasites are highly dependent on the fermentation of glucose for energy generation—while these parasites do contain mitochondria, these organelles lack the usual array of cristae in merozoites, and the enzymes needed for a functional TCA cycle and oxidative glucose metabolism are not expressed in all parasite stages (Lang-Unnasch, "*Plasmodium falciparum*: Antiserum to Malate Dehydrogenase," *Exp. Parasitol.* 80:357-359 (1995); Lang-Unnasch, "Purification and Properties of *Plasmodium falciparum* Malate Dehydrogenase," *Mol. Biochem. Parasitol.* 50:17-25 (1992); Meis et al., "Histochemical Observations on the Exoerythrocytic Malaria Parasite *Plasmodium berghei* in Rat Liver," *Histochemistry* 81:417-425 (1984); Lang-Unnasch & Murphy, "Metabolic Changes of the Malaria Parasite During the Transition From the Human to the Mosquito Host," *Annu. Rev. Microbiol.* 52:561-590 (1998), which are hereby incorporated by reference in their entirety). While there are several sequence differences between human and *Plasmodium* Aldolase, the sequence and structure of the enzyme's catalytic site is highly conserved between these species (Kim et al., "Crystal Structure of Fructose-1,6-Bisphosphate Aldolase From the Human Malaria Parasite *Plasmodium falciparum*," *Biochemistry* 37:4388-4396 (1998), which is hereby incorporated by reference in its entirety).

A recent study in *Toxoplasma gondii* demonstrated that the regions on Aldolase responsible for its two key roles—motility and enzyme activity—represented two overlapping but distinct domains (Starnes et al., "Aldolase is Essential for Energy Production and Bridging Adhesin-Actin Cytoskeletal Interactions During Parasite Invasion of Host Cells," *Cell Host Microbe* 5:353-364 (2009), which is hereby incorporated by reference in its entirety). However, the question of whether the same pool of Aldolase participates in both roles remains unclear. The same study failed to reproduce earlier results that demonstrated a relocalization of a single Aldolase pool to the *Toxoplasma* pellicle during cellular invasion (Pomel et al., "Host Cell Egress and Invasion Induce Marked Relocations of Glycolytic Enzymes in *Toxoplasma gondii* Tachyzoites," *PLoS Pathog.* 4:e1000188 (2008), which is hereby incorporated by reference in its entirety). Additionally, while numerous reports place both the TRAP and F-actin binding domains in overlapping regions near the Aldolase active site (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007); Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007); St-Jean et al., "A Hydrophobic Pocket in the Active Site of Glycolytic Aldolase Mediates Interactions With Wiskott-Aldrich Syndrome Protein," *J. Biol. Chem.* 282(19):14309-15 (2007); Starnes et al., "Aldolase is Essential for Energy Production and Bridging Adhesin-Actin Cytoskeletal Interactions During Parasite Invasion of Host Cells," *Cell Host Microbe* 5:353-364 (2009); Wang et al., "The Molecular Nature of the F-Actin Binding Activity of Aldolase Revealed With Site-Directed Mutants," *J. Biol. Chem.* 271:6861-6865 (1996); O'Reilly & Clarke, "Identification of an Actin Binding Region in Aldolase," *FEBS Lett.* 321:69-72 (1993), which are hereby incorporated by reference in their entirety), the precise stoichiometry of this interaction—as well as the spatial arrangement of the complete actin-Aldolase-TRAP complex—remains an open question.

Amino acid or nucleic acid sequences and three-dimensional structures corresponding to Aldolases, which may be used for the purposes of the present invention, can be obtained from protein databases such as UniProt. The Universal Protein Resource (UniProt) is a comprehensive resource for protein sequence and annotation data. A person of ordinary skill in the art would be able to readily identify a relevant Aldolase sequence based on database search and sequence comparison. Some of the example of Aldolases which can be used for the purposes of present invention are described in Table 1 below:

TABLE 1

Available Aldolase Structures with Homology to *Plasmodium* Aldolase

| PDB code | Species | # of Subunits | Ligands Present | Mutations | Resolution (Å) | Reference[a] |
|---|---|---|---|---|---|---|
| 1A5C | *P. falciparum* | 2 | | | 3 | Kim, et al. (1998) Biochemistry. 37(13): 4388-96. |
| 2pc4 | *P. falciparum* | 4 | TRAP peptide | | 2.4 | Bosch, et al. (2007) Proc. Natl. Acad. Sci. USA 104(17): 7015-7020. |
| 2eph | *P. falciparum* | 4 | TRAP peptide | | 2.7 | Bosch, et al. (2007) Proc. Natl. Acad. Sci. USA 104(17): 7015-7020. |
| 1EPX | *L. mexicana* | 4 | | | 1.8 | Chudzik, et al. (2000) J Mol. Biol. 300(4): 697-707. |
| 2QAP | *L. mexicana* | 4 | Phosphate | | 1.6 | Lafrance-Vanasse and Sygusch (2007) Biochemistry 46(33): 9533-9540. |
| 2QDG | *L. mexicana* | 4 | F16P; Phosphate | | 2.2 | Lafrance-Vanasse and Sygusch (2007) Biochemistry 46(33): 9533-9540. |
| 2QDH | *L. mexicana* | 4 | D-mannitol-1,6-Bisphosphate | | 1.9 | Lafrance-Vanasse and Sygusch (2007) Biochemistry 46(33): 9533-9540. |
| 1F2J | *T. brucei* | 1 | | | 1.9 | Chudzik, et al. (2000) J Mol. Biol. 300(4): 697-707. |
| 1FBA | *D. melanogaster* | 4 | | | 2.5 | Hester, et al. (1991) FEBS Lett. 292(1-2): 237-42. |
| 1ZAI | Rabbit (muscle) | 4 | F16P | | 1.76 | St-Jean, et al. (2005) J Biol Chem. 280(29): 27262-70. |
| 1ZAH | Rabbit (muscle) | 4 | | | 1.8 | St-Jean, et al. (2005) J Biol Chem. 280(29): 27262-70. |
| 1ZAL | Rabbit (muscle) | 4 | Tagatose-1,6-Bisphosphate | | 1.89 | St-Jean, et al. (2005) J Biol Chem. 280(29): 27262-70. |
| 1ZAJ | Rabbit (muscle) | 4 | D-Mannitol-1,6-Diphosphate | | 1.89 | St-Jean, et al. (2005) J Biol Chem. 280(29): 27262-70. |
| 1ADO | Rabbit (muscle) | 4 | 1,3-DHAP; Sulfate ion | | 1.9 | Blom and Sygusch (1997) Nat Struct Biol 4(1): 36-9. |
| 1EWG | Rabbit (muscle) | 4 | | E187Q | 2 | Maurady, et al. (2002) J Biol Chem. 277(11): 9474-83. |
| 1EX5 | Rabbit (muscle) | 4 | | E187A | 2.2 | Maurady, et al. (2002) J Biol Chem. 277(11): 9474-83. |
| 6ALD | Rabbit (muscle) | 4 | F16P | K146A | 2.3 | Choi, et al. (1999) Biochemistry 38(39): 12655-64. |
| 1EWD | Rabbit (muscle) | 4 | | K107M | 2.46 | Maurady, et al. (2002) J Biol Chem. 277(11): 9474-83. |
| 1EWE | Rabbit (muscle) | 4 | | K107M | 2.6 | Maurady, et al. (2002) J Biol Chem. 277(11): 9474-83. |
| 1J4E | Rabbit (muscle) | 4 | 1,3-DHAP | C72A, C239A, C289A, C338A | 2.65 | Choi, et al. (2001) Biochemistry. 40(46): 13868-75. |
| 2OT0 | Rabbit (muscle) | 4 | WASp peptide | | 2.05 | St-Jean, et al. (2007) J Biol Chem. 282(19): 14309-14315. |
| 2OT1 | Rabbit (muscle) | 4 | Napthol-AS-E-Phosphate | | 2.05 | St-Jean, et al. (2007) J Biol Chem. 282(19): 14309-14315. |
| 1ALD | Human (muscle) | 1 | | | 2 | Gamblin, et al. (1991) J Mol Biol. 219(4): 573-6. |
| 2ALD | Human (muscle) | 1 | | | 2.1 | Dalby, et al. (1999) Protein Sci. 8(2): 291-7. |
| 4ALD | Human (muscle) | 1 | F16P | | 2.8 | Dalby, et al. (1999) Protein Sci. 8(2): 291-7. |

Figure 26:
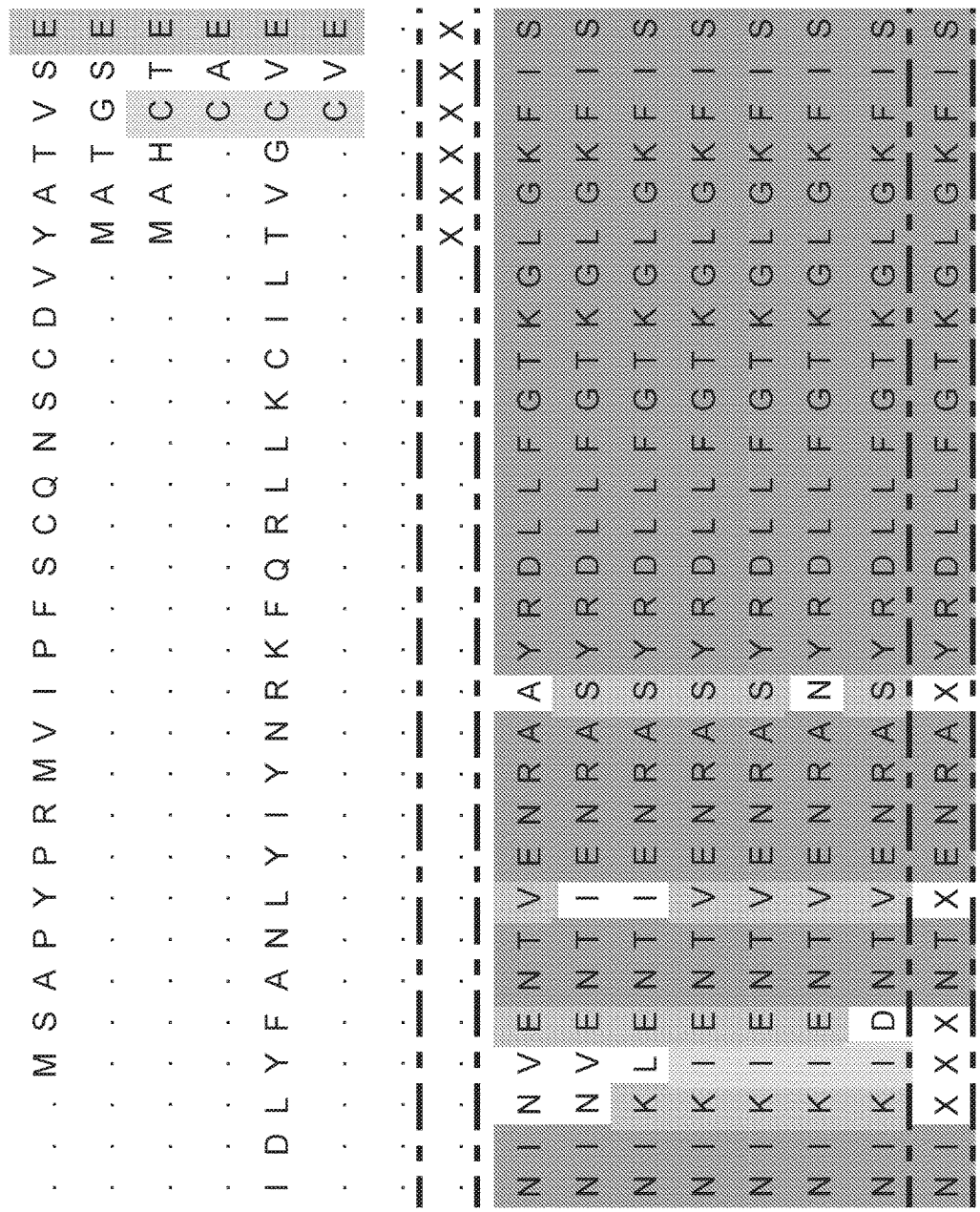
FIG. 26 shows ClustalW alignment of Aldolase proteins obtained from various apicomplexan organisms (SEQ ID NOS: 2 to 8).
Figure 26:
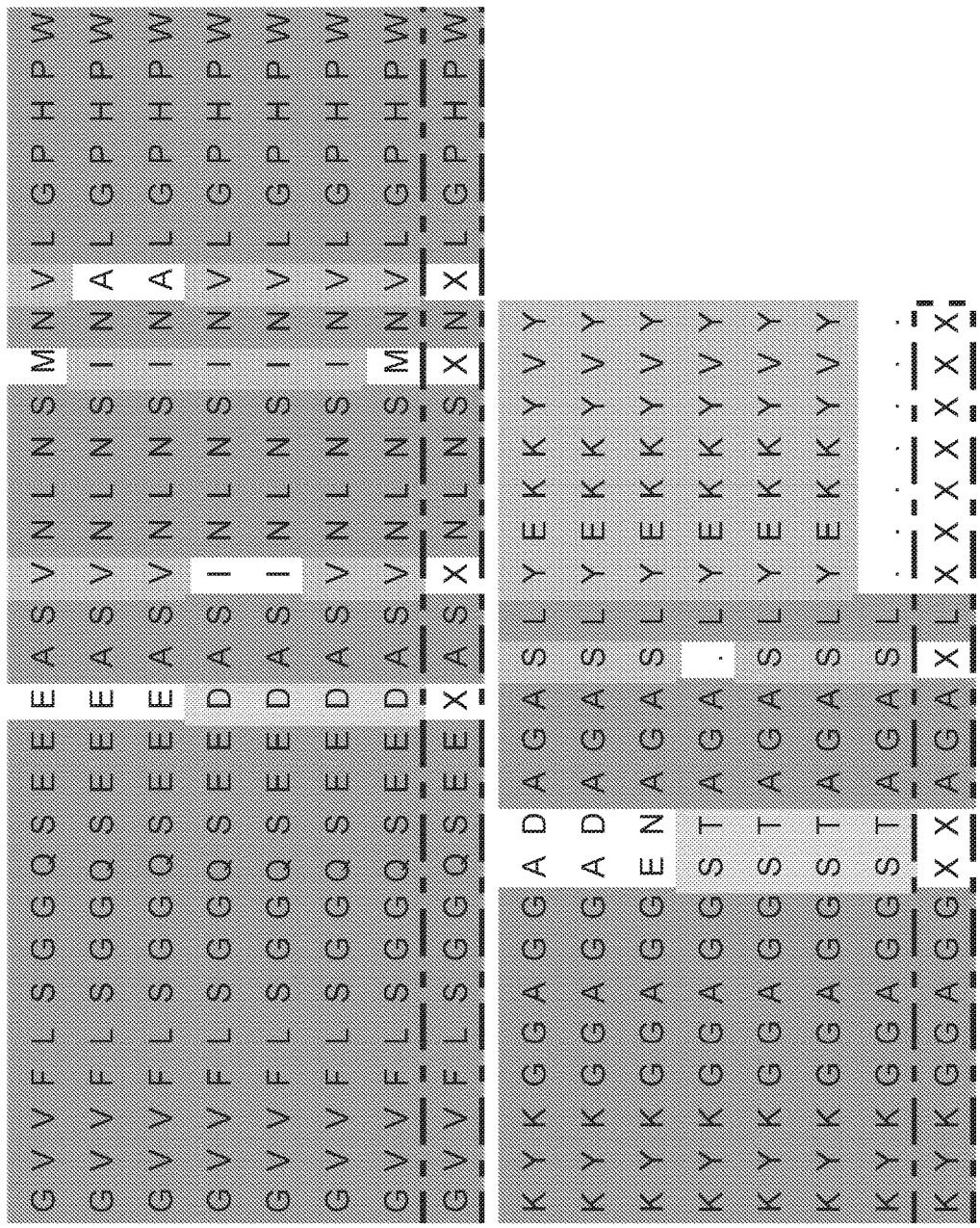

[a] All the references cited herein are incorporated by reference in their entirety A consensus sequence is used in the present invention to define the residue number of an amino acid residue. Residues which correspond to a particular position or the numbering of a residue can be easily identified by a person of skill in the art by sequence alignment. For example, a sequence alignment of Aldolases is shown in FIG. 26. The residue which is aligned to a particular residue of the consensus sequence is the corresponding residue with respect to that position in the consensus sequence. The amino acid sequence for the consensus sequence of Aldolase is as follows ("X" can be any amino acid or gap in the sequence) (SEQ ID NO: 1):

```
  1   XXXXXXXXXX XXKLPXXVAX EXAXTAXKLV XXGKGILAAD
      ESTQTIKKRF

51   DNIXXXNTXE NRAXYRDLLF GTKGLGKFIS GAILFEETLF
      QKNEAGVPXV

101   NLLHXXXIIP GIKVDKGLVX IPCTDXEKST QGLDGLAERC
      KEYYKAGARF

151   AKWRXVLVID XXKGKPTDLS IXEXXWGLAR YAXICQQNXL
      VPIVEPEILA

201   DGXHXIEVCA XVTQKVLXXV FKALXXXGXL LEGALLKPNM
      VTAGYXCXXK

251   TXTXDXGFXT VRTLXRTVPP XLPGVVFLSG GQSEEXASXN
      LNSXNXLGPH

301   PWALTFSYGR ALQASVLXTW XGKKENXXKA XXVLLXRAEA
      NSLATYGKYK

351   GGAGGXXAGA XLXXXXXXX
```

The Aldolase which may be used for the purposes of the present invention can be derived from an apicomplexan organism. The apicomplexan organism can be, for example, *Plasmodium falciparum*, *Plasmodium yoelii*, *Plasmodium chabaudi*, *Plasmodium berghei*, *Plasmodium knowlesi*, *Plasmodium vivax*, *Plasmodium vinckei*, *Theileria annulata*, *Theileria parva*, *Babesia bovis*, *Cryptosporidium parvum*, *Cryptosporidium hominis*, *Toxoplasma gondii*, *Cyclospora cayetanensis*, *Isospora belli*, *Sarcocystis* spp, or *Eimeria* spp.

FIG. 26 shows the sequence alignment of sequences described below. The amino acid sequences for the Aldolases from apicomplexan organisms are as follows:

```
DEFINITION tr|Q4YV79|Q4YV79_PLABA
Fructose-bisphosphate Aldolase Fragment)
OS = Plasmodium berghei (strain Anka)
                                        SEQ ID NO: 2
  1   CAEYKNAPMK LPKEVAQELA ETAKKLVAAG KGILAADEST
      QTIKKRFDNI

51   KIENTVENRA SYRDLLFGTK GLGKFISGAI LFEETLFQKN
      EAGVPLVNLL

101   HDEGIIPGIK VDKGLVSIPC TDDEKSTQGL DGLAERCKEY
      YKAGARFAKW

151   RAVLVIDPAK GKPTDLSIQE VSWGLARYAS ICQQNKLVPI
      VEPEILADGA

201   HTIEVCATVT QKVLASVFKA LHDNGVLLEG ALLKPNMVTA
      GYDCTEKTKT

251   DDIGFFTVRT LRRTVPPALP GVVFLSGGQS EEDASINLNS
      INVLGPHPWA

301   LTFSYGRALQ ASVLNTWQGK KENVAKARAV LLQRAEANSL
      ATYGKYKGGA

351   GGSTAGALYE KKYVY

DEFINITION tr|Q4XW14|Q4XW14_PLACH
Fructose-bisphosphate Aldolase Fragment)
OS = Plasmodium chabaudi
                                        SEQ ID NO: 3
  1   CVEYKNAPMK LPKEVAHELA ETAKKLVAPG KGILAADEST
      QTIKKRFDNI

51   KIENTVENRA NYRDLLFGTK GLGKFISGAI LFEETLFQKN
      EAGVPLVNLL

101   HDEDIIPGIK VDKGLVSIPC TDDEKSTQGL DGLAERCKEY
      YKAGARFAKW

151   RAVLVIDPVK GKPTDLSIHE VSWGLARYAA ICQQNKLVPI
      VEPEILADGG

201   HTIEVCATVT QKVLASVFKA LHDNGVLLEG ALLKPNMVTA
      GYDCTEKTKT

251   DDIGFFTVRT LRRTVPPALP GVVFLSGGQS EEDASVNLNS
      INVLGPHPWA

301   LTFSYGRALQ ASVLSTWQGK KENVAKAREV LLQRAEANSL
      ATYGKYKGGA

351   GGSTAGASLY EKKYVY

DEFINITION sp|P14223|ALF_PLAFA Fructose-bisphos-
phate
Aldolase OS = Plasmodium falciparum
                                        SEQ ID NO: 4
  1   MAHCTEYMNA PKKLPADVAE ELATTAQKLV QAGKGILAAD
      ESTQTIKKRF

51   DNIKLENTIE NRASYRDLLF GTKGLGKFIS GAILFEETLF
      QKNEAGVPMV

101   NLLHNENIIP GIKVDKGLVN IPCTDEEKST QGLDGLAERC
      KEYYKAGARF

151   AKWRTVLVID TAKGKPTDLS IHETAWGLAR YASICQQNRL
      VPIVEPEILA

201   DGPHSIEVCA VVTQKVLSCV FKALQENGVL LEGALLKPNM
      VTAGYECTAK

251   TTTQDVGFLT VRTLRRTVPP ALPGVVFLSG GQSEEEASVN
      LNSINALGPH

301   PWALTFSYGR ALQASVLNTW QGKKENVAKA REVLLQRAEA
      NSLATYGKYK

351   GGAGGENAGA SLYEKKYVY

DEFINITION tr|B3L9W9|B3L9W9_PLAKH Fructose-
bisphosphate Aldolase OS = Plasmodium
knowlesi (strain H)
                                        SEQ ID NO: 5
  1   MSAPYPRMVI PFSCQNSCDV YATVSEYKNA PLKLPADVAE
      EIATTAKKLV

51   QAGKGILAAD ESTQTIKKRF DNINVENTVE NRAAYRDLLF
      GTKGLGKFIS

101   GAILFEETLF QKNEAGVPLV NLLHDEGIIP GIKVDKGLVT
      IPCTDDEKST

151   QGLDGLAERC KEYYKAGARF AKWRAVLVID PVKGKPTDLS
      IQETAWGLAR

201   YASICQQNKL VPIVEPEILA DGSHTIEVCA TVTQKVLACV
      FKALHDQGIL

251   LEGALLKPNM VTAGYDCTVK TKTQDIGFLT VRTLSRTVPP
      ALPGVVFLSG
```

-continued

```
301   GQSEEEASVN LNSMNVLGPH PWALTFSYGR ALQASVLNTW
      KGKKENVAKA

351   REVLLKRAEA NSLATYGKYK GGAGGADAGA SLYEKKYVY

DEFINITION tr|Q968W1|Q968W1_PLAVN Fructose-
bisphosphate Aldolase (Fragment)
OS = Plasmodium vinckei
                                              SEQ ID NO: 6
  1   MKLPKEVAQE LADTAKKLVA PGKGILAADE STQTIKKRFD
      NIKIDNTVEN

51   RASYRDLLFG TKGLGKFISG AILFEETLFQ KNEAGVPLVN
      LLHDQNIIPG

101   IKVDKGLVAI PCTDDEKSTQ GLDGLAERCK EYYKAGARFA
      KWRAVLVIDP

151   AKGKPTDLSI QEVSWGLARY AAICQQNKLV PIVEPEILAD
      GAHTIEVCAA

201   VTQKVLASVF KALHDNGVLL EGALLKPNMV TAGYDCPEKT
      KTEDIGFFTV

251   RTLSRTVPPA LPGVVFLSGG QSEEDASVNL NSMNVLGPHP
      WALTFSYGRA

301   LQASVLSTWQ GKKENAAKAQ EVLLQRAEAN SLATYGKYKG
      GAGGSTAGAS

351   L

DEFINITION tr|Q968V9|Q968V9_PLAVI Fructose-
bisphosphate Aldolase OS = Plasmodium vivax
                                              SEQ ID NO: 7
  1   MATGSEYKNA PLKLPAEVAE EIATTAKKLV EAGKGILAAD
      ESTQTIKKRF

51   DNINVENTIE NRASYRDLLF GTKGLGKFIS GAILFEETLF
      QKNEAGVPLV

101   NLLHDEGIIP GIKVDKGLVT IPCTDDEKST QGLDGLAERC
      KEYYKAGARF

151   AKWRAVLVID PVKGKPTDLS IQETAWGLAR YASICQQNKL
      VPIVEPEILA

201   DGSHTIEVCA TVTQKVLASV FKALHDQGVL LEGALLKPNM
      VTAGYDCAVK

251   TNTQDIGFLT VRTLSRTVPP SLPGVVFLSG GQSEEEASVN
      LNSINALGPH

301   PWALTFSYGR ALQASVLNTW KGKKENVEKA REVLLKRAEA
      NSLATYGKYK

351   GGAGGADAGA SLYEKKYVY

DEFINITION tr|Q7RIB6|Q7RIB6_PLAYO Fructose-
bisphosphate Aldolase OS = Plasmodium yoelii
                                              SEQ ID NO: 8
  1   MYRTCSLNES KCDDKIYIDL YFANLYIYNR KFQRLLKCIL
      TVGCVEYKNA

51   PMKLPKEVAQ ELAETAKKLV AAGKGILAAD ESTQTIKKRF
      DNIKIENTVE

101   NRASYRDLLF GTKGLGKFIS GAILFEETLF QKNEAGVPLV
      NLLHDEGIIP

151   GIKVDKGLVS IPCTDDEKST QGLDGLAERC KEYYKAGARF
      AKWRAVLVID

201   PAKGKPTDLS IQESWGLAR YASICQQNKL VPIVEPEILA
      DGAHTIEVCA

251   TVTQKVLASV FKALHDNGVL LEGALLKPNM VTAGYDCTEK
      TKTDDIGFFT

301   VRTLRRTVPP ALPGVVFLSG GQSEEDASIN LNSINVLGPH
      PWALTFSYGR

351   ALQASVLNTW QGKKENVAKA REVLLQRAEA NSLATYGKYK
      GGAGGSTAGA

401   SLYEKKYVY
```

A second aspect of the present invention relates to a method of identifying compounds useful in stabilizing a complex between Aldolase and thrombospondin-related anonymous protein (TRAP) or a portion thereof. The method includes providing a complex of first model comprising Aldolase or residues of the amino acid sequence corresponding to SEQ ID NO: 1, said residues being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347; and a second model comprising TRAP or residues of the amino acid sequence corresponding to SEQ ID NO: 38, said residues being at amino acid positions selected from the group consisting of 554, 555, 556, 557, 558, and 559. The method further includes providing one or more candidate compounds and examining contact between the candidate compounds and the complex between the first and the second model to determine which of the one or more candidate compounds have an ability to bind to and/or fit in the complex between the first and the second model. Compounds which, based on said examining, have the ability to bind to and/or fit in the complex between the first and the second model are identified as compounds potentially useful for stabilizing the complex.

One example of a full length amino acid sequence for TRAP sequence is:

```
DEFINITION tr| P16893| TRAP_PLAFA
Thrombospondin-related anonymous protein
OS = Plasmodium falciparum
                                             SEQ ID NO: 37
  1   MNHLGNVKYL VIVFLIFFDL FLVNGRDVQN NIVDEIKYSE
      EVCNDQVDLY

51   LLMDCSGSIR RHNWVNHAVP LAMKLIQQLN LNDNAIHLYV
      NVFSNNAKEI

101   IRLHSDASKN KEKALIIIRS LLSTNLPYGR TNLTDALLQV
      RKHLNDRINR

151   ENANQLVVIL TDGIPDSIQD SLKESRKLSD RGVKIAVFGI
      GQGINVAFNR

201   FLVGCHPSDG KCNLYADSAW ENVKNVIGPF MKAVCVEVEK
      TASCGVWDEW

251   SPCSVTCGKG TRSRKREILH EGCTSEIQEQ CEEERCPPKW
      EPLDVPDEPE

301   DDQPRPRGDN SSVQKPEENI IDNNPQEPSP NPEEGKDENP
      NGFDLDENPE

351   NPPNPDIPEQ KPNIPEDSEK EVPSDVPKNP EDDREENFDI
      PKKPENKHDN

401   QNNLPNDKSD RNIPYSPLPP KVLDNERKQS DPQSQDNNGN
      RHVPNSEDRE

451   TRPHGRNNEN RSYNRKYNDT PKHPEREEHE KPDNNKKKGE
      SDNKYKIAGG
```

```
501  IAGGLALLAC AGLAYKFVVP GAATPYAGEP APFDETLGEE
     DKDLDEPEQF

551  RLPEENEWN
```

For the purposes of the present invention, just the C-terminal intracellular tail may be used. The consensus sequence (SEQ ID NO: 38) for TRAP tail is $X_{547}XXXXXXX_{554}X_{555}XXWX_{559}$ where "X" can be any amino acid or gap in the sequence, "$X_{554}$" and "$X_{555}$" indicate negatively charged amino acids aspartic acid (D) or glutamic acid (E) or in some cases asparagine (N). FIG. 27 shows an alignment of the TRAP C-terminal intracellular tail sequences from P. falciparum and P. vivax. The residue numbering in the consensus sequence for TRAP corresponds to TRAP sequence from P. falciparum. Residues which correspond to a particular position or the numbering of a residue can be easily identified by a person of skill in the art by sequence alignment as shown in FIG. 27.

The method further includes screening the identified compounds in vitro for their ability to kill and/or inhibit growth of an apicomplexan organism and designating the screened compounds which kill and/or inhibit an apicomplexan organism as a therapeutic targeting apicomplexan organisms.

TRAP (Thrombospondin-Related Anonymous Protein)

TRAP is the founding member of a growing family of apicomplexan adhesive proteins that include, for example, MTRAP from the merozoite stage of Plasmodium (Baum et al., "A Conserved Molecular Motor Drives Cell Invasion and Gliding Motility Across Malaria Life Cycle Stages and Other Apicomplexan Parasites," J. Biol. Chem. 281:5197-5208 (2006), which is hereby incorporated by reference in its entirety), Toxoplasma MIC2 (Microneme Protein 2) (Wan et al., "Molecular Characterisation of an Expressed Sequence Tag Locus of Toxoplasma gondii Encoding the Micronemal Protein MIC2," Mol. Biochem. Parasitol. 84:203-214 (1997), which is hereby incorporated by reference in its entirety), Eimeria Etp100 (Tomley et al., "Sequence of the Gene Encoding an Immunodominant Microneme Protein of Eimeria tenella," Mol. Biochem. Parasitol. 49:277-288 (1991), which is hereby incorporated by reference in its entirety), Cryptosporidium TRAPC1 (Spano et al., "Molecular Cloning and Expression Analysis of a Cryptosporidium Parvum Gene Encoding a New Member of the Thrombospondin Family," Mol. Biochem. Parasitol. 92:147-162 (1998), which is hereby incorporated by reference in its entirety), Plasmodium CTRP (Trottein et al., "Molecular Cloning of a Gene From Plasmodium falciparum That Codes for a Protein Sharing Motifs Found in Adhesive Molecules From Mammals and Plasmodia," Mol. Biochem. Parasitol. 74:129-141 (1995), which is hereby incorporated by reference in its entirety), and TLP (TRAP-like Protein) (Heiss et al., "Functional Characterization of a Redundant Plasmodium TRAP Family Invasin, TRAP-Like Protein, by Aldolase Binding and a Genetic Complementation Test," Eukaryot. Cell 7:1062-1070 (2008); Moreira et al., "The Plasmodium TRAP/MIC2 Family Member, TRAP-Like Protein (TLP), is Involved in Tissue Traversal by Sporozoites," Cell. Microbiol. 10:1505-1516 (2008), which are hereby incorporated by reference in their entirety), Neospora NcMIC2 (Lovett et al., "Molecular Characterization of a Thrombospondin-Related Anonymous Protein Homologue in Neospora Caninum," Mol. Biochem. Parasitol. 107:33-43 (2000), which is hereby incorporated by reference in its entirety), and recently, TREP (TRAP-related protein) in Plasmodium oocyst-stages porozoites (Combe et al. "TREP, a Novel Protein Necessary for Gliding Motility of the Malaria Sporozoite," Int. J. Parasitol. 39:489-496 (2009), which is hereby incorporated by reference in its entirety). All these apicomplexan adhesive proteins, described herein, can be used for the purposes of the present invention. Hereafter, the term TRAP in intended to include all apicomplexan adhesive proteins.

Figure 2:
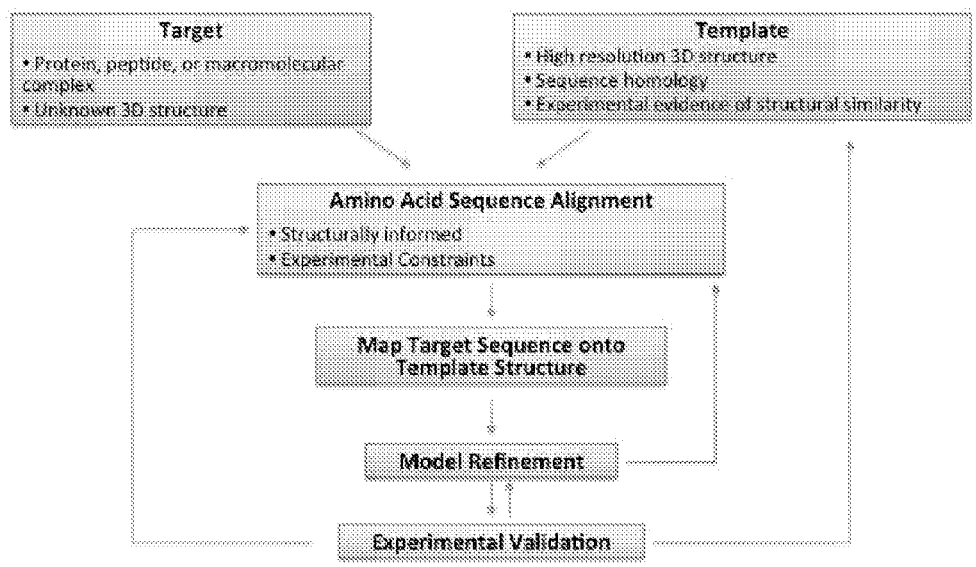
FIG. 2 shows the method used for homology modeling.

TRAP family members are type 1 transmembrane proteins with several extracellular adhesive domains, including a thrombospondin type 1 repeat (TSR) and an integrin-like A domain (FIG. 2). The TSR and related domains contain basic residues that are thought to bind to receptors and heparan sulfate proteoglycans (HSPGs) on the surface of human and mosquito host cells (Kappe et al., "Plasmodium Sporozoite Molecular Cell Biology," Annu. Rev. Cell Dev. Biol. 20:29-59 (2004), which is hereby incorporated by reference in its entirety). The C-termini of TRAP and MTRAP are intracellular and bind Aldolase (Baum et al., "A Conserved Molecular Motor Drives Cell Invasion and Gliding Motility Across Malaria Life Cycle Stages and Other Apicomplexan Parasites," J. Biol. Chem. 281:5197-5208 (2006); Buscaglia et al., "Sites of Interaction Between Aldolase and Thrombospondin-Related Anonymous Protein in Plasmodium," Mol. Biol. Cell. 14:4947-4957 (2003); Green et al., "The MTIP-Myosin A Complex in Blood Stage Malaria Parasites," J. Mol. Biol. 355:933-941 (2006); Buscaglia et al., "Modeling the Interaction Between Aldolase and the Thrombospondin-Related Anonymous Protein, a Key Connection of the Malaria Parasite Invasion Machinery," Proteins 66:528-537 (2007); Bosch et al., "Aldolase Provides an Unusual Binding Site for Thrombospondin-Related Anonymous Protein in the Invasion Machinery of the Malaria Parasite," Proc. Nat'l. Acad. Sci. USA 104(17): 7015-20 (2007), which are hereby incorporated by reference in their entirety). TRAP and a second Plasmodium adhesin, circumsporozoite protein (CSp)—which also contains a TSR, but is extracellular and GPI-anchored—play critical roles in parasite motility and invasion of mosquito salivary glands and mammalian liver cells (Buscaglia et al., "Sites of Interaction Between Aldolase and Thrombospondin-Related Anonymous Protein in Plasmodium," Mol. Biol. Cell. 14:4947-4957 (2003); Sultan et al., "TRAP is Necessary for Gliding Motility and Infectivity of Plasmodium Sporozoites," Cell 90:511-522 (1997); Kappe et al., "Conservation of a Gliding Motility and Cell Invasion Machinery in Apicomplexan Parasites," J. Cell. Biol. 147:937-944 (1999); Buscaglia et al., "Modeling the Interaction Between Aldolase and the Thrombospondin-Related Anonymous Protein, a Key Connection of the Malaria Parasite Invasion Machinery," Proteins 66:528-537 (2007), which are hereby incorporated by reference in their entirety), while MTRAP appears essential to merozoite development (Baum et al., "A Conserved Molecular Motor Drives Cell Invasion and Gliding Motility Across Malaria Life Cycle Stages and Other Apicomplexan Parasites," J. Biol. Chem. 281:5197-5208 (2006), which is hereby incorporated by reference in its entirety).

After synthesis by ribosomes associated with the rough endoplasmic reticulum, TRAP is targeted to micronemes and the sporozoite surface via a YXXΦ motif (XX=any amino acid, Φ=hydrophobic residue; residues 562-YNFI-566 in P. berghei and 515-YKFV-518 in P. falciparum) (Bhanot et al., "Defective Sorting of the Thrombospondin-Related Anonymous Protein (TRAP) Inhibits Plasmodium Infectivity," Mol. Biochem. Parasitol. 126:263-273 (2003), which is hereby incorporated by reference in its entirety). CSp, TRAP, MTRAP and their orthologs (Robson et al., "Cloning and Expression of the Thrombospondin Related Adhesive Protein Gene of *Plasmodium Berghei*," *Mol. Biochem. Parasitol.* 84:1-12 (1997); Rogers et al., "Characterization of *Plasmodium falciparum* Sporozoite Surface Protein 2," *Proc. Nat'l. Acad. Sci. USA* 89:9176-9180 (1992); Robson et al., A Highly Conserved Amino-Acid Sequence in Thrombospondin, Properdin and in Proteins From Sporozoites and Blood Stages of a Human Malaria Parasite," *Nature* 335:79-82 (1988); Hedstrom et al., "A Malaria Sporozoite Surface Antigen Distinct From the Circumsporozoite Protein," *Bull. World Health Organ.* 68:152-157 (1990), which are hereby incorporated by reference in their entirety) are secreted from the apical micronemes in a $Ca^{2+}$ dependent manner when the parasites contact their target cells (Carruthers & Sibley, "Mobilization of Intracellular Calcium Stimulates Microneme Discharge in *Toxoplasma gondii*," *Mol. Microbiol.* 31:421-428 (1999); Gantt et al., "Antibodies Against Thrombospondin-Related Anonymous Protein Do Not Inhibit *Plasmodium* Sporozoite Infectivity In Vivo," *Infect. Immun.* 68:3667-3673 (2000); Vieira & Moreno, "Mobilization of Intracellular Calcium Upon Attachment of *Toxoplasma gondii* Tachyzoites to Human Fibroblasts is Required for Invasion," *Mol. Biochem. Parasitol.* 106:157-162 (2000), which are hereby incorporated by reference in their entirety). Movement of MyoA along F-actin then pulls TRAP or MTRAP backwards along the sporozoite or merozoite surface, pushing the parasite forward into the cell, and excavating the parasitophorous vacuole described above (Kappe et al., "*Plasmodium* Sporozoite Molecular Cell Biology," *Annu. Rev. Cell Dev. Biol.* 20:29-59 (2004); Kappe et al., "Apicomplexan Gliding Motility and Host Cell Invasion: Overhauling the Motor Model," *Trends Parasitol.* 20:13-16 (2004), which are hereby incorporated by reference in their entirety).

The cytoplasmic tails of TRAP proteins are characterized by numerous acidic residues and a conserved tryptophan near the C-terminus (Menard, "Gliding Motility and Cell Invasion by Apicomplexa: Insights From the *Plasmodium* Sporozoite," *Cell. Microbiol.* 3:63-73 (2001); Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006); Starnes et al., "Two Separate, Conserved Acidic Amino Acid Domains Within the *Toxoplasma gondii* MIC2 Cytoplasmic Tail are Required for Parasite Survival," *J. Biol. Chem.* 281:30745-30754 (2006), which are hereby incorporated by reference in their entirety), and appear to serve similar functions—the cytoplasmic tails of *Plasmodium* TRAP and *Toxoplasma* MIC2 were found to be interchangeable with each other in terms of their roles in parasite motility and infectivity (Kappe et al., "Conservation of a Gliding Motility and Cell Invasion Machinery in Apicomplexan Parasites," *J. Cell. Biol.* 147:937-944 (1999), which is hereby incorporated by reference in its entirety). Deletions or mutations of the TRAP cytoplasmic domain in malaria sporozoites result in impaired gliding and infectivity, suggesting that this region interacts with the motor (Kappe et al., "Conservation of a Gliding Motility and Cell Invasion Machinery in Apicomplexan Parasites," *J. Cell. Biol.* 147:937-944 (1999), which is hereby incorporated by reference in its entirety). This hypothesis was confirmed by the demonstration that the C-terminal tail of TRAP bound *Plasmodium* Aldolase (Buscaglia et al., "Sites of Interaction Between Aldolase and Thrombospondin-Related Anonymous Protein in *Plasmodium*," *Mol. Biol. Cell.* 14:4947-4957 (2003), which is hereby incorporated by reference in its entirety), a protein previously known to bind actin. Independent modeling and crystallographic studies demonstrated that the conserved tryptophan in the cytoplasmic tail of TRAP binds tightly into a cleft in Aldolase near the enzyme's active site (Buscaglia et al., "Modeling the Interaction Between Aldolase and the Thrombospondin-Related Anonymous Protein, a Key Connection of the Malaria Parasite Invasion Machinery," *Proteins* 66:528-537 (2007); Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which are hereby incorporated by reference in their entirety).

Recent crystallographic structures demonstrate that the human WASp (St-Jean et al., "A Hydrophobic Pocket in the Active Site of Glycolytic Aldolase Mediates Interactions With Wiskott-Aldrich Syndrome Protein," *J. Biol. Chem.* 282(19):14309-15 (2007), which is hereby incorporated by reference in its entirety) proteins interact with Aldolase in an identical manner. Other studies demonstrate that CTRP, a TRAP family member found in *Plasmodium* ookinetes, has properties similar to TRAP, as does TLP, which is expressed in mosquito salivary gland sporozoites (Heiss et al., "Functional Characterization of a Redundant *Plasmodium* TRAP Family Invasin, TRAP-Like Protein, by Aldolase Binding and a Genetic Complementation Test," *Eukaryot. Cell* 7:1062-1070 (2008); Moreira et al., "The *Plasmodium* TRAP/MIC2 Family Member, TRAP-Like Protein (TLP), is Involved in Tissue Traversal by Sporozoites," *Cell. Microbiol.* 10:1505-1516 (2008), which are hereby incorporated by reference in their entirety). The ookinetes from CTRP(−) parasites do not move, and are unable to invade cells from the mosquito midgut (Dessens et al., "CTRP is Essential for Mosquito Infection by Malaria Ookinetes," *Embo J.* 18:6221-6227 (1999); Yuda et al., "Targeted Disruption of the *Plasmodium Berghei* CTRP Gene Reveals Its Essential Role in Malaria Infection of the Vector Mosquito," *J. Exp. Med.* 190:1711-1716 (1999); Templeton et al., "Developmental Arrest of the Human Malaria Parasite *Plasmodium falciparum* Within the Mosquito Midgut Via CTRP Gene Disruption," *Mol. Microbiol.* 36:1-9 (2000), which are hereby incorporated by reference in their entirety). Sporozoites lacking TRAP cannot glide normally and are unable to invade host cells, and organisms harboring TRAP mutations that prevent its binding to Aldolase are also defective in these processes (Buscaglia et al., "Sites of Interaction Between Aldolase and Thrombospondin-Related Anonymous Protein in *Plasmodium*," *Mol. Biol. Cell.* 14:4947-4957 (2003); Sultan et al., "TRAP is Necessary for Gliding Motility and Infectivity of *Plasmodium* Sporozoites," *Cell* 90:511-522 (1997); Kappe et al., "Conservation of a Gliding Motility and Cell Invasion Machinery in Apicomplexan Parasites," *J. Cell. Biol.* 147:937-944 (1999); Buscaglia et al., "Modeling the Interaction Between Aldolase and the Thrombospondin-Related Anonymous Protein, a Key Connection of the Malaria Parasite Invasion Machinery," *Proteins* 66:528-537 (2007), which are hereby incorporated by reference in their entirety). Finally, a "TRAP-like" transmembrane protein, MTRAP, was identified in *Plasmodium* merozoites. The extracellular domain of this merozoite TRAP may bind specifically to the surface of erythrocytes, and its cytoplasmic tail may interact with Aldolase and the conserved molecular motor in the same way as sporozoite TRAP (Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006), which is hereby incorporated by reference in its entirety). The mode of interaction of TRAP with Aldolase thus appears to be a prototype for a large class of similar juxta-membrane interactions across apicomplexan species and within certain mammalian cell types.

Motility and invasiveness are key features of the sporozoite and merozoite stages of *Plasmodium* species, and are prerequisites for malarial infection. Notably, the mechanism of motility and invasion utilized by the malaria parasite is common to other apicomplexan organisms of medical interest as well, including *Babesia, Cryptosporidium parvum, Cyclospora cayetanensis, Toxoplasma gondii*, and *Eimeria*.

Several lines of evidence suggest that the same molecules and similar mechanisms are involved in both malarial motility and invasion—of hepatocytes and mosquito salivary gland cells by sporozoites and of erythrocytes by merozoites (Kappe et al., "*Plasmodium* Sporozoite Molecular Cell Biology," *Annu. Rev. Cell Dev. Biol.* 20:29-59 (2004); Wetzel et al., "Actin Filament Polymerizaiton Regulates Gliding Motility by Apicomplexan Parasites," *Mol. Biol. Cell* 14:396-406 (2003); Opitz & Soldati, "'The Glideosome': A Dynamic Complex Powering Gliding Motion and Host Cell Invasion by *Toxoplasma gondii*," *Mol. Microbiol.* 45:597-604 (2002); Menard, "Gliding Motility and Cell Invasion by Apicomplexa: Insights From the *Plasmodium* Sporozoite," *Cell. Microbiol.* 3:63-73 (2001); Meissner et al., "Role of *Toxoplasma gondii* Myosin A in Powering Parasite Gliding and Host Cell Invasion," *Science* 298:837-840 (2002); Dobrowolski & Sibley, "*Toxoplasma* Invasion of Mammalian Cells is Powered by the Actin Cytoskeleton of the Parasite," *Cell* 84:933-939 (1996); King, "Cell Motility of Sporozoan Protozoa," *Parasitol. Today* 4:315-319 (1988); Chitnis & Blackman, "Host Cell Invasion by Malaria Parasites," *Parasitol. Today* 16:411-415 (2000); Baum et al., "A Conserved Molecular Motor Drives Cell Invasion and Gliding Motility Across Malaria Life Cycle Stages and Other Apicomplexan Parasites," *J. Biol. Chem.* 281:5197-5208 (2006); Pinder et al., "Motile Systems in Malaria Merozoites: How is the Red Blood Cell Invaded?" *Parasitol. Today* 16:240-245 (2000); Pinder et al., "Actomyosin Motor in the Merozoite of the Malaria Parasite, *Plasmodium falciparum*: Implications for Red Cell Invasion," *J. Cell. Sci.* 111:1831-1839 (1998); Buscaglia et al., "Sites of Interaction Between Aldolase and Thrombospondin-Related Anonymous Protein in *Plasmodium*," *Mol. Biol. Cell*. 14:4947-4957 (2003); Kappe et al., "Apicomplexan Gliding Motility and Host Cell Invasion: Overhauling the Motor Model," *Trends Parasitol.* 20:13-16 (2004); Matuschewski et al., "*Plasmodium* Sporozoite Invasion Into Insect and Mammalian Cells is Directed by the Same Dual Binding System," *Embo J.* 21:1597-1606 (2002); Menard, "The Journey of the Malaria Sporozoite Through Its Hosts: Two Parasite Proteins Lead the Way," *Microbes Infect.* 2:633-642 (2000); Mota & Rodriguez, "Invasion of Mammalian Host Cells by *Plasmodium* Sporozoites," *Bioessays* 24:149-156 (2002); Muller et al., "Thrombospondin Related Anonymous Protein (TRAP) of *Plasmodium falciparum* in Parasite-Host Cell Interactions," *Parassitologia* 35 Suppl:69-72 (1993); Sultan, "Molecular Mechanisms of Malaria Sporozoite Motility and Invasion of Host Cells," *Int. Microbiol.* 2:155-160 (1999); Sultan et al., "TRAP is Necessary for Gliding Motility and Infectivity of *Plasmodium* Sporozoites," *Cell* 90:511-522 (1997); Kappe et al., "Conservation of a Gliding Motility and Cell Invasion Machinery in Apicomplexan Parasites," *J. Cell. Biol.* 147: 937-944 (1999), which are hereby incorporated by reference in their entirety). Like other apicomplexan parasites, *Plasmodium* organisms lack cilia or flagella, and do not form pseudopods during parasite movement. Instead, they employ an actin-myosin based method of locomotion called "substrate dependent gliding motility".

The thrombospondin-related anonymous protein (TRAP) can be derived from an apicomplexan organism. The apicomplexan organism can be, for example, from *Plasmodium falciparum, Plasmodium yoelii, Plasmodium chabaudi, Plasmodium berghei, Plasmodium knowlesi, Plasmodium vivax, Plasmodium Vinckei, Theileria annulata, Theileria parva, Babesia bovis, Cryptosporidium parvum, Cryptosporidium hominis, Toxoplasma gondii, Cyclospora cayetanensis, Isospora belli, Sarcocystis* spp, or *Eimeria* spp.

A person of skill in the art will appreciate that whole Aldolase molecule, whole TRAP molecule or their domains or fragments could be used for model building and for the purposes of the present invention. Relevant domains or fragments of Aldolase may comprise residues such 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345 of SEQ ID NO: 1. Once an appropriate model is obtained, domains or fragments of this model can be obtained by, for example, modifying the atomic coordinates of the model to provide atomic coordinates for domains or fragments or by selectively defining the relevant domains of the model in an input file that is to be used for computational calculations.

As is well known in the art, there are many ways available to provide a model for a protein or other macromolecule. As the art improves, much more sophisticated methods might become available for use in modeling the structure of molecules of the present invention. The description provided below is intended to provide non limiting examples of methods which can be used for providing a model for Aldolase or its fragments and TRAP or its fragments. Typically experimental techniques such as X-ray crystallography (Clegg W, *Crystal Structure Determination* (*Oxford Chemistry Primer*), Oxford: Oxford University Press (1998); Drenth J, *Principles of Protein X-Ray Crystallography*, New York: Springer-Verlag (1999), which are hereby incorporated by reference in their entirety) or Nuclear Magnetic Resonance (NMR) (T. Kevin Hitchens, *Fundamentals of Protein NMR Spectroscopy* (*Focus on Structural Biology*), Berlin: Springer (2005); Quincy Teng, *Structural Biology: Practical NMR Applications*, Berlin: Springer (2005), which are hereby incorporated by reference in their entirety) could be used to generate the structural models of the present invention. These two experimental techniques can provide high resolution structures of macromolecules.

Optionally molecular modeling techniques may also be used to generate the models of the present invention, including the first model, the second model and a complex between the first and second model. Molecular modeling can also be used for protein structure prediction. Molecular modeling approaches to protein structure prediction is of importance in medicine (for example, in drug design) and biotechnology (for example, in the design of novel enzymes). The ultimate goal of protein structure prediction, in general, is the prediction of the three-dimensional structure of a protein from just its amino acid sequence.

Molecular modeling can be used to generate one or more 3D models of a structural feature of a macromolecule, for example, a ligand binding site, a catalytic site. Molecular modeling techniques can be performed manually, with the aid of a computer, or with a combination of these. For example, molecular modeling techniques can be applied to generate the atomic co-ordinates of Aldolase or TRAP to derive a range of 3D models and to investigate the structure of active/catalytic site of Aldolase or TRAP.

Molecular modeling approaches to protein structure prediction can be broadly divided in to two categories: comparative modeling and ab initio-modeling. In both cases, an energy function is needed to recognize the native structure, and to guide the search for the native structure. In a comparative structure prediction approach to molecular modeling (also called homology modeling), the search space is pruned by the assumption that the protein in question adopts a structure that is reasonably close to the structure of at least one known protein. Comparative protein modeling uses previously solved structures as starting points, or templates. This is effective because it appears that although the number of actual proteins is vast, there is a limited set of tertiary structural motifs to which most proteins belong. These comparative methods can also be split into two groups: homology-based modeling and protein threading.

Homology modeling is based on the reasonable assumption that two homologous proteins will share very similar structures. Because a protein's fold is more evolutionarily conserved than its amino acid sequence, a target sequence can be modeled with reasonable accuracy on a very distantly related template, provided that the relationship between target and template can be discerned through sequence alignment. It has been suggested that the primary bottleneck in comparative modeling arises from difficulties in alignment rather than from errors in structure prediction given a known-good alignment (Zhang et al., "Progress and Challenges in Protein Structure Prediction," *Curr Opin Struct Biol* 18: 342-348 (2008), which is hereby incorporated by reference in its entirety). Unsurprisingly, homology modeling is most accurate when the target and template have similar sequences.

Protein threading (Bowie et al., "A Method to Identify Protein Sequences that Fold into a Known Three-dimensional Structure," *Science* 253: 164-170 (1991), which is hereby incorporated by reference in its entirety) scans the amino acid sequence of an unknown structure against a database of solved structures. In each case, a scoring function is used to assess the compatibility of the sequence to the structure, thus yielding possible three-dimensional models. This type of method is also known as 3D-1D fold recognition due to its compatibility analysis between three-dimensional structures and linear protein sequences. This method has also given rise to methods performing an inverse folding search by evaluating the compatibility of a given structure with a large database of sequences, thus predicting which sequences have the potential to produce a given fold.

In de novo or ab initio structure prediction, no assumption of structural similarity between two homologous proteins is made, which results in a much harder search problem. Ab initio- or de-novo-protein modeling methods seek to build three-dimensional protein models "from scratch", i.e., based on physical principles rather than (directly) on previously solved structures. There are many possible procedures that either attempt to mimic protein folding or apply some stochastic method to search possible solutions (i.e., global optimization of a suitable energy function). These procedures tend to require vast computational resources.

In the case of complexes involving two or more proteins, for example, docking between the first and the second model of the present invention, where the structures of the proteins are known or can be predicted with high accuracy, protein-protein docking methods can also be used to predict the structure of the complex. Information of the effect of mutations at specific sites on the affinity of the complex helps to understand the complex structure and to guide docking methods.

Many software tools are available for molecular modeling. For example, MODELLER is a popular software tool for producing homology models using methodology derived from NMR spectroscopy data processing. SwissModel provides an automated web server for basic homology modeling. I-TASSER is a server for protein structure prediction according to the recent CASP experiments (CASP7 and CASP8). Common software tools for protein threading are HHpred/HHsearch, Robetta, and Phyre. RAPTOR is a protein threading software that is based on integer programming. The basic algorithm for threading is described in Bowie et al., "A Method to Identify Protein Sequences that Fold into a Known Three-dimensional Structure," *Science* 253: 164-170 (1991), which is hereby incorporated by reference in its entirety, and is fairly straightforward to implement. Abalone is a Molecular Dynamics program for folding simulations with explicit or implicit water models.

Typical suites of software include CERIUS$^2$ (Accelrys, San Diego, Calif.), SYBYL (Tripos Inc., St. Louis, Mo.), AMBER (University of California, San Francisco), HYPERCHEM (Hypercube Inc., Gainesville, Fla.), INSIGHT II (Accelrys, San Diego, Calif.), CATALYST (Accelrys, San Diego, Calif.), CHEMSITE (ChemSW, Fairfield, Calif.), QUANTA (Accelrys, San Diego, Calif.). These packages implement many different algorithms that may be used according to the present invention (e.g. CHARMM molecular mechanics (Brooks et al., "CHARMM: A Program for Macromolecular Energy, Minimization, and Dynamics Calculations," *J. Comp. Chem.* 4, 187-217 (1983), which is hereby incorporated by reference in its entirety). Their uses in the methods of the present invention include, but are not limited to: (a) interactive modeling of the structure with concurrent geometry optimization (e.g. QUANTA); (b) molecular dynamics simulation of Aldolase or its fragments and TRAP or its fragments (e.g. CHARMM, AMBER); (c) normal mode dynamics simulation of Aldolase or its fragments and TRAP or its fragments (e.g. CHARMM). Modeling may include one or more steps of energy minimization with standard molecular mechanics force fields, such as those used in CHARMM and AMBER. These molecular modeling software usually allow the construction of structural models that can be further used for de-novo drug design or for combinatorial approaches towards drug design.

Further reviews of software for structure prediction can be found in Nayeem et al., "A Comparative Study of Available Software for High-accuracy Homology Modeling From Sequence Alignments to Structural Models," *Protein Sci* 15: 808-824 (2006), which is hereby incorporated by reference in its entirety. The progress and challenges in protein structure prediction has been reviewed by Zhang et al., "Progress and Challenges in Protein Structure Prediction," *Curr Opin Struct Biol* 18: 342-348 (2008), which is hereby incorporated by reference in its entirety.

The methods of the present invention comprise providing one or more candidate compounds. This can be done by many methods known in the art. The most important issue when selecting the candidate compounds is to be able to identify key molecular features of the candidate compound and the target which make binding between the compound and the candidate possible. The process of selecting candidate compounds may involve various steps such as the identification of candidates, synthesis, characterization, screening, and assays for therapeutic efficacy.

Among the most important advances in drug development have been advances in combinatorial synthesis of chemical libraries. In conventional drug screening with purified enzyme targets, combinatorial chemistries can often help create new derivatives of a lead compound that will also inhibit the target enzyme but with some different and desirable property. Well designed chemical libraries are an essential part of drug design. The present invention could be practiced by either screening for drug compounds and/or by de novo design of drug compounds against the Aldolase, TRAP, their complex or their fragments. There is a large chemical space available for drug-candidate molecules and conducting an effective search has been difficult in the past. Drug candidates can be identified using de-novo design, which can be helpful in producing novel molecular structures with desired pharmacological properties and also in narrowing down the chemical search space. It provides a substitute for a systematic construction and evaluation of individual compounds and relies on some kind of structure optimization algorithm, described below, where an optimization of the interactions between the candidate drug and the target is carried out. Often the aim is to incorporate as much chemical knowledge as possible about the structure of the target and the candidate drug into the search or design algorithms to restrict the search space and therefore facilitate the directed navigation to the drug which interacts effectively with the target.

Evaluation and/or screening of candidate compounds and chemical libraries can be done by various methods known the art. High throughput screening is a method of drug discovery that involves a brute force approach where tens of thousands of compounds are tested against a particular target. Compound libraries can have millions of compounds, selected for drug-like characteristics such as solubility, partition coefficient (log P), molecular weight, and number of hydrogen bond donors/acceptors. Generally, high throughput screening involves modern robotics, sophisticated control software, advanced liquid handling, and sensitive detection methods. The hits generated during HTS can be used as the starting point for a drug discovery effort. Typically, hits are refined through medicinal chemistry and lower-throughput assays. High throughput assays can be classified as either functional or nonfunctional. Functional assays measure the activity of a compound in modifying the actual function of a target protein (e.g., ion currents through hERG channels). Nonfunctional assays often simply measure binding of a compound to the target protein or use some indirect measure of target activity. Examples of nonfunctional assays include tritiated binding assays, the measure of fluorescence activity associated with calcium signaling, or techniques such as fluorescence resonance energy transfer (FRET). Functional assays are preferred since they are less prone to false positive hits. High throughput assays refer to assays that allow the screening of between 10,000 and 100,000 compounds per day. Ultra-high throughput assays refer to assays that allow the screening of over 100,000 compounds per day.

High throughput screening/evaluation through these libraries is well known in the art as a method to rapidly scan and analyze these libraries. A key factor for success of high throughput searching is the design of the library itself and whether the design increases a probability of retrieving promising lead compounds. The chemical libraries used in the art could basically be categorized into two types: experimental chemical libraries and virtual chemical libraries. Experimental chemical libraries comprise real chemical compounds that are screened in vitro. Virtual chemical libraries comprise 3-dimensional representations of chemical compounds that are screened computationally (in silico). These two kinds of libraries often complement each other.

In one embodiment of the present invention, the candidate compounds can be designed de novo based on identification of certain compounds that have the ability to bind to and/or fit in the models of the present invention. Earlier in the art, virtual libraries consisted of large set of compounds, often chosen randomly, without giving consideration to rational design directed specifically to the target molecule. The libraries were more-or-less a random collection of compounds. Essentially, the basic approach was to screen as many compounds, in a given period of time, as possible against the target molecule. These libraries typically could include up to one million small-molecule compounds, which were screened relatively quickly in perhaps a few days to a week of run time. The general belief was that drug leads could be derived from the sheer number of compounds screened. Although these efforts led to some notable successes in finding drug leads, it is believed that the screening results are not as fruitful as expected.

In order to improve the capability of finding drug leads against the target, the present invention is directed towards specific design of virtual libraries, where compounds, their parts, or fragments are selectively identified based upon interaction criteria, such as hydrophobic interactions, hydrophilic interactions, hydrogen bonding, van der Waals interactions, electrostatic complementarity, and used to generate target libraries. The compound memberships are based on design strategies such as diversity-oriented design and/or target-oriented design.

The goal of diversity-oriented design is to generate libraries with a highly diverse set of chemical compounds. By using a diverse set of compounds, there should be a greater likelihood that query molecules will "hit" one or several novel target compounds. Numerous methods are available for creating such diversity. Skeletal diversity, for example, is a strategy where the core, backbone, or scaffold elements of chemical compounds are chosen to maximize their variation in 3D shape, electrostatics, or molecular properties. Stereochemical diversity involves the 3D spatial arrangements of atoms and functional groups in molecules, and is maximized such that a range of molecular conformations is sampled during screening runs. Molecular property diversity is another method for generating compound diversity. Here, molecular properties available for modification include hydrogen bond donor groups, hydrogen bond acceptor groups, polarizable groups, charge distributions, hydrophobic and lipophobic groups, and numerous other chemical or physical properties. The diversity of the libraries resulting from these methods is often measured using statistical techniques, such as cluster analysis and principal components analysis.

Target-oriented design seeks to create libraries that are focused around specific chemotypes, molecular species, or classes of compounds. Target-oriented design results in focused libraries with a limited number of well-defined compounds. For example, scaffold compounds can be used as "seed" elements with various functional groups systemically added to the seed scaffolds to create sets of analogue compounds. Target-oriented design methods use 3D shape, 3D electrostatics, pharmacophore models, molecular descriptors, and other methods to generate focused libraries. And if compounds of known 3D structure bind to active sites, they can also be used as seeds for libraries. When building targeted libraries, a common design method is to take existing drug leads and generate neighbors (analogues) of the leads in chemistry space using combinatorial methods and conformational expansions of the lead compounds. The resulting compound libraries thus include many analogues of the lead compounds, which can be used in additional screens for novel leads.

Whether virtual high throughput screening (vHTS) libraries are designed for diversity or focused around specific chemotypes, they often use molecular property profiles in the design process. Generally, chemical compounds need to satisfy a variety of constraints before they become marketable drugs, for example, solubility, oral bioavailability, cell membrane permeability, liver enzyme activity (i.e. the cytochrome series), plasma protein binding, penetration of the blood-brain barrier, toxicity (mutagenicity, carcinogenicity, LD50), and many others. For example, a common design approach is focusing molecular properties around Lipinski's rules. This is a set of rules that describes common molecular properties of many currently marketed drugs. Lipinski's rules place limits on molecular weight, the number of hydrogen bond donors and acceptors, the number of rotatable bonds, and solubility. Applying Lipinski's rules in library design acts as a molecular property filter, you can effectively restrict the set of compounds to those with drug-like characteristics.

Compounds in these in silico libraries can also be evaluated for their ability to interact with the target by using their respective atomic co-ordinates in automated docking algorithms. An automated docking algorithm is one which permits the prediction of interactions of a number of compounds with a molecule having a given atomic structure.

Suitable docking algorithms include: DOCK (Kuntz et al., "A Geometric Approach to Macromolecule-ligand Interactions," *J Mol Biol.* 161(2):269-88 (1982), which is hereby incorporated by reference in its entirety), AUTODOCK (Goodsell et al. *Proteins: Structure, Function and Genetics* 8:195-202 (1990), which is hereby incorporated by reference in its entirety), MOE-DOCK (Chemical Computing Group, Montreal Canada) or FLEXX (BioSolveIT GmbH, Sankt Augustine, Germany). Docking algorithms can also be used to verify interactions with ligands designed de novo.

De novo compound design can also involve a process whereby binding surfaces or sequences within a target macromolecule (e.g., a nucleic acid or polypeptide) are determined, and those surfaces are used as a platform or basis for the rational design of compounds such that the compounds will interact with those surfaces. The molecular modeling steps used in the methods of the invention may use the atomic co-ordinates of Aldolase and/or TRAP or their fragments, and models derived therefrom, to determine binding surfaces. This preferably reveals essential molecular interactions, for example, van der Waals contacts, electrostatic interactions, and/or hydrogen bonding.

These binding surfaces will typically be used by grid-based techniques (e.g. GRID (Goodford, P. J., "A Computational Procedure for Determining Energetically Favourable Binding Sites on Biologically Important Macromolecules," *J. Med. Chem.*, 28: 849-857 (1985), which is hereby incorporated by reference in its entirety), CERIUS$^2$ (Accelrys, San Diego, Calif.) and/or multiple copy simultaneous search (MCSS) techniques (Miranker et al., "Functionality Maps of Binding Sites: A Multiple Copy Simultaneous Search Method," *Proteins, Structure, Function and Genetics* 11: 29-34 (1991); Caflish et al., "Multiple Copy Simultaneous Search and Construction of Ligands in Binding Sites: Application to Inhibitors of HIV-1 Aspartic Proteinase," *J. Med. Chem.* 36: 2142-2167 (1993); Eisen et al., "HOOK: A Program for Finding Novel Molecular Architectures that Satisfy the Chemical and Steric Requirements of a Macromolecule Binding Site," *Proteins Structure, Function and Genetics* 19: 199-221 (1994), which are hereby incorporated by reference in their entirety) to map favorable interaction positions for functional groups. This preferably reveals positions in Aldolase or TRAP or both for interactions such as, but not limited to, those with protons, hydroxyl groups, amine groups, hydrophobic groups (e.g. methyl, ethyl, benzyl) and/or divalent cations. The term "functional group" refers to chemical groups that interact with one or more sites on an interaction surface of a macromolecule. A "small molecule" is a compound having molecular mass of less than 3000 Daltons, preferably less than 2000 or 1500, still more preferably less than 1000, and most preferably less than 600 Daltons. A "small molecule fragment" is a portion of a small molecule that has at least one functional group. A "small organic molecule" is a small molecule that comprises carbon.

In one embodiment of the present invention, the designing comprises linking functional groups or small molecule fragments of the identified compounds to form de novo compounds. Once functional groups or small molecule fragments which can interact with specific sites in the binding surface of the target have been identified, they can be linked in a single compound using either bridging fragments with the correct size and geometry or frameworks which can support the functional groups at favorable orientations, thereby providing a compound according to the present invention. Whilst linking of functional groups in this way can be done manually, perhaps with the help of software such as QUANTA (Accelrys, San Diego, Calif.) or SYBYL (Tripos Inc., St. Louis, Mo.), the following software may be used for assistance: HOOK (Eisen, et al., "HOOK: A program for finding novel molecular architectures that satisfy the chemical and steric requirements of a macromolecule binding site," *Proteins Structure, Function and Genetics* 19: 199-221 (1994), which is hereby incorporated by reference in its entirety), which links multiple functional groups with molecular templates taken from a database, and/or CAVEAT (Lauri, G. et al., "CAVEAT: A Program to Facilitate the Design of Organic Molecules," *J. Comp. Aided Mol. Design* 8: 51-66 (1994), which is hereby incorporated by reference in its entirety), which designs linking units to constrain acyclic molecules.

Other computer-based approaches to de novo compound design that can be used with the 3-dimensional atomic coordinates include LUDI (Böhm, H. J., "The Computer Program LUDI: A New Method for the de novo Design of Enzyme Inhibitors," *J. Comp. Aided Molec. Design,* 6: 61-78 (1992), which is hereby incorporated by reference in its entirety), SPROUT (Valerie et al., "Sprout: Recent Developments in the de novo Design of Molecules," *J. Chem. Inf. Comput. Sci.* 34:207-217 (1994); Valerie et al., "Sprout: A Program for Structure Generation," *J. Comput.-Aided Mol. Design* 7:127-153 (1993), which are hereby incorporated by reference in their entirety) and LEAPFROG™ (Tripos Inc., St. Louis, Mo.).

As well as using de novo design, a pharmacophore of the target molecule, for example Aldolase and/or TRAP or their complex or fragments thereof, can be defined i.e. a collection of chemical features and 3D constraints that expresses specific characteristics responsible for biological activity. The pharmacophore preferably includes surface-accessible features, more preferably including hydrogen bond donors and acceptors, charged/ionizable groups, and/or hydrophobic patches. These may be weighted depending on their relative importance in conferring activity (Han Van de Waterbeemd, *Computer Assisted Lead Finding and Optimization* Wiley-VCH (1997), which is hereby incorporated by reference in its entirety).

Pharmacophores can be determined using software such as CATALYST (including HypoGen or HipHop) (Accelrys, San Diego, Calif.), CERIUS$^2$ (Accelrys, San Diego, Calif.), or constructed by hand from a known conformation of a lead compound. The pharmacophore can be used to screen in silico compound libraries, using a program such as CATALYST (Accelrys, San Diego, Calif.). Langer et al. provides a discussion on the generation and use of virtual compound libraries, and on studies in which chemical feature-based pharmacophore models are used in combination with in silico screening (Langer et al., "Chemical Feature-based Pharmacophores and Virtual Library Screening for Discovery of New Leads," *Curr Opin Drug Discov Devel.* 6: 370-6 (2003), which is hereby incorporated by reference in its entirety). These procedures are generally used to obtain hits (or leads) that are more likely to give successful clinical candidates against a target molecule(s) of the present invention.

Suitable in silico libraries include commercially or publicly available chemical libraries, for example, the Available Chemical Directory (MDL Inc), the Derwent World Drug Index (WDI), BioByteMasterFile, the National Cancer Institute database (NCI), and the Maybridge catalog can also be used for the purposes of the present invention.

The methods according to the present invention involve evaluating contact between the candidate compounds and the model to determine which of the one or more candidate compounds have an ability to bind to and/or fit in a model of the present invention. The evaluation of the candidate compounds, which may be a part of a library of compounds, is a central task in the drug-design process. The evaluation of candidate compounds is a means to assess the binding properties of the candidate compounds and ascertain the most promising candidates. There are many ways known in the art which can be used to evaluate the candidate compounds and are described (Kitchen et al., "Docking and Scoring in Virtual Screening for Drug Discovery: Methods and Applications," *Nature Reviews. Drug Discovery* 3: 935-49 (2004); Lengauer et al., "Computational Methods for Biomolecular Docking," *Curr. Opin. Struct. Biol.* 6: 402-6 (1996); Wei et al., "Testing a Flexible-receptor Docking Algorithm in a Model Binding Site," *J. Mol. Biol.* 337: 1161-82 (2004); Meng et al., "Automated Docking with Grid-based Energy Evaluation," *Journal of Computational Chemistry* 13: 505-524 (2004); Morris et al., "Automated Docking Using a Lamarckian Genetic Algorithm and an Empirical Binding Free Energy Function," *Journal of Computational Chemistry* 19: 1639-1662 (1998); Schneider et al., "Computer based de novo Design of Drug-like Molecules," *Nature Reviews* 4:649-663, which are hereby incorporated by reference in their entirety). Scoring functions can rank the candidate compounds based on their binding to the target and also provide a guide during the design process through the search space.

In one embodiment of the present invention, the binding and/or interactions between the candidate drug and a model of the present invention are evaluated using automated docking algorithms.

Virtual Library/Ligand Screening (VLS) is a structure-based approach to drug discovery performed in silico. VLS requires a 3D model of the protein target ("receptor"), a collection of small molecules ("ligands") to test against the target, and an algorithm to dock the two together and score the predicted interactions (Brive & Abagyan, "Computational Structural Proteomics," *Ernst Schering Res. Found. Workshop,* 149-166 (2002); Abagyan & Totrov, "High-Throughput Docking for Lead Generation," *Curr. Opin. Chem. Biol.* 5:375-382 (2001); Cardozo & Abagyan, "Druggability of SCF Ubiquitin Ligase-Protein Interfaces. in *Ubiquitin and Protein Degradation, Part B*, Vol. 399 (ed. Deshaies, R. J.) Elsevier Academic Press:San Diego, pp. 634-653 (2005), which are hereby incorporated by reference in their entirety). The steps involved in a virtual ligand screen are outlined below and summarized in FIG. 5.

Once the protein target structure and small molecule library are prepared, a computer algorithm is used to dock the library compounds to the target. In silico docking involves searching the entire space in and around the receptor for the best (i.e. most energetically favorable) position and conformation for the ligand. In the case of VLS, this procedure is repeated for every compound in the chemical library. The molecules are then ranked according to the fitness or energy score of their interaction with the target protein (Abagyan & Totrov, "High-Throughput Docking for Lead Generation," *Curr. Opin. Chem. Biol.* 5:375-382 (2001), which is hereby incorporated by reference in its entirety).

The highest ranking compounds are then curated as appropriate to the objective of the invention. For example, based on prior work for a given drug target, it may be desirable to have a certain level of chemical diversity or a specific range of physicochemical properties present in the final hitlist. The final set of compounds in the curated hitlist are advanced for further testing, including in vitro and/or in vivo validation of their activity, as well as various lead optimization methods to increase their potency and specificity (Brive & Abagyan, "Computational Structural Proteomics," *Ernst Schering Res. Found. Workshop,* 149-166 (2002); Abagyan & Totrov, "High-Throughput Docking for Lead Generation," *Curr. Opin. Chem. Biol.* 5:375-382 (2001), which is hereby incorporated by reference in its entirety).

Without any intentions of limiting the methods that can be used for the purposes of evaluating the candidate compounds and their interactions with the models of the present invention, the evaluation methods can be broadly categorized into: steric scoring, receptor based scoring, and ligand based scoring.

In the steric scoring, for example, the evaluation of the candidate compounds can be done based on a simple steric constraints to guide the selection process (Lewis et al., "Automated Site-directed Drug Design Using Molecular Lattices," *J. Mol. Graphics.* 10:66-78 (1992); Roe et al., "BUILDER v.2: Improving the Chemistry of a de novo Design Strategy," *J. Comput. Aided Mol. Des.* 9:269-282 (1995); Tschinke, et al., "The NEWLEAD Program: A New Method for the Design of Candidate Structures from Pharmacophoric Hypothesis," *J. Med. Chem.* 36:3863-3870 (1993); Lewis et al., Automated Site-directed Drug Design: The Formation of Molecular Templates in Primary Structure Generation," *Proc. R. Soc. Lond. B* 236:141-162 (1989); Gillett, et al., "Automated Structure Design in 3D," *Tetrahedron Comput. Method.* 3:681-696 (1990); Lewis, R. A. Automated Site-directed Drug Design: Approaches to the Formation of 3D Molecular Graphs," *J. Comput. Aided Mol. Des.* 4:205-210 (1990); Rotstein, et al., "GenStar: A Method for de novo Drug Design," *J. Comput. Aided. Mol. Des.* 7:23-43 (1993), which are hereby incorporated by reference in their entirety).

Receptor based scoring can be sub-divided into explicit force field methods, empirical scoring functions, and knowledge based scoring functions. These methods attempt to approximate the binding free energy (Schneider et al., "Computer based de novo Design of Drug-like Molecules," *Nature Reviews* 4:649-663, which is hereby incorporated by reference in its entirety). Force fields are computationally more costly than the other two types of scoring functions. LEGEND (Nishibata et al., "Automatic Creation of Drug Candidate Structures Based on Receptor Structure. Starting Point for Artificial Lead Generation," *Tetrahedron* 47:8985-8990 (1991), which is hereby incorporated by reference in its entirety) was the first program that used a force field to evaluate candidate compounds. Many others now use this to evaluate candidate compounds (Rotstein et al., "GroupBuild: A Fragment Based Method for de novo Drug Design," *J. Med. Chem.* 36: 1700-1710 (1993); Luo et al., "RASSE: A New Method for Structure-based Drug Design," *J. Chem. Inf. Comput. Sci.* 36: 1187-1194 (1996); Pearlman et al., "CONCERTS: Dynamic Connection of Fragments as an Approach to de novo Ligand Design," *J. Med. Chem.* 39: 1651-1663 (1996); Liu et al., "Structure-based Ligand Design by Dynamically Assembling Molecular Building Blocks at Binding Site," *Proteins* 36: 462-470 (1999); Zhu, et al., Design of Selective Inhibitors of Cyclooxygenase-2 Dynamic Assembly of Molecular Building Blocks," *J. Comput. Aided Mol. Des.* 15: 447-463 (2001); Zhu et al., "Structure-based Ligand Design for Flexible Proteins: Application of New F-Dyco Block," *J. Comput. Aided Mol. Des.* 15: 979-996 (2001), which are hereby incorporated by reference in their entirety). Empirical scoring functions are a weighted sum of individual ligand-receptor interaction types, usually supplemented by penalty terms, for example, the number of rotatable bonds. These methods are fast and have proven suitability for de novo design methods and programs (Clark et al., "PRO LIGAND: An Approach to de novo Molecular Design. 1. Application to the Design of Organic Molecules," *J. Comput. Aided Mol. Des.* 9: 13-32 (1995); Murray et al., "PRO_SELECT: Combining Structure Based Drug Design and Combinatorial Chemistry for Rapid Lead Discovery. 1. Technology," *J. Comp. Aided Mol. Des.* 11: 193-207 (1997); Bohacek et al., "Multiple Highly Diverse Structures Complementary to Enzyme Binding Sites: Results of Extensive Application of a de novo Design Method Incorporating Combinatorial Growth," *J. Am. Chem. Soc.* 116: 5560-5571 (1994); Wang et al., "LigBuilder: A Multi-purpose Program for Structure-based Drug Design," *J. Mol. Model.* 6: 498-516 (2000); Pearlman et al., "CONCEPTS: New Dynamic Algorithm for de novo Design Suggestion," *J. Comput. Chem.* 14: 1184-1193 (1993); Eldridge et al., "Empirical Scoring Functions: I. The Development of a Fast Empirical Scoring Function to Estimate the Binding Affinity of Ligands in Receptor Complexes," *J. Comput. Aided Mol. Des.* 11: 425-445 (1997), which are hereby incorporated by reference in their entirety). Knowledge-based scoring is grounded on a statistical analysis of ligand-receptor complex structures. The frequencies of each possible pair of atoms in contact to each other are determined. Interactions found to occur more frequently than would be randomly expected are considered attractive; interactions that occur less frequently are considered repulsive. A de novo design program, SmoG, uses implementation of this type of scoring function (DeWitte et al., "SMoG de novo Design Method Based on Simple, Fast, and Accurate Free Energy Estimates. 1. Methodology and Supporting Evidence," *J. Am. Chem. Soc.* 118: 11733-11744 (1996); Ishchenko et al., "Small Molecule Growth 2001 (SMoG2001): An Improved Knowledge Based Scoring Function for Protein-ligand Interactions," *J. Med. Chem.* 45: 2770-2780 (2002), which are hereby incorporated by reference in their entirety).

If a three-dimensional structure of a particular biological target is unavailable but one or more binding molecules are known, ligand-based scoring provides an alternative strategy. Receptor-based structure generation has a huge conformational complexity. A ligand-based strategy, in contrast, can either consider the three-dimensional or the topological structure of one or more known ligands. One way to use the information inherent to the known actives is the derivation of a three-dimensional ligand pharmacophore model. Once established, it can be used to obtain a pseudo-receptor model (Waszkowycz et al., "PRO LIGAND: An Approach to de novo Molecular Design. 2. Design of Novel Molecules from Molecular Field Analysis (MFA) Models and Pharmacophores," *J. Med. Chem.* 37: 3994-4002 (1994), which is hereby incorporated by reference in its entirety). This facilitates the application of de novo design programs that were originally developed with a receptor-based strategy in mind to ligand-based design.

The best protein model for use with VLS would be a high resolution (<2.5 Å) crystallographic or NMR structure of the drug target, although in some circumstances a lower resolution structure or homology model will suffice. This structure should represent the receptor in a conformation appropriate to the drug design strategy employed (i.e., active, inactive, ligand-bound, or free receptor depending on whether the screen is meant to identify agonists, antagonists, competitive vs. noncompetitive inhibitors).

The part of the structure that one would like a drug to interact with (i.e. the functionally sensitive region on the receptor) should have a surface or "pocket" suitable for ligand binding. Previous drug discovery trials have shown that pockets with volume-to-area ratios between 100 and 500 are more likely to yield successful results (Cardozo & Abagyan, "Druggability of SCF Ubiquitin Ligase-Protein Interfaces. in *Ubiquitin and Protein Degradation, Part B*, Vol. 399 (ed. Deshaies, R. J.) Elsevier Academic Press:San Diego, pp. 634-653 (2005), which is hereby incorporated by reference in its entirety). In the present invention, the PocketFinder module included with the ICM software (Molsoft, LLC, La Jolla, Calif.) was used to identify potential drug-binding pockets within the receptors used for VLS. The PocketFinder algorithm uses a transformation of the Lennard-Jones potential to create grid potential maps of regions on the receptor with consistently high van der Waals attraction. Putative ligand envelopes demonstrating the sizes and shapes of the available ligand-binding volumes are then created by contouring these maps (An et al., "Pocketome Via Comprehensive Identification and Classification of Ligand Binding Envelopes," *Mol. Cell. Proteomics* 4:752-761 (2005), which is hereby incorporated by reference in its entirety).

The library of small molecules used for VLS should be large and diverse, to increase the chances of finding "hits" or drug leads. Since the ultimate goal of a VLS project is the development of a drug, it would be advantageous if the compounds in the library were "drug-like" and relatively easy to synthesize. Lipinski's "Rule of 5," which describes characteristics common to most successful drugs on the market today, can be used to exclude non-suitable molecules from the screen. These rules are based on the observations that most compounds with favorable bioavailability and activity profiles have five or fewer hydrogen bond donors, ten or fewer hydrogen bond acceptors, a molecular weight less than 500 Daltons and a log P less than or equal to five (Lipinski et al., "Experimental and Computational Approaches to Estimate Solubility and Permeability in Drug Discovery and Development Settings," *Adv. Drug Deliv. Rev.* 46:3-26 (2001), which is hereby incorporated by reference in its entirety). For VLS studies, a chemical library supplied by the ChemBridge Corporation (San Diego, Calif.) was used. This library contains >300,000 diverse structures, most of which should be drug-like. Any library compounds that do not conform to the Lipinski rules were filtered out by the ICM-VLS software.

The main advantage of computer-aided structure-based drug design is the ability to rapidly find compounds with a high degree of both potency and specificity. If properly designed, the VLS approach should yield promising chemotypes with at least some degree of specificity and affinity for their target. These initial leads can then be derivatized and optimized using a variety of cheminformatics and medicinal chemistry techniques.

In a substructure search, molecular comparison algorithms (e.g. Tanimoto Distance calculations) are utilized to search large chemical databases for compounds containing a chemical scaffold identified by VLS or other drug discovery methods. These additional leads can then be screened against the target—virtually or at the bench—in order to identify derivatives with optimal features (Schneider & Baringaus, *Molecular Design: Concepts and Applications*, (Wiley-VCH, Weinheim, Germany, 2008); Opera, *Chemoinformatics in Drug Discovery*, (Wiley-VCH, Weinheim, Germany, 2005), which are hereby incorporated by reference in their entirety).

In a variation of the substructure search, the search query is represented as a pharmacophore instead of as an explicit chemical structure. In this case, the goal is to obtain novel compounds with a particular geometric arrangement of reactive groups (i.e. H-bond donor, hydroxyl, aliphatic moiety, methyl group, positive charge, etc. at particular distances and angles from each other) previously identified as contributing to receptor-ligand binding. As such, a pharmacophore search can be a key step in "scaffold hopping"—identifying novel active chemotypes and scaffolds that can then serve as starting points for derivatization and optimization (Schneider & Baringaus, *Molecular Design: Concepts and Applications*, (Wiley-VCH, Weinheim, Germany, 2008); Opera, *Chemoinformatics in Drug Discovery*, (Wiley-VCH, Weinheim, Germany, 2005), which are hereby incorporated by reference in their entirety).

In general, these search algorithms are much faster and require less computation than docking, making them ideally suited to scanning extremely large chemical databases. In the hands of extremely competent computational biologists and medicinal chemists, these techniques can allow the development of extremely potent and highly selective leads in a very short time (Schneider & Baringaus, Molecular Design Concepts and Applications, (Wiley-VCH, Weinheim, Germany, 2008); Opera, *Chemoinformatics in Drug Discovery*, (Wiley-VCH, Weinheim, Germany, 2005), which are hereby incorporated by reference in their entirety).

A three-dimensional ligand pharmacophore model can be used directly in a similarity design method (Waszkowycz et al., "PRO_LIGAND: An Approach to de novo Molecular Design. 2. Design of Novel Molecules from Molecular Field Analysis (MFA) Models and Pharmacophores," *J. Med. Chem.* 37: 3994-4002 (1994), which is hereby incorporated by reference in its entirety). Whereas a (pseudo)receptor guides the design of structures that are complementary to the primary target constraints, a ligand pharmacophore model can be applied to designing structures that are similar to these constraints. A set of known ligands can also be taken as an input for the development of a target-specific quantitative structure-activity relationship (QSAR) model. The established model then serves as a scoring function (Nachbar et al., "Molecular Evolution: Automated Manipulation of Hierarchical Chemical Topology and its Application to Average Molecular Structures," *Genet. Programming Evolvable Machines* 1: 57-94 (2000); Pellegrini et al., "Development and Testing of a de novo Drug-design Algorithm," *J. Comp. Aided Mol. Des.* 17: 621-641 (2003); Douguet et al., "A Genetic Algorithm for the Automated Generation of Small Organic Molecules: Drug Design Using an Evolutionary Algorithm," *J. Comput. Aided Mol. Des.* 14: 449-466 (2000), which are hereby incorporated by reference in their entirety).

The methods of the present invention include identifying the compounds which, based on evaluation, have the ability to bind to and/or fit in a model of the present invention as compounds potentially useful for modifying the activity of Aldolase. Similarly, the methods of the present invention also include identifying the compounds, which based on evaluation, have the ability to stabilize a complex between the first model and the second model as compounds useful for stabilizing the complex. Candidate compounds can be identified using any of the techniques mentioned supra such as screening, de novo design, molecular modeling, and contacting the compound with Aldolase and/or its fragments and assaying the interaction between them. Scoring functions described above may be used to provide a cut off limit and used to assist in identification of compounds with increased potential to modify the activity of Aldolase. Various other criteria such as contact area, binding energy calculations, free energy calculations, visual inspection, evaluation of steric hindrances and hydrogen bonding potential can be used to identify compounds with potential to modify the activity of Aldolase. Modifying the activity of Aldolase includes enhancing the activity of Aldolase or inhibiting the activity of Aldolase.

Various methods which use in vitro or in vivo assays for the activity of Aldolase in the presence of a compound are well known in the art and can be used to indentify the compounds and/or to rank compounds according to their inhibition potential.

In another aspect, the present invention is directed to a pharmaceutical composition comprising a compound selected from the group consisting of:
(1) a compound of formula (I)

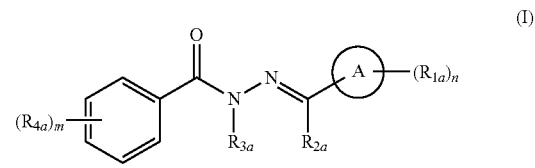

wherein:
n is an integer from 0 to 4;
m is an integer from 0 to 4;
$R_{1a}$ is independently at each occurrence H, halogen, $CF_3$, $CHF_2$, $CH_2F$, OH, $NH_2$, CN, $NO_2$, —C(O)$R_{5a}$, —S$R_{5a}$, —S(O)$R_{5a}$, —S(O)$_2R_{5a}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur; or two adjacent $R_{1a}$ groups may combine to form a 3- to 7-membered heterocyclic ring containing from 1 to 5 heteroatoms selected from the group consisting of oxygen, nitrogen, and sulfur;

$R_{2a}$ is independently H, halogen, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;

$R_{3a}$ is independently H, —$SR_{5a}$, —$S(O)R_{5a}$, —$S(O)_2R_{5a}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;

$R_{4a}$ is independently at each occurrence H, halogen, $CF_3$, $CHF_2$, $CH_2F$, OH, $OR_{5a}$, $O(CH_2)_2OR_{5a}$, —$C(O)R_{5a}$, —$OC(O)R_{5a}$, —$NHC(O)R_{5a}$, —$NHC(O)OR_{5a}$—$C(O)OR_{5a}$, —$C(O)NR_{5a}R_{6a}$, —$NHR_{5a}$, —$NR_{5a}R_{6a}$, —$SR_{5a}$, —$S(O)R_{5a}$, —$S(O)_2R_{5a}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl;

two adjacent $R_{4a}$ groups may combine to form a 3- to 7-membered heterocyclic ring containing from 1 to 5 heteroatoms selected from the group consisting of oxygen, nitrogen, sulfur, and bismuth, wherein heterocycyclic ring can be unsaturated or saturated and optionally substituted with from 1-2 substituents independently selected at each occurrence thereof from OH, F and $C_1$-$C_6$ alkyl;

$R_{5a}$ and $R_{6a}$ are independently H, $CHF_2$, $CH_2Ph$, $CH_2C(O)NH_2$, $CH_2CH_2NHSO_2Me$, $C_1$-$C_{16}$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur; and wherein $CH_2Ph$ is optionally substituted with from 1-3 substituents independently selected at each occurrence thereof from F, Cl, OMe; and A is a substituted or unsubstituted mono or polycyclic aryl or substituted or unsubstituted mono or polycyclic heteroaryl containing from 1 to 5 heteroatoms selected from the group consisting of oxygen, nitrogen, and sulfur;

(2) a compound of formula (II)

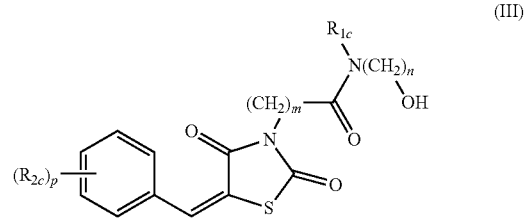

wherein:
X is O, S, or NH;
n is an integer from 0 to 3;
m is an integer from 0 to 3;
$R_{1b}$ is independently H, halogen, $CF_3$, $CHF_2$, $CH_2F$, OH, $NH_2$, CN, $NO_2$, $OR_{5b}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;

$R_{2b}$ and $R_{3b}$ is independently H, —$SR_{5b}$, —$S(O)R_{5b}$, —$S(O)_2R_{5b}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;

$R_{4b}$ is independently at each occurrence H, halogen, $CF_3$, $CHF_2$, $CH_2F$, OH, $OR_{5b}$, —$C(O)R_{5b}$, —$C(O)OR_{5b}$, —$C(O)NR_{5b}R_{6b}$, —$NHR_{5b}$, —$NR_{5b}R_{6b}$, —$SR_{5b}$, —$S(O)R_{5b}$, —$S(O)_2R_{5b}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and $R_{5b}$ and $R_{6b}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each monocyclic aryl or monocyclic heteroaryl optionally substituted from 1 to 4 times with substituents selected from the group consisting of H, halogen, $CF_3$, $CHF_2$, $CH_2F$, OH, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl;

(3) a compound of formula (III):

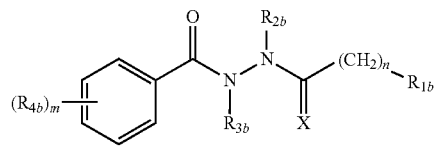

wherein:
m, n, and p are independently integers from 0 to 3;
$R_{1c}$ is H, —$SR_{3c}$, —$S(O)R_{3c}$, —$S(O)_2R_{3c}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur;

$R_{2c}$ is independently at each occurrence H, halogen, $CF_3$, $CHF_2$, $CH_2F$, OH, $OR_{3c}$, —$C(O)R_{3c}$, —$C(O)OR_{3c}$, —$C(O)NR_{3c}R_{4c}$, —$NHR_{3c}$, —$NR_{3c}R_{4c}$, —$SR_{3c}$, —$S(O)R_{3c}$, —$S(O)_2R_{3c}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl; and $R_{3c}$ and $R_{4c}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur;

(4) a compound of formula (IV):

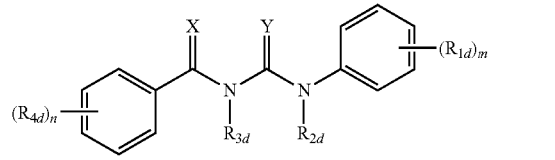

wherein:

m and n are integers from 0 to 3;

X and Y are independently O or S;

$R_{1d}$ and $R_{4d}$ are independently at each occurrence H, halogen, $CF_3$, $CHF_2$, $CH_2F$, OH, $OR_{5d}$, $-C(O)R_{5d}$, $-C(O)OR_{5d}$, $-C(O)NR_{5d}R_{6d}$, $-NHR_{5d}$, $-NR_{5d}R_{6d}$, $-SR_{5d}$, $-S(OR_{5d}$, $-S(O)_2R_{5d}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl;

$R_{2d}$ and $R_{3d}$ are independently H, $-SR_{5d}$, $-S(O)R_{5d}$, $-S(O)_2R_{5d}$, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1-5 heteroatoms selected from the group consisting of nitrogen, oxygen, and sulfur; and $R_{5d}$ and $R_{6d}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur;

(5) a compound of formula V:

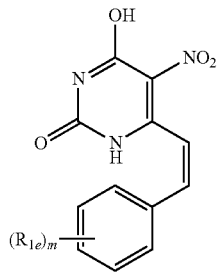

(V)

wherein:

m is an integer from 0 to 3 and $R_{1e}$ is independently at each occurrence H, halogen, $CF_3$, $CHF_2$, $CH_2F$, OH, $OR_{5e}$, $-C(O)R_{5e}$, $-C(O)OR_{5e}$, $-C(O)NR_{5e}R_{6e}$, $-NHR_{5e}$, $-NR_{5e}R_{6e}$, $-SR_{5e}$, $-S(O)R_{5e}$, $-S(O)_2R_{5e}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl or mono or polycyclic heterocycle containing from 1-5 heteroatoms selected from the group consisting of nitrogen, oxygen, and sulfur.

As used above, and throughout the description of the present invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "halo" or "halogen" means fluoro, chloro, bromo, or iodo.

The term "optionally substituted" indicates that a group may have a substituent at each substitutable atom of the group (including more than one substituent on a single atom), and the identity of each substituent is independent of the others.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. Exemplary substitutents include, without limitation, oxo, thio (i.e. =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic hetereoaryl, polycyclic aryl, and polycyclic heteroaryl.

The term "monocyclic" indicates a molecular structure having one ring.

The term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methyl-butynyl, and n-pentynyl.

The term "alkoxy" means an alkyl-O—, alkenyl-O—, or alkynyl-O-group wherein the alkyl, alkenyl, or alkynyl group is described above. Exemplary alkoxy groups include methoxy, ethoxy, n-propoxy, i-propoxy, n-butoxy, pentoxy, and hexoxy.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

The term "cycloalkylalkyl" refers to a radical of the formula $-R^aR^b$ where $R^a$ is an alkyl radical as defined above and $R^b$ is a cycloalkyl radical as defined above. The alkyl radical and the cycloalkyl radical may be optionally substituted as defined above.

The term "aryl" refers to aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula —R$^a$R$^b$ where R$^a$ is an alkyl radical as defined above and R$^b$ is an aryl radical as defined above. The alkyl radical and the cycloalkyl radical may be optionally substituted as defined above.

The term "aryarylalkyl" refers to a radical of the formula —R$^a$R$^b$R$^c$ where R$^a$ is an alkyl as defined above, R$^b$ is an aryl radical as defined above, and R$^c$ is an aryl radical as defined above. The alkyl radical and both aryl radicals may be optionally substituted as defined above.

The term "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" refers to an aromatic ring radical which consists of carbon atoms and from one to five heteroatoms selected from the group consisting of nitrogen, oxygen, and sulfur. For purposes of this invention the heteroarayl may be a monocyclic or polycyclic ring system; and the nitrogen, carbon, and sulfur atoms in the heteroaryl ring may be optionally oxidized; the nitrogen may optionally be quaternized. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

Further heterocycles and heteraryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

The term "compounds of the invention", and equivalent expressions are meant to embrace compounds of formula (I) to (V) as herein before described, which expression includes the prodrugs, the pharmaceutically acceptable salts, and the solvates, e.g., hydrates, where the context so permits. Similarly, reference to intermediates, whether or not they themselves are claimed, is meant to embrace their salts and solvates, where the context so permits. For the sake of clarity, particular instances, when the context so permits, are sometimes indicated in the text, but these instances are purely illustrative and it is not intended to exclude other instances when the context so permits.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

One way to make compounds of the Formula (I) is shown on the Scheme 1.

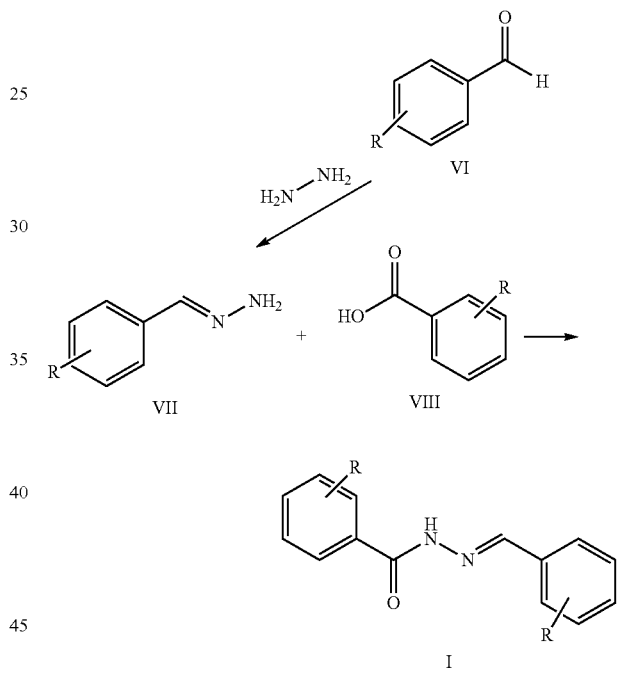

Scheme 1.

By Scheme 1, aldehydes of Formula (VI) may be converted to compounds of Formula (VII) by treatment with hydrazine hydrate. Reaction between Intermediate (VII) and Acid (VIII) generates compounds of Formula (I).

One way to make Compound 24 of the Formula (I) is shown on the Schemes 2-3.

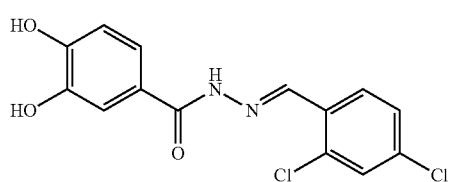

Scheme 2.

Retrosynthetic Analysis:
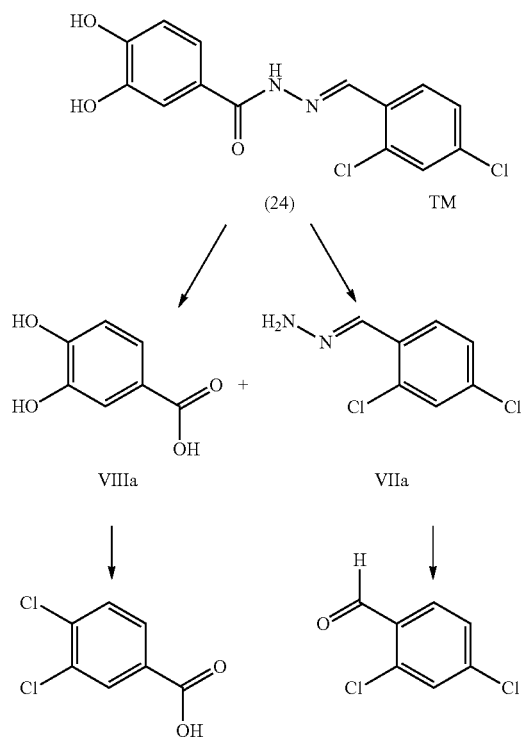
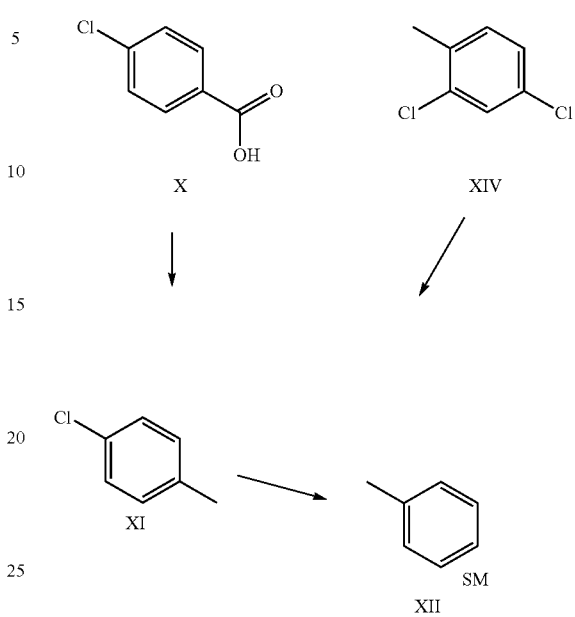
Retrosynthetic analysis (Scheme 2) showed that Compound 24 of the Formula (I) can be prepared from Compound (VIIa) and Acid (VIIIa). Both Compound (VIIa) and Compound (VIIIa) can be prepared from the same starting material toluene (XII).
Scheme 3.
Synthesis of Compound #24:
(24)
Start:
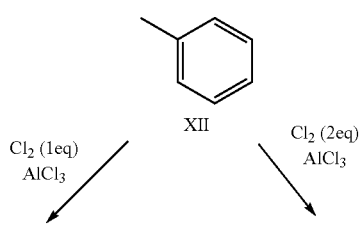

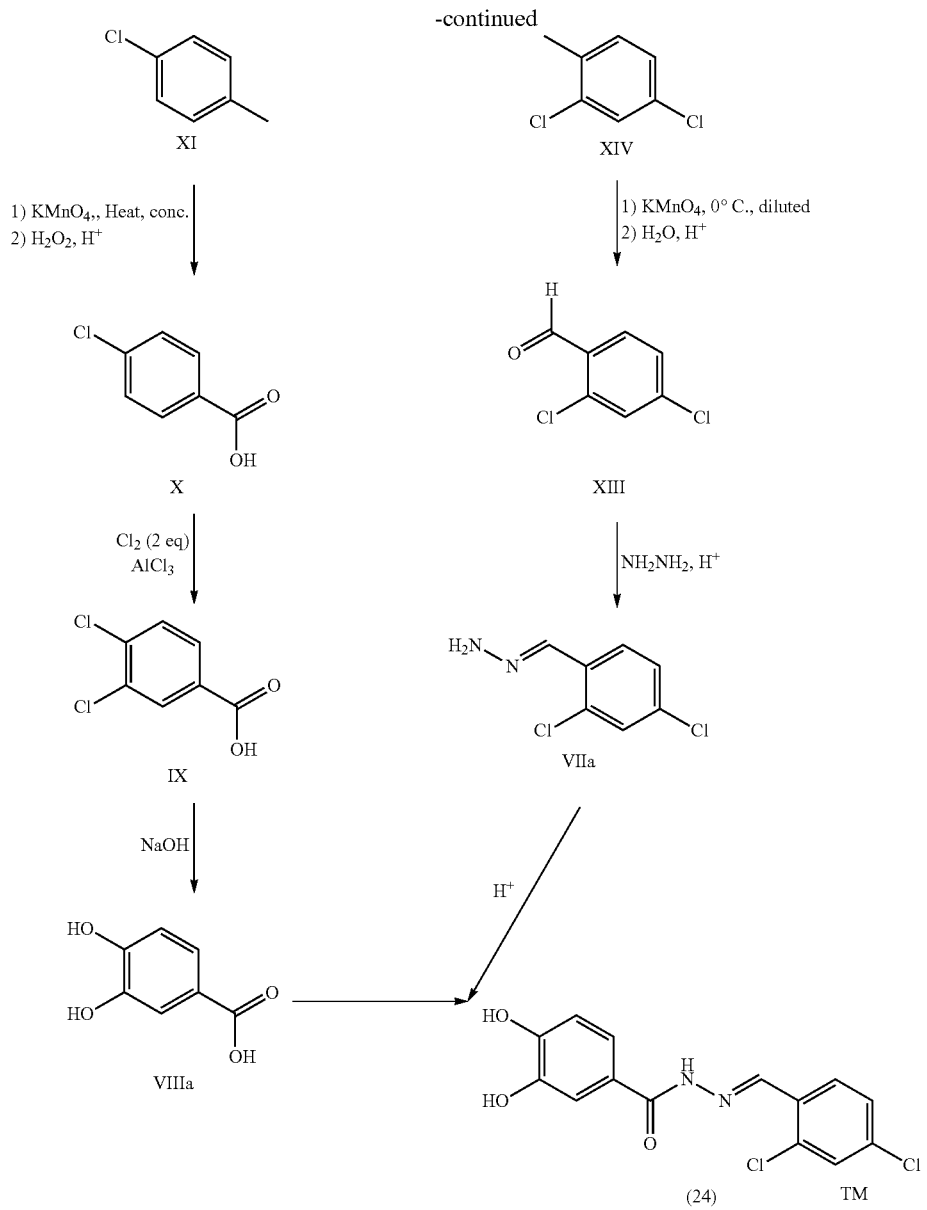

Chlorination of the toluene (XII) in the presence of a Lewis acid catalyst generates a compound of Formula (XI) (Scheme 3). Compound (XI) can be converted to Acid (X) by treatment with potassium permanganate. Chlorination of Compound (X) results in the formation of Compound (IX). Compound (IX) can be further converted into Compound (VIIIa) by reaction with sodium hydroxide. Chlorination of toluene (XII) in the presence of a Lewis acid catalyst can generate a compound of Formula (XIV). Oxidation of Compound (XIV) in the presence of potassium permanganate leads to formation of aldehyde (XIII). Compound (XIII) can be converted to a compound of Formula (VIIa) by treatment with hydrazine hydrate. Reaction between Compound (VIIa) and Compound (VIIIa) leads to formation of Compound 24.

One way to make Compound 42 of the Formula (I) is shown on the Schemes 4-5.

Retrosynthetic analysis (Scheme 4) showed that Compound 42 of the Formula (I) can be prepared from Compound (VIIb) and Acid (VIIIb). Both Compound (VIIb) and Compound (VIIIb) can be prepared from the same starting material toluene (XII).

Scheme 4.

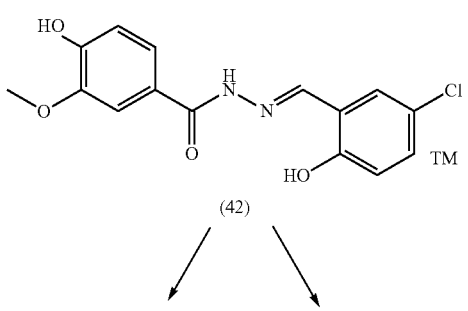

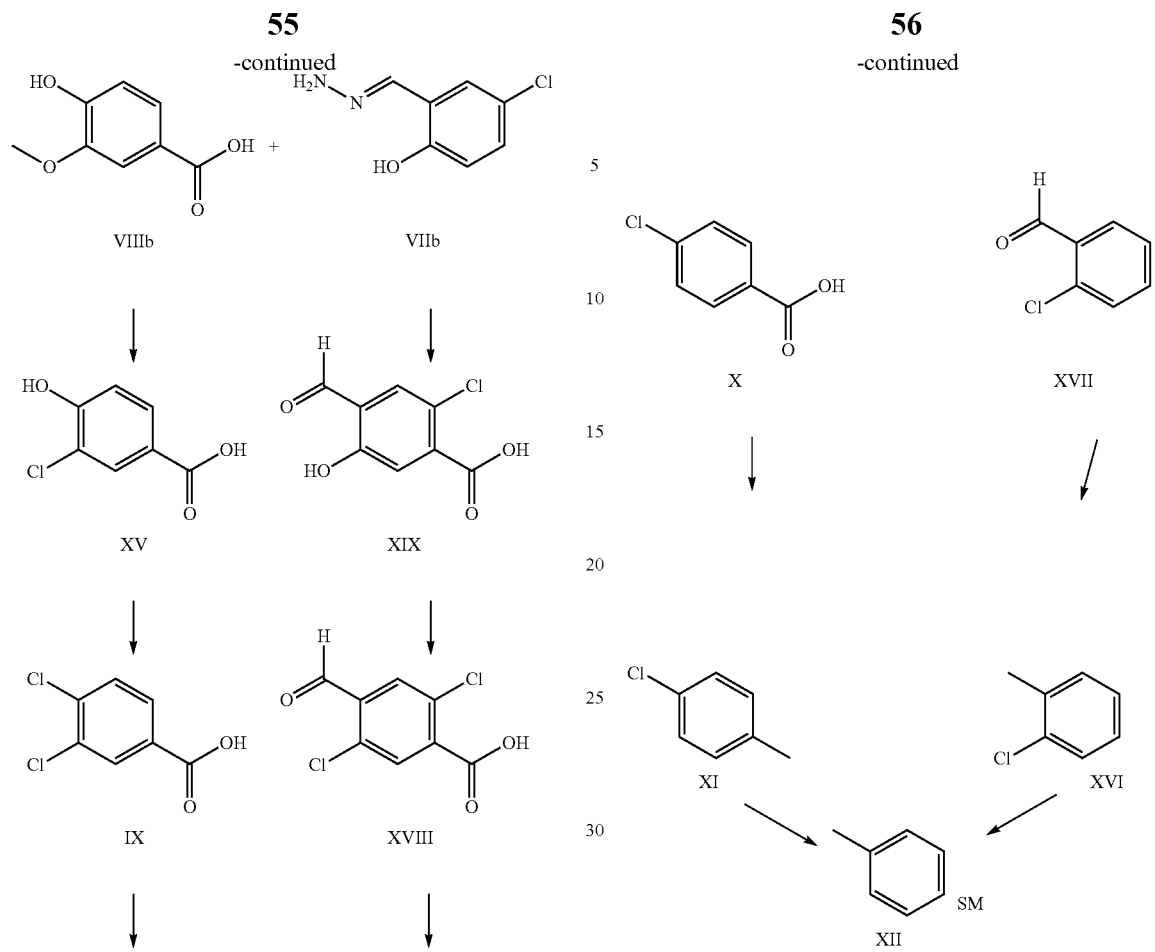
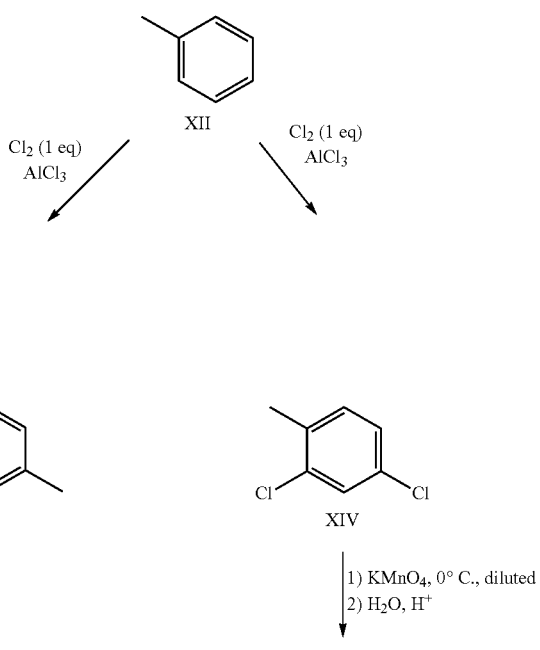
Scheme 5.

-continued

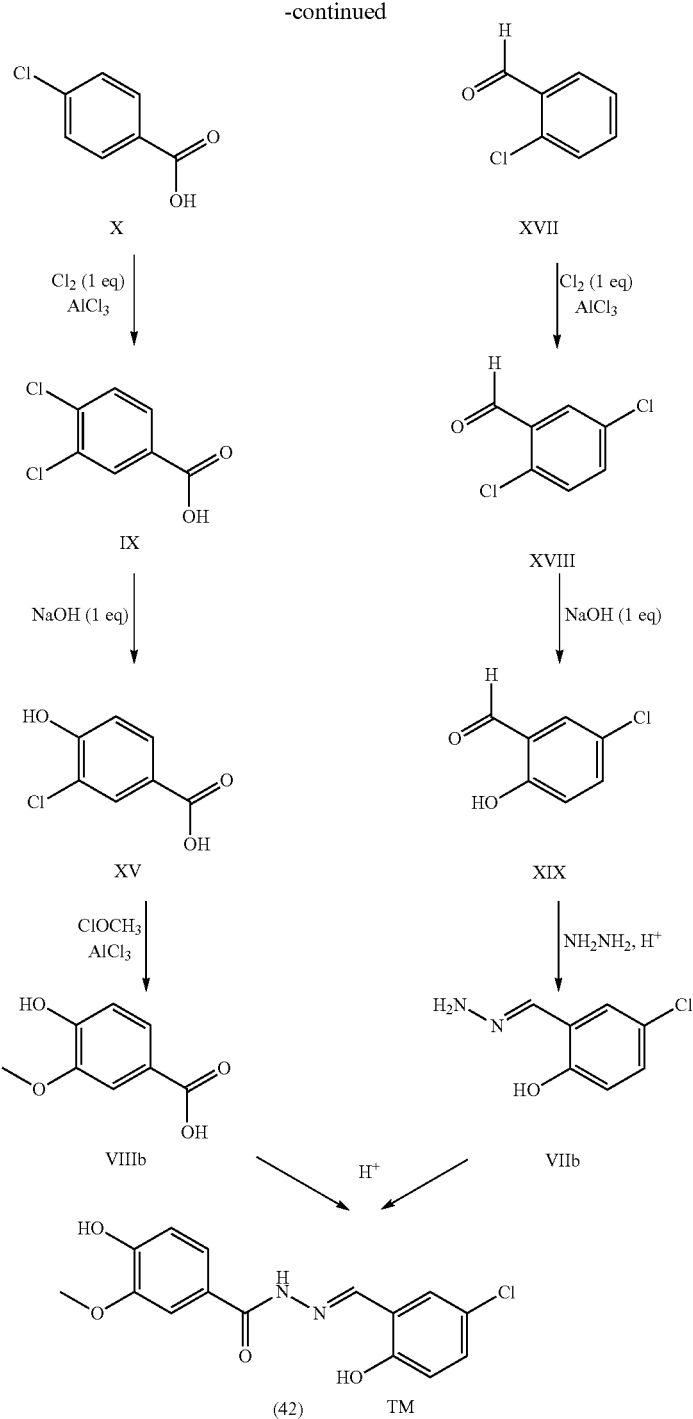

Chlorination of the toluene (XII) in the presence of a Lewis acid catalyst generates a compound of Formula (XI) (Scheme 5). Compound (XI) can be converted to Acid (X) by treatment with potassium permanganate. Chlorination of Compound (X) results in the formation of Compound (IX). Compound (IX) can be converted into Compound (XV) by the reaction with sodium hydroxide. Compound (XV) can be further converted into Compound (8b). Chlorination of toluene (XII) in the presence of a Lewis acid catalyst can also a generate compound of Formula (XVI). Oxidation of the Compound (XVI) in the presence of potassium permanganate leads to formation of aldehyde (XVIII). Compound (XVIII) can be converted into Compound (XIX) by the reaction with sodium hydroxide. Compound (XIX) can be further converted to a compound of Formula (VIIb) by treatment with hydrazine hydrate. Reaction between Compound (VIIb) and Compound (VIIIb) leads to formation of the Compound 24.

Compounds of the Formula (I) and their chemical analysis are shown in the Table 2.

TABLE 2

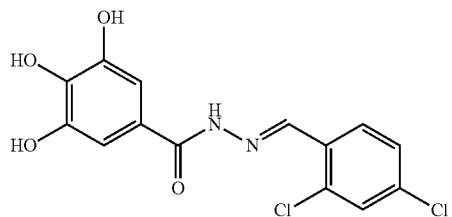

Chemical Formula: $C_{14}H_{10}Cl_2N_2O_4$
Exact Mass: 340.00
Molecular Weight: 341.15
m/z: 340.00 (100.0%), 342.00 (64.0%), 341.01 (15.4%),
344.00 (10.8%), 343.00 (10.3%), 342.01 (1.9%),
345.00 (1.6%)
Elemental Analysis: C, 49.29; H, 2.95; Cl, 20.78; N, 8.21;
O, 18.76

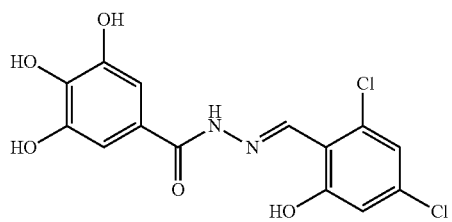

Chemical Formula: $C_{14}H_{10}Cl_2N_2O_5$
Exact Mass: 356.00
Molecular Weight: 357.15
m/z: 356.00 (100.0%), 357.99 (63.9%), 357.00 (15.4%),
359.99 (10.3%), 359.00 (10.0%), 358.00 (2.2 %),
360.99 (1.6%), 360.00 (1.4 %)
Elemental Analysis: C, 47.08; H, 2.82; Cl, 19.85; N, 7.84;
O, 22.40

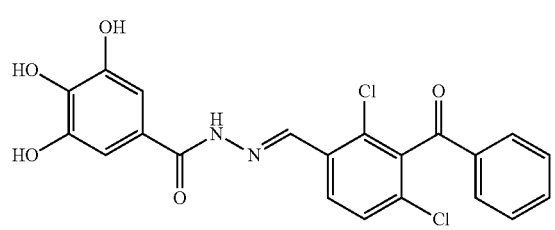

Chemical Formula: $C_{21}H_{14}Cl_2N_2O_5$
Exact Mass: 444.03
Molecular Weight: 445.25
m/z: 444.03 (100.0%), 446.03 (67.6%), 445.03 (23.8%),
447.03 (14.8%), 448.02 (10.2%), 449.03 (2.5 %),
448.03 (2.4%)
Elemental Analysis: C, 56.65; H, 3.17; Cl, 15.92; N, 6.29; O, 17.97

TABLE 2-continued

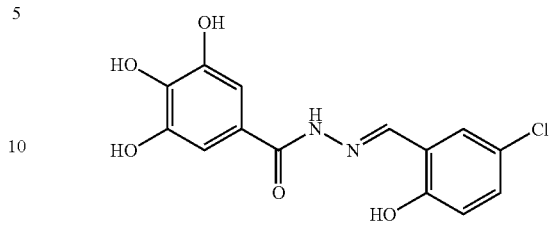

Chemical Formula: $C_{14}H_{11}ClN_2O_5$
Exact Mass: 322.04
Molecular Weight: 322.70
m/z: 322.04 (100.0%), 324.03 (32.0%), 323.04 (15.5%),
325.04 (5.1%), 324.04 (2.2%)
Elemental Analysis: C, 52.11; H, 3.44; Cl, 10.99;
N, 8.68; O, 24.79

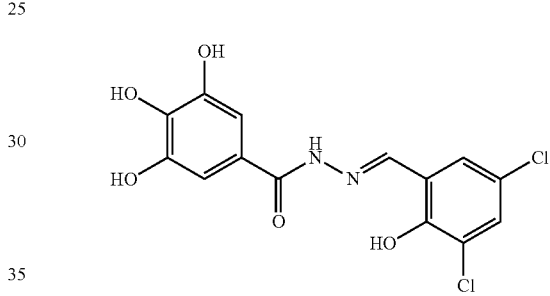

Chemical Formula: $C_{14}H_{10}Cl_2N_2O_5$
Exact Mass: 356.00
Molecular Weight: 357.15
m/z: 356.00 (100.0%), 357.99 (63.9%), 357.00 (15.4%),
359.99 (10.3%), 359.00 (10.0%), 358.00 (2.2 %),
360.99 (1.6%), 360.00 (1.4 %)
Elemental Analysis: C, 47.08; H, 2.82; Cl, 19.85; N, 7.84;
O, 22.40

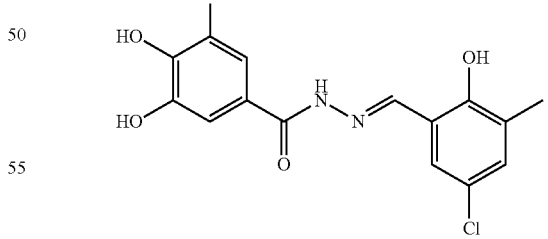

Chemical Formula: $C_{15}H_{13}ClN_2O_5$
Exact Mass: 336.05
Molecular Weight: 336.73
m/z: 336.05 (100%), 338.05 (32.1%), 337.05 (17.0%),
339.05 (5.5%), 338.06 (2.3%)
Elemental Analysis: C, 53.50; H, 3.89; Cl, 10.53; N, 8.32;
O, 23.76

TABLE 2-continued

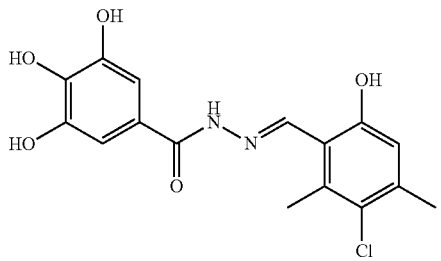

Chemical Formula: $C_{16}H_{15}ClN_2O_5$
Exact Mass: 350.07
Molecular Weight: 350.75
m/z: 350.07 (100.0%), 352.06 (32.0%), 351.07 (17.7%),
353.07 (5.8%), 352.07 (2.6%)
Elemental Analysis: C, 54.79; H, 4.31; Cl, 10.11; N, 7.99;
O, 22.81

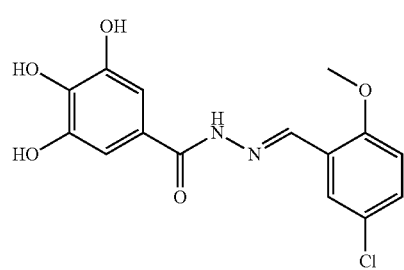

Chemical Formula: $C_{15}H_{13}ClN_2O_5$
Exact Mass: 336.05
Molecular Weight: 336.73
m/z: 336.05 (100.0%), 338.05 (32.1%), 337.05
(17.0%), 339.05 (5.5%), 338.06 (2.3%)
Elemental Analysis: C, 53.50; H, 3.89; Cl, 10.53;
N, 8.32; O, 23.76

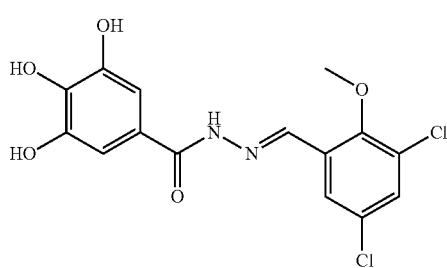

Chemical Formula: $C_{15}H_{12}Cl_2N_2O_5$
Exact Mass: 370.01
Molecular Weight: 371.17
m/z: 370.01 (100.0%), 372.01 (64.0%), 371.02 (16.6%),
373.01 (11.0%), 374.01 (11.0%), 372.02 (2.3%),
375.01 (1.7%)
Elemental Analysis: C, 48.54; H, 3.26; Cl, 19.10; N, 7.55;
O, 21.55

TABLE 2-continued

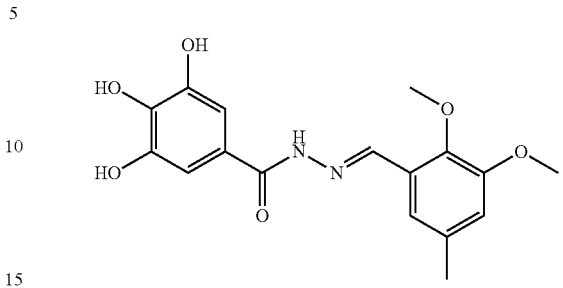

Chemical Formula: $C_{17}H_{18}N_2O_6$
Exact Mass: 346.12
Molecular Weight: 346.33
m/z: 346.12 (100.0%), 347.12 (18.8%), 348.12 (3.0%),
Elemental Analysis: C, 58.96; H, 5.24; N, 8.09; O, 27.72

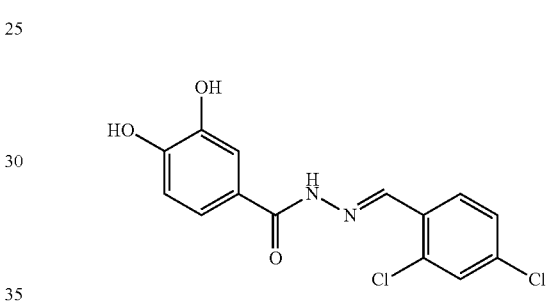

Chemical Formula: $C_{14}H_{10}Cl_2N_2O_3$
Exact Mass: 324.01
Molecular Weight: 325.15
m/z: 324.01 (100.0%), 326.00 (63.9%), 325.01 (15.4%),
328.00 (10.3%), 327.01 (9.9%), 326.01 (1.8%),
329.00 (1.6%), 328.01 (1.1%)
Elemental Analysis: C, 51.72; H, 3.10; Cl, 21.81; N, 8.62;
O, 14.76

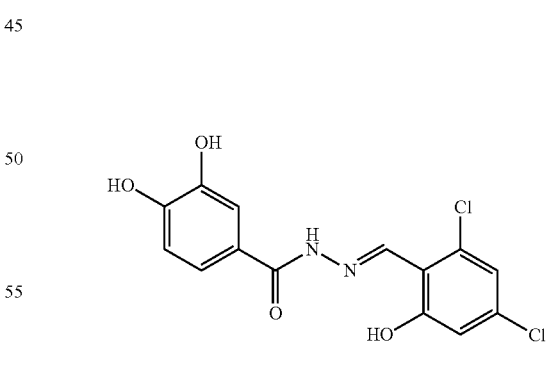

Chemical Formula: $C_{14}H_{10}Cl_2N_2O_4$
Exact Mass: 340.00
Molecular Weight: 341.15
m/z: 340.00 (100.0%), 342.00 (64.0%), 341.01 (15.4%),
344.00 (10.8%), 343.00 (10.3%), 342.01 (1.9%),
345.00 (1.6%)
Elemental Analysis: C, 49.29; H, 2.95; Cl, 20.78; N, 8.21;
O, 18.76

TABLE 2-continued

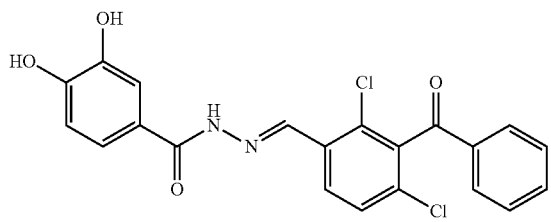

Chemical Formula: $C_{21}H_{14}Cl_2N_2O_4$
Exact Mass: 428.03
Molecular Weight: 429.25
m/z: 428.03 (100.0%), 430.03 (64.1%), 429.04 (23.0%),
431.03 (15.1%), 432.03 (10.8%), 430.04 (3.4%),
433.03 (2.4%), 432.04 (1.6%)
Elemental Analysis: C, 58.76; H, 3.29; Cl, 16.52; N, 6.53; O, 14.91

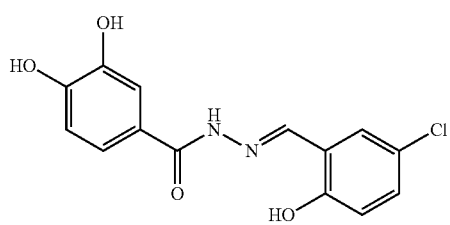

Chemical Formula: $C_{14}H_{11}ClN_2O_4$
Exact Mass: 306.04
Molecular Weight: 306.70
m/z: 306.04 (100.0%), 308.04 (32.9%), 307.04 (16.0%),
309.04 (4.9%), 308.05 (1.1%)
Elemental Analysis: C, 54.83; H, 3.62; Cl, 11.56; N, 9.13;
O, 20.87

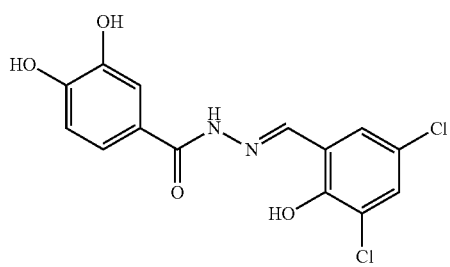

Chemical Formula: $C_{14}H_{10}Cl_2N_2O_4$
Exact Mass: 340.00
Molecular Weight: 341.15
m/z: 340.00 (100.0%), 342.00 (64.0%), 341.01 (15.4%),
344.00 (10.8%), 343.00 (10.3%), 342.01 (1.9%),
345.00 (1.6%)
Elemental Analysis: C, 49.29; H, 2.95; Cl, 20.78; N, 8.21;
O, 18.76

TABLE 2-continued

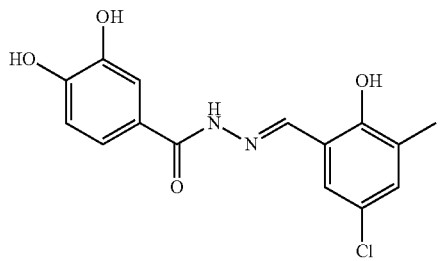

Chemical Formula: $C_{15}H_{13}ClN_2O_4$
Exact Mass: 320.06
Molecular Weight: 320.73
m/z: 320.06 (100.0%), 322.05 (32.0%), 321.06 (16.5%),
323.06 (5.4%), 322.06 (2.2%)
Elemental Analysis: C, 56.17; H, 4.09; Cl, 11.05; N, 8.73;
O, 19.95

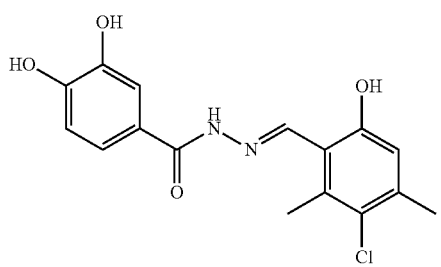

Chemical Formula: $C_{16}H_{15}ClN_2O_4$
Exact Mass: 334.07
Molecular Weight: 334.75
m/z: 334.07 (100.0%), 336.07 (32.1%), 335.08 (17.6%),
337.07 (5.8%), 336.08 (2.3%)
Elemental Analysis: C, 57.41; H, 4.52; Cl, 10.59;
N, 8.37; O, 19.12

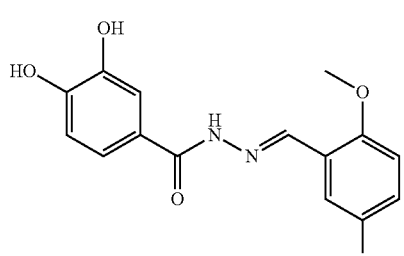

Chemical Formula: $C_{15}H_{13}ClN_2O_4$
Exact Mass: 320.06
Molecular Weight: 320.73
m/z: 320.06 (100.0%), 322.05 (32.0%), 321.06
(16.5%), 323.06 (5.4%), 322.06 (2.2%)
Elemental Analysis: C, 56.17; H, 4.09;
Cl, 11.05; N, 8.73; O, 19.95

TABLE 2-continued

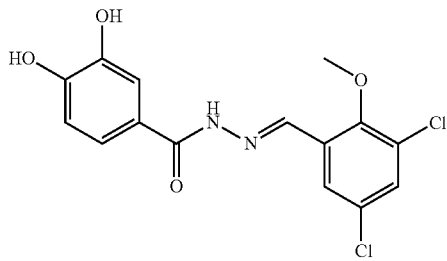

Chemical Formula: $C_{15}H_{12}Cl_2N_2O_4$
Exact Mass: 354.02
Molecular Weight: 355.17
m/z: 354.02 (100.0%), 356.01 (63.9%), 355.02 (16.5%),
357.02 (10.6%), 358.01 (10.3%), 356.02 (2.2%),
359.01 (1.7%), 358.02 (1.3%)
Elemental Analysis: C, 50.72; H, 3.41; Cl, 19.96; N, 7.89;
O, 18.02

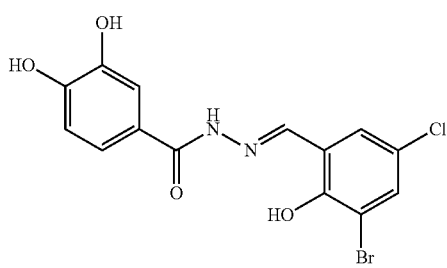

Chemical Formula: $C_{14}H_{10}BrClN_2O_4$
Exact Mass: 383.95
Molecular Weight: 385.60
m/z: 385.95 (100.0%), 383.95 (77.3%), 387.95 (25.0%),
386.95 (16.1%), 384.95 (12.3%), 388.95 (3.7%),
385.96 (1.5%), 387.96 (1.1%)
Elemental Analysis: C, 43.61; H, 2.61; Br 20.72; Cl, 9.19;
N, 7.26; O, 16.60

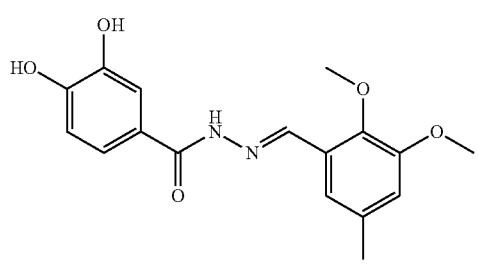

Chemical Formula: $C_{17}H_{18}N_2O_5$
Exact Mass: 330.12
Molecular Weight: 330.34
m/z: 330.12 (100.0%), 331.12 (19.1%), 332.13 (2.7%)
Elemental Analysis: C, 61.81; H, 5.49; N, 8.48; O, 24.22

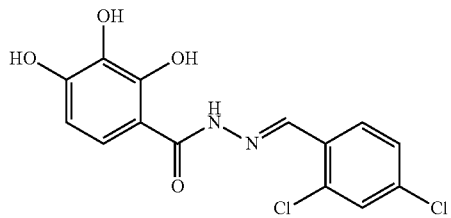

Chemical Formula: $C_{14}H_{10}Cl_2N_2O_4$
Exact Mass: 340.00
Molecular Weight: 341.15
m/z: 340.00 (100.0%), 342.00 (64.0%), 341.01 (15.4%),
344.00 (10.8%), 343.00 (10.3%), 342.01 (1.9%),
345.00 (1.6%)
Elemental Analysis: C, 49.29; H, 2.95; Cl, 20.78; N, 8.21;
O, 18.76

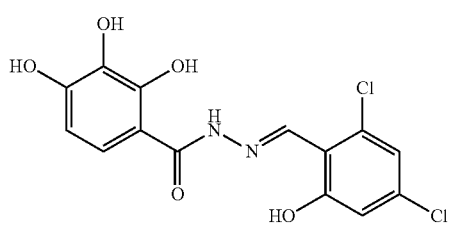

Chemical Formula: $C_{14}H_{10}Cl_2N_2O_5$
Exact Mass: 356.00
Molecular Weight: 357.15
m/z: 356.00 (100.0%), 357.99 (63.9%), 357.00 (15.4%),
359.99 (10.3%), 359.00 (10.0%), 358.00 (2.2%),
360.99 (1.6%), 360.00 (1.4%)
Elemental Analysis: C, 47.08; H, 2.82; Cl, 19.85; N, 7.84;
O, 22.40

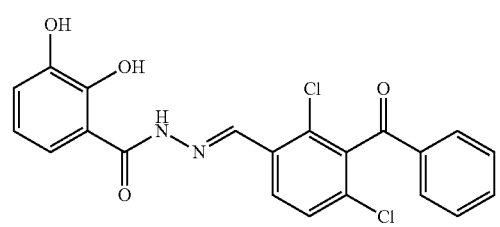

Chemical Formula: $C_{21}H_{14}Cl_2N_2O_4$
Exact Mass: 428.03
Molecular Weight: 429.25
m/z: 428.03 (100.0%), 430.03 (64.1%), 429.04 (23.0%),
431.03 (15.1%), 432.03 (10.8%), 430.04 (3.4%),
433.03 (2.4%), 432.04 (1.6%)
Elemental Analysis: C, 58.76; H, 3.29; Cl, 16.52; N, 6.53;
O, 14.91

TABLE 2-continued

Chemical Formula: C$_{14}$H$_{11}$ClN$_2$O$_5$
Exact Mass: 322.04
Molecular Weight: 322.70
m/z: 322.04 (100.0%), 324.03 (32.0%), 323.04 (15.5%),
325.04 (5.1%), 324.04 (2.2%)
Elemental Analysis: C, 52.11; H, 3.44; Cl, 10.99; N, 8.68;
O, 24.79

Chemical Formula: C$_{14}$H$_{10}$Cl$_2$N$_2$O$_5$
Exact Mass: 356.00
Molecular Weight: 357.15
m/z: 356.00 (100.0%), 357.99 (63.9%), 357.00 (15.4%),
359.99 (10.3%), 359.00 (10.0%), 358.00 (2.2%),
360.99 (1.6%), 360.00 (1.4%)
Elemental Analysis: C, 47.08; H, 2.82; Cl, 19.85; N, 7.84;
O, 22.40

Chemical Formula: C$_{15}$H$_{13}$ClN$_2$O$_5$
Exact Mass: 336.05
Molecular Weight: 336.73
m/z: 336.05 (100.0%), 338.05 (32.1%), 337.05 (17.0%),
339.05 (5.5%), 338.06 (2.3%)
Elemental Analysis: C, 53.50; H, 3.89; Cl, 10.53; N, 8.32;
O, 23.76

TABLE 2-continued

Chemical Formula: C$_{16}$H$_{15}$ClN$_2$O$_5$
Exact Mass: 350.07
Molecular Weight: 350.75
m/z: 350.07 (100.0%), 352.06 (32.0%), 351.07 (17.7%),
353.07 (5.8%), 352.07 (2.6%)
Elemental Analysis: C, 54.79; H, 4.31; Cl, 10.11; N, 7.99;
O, 22.81

Chemical Formula: C$_{15}$H$_{13}$ClN$_2$O$_5$
Exact Mass: 336.05
Molecular Weight: 336.73
m/z: 336.05 (100.0%), 338.05 (32.1%),
337.05 (17.0%), 339.05 (5.5%), 338.06 (2.3%)
Elemental Analysis: C, 53.50; H, 3.89; Cl, 10.53;
N, 8.32; O, 23.76

Chemical Formula: C$_{15}$H$_{12}$Cl$_2$N$_2$O$_5$
Exact Mass: 370.01
Molecular Weight: 371.17
m/z: 370.01 (100.0%), 372.01 (64.0%), 371.02 (16.6%),
373.01 (11.0%), 374.01 (11.0%), 372.02 (2.3%),
375.01 (1.7%)
Elemental Analysis: C, 48.54; H, 3.26; Cl, 19.10; N, 7.55;
O, 21.55

TABLE 2-continued

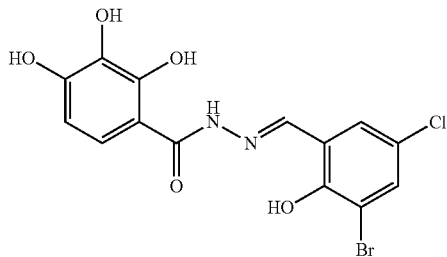

Chemical Formula: $C_{14}H_{10}BrClN_2O_5$
Exact Mass: 399.95
Molecular Weight: 401.60
m/z: 401.94 (100.0%), 399.95 (77.4%), 403.94 (24.2%),
402.95 (15.6%), 400.95 (12.0%), 404.94 (3.8%),
403.95 (2.1%), 401.95 (1.7%)
Elemental Analysis: C, 41.87; H, 2.51; Br, 19.90; Cl, 8.83;
N, 6.98; O, 19.92

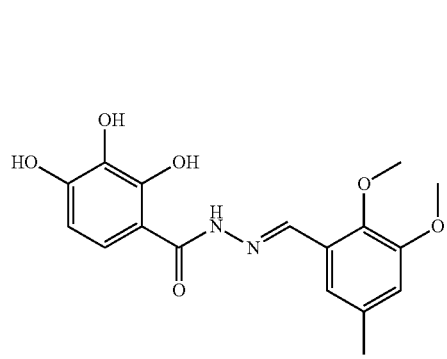

Chemical Formula: $C_{17}H_{18}N_2O_6$
Exact Mass: 346.12
Molecular Weight: 346.33
m/z: 346.12 (100.0%), 347.12 (18.8%), 348.12 (3.0%)
Elemental Analysis: C, 58.96; H, 5.24; N, 8.09; O, 27.72

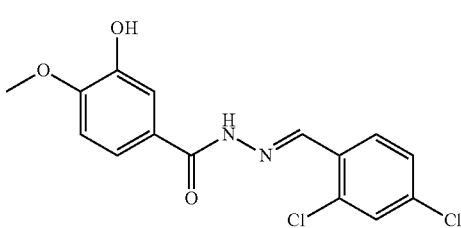

Chemical Formula: $C_{15}H_{12}Cl_2N_2O_3$
Exact Mass: 338.02
Molecular Weight: 339.17
m/z: 338.02 (100.0%), 340.02 (64.0%), 339.03 (16.5%),
341.02 (10.9%), 342.02 (10.7%), 340.03 (1.9%),
343.02 (1.7%)
Elemental Analysis: C, 53.12; H, 3.57; Cl, 20.91; N, 8.26;
O, 14.15

TABLE 2-continued

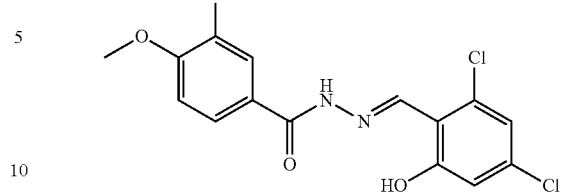

Chemical Formula: $C_{15}H_{12}Cl_2N_2O_4$
Exact Mass: 354.02
Molecular Weight: 355.17
m/z: 354.02 (100.0%), 356.01 (63.9%), 355.02 (16.5%),
357.02 (10.6%), 358.01 (10.3%), 356.02 (2.2%),
359.01 (1.7%), 358.02 (1.3%)
Elemental Analysis: C, 50.72; H, 3.41; Cl, 19.96; N, 7.89;
O, 18.02

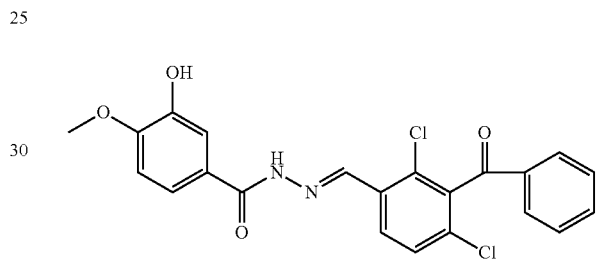

Chemical Formula: $C_{22}H_{16}Cl_2N_2O_4$
Exact Mass: 442.05
Molecular Weight: 443.28
m/z: 442.05 (100.0%), 444.05 (64.9%), 443.05 (24.9%),
445.05 (15.5%), 446.04 (10.2%), 444.06 (2.8%),
447.05 (2.6%), 446.05 (2.4%)
Elemental Analysis: C, 59.61; H, 3.64; Cl, 16.00; N, 6.32; O, 14.44

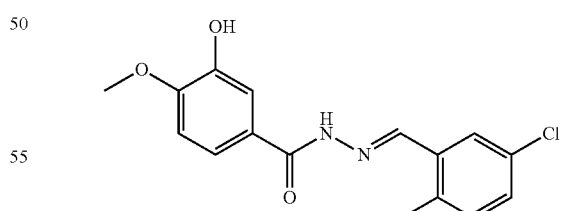

Chemical Formula: $C_{15}H_{13}ClN_2O_4$
Exact Mass: 320.06
Molecular Weight: 320.73
m/z: 320.06 (100.0%), 322.05 (32.0%), 321.06 (16.5%),
323.06 (5.4%), 322.06 (2.2%)
Elemental Analysis: C, 56.17; H, 4.09; Cl, 11.05; N, 8.73;
O, 19.95

TABLE 2-continued

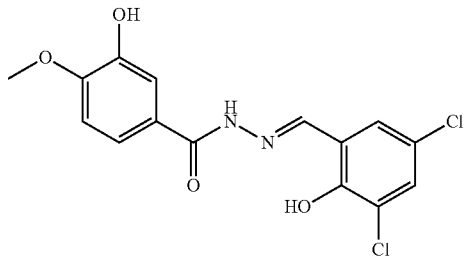

Chemical Formula: $C_{15}H_{12}Cl_2N_2O_4$
Exact Mass: 354.02
Molecular Weight: 355.17
m/z: 354.02 (100.0%), 356.01 (63.9%), 355.02 (16.5%),
357.02 (10.6%), 358.01 (10.3%), 356.02 (2.2%),
359.01 (1.7%), 358.02 (1.3%)
Elemental Analysis: C, 50.72; H, 3.41; Cl, 19.96; N, 7.89;
O, 18.02

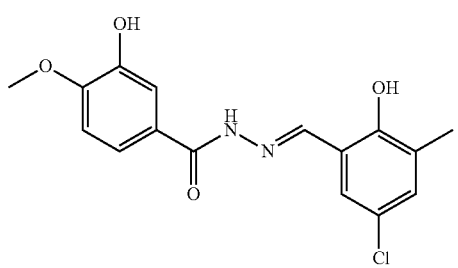

Chemical Formula: $C_{16}H_{15}ClN_2O_4$
Exact Mass: 334.07
Molecular Weight: 334.75
m/z: 334.07 (100.0%), 336.07 (32.1%), 335.08 (17.6%),
337.07 (5.8%), 336.08 (2.3%)
Elemental Analysis: C, 57.41; H, 4.52; Cl, 10.59; N, 8.37;
O, 19.12

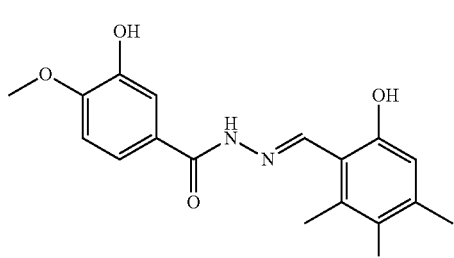

Chemical Formula: $C_{17}H_{17}ClN_2O_4$
Exact Mass: 348.09
Molecular Weight: 348.78
m/z: 348.09 (100.0%), 350.08 (32.0%), 349.09 (18.7%),
351.09 (6.0%), 350.09 (2.6%)
Elemental Analysis: C, 58.54; H, 4.91; Cl, 10.16; N, 8.03;
O, 18.35

TABLE 2-continued

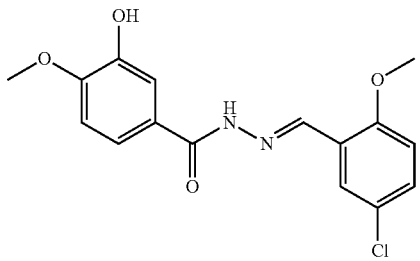

Chemical Formula: $C_{16}H_{15}ClN_2O_4$
Exact Mass: 334.07
Molecular Weight: 334.75
m/z: 334.07 (100.0%), 336.07 (32.1%), 335.08
(17.6%), 337.07 (5.8%), 336.08 (2.3%)
Elemental Analysis: C, 57.41; H, 4.52; Cl, 10.59;
N, 8.37; O, 19.12

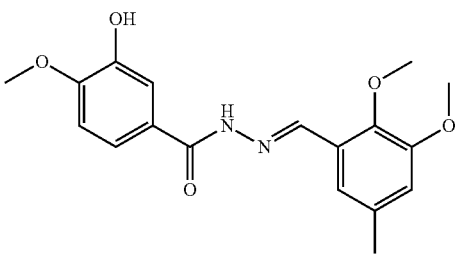

Chemical Formula: $C_{18}H_{20}N_2O_5$
Exact Mass: 344.14
Molecular Weight: 344.36
m/z: 344.14 (100.0%), 345.14 (19.9%), 346.14 (3.0%)
Elemental Analysis: C, 62.78; H, 5.85; N, 8.13; O, 23.23

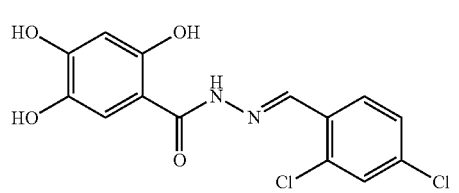

Chemical Formula: $C_{14}H_{10}Cl_2N_2O_4$
Exact Mass: 340.00
Molecular Weight: 341.15
m/z: 340.00 (100.0%), 342.00 (64.0%), 341.01 (15.4%),
344.00 (10.8%), 343.00 (10.3%), 342.01 (1.9%),
345.00 (1.6%)
Elemental Analysis: C, 49.29; H, 2.95; Cl, 20.78; N, 8.21;
O, 18.76

TABLE 2-continued

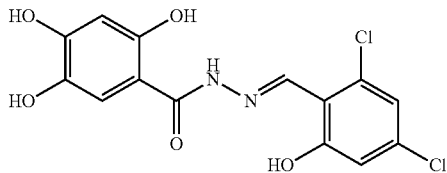

Chemical Formula: $C_{14}H_{10}Cl_2N_2O_5$
Exact Mass: 356.00
Molecular Weight: 357.15
m/z: 356.00 (100.0%), 357.99 (63.9%), 357.00 (15.4%), 359.99 (10.3%), 359.00 (10.0%), 358.00 (2.2%), 360.99 (1.6%), 360.00 (1.4%)
Elemental Analysis: C, 47.08; H, 2.82; Cl, 19.85; N, 7.84; O, 22.40

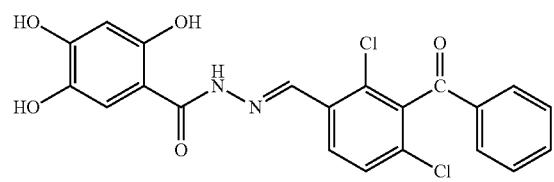

Chemical Formula: $C_{21}H_{14}Cl_2N_2O_5$
Exact Mass: 444.03
Molecular Weight: 445.25
m/z: 444.03 (100.0%), 446.03 (67.6%), 445.03 (23.8%), 447.03 (14.8%), 448.02 (10.2%), 449.03 (2.5%), 448.03 (2.4%)
Elemental Analysis: C, 56.65; H, 3.17; Cl, 15.92; N, 6.29; O, 17.97

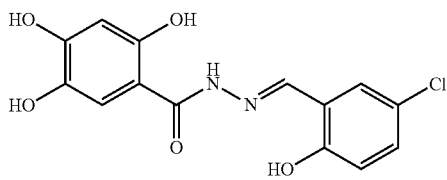

Chemical Formula: $C_{14}H_{11}ClN_2O_5$
Exact Mass: 322.04
Molecular Weight: 322.70
m/z: 322.04 (100.0%), 324.03 (32.0%), 323.04 (15.5%), 325.04 (5.1%), 324.04 (2.2%)
Elemental Analysis: C, 52.11; H, 3.44; Cl, 10.99; N, 8.68; O, 24.79

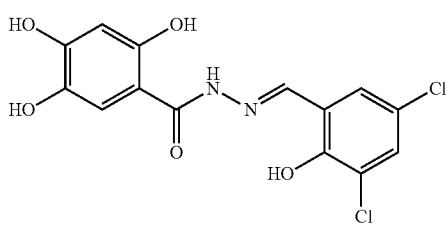

Chemical Formula: $C_{14}H_{10}Cl_2N_2O_5$
Exact Mass: 356.00
Molecular Weight: 357.15
m/z: 356.00 (100.0%), 357.99 (63.9%), 357.00 (15.4%), 359.99 (10.3%), 359.00 (10.0%), 358.00 (2.2%), 360.99 (1.6%), 360.00 (1.4%)
Elemental Analysis: C, 47.08; H, 2.82; Cl, 19.85; N, 7.84; O, 22.40

TABLE 2-continued

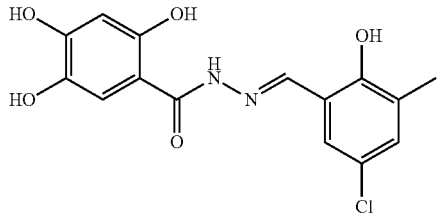

Chemical Formula: $C_{15}H_{13}ClN_2O_5$
Exact Mass: 336.05
Molecular Weight: 336.73
m/z: 336.05 (100.0%), 338.05 (32.1%), 337.05 (17.0%), 339.05 (5.5%), 338.06 (2.3%)
Elemental Analysis: C, 53.50; H, 3.89; Cl, 10.53; N, 8.32; O, 23.76

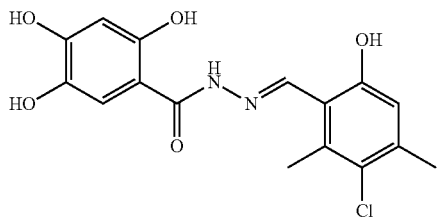

Chemical Formula: $C_{16}H_{15}ClN_2O_5$
Exact Mass: 350.07
Molecular Weight: 350.75
m/z: 350.07 (100.0%), 352.06 (32.0%), 351.07 (17.7%), 353.07 (5.8%), 352.07 (2.6%)
Elemental Analysis: C, 54.79; H, 4.31; Cl, 10.11; N, 7.99; O, 22.81

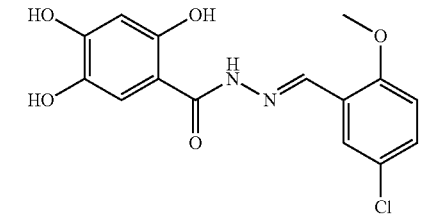

Chemical Formula: $C_{15}H_{13}ClN_2O_5$
Exact Mass: 336.05
Molecular Weight: 336.73
m/z: 336.05 (100.0%), 338.05 (32.1%), 337.05 (17.0%), 339.05 (5.5%), 338.06 (2.3%)
Elemental Analysis: C, 53.50; H, 3.89; Cl, 10.53; N, 8.32; O, 23.76

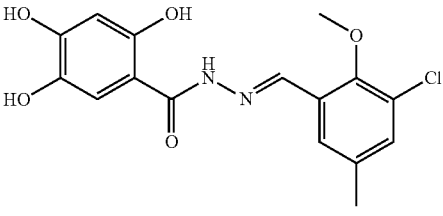

Chemical Formula: $C_{16}H_{15}ClN_2O_5$
Exact Mass: 350.07
Molecular Weight: 350.75
m/z: 350.07 (100.0%), 352.06 (32.0%), 351.07 (17.7%), 353.07 (5.8%), 352.07 (2.6%)
Elemental Analysis: C, 54.79; H, 4.31; Cl, 10.11; N, 7.99; O, 22.81

TABLE 2-continued

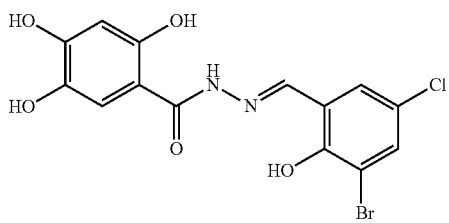

Chemical Formula: $C_{14}H_{10}BrClN_2O_5$
Exact Mass: 399.95
Molecular Weight: 401.60
m/z: 401.94 (100.0%), 399.95 (77.4%), 403.94 (24.2%),
402.95 (15.6%), 400.95 (12.0%), 404.94 (3.8%),
403.95 (2.1%), 401.95 (1.7%)
Elemental Analysis: C, 41.87; H, 2.51; Br, 19.90;
Cl, 8.83; N, 6.98; O, 19.92

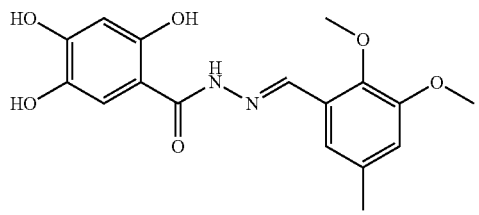

Chemical Formula: $C_{17}H_{18}N_2O_6$
Exact Mass: 346.12
Molecular Weight: 346.33
m/z: 346.12 (100.0%), 347.12 (18.8%), 348.12 (3.0%)
Elemental Analysis: C, 58.96; H, 5.24; N, 8.09; O, 27.72

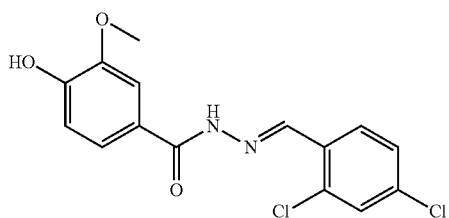

Chemical Formula: $C_{15}H_{12}Cl_2N_2O_3$
Exact Mass: 338.02
Molecular Weight: 339.17
m/z: 338.02 (100.0%), 340.02 (64.0%), 339.03 (16.5%),
341.02 (10.9%), 342.02 (10.7%), 340.03 (1.9%),
343.02 (1.7%)
Elemental Analysis: C, 53.12; H, 3.57; Cl, 20.91; N, 8.26;
O, 14.15

TABLE 2-continued

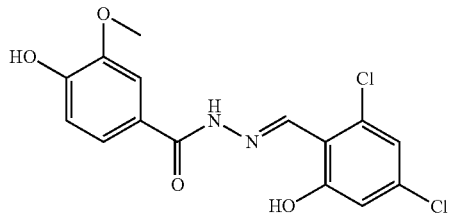

Chemical Formula: $C_{15}H_{12}Cl_2N_2O_4$
Exact Mass: 354.02
Molecular Weight: 355.17
m/z: 354.02 (100.0%), 356.01 (63.9%), 355.02 (16.5%),
357.02 (10.6%), 358.01 (10.3%), 356.02 (2.2%),
359.01 (1.7%), 358.02 (1.3%)
Elemental Analysis: C, 50.72; H, 3.41; Cl, 19.96; N, 7.89;
O, 18.02

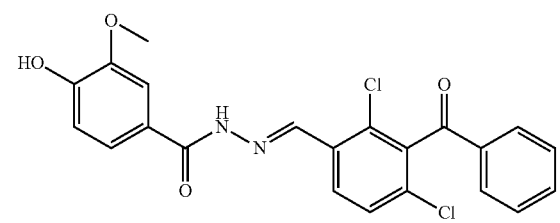

Chemical Formula: $C_{22}H_{16}Cl_2N_2O_4$
Exact Mass: 442.05
Molecular Weight: 443.28
m/z: 442.05 (100.0%), 444.05 (64.9%), 443.05 (24.9%),
445.05 (15.5%), 446.04 (10.2%), 444.06 (2.8%),
447.05 (2.6%), 446.05 (2.4%)
Elemental Analysis: C, 59.61; H, 3.64; Cl, 16.00; N, 6.32; O, 14.44

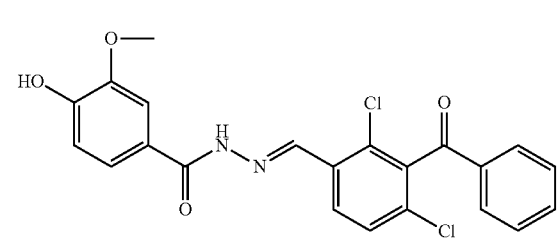

Chemical Formula: $C_{22}H_{16}Cl_2N_2O_4$
Exact Mass: 442.05
Molecular Weight: 443.28
m/z: 442.05 (100.0%), 444.05 (64.9%), 443.05 (24.9%),
445.05 (15.5%), 446.04 (10.2%), 444.06 (2.8%),
447.05 (2.6%), 446.05 (2.4%)
Elemental Analysis: C, 59.61; H, 3.64; Cl, 16.00; N, 6.32; O, 14.44

TABLE 2-continued

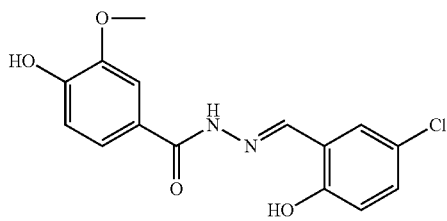

Chemical Formula: $C_{15}H_{13}ClN_2O_4$
Exact Mass: 320.06
Molecular Weight: 320.73
m/z: 320.06 (100.0%), 322.05 (32.0%), 321.06 (16.5%), 323.06 (5.4%), 322.06 (2.2%)
Elemental Analysis: C, 56.17; H, 4.09; Cl, 11.05; N, 8.73; O, 19.95

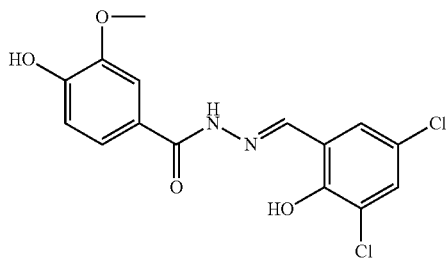

Chemical Formula: $C_{15}H_{12}Cl_2N_2O_4$
Exact Mass: 354.02
Molecular Weight: 355.17
m/z: 354.02 (100.0%), 356.01 (63.9%), 355.02 (16.5%), 357.02 (10.6%), 358.01 (10.3%), 356.02 (2.2%), 359.01 (1.7%), 358.02 (1.3%)
Elemental Analysis: C, 50.72; H, 3.41; Cl, 19.96; N, 7.89; O, 18.02

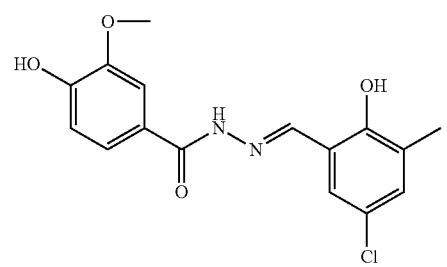

Chemical Formula: $C_{16}H_{15}ClN_2O_4$
Exact Mass: 334.07
Molecular Weight: 334.75
m/z: 334.07 (100.0%), 336.07 (32.1%), 335.08 (17.6%), 337.07 (5.8%), 336.08 (2.3%)
Elemental Analysis: C, 57.41; H, 4.52; Cl, 10.59; N, 8.37; O, 19.12

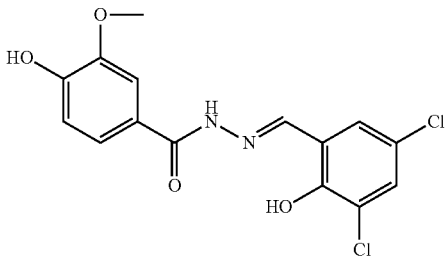

Chemical Formula: $C_{15}H_{12}Cl_2N_2O_4$
Exact Mass: 354.02
Molecular Weight: 355.17
m/z: 354.02 (100.0%), 356.01 (63.9%), 355.02 (16.5%), 357.02 (10.6%), 358.01 (10.3%), 356.02 (2.2%), 359.01 (1.7%), 358.02 (1.3%)
Elemental Analysis: C, 50.72; H, 3.41; Cl, 19.96; N, 7.89; O, 18.02

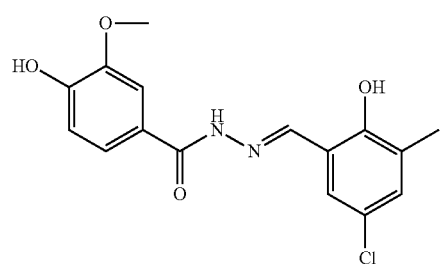

Chemical Formula: $C_{16}H_{15}ClN_2O_4$
Exact Mass: 334.07
Molecular Weight: 334.75
m/z: 334.07 (100.0%), 336.07 (32.1%), 335.08 (17.6%), 337.07 (5.8%), 336.08 (2.3%)
Elemental Analysis: C, 57.41; H, 4.52; Cl, 10.59; N, 8.37; O, 19.12

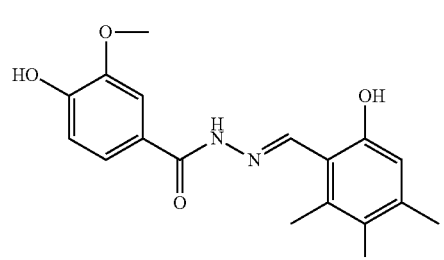

Chemical Formula: $C_{17}H_{17}ClN_2O_4$
Exact Mass: 348.09
Molecular Weight: 348.78
m/z: 348.09 (100.0%), 350.08 (32.0%), 349.09 (18.7%), 351.09 (6.0%), 350.09 (2.6%)
Elemental Analysis: C, 58.54; H, 4.91; Cl, 10.16; N, 8.03; O, 18.35

TABLE 2-continued

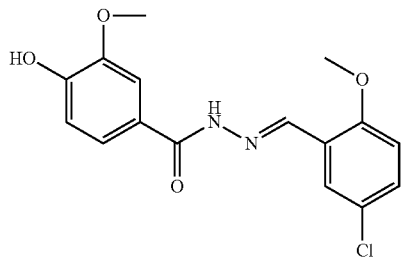

Chemical Formula: $C_{16}H_{15}ClN_2O_4$
Exact Mass: 334.07
Molecular Weight: 334.75
m/z: 334.07 (100.0%), 336.07 (32.1%), 335.08
(17.6%), 337.07 (5.8%), 336.08 (2.3%)
Elemental Analysis: C, 57.41; H, 4.52; Cl, 10.59;
N, 8.37; O, 19.12

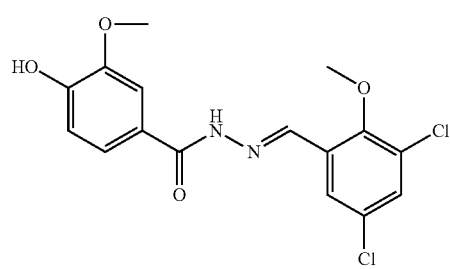

Chemical Formula: $C_{16}H_{14}Cl_2N_2O_4$
Exact Mass: 368.03
Molecular Weight: 369.20
m/z: 368.03 (100.0%), 370.03 (64.1%), 369.04 (17.6%),
371.03 (11.6%), 372.03 (10.8%), 370.04 (2.3%),
373.03 (1.8%)
Elemental Analysis: C, 52.05; H, 3.82; Cl, 19.21; N, 7.59;
O, 17.33

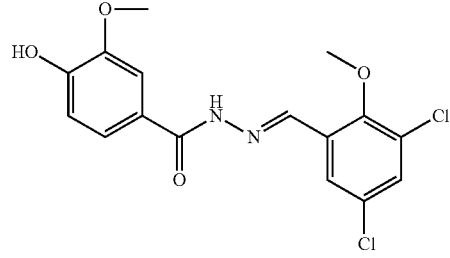

Chemical Formula: $C_{16}H_{14}Cl_2N_2O_4$
Exact Mass: 368.03
Molecular Weight: 369.20
m/z: 368.03 (100.0%), 370.03 (64.1%), 369.04 (17.6%),
371.03 (11.6%), 372.03 (10.8%), 370.04 (2.3%),
373.03 (1.8%)
Elemental Analysis: C, 52.05; H, 3.82; Cl, 19.21;
N, 7.59; O, 17.33

TABLE 2-continued

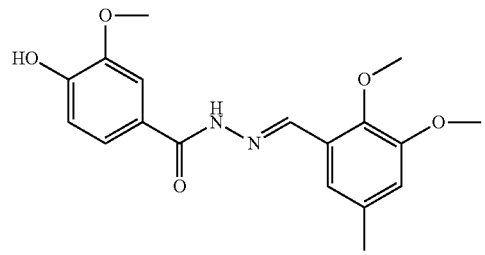

Chemical Formula: $C_{18}H_{20}N_2O_5$
Exact Mass: 344.14
Molecular Weight: 344.36
m/z: 344.14 (100.0%), 345.14 (19.9%), 346.14 (3.0%)
Elemental Analysis: C, 62.78; H, 5.85; N, 8.13; O, 23.23

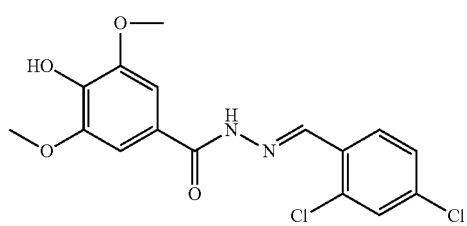

Chemical Formula: $C_{16}H_{14}Cl_2N_2O_4$
Exact Mass: 368.03
Molecular Weight: 369.20
m/z: 368.03 (100.0%), 370.03 (64.1%), 369.04 (17.6%),
371.03 (11.6%), 372.03 (10.8%), 370.04 (2.3%),
373.03 (1.8%)
Elemental Analysis: C, 52.05; H, 3.82; Cl, 19.21; N, 7.59;
O, 17.33

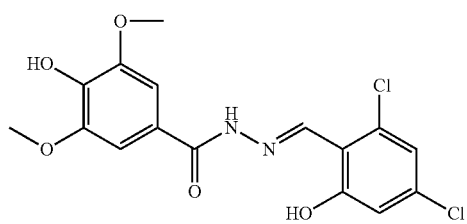

Chemical Formula: $C_{16}H_{14}Cl_2N_2O_5$
Exact Mass: 384.03
Molecular Weight: 385.20
m/z: 384.03 (100.0%), 386.03 (66.5%), 385.03 (18.4%),
387.03 (11.3%), 388.02 (10.2%), 389.03 (1.9%),
388.03 (1.7%)
Elemental Analysis: C, 49.89; H, 3.66; Cl, 18.41; N, 7.27;
O, 20.77

TABLE 2-continued

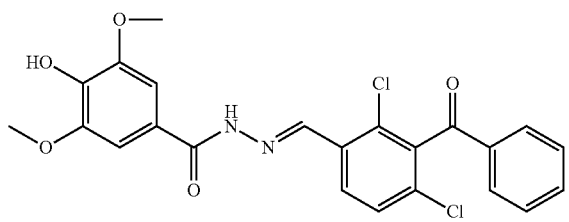

Chemical Formula: $C_{23}H_{18}Cl_2N_2O_5$
Exact Mass: 472.06
Molecular Weight: 473.31
m/z: 472.06 (100.0%), 474.06 (65.1%), 473.06 (25.8%),
475.06 (16.2%), 476.05 (10.2%), 474.07 (3.1%),
477.06 (2.8%), 476.06 (2.7%)
Elemental Analysis: C, 58.37; H, 3.83; Cl, 14.98; N, 5.92; O, 16.90

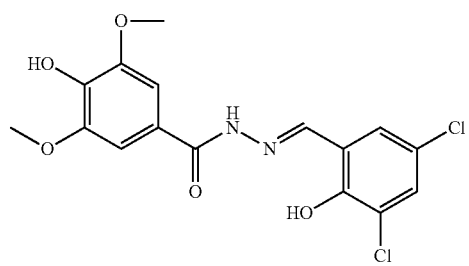

Chemical Formula: $C_{16}H_{14}Cl_2N_2O_5$
Exact Mass: 384.03
Molecular Weight: 385.20
m/z: 384.03 (100.0%), 386.03 (66.5%), 385.03 (18.4%),
387.03 (11.3%), 388.02 (10.2%), 389.03 (1.9%),
388.03 (1.7%)
Elemental Analysis: C, 49.89; H, 3.66; Cl, 18.41; N, 7.27;
O, 20.77

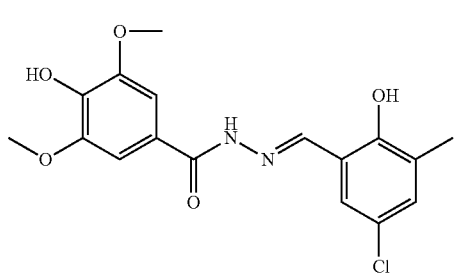

Chemical Formula: $C_{17}H_{17}ClN_2O_5$
Exact Mass: 364.08
Molecular Weight: 364.78
m/z: 364.08 (100.0%), 366.08 (32.1%), 365.09 (18.8%),
367.08 (6.2%), 366.09 (2.7%)
Elemental Analysis: C, 55.97; H, 4.70; Cl, 9.72; N, 7.68;
O, 21.93

TABLE 2-continued

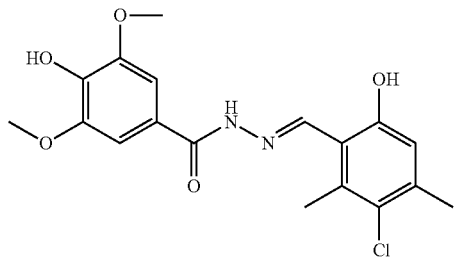

Chemical Formula: $C_{18}H_{19}ClN_2O_5$
Exact Mass: 378.10
Molecular Weight: 378.81
m/z: 378.10 (100.0%), 380.10 (34.9%), 379.10 (20.6%),
381.10 (6.4%)
Elemental Analysis: C, 57.07; H, 5.06; Cl, 9.36; N, 7.40;
O, 21.12

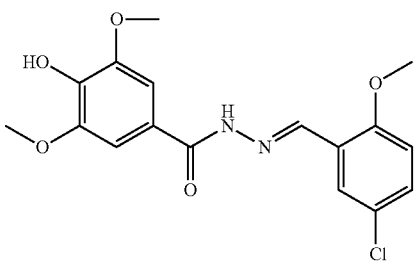

Chemical Formula: $C_{17}H_{17}ClN_2O_5$
Exact Mass: 364.08
Molecular Weight: 364.78
m/z: 364.08 (100.0%), 366.08 (32.1%), 365.09 (18.8%),
367.08 (6.2%), 366.09 (2.7%)
Elemental Analysis: C, 55.97; H, 4.70; Cl, 9.72; N, 7.68;
O, 21.93

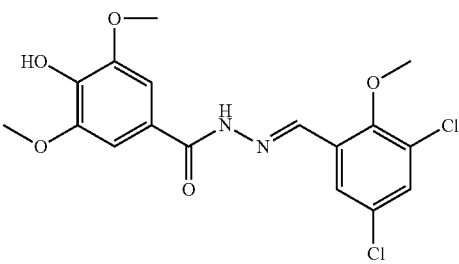

Chemical Formula: $C_{17}H_{16}Cl_2N_2O_5$
Exact Mass: 398.04
Molecular Weight: 399.23
m/z: 398.04 (100.0%), 400.04 (64.1%), 399.05 (18.8%),
401.04 (12.4%), 402.04 (11.0%), 400.05 (2.7%),
403.04 (1.9%), 402.05 (1.1%)
Elemental Analysis: C, 51.14; H, 4.04; Cl, 17.76; N, 7.02;
O, 20.04

TABLE 2-continued

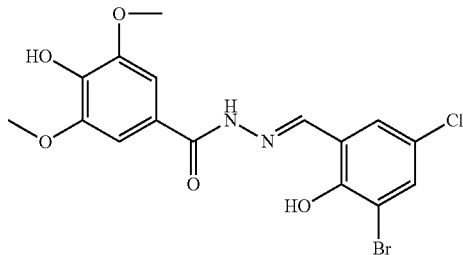

Chemical Formula: C₁₆H₁₄BrClN₂O₅
Exact Mass: 427.98
Molecular Weight: 429.65
m/z: 427.98 (100.0%), 429.98 (99.8%), 429.97 (32.0%),
431.97 (31.1%), 430.98 (22.8%), 428.98 (17.7%),
432.98 (5.8%), 431.98 (3.3%)
Elemental Analysis: C, 44.73; H, 3.28; Br, 18.60; Cl, 8.25;
N, 6.52; O, 18.62

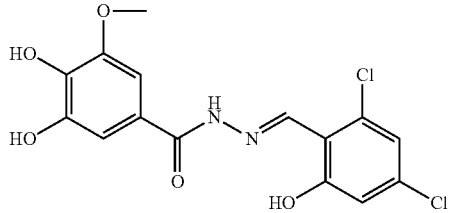

Chemical Formula: C₁₅H₁₂Cl₂N₂O₅
Exact Mass: 370.01
Molecular Weight: 371.17
m/z: 370.01 (100.0%), 372.01 (64.0%), 371.02 (16.6%),
373.01 (11.0%), 374.01 (11.0%), 372.02 (2.3%),
375.01 (1.7%)
Elemental Analysis: C, 48.54; H, 3.26; Cl, 19.10; N, 7.55;
O, 21.55

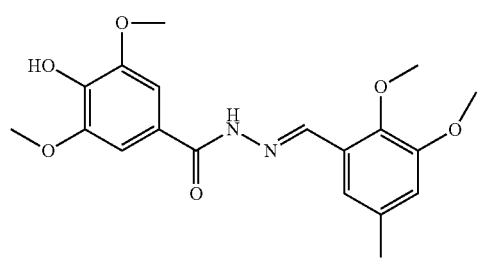

Chemical Formula: C₁₉H₂₂N₂O₆
Exact Mass: 374.15
Molecular Weight: 374.39
m/z: 374.15 (100.0%), 375.15 (21.0%), 376.15 (3.4%),
Elemental Analysis: C, 60.95; H, 5.92; N, 7.48; O, 25.64

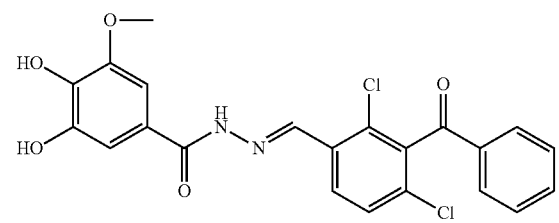

Chemical Formula: C₂₂H₁₆Cl₂N₂O₅
Exact Mass: 458.04
Molecular Weight: 459.28
m/z: 458.04 (100.0%), 460.04 (64.1%), 459.05 (24.2%),
461.04 (15.8%), 462.04 (11.0%), 460.05 (3.8%),
463.04 (2.5%), 462.05 (1.8%)
Elemental Analysis: C, 57.53; H, 3.51; Cl, 15.44; N, 6.10; O, 17.42

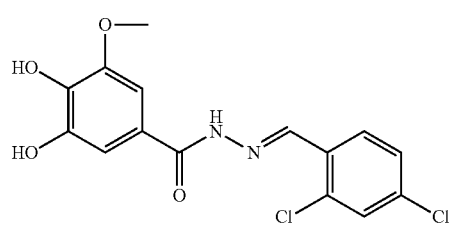

Chemical Formula: C₁₅H₁₂Cl₂N₂O₄
Exact Mass: 354.02
Molecular Weight: 355.17
m/z: 354.02 (100.0%), 356.01 (63.9%), 355.02 (16.5%),
357.02 (10.6%), 358.01 (10.3%), 356.02 (2.2%),
359.01 (1.7%), 358.02 (1.3%)
Elemental Analysis: C, 50.72; H, 3.41; Cl, 19.96; N, 7.89;
O, 18.02

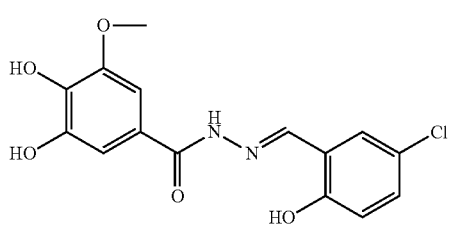

Chemical Formula: C₁₅H₁₃ClN₂O₅
Exact Mass: 336.05
Molecular Weight: 336.73
m/z: 336.05 (100.0%), 338.05 (32.1%), 337.05 (17.0%),
339.05 (5.5%), 338.06 (2.3%)
Elemental Analysis: C, 53.50; H, 3.89; Cl, 10.53; N, 8.32;
O, 23.76

TABLE 2-continued

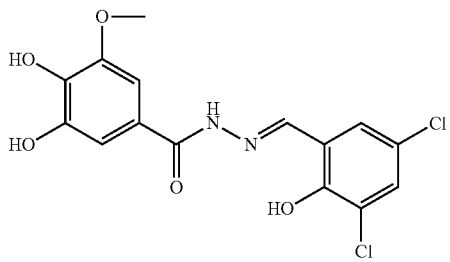

Chemical Formula: $C_{15}H_{12}Cl_2N_2O_5$
Exact Mass: 370.01
Molecular Weight: 371.17
m/z: 370.10 (100.0%), 372.01 (64.0%), 371.02 (16.6%),
373.01 (11.0%), 374.01 (11.0%), 372.02 (2.3%),
375.01 (1.7%)
Elemental Analysis: C, 48.54; H, 3.26; Cl, 19.10; N, 7.55;
O, 21.55

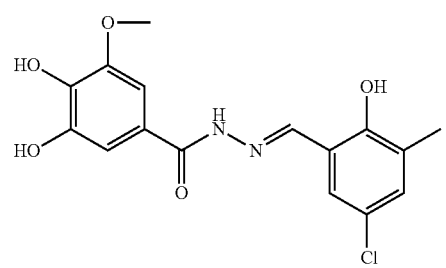

Chemical Formula: $C_{16}H_{15}ClN_2O_5$
Exact Mass: 350.07
Molecular Weight: 350.75
m/z: 350.07 (100.0%), 352.06 (32.0%), 351.07 (17.7%),
353.07 (5.8%), 352.07 (2.6%)
Elemental Analysis: C, 54.79; H, 4.31; Cl, 10.11; N, 7.99;
O, 22.81

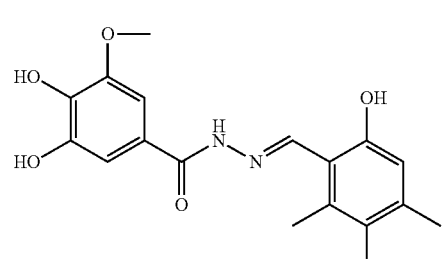

Chemical Formula: $C_{17}H_{17}ClN_2O_5$
Exact Mass: 364.08
Molecular Weight: 364.78
m/z: 364.08 (100.0%), 366.08 (32.1%), 365.09 (18.8%),
367.08 (6.2%), 366.09 (2.7%)
Elemental Analysis: C, 55.97; H, 4.70; Cl, 9.72; N, 7.68;
O, 21.93

TABLE 2-continued

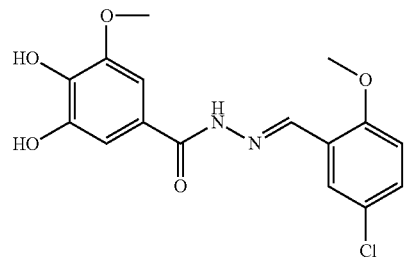

Chemical Formula: $C_{16}H_{15}ClN_2O_5$
Exact Mass: 350.07
Molecular Weight: 350.75
m/z: 350.07 (100.0%), 352.06 (32.0%), 351.07
(17.7%), 353.07 (5.8%), 352.07 (2.6%)
Elemental Analysis: C, 54.79; H, 4.31; Cl, 10.11;
N, 7.99; O, 22.81

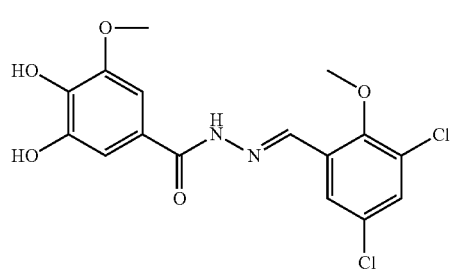

Chemical Formula: $C_{16}H_{14}Cl_2N_2O_5$
Exact Mass: 384.03
Molecular Weight: 385.20
m/z: 384.03 (100.0%), 386.03 (66.5%), 385.03 (18.4%),
387.03 (11.3%), 388.02 (10.2%), 389.03 (1.9%),
388.03 (1.7%)
Elemental Analysis: C, 49.89; H, 3.66; Cl, 18.41; N, 7.27;
O, 20.77

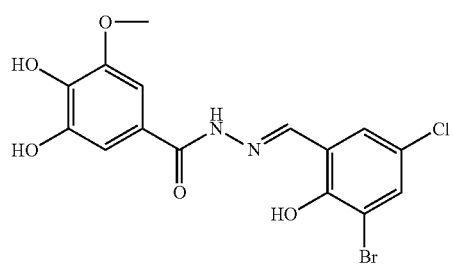

Chemical Formula: $C_{15}H_{12}BrClN_2O_5$
Exact Mass: 413.96
Molecular Weight: 415.62
m/z: 415.96 (100.0%), 413.96 (77.3%), 417.96 (25.2%),
416.96 (17.1%), 414.97 (12.8%), 418.96 (4.0%),
415.97 (1.8%), 417.97 (1.3%)
Elemental Analysis: C, 43.35; H, 2.91; Br, 19.23; Cl, 8.53;
N, 6.74; O, 19.25

TABLE 2-continued

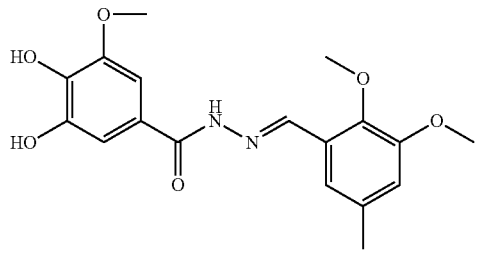

Chemical Formula: $C_{18}H_{20}Cl_2N_2O_6$
Exact Mass: 360.13
Molecular Weight: 360.36
m/z: 360.13 (100.0%), 361.14 (19.9%), 362.14 (3.1%)
Elemental Analysis: C, 59.99; H, 5.59; N, 7.77; O, 26.64

A fourth aspect of the present invention is related to a method of modifying activity of Aldolase in an apicomplexan organism. The method includes providing an apicomplexan organism, providing the pharmaceutical composition of the present invention, and contacting the pharmaceutical composition with the apicomplexan organism. The contacting modifies the activity of Aldolase in the apicomplexan organism.

In one embodiment the activity of Aldolase is inhibited. In another embodiment the activity of Aldolase is enhanced.

A fifth aspect of the present invention is related to a method of stabilizing a complex between Aldolase or portions thereof and thrombospondin-related anonymous protein (TRAP) or portions thereof. The method includes providing an apicomplexan organism, providing the pharmaceutical composition of the present invention, and contacting the pharmaceutical composition with the apicomplexan organism under conditions effective to stabilize the complex between Aldolase or portions thereof and thrombospondin-related anonymous protein (TRAP) or portions thereof.

A sixth aspect of the present invention is related to a method of inhibiting dissociation of cytoplasmic TRAP tail from glideosome in an apicomplexan organism including providing an apicomplexan organism and providing a pharmaceutical composition according to the third aspect of the present invention. The pharmaceutical composition is contacted with the apicomplexan organism under conditions effective to inhibit the dissociation of cytoplasmic TRAP tail from the glideosome.

A seventh aspect of the present invention is related to a method of inhibiting activity and/or survival of an apicomplexan organism. The method includes selecting apicomplexan organism and administering to the selected apicomplexan organism the pharmaceutical composition of the present invention under conditions effective to inhibit the activity and/or survival of the apicomplexan organism.

An eighth aspect of the present invention is related to a method of treating or preventing infection caused by an apicomplexan organism in a subject. The method includes selecting a subject having or susceptible to an infection caused by an apicomplexan organism and administering to the selected subject the pharmaceutical composition of the present invention under conditions effective to prevent or treat the infection caused by an apicomplexan organism.

A ninth aspect of the present invention is related to a method of treating or preventing malarial infection in a subject. The method includes selecting a subject susceptible to or having the malarial infection. A compound is provided which binds to and/or fits in:

a) a first model comprising Aldolase or residues of the amino acid sequence corresponding to SEQ ID NO: 1 being at amino acid positions selected from the group consisting of 10-13, 26, 27, 29, 30, 31, 32, 33, 37, 39, 40, 41, 43, 44, 47, 48, 51, 52, 60, 63, 66, 79, 84, 85, 92, 93, 103, 106-109, 112-117, 138, 142, 146, 148, 151, 153, 179, 182, 183, 185, 186, 194, 196, 197, 198, 199, 208, 226-228, 231-269, 270, 272, 277-283, 285-289, 294, 295, 297-299, 301-304, 306-310, 312, 313, 316, 317, 319, 321, 323, 326, 330, 344, 345, and 347; and/or b) a complex between said first model and a second model comprising a thrombospondin-related anonymous protein (TRAP) or residues of the amino acid sequence corresponding to SEQ ID NO: 38 said residues being at amino acid positions selected from the group consisting of 554, 555, 556, 557, 558, and 559. The compound is administered to the selected subject under conditions effective to treat the malarial infection in the subject.

As will be apparent to one of ordinary skill in the art, administering any of the pharmaceutical compounds or compositions of the present invention may be carried out using generally known methods. Typically, the agents of the present invention can be administered orally, parenterally, for example, subcutaneously, intravenously, intramuscularly, intraperitoneally, by intranasal instillation, by application to mucous membranes, such as, that of the nose, throat, and bronchial tubes or by direct contact to the cells of a subject, by direct injection into the subjects cells or by intratumoral injection. They may be administered alone or with suitable pharmaceutical carriers, and can be in solid or liquid form such as, tablets, capsules, powders, solutions, suspensions, or emulsions. The amount of vector(s) to be administered will depend on several factors, such as route of administration, the condition of the individual, stage of the disease, and the degree of aggressiveness of the malignancy, if the disease is cancer. Effective doses of the pharmaceutical compound or composition of the present invention may also be extrapolated from dose-response curves derived from animal model test systems. Also, the pharmaceutical compound or composition may be used in conjunction with other treatment modalities. Formulations also include lyophilized and/or reconstituted forms of the vectors (including those packaged as a virus) of the present invention.

The pharmaceutical compounds or compositions of the present invention may include a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The pharmaceutical compounds or compositions of the present invention may be orally administered, for example, with an inert diluent, with an assimilable edible carrier, enclosed in hard or soft shell capsules, compressed into tablets, or incorporated directly with the food of the diet. Such compositions and preparations should contain at least 0.1% of active compound. The percentage of the active agent or compound in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 250 mg of active compound.

Pharmaceutically acceptable carriers for oral administration are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration. The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both.

These pharmaceutical compounds or compositions may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms. Formulations for parenteral and nonparenteral drug delivery are known in the art and are set forth in *Remington's Pharmaceutical Sciences*, 19th Edition, Mack Publishing (1995), which is hereby incorporated by reference in its entirety.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Suitable subjects to be treated in accordance with the present invention include human and non-human animals, preferably mammals or avian species. Exemplary mammalian subjects include, without limitation, humans, non-human primates, dogs, cats, rodents, cattle, horses, sheep, and pigs. Exemplary avian subjects include, without limitation, chicken, quail, turkey, duck or goose. In a preferred embodiment the subject is human.

The present invention is illustrated, but not limited, by the following examples.

EXAMPLES

Example 1—Computational Studies

The computational experiments described herein entail protein-protein docking, homology modeling, small molecule docking, VLS, and substructure searching. For VLS and docking of other small molecules to Aldolase, a grid representation of Aldolase and a full atom representation of the small molecule were used. The receptor (i.e., Aldolase) was held rigid, while maintaining the flexibility of the ligand (i.e., small molecule). For protein-protein docking, both the receptor (i.e., Aldolase) and ligand (i.e., Band 3 or actin peptides) were represented by potential energy grids, and in some cases the ligand was held rigid as well. While this method may not detect certain ligand-receptor interactions that involve a large amount of induced fit, it does allow for rapid and efficient searching of the conformational space by significantly reducing the number of variables (i.e. bond lengths, bond angles, torsion, and phase angles) to be evaluated (Brive and Abagyan, "Computational Structural Proteomics," *Ernst Schering Res. Found. Workshop*, 149-166 (2002); Abagyan & Totrov, "High-Throughput Docking for Lead Generation," *Curr. Opin. Chem. Biol.* 5:375-382 (2001); Totrov and Abagyan, "Flexible Protein-Ligand Docking by Global Energy Optimization in Internal Coordinates," *Proteins Suppl* 1:215-220 (1997); Sternberg et al., "Predictive Docking of Protein-Protein and Protein-DNA Complexes," *Curr. Opin. Struct. Biol.* 8:250-256 (1998), which are hereby incorporated by reference in their entirety).

All computational work was completed using the Internal Coordinate Mechanics (ICM) modeling, docking, VLS, and cheminformatics software produced by Molsoft, LLC (La Jolla, Calif.). ICM offers several technical advantages that made it effective for the current study. This program represents full-atom structures in internal coordinate space as opposed to Cartesian, which significantly reduces the computational burden involved in molecular modeling and docking studies by reducing the number of variables to be considered. Because bond lengths, bond angles, torsion, and phase angles are considered as independent variables, operations can be performed on arbitrarily fixed multimolecular systems.

The ICM software utilizes a global energy optimization procedure that includes pseudo-Brownian motion, Biased Probability Monte Carlo conformational searches, and local deformation loop movements to obtain the best conformations for side chains, loops, and/or receptor-ligand interactions. Proteins, small molecules, and complex structures are scored and ranked based on the optimization of several energy terms including entropy, van der Waals forces, hydrogen bonding, electrostatic interactions, hydrophobic interactions, and solvation energy (Abagyan & Totrov, "High-Throughput Docking for Lead Generation," *Curr. Opin. Chem. Biol.* 5:375-382 (2001); Totrov & Abagyan, "Flexible Protein-Ligand Docking by Global Energy Optimization in Internal Coordinates," *Proteins* Suppl 1:215-220 (1997); Abagyan & Mazur, "New Methodology for Computer-Aided Modelling of Biomolecular Structure and Dynamics. 2. Local Deformations and Cycles," *J. Biomol. Struct. Dyn.* 6:833-845 (1989); Mazur & Abagyan, "New Methodology for Computer-Aided Modelling of Biomolecular Structure and Dynamics. 1. Non-Cyclic Structures," *J. Biomol. Struct. Dyn.* 6:815-832 (1989); Abagyan et al., "ICM—A New Method for Protein Modeling and Design: Applications to Docking and Structure Prediction from the Distorted Native Conformation," *J. Computational Chem.* 15:488-506 (1994); Cardozo et al., "Homology Modeling by the ICM Method," *Proteins* 23:403-414 (1995); Abagyan, et al., "Homology Modeling With Internal Coordinate Mechanics: Deformation Zone Mapping and Improvements of Models Via Conformational Search," *Proteins* Suppl 1:29-37 (1997); Abagyan & Totrov, "Biased Probability Monte Carlo Conformational Searches and Electrostatic Calculations for Peptides and Proteins," *J. Mol. Biol.* 235: 983-1002 (1994), which are hereby incorporated by reference in their entirety). The ICM algorithms have proven highly successful at blind structure prediction, homology modeling, docking, and VLS in several different labs (Chen et al., "On Evaluating Molecular-Docking Methods for Pose Prediction and Enrichment Factors," *J. Chem. Inf. Model* 46:401-415 (2006); Cardozo et al., "Homology Modeling by the ICM Method," *Proteins* 23:403-414 (1995); Bursulaya et al., "3rd. Comparative Study of Several Algorithms for Flexible Ligand Docking," *J. Comput. Aided Mol. Des.* 17:755-763 (2003); Schapira et al., "Discovery of Diverse Thyroid Hormone Receptor Antagonists by High-Throughput Docking," *Proc. Nat'l. Acad. Sci. U.S.A.* 100:7354-7359 (2003), which are hereby incorporated by reference in their entirety).

Example 2—Aldolase Mutagenesis, Expression, and Purification

Nearly every part of this study required the expression and purification of *P. falciparum* Aldolase or mutants thereof. Consequently, the protein was produced using various protocols. Crystallography-grade *P. falciparum* and *P. berghei* Aldolase was expressed and purified using the standard procedures described in Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17): 7015-20 (2007); Kim et al., "Crystal Structure of Fructose-1,6-Bisphosphate Aldolase From the Human Malaria Parasite *Plasmodium falciparum*," *Biochemistry* 37:4388-4396 (1998), which are hereby incorporated by reference in their entirety. GST-tagged *P. falciparum* Aldolase in *E. coli* from plasmids was expressed and purified using the following procedures.

Example 3—Site-Directed Mutagenesis of Aldolase

*P. falciparum* Aldolase and site-specific mutants thereof were cloned into pGEX-4T-1 or pGEX-5X-1 vectors (GE Healthcare, Piscataway, N.J.) by PCR and checked by DNA sequencing as previously described (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007), which are hereby incorporated by reference in their entirety).

Example 4—Aldolase Expression and Purification in *E. coli*

Plasmids containing the *P. falciparum* Aldolase sequence fused to GST were transformed into chemically competent BL21 cells via heat shocking Transformed cells were grown in 1 ml Luria Bertani (LB) media at 37° C., with shaking at 200-220 RPM, for 1-2 hours. 100 µl of the liquid culture was then plated on LB-agar plates, supplemented with 50 µg/ml ampicillin. (An additional 100 µl was resuspended with an equal amount of glycerol and stored at −80° C., as a 50% glycerol stock for future use.) Plates were incubated at 37° C. for 12-16 hours, at which point single colonies were picked and used to inoculate 5 ml of LB supplemented with 100 µm/ml ampicillin. Cultures were grown overnight, at 37° C., with shaking, and then used to seed larger cultures (ranging from 100-450 ml LB+100 µm/ml ampicillin), which were grown to an OD of 0.6-0.8. GST-Aldolase expression was induced with 0.5 mM IPTG, after which colonies continued to grow under the same conditions for 4-6 hours. The bacteria were then collected by centrifugation at 4200 RPM for 10 minutes at 4° C. At that point, the protein was either purified immediately, or pellets were stored at −80° C. and then thawed on ice before purification at a later date.

The bacterial pellet was resuspended in ice-cold Lysis Buffer (1 mM DTT, 1 mM PMSF, 1 mM EDTA, 10% glycerol, 0.1% Triton-X 100, in PBS at pH7.4). 5 ml of Lysis Buffer, supplemented with ½ of a Roche Complete® Protease Inhibitor tablet (Indianapolis, Ind.), was used for every 200 ml of bacterial culture. Additional Triton-X 100 was added to the resuspended cells to a final concentration of 1.1%. The suspensions were divided into 5 ml batches and lysed by sonication on ice (3×15 pulses, with 1 minute incubations in between sets). Lysed cells were incubated on ice for 20 minutes before lysate collection by centrifugation at 12,000 RPM, at 4° C. for 30-45 minutes. Supernatants were filtered through a 0.45 µM syringe filter.

Subsequent purification steps were carried out in the cold room: Filtered lysates were incubated with glutathione-sepharose beads (GE Healthcare, Piscataway, N.J.) pre-equilibrated with Wash Buffer (1 mM PMSF, 1 mM EDTA, 10% glycerol, 1% Triton-X-100, in PBS, pH 7.4) for 1 hour, and then the lysates and beads were transferred to polypropylene columns. The initial flow-through was reloaded onto the column, which was then mounted on a Vac-Man® laboratory vacuum manifold (Promega, Madison, Wis.). Columns were washed with 5 ml Wash Buffer, 3 ml Wash Buffer supplemented with 200 mM NaCl, and 3 additional washes with 5 ml Wash Buffer. The columns were then equilibrated 3 times with 5 ml Factor Xa Buffer (100 mM NaCl, 5 mM $CaCl_2$, in 50 mM Tris-HCl at pH 8.0), and the samples were resuspended in 750 µl Factor Xa Buffer and transferred to microcentrifuge tubes for GST cleavage.

The GST tags were removed from the purified proteins, and Factor Xa removed from the cleaved samples using the Novagen® Factor Xa Cleavage-Capture Kit (Madison, Wis.), following the manufacturer's instructions. Optimal cleavage and protein yields were obtained by rotating the samples at room temperature, for 18 hours, with 1 unit of Factor Xa per 20 µg Aldolase.

The purified, untagged, Aldolase was dialyzed overnight, and then for 2 additional 3-4 hour periods, against ice-cold PBS (pH 7.2-7.4), using 3500 Da molecular weight cut-off Pierce Slide-A-Lyzer Dialysis Cassettes (Thermo Fisher Scientific, Rockford, Ill.).

The identity of the purified proteins was confirmed via Western blot, using rabbit polyclonal antibodies to *P. falciparum* Aldolase (Abcam, Cambridge, Mass.). Aldolase purity was assessed via Coomassie staining, and the preparations were quantitated using the Pierce BCA kit (Thermo Fisher Scientific, Rockford, Ill.). Aliquots were stored at −80° C. with 10% glycerol. (Note: Whenever possible, Aldolase aliquots were not refrozen more than once, and fresh batches of protein were purified at regular intervals.)

Example 5—Actin Protein and Peptide Expression and Purification

Several variants of *P. falciparum* actin were needed during the course of the actin-Aldolase modeling studies. GST- and His-tagged actin peptides were expressed in *E. coli* and His-tagged full-length actin was produced in baculovirus as the protein aggregated in the prokaryotic cells. His-tagged variants were generated to allow for the use of HisGRAB ELISA plates, thereby reducing differences in coating efficiency due to variations in peptide size and hydrophobicity.

Example 6—Cloning and Expression of GST Fusion Proteins Derived from *P. falciparum* Actin To generate GST-15 in which GST is fused to the 15 amino acid C-terminal actin loop (GST-$_{353}$FQQMWIT-KEEYDESG$_{367}$ (SEQ ID NO: 9)), pGEX-5X-1 (Amersham Biosciences, Piscataway, N.J.) was first linearized with BamHI and EcoRI (New England Biolabs, Ipswich, Mass.). Oligonucleotides GST15-fwd (5'GATCTTTCAACAAAT-GTGGATCACAAAAGAGGAATACGATGAATCAGG ATAAGAGCTC3'(SEQ ID NO: 10)) and GST15-rev (5'AT-TGAGCTCTTATCCTGATTCATCGTATTCCTCTTTTGT-GATTGCCATTT GTTGAAA3' (SEQ ID NO: 11)) (Integrated DNA Technologies, Coralville, Iowa) were resuspended in sterile water to a final concentration of 10 μM and equal amounts were mixed and annealed by heating to 95° C. for 10 minutes, then left to cool gradually to room temperature. The annealed oligonucleotides were resuspended 1:50 in sterile water, cloned into the linearized vector by using the Rapid DNA Ligation Kit (Roche Applied Science, Indianapolis, Ind.) and transformed into chemically competent DH5a cells (Invitrogen, Carlsbad, Calif.). Recombinant clones were screened by digestion with SacI (New England Biolabs, Ipswich, Mass.), at a site that was introduced downstream of the stop codon and was not present in the original vector. Positive recombinant clones confirmed by sequencing were transformed into BL21 (DE3) chemically competent cells (Invitrogen, Carlsbad, Calif.). Single colonies were inoculated in LB media supplemented with 100 μg/ml ampicillin (Sigma-Aldrich, St. Louis, Mo.) and protein expression was induced with 0.5 mM IPTG. Cell pellets were resuspended in phosphate buffered saline supplemented with 1% Triton-X and Complete™ protease inhibitors (Roche Applied Science, Indianapolis, Ind.), lysed by sonication, and centrifuged at 14,000 RPM for 30 minutes at 4° C. The cleared lysates were loaded on a Glutathione Sepharose 4 Fast Flow matrix (GE Healthcare, Piscataway, N.J.), and, after extensive washes of the column, GST fusion proteins were eluted with 5 column volumes of 20 mM GSH elution buffer at pH 7.5. The protein was dialyzed three times for 4 hours each in 10 kDa cut-off dialysis cassettes (Pierce Chemical, Rockford, Ill.) and concentrated with VivaSpin 3000 concentrators (Viva-Science, Edgewood, N.Y.). The same approach was used to clone GST-15 mutants (GST-15 Y→A: GST-$_{353}$FQQMWIT-KEE$\underline{A}$DESG$_{367}$ (SEQ ID NO: 12); GST-15 W→A: GST-$_{353}$FQQM$\underline{A}$ITKEEYDESG$_{367}$ (SEQ ID NO: 13); and GST-15 WY→AA: GST-$_{353}$FQQM$\underline{A}$ITKEE$\underline{A}$DESG$_{367}$ (SEQ ID NO: 14)), as well as GST-9 (GST-AAA-$_{357}$WIT-KEEYDE$_{365}$ (SEQ ID NO: 15)), and site-specific mutants derived from it (GST-9 EE→QQ: GST-AAA-$_{357}$WITK$\underline{QQ}$YDE$_{365}$ (SEQ ID NO: 16) and GST-9 DE→NO: GST-AAA-$_{357}$WITKEEY$\underline{NQ}_{365}$ (SEQ ID NO: 17)). A stretch of three alanine residues preceding the nine amino acid sequences were included in GST-9 in order to ensure flexibility of the resulting short peptide with respect to the globular GST moiety.

Example 7—Cloning and Expression of his-Tagged *P. Falciparum* Actin Peptides

Proteins containing only actin's C-terminal 72 amino acids (His-72), and truncated versions of His-72 lacking its extreme C-terminal residues (His-51 and His-46) were generated in *E. coli*. The choice of construct for His-72 was based on secondary structure predictions of actin and intended to preserve the structural motifs at the actin C-terminus.

To generate His-72, primers pHis72fwd (5'-ATCGATG-GATCCGGAGGTAACTACTATGTATGAAGGT-3' (SEQ ID NO: 18)) and pHis72rev (5'-GCTACTCGAGGCGGC-CGCTTATCTGTGGACAATACTTGGTCCTGA-3' (SEQ ID NO: 19)) (Integrated DNA Technologies, Coralville, Iowa) were used to amplify a short protein containing 72 amino acids from the C-terminus of actin, and excluding three extreme C-terminal residues that contain an unpaired cysteine, with *P. falciparum* genomic DNA as the template. The approximately 240 bp PCR product was digested with EcoRI and BamHI (New England Biolabs, Ipswich, Mass.), and after purification from a 2% agarose gel, the DNA fragment was ligated into a pTrcHisB vector (Invitrogen, Carlsbad, Calif.) that was previously linearized with the same two restriction enzymes. Ligation reactions were transformed into DH5α chemically competent cells and clones were screened by SacI digestion to identify recombinants. Positive clones were transformed into BL21 (DE3) chemically competent cells. A single colony was inoculated in 5 ml LB media supplemented with 100 μg/ml ampicillin, and a culture was grown at 37° C. overnight. The culture was then inoculated 1:1000 into a 100 ml culture that was grown with shaking at 37° C. until it reached OD=0.6, at which point protein expression was induced with 0.5 mM IPTG. Pellets were collected after 3 more hours of growth at 37° C., and resuspended in Resuspension Buffer (50 mM NaH$_2$PO$_4$, 150 mM NaCl, 10 mM imidazole, pH=8). The cells were lysed by sonication (3 pulses, 10 seconds each, repeated 4 times). Lysates were incubated on ice for 30 minutes, then centrifuged at 14,000 RPM for 45 minutes at 4° C. and incubated with 150 μl Ni-NTA beads for 1 hour on a rotating platform in a cold room. The matrix was packed into polypropylene columns (BioRad Laboratories, Hercules, Calif.) and washed with 10 column volumes of Washing Buffer (50 mM NaH$_2$PO$_4$, 150 mM NaCl, 20 mM imidazole, pH=8), and the protein was eluted with 5 column volumes of Elution Buffer (50 mM NaH$_2$PO$_4$, 150 mM NaCl, 1M imidazole, pH=8). The protein was subsequently dialyzed 3 times for 3 hours each against phosphate buffer saline at pH=7.4 using 2 kDa cut-off dialysis cassettes (Pierce Chemical, Rockford, Ill.).

Example 8—Cloning and Expression of his-Tagged Full-Length *P. Falciparum* Actin in Baculovirus Full-length *P. falciparum* G-actin (globular actin) was amplified from *P. falciparum* genomic DNA with pPfactinfwd (5'-ATCGATCTCGAGGCATGGGAGAAGAAGAT-GTTCAAGCT-3' (SEQ ID NO: 20)) and pPfactin-rev (5'-TCGATCGCGGCCGCTTAGAAGCATTTTCTGTGGAC-AAT-3' (SEQ ID NO: 21)) primers. The amplification product was digested with XhoI and NotI (New England Biolabs, Ipswich, Mass.), gel-purified and ligated into the multiple cloning site of a pAcHLT-B vector (BD Biosciences, San Diego, Calif.) that was previously double-digested with the same two enzymes. Ligations were transformed into One-Shot Match-1 chemically competent cells (Invitrogen, Carlsbad, Calif.). Ampicillin-resistant colonies were grown in LB supplemented with 100 µg/ml ampicillin, then digested with NcoI to identify recombinants. Positive clones were sequenced, and a 1 liter culture was grown to isolate an endonuclease-free plasmid Maxiprep (QIAGEN, Valencia, Calif.), 2 µg of which were then used together with 0.5 µg linearized baculovirus Baculo Gold DNA (BD Biosciences, San Jose, Calif.) to co-transfect a 50% confluent culture of adhering Sf9 insect cells in 6-well plates, according to manufacturer's instructions. After 5 days, the supernatants were collected (P1 viral supernatant) and 100 µl were used to infect an adherent culture of Sf9 cells grown in TNM-FH to 50% confluency on 10 cm tissue culture plates. After 5 days, 100 µl of this second supernatant (P2 viral supernatant) was used to amplify the viral stock for a new 5-day amplification cycle. 2 ml of the P3 viral supernatant were used to infect an adherent monolayer of Hi5 cells. After 48 hours, the cells were collected by centrifugation for 10 minutes at 1000 RPM and lysed in Lysis Buffer (5 mM TrisCl, 100 mM NaCl, 50 mM NaF1, 0.2 mM ATP, 1 mM $CaCl_2$, 0.2% Triton-X100) supplemented with Complete™ protease inhibitors (Roche Applied Science, Indianapolis, Ind.). After 30 minutes of incubation on ice, lysates were centrifuged for 30 minutes at 14,000 RPM and incubated for 2 hours at 4° C. with Ni-NTA beads (QIAGEN, Valencia, Calif.) that were previously washed 3 times with washing buffer. Lysates were then loaded on polypropylene columns (BioRad Laboratories, Hercules, Calif.) and after washing with 10 column volumes of Washing Buffer (5 mM TrisCl, 100 mMNaCl, 0.2 mMATP, 1 mM $CaCl_2$), G-actin was eluted with 5 column volumes of elution buffer supplemented with Complete™ protease inhibitors (Roche Applied Science, Indianapolis, Ind.) and dialyzed (Pierce Chemical, Rockford, Ill.). The same approach was used to amplify the PfActin A24 and PfActin WY→AA proteins.

Example 9—Synthetic Peptides

Synthetic peptides derived from *P. falciparum* actin were custom-synthesized by Genemed Synthesis, Inc (San Antonio, Tex.). Their sequences are WITKEEYDE (wild-type peptide, (SEQ ID NO: 22)), EDWYIKTEE (scrambled peptide, (SEQ ID NO: 23)) and NITKQQNDE (mutant peptide, (SEQ ID NO: 24)). Peptides were initially resuspended in 1M TrisCl to a final concentration of 10 mg/ml, and the pH of the solution was adjusted to 7.4 by using a few microliters of 10% $Na_2CO_3$. For ELISA, 20 µl of serial dilutions of the peptide solutions were added to the wells, and as a control, the same volume of 1M TrisCl was used.

Synthetic peptides derived from the cytoplasmic tails of *P. falciparum* and *P. berghei* TRAP were similarly produced by Genemed Synthesis, Inc (Texas). These included PfTRAP25 (ETLGEEDKDLDEPEQFRLPEENEWN, (SEQ ID NO: 25)), PfTRAP6 (EENEWN, (SEQ ID NO: 26)), PbTRAP25 (VMADDEKGIVEDEGFKLPEDNDWN, (SEQ ID NO: 27)), and PbTRAP6 (EDNDWN, (SEQ ID NO: 28)). Lyophilized peptides were stored at 4° C. Peptides used for the catalysis assays were resuspended in Catalysis Buffer (see below) and aliquots were stored at −80° C. Whenever possible, excess peptides were not refrozen after thawing, and frozen samples were discarded and replenished at regular intervals.

Example 10—ELISA-Based Binding and Inhibition Assays

The key residues involved in Aldolase-actin binding were mapped via ELISA-based binding and inhibition assays using the protocol described below.

Polystyrene ELISA MaxiSorp 96-well microplates (Nunc A/S, Roskilde, Denmark) were coated overnight with 1 nmol/well G-actin dissolved in 50 mM Carbonate Buffer (15 mM $Na_2CO_3$ and 35 mM $NaHCO_3$) at pH 9.5. After blocking for 2 hours in ELISA Buffer (10 mM imidazole acetate, pH 7.3, 50 mM KCl and 0.2% Tween20) supplemented with 3% BSA, *P. falciparum* Aldolase dissolved in ELISA buffer was added and plates were incubated for 2 hours. After five washes with 180 µl ELISA buffer, plates were incubated with custom-made rabbit anti-Pf Aldolase antibodies (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007), which are hereby incorporated by reference in their entirety) (1:1, 200) for 1 hour, and after five additional washes as described (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007), which are hereby incorporated by reference in their entirety) plates were incubated with secondary anti-rabbit horseradish peroxidase (HRP) antibodies (Pierce Chemical, Rockford, Ill.) diluted 1:5,000. After five additional washes, 100 µl 1-step slow TMB (3,3',5,5'-tetramethylbenzidine) (Pierce Chemical, Rockford, Ill.) was added to each well, reactions were stopped with 100 µl 0.5N sulfuric acid, and absorbances were read at 450 nm. For experiments that compared the binding of Aldolase mutants to actin, GST-Aldolases and anti-GST primary antibodies (GE Healthcare, Piscataway, N.J.) diluted 1:1,0000 and anti-goat HRP (Promega, Madison, Wis.) secondary antibodies diluted 1:5,000 were used. For experiments performed with GST fusion proteins or peptides, equimolar amounts of GST were used in parallel and their values were subtracted from the experimental results. For competition assays, various amounts of competitor dissolved in 20 µl PBS or, as a control, 20 µl PBS without competitor, were added to the plates with Aldolase.

Example 11—Compounds Used for Screening

The ChemBridge library (San Deigo, Calif.) was used for the initial VLS screen. VLS hits were ordered from ChemBridge via the Hit2Lead system, in powdered form. The chemicals were dissolved in DMSO, and 100 mM stocks were stored at 4° C. Fresh working solutions of the compounds in the relevant assay buffers were created as close as possible to the time of the assay. Note that some compounds could not be tested in all assays as they were not all soluble in all buffers used.

Example 12—In Vitro Compound Activity Assays

Thermal shift assays were used to test the affect of the VLS hits on the stability of the TRAP-Aldolase complex. In the thermal shift assay Sypro Orange (Invitrogen, Carlsbad, Calif.) was used as the reporter dye. In this assay, proteins are thermally denatured (with or without the VLS compounds), in the presence of an environmentally sensitive dye that increases in fluorescence when exposed to the hydrophobic core of the unfolded proteins. The melting point of the protein (or protein complex) can be determined from the minimum of the first derivative of the fluorescence curve. The results reported here measured the effect of the VLS hits on a complex of recombinant P. falciparum Aldolase and the PbTRAP6 peptide described above. The assays were conducted and analyzed as per previously published protocols (Ericsson et al., "Thermofluor-Based High-Throughput Stability Optimization of Proteins for Structural Studies," Anal. Biochem. 357:289-298 (2006); Crowther et al., "Use of Thermal Melt Curves to Assess the Quality of Enzyme Preparations," Anal. Biochem. 399:268-275 (2010), which are hereby incorporated by reference in their entirety).

Example 13—Catalysis Assays

It is very difficult to measure Aldolase activity directly. Therefore, Aldolase catalysis was measured by coupling the Aldolase reaction to those that follow it during the glycolytic cycle—the interconversion of glyceraldehyde-3-phosphate (G3P) and dihydroxyacetone phosphate (DHAP) by triosephosphate isomerase (TPI or TIM), and G3P and 1,3-bisphosphoglycerate (1,3-BPG) by glyceraldehyde-3-phosphate dehydrogenase ($\alpha$-GDH). These reactions utilize NADH, which can be used as an indirect measure of F16P cleavage by Aldolase.

The protocol utilized here was based on that provided by Sigma-Aldrich® (St. Louis, Mo.), and all of the reagents (listed below) other than drugs, TRAP, and Aldolase were obtained from that company as well. Briefly, Aldolase was preincubated for 10 minutes±TRAP peptide (PfTRAP25, described above)±compound or DMSO at room temperature. The other reagents ($\alpha$-GDH/TPI, $\beta$-NADH, F16P in order) were then added, yielding a final reaction mixture containing 0.02 units/ml Aldolase (1 unit=amount of Aldolase required to convert 1 µmole of F16P to DHAP and G3P per minute at pH 7.4 and 25° C.; for these studies, this usually amounted to ~50 nM Aldolase, based on an estimated purification yield of 10 units/mg Aldolase), 2 mM F16P, 0.13 mM $\beta$-NADH, 2 units/ml $\alpha$-GDH/TPI (1 unit=amount of $\alpha$GDH required to convert 1.0 µmole of DHAP to $\alpha$-glycerophosphate per min at pH 7.4 and 25° C.), 100 nM TRAP (or DMSO), and 5-100 µM compound (or DMSO) in Catalysis Buffer (0.2 M glycine titrated to pH 7.3 with Trizma Base). The use of a low concentration of F16P ensured a slower reaction so that the affects of the compounds could easily be seen, and an anionic buffer was used so as not to interfere with the electrostatic interactions between Aldolase and TRAP. Reactions were carried out in a final volume of 1 ml, in standard plastic cuvettes. NADH consumption was measured at 340 nm for 10 minutes at 25° C., using a SpectraMax M2e Microplate Reader (Molecular Devices, Sunnyvale, Calif.). As many of the compounds had measurable inherent absorbance at 340 nM, the baseline absorbance of each compound when dissolved in Catalysis Buffer at the tested concentration was measured and subtracted from the values obtained during the kinetic run. The kinetic data was analyzed using SoftMax Pro® software provided with the instrument, as well as with Microsoft® Excel. Suramin (Sigma-Aldrich®, St. Louis, Mo.), a known Aldolase inhibitor, was used as a positive control for Aldolase inhibition.

Example 14—In Vivo Compound Activity Assays

Sporozoite motility assay was used to test compounds for their affect on P. berghei sporozoite motility by using established protocols (Coppi et al., "Antimalarial Activity of Allicin, a Biologically Active Compound From Garlic Cloves," Antimicrob. Agents Chemother. 50:1731-1737 (2006); Kortagere et al., "Structure-Based Design of Novel Small-Molecule Inhibitors of Plasmodium falciparum," J. Chem. Inf. Model 50:840-849 (2010), which are hereby incorporated by reference in their entirety). Briefly, the method consists of allowing the parasites to glide on glass slides that are coated with an antibody to CSp. As the parasites move, they shed their surface CSp which is captured by the antibody, allowing for the parasites' trails to be visualized with a biotinylated antibody specific for CSp. For the assays described here, sporozoites were preincubated with each compound (or DMSO) at 500 µM for 10 min at 28° C. and the sporozoites remained in the presence of the compound (or DMSO) during the hour long assay at 37° C. The quantity of motile parasites and the numbers of their trails were then calculated to assess the compounds' affects. "Normal" parasites tend to deposit >10 complete trails during a one hour period.

Example 15—In Vivo Compound Toxicity Assays

HepG2 HC-04 toxicity screen was used to conduct preliminary cytotoxicity screens of the VLS hits, using established protocols (Koopman et al., "Annexin V for Flow Cytometric Detection of Phosphatidylserine Expression on B Cells Undergoing Apoptosis," Blood 84:1415-1420 (1994); Guerreiro-Cacais et al., "B Cell Receptor Triggering Sensitizes Human B Cells to TRAIL-Induced Apoptosis," J. Leukoc. Biol. 88(5):937-45 (2010); Vermes et al., "A Novel Assay for Apoptosis. Flow Cytometric Detection of Phosphatidylserine Expression on Early Apoptotic Cells Using Fluorescein Labelled Annexin V," J. Immunol. Methods 184:39-51 (1995), which are hereby incorporated by reference in their entirety). Briefly, cultured hepatocytes (HC-04 cells) were treated with 100 µM of the compounds, and then stained with Annexin V-APC and Propidium Iodide. The presence of apoptotic markers (i.e. accessibility of phosphatidylserine to Annexin V staining and cell permeability to Propidium Iodide) was then assessed by flow cytometry.

Example 16—X-Ray Crystallography

All of the crystallography work described in this study was done using previously published protocols in Bosch et al., "Aldolase Provides an Unusual Binding Site for Thrombospondin-Related Anonymous Protein in the Invasion Machinery of the Malaria Parasite," Proc. Nat'l. Acad. Sci. USA 104(17):7015-20 (2007); Bosch et al., "Using Fragment Cocktail Crystallography to Assist Inhibitor Design of Trypanosoma brucei Nucleoside 2-Deoxyribosyltransferase," J. Med. Chem. 49:5939-5946 (2006), which are hereby incorporated by reference in their entirety. Crystals were grown, processed, and analyzed using protocols described in these references.

Co-crystallization screening was performed using recombinant P. falciparum Aldolase with either P. berghei or P.

falciparum TRAP hexa-peptides and one compound per crystallization drop. Compounds identified either through thermal shift assay or gliding motility assay having an effect on the stability of Aldolase or decreased capapbilities in motility and invasion of cells were added between 1-5 mM concentration. Co-crystals of the presumably ternary complex of Aldolase-TRAP-Compound were then tested for X-ray diffraction using synchrotron radiation. Using molecular replacement with 2PC4 as a template, the co-crystal structures were solved. To identify additional bound compounds in the co-crystal structure, a difference density map Fo-Fc was calculated. Refinement of the structures was carried out using PHENIX (Adams P. D. et al., "PHENIX: A Comprehensive Python-based System for Macromolecular Structure Solution," *Acta Crystallogr. D Biol Crystallogr.* 66:213-21 (2010), which is hereby incorporated by reference in its entirety) until convergence of the model.

Example 17—The TRAP-Aldolase Interface

The malarial motor complex represents a promising target for anti-malarial drug design. In particular, the availability of high-resolution structural information regarding the Aldolase-TRAP interface afforded us the opportunity to use virtual library screening to discover novel anti-malarials targeting that part of the glideosome.

A recent effort elucidated the structural basis of the TRAP-Aldolase interaction (Buscaglia et al., "Sites of Interaction Between Aldolase and Thrombospondin-Related Anonymous Protein in *Plasmodium*," *Mol. Biol. Cell.* 14:4947-4957 (2003); Buscaglia et al., "Modeling the Interaction Between Aldolase and the Thrombospondin-Related Anonymous Protein, a Key Connection of the Malaria Parasite Invasion Machinery," *Proteins* 66:528-537 (2007); Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which are hereby incorporated by reference in their entirety). Experimental studies showed that TRAP localizes to Aldolase's active site and inhibits binding of fructose-1,6-bisphophate (F16P), the enzyme's natural substrate. TRAP's subterminal tryptophan residue is essential for this interaction, and is buried within a hydrophobic pocket deep within the enzyme's active site. In silico docking of the terminal 6 residues of TRAP to a homology model of *P. falciparum* Aldolase demonstrated that a helix-loop-helix bordering the enzyme's active site rotates outward to accommodate TRAP binding. As shown in FIG. 4a, this conformational shift was confirmed by x-ray crystallography, and explains why TRAP inhibits Aldolase catalysis—TRAP forces the enzyme into an alternate conformation that cannot bind F16P.

Example 18—Aldolase-TRAP as a Drug Target

As previously discussed, the binding of TRAP to Aldolase is essential to malarial motility and infectivity (Buscaglia et al., "Sites of Interaction Between Aldolase and Thrombospondin-Related Anonymous Protein in *Plasmodium*," *Mol. Biol. Cell.* 14:4947-4957 (2003); Sultan et al., "TRAP is Necessary for Gliding Motility and Infectivity of *Plasmodium* Sporozoites," *Cell* 90:511-522 (1997); Kappe et al., "Conservation of a Gliding Motility and Cell Invasion Machinery in Apicomplexan Parasites," *J. Cell. Biol.* 147: 937-944 (1999); Buscaglia et al., "Modeling the Interaction Between Aldolase and the Thrombospondin-Related Anonymous Protein, a Key Connection of the Malaria Parasite Invasion Machinery," *Proteins* 66:528-537 (2007), which are hereby incorporated by reference in their entirety). The present study is directed towards in silico docking and modeling studies with the aim to design glideosome inhibitors targeting the TRAP-Aldolase interface.

Figure 4B:
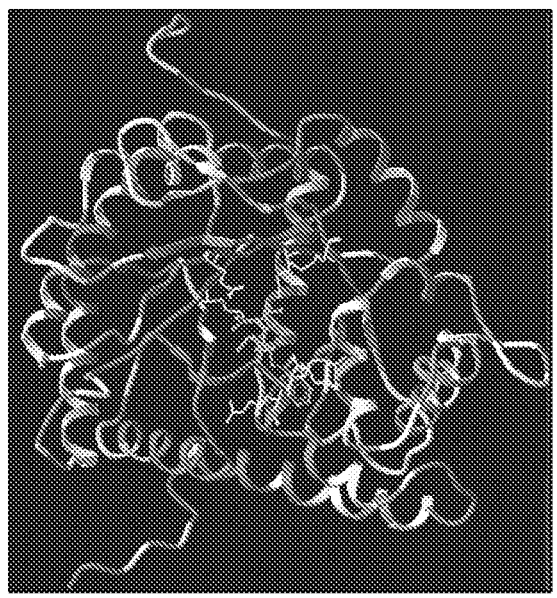
FIGS. 4A-B show a model of the TRAP-Aldolase interface.
Figure 4A:

Notably, the region that TRAP binds—the Aldolase active site—is highly conserved among Aldolases from different species (FIG. 4b). Since Aldolase is also present in human cells, where it represents a key enzyme in the glycolytic pathway, it was important to minimize the effects of this inhibitor on the human Aldolase enzyme. Therefore, the compound should affect the *P. falciparum* Aldolase-TRAP interaction with a high level of potency and specificity.

It has been demonstrated that apicomplexan Aldolases can be blocked without interfering with their human or rabbit homologs. Dobeli et al. generated rabbit antibodies against *P. falciparum* Aldolase that showed no cross-reactivity with the human enzyme (Dobeli et al., "Expression, Purification, Biochemical Characterization and Inhibition of Recombinant *Plasmodium falciparum* Aldolase," *Mol. Biochem. Parasitol* 41:259-268 (1990), which is hereby incorporated by reference in its entirety), and Itin et al. selectively inhibited parasite Aldolase with a peptide derived from a α-tubulin (Itin et al., "Selective Inhibition of *Plasmodium falciparum* Aldolase by a Tubulin Derived Peptide and Identification of the Binding Site," *Mol. Biochem. Parasitol* 58:135-143 (1993), which is hereby incorporated by reference in its entirety). Additionally, Dax et al. synthesized a small molecule inhibitor highly selective towards Aldolase from the apicomplexan parasites, *Trypanosoma brucei, Leishmania mexicana*, and *Plasmodium falciparum* (Dax et al., "Selective Irreversible Inhibition of Fructose 1,6-Bisphosphate Aldolase From *Trypanosoma* Brucei," *J. Med. Chem.* 49:1499-1502 (2006), which is hereby incorporated by reference in its entirety).

Example 19—Drug Design Strategy

When *Plasmodium* sporozoites glide over a host cell's surface or artificial substrate, TRAP and other adhesive proteins are translocated from the anterior to the posterior end of the parasite. Upon reaching the posterior end, the adhesins are cleaved within their transmembrane domains by rhomboid proteases and remain bound to the substrate or host cell (Baker et al., "Two *Plasmodium* Rhomboid Proteases Preferentially Cleave Different Adhesins Implicated in all Invasive Stages of Malaria," *PLoS Pathog.* 2:e113 (2006), which is hereby incorporated by reference in its entirety). Disruption of this cleavage reaction in related apicomplexan parasites severely impairs their gliding and invasive capabilities (Kappe et al., "Conservation of a Gliding Motility and Cell Invasion Machinery in Apicomplexan Parasites," *J. Cell. Biol.* 147:937-944 (1999); Brossier et al., "C-Terminal Processing of the *Toxoplasma* Protein MIC2 is Essential for Invasion Into Host Cells," *J. Biol. Chem.* 278:6229-6234 (2003); Kim, "Role of Proteases in Host Cell Invasion by *Toxoplasma gondii* and Other Apicomplexa," *Acta Trop.* 91:69-81 (2004), which are hereby incorporated by reference in their entirety). After this proteolytic cleavage, the remaining TRAP tail must presumably disassociate from the Aldolase tetramer to allow the enzyme to engage another TRAP protein and participate in the next round of motion.

The present study was directed towards the inhibition this disassembly and subsequent reassembly of the malarial motor complex by stabilizing the interaction between TRAP and Aldolase. Doing so would prevent the continued productive motion of the parasite, and as a result, impede its ability to invade host cells. Additionally, as the binding of TRAP and F16P to Aldolase are mutually exclusive, stabilizing the TRAP-Aldolase interaction would also selectively inhibit the catalytic activity of the malarial enzyme, thereby disrupting the glycolytic cycle upon which *Plasmodium falciparum* parasites are exquisitely dependent for ATP generation (Sherman, "Antimalarial Drugs, Chapter 2: Metabolism," in *Handbook of Experimental Pharmacology*, Vol. 68 (eds. Peters, W. & Richards, W. H. G.) Springer-Verlag:Berlin, pp. 31-81 (1984), which is hereby incorporated by reference in its entirety).

This was done by conducting a virtual library screen (VLS) against the TRAP-Aldolase interface—elucidated in the co-crystal structure of a C-terminal TRAP hexapeptide bound to Aldolase (PDB ID: 2pc4, 2.4 Å resolution structure as taught by Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety—in order to find small molecule enhancers of TRAP-Aldolase binding. Various in vitro and in vivo techniques were then used to validate the resultant VLS hits.

This strategy was especially attractive because using TRAP as part of the target area significantly improved the likelihood of the compounds found in the screen being specific for *Plasmodium* and not human Aldolase. Additionally, as the screen targeted an area at or near the enzyme's active site, and was designed to favor compounds that interact with non-conserved Aldolase residues, all the resulting hits were potential specific inhibitors of Plasmodial glycolysis, irrespective of their affect on TRAP-Aldolase binding.

Example 20—Target Validation: Receptor "Pocket" Analysis

As discussed supra, an important feature of protein structures amenable to VLS are "druggable pockets" (Cardozo and Abagyan, "Druggability of SCF Ubiquitin Ligase-Protein Interfaces. in *Ubiquitin and Protein Degradation, Part B*, Vol. 399 (ed. Deshaies, R. J.) Elsevier Academic Press: San Diego, pp. 634-653 (2005), which is hereby incorporated by reference in its entirety). The PocketFinder (An et al., "Pocketome Via Comprehensive Identification and Classification of Ligand Binding Envelopes," *Mol. Cell. Proteomics* 4:752-761 (2005), which is hereby incorporated by reference in its entirety) module within the ICM software package was used to locate ligand-accessible cavities and surfaces ("pockets") on *Plasmodium falciparum* Aldolase crystal structures.

Figure 5A:
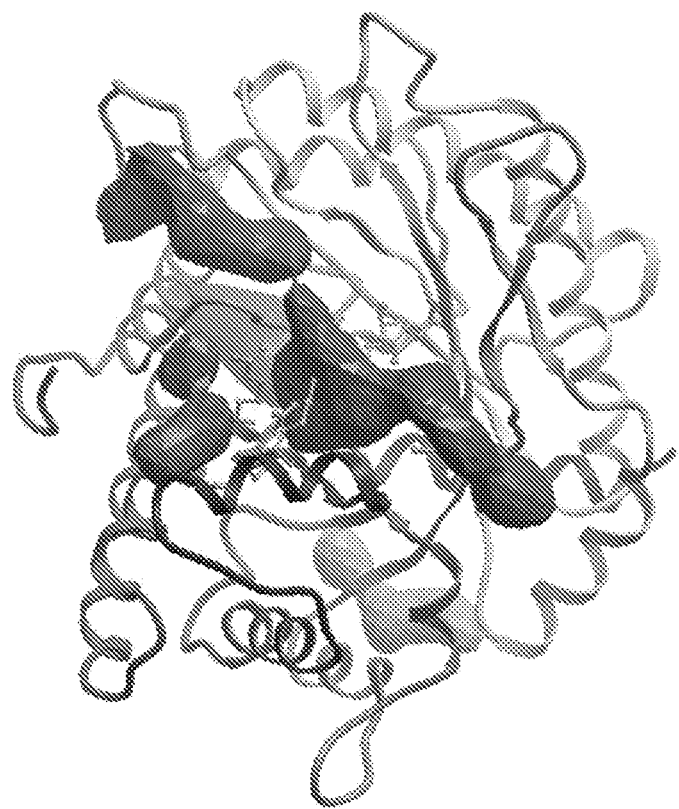
FIGS. 5A-C show "pockets" in the crystal structure of unliganded *Plasmodium falciparum* Aldolase. Potential ligand-binding pockets were rendered using the Pocket-Finder module in ICM.
Figure 5B:
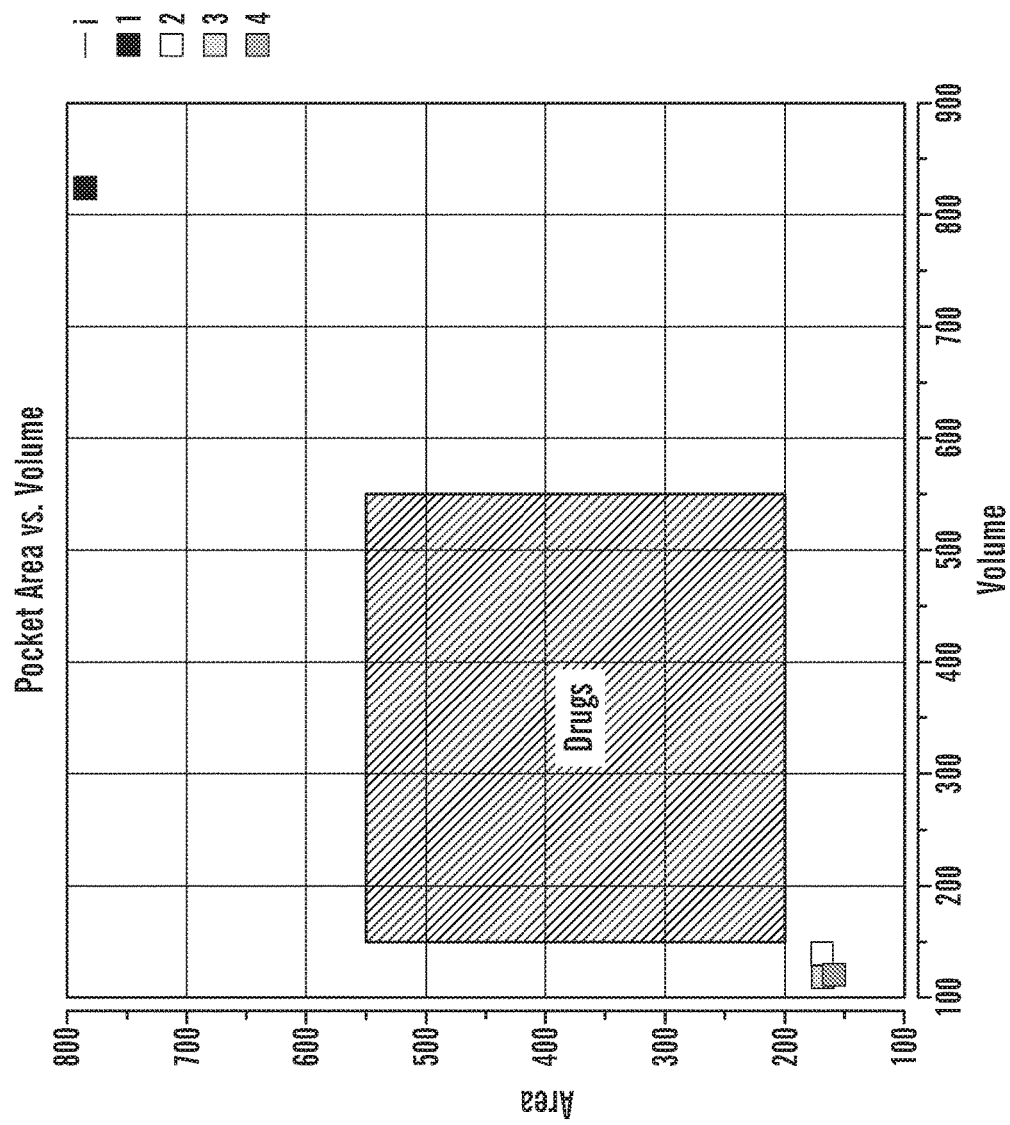
Figure 5C:
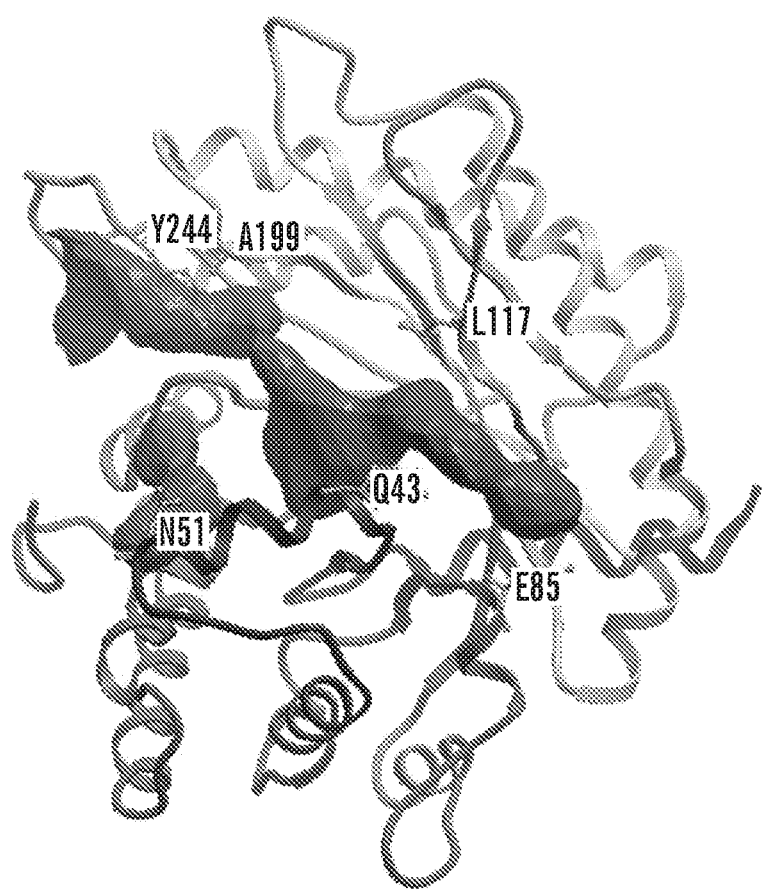

As shown in FIG. 5 and Table 2, the unliganded form of malarial Aldolase (PDB code 1a5c, 3.0 Å resolution structure taught by Kim et al., "Crystal Structure of Fructose-1, 6-Bisphosphate Aldolase From the Human Malaria Parasite *Plasmodium falciparum*," *Biochemistry* 37:4388-4396 (1998), which is hereby incorporated by reference in its entirety) contains 4 pockets. At first glance, none of these pockets are of the proper size and shape for drug-binding (FIG. 5B); however, pocket 1 (colored blue in FIG. 5A) appears to contain two smaller pockets joined by a narrow segment in the middle, one of which could be amenable to drug binding. As the enzyme's natural substrate, fructose-1,6-bisphosphate, binds to this area, and is itself a small molecule, this is likely to be the case. Pockets 1 and 4 (blue and purple in FIG. 5C) are located in the area of interest for this study, i.e. near Aldolase's TRAP-binding site. These pockets are contacted by several residues that are not conserved in any of the three human isoforms of Aldolase (muscle, $H_sA$; liver, $H_sB$; and brain, $H_sC$), including Q43, N51, E85, L117, A199, and Y244 (displayed as balls-and-sticks in FIG. 5C and shown as bold in Table 3).

TABLE 3

Pockets in the unliganded *P. falciparum* Aldolase crystal structure (PDB ID: 1a5c, which is here by incorporated by reference in its entirety). Key pockets are italicized, and non-conserved residues contacting these pockets are listed in bold.

| Pocket # | Volume ($Å^3$) | Area ($Å^2$) | Radius (Å) | Nonsphericity | Aldolase Residues Contacting Pocket |
|---|---|---|---|---|---|
| 1 | *821.42* | *786.40* | *5.81* | *1.85* | *A37, D39-S41, Q43, T44, R48, F84, E85, K112-L117, R138, Y142, K151, R153, E194, E196-A199, K236, N238, M239, T241-Y244, C246, K249-T252, V255, L277-Q281, E285, N289, S306-R309* |
| 2 | 139.29 | 171.17 | 3.22 | 1.32 | V29, A31, G32, N294, G297-H299, W301-T304, T344, Y345 |
| 3 | 116.77 | 169.54 | 3.03 | 1.47 | K27, Q30, K33, S79, H103, N106-P109, G146, R148 |
| 4 | *119.72* | *160.73* | *3.06* | *1.37* | *R48, N51, I52, G280-E283, R309, A310, A313, L316, N317* |

Figure 6A:
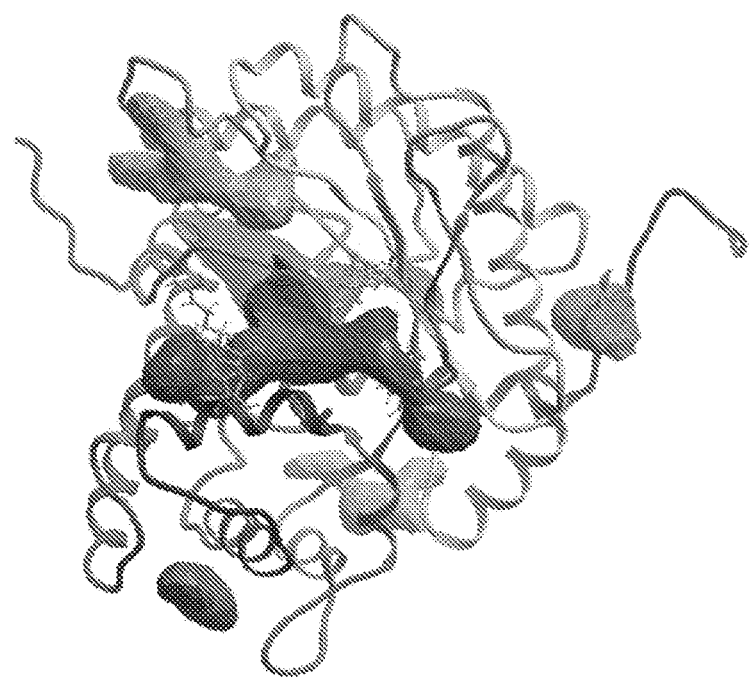
FIGS. 6A-C show "pockets" in the *Plasmodium* Aldolase-TRAP co-crystal structure with TRAP removed. Potential ligand-binding pockets were rendered using the Pocket-Finder module in ICM.
Figure 6B:
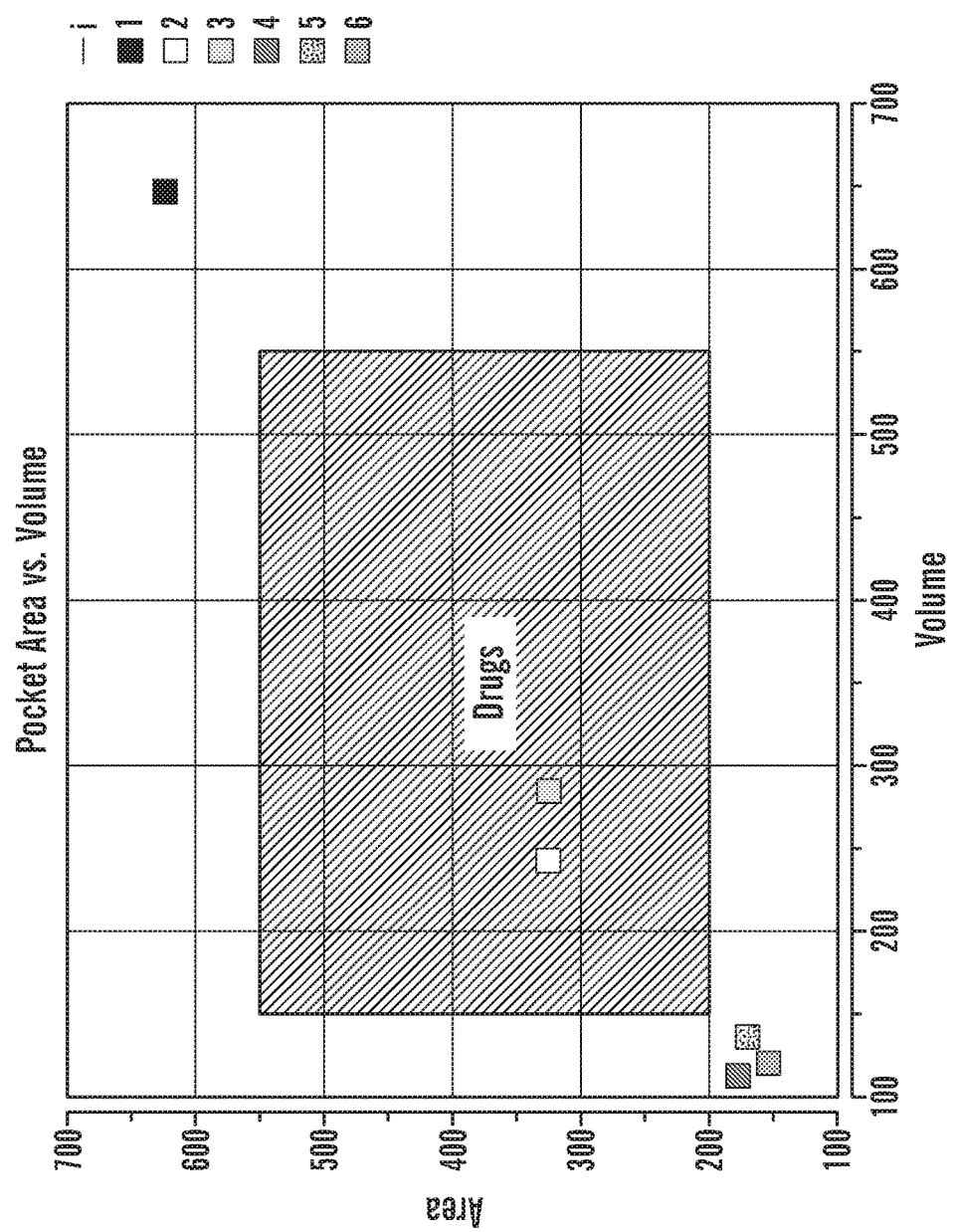
Figure 6C:
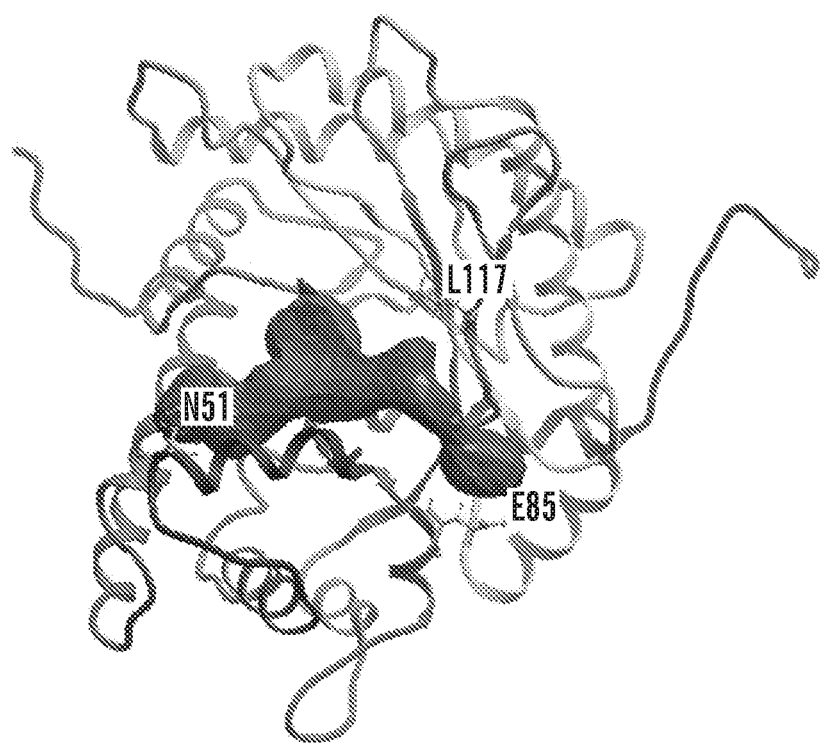
Figure 7A:
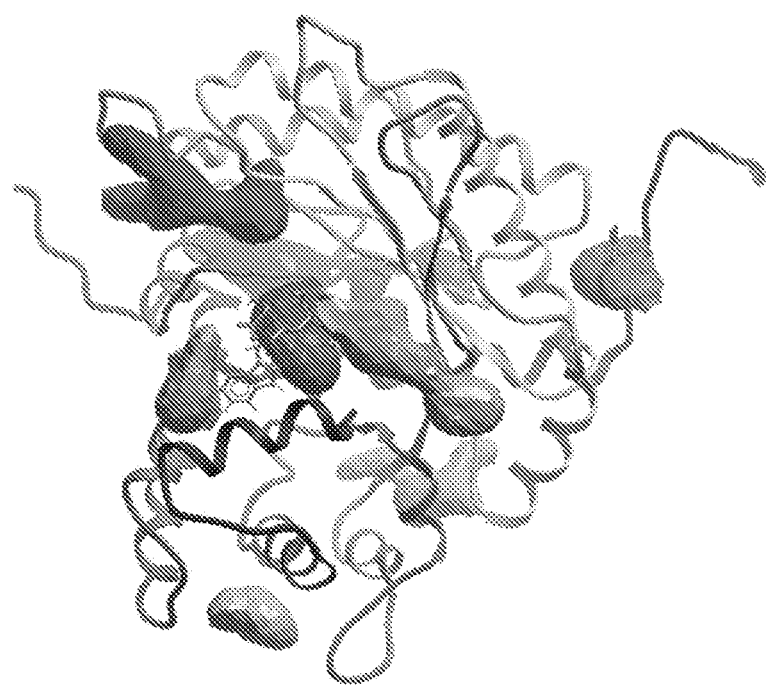
FIGS. 7A-C show "pockets" in the *Plasmodium* Aldolase-TRAP co-crystal structure with TRAP present. Potential ligand-binding pockets were rendered using the Pocket-Finder module in ICM.
Figure 7B:
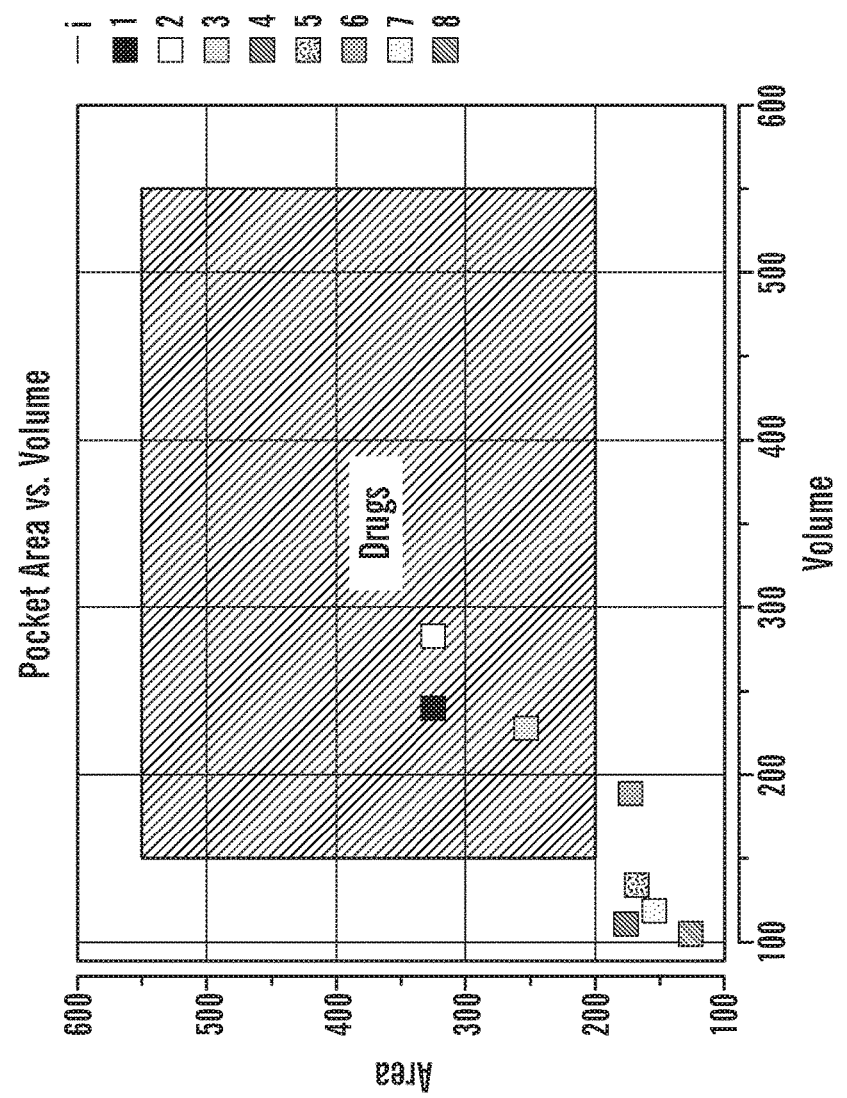
Figure 7C:
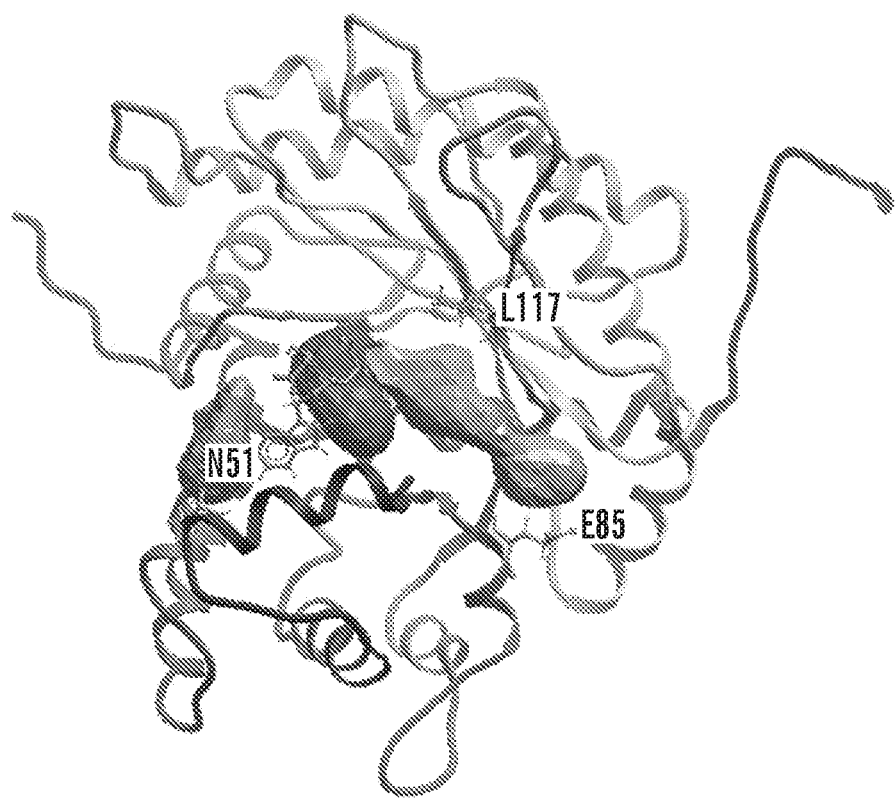

The structure obtained from the co-crystallization of *P. falciparum* Aldolase and a *P. berghei* TRAP hexamer (PDB code 2pc4, 2.4 Å resolution structure taught by Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety) was analyzed without (FIG. 6 and Table 4) and with the TRAP peptide present (FIG. 7 and Table 5). In the absence of TRAP, this structure contains 6 pockets. Pocket 1 (colored blue in FIG. 6) is the only pocket to overlay the TRAP-binding region, and contacts non-conserved residues N51, E85, and L117 (displayed as balls-and-sticks and shown as bold in FIG. 6).

TABLE 4

Pockets in the Aldolase-TRAP co-crystal structure with TRAP removed (PDB ID: 2pc4, which is here by incorporated by reference in its entirety). Key pockets are italicized, and non-conserved residues contacting these pockets are listed in bold.

| Pocket # | Volume (Å³) | Area (Å²) | Radius (Å) | Nonsphericity | Aldolase Residues Contacting Pocket |
|---|---|---|---|---|---|
| 1 | *645.12* | *625.13* | *5.36* | *1.73* | *A37, D39-S41, T44, R48,N51, I52, F84,* *E85, K112-L117, R138, Y142, K151, R153, E194, E196, K236, L277-G279, S306-R309, Q312, A313, L316, N317* |
| 2 | 240.71 | 327.29 | 3.86 | 1.75 | Q26, V29-G32, E231, P269, A270, P272, N294, A295, G297-H299, W301-T304, T344, Y345, K347 |
| 3 | 282.55 | 326.79 | 4.07 | 1.57 | E196-A199, C208, N238, M239, T241-Y244, C246-A248, T250-T252, V255, L277-Q281, E285, N289 |
| 4 | 110.52 | 180.05 | 2.98 | 1.62 | K27, Q30, K33, H103, N106-P109, R148 |
| 5 | 134.05 | 170.67 | 3.17 | 1.35 | P10-L13, R179, S182, I183, Q185, Q186, N226-V228 |
| 6 | 119.24 | 156.75 | 3.05 | 1.34 | N60, S63, D66, N92, E93, W319, G321, K323, V326, R330 |

TABLE 5

Pockets in the Aldolase-TRAP co-crystal structure with TRAP present (PDB ID: 2pc4, which is here by incorporated by reference in its entirety). Key pockets are italicized, and non-conserved residues are listed in bold.

| Pocket # | Volume (Å³) | Area (Å²) | Radius (Å) | Nonsphericity | Aldolase Residues Contacting Pocket | TRAP Residues Contacting Pocket |
|---|---|---|---|---|---|---|
| 1 | 239.11 | 325.36 | 3.85 | 1.75 | Q26, V29-G32, E231, P269, A270, P272, N294, A295, G297-H299, W301-T304, T344, Y345, K347 | |
| 2 | 281.97 | 326.56 | 4.07 | 1.57 | E196-A199, C208, N238-M239, T241-Y244, C246-A248, T250-T252, V255, L277-Q281, E285, N289 | |
| 3 | *227.86* | *255.05* | *3.79* | *1.41* | *S41, T44, F84,E85, K112-L117, R138, Y142, R153* | *N606, corresponding to N559 of SEQ ID NO: 38* |
| 4 | 109.52 | 179.08 | 2.97 | 1.62 | K27, Q30, K33, H103, N106-P109, R148 | |
| 5 | 133.22 | 169.82 | 3.17 | 1.35 | P10-L13, R179, S182, I183, Q185, Q186, N226-V228 | |
| 6 | *188.41* | *174.08* | *3.56* | *1.10* | *A37, D39, E40, K151, E194, K236, L277-G279, S306-A310* | *W605, N606, corresponding to W558 and N559 of SEQ ID NO: 38, respectively* |
| 7 | 118.41 | 156.06 | 3.05 | 1.34 | N60, S63, D66, N92, E93, W319, G321, K323, V326 | |
| 8 | *102.94* | *126.75* | *2.91* | *1.19* | *K47, R48,N51, I52, R309, A313, L316, N317* | *W605, corresponding to W558 of SEQ ID NO: 38* |

With TRAP present, eight pockets are created. Pockets 3, 6, and 8 (colored yellow, purple, and rose, respectively, in FIG. 7) juxtapose with the TRAP binding site, and contact the non-conserved residues, N51, E85, and L117, as well as TRAP itself (balls-and-sticks in FIG. 7). While pockets 6 and 8 individually do not have desirable area-to-volume ratios for drug binding, their combined space could prove adequate. Additionally, their key locations within the target region justified including them in the area to be screened against.

Example 21—Target and Technology Validation: Self- and Cross-Dockings with ICM Software As discussed supra, crystal structures with resolutions better than 2.5 Å are usually suitable for VLS. Additionally, a structure with low resolution overall may still have sufficiently high resolution within a domain of interest. Conversely, a high-resolution structure may not display clear density within a target region. Therefore, it is best to test the suitability of all structures before commencing with VLS (Abagyan & Totrov, "High-Throughput Docking for Lead Generation," *Curr. Opin. Chem. Biol.* 5:375-382 (2001); Cardozo & Abagyan, "Druggability of SCF Ubiquitin Ligase-Protein Interfaces. in *Ubiquitin and Protein Degradation, Part B*, Vol. 399 (ed. Deshaies, R. J.) Elsevier Academic Press:San Diego, pp. 634-653 (2005), which are hereby incorporated by reference in their entirety). The simplest way of doing so is by docking known binders to the candidate structures and comparing the results to published co-crystals, if available, and/or biochemical and genetic data.

This method has the advantage of simultaneously serving as a test of the proposed screening method. VLS is, in effect, a series of repeated dockings, and utilizes the same algorithms and energy function. If the algorithm and energy function are reliable, the docking software should correctly place known binders within the structures and assign those complexes good energy scores. Finally, the scores obtained for known binders may guide the choice of score threshold used in the subsequent virtual library screen.

To date, co-crystal structures are available for mammalian Aldolases bound to their natural substrates, F16P, DHAP, and G3P, and the substrate analogues, tagatose-1,6-bisphosphate and D-mannitol-1,6-diphosphate (PDB ID: 4ald as taught by Dalby et al., "Crystal Structure of Human Muscle Aldolase Complexed With Fructose 1,6-Bisphosphate: Mechanistic Implications," *Protein Sci.* 8:291-297 (1999), which is hereby incorporated by reference in its entirety; PDB ID: bald as taught by (Choi et al., "Structure of a Fructose-1,6-bis(phosphate) Aldolase Liganded to its Natural Substrate in a Cleavage-Defective Mutant at 2.3 Å," *Biochemistry* 38:12655-12664 (1999), which is hereby incorporated by reference in its entirety; PDB ID: 1zai as taught by St-Jean et al., "High Resolution Reaction Intermediates of Rabbit Muscle Fructose-1,6-Bisphosphate Aldolase: Substrate Cleavage and Induced Fit," *J. Biol. Chem.* 280:27262-27270 (2005), which is hereby incorporated by reference in its entirety; PDB ID: 1j4e as taught by Choi et al., "Snapshots of Catalysis: The Structure of Fructose-1,6-(bis)phosphate Aldolase Covalently Bound to the Substrate Dihydroxyacetone Phosphate," *Biochemistry* 40:13868-13875 (2001), which is hereby incorporated by reference in its entirety; PDB ID: lado as taught by Blom and Sygusch, "Product Binding and Role of the C-Terminal Region in Class I D-Fructose 1,6-Bisphosphate Aldolase," *Nat. Struct. Biol.* 4:36-39 (1997), which is hereby incorporated by reference in its entirety; PDB ID: 1f2jas taught by Chudzik et al., "Structures of Type 2 Peroxisomal Targeting Signals in two Trypanosomatid Aldolases," *J. Mol. Biol.* 300:697-707 (2000), which is hereby incorporated by reference in its entirety; PDB ID: 1za1 as taught by St-Jean et al., "High Resolution Reaction Intermediates of Rabbit Muscle Fructose-1,6-Bisphosphate Aldolase: Substrate Cleavage and Induced Fit," *J. Biol. Chem.* 280:27262-27270 (2005), which is hereby incorporated by reference in its entirety, and PDB ID: 1zaj as taught by St-Jean et al., "High Resolution Reaction Intermediates of Rabbit Muscle Fructose-1,6-Bisphosphate Aldolase: Substrate Cleavage and Induced Fit," *J. Biol. Chem.* 280:27262-27270 (2005), which is hereby incorporated by reference in its entirety. Additionally, rabbit muscle Aldolase has been co-crystallized while bound to a peptide derived from Wiskott-Aldritch Syndrome protein (WASp) and to an inhibitor of WASp binding, Napthol AS-E phosphate (NASEP), and *Plasmodium falciparum* Aldolase has been co-crystallized in the presence of TRAP (PDB ID: 2ot0 as taught by St-Jean et al., "A Hydrophobic Pocket in the Active Site of Glycolytic Aldolase Mediates Interactions With Wiskott-Aldrich Syndrome Protein," *J. Biol. Chem.* 282(19):14309-15 (2007), which is hereby incorporated by reference in its entirety; PDB ID: 2ot1 as taught by St-Jean et al., "A Hydrophobic Pocket in the Active Site of Glycolytic Aldolase Mediates Interactions With Wiskott-Aldrich Syndrome Protein," *J. Biol. Chem.* 282(19):14309-15 (2007), which is hereby incorporated by reference in its entirety; PDB ID: 2pc4 as taught by Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety; and PDB ID: 2eph as taught by Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety. The structures that would potentially be used for VLS were therefore docked to a subset of these ligands and the predicted conformations were compared to the relevant co-crystal structures and examined for their fit to published experimental data. In the cases where the structure in question was itself derived from a co-crystallization experiment, the complexed ligand was deleted from the structure before docking.

Figure 8:
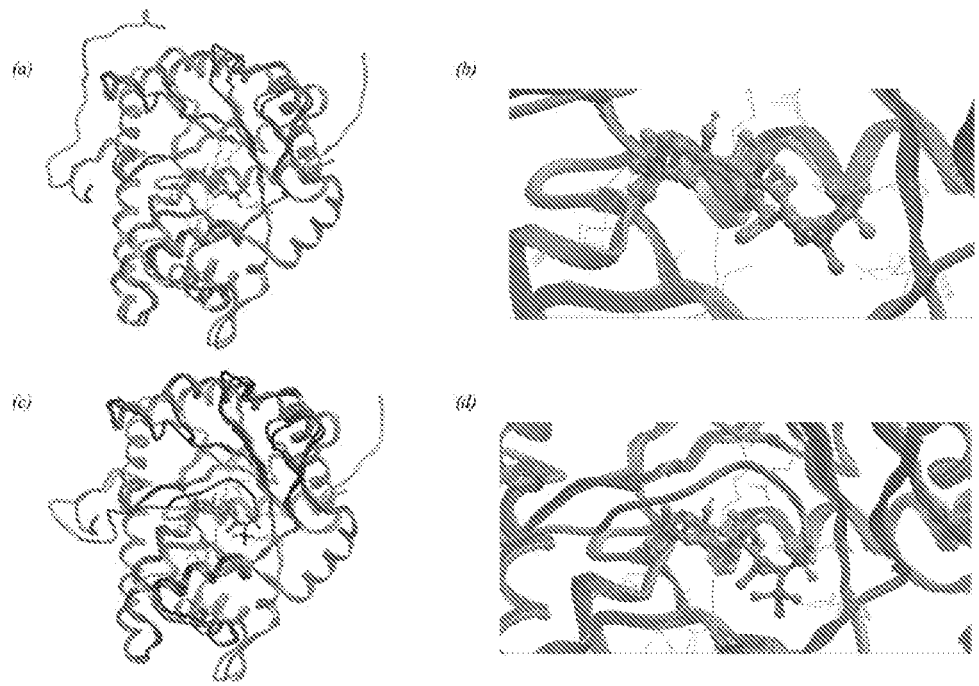
FIGS. 8A-D show a model of F16P docked to the active site of unliganded *P. falciparum* Aldolase. F16P was docked to *P. falciparum* Aldolase (PDB ID: 1a5c, Kim et al., "Crystal Structure of Fructose-1,6-Bisphosphate Aldolase From the Human Malaria Parasite *Plasmodium falciparum*," *Biochemistry* 37:4388-4396 (1998), which is hereby incorporated by reference in its entirety) using the ICM small-molecule docking module. F16P localized to the enzyme's active site, and established most of the expected interactions with active-site residues.
Figure 9:
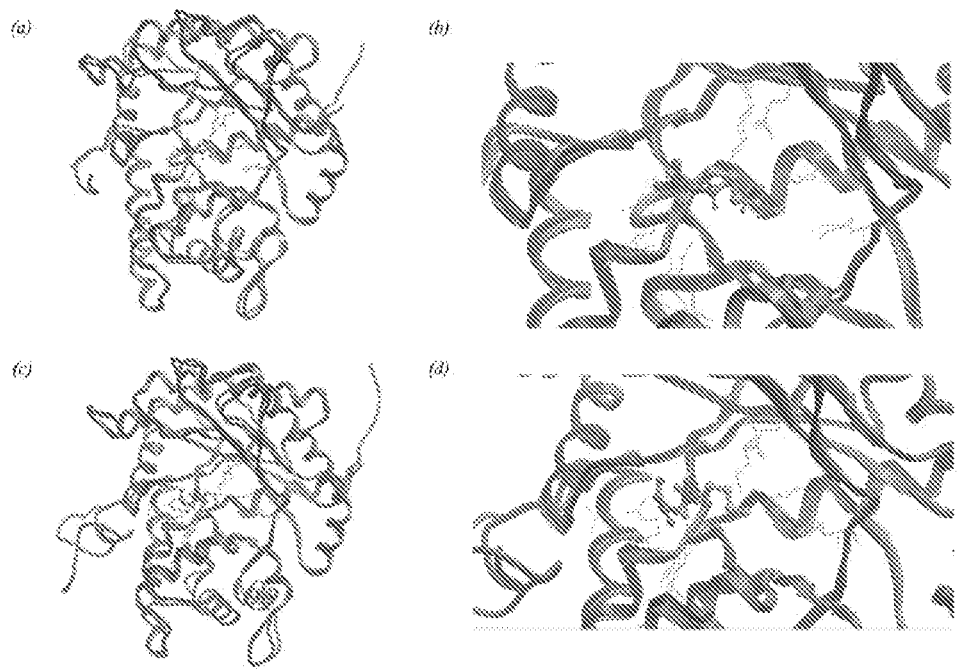
FIGS. 9A-D shows a model of DHAP docked to the active site of unliganded P. falciparum Aldolase. DHAP was docked to P. falciparum Aldolase (PDB ID: 1a5c (Kim et al., "Crystal Structure of Fructose-1,6-Bisphosphate Aldolase From the Human Malaria Parasite Plasmodium falciparum," Biochemistry 37:4388-4396 (1998), which is hereby incorporated by reference in its entirety)) using the ICM small-molecule docking module. DHAP localized to the enzyme's active site, and established most of the expected interactions with active-site residues.

Both F16P and DHAP localized to the enzyme's active site when docked to a 3 Å resolution crystallographic structure of unliganded *P. falciparum* Aldolase (PDB code: 1a5c as taught by Kim et al., "Crystal Structure of Fructose-1,6-Bisphosphate Aldolase From the Human Malaria Parasite *Plasmodium falciparum*," *Biochemistry* 37:4388-4396 (1998), which is hereby incorporated by reference in its entirety), with their phosphate groups properly positioned and the majority of the expected interactions conserved. Superimposition demonstrates that the docked complexes demonstrate differences in structure relative to co-crystal structures of mammalian Aldolases bound to F16P or DHAP that are no greater than those found between the co-crystal structures themselves (FIG. 8 and FIG. 9).

Figure 10:
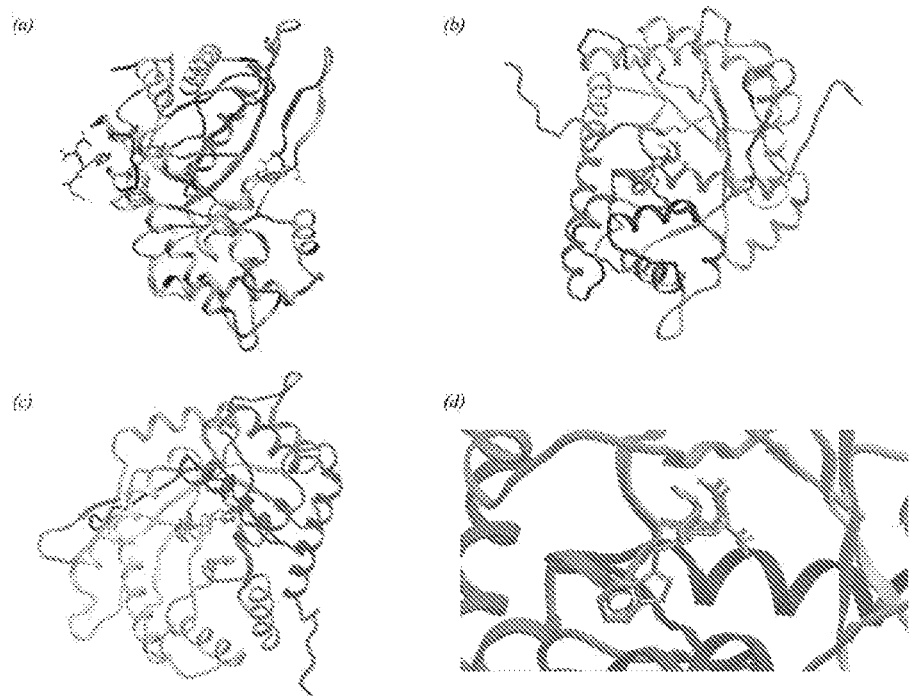
FIGS. 10A-D show a TRAP peptide docked to Aldolase. The TRAP peptide was removed from the TRAP-Aldolase co-crystal structure (PDB ID: 2pc4, Bosch et al., "Aldolase Provides an Unusual Binding Site for Thrombospondin-Related Anonymous Protein in the Invasion Machinery of the Malaria Parasite," Proc. Nat'l. Acad. Sci. USA 104(17): 7015-20 (2007), which is hereby incorporated by reference in its entirety)) and then re-docked to Aldolase.

The ICM software also successfully re-docked a TRAP peptide to the 2.4 Å resolution structure of the TRAP-Aldolase complex (PDB ID: 2pc4 as taught by Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety; FIG. 10). The TRAP tripeptide was removed from the co-crystal structure and then docked back to Aldolase. The lowest energy conformation for the docked structure placed the TRAP peptide at the enzyme's C-terminus. However, upon closer inspection, it is apparent that this result is probably artifactual—the C-terminal portion of Aldolase displays a high b-factor relative to the rest of the enzyme in this structure, and likely represents an artificial docking surface that is not present in vivo. (FIG. 10A) When this region is ignored, the lowest energy conformation of the docked structure superimposes remarkably well with the co-crystallized complex (FIG. 4B-D).

Example 22—Receptor Modeling

Based on the results of the pocket analysis and preliminary docking studies, both the available *Plasmodium* Aldolase crystal structures and the ICM docking algorithm were suitable for proposed virtual library screen. In keeping with the strategy of screening for enhancers of the Aldolase-TRAP interaction, TRAP-Aldolase co-crystal structure with TRAP present (PDB ID: 2pc4, 2.4 Å resolution as taught by Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which is hereby incorporated by reference in its entirety) for VLS was prepared.

After careful inspection of the structure, it became apparent that at least two additional receptor models based on this structure would be necessary for the screen to succeed.

In the structure, *P. falciparum* Aldolase was crystallized with a peptide derived from *P. berghei* TRAP rather than *P. falciparum* TRAP. The two peptides differ in position 604 of TRAP—*P. berghei* has an aspartate residue in this position, while *P. falciparum* contains a glutamate (amino acid residue 557). As this polymorphism affects the positioning of a charged group within the drug-binding pocket, it can have a relatively large effect on the VLS results. A model was generated of the complex containing the *P. falciparum* TRAP sequence for use in a parallel VLS run. This was accomplished by mutating the residue in silico and then briefly refining the mutated residue and its neighboring side-chains using ICM's Biased Probability Montecarlo conformational search and energy minimization algorithms.

Ligand-induced conformational changes of individual amino acid side chains or entire backbone regions cannot be easily incorporated in VLS. In many cases, a particular side change may be positioned in such a way as to block the correct docking pose of a VLS ligand. In vitro, the side chain would move out of the way, but with VLS, the docking is done to a rigid receptor. It was anticipated that TRAP's C-terminal arginine could pose such a problem. N606 does not appear to make essential contacts with Aldolase. However, it is a relatively large amino acid and its fixed position within the crystal structure may artificially block entry of some VLS ligands into the docking pocket, generating many false negatives. Studies have shown that in situations like this, in silico alanine scanning mutagenesis can simulate a certain amount of induced fit (Bottegoni et al., "A New Method for Ligand Docking to Flexible Receptors by Dual Alanine Scanning and Refinement (SCARE)," *J. Comput. Aided Mol. Des.* 22(5):311-325 (2008), which is hereby incorporated by reference in its entirety). A screen against a model of the TRAP-Aldolase complex in which N606 is replaced by alanine was also done.

Figure 11:
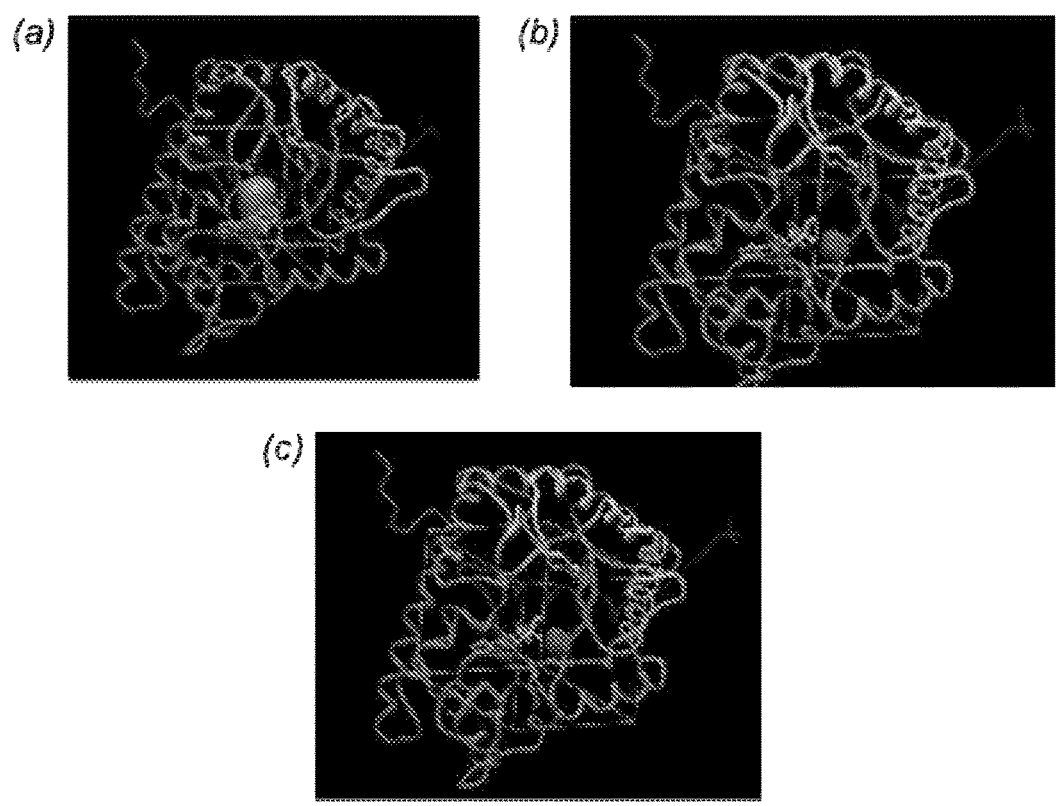
FIGS. 11A-C show receptor models for VLS and docking boxes. Aldolase is shown as a ribbon colored in a gradient from blue at its N-terminus to red at its C-terminus. TRAP peptides are shown in ball-and-stick depiction with standard atom-coded colors (oxygen=red, nitrogen=blue, hydrogen=grey, carbon=yellow). The red balls represent the initial docking "probe," which is where each ligand was placed at the start of each docking procedure. The VLS "boxes" in purple represent the regions in which the docking algorithm concentrated its search.

The final three receptor models used for VLS, as well as the "box" within which docking was concentrated, are shown in FIG. 11. In the remainder of this document, each model will be referred to as follows:

"2pc4 model"—the unmodified co-crystal structure, with *P. falciparum* Aldolase and *P. bergheii* TRAP, DWN
"falciparum model"—the co-crystal structure modified to contain the *P. falciparum* TRAP sequence, EWN
"gapped-pocket model"—the co-crystal structure modified to simulate induced-fit, with the TRAP sequence altered to DWA Example 23—The VLS Library For the VLS studies, a chemical library supplied by the ChemBridge Corporation (San Diego, Calif.) was utilized. This library contained data on 315,102 compounds with diverse structures, most of which should be drug-like. Any library compounds that did not conform to the Lipinski rules were filtered out prior to docking by the ICM-VLS software. Importantly, the majority of the compounds within this library were easily obtainable from ChemBridge at the time of screening.

Example 24—Small-Molecule Docking and Hitlist Post-Processing

It is beneficial to run multiple screens against the same target in order to ensure full coverage of the conformational space of the chemicals in the library, as a random assortment of ligand conformations are explored during each screen. It has been experienced that the point of diminishing returns is reached by the fourth screen, and that an initial energy-score cut-off of −32 allows for a reasonable balance between stringency of compound fit and allowance for compounds that might score better with slight receptor side-chain rearrangements (Schapira et al., "Rational Discovery of Novel Nuclear Hormone Receptor Antagonists," *Proc. Nat'l. Acad. Sci. U.S.A.* 97:1008-1013 (2000), which is hereby incorporated by reference in its entirety). A total of three independent screens were run against each of the 3 receptor models in parallel using ICM-VLS. These screens generated 182 unique small molecule "hits." These hits were then redocked to the target complexes using ICM-DOCK, which is a slower, more robust docking algorithm, and compounds whose re-docked poses and/or energy scores differed significantly from the VLS results were eliminated. This step identified 76 unique compounds.

Compounds which have predicted chemistries unfavorable for use as orally-available drugs (i.e. c Log P<−2 or >4) were filtered out (Lipinski et al., "Experimental and Computational Approaches to Estimate Solubility and Permeability in Drug Discovery and Development Settings," *Adv. Drug Deliv. Rev.* 46:3-26 (2001), which is hereby incorporated by reference in its entirety). Sixty-nine compounds remained after this analysis.

The final 69 compounds and their docking poses were manually inspected to ensure full coverage of all of the receptor models: 5 compounds docked only to the 2pc4 model, 11 only to the falciparum model, and 51 docked only to the gapped-pocket model; one compound docked to both the 2pc4 and falciparum models, while another docked to all three models.

Figures 12A, 12B, 12C:
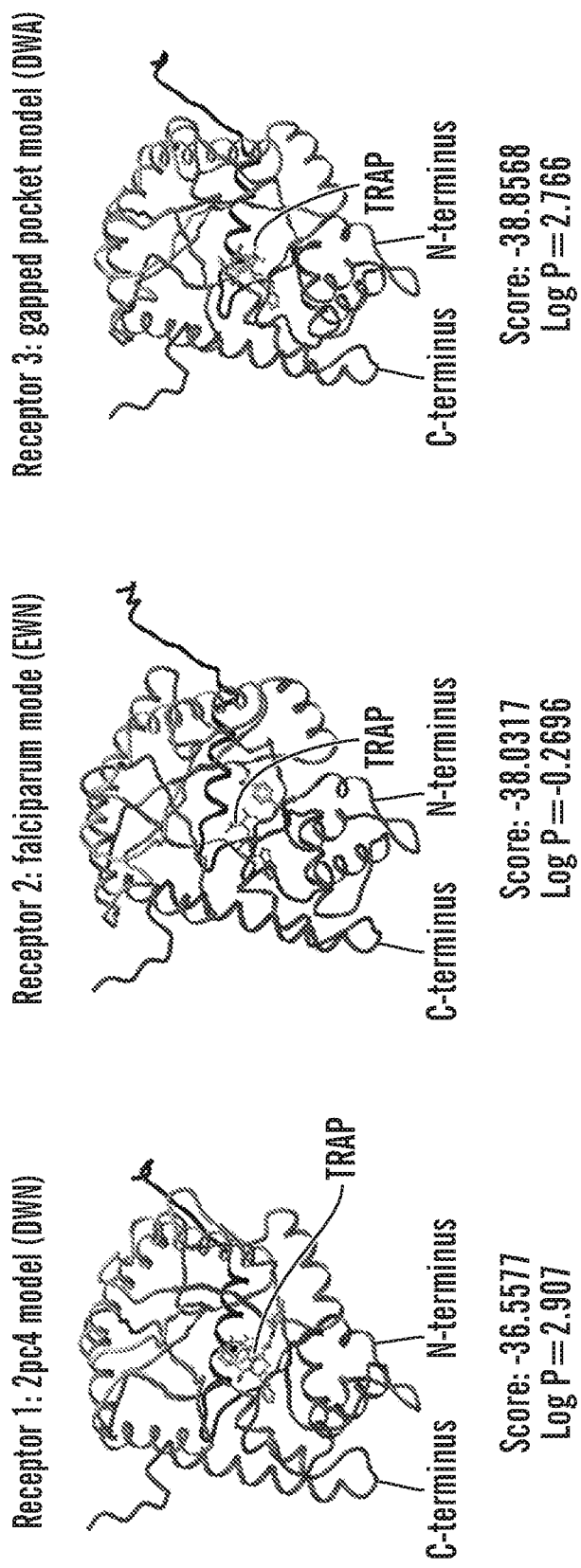
FIGS. 12A-C show representative compounds and their docked poses from the VLS hitlist. Aldolase is shown as a ribbon colored in a gradient from blue at its N-terminus to red at its C-terminus. VLS hits are shown in ball-and-stick depiction with standard atom-coded colors (oxygen=red, nitrogen=blue, hydrogen=grey, carbon=yellow). The TRAP peptide for each receptor model is shown in stick depiction and colored according to the receptor label. The docking score and calculated Log P is shown for each compound. The final hitlist covered all of the receptor models, with a wide range of docking poses, and diverse chemical structures.

Additionally, the hit list contained compounds that docked throughout the target region, with some docking above, below, and behind TRAP when the receptor is viewed with the flexible helix-loop-helix in front of the Aldolase core and below TRAP (FIG. 12). This feature of the hit list is very desirable, as it demonstrates that the ICM-VLS algorithm fully sampled the receptor area. Additionally, it may allow for the future synthesis of multi-valent compound derivatives by linking promising compounds with non-overlapping docking poses.

Sixty of the sixty nine compounds were purchased in the final hit list from ChemBridge for experimental validation studies. The structural and chemical features of these compounds are described in Table 6:

TABLE 6

Structural and Chemical Features of Compounds

| Compound No. | Chembridge ID No. | Chemical Structure | Name |
|---|---|---|---|
| 1 | 5112957 | 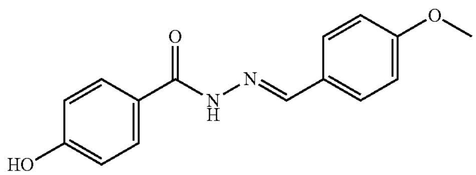 [SMILES: COc1ccc(/C=N/NC(=O)c2ccc(O)cc2)cc1] | 4-hydroxy-N'-(4-methoxybenzylidene)benzohydrazide |
| 2 | 5112979 | 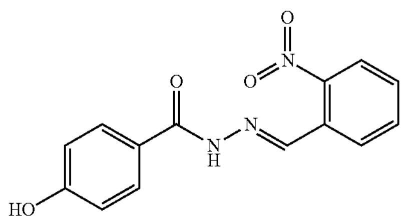 [SMILES: O=C(N/N=C/c1ccccc1[N+](=O)[O-])c1ccc(O)cc1] | 4-hydroxy-N'-(2-nitrobenzylidene)benzohydrazide |
| 3 | 5121901 | 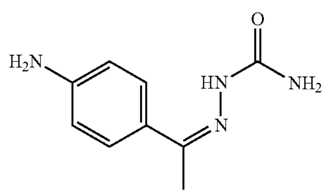 | 1-(4-aminophenyl)-1-ethanone semicarbazone |
| 4 | 5153389 | 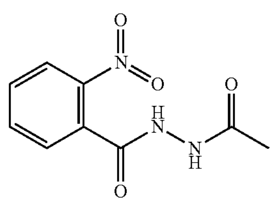 [SMILES: CC(=O)NNC(=O)c1ccccc1[N+](=O)[O-]] | N'-acetyl-2-nitrobenzohydrazide |
| 5 | 5153799 | 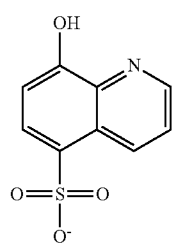 [SMILES: O=S(=O)([O-])c1ccc(O)c2ncccc12] | 8-hydroxy-5-quinolinesulfonic acid |
| 6 | 5227275 | 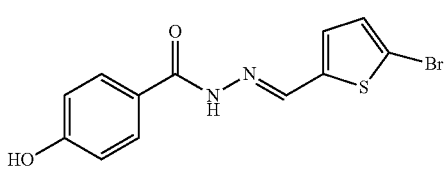 [SMILES: O=C(N/N=C/c1ccc(Br)s1)c1ccc(O)cc1] | N'-[(5-bromo-2-thienyl)methylene]-4-hydroxybenzohydrazide |
| 7 | 5227278 | 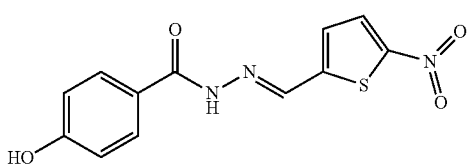 [SMILES: O=C(N/N=C/c1ccc([N+](=O)[O-])s1)c1ccc(O)cc1] | 4-hydroxy-N'-[(5-nitro-2-thienyl)methylene]benzohydrazide |

TABLE 6-continued

Structural and Chemical Features of Compounds

| Compound No. | Chembridge ID No. | Chemical Structure | Name |
|---|---|---|---|
| 8 | 5227280 | 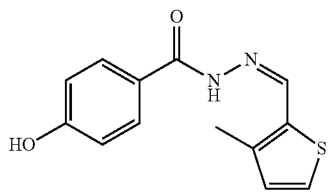 [SMILES: Cc1ccsc1/C=N\NC(=O)c1ccc(O)cc1] | 4-hydroxy-N'-[(3-methyl-2-thienyl)methylene]benzohydrazide |
| 9 | 5227289 | 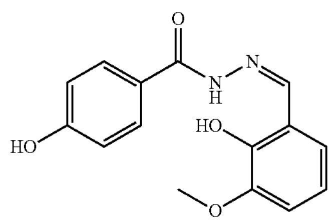 [SMILES: COc1cccc(/C=N\NC(=O)c2ccc(O)cc2)c1O] | 4-hydroxy-N'-(2-hydroxy-3-methoxybenzylidene)benzohydrazide |
| 10 | 5227292 | 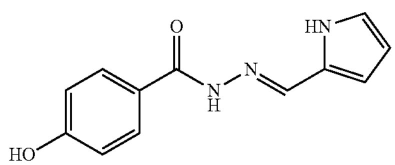 [SMILES: O=C(N/N=C/c1ccc[nH]1)c1ccc(O)cc1] | 4-hydroxy-N'-(1H-pyrrol-2-ylmethylene)benzohydrazide |
| 11 | 5227298 | 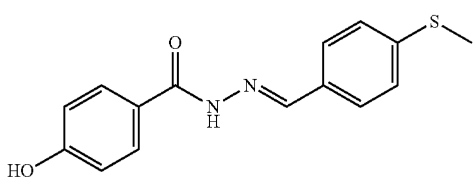 | 4-hydroxy-N'-[4-(methylthio)benzylidene]benzohydrazide |
| 12 | 5227303 | 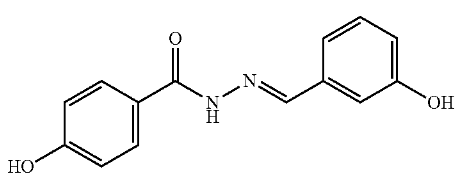 [SMILES: O=C(N/N=C/c1cccc(O)c1)c1ccc(O)cc1] | 4-hydroxy-N'-(3-hydroxybenzylidene)benzohydrazide |
| 13 | 5227326 | 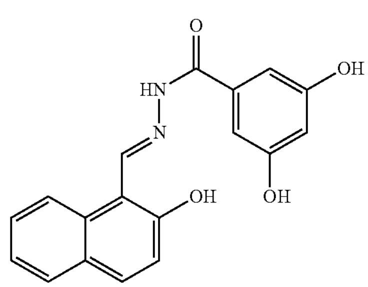 [SMILES: O=C(N/N=C/c1c(O)ccc2ccccc12)c1cc(O)cc(O)c1] | 3,5-dihydroxy-N'-[(2-hydroxy-1-naphthyl)methylene]benzohydrazide |
| 14 | 5252622 | 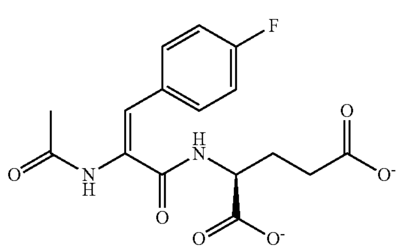 [SMILES: CC(=O)N/C(=C/c1ccc(F)cc1)C(=O)N[C@@H](CCC(=O)[O-])C(=O)[O-]] | N-[2-(acetylamino)-3-(4-fluorophenyl)acryloyl]glutamic acid |

TABLE 6-continued

Structural and Chemical Features of Compounds

| Compound No. | Chembridge ID No. | Chemical Structure | Name |
|---|---|---|---|
| 15 | 5256251 | 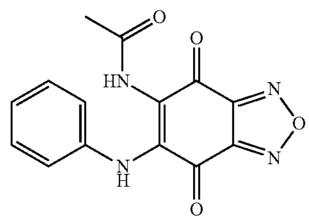 [SMILES: CC(=O)NC1=C(Nc2ccccc2)C(=O)c2nonc2C1=O] | N-(6-anilino-4,7-dioxo-4,7-dihydro-2,1,3-benzoxadiazol-5-yl)acetamide |
| 16 | 5256921 | 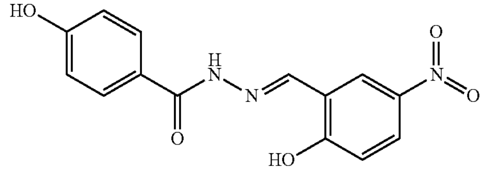 [SMILES: O=C(N/N=C/c1cc([N+](=O)[O-])ccc1O)c1ccc(O)cc1] | 4-hydroxy-N'-(2-hydroxy-5-nitrobenzylidene)benzohydrazide |
| 17 | 5264148 | 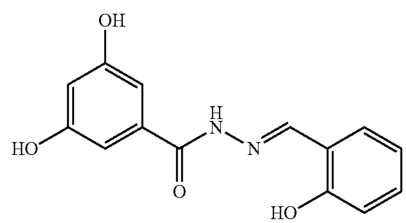 [SMILES: O=C(N/N=C/c1ccccc1O)c1cc(O)cc(O)c1] | 3,5-dihydroxy-N'-(2-hydroxybenzylidene)benzohydrazide |
| 18 | 5266986 | 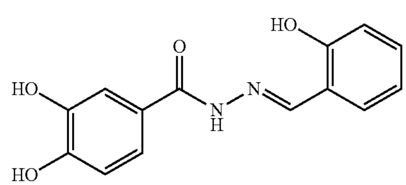 [SMILES: O=C(N/N=C/c1ccccc1O)c1ccc(O)c(O)c1] | 3,4-dihydroxy-N'-(2-hydroxybenzylidene)benzohydrazide |
| 19 | 5267209 | 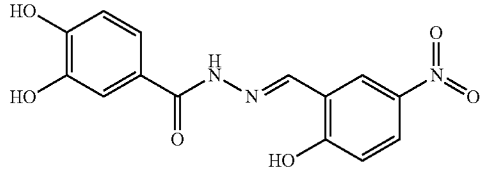 [SMILES: O=C(N/N=C/c1cc([N+](=O)[O-])ccc1O)c1ccc(O)c(O)c1] | 3,4-dihydroxy-N'-(2-hydroxy-5-nitrobenzylidene)benzohydrazide |
| 20 | 5267603 | 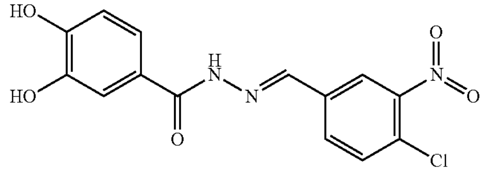 [SMILES: O=C(N/N=C/c1ccc(Cl)c([N+](=O)[O-])c1)c1ccc(O)c(O)c1] | N'-(4-chloro-3-nitrobenzylidene)-3,4-dihydroxybenzohydrazide |
| 21 | 5280090 | 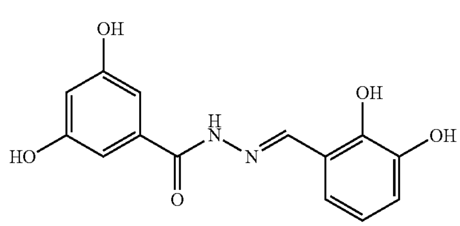 [SMILES: O=C(N/N=C/c1cccc(O)c1O)c1cc(O)cc(O)c1] | N'-(2,3-dihydroxybenzylidene)-3,5-dihydroxybenzohydrazide |

TABLE 6-continued

Structural and Chemical Features of Compounds

| Compound No. | Chembridge ID No. | Chemical Structure | Name |
|---|---|---|---|
| 22 | 5302171 | 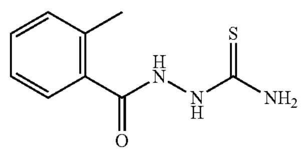 | 2-(2-methylbenzoyl)hydrazine-carbothioamide |
| 23 | 5312165 | 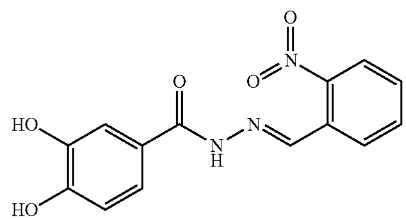 [SMILES: O=C(N/N=C/c1ccccc1[N+](=O)[O-])c1ccc(O)c(O)c1] | 3,4-dihydroxy-N'-(2-nitrobenzylidene)benzohydrazide |
| 24 | 5315106 | 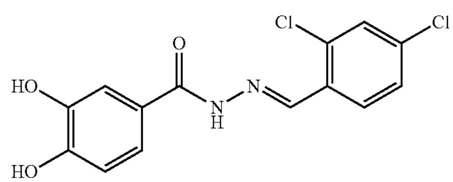 [SMILES: O=C(N/N=C/c1ccc(Cl)cc1Cl)c1ccc(O)c(O)c1] | N'-(2,4-dichlorobenzylidene)-3,4-dihydroxybenzohydrazide |
| 25 | 5316181 | 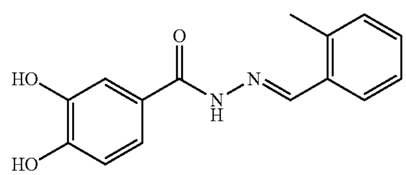 [SMILES: Cc1ccccc1/C=N/NC(=O)c1ccc(O)c(O)c1] | 3,4-dihydroxy-N'-(2-methylbenzylidene)benzohydrazide |
| 26 | 5318411 | 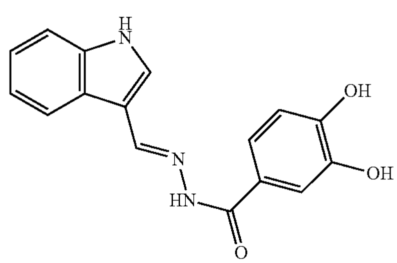 [SMILES: O=C(N/N=C/c1c[nH]c2ccccc12)c1ccc(O)c(O)c1] | 3,4-dihyroxy-N'-(1H-indol-3-ylmethylene)benzohydrazide |
| 27 | 5320663 | 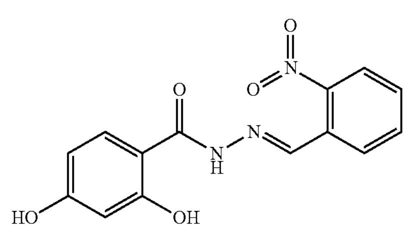 [SMILES: O=C(N/N=C/c1ccccc1[N+](=O)[O-])c1ccc(O)cc1O] | 2,4-dihydroxy-N'-(2-nitrobenzylidene)benzohydrazide |

TABLE 6-continued

Structural and Chemical Features of Compounds

| Compound No. | Chembridge ID No. | Chemical Structure | Name |
|---|---|---|---|
| 28 | 5321784 | 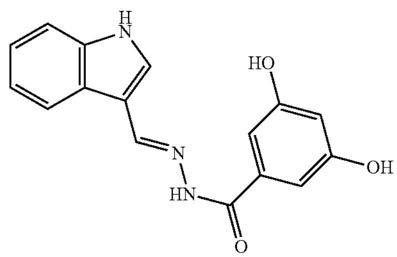 [SMILES: O=C(N/N=C/c1c[nH]c2ccccc12)c1cc(O)cc(O)c1] | 3,5-dihydroxy-N'-(1H-indol-3-ylmethylene)benzohydrazide |
| 29 | 5322358 | 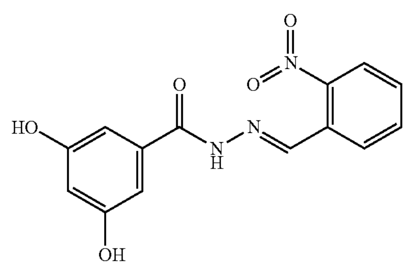 [SMILES: O=C(N/N=C/c1ccccc1[N+](=O)[O-])c1cc(O)cc(O)c1] | 3,5-dihydroxy-N'-(2-nitrobenzylidene)benzohydrazide |
| 30 | 5331708 | 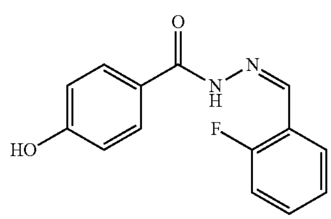 [SMILES: O=C(N/N=C\c1ccccc1F)c1ccc(O)cc1] | N'-(2-fluorobenzylidene)-4-hydroxybenzohydrazide |
| 31 | 5336667 | 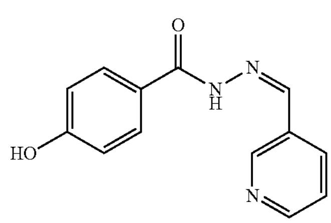 [SMILES: O=C(N/N=C\c1cccnc1)c1ccc(O)cc1] | 4-hydroxy-N'-(3-pyridinylmethylene)benzohydrazide |
| 32 | 5377378 | 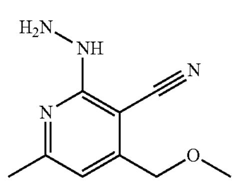 | 2-hydrazino-4-(methoxymethyl)-6-methylnicotinonitrile |
| 33 | 5468567 | 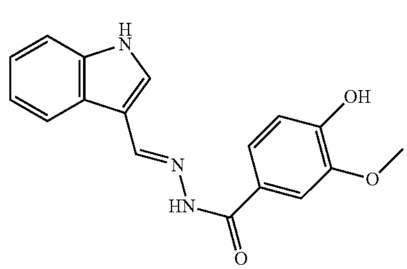 [SMILES: COc1cc(C(=O)N/N=C/c2c[nH]c3ccccc23)ccc1O] | 4-hydroxy-N'-(1H-indol-3-ylmethylene)-3-methoxybenzohydrazide |

TABLE 6-continued

Structural and Chemical Features of Compounds

| Compound No. | Chembridge ID No. | Chemical Structure | Name |
|---|---|---|---|
| 34 | 5466778 | 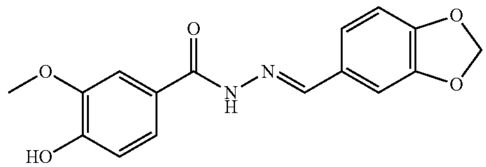 [SMILES: COc1cc(C(=O)N/N=C/c2ccc3c(c2)OCO3)ccc1O] | N'-(1,3-benzodioxol-5-ylmethylene)-4-hydroxy-3-methoxybenzohydrazide |
| 35 | 5475747 | 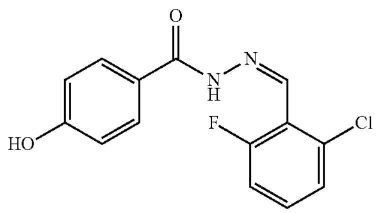 [SMILES: O=C(N/N=C\c1c(F)cccc1Cl)c1ccc(O)cc1] | N'-(2-chloro-6-fluorobenzylidene)-4-hydroxybenzohydrazide |
| 36 | 5493440 | 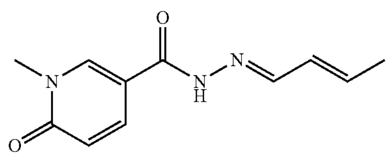 [SMILES: C/C=C/C=N/NC(=O)c1ccc(=O)n(C)c1] | N'-2-buten-1-ylidene-1-methyl-6-oxo-1,6-dihydro-3-pyridinecarbohydrazide |
| 37 | 5511358 | 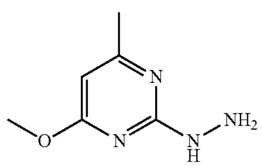 | 2-hydrazino-4-methoxy-6-methylpyrimidine |
| 38 | 5521698 | 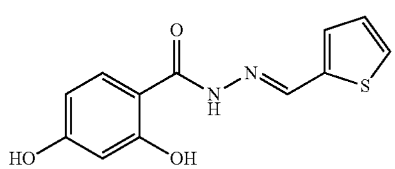 [SMILES: O=C(N/N=C/c1cccs1)c1ccc(O)cc1O] | 2,4-dihydroxy-N'-(2-thienylmethylene)benzohydrazide |
| 39 | 5532286 | 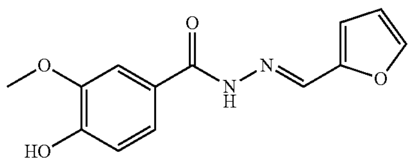 [SMILES: COc1cc(C(=O)N/N=C/c2ccco2)ccc1O] | N'-(2-furylmethylene)-4-hydroxy-3-methoxybenzohydrazide |
| 40 | 5562286 | 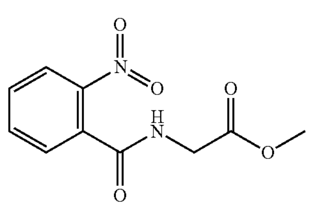 [SMILES: COC(=O)CNC(=O)c1ccccc1[N+](=O)[O-]] | methyl N-(4-nitrobenzoyl)glycinate |
| 41 | 5567417 | 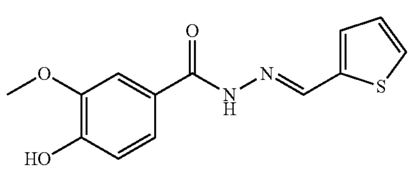 [SMILES: COc1cc(C(=O)N/N=C/c2cccs2)ccc1O] | 4-hydroxy-3-methoxy-N'-(2-thienylmethylene)benzohydrazide |

TABLE 6-continued

Structural and Chemical Features of Compounds

| Compound No. | Chembridge ID No. | Chemical Structure | Name |
|---|---|---|---|
| 42 | 530714 | 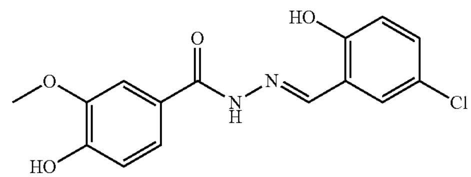 [SMILES: COc1cc(C(=O)N/N=C/c2cc(Cl)ccc2O)ccc1O] | N'-(5-chloro-2-hydroxybenzylidene)-4-hydroxy-3-methoxybenzohydrazide |
| 43 | 5774457 | 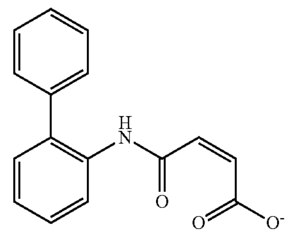 [SMILES: O=C([O-])/C=C\C(=O)Nc1ccccc1-c1ccccc1] | 4-(2-biphenylylamino)-4-oxo-2-butenoic acid |
| 44 | 5798683 | 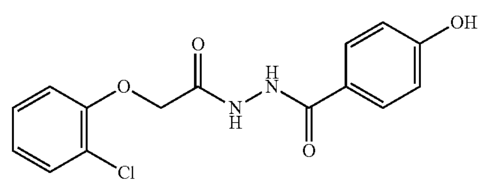 [SMILES: O=C(COc1ccccc1Cl)NNC(=O)c1ccc(O)cc1] | N'-[(2-chlorophenoxy)acetyl]-4-hydroxybenzohydrazide |
| 45 | 5799663 | 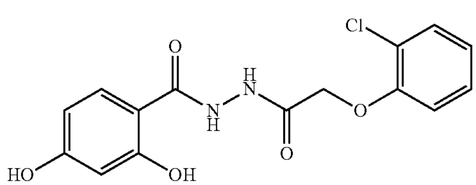 [SMILES: O=C(COc1ccccc1Cl)NNC(=O)c1ccc(O)cc1O] | N'-[(2-chlorophenoxy)acetyl]-2,4-dihydroxybenzohydrazide |
| 46 | 5851839 | 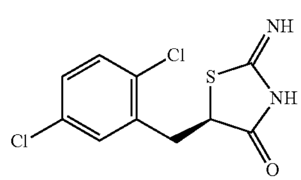 [SMILES: N=C1NC(=O)[C@@H](Cc2cc(Cl)ccc2Cl)S1] | 5-(2,5-dichlorobenzyl)-2-imino-1,3-thiazolidin-4-one |
| 47 | 5853551 | 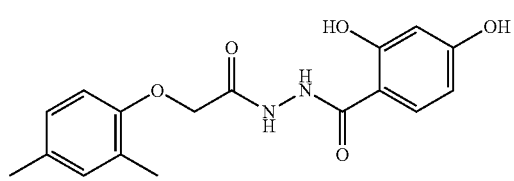 [SMILES: Cc1ccc(OCC(=O)NNC(=O)c2ccc(O)cc2O)c(C)c1] | N'-[(2,4-dimethylphenoxy)acetyl]-2,4-dihydroxybenzohydrazide |
| 48 | 6213095 | 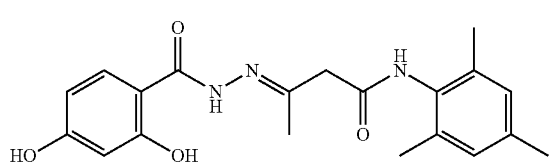 [SMILES: C/C(CC(=O)Nc1c(C)cc(C)cc1C)=N\NC(=O)c1ccc(O)cc1O] | 3-[(2,4-dihydroxybenzoyl)hydrazono]-N-mesitylbutanamide |

TABLE 6-continued

Structural and Chemical Features of Compounds

| Compound No. | Chembridge ID No. | Chemical Structure | Name |
|---|---|---|---|
| 49 | 6326744 | 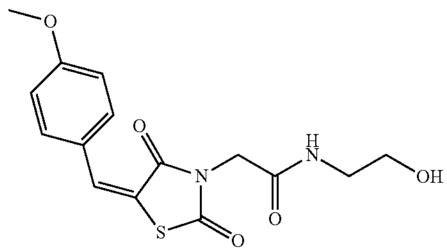 [SMILES: COc1ccc(/C=C2/SC(=O)N(CC(=O)NCCO)C2=O)cc1] | N-(2-hydroxyethyl)-2-[5-(4-methoxybenzylidene)-2,4-dioxo-1,3-thiazolidin-3-yl]acetamide |
| 50 | 6348549 | 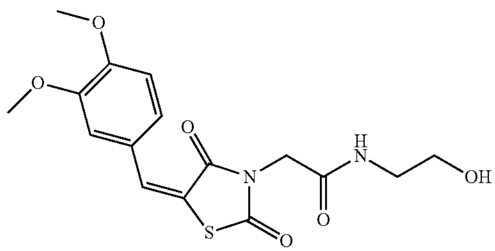 [SMILES: COc1ccc(/C=C2/SC(=O)N(CC(=O)NCCO)C2=O)cc1OC] | 2-[5-(3,4-dimethoxybenzylidene)-2,4-dioxo-1,3-thiazolidin-3-yl]-N-(2-hydroxyethyl)acetamide |
| 51 | 6356536 | 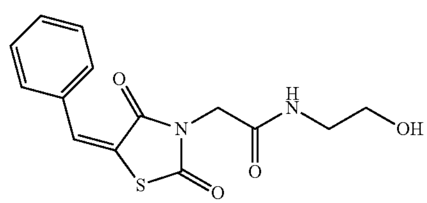 [SMILES: O=C(CN1C(=O)S/C(=C/c2ccccc2)C1=O)NCCO] | 2-(5-benzylidene-2,4-dioxo-1,3-thiazolidin-3-yl)-N-(2-hydroxyethyl)acetamide |
| 52 | 6631742 | 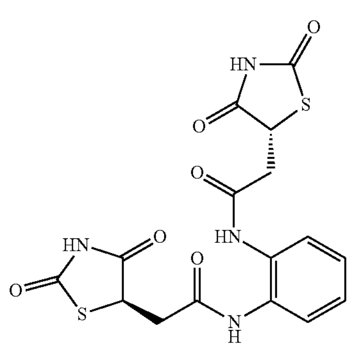 [SMILES: O=C(C[C@H]1SC(=O)NC1=O)Nc1ccccc1NC(=O)C[C@H]1SC(=O)NC1=O] | N,N'-1,2-phenylenebis[2-(2,4-dioxo-1,3-thiazolidin-5-yl)acetamide] |
| 53 | 6946462 | 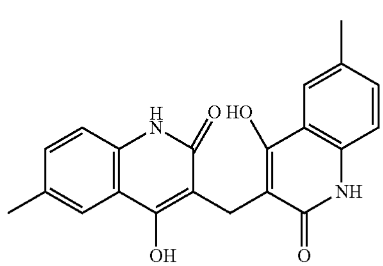 [SMILES: Cc1ccc2[nH]c(=O)c(Cc3c(O)c4cc(C)ccc4[nH]c3=O)c(O)c2c1] | 3,3'-methylenebis (4-hydroxy-6-methyl-2(1H)-quinolinone) |

TABLE 6-continued

Structural and Chemical Features of Compounds

| Compound No. | Chembridge ID No. | Chemical Structure | Name |
|---|---|---|---|
| 54 | 6949907 | 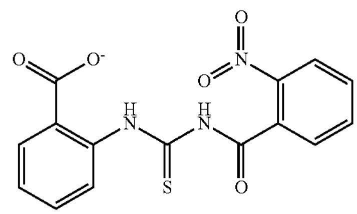 [SMILES: O=C([O-])c1ccccc1NC(=S)NC(=O)c1ccccc1[N+](=O)[O-]] | 2-({[(2-nitrobenzoyl)amino]carbonothioyl}amino)benzoic acid |
| 55 | 6988892 | 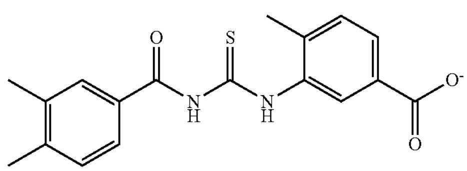 [SMILES: Cc1ccc(C(=O)NC(=S)Nc2cc(C(=O)[O-])ccc2C)cc1C] | 3-({[(3,4-dimethylbenzoyl)amino]carbonothioyl}amino)-4-methylbenzoic acid |
| 56 | 7446357 | 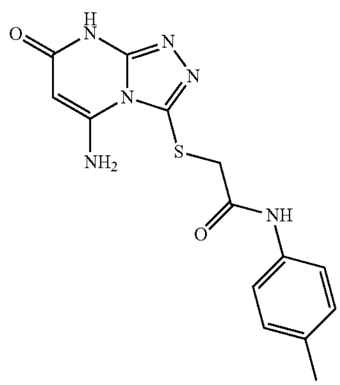 [SMILES: Cc1ccc(NC(=O)CSc2nnc3[nH]c(=O)cc(N)n23)cc1] | 2-[(5-amino-7-oxo-7,8-dihydro[1,2,4]triazolo[4,3-a]pyrimidin-3-yl)thio]-N-(4-methylphenyl)acetamide |
| 57 | 7507803 | 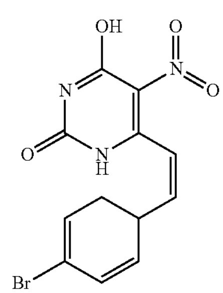 [SMILES: O=c1nc(O)c([N+](=O)[O-])c(/C=C\C2C=CC(Br)=CC2)[nH]1] | 6-[2-(4-bromophenyl)vinyl]-4-hydroxy-5-nitro-2(1H)-pyrimidinone |
| 58 | 7530375 | 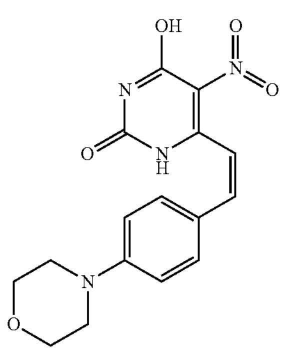 [SMILES: O=c1nc(O)c([N+](=O)[O-])c(/C=C\c2ccc(N3CCOCC3)cc2)[nH]1] | 4-hydroxy-6-(2-(4-(4-morpholinyl)phenyl)vinyl)-5-nitro-2(1H)pyrimidinone |

TABLE 6-continued

Structural and Chemical Features of Compounds

| Compound No. | Chembridge ID No. | Chemical Structure | Name |
|---|---|---|---|
| 59 | 7608933 | 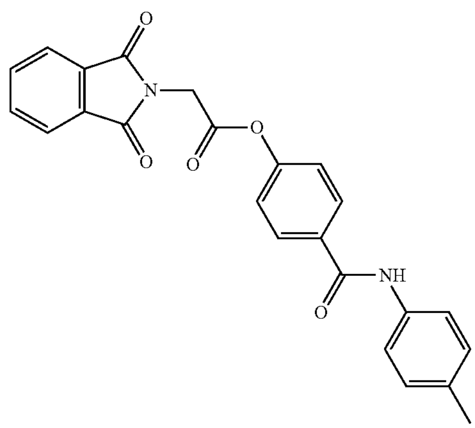 [SMILES: Cc1ccc(NC(=O)c2ccc(OC(=O)CN3C(=O)c4ccccc4C3=O)cc2)cc1] | 4-([[(4-methylphenyl)amino]carbonyl)phenyl(1,3-dioxo-1,3-dihydro-2H-isoindol-2-yl)acetate |
| 60 | 7666888 | 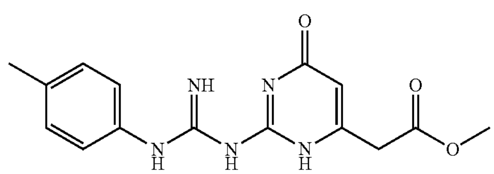 | methyl[2-({imino[(4-methylphenyl)amino]methyl}amino)-6-oxo-3,6-dihydro-4-pyrimidinyl]acetate |

Example 25—In Vitro Hit Validation

In order to validate these VLS hits as Aldolase-TRAP enhancers, they were assayed in vitro for their ability to stabilize the complex using two independent assays. A "thermal shift" assay, which utilizes an environmentally-sensitive fluorescent dye to measure the effects of candidate drugs on the melting point (i.e., stability) of the TRAP-Aldolase complex. An "Aldolase catalysis" assay, as drugs that stabilize the Aldolase-TRAP interaction should enhance the normally weak inhibition of the enzyme by TRAP. Validated hits would be those that preferentially inhibit Aldolase activity in the presence vs. absence of TRAP.

Example 26—Stabilization of the TRAP-Aldolase Complex

Figure 13:
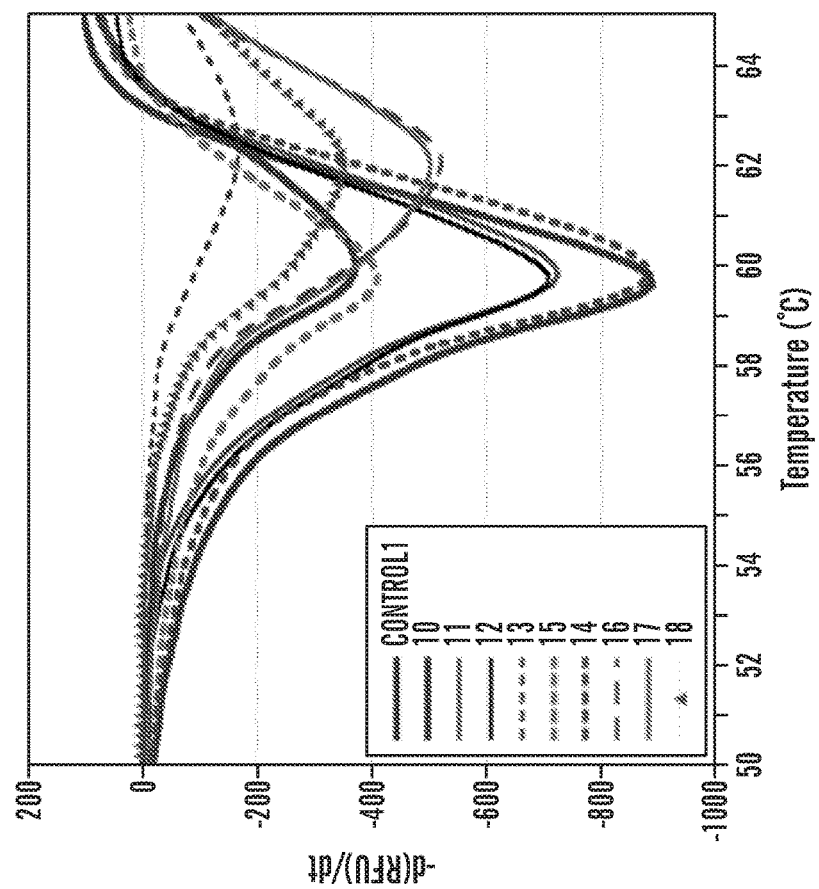
FIG. 13 shows stabilization of the Aldolase-TRAP complex upon the addition of VLS hits. The results of the thermal shift assay for nine of the VLS hits are shown. The curves represent the first derivative plots of the fluorescence curves obtained during the assay (RFU=relative fluorescence units). The minimum of each curve represents the sample's melting point ($T_m$). The $T_m$ for the Aldolase-TRAP complex plus DMSO (control 1, lower solid blue curve) is approximately 59.5+/−1° C. The addition of compounds 13, 16, 17, and 18 to the complex (blue dashed line, thin green dashed line, red solid line, and grey triangles, respectively) each resulted in an increase in $T_m$ greater than 2° C., indicating a stabilizing effect on the TRAP-Aldolase complex.

The effects of the compounds on the stability of the Aldolase-TRAP complex was measured by thermally denaturing the complex in the presence of Sypro Orange, which increases in fluorescence as it is exposed to the hydrophobic cores of the denatured proteins. The first derivative curves of the fluorescence readings obtained for nine of the VLS hits are shown in FIG. 13, demonstrating an upward shift in melting point ($T_m$) upon the addition of four of the compounds to the TRAP-Aldolase complex (i.e. the minima of the curves are shifted to the right. All told, 8 compounds produced an upward shift of >2° C. in the $T_m$ of the Aldolase-TRAP complex (compounds 5, 9, 13, 16, 17, 18, 45, and 52), suggesting a stabilizing effect.

Interestingly, 3 compounds produced a downward shift of >2° C. in the $T_m$ (compounds 37, 49, and 50). As noted above, only the last 3 residues of TRAP were visible in the crystal structure and receptor models that were screened against it. It is possible that these compounds interact in an inhibitory way with upstream TRAP residues that could not be accounted for in these screens.

The results of the thermal shift assay for all 60 compounds are detailed in FIG. 24.

Example 27—Selective Aldolase Catalysis Inhibition in the Presence of TRAP

Figure 14:
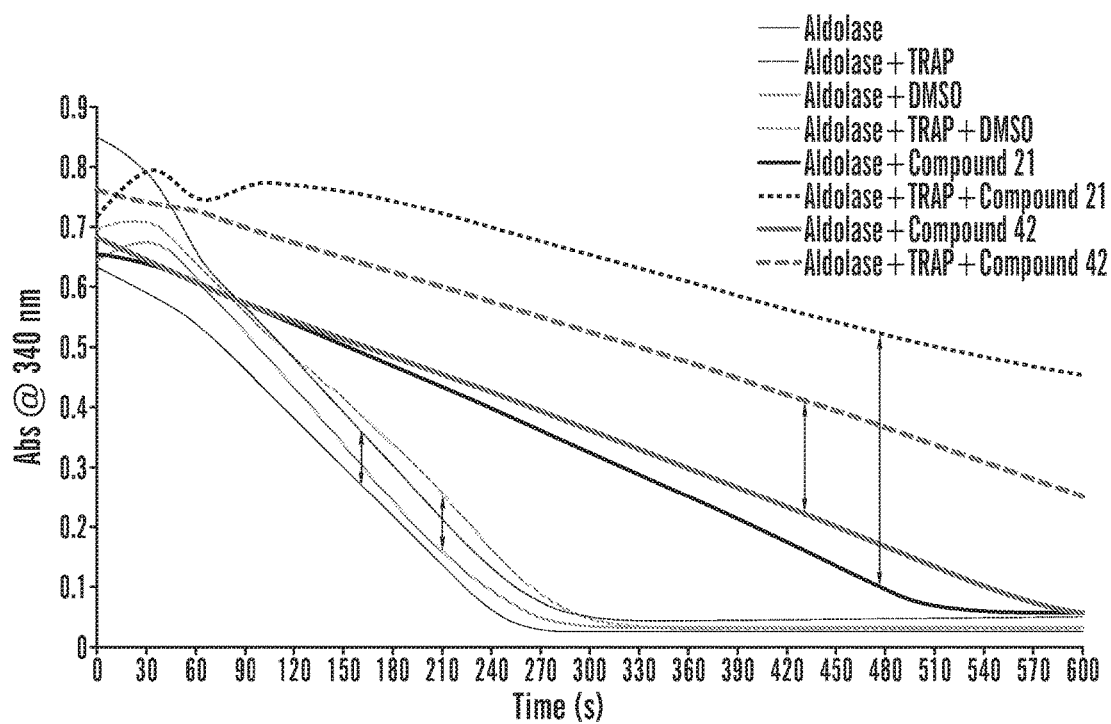
FIG. 14 shows enhanced TRAP inhibition of Aldolase activity in the presence of VLS hits. At 100 nM, TRAP has a very small effect on the rate of NADH consumption (rate of decrease in absorbance at 340 nm, brown double-headed arrow). The affect of TRAP on Aldolase catalysis is not increased by DMSO (blue arrow). However, when 50 μM of compounds 21 or 42 were added to the assay mix, the ability of TRAP to inhibit Aldolase activity was noticeably increased (green and purple arrows, respectively). (Note: The curves shown have been corrected for the compounds' inherent absorbances at 340 nM.)

The effects of the VLS hits on Aldolase activity were measured in the presence and absence of TRAP, by coupling the Aldolase reaction to the α-GDH/TPI reaction which consumes NADH. Drug candidates were considered potential Aldolase-TRAP stabilizers if they promoted an increase in Aldolase inhibition in the presence vs. absence of TRAP. The results of a catalysis assay for two of the VLS hits are shown in FIG. 14. Note that while the drugs do appear to inhibit the activity of Aldolase on their own, there is a far greater decrease in the rate of NADH consumption (detected by a decrease in absorbance at 340 nm) in the presence of TRAP.

Figure 15:
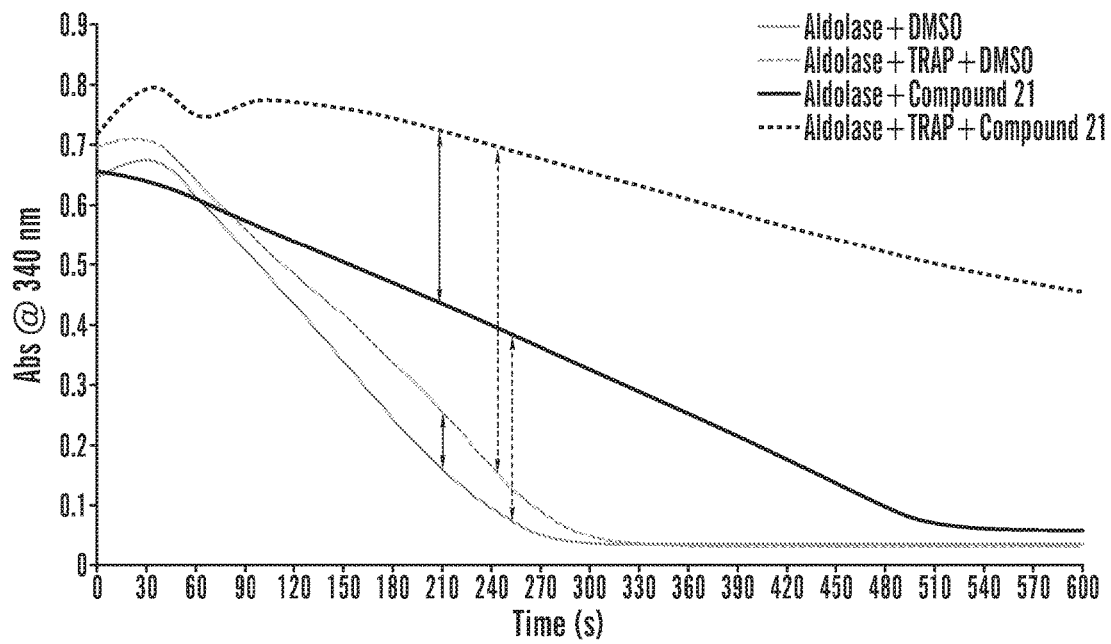
FIG. 15 shows derivation of TRAP Enhancement and Complex Dependence Scores for the VLS hits. This figure is a simplified version of FIG. 14 for the purpose of illustrating the rationale behind the use of the TRAP Enhancement and Complex Dependence Scores to describe the catalysis assay results for each compound. The solid arrows represent the inhibition of Aldolase by TRAP in the presence of DMSO (blue; the denominator in Equation 1) or a candidate drug (purple; the numerator in equation Equation 1). The dashed arrows represent the inhibition of Aldolase by a candidate drug—relative to the DMSO control—in the presence (purple; numerator in Equation 2) vs. absence (pink; denominator in Equation 2) of TRAP.

Two scores were calculated for the compounds based on the NADH absorbance curves for the catalysis assays:
1. An "enhancement of TRAP activity against Aldolase" score, which was meant to indicate the change in TRAP's ability to inhibit Aldolase activity due to the compound relative to the DMSO control—i.e. the ratio of the purple and blue solid arrows in FIG. 15.

(TRAP Enhancement Score, Equation 1)

$$\frac{AUC_{drug+TRAP} - AUC_{drug}}{AUC_{DMSO+TRAP} - AUC_{DMSO}}$$

This score is meant to reflect the compound's ability to increase the inhibition of Aldolase by TRAP—i.e. the compound's ability to stabilize the Aldolase-TRAP complex. (AUC=Area Under the absorbance Curve; drug+TRAP=assay conditions in which both TRAP and the drug are present; drug=assay with the drug but no TRAP; DMSO+TRAP=DMSO control with TRAP present; DMSO=DMSO control without TRAP.)

2. Since the goal was not simply to find compounds that help TRAP inhibit Aldolase, but rather to find compounds that simultaneously do not inhibit Aldolase by themselves—i.e. the ratio between the dotted arrows in FIG. 15—a second "inhibition of Aldolase only in the presence of TRAP" score for each compound was also calculated.

(Complex Dependence Score, Equation 2)

$$\frac{AUC_{drug+TRAP} - AUC_{DMSO+TRAP}}{AUC_{drug} - AUC_{DMSO}}$$

This score is meant to reflect the difference in affinity of the compound for the Aldolase-TRAP complex vs. for Aldolase alone. (AUC=Area Under the absorbance Curve; drug+TRAP=assay conditions in which both TRAP and the drug are present; drug=assay with the drug but no TRAP; DMSO+TRAP=DMSO control with TRAP present; DMSO=DMSO control without TRAP.)

For the purpose of this study, compounds that obtained a TRAP Enhancement Score ≥1.5 and a Complex Dependence Score >1 or a TRAP Enhancement Score >1 and a Complex Dependence Score ≥1.5 in any one experiment were considered "active" in the catalysis assay. Additionally, since a small but reproducible effect of DMSO on the assay was noted (see FIG. 25), scores were also calculated relative to Aldolase alone, and included compounds that met the criteria above with these scores in the initial "active" list as well. Eleven of the initial 60 compounds met these criteria when assayed at 50 µM, including compounds 1, 5, 17, 18, 19, 21, 32, 36, 39, 42, and 43, while 15 of the compounds were not soluble in the assay buffer at that concentration. (The kinetic curves and scores for all of the compounds tested are shown in FIG. 25)

These permissive cut-off values were chosen so as to minimize the number of false negatives. While this likely resulted in a higher false-positive rate, it was felt that at this early stage in the analysis, it was better to include as many compounds as possible for further testing. For example, compound 24 could not be adequately tested for its Aldolase catalysis inhibition properties due to it's unpredictable solubility; however, as will be shown below, crystallographic data demonstrated it's binding within the enzyme active site, cross-linking TRAP and Aldolase. This compound also inhibited parasite gliding in vivo (see below), justifying the reluctance to rule out compounds based solely on their performance in the catalysis (or thermal shift) assay(s).

Example 28—Crystallographic Hit Validation

In order to aid in the interpretation of the catalysis assay and thermal shift results, and to further validate the VLS approach, as well as to obtain additional high-resolution receptor structures for future drug design projects, TRAP-Aldolase crystals were soaked in solutions containing some of the VLS compounds and also attempted to grow de novo crystals with Aldolase, TRAP, and the candidate drugs.

To date, well-diffracting crystals were obtained for compounds 1, 24, and 43, and the preliminary crystallographic data suggests that these chemicals do in fact cross-link the two proteins. In one case—that of compound 24—electron density was seen for both TRAP and the compound in all 4 subunits of the Aldolase tetramer (FIG. 16). Notably, in the previously published Aldolase-TRAP co-crystal structure (PDB ID: 2pc4), TRAP could only be seen in one Aldolase subunit (Bosch et al., "Aldolase Provides an Unusual Binding Site for Thrombospondin-Related Anonymous Protein in the Invasion Machinery of the Malaria Parasite," Proc. Nat'l. Acad. Sci. USA 104(17):7015-20 (2007), which is hereby incorporated by reference in its entirety), further highlighting the stabilizing effect of this compound on the complex.

Example 29—In Vivo Hit Validation

Figure 17:
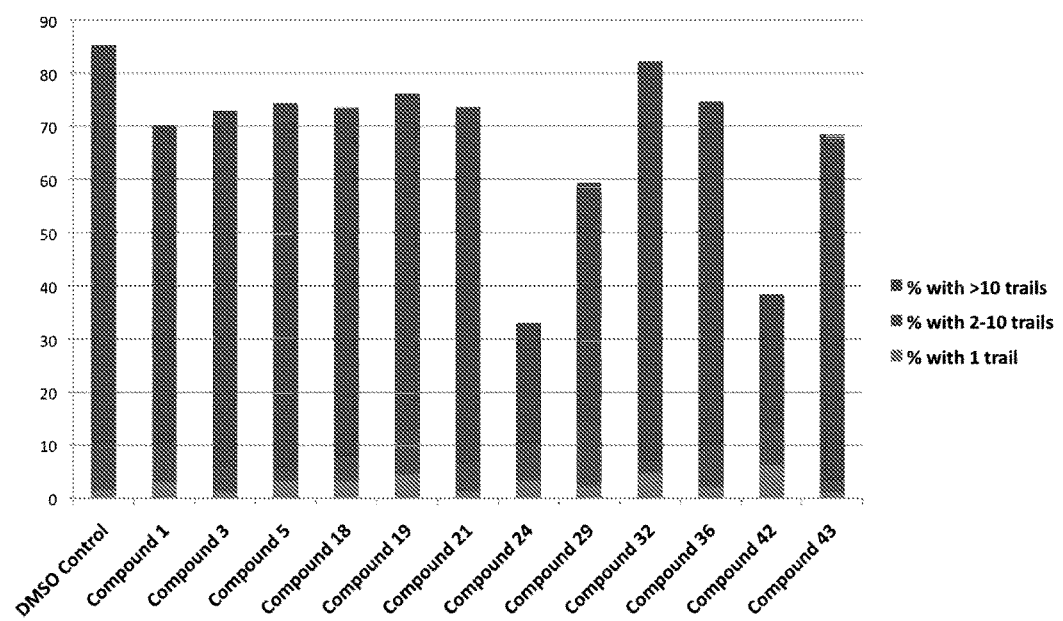
FIG. 17 shows the effect of VLS hits on sporozoite motility. The total heights of the bars represent the percentage of sporozoites that were motile (produced 1 or more trails on a glass slide) during the assay period. "Normal" sporozoites produce >10 trails under the assay conditions. As shown here, sporozoites treated with compounds 24 or 42 were less motile overall and produced fewer trails than the DMSO controls. In this experiment, treatment with DMSO, compound 24, or compound 42 produced 85, 33, and 38% motile sporozoites, respectively. (Detailed counts of motile and non-motile sporozoites, as well as the results of repeated assays with compounds 24 and 42, are tabulated in Table 6 and 7.
Figure 18:
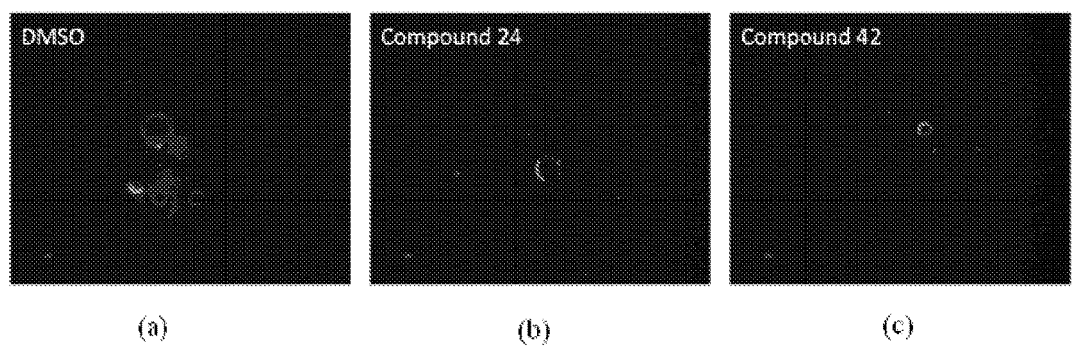
FIGS. 18A-C show that compounds 24 and 42 inhibit sporozoite motility. Fluorescent microscopy images of a representative sporozoite (green cresent) and it's gliding path (green spirals) for 3 assay treatments: DMSO control (FIG. 18A), compound 24 (FIG. 18B), and compound 42 (FIG. 18C). Sporozoite trails were visualized using a biotinylated antibody to CSp. While some sporozoites treated with compounds 24 or 42 did produce >10 trails, most of them produced no or few trails as shown here.

The effect of 12 of the active compounds on parasite motility was assayed. As shown in FIG. 17 and FIG. 18, two of the compounds—24 and 42—produced a pronounced inhibition of gliding motility when assayed at 500 µM against P. berghei sporozoites. The effect on sporozoite motility was measured for a subset of the VLS hits. As a reference, "normal" motile sporozoites generally produce >10 trails in the assay conditions used.

TABLE 7

Sporozoite motility

| Compound # | # of parasites counted | % motile cells | % with 1 trail | % with 2-10 trails | % with >10 trails |
|---|---|---|---|---|---|
| DMSO | 136 | 85 | 1 | 9 | 75 |
| 1 | 97 | 70 | 3 | 7 | 60 |
| 3 | 85 | 73 | 1 | 5 | 67 |
| 5 | 90 | 74 | 3 | 2 | 69 |
| 18 | 91 | 74 | 3 | 4 | 66 |
| 19 | 88 | 76 | 5 | 8 | 64 |
| 21 | 76 | 74 | 1 | 5 | 67 |
| 24 | 145 | 33 | 3 | 7 | 23 |
| 29 | 86 | 59 | 2 | 12 | 45 |
| 32 | 85 | 82 | 5 | 2 | 75 |
| 36 | 91 | 75 | 2 | 8 | 65 |
| 42 | 177 | 38 | 6 | 7 | 25 |
| 43 | 92 | 68 | 1 | 2 | 65 |

The motility assay was repeated in triplicate for compounds 24 and 42. The results are shown below in Table 8:

TABLE 8

Sporozoite motility for compound 24 and 42

| Compound # | # of parasites counted | % motile cells | % with 1 trail | % with 2-10 trails | % with >10 trails |
|---|---|---|---|---|---|
| DMSO (1) | 124 | 82 | 2 | 10 | 70 |
| DMSO (2) | 106 | 83 | 4 | 9 | 70 |
| DMSO (3) | 115 | 78 | 2 | 8 | 69 |
| DMSO Average | 115 | 81 | 3 | 9 | 70 |
| 24 (1) | 116 | 32 | 3 | 8 | 21 |
| 24 (2) | 125 | 26 | 0 | 2 | 24 |
| 24 (3) | 126 | 21 | 2 | 5 | 14 |
| 24 Average | 122 | 26 | 2 | 5 | 20 |
| 42 (1) | 129 | 46 | 7 | 9 | 30 |
| 42 (2) | 128 | 53 | 5 | 14 | 34 |
| 42 (3) | 121 | 50 | 5 | 17 | 28 |
| 42 Average | 126 | 50 | 6 | 13 | 31 |

As discussed above, the TRAP sequence is slightly different between P. berghei and P. falciparum. It is therefore possible that some of the compounds that were not active against P. berghei will prove to be active against P. falciparum, and vice versa.

Figure 19A:
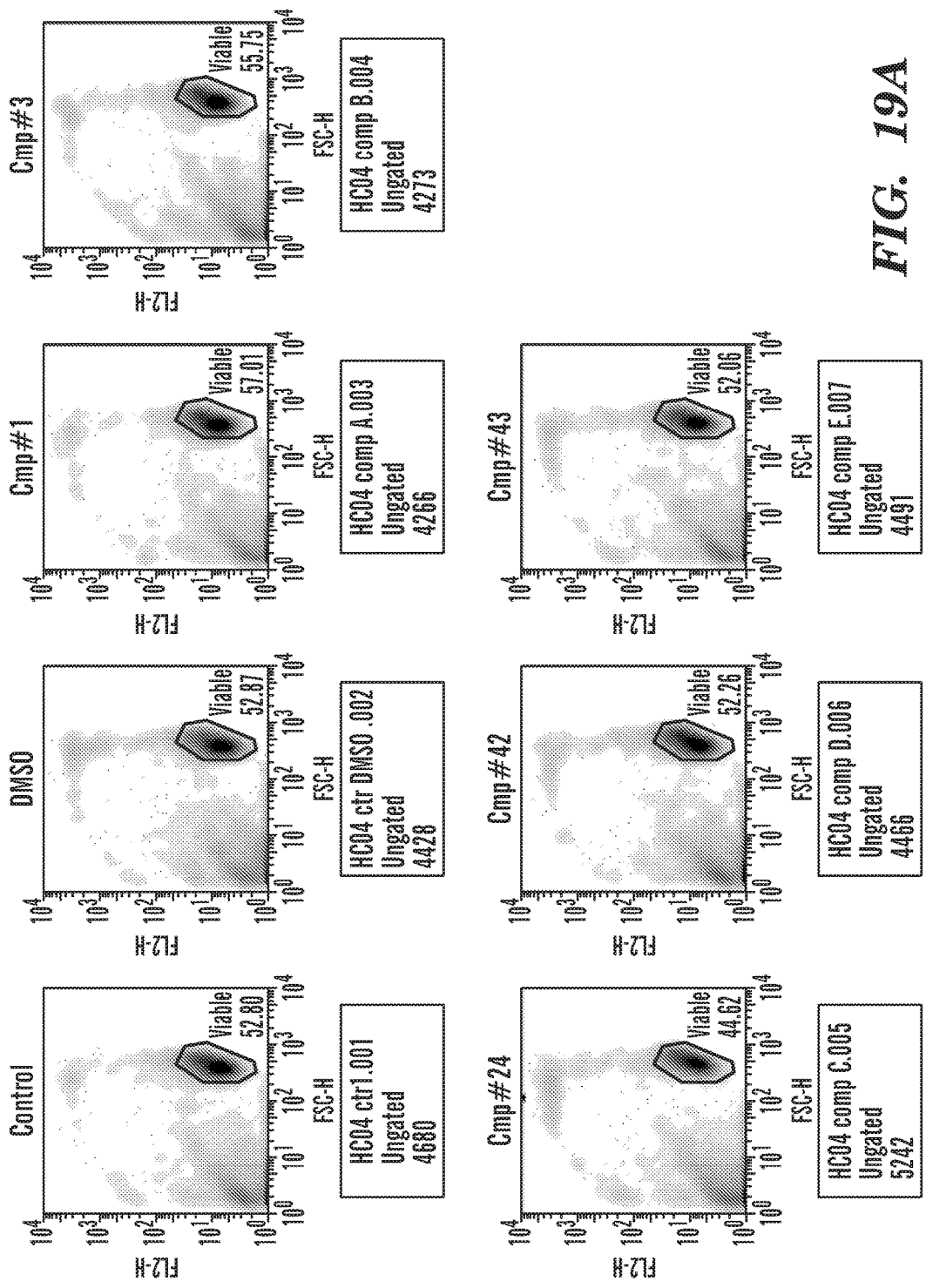
FIGS. 19A-B shows that lead candidates do not cause cytotoxicity in human hepatocytes. Human hepatocytes (HC-04 cells) were treated with 100 µM of the compounds, and then analyzed for the expression of apoptotic markers (via Annexin V-APC and Propidium Iodide staining) by flow cytometry. These are representative examples of the compounds tested to date.
Figure 19B:
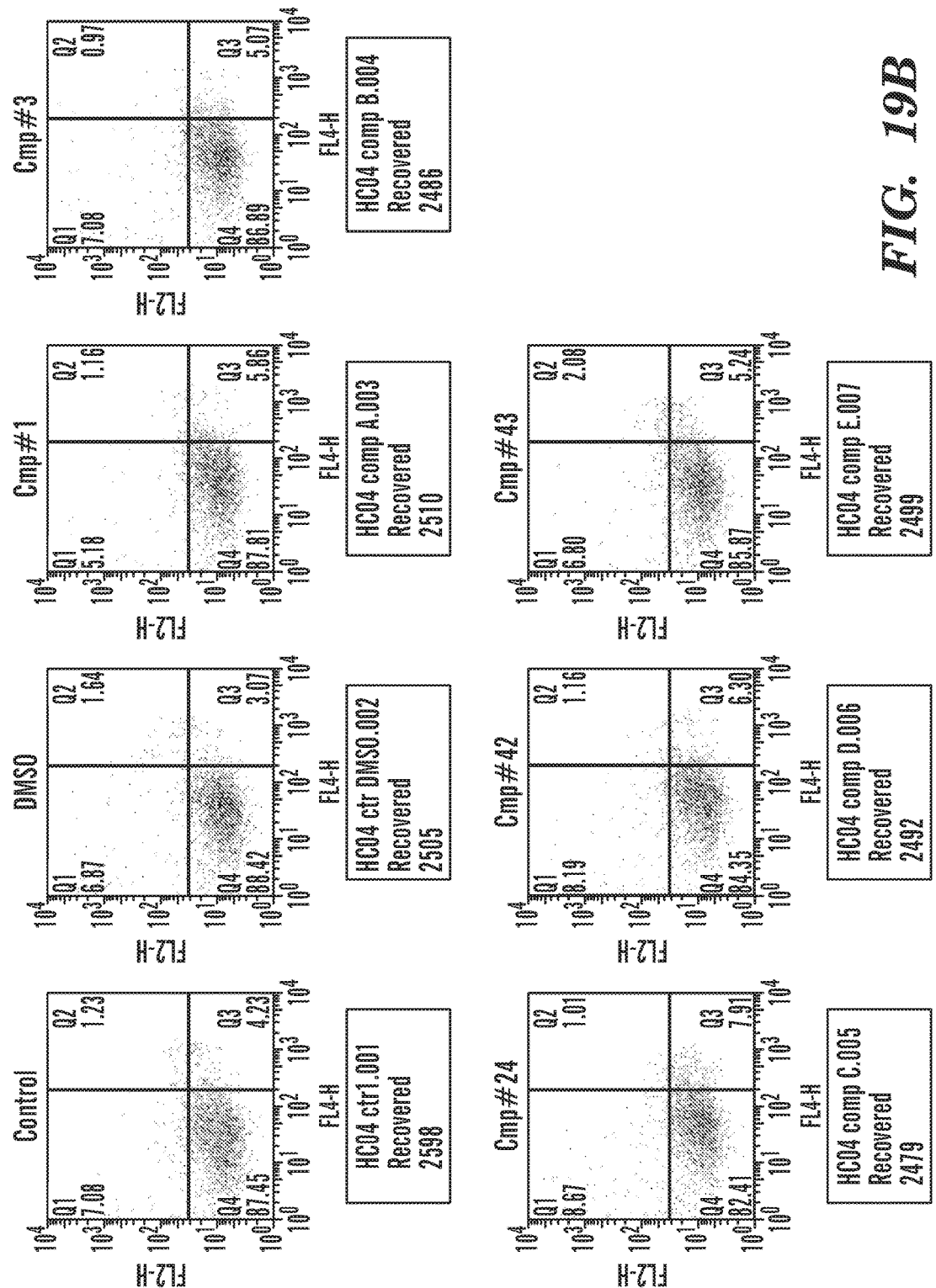

The compounds that showed activity in vitro or in vivo were assayed for their effects on the viability of human livercells. As shown in FIG. 19, preliminary studies using 100 μM of the compounds do not show the induction of apoptotic markers. These results suggest that the identified compounds are indeed parasite-specific. This can be confirmed by repeating the in vitro studies (thermal shift and catalysis assays) using human Aldolase and WASp, a human protein that binds Aldolase in a similar manner as TRAP.

Example 30—Cell Cytotoxicity: Sulforthadamine-B Cell Proliferation Assay

Staining of Cellular Mass/100 μL of HeLa cells were seeded in 96-well plates at a concentration of $2 \times 10^4$ cells/mL. The last column of the plate was left without cells as a Blank control. Cells were incubated at 37° C. in 5% $CO_2$ humidified incubator for 24 hr. The cells were dosed with the different drug solutions: 6 wells per plate for any given concentration and two plates per experiments. A total of two experiments were conducted. The controls for the experiments were: Blank wells (No cells/No drug); Dosed Blanks (No cells/Yes Drugs); Negative Control (Yes Cells/No Drug); Positive Controls Low Dose (Yes Cells/No Drug/Yes $H_2O_2$ [100 μM]); Positive Controls High Dose (Yes Cells/No Drugs/Yes $H_2O_2$ [500 μM]). The dosed plates were incubated for 72 hrs with the drug solutions but only for 2 hrs with $H_2O_2$ at the different concentrations. Drug solution was then aspirated and cells were fixed with 10% TCA for 1 hr at 4° C. The wells were washed once with 150 μL of DD $H_2O$ and then stained with 50 μL of 4% SRB in 1% HAc and incubated at room temp. for 15 min. The wells were washed, air-dried and then the dye was dissolved and Absorbance was measured at 570 nm. (n=12 for each determination)

Example 31—Cell Cytotoxicity: Presto-Blue Cell Viability Assay

The cells were treated as above until incubated with drug solution for 72 hr. After the incubation period, 11.14, of the Presto-Blue Dye was added to each well and fluorescence was measured at 570 nm as a function of time for a 2 hr period. In between measurements, the plates were incubated at room temperature covered from light exposure.

Figure 28A:
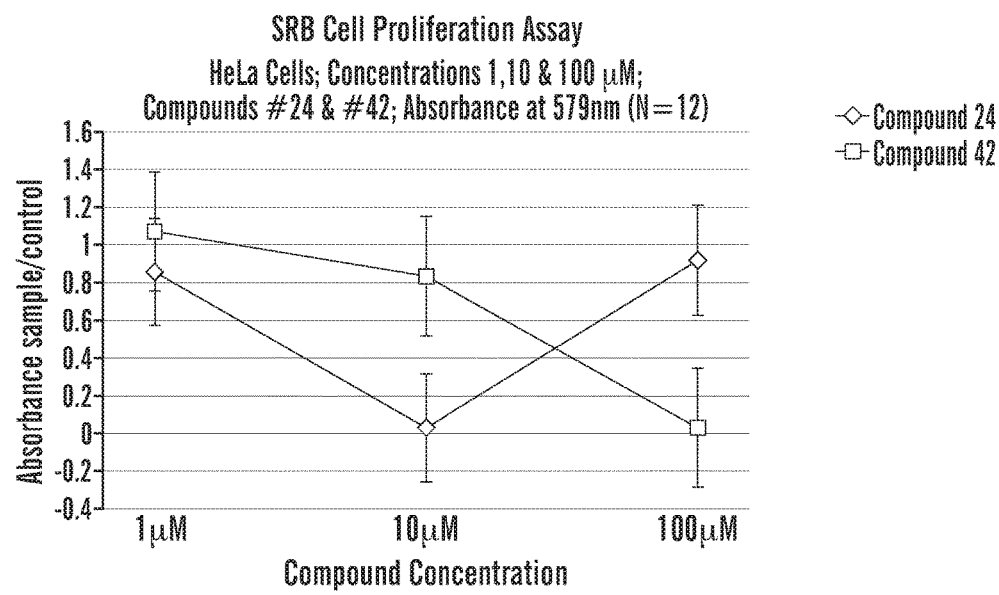
FIGS. 28 A-B show the results of the Cell Cytotoxicity Assay. HeLa cells were incubated in a 96-well plate for 72 hr in the presence of the compounds at various concentrations, and the compounds cytotoxicity was determined.
Figure 28B:
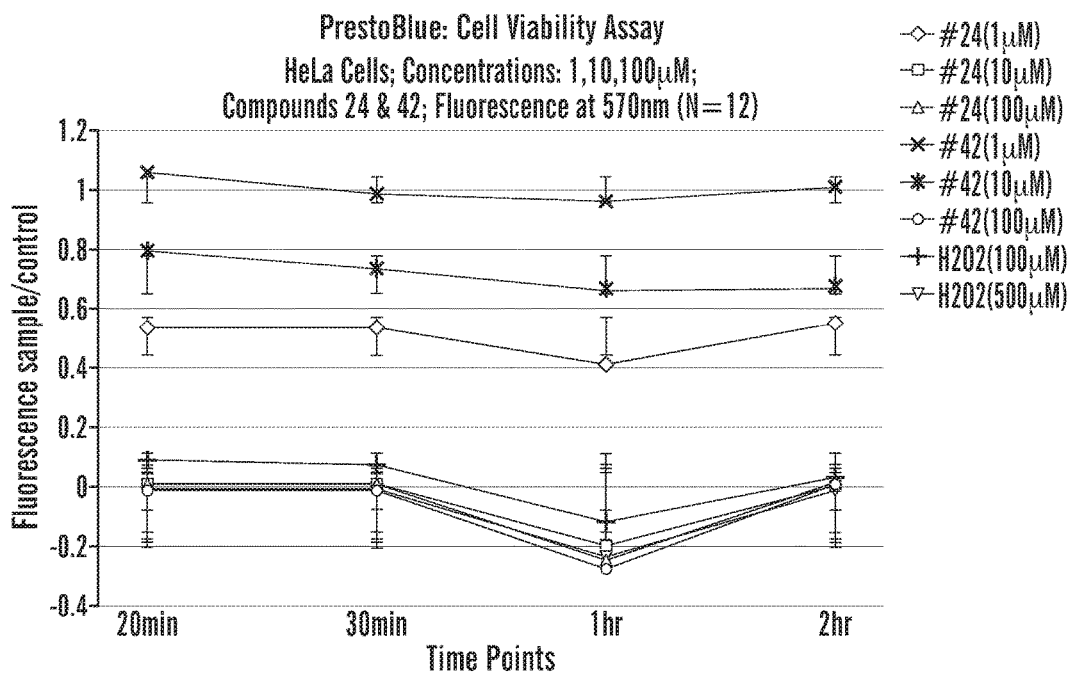

Two separate Cell based Cytotoxicity Assays were performed in HeLa cells after treatment with the compounds for 72 hr at different concentrations. SRB Cell proliferation assay (with fixed cells) (FIG. 28A) and Presto Blue Cell Viability Assay (with live cells) (FIG. 28B) suggest that compound #24 is around 10× more toxic than compound #42 as evidenced by their IC50's. Furthermore, compound #24 does not appear to affect cell proliferation at concentrations of 100 μM. Nevertheless, it is suspected that these cells are not viable as the Presto Blue Assay suggests and that cell-survival response that results from exposure to a very toxic environment is observed. The incubation period of 72 h is more than enough time for protein synthesis and/or Chromatin modifications both of which could result in drug-induced-drug resistance.

Example 32—Preliminary SAR Analysis and Possibilities for Future Optimization

Figure 20:
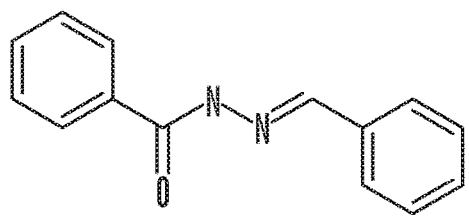
FIG. 20 shows the N-(benzylideneamino)benzamide, a chemical scaffold shared by many of the active compounds of the present invention.

As can be seen in Table 8 many of the VLS hits share similar chemical scaffolds. In particular, many of the compounds that were active in the catalysis or thermal shift assays, including compounds 1, 9, 13, 16, 17, 18, 19, and 21, as well as compounds 24 and 42, which were also active in vivo, contained the basic structure shown in FIG. 20, consisting of 2 benzene rings connected by a carboxyl-nitrogen-nitrogen-carbon linker.

TABLE 9

VLS Results and Compound Data

| Compound # | VLS Score | Docking Score | Score Difference | RMSD (Å) |
|---|---|---|---|---|
| VLS hits for the "2pc4 model" | | | | |
| 4 | −37.50 | −36.92 | 0.58 | 0.08 |
| 40 | −34.07 | −37.10 | −3.03 | 0.00 |
| 44 | −43.32 | −43.28 | 0.05 | 0.00 |
| 45 | −46.36 | −36.59 | 9.77 | 1.98 |
| 47 | −36.64 | −37.11 | −0.47 | 2.14 |
| 56 | −32.92 | −32.18 | 0.75 | 1.73 |
| VLS hits for the "falciparum model" | | | | |
| 3 | −36.51 | −36.50 | 0.01 | 0.00 |
| 5 | −33.66 | −33.42 | 0.24 | 0.75 |
| 15 | −36.22 | −33.04 | 3.18 | 0.21 |
| 22 | −33.63 | −35.83 | −2.20 | 0.05 |
| 32 | −37.62 | −34.41 | 3.21 | 0.48 |
| 37 | −34.12 | −33.16 | 0.96 | 0.09 |
| 40 | −33.30 | −36.58 | −3.28 | 0.08 |
| 43 | −32.39 | −32.34 | 0.06 | 0.02 |
| 46 | −32.55 | −32.56 | −0.01 | 0.00 |
| 53 | −32.21 | −32.23 | −0.03 | 0.01 |
| 55 | −37.23 | −37.01 | 0.22 | 0.10 |
| VLS hits for the "gapped-pocket model" | | | | |
| 1 | −32.43 | −33.19 | −0.76 | 0.03 |
| 2 | −36.41 | −42.87 | −6.47 | 0.07 |
| 5 | −36.46 | −36.53 | −0.06 | 0.75 |
| 6 | −37.08 | −36.52 | 0.56 | 0.03 |
| 7 | −35.10 | −35.59 | −0.49 | 0.05 |
| 8 | −33.05 | −33.11 | −0.06 | 0.03 |
| 9 | −36.10 | −33.41 | 2.69 | 0.17 |
| 10 | −35.37 | −35.32 | 0.05 | 1.87 |
| 11 | −32.71 | −32.41 | 0.30 | 1.70 |
| 12 | −35.11 | −32.30 | 2.81 | 2.72 |
| 13 | −33.02 | −34.97 | −1.95 | 2.12 |
| 14 | −35.00 | −34.46 | 0.54 | 0.01 |
| 16 | −35.12 | −34.91 | 0.21 | 0.00 |
| 17 | −34.25 | −34.32 | −0.07 | 0.02 |
| 18 | −35.05 | −34.92 | 0.13 | 0.00 |
| 19 | −34.49 | −34.12 | 0.37 | 0.00 |
| 20 | −34.78 | −32.09 | 2.69 | 2.22 |
| 21 | −35.30 | −35.28 | 0.02 | 0.03 |
| 23 | −37.96 | −43.33 | −5.37 | 0.09 |
| 24 | −32.67 | −32.79 | −0.11 | 0.03 |
| 25 | −32.61 | −32.44 | 0.17 | 0.01 |
| 26 | −37.45 | −37.65 | −0.20 | 0.00 |
| 27 | −35.54 | −41.36 | −5.83 | 0.05 |
| 28 | −34.21 | −33.17 | 1.03 | 2.21 |
| 29 | −35.18 | −42.15 | −6.97 | 2.27 |
| 30 | −33.65 | −33.36 | 0.30 | 1.81 |
| 31 | −34.27 | −33.76 | 0.51 | 0.02 |
| 33 | −39.25 | −38.68 | 0.57 | 0.03 |
| 34 | −36.53 | −36.82 | −0.29 | 0.00 |
| 35 | −32.47 | −33.42 | −0.95 | 1.81 |
| 36 | −33.16 | −32.87 | 0.29 | 0.01 |
| 38 | −35.19 | −35.18 | 0.01 | 0.00 |
| 39 | −38.55 | −37.22 | 1.34 | 0.04 |
| 41 | −38.86 | −38.45 | 0.41 | 0.00 |
| 42 | −34.08 | −34.01 | 0.08 | 0.00 |
| 48 | −32.34 | −33.15 | −0.81 | 4.14 |
| 49 | −37.85 | −37.39 | 0.46 | 0.03 |

TABLE 9-continued

VLS Results and Compound Data

| Compound # | VLS Score | Docking Score | Score Difference | RMSD (Å) |
|---|---|---|---|---|
| 50 | −32.98 | −36.85 | −3.87 | 0.68 |
| 51 | −37.08 | −37.01 | 0.08 | 0.03 |
| 52 | −38.58 | −37.99 | 0.60 | 6.84 |
| 54 | −35.14 | −41.21 | −6.06 | 0.09 |
| 57 | −35.55 | −35.89 | −0.34 | 0.00 |
| 58 | −33.41 | −33.16 | 0.25 | 1.66 |
| 59 | −32.74 | −32.69 | 0.05 | 2.26 |
| 60 | −34.63 | −32.09 | 2.53 | 0.02 |

The docking results and the preliminary crystallographic data for the active compounds suggest that several of these hits also make similar hydrogen-bonding and electrostatic contacts with the Aldolase-TRAP complex via functional groups extending off of the scaffold's two benzene rings. This may indicate that this particular scaffold is ideally suited to fit the biophysical and geometric constraints for binding at the Aldolase-TRAP interface.

In order to explore this hypothesis, initial substructure searches were initiated using PubChem and ICM-Molcart databases, which together contain greater than 30 million unique compounds, to identify additional chemicals and derivatives of the current hit list that contain this scaffold. These substructure search hits were then docked to the VLS receptor models to identify compounds that replicate the pharmacophoric features seen thus far for the active compounds. The most promising hits from these screens can then be assayed for their activity using the methods described above.

Figure 21:
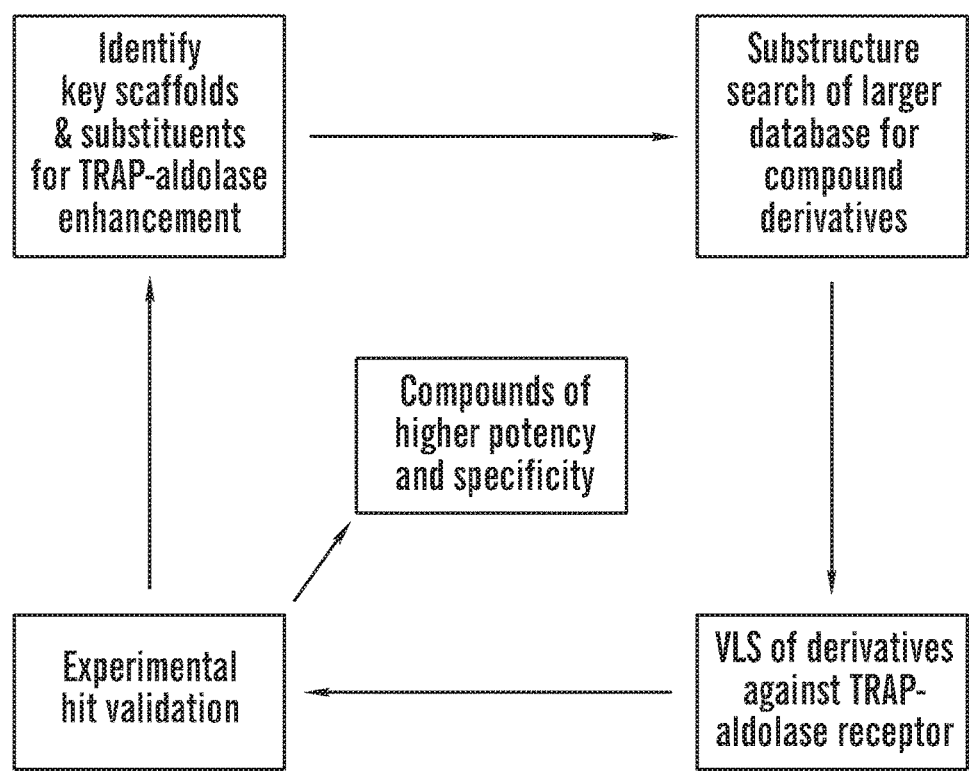
FIG. 21 shows a schematic of lead optimization process.

The methods described in the present invention can be used to find additional scaffolds or compounds amenable to this type of derivatization and optimization as well. An in-depth analysis can be performed of the pharmacophore space occupied by the initial VLS hitlist. Then testing of the resultant derivatives can be done experimentally. As illustrated in FIG. 21, this is an iterative process and can be used to identify compounds of increasing potency and specificity.

Example 33—Docking Simulations

In-silico compound docking simulations were performed with the ICM software. The PDB "2pc4", which contains a monomer of the aldolase protein linked to a C-terminal peptide of *P. berghei*'s TRAP, was mutated in order to represent *P. falciparum*'s TRAP peptide instead as part of the discovery procedure. Compound 24 was built in silico from SMILES strings and the docking simulation was conducted by a previously described method (Wang et al., "Structural determinants of PERK inhibitor potency and selectivity," *Chemical Biology & Drug Design* 76(6):480-95 (2010), which is hereby incorporated by reference in its entirety). Analysis of this simulation revealed that compound #24 (see Table 6) was able to successfully dock with good "scores" in two conformations: one that has the carbonyl of the general scaffold facing the inside of the pocket (named:"Inside" conformation; represented by: →) and one with the carbonyl of the scaffold facing the outside of the pocket ("Outside" conformation; ←). The "Outside" conformation is the one observed in the crystal structure (FIG. 16), so it is the more likely conformation, but the docking does not rule out a second binding mode for the compound at the target site on aldolase.

In either conformation, the atoms of the compound in close proximity with those of TRAP's peptide and capable of forming hydrogen bonds (H-bonds) were noted. Using the ideas of this work, these atoms, if they do not make H-bonds, may be chemically modified in a derivative of compound 24 to improve the potency of binding. The "distance-between-two-atoms" function of ICM was used to determine the distance between compound atoms and all nitrogen and oxygen atoms in the TRAP peptide. Only those in close proximity to the location of binding were actually considered for the design of the derivatives. Many starting materials for the synthesis of compound 24 are available for purchase from chemical companies such as Sigma and their inclusion into the synthesis of compound 24 would result in the derivatives represented in the "substituent combination" table (FIG. 29B). Based on this table and the H-bond information from the docking, the derivatives were designed and their binding conformation (orientation) was predicted by docking.

Each of the derivatives were docked into the target binding site. Results for the best 103 derivatives are shown in Table 10. Conformation of binding symbol ↔ indicates that the derivative docks in both orientations, conformation of binding symbol → shows that the derivative docks in the carbonyl "inside" conformation, and conformation of binding symbol ← indicates the derivative docks in the carbonyl "outside" conformation. Structure #1 in Table 10 shows the whole derivative of compound 24 with methoxy groups substituting for substituent positions $Y_3$ and $Y_4$ (see FIG. 29B). The other structures show only the aromatic ring in FIG. 29B bearing substituents $Y_{2-4}$ and $X_1$ and $X_5$.

Analysis of the bonds that compose the general scaffold of the compounds reveals positions for functional groups that are identical from the point of view of chemical synthesis/spectroscopy, or different from the point of view of chemical synthesis (FIG. 29 A). For example, the chemical environment of positions X1 and X5 are identical, and a chemical reaction intended to add a hydroxyl group to one of these positions would probably add it to both, whereas the chemical environment between X1 and Y3 is different and can be distinguished spectroscopically. From a chemical synthesis point of view, therefore, only combinations of groups from different chemical environments can be achieved by mixing and matching starting materials for the synthesis of compound 24 Scheme 1). These different combinations are shown in FIG. 29B and result in 720 different possible combinations. The aldolase-TRAP-compatible subset of 103 of the resulting derivatives from these combinations are shown in Table 10.

TABLE 10

| # | Structure | Conf. of Binding |
|---|---|---|
| 1 | 3,4-dimethoxy-N'-(2,4-dichlorobenzylidene)benzohydrazide | ↔ |
| 2 | 3,4,5-trihydroxybenzoic acid (gallic acid) | ↔ |
| 3 | 3,4-dihydroxybenzoic acid | ↔ |
| 4 | 2,3,4-trihydroxybenzoic acid | ↔ |
| 5 | sodium 3,4,5-trihydroxybenzoate | ↔ |
| 6 | 4-methoxy-3-hydroxybenzoic acid | ↔ |
| 7 | 2,4,5-trihydroxybenzoic acid | ↔ |

TABLE 10-continued

| # | Structure | Conf. of Binding |
|---|-----------|------------------|
| 8 | 4-hydroxy-3-methoxybenzoic acid (vanillic acid) | ↔ |
| 9 | bismuth catecholate of 3,4-dihydroxy-5-hydroxybenzoic acid ·xH₂O | ↔ |
| 10 | bismuth catecholate of 3,4-dihydroxy-5-hydroxybenzoic acid | ↔ |
| 11 | 4-hydroxy-3,5-dimethoxybenzoic acid (syringic acid) | ↔ |
| 12 | 3,4-dihydroxy-5-methoxybenzoic acid | ↔ |
| 13 | 3,4-dimethoxybenzoic acid (veratric acid) | ↔ |
| 14 | 3,4,5-trimethoxybenzoic acid | ↔ |

TABLE 10-continued

| # | Structure | Conf. of Binding |
|---|---|---|
| 15 | 4-ethoxy-3-methoxybenzoic acid | ↔ |
| 16 | 3-isopropoxy-4-methoxybenzoic acid | ↔ |
| 17 | 3-ethoxy-4-methoxybenzoic acid | ↔ |
| 18 | 3,4-diethoxybenzoic acid | ↔ |
| 19 | 2-hydroxy-3,4-dimethoxybenzoic acid | ↔ |
| 20 | 2-formyl-4,5-dimethoxybenzoic acid | ↔ |
| 21 | 4-(allyloxy)-3-methoxybenzoic acid | → |

TABLE 10-continued

| # | Structure | Conf. of Binding |
|---|---|---|
| 22 | 4-acetoxy-3-acetoxybenzoic acid | ↔ |
| 23 | 4-benzyloxy-3-ethoxybenzoic acid | → |
| 24 | 4-butoxy-3-methoxybenzoic acid | → |
| 25 | 3-benzyloxy-4-methoxybenzoic acid | → |
| 26 | 3-methoxy-4-benzyloxybenzoic acid | → |
| 27 | 3-butoxy-4-methoxybenzoic acid | → |
| 28 | 3-propoxy-4-methoxybenzoic acid | → |

TABLE 10-continued

| # | Structure | Conf. of Binding |
|---|---|---|
| 29 | (isopentyloxy-3-methoxybenzoic acid) | → |
| 30 | (2,3,4-trimethoxybenzoic acid) | ↔ |
| 31 | (4-acetoxy-3,5-dimethoxybenzoic acid) | ↔ |
| 32 | (4-(carbamoylmethoxy)-3-methoxybenzoic acid) | → |
| 33 | (3-chloro-4-hydroxy-5-methoxybenzoic acid) | ↔ |
| 34 | (3-cyclopentyloxy-4-methoxybenzoic acid) | ↔ |
| 35 | (3-chloro-4,5-dimethoxybenzoic acid) | ↔ |

TABLE 10-continued

| # | Structure | Conf. of Binding |
|---|---|---|
| 36 | 4-(difluoromethoxy)-3-methoxybenzoic acid | ↔ |
| 37 | 2-chloro-3,4-dimethoxybenzoic acid | → |
| 38 | 2-amino-3,4,5-trimethoxybenzoic acid | → |
| 39 | 2,3-dichloro-4-hydroxy-5-methoxybenzoic acid | → |
| 40 | 2,4,5-trimethoxybenzoic acid | → |
| 41 | 5-(benzyloxy)-4-methoxy-2-methylbenzoic acid | → |

TABLE 10-continued

| # | Structure | Conf. of Binding |
|---|---|---|
| 42 | 4-(hexadecyloxy)-3-methoxybenzoic acid | → |
| 43 | 4-(cyclopentylmethyl)-3-methoxybenzoic acid | → |
| 44 | 2-chloro-4,5-dimethoxybenzoic acid | → |
| 45 | 3-(cyclopentyloxy)-4-methoxybenzoic acid | → |
| 46 | 2-amino-4,5-dimethoxybenzoic acid | → |
| 47 | 3,4,5-trimethoxyphthalic acid | → |
| 48 | 4-(difluoromethoxy)-3-methoxybenzoic acid | ↔ |

TABLE 10-continued

| # | Structure | Conf. of Binding |
|---|---|---|
| 49 | 3-bromo-4,5-dihydroxybenzoic acid | ↔ |
| 50 | 2-amino-3,4-dimethoxybenzoic acid | → |
| 51 | 2-chloro-3,4-dimethoxybenzoic acid | → |
| 52 | 4-[(4-chlorobenzyl)oxy]-3-methoxybenzoic acid | → |
| 53 | 2-amino-3,4,5-trimethoxybenzoic acid | → |
| 54 | 2,3-dichloro-4-hydroxy-5-methoxybenzoic acid | → |
| 55 | 4-[(2-chlorobenzyl)oxy]-3-ethoxybenzoic acid | → |

TABLE 10-continued

| # | Structure | Conf. of Binding |
|---|---|---|
| 56 | (3-chloro-4-ethoxy-5-methoxybenzoic acid) | ↔ |
| 57 | (4-((2-chlorobenzyl)oxy)-3-methoxybenzoic acid) | → |
| 58 | (4-(2-(methylsulfonamido)ethoxy)-3-methoxybenzoic acid) | → |
| 59 | (2-amino-3,4-diethoxybenzoic acid) | ↔ |
| 60 | (2-amino-4-(2-methoxyethoxy)-5-methoxybenzoic acid) | → |
| 61 | (3-allyl-4,5-dimethoxybenzoic acid) | ↔ |

TABLE 10-continued

| # | Structure | Conf. of Binding |
|---|-----------|------------------|
| 62 | 3-ethoxy-5-chloro-4-(benzyloxy)benzoic acid | → |
| 63 | 2-bromo-4,5-dimethoxybenzoic acid | → |
| 64 | 4-((4-fluorobenzyl)oxy)-3-methoxybenzoic acid | → |
| 65 | 3-bromo-4-hydroxy-5-methoxybenzoic acid | → |
| 66 | 3-chloro-4-((2-chlorobenzyl)oxy)-5-ethoxybenzoic acid | → |
| 67 | 3-bromo-4,5-dimethoxybenzoic acid | → |

TABLE 10-continued

| # | Structure | Conf. of Binding |
|---|-----------|------------------|
| 68 | 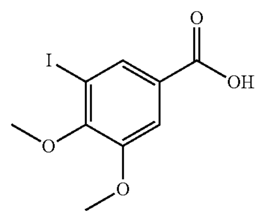 | ↔ |
| 69 | 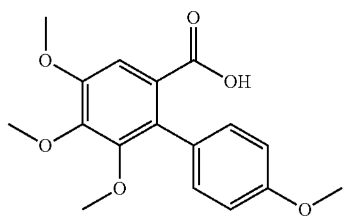 | → |
| 70 | 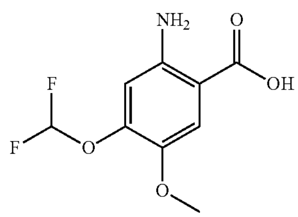 [SMILES: COc1cc(C(=O)O)c(N)cc1OC(F)F] | → |
| 71 | 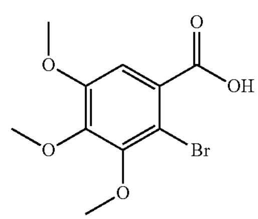 [SMILES: COc1cc(C(=O)O)c(Br)c(OC)c1OC] | ↔ |
| 72 | 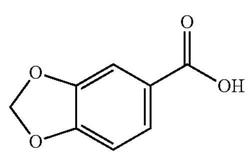 [SMILES: O=C(O)c1ccc2c(c1)OCO2] | |
| 73 | 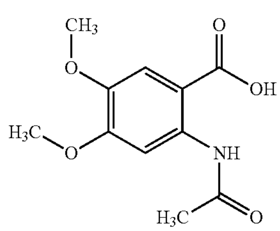 [SMILES: COc1cc(NC(C)=O)c(C(=O)O)cc1OC] | → |
| 74 | 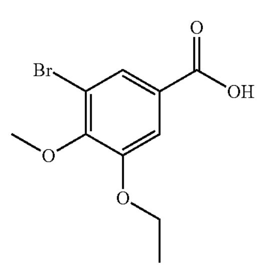 | ↔ |

TABLE 10-continued

| # | Structure | Conf. of Binding |
|---|-----------|------------------|
| 75 | 3-bromo-4-ethoxy-5-methoxybenzoic acid | ↔ |
| 76 | 2,3-dihydro-1,4-benzodioxine-6-carboxylic acid | ↔ |
| 77 | 8-methoxy-2,3-dihydro-1,4-benzodioxine-6-carboxylic acid | ↔ |
| 78 | 4,5-dimethoxy-2-nitrobenzoic acid | → |
| 79 | 3,4-dihydro-2H-1,5-benzodioxepine-7-carboxylic acid | ↔ |
| 80 | 3-acetoxy-2-bromo-4-methoxybenzoic acid | → |
| 81 | 2-benzamido-4,5-dimethoxybenzoic acid | → |

TABLE 10-continued

| # | Structure | Conf. of Binding |
|---|---|---|
| 82 | 4,5-dimethoxy-2-(ethoxycarbonylamino)benzoic acid | → |
| 83 | 8-chloro-2,3-dihydro-1,4-benzodioxine-6-carboxylic acid | ↔ |
| 84 | 2,2-difluoro-1,3-benzodioxole-5-carboxylic acid | ↔ |
| 85 | 9-chloro-3,4-dihydro-2H-1,5-benzodioxepine-7-carboxylic acid | → |
| 86 | 4-[(hydroxymethyl-trihydroxy-cyclohexyl)methyl]-3-methoxybenzoic acid | → |
| 87 | 3-(benzyloxy)-4-methoxy-2-nitrobenzoic acid | → |
| 88 | 6-bromo-1,3-benzodioxole-5-carboxylic acid | → |

TABLE 10-continued

| # | Structure | Conf. of Binding |
|---|-----------|------------------|
| 89 | 2,3-dihydro-1,4-benzodioxine-6-carboxylic acid with Br | → |
| 90 | 7-methoxy-2-methyl-2,3-dihydrobenzofuran-5-carboxylic acid | → |
| 91 | 6-hydroxy-4,7-dimethoxybenzofuran-5-carboxylic acid | → |
| 92 | 2,2-dimethyl-7,8-dihydroxychroman-6-carboxylic acid | → |
| 93 | 2,4-dichlorobenzaldehyde | N/A |
| 94 | 2,4-dichloro-6-hydroxybenzaldehyde | N/A |
| 95 | 2,6-dichloro-3-benzoylbenzaldehyde | N/A |
| 96 | 5-chloro-2-hydroxybenzaldehyde | N/A |

TABLE 10-continued
| # | Structure | Conf. of Binding |
|---|---|---|
| 97 | 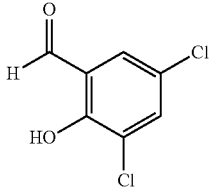 [SMILES: O=Cc1cc(Cl)cc(Cl)c1O] | N/A |
| 98 | 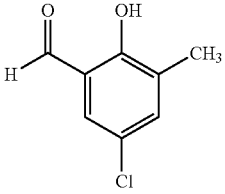 | N/A |
| 99 | 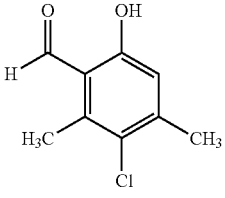 | N/A |
| 100 | 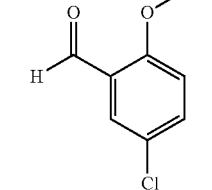 | N/A |
| 101 | 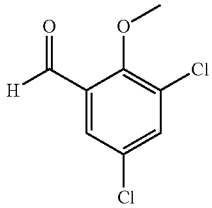 | N/A |
| 102 | 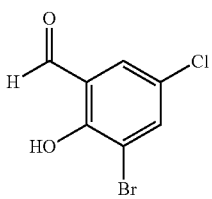 | N/A |
| 103 | 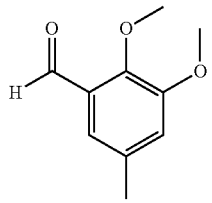 | N/A |

Example 34—Implications of the Results

The computational, enzymatic, crystallographic, and cellular data on the activities of several novel small molecules with potential or likely anti-malarial activity are described above. These chemicals can now be advanced for further optimization and pre-clinical testing in animal models of malarial infection.

Figure 22:
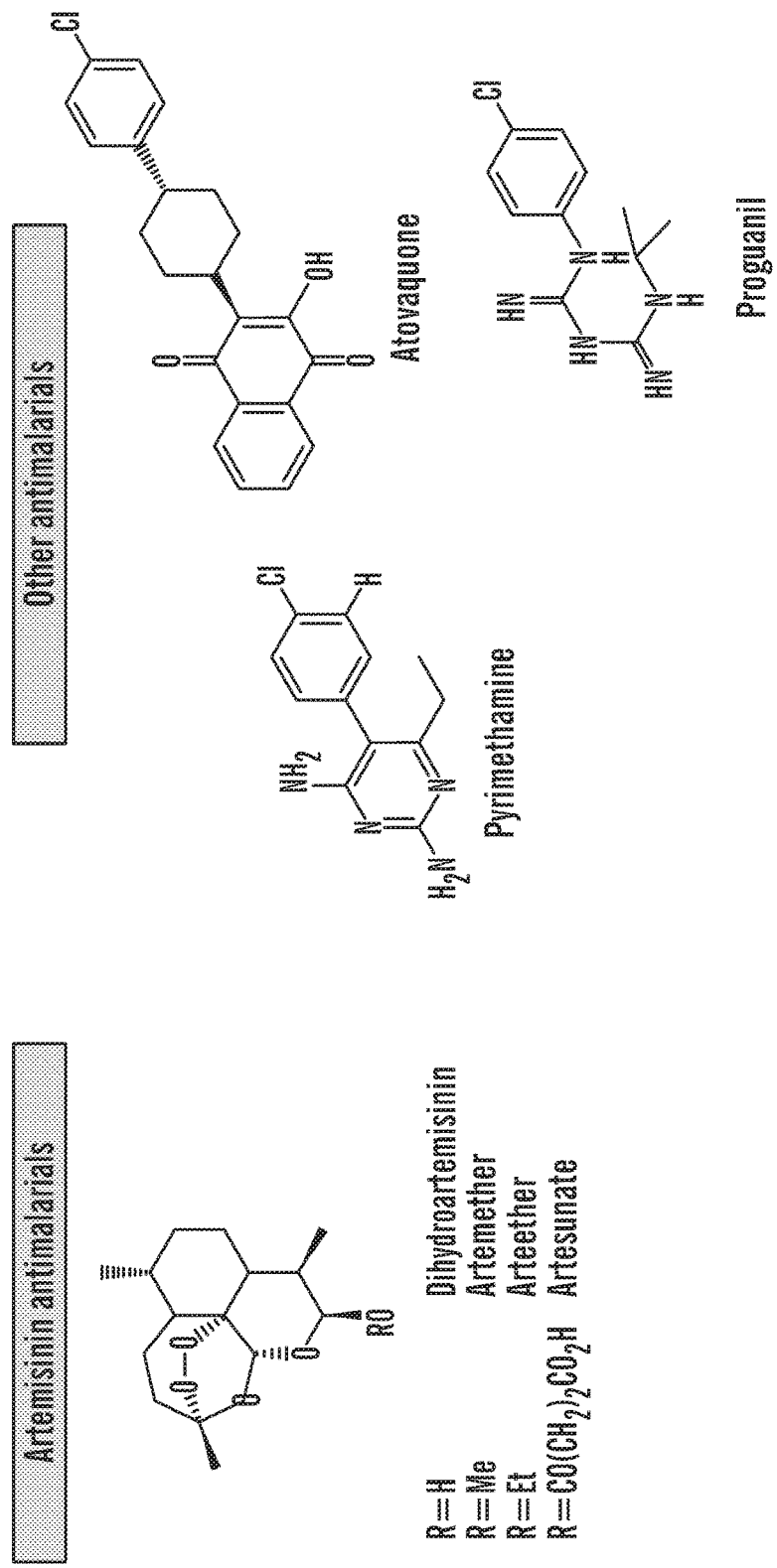
FIG. 22 shows structures of anti-malarial drugs in clinical use. None of the drugs currently prescribed to treat malaria possess the chemical scaffold identified here and shown in FIG. 20. Reproduced, with permission, from Ridley, *Nature*, 2002 (Ridley, "Medical Need, Scientific Opportunity and the Drive for Antimalarial Drugs," *Nature* 415:686-693 (2002), which is hereby incorporated by reference in its entirety).

It is important to note that the compounds and chemical scaffolds identified here are not found among the anti-malarials currently in clinical use (FIG. 22). This effort, therefore, represents a successful "scaffold hop" in anti-malarial drug discovery. If ultimately successful, these drugs and their derivatives would constitute a novel class or classes of anti-malarial agents, as well as the first drugs to target the Aldolase-TRAP interaction. Additionally, as designed, these drugs should be effective against the parasite's liver stages, and may therefore be ideally suited for anti-malarial prophylaxis or the treatment of latent infections.

The vulnerability of the apicomplexan glideosome to anti-malarial drug design has historically been under-appreciated. The obstacles of drug-specificity and the challenges of targeting the semi-conserved protein-protein interfaces within the glideosome can be overcome by striving to enhance, rather than inhibit, the Aldolase-TRAP interaction.

Finally, there are marketed drugs that stabilize protein-protein interactions. However, none of them were intentionally designed to do so. Rather, they were discovered in biological assays or derived from natural products based on their efficacy in treating an illness, but their exact mechanism of action was only appreciated later on. On the other hand, a recent attempt to use VLS to develop herbicides that stabilize an inhibitory interaction within the plant proton pump failed to produce compounds with validated activity in vitro (Block et al., "Strategies to Search and Design Stabilizers of Protein-Protein Interactions: A Feasibility Study," Proteins 68:170-186 (2007), which is hereby incorporated by reference in its entirety). The present invention is the first successful case of small molecules rationally designed to enhance the TRAP-Aldolase or any other protein-protein interaction.

Example 35—Summary of Results

Computational, experimental, and structural data were successfully integrated to elucidate key features of the actin-Aldolase interface in Plasmodium falciparum and the malarial glideosome as a whole. The results included the following:
a) In silico visualization of the band 3-Aldolase complex via protein-protein docking Modeling this complex was an intermediate step in visualizing the actin-Aldolase complex by homology to it.
b) Identification of actin's Aldolase binding region by homology and ELISA-based binding and inhibition assays.
c) In silico visualization and biochemical validation of the P. falciparum actin-Aldolase complex via homology modeling, protein-protein docking, Aldolase mutagenesis, and ELISA-based binding assays.
d) In silico visualization of the P. falciparum actin-Aldolase-TRAP complex via protein-protein docking
e) Crystallographic resolution of the Plasmodium actin-Aldolase- (and possibly TRAP) complex.

Taken together, the data represent the first visualization of the actin-Aldolase-TRAP complex in atomic detail, and suggest the existence of several alternative interfaces between the proteins of the glideosome that are in equilibrium with one another. This represents a dynamic view of the complex, and opens up new avenues of exploration for future drug discovery efforts targeting this complex.

It was also demonstrated that there is potential for structure-based anti-malarial drug design with VLS. It is possible to perform in silico discovery of potential small molecule enhancers of the Aldolase-TRAP complex.

Biochemical and crystallographic validation of compounds as stabilizers of the Aldolase-TRAP complex and TRAP-dependent inhibitors of Plasmodium Aldolase's catalytic activity can also be performed successfully.

In vivo validation can be done of the identified lead compounds as inhibitors of sporozoite motility that are nontoxic to human cells. Using the methods described herein, a successful "scaffold hop" and development of novel classes of anti-malarial agents targeting the glideosome can be done.

Crystallographic resolution of additional glideosome conformations for future drug design projects can also be obtained using the methods described herein.

These results constitute a proof-of-principle for the drug targeting strategy, and may be the first examples of drugs intentionally designed to enhance, rather than inhibit, a protein-protein interaction.

The broader implications of these results for malarial biology, anti-malarial drug discovery, and structure-based drug design in general are discussed below.

Example 36—Insights into the Malarial Motor Complex

The body of work described here highlights the dynamic nature of the malarial motor apparatus. Actin appears to have multiple binding sites on Aldolase, which can be modulated by TRAP and F16P. The success demonstrated in inhibiting gliding by stabilizing the TRAP-Aldolase interface shows the processive nature of the Aldolase-TRAP interaction.

The precise arrangement of Aldolase, F-actin, TRAP, and F16P in vivo is as yet unknown, and may be too complex to visualize as a static image. It may be possible to explore the spatial arrangements and temporal sequence of conformations of this complex in vivo through selective mutagenesis of the interacting residues in each protein or by well-designed co-localization or fluorescence resonance energy transfer analyses. Additionally, the use of small molecules that selectively modulate specific components of the glideosome—such as the Aldolase-TRAP stabilizers identified here—may also help tease out the variations in affinity of Aldolase for TRAP, actin, or F16P. As described herein, modeling and crystallographic studies should help define additional receptor pockets and conformations that can be exploited to design compounds that target different aspects of the glideosome.

Example 37—Modeling and Crystallography

The success of this study relied on the complementary and integrative use of computational modeling and x-ray crystallography. Previous attempts to co-crystallize actin and Aldolase failed. However, once the biochemical and modeling efforts identified actin's Aldolase binding region, crystals of the corresponding actin peptide bound to Aldolase were resolved relatively quickly. Prior to this work, the resolution of the TRAP-Aldolase structure was similarly guided by homology modeling studies (Buscaglia et al., "Modeling the Interaction Between Aldolase and the Thrombospondin-Related Anonymous Protein, a Key Connection of the Malaria Parasite Invasion Machinery," *Proteins* 66:528-537 (2007); Bosch et al., "Aldolase Provides an Unusual Binding Site for Thrombospondin-Related Anonymous Protein in the Invasion Machinery of the Malaria Parasite," *Proc. Nat'l. Acad. Sci. USA* 104(17):7015-20 (2007), which are hereby incorporated by reference in their entirety). Additionally, the success of the drug design study hinged upon the high resolution of the crystallographic Aldolase structures against which the compounds were screened. The compounds that were identified by VLS then aided in the elucidation of additional high resolution Aldolase-TRAP structures, which can also provide starting points for further rounds of drug design.

These paradigms of model-guided crystallography and crystallographically-targeted computational drug design can be broadly applied to many biological systems. The combination of in silico and crystallographic structure prediction may assist in resolving difficult structures, including membrane proteins or multi-component protein complexes of importance to human health. VLS and other docking technologies can then be harnessed to therapeutically modulate those proteins or protein complexes.

Example 38—Computer Aided Drug Design (CADD) and High Throughput Screening (HTS)

Recent literature seems to demonstrate a tug-of-war between proponents of computer-aided, structure-based drug design and supporters of drug discovery through HTS and cell-based assays (Wells, "Microbiology. Is the Tide Turning for New Malaria Medicines?" *Science* 329:1153-1154 (2010), which is hereby incorporated by reference in its entirety). On the one hand, a lot of work must be done to identify, validate, and visualize a druggable target before a structure-based approach can begin, whereas HTS can rapidly identify compounds with in vivo activity without prior knowledge of their targets. On the other hand, detailed knowledge of the atomic contacts made between the lead compounds and their target provides the opportunity for rapid lead optimization and the ability to predict and circumvent resistance mutations, whereas HTS hits must be optimized in the chemical space alone, and without knowledge of the drug's receptor structure to guide the creation of second generation compounds. VLS can be cheaper and faster than HTS, though the target identification and validation process may take years and be at great expense, while some industrial HTS efforts can process tens of thousands of compounds per day and make use of a rich array of genomic and proteomic resources to speed up identification of their hits' mechanisms of action. Of course, neither method can provide a foolproof guarantee of target specificity—many drugs that were designed or hypothesized to alter specific cellular pathways or molecular interactions were later found to exert their activity through larger and unexpected "off-target" affects.

This past year saw the preliminary successes of antimalarial drug discovery efforts using both methods. The GSK, St. Jude, and Novartis anti-malarial candidates were found by HTS, using whole-cell in vitro or in vivo proliferation assays (Gamo et al., "Thousands of Chemical Starting Points for Antimalarial Lead Identification," *Nature* 465:305-310 (2010); Gamo et al., "GSK TCAMS Dataset. ChEMBL—Neglected Tropical Disease Archive; Guiguemde et al. "Chemical Genetics of *Plasmodium falciparum*," *Nature* 465:311-315 (2010); Guiguemde et al., St. Jude Children's Research Hospital Malaria Dataset. ChEMBL—Neglected Tropical Disease Archive; Gagaring et al., Novartis-GNF Malaria Box. ChEMBL—Neglected Tropical Disease Archive, which are hereby incorporated by reference in their entirety), whereas the MTIP-MyoA inhibitor was identified using VLS (Kortagere et al., "Structure-Based Design of Novel Small-Molecule Inhibitors of *Plasmodium falciparum*," *J. Chem. Inf. Model* 50:840-849 (2010), which is hereby incorporated by reference in its entirety). In the case of MTIP-MyoA, the researchers first created a homology model of the *P. falciparum* MTIP-MyoA complex based on the published crystallographic structure of the *P. knowlesi* MTIP-*P. yoelii* MyoA complex. They then generated a hybrid receptor-ligand pharmacophore map based on their model, and screened an electronic database of small molecules for those that would fit that pharmacophore. Promising compounds were docked to the receptor's binding site and the resultant hits were assayed for their affects on parasite growth and motility. Active compounds were then subjected to SAR analysis and used as starting points to identify more potent derivatives. Unfortunately, the compounds were not directly tested to analyze their affect on the MTIP-MyoA interaction in vitro, so it is not certain that they exert their affects through this complex; however, the affect of their compounds on sporozoite motility suggests that their hypothesized mechanism of action is correct for at least some of their VLS leads (Kortagere et al., "Structure-Based Design of Novel Small-Molecule Inhibitors of *Plasmodium falciparum*," *J. Chem. Inf. Model* 50:840-849 (2010), which is hereby incorporated by reference in its entirety).

The computational structure-based approach used to identify the MTIP-MyoA inhibitor (Kortagere et al., "Structure-Based Design of Novel Small-Molecule Inhibitors of *Plasmodium falciparum*," *J. Chem. Inf. Model* 50:840-849 (2010), which is hereby incorporated by reference in its entirety) was accomplished by a smaller, and presumably less generously funded, group of academic researchers, while the Novartis, GSK, and St. Jude whole-cell HTS projects required the resources and time of large pharmaceutical corporations. The computational work allowed for very rapid detailed SAR analysis and derivative design, whereas much work will need to be done to precisely define the targets of the HTS hits. However, the computational work would not have been possible before the publication of the *Plasmodium* MTIP-MyoA structures (Bosch et al., "The Closed MTIP-Myosin A-Tail Complex from the Malaria Parasite Invasion Machinery," *J. Mol. Biol.* 372(1):77-88 (2007); Bosch et al., "Structure of the MTIP-MyoA Complex, a Key Component of the Malaria Parasite Invasion Motor," *Proc. Nat'l. Acad. Sci. U.S.A.* 103:4852-4857 (2006), which are hereby incorporated by reference in their entirety).

Computer-aided approaches are ideally suited to take advantage of advances in malaria research and structural biology; cheminformatics methods can rapidly optimize existing drugs or find novel compounds with matching pharmacophores; and high-throughput whole-cell assays can accelerate the identification of new targets and novel mechanisms of action.

Figure 23:
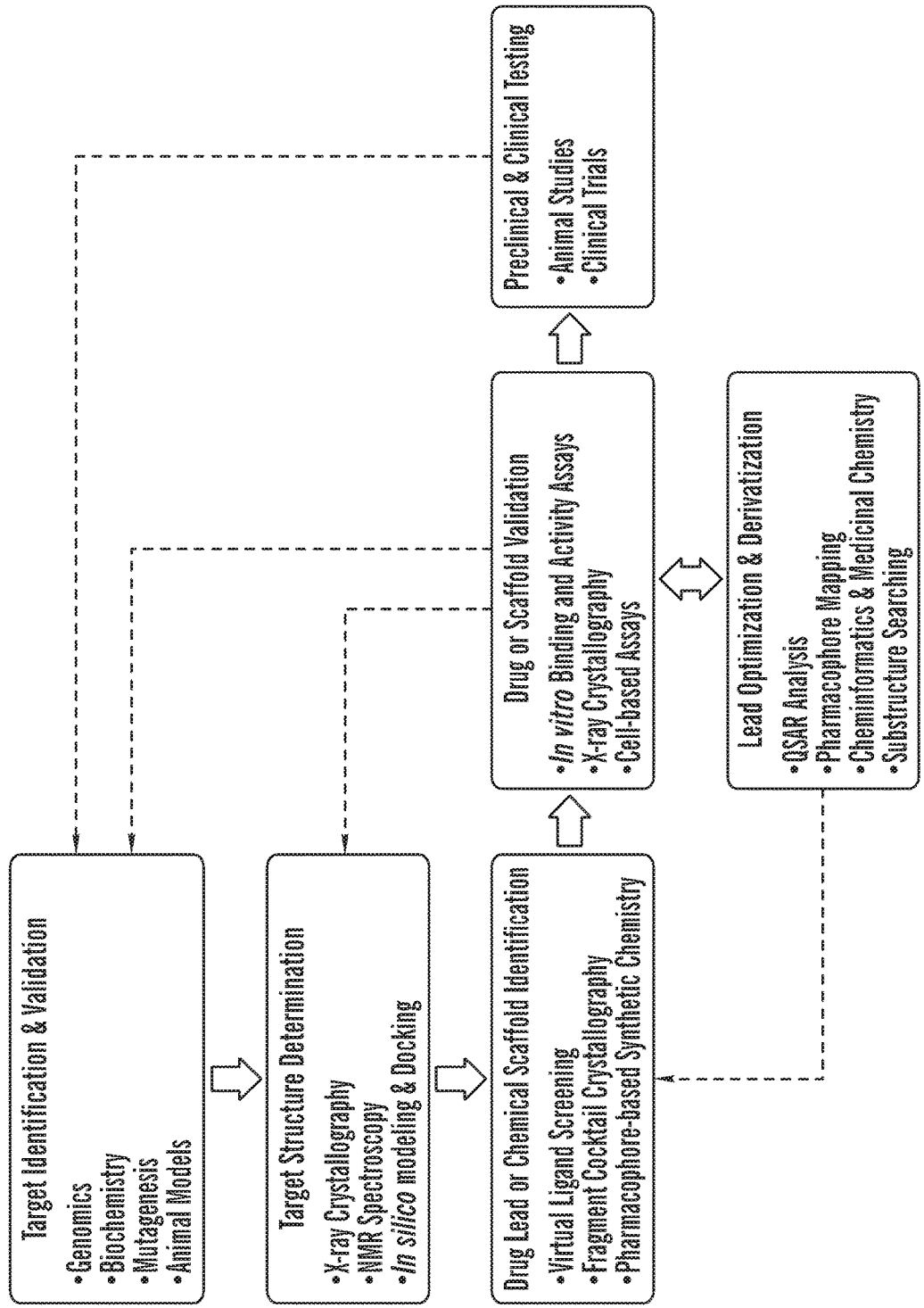
FIG. 23 shows the idealized Drug Design Workflow.
Figure 24D:
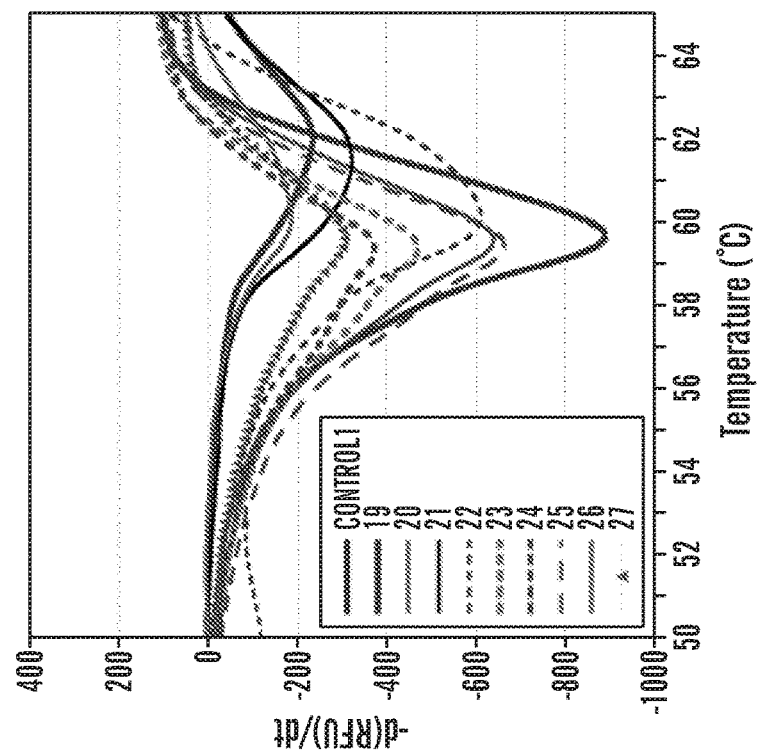
Figure 24C:
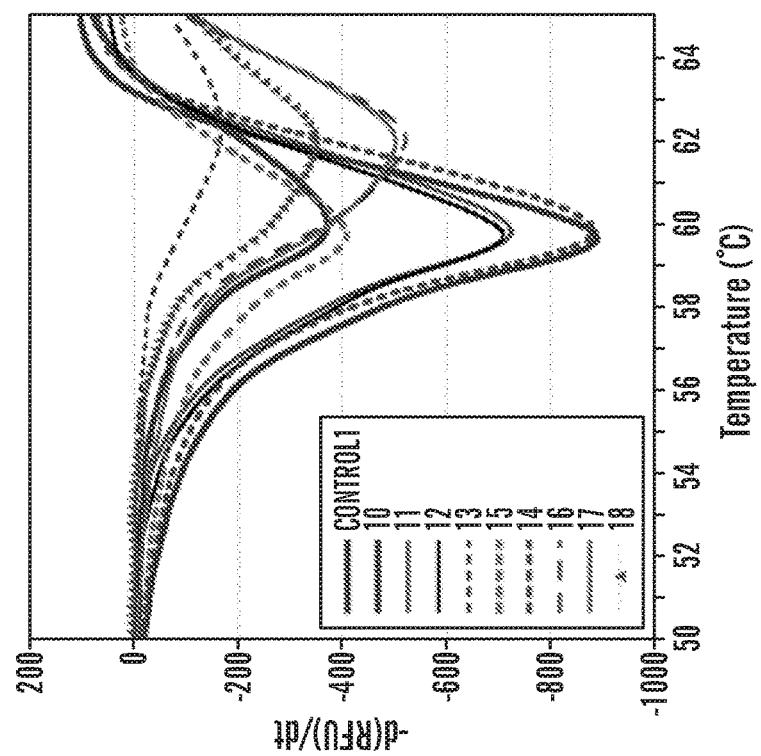
Figure 24F:
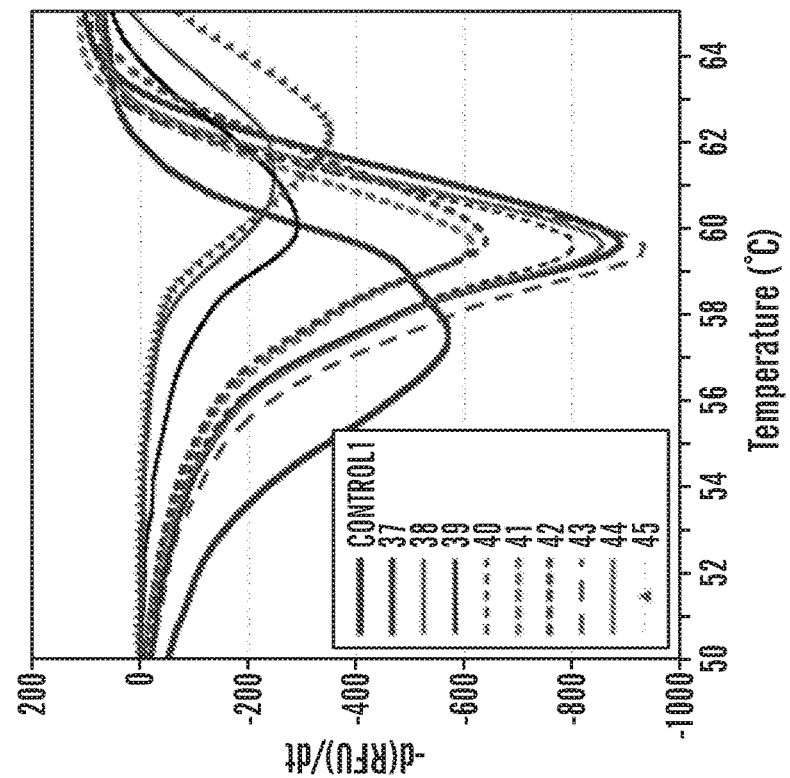
Figure 24E:
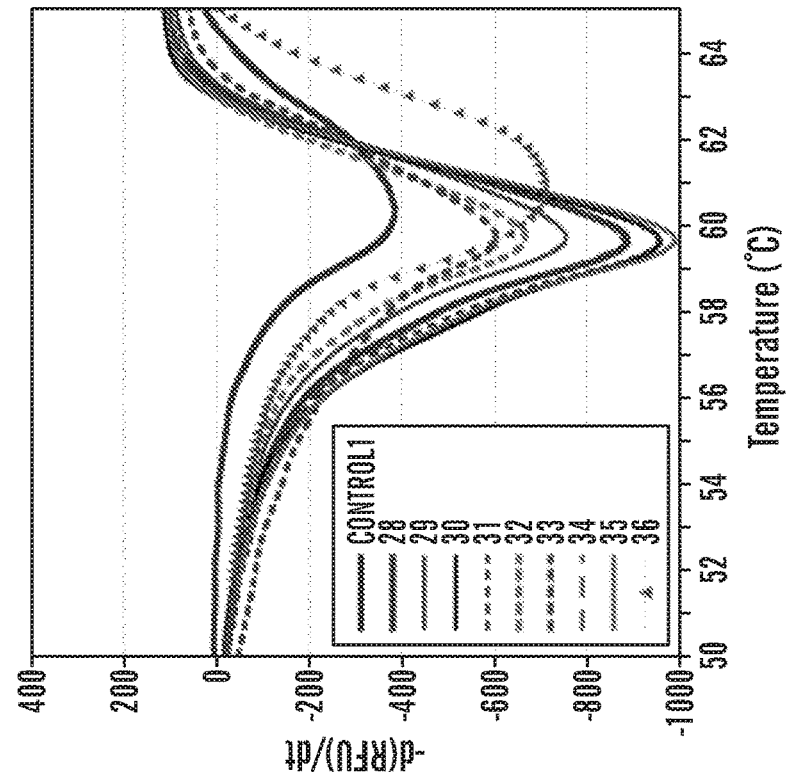
Figure 24H:
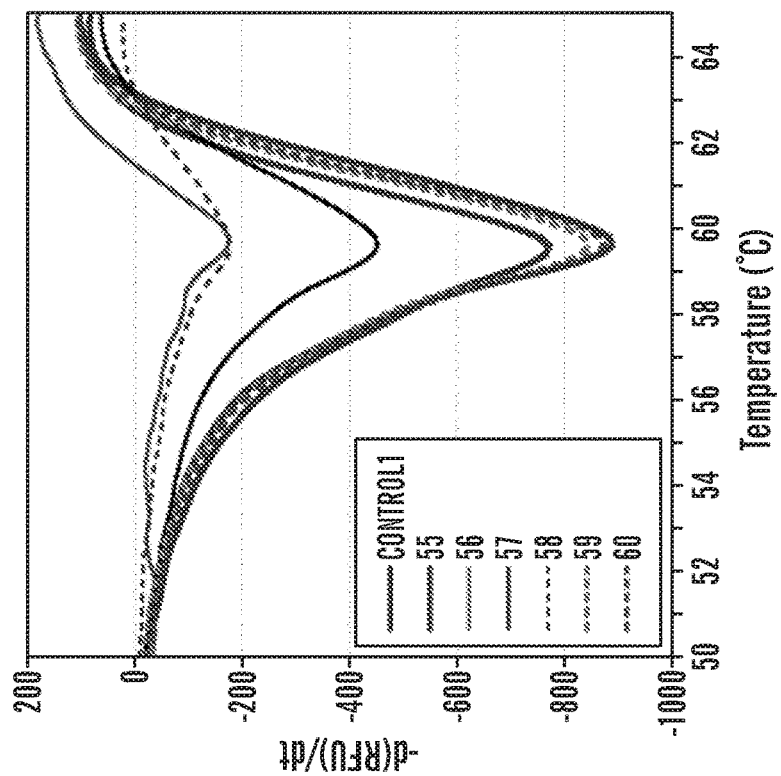
Figure 24G:
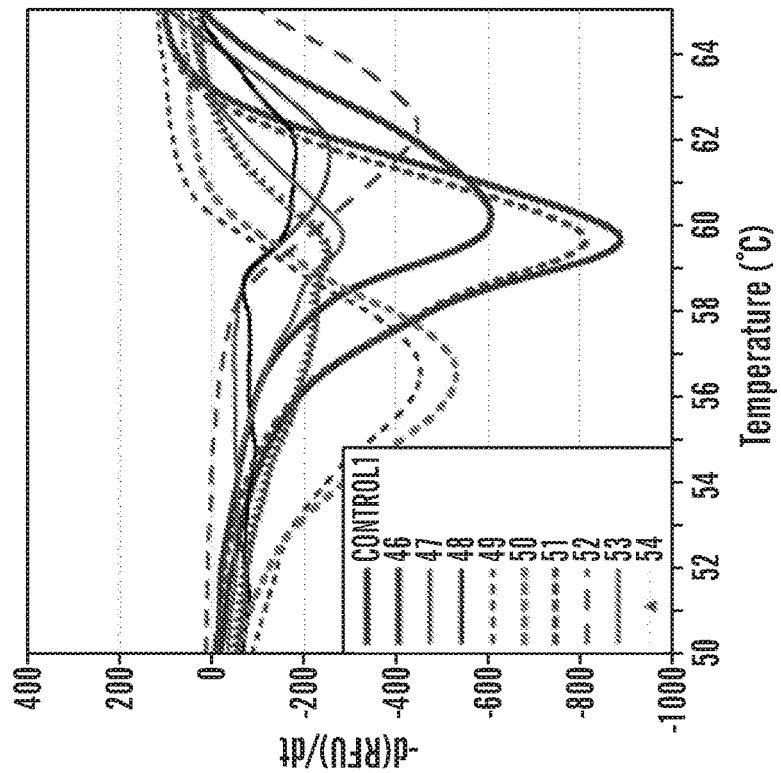
Figure 25A:
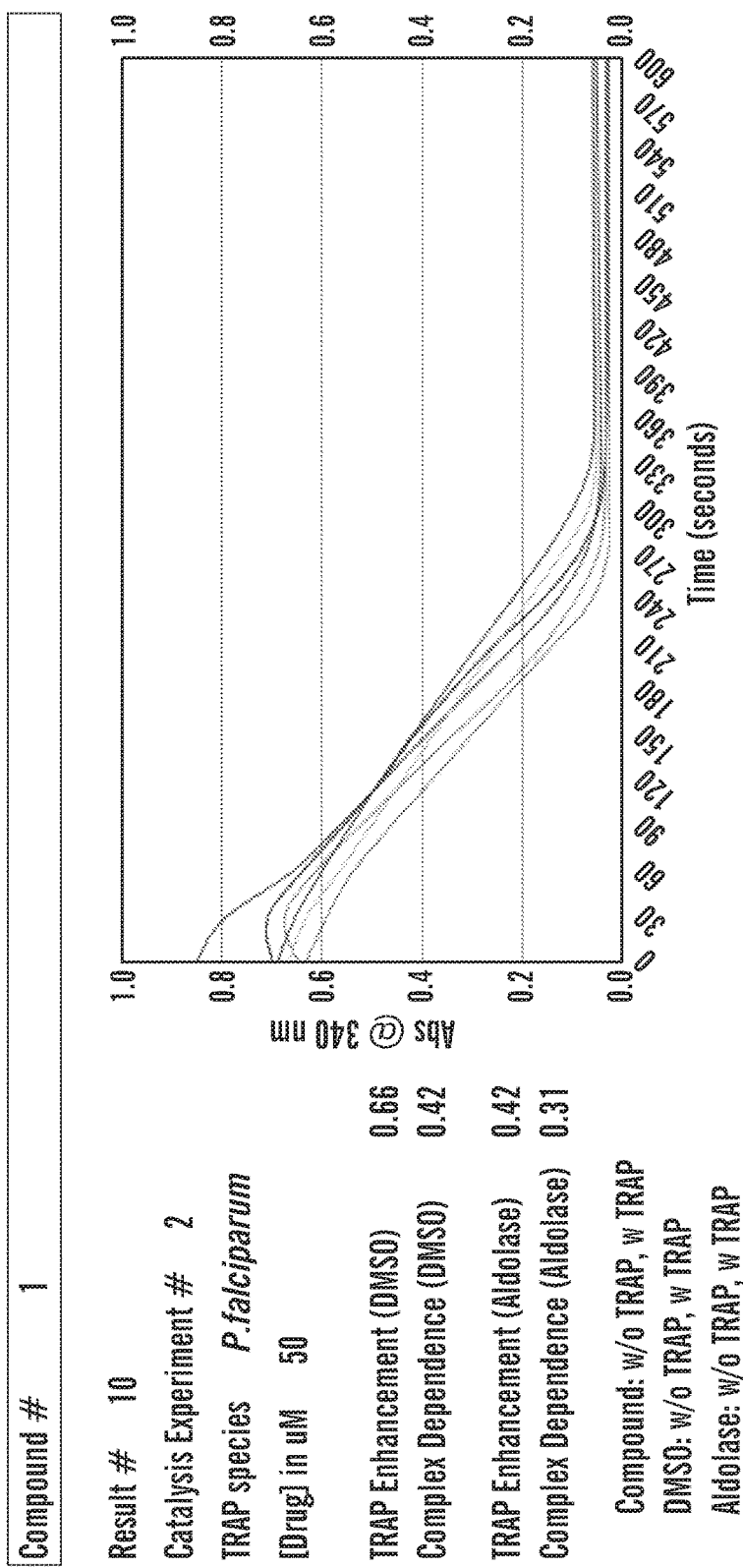
FIGS. 25A-PPPP show the effects of the VLS hits on Aldolase activity when measured in the presence and absence of TRAP. The figure shows the absorbance curves (i.e. NADH consumption/Aldolase catalysis curves) obtained for each compound over multiple 10 minute experiments. "TRAP species" refers to the TRAP peptide used during the experiment—*P. falciparum* indicates a peptide containing the 25 C-terminal residues of *P. falciparum* TRAP (PfTRAP25), while *P. berghei* indicates a peptide containing the 25 C-terminal residues of *P. berghei* TRAP (PbTRAP25). The concentration of drug used, the TRAP Enhancement, and Complex Dependence Scores obtained relative to both DMSO and Aldolase alone, and the Aldolase and DMSO control curves are shown for each experiment as well. Results are sorted by compound number, and scores were analyzed for the linear portions of the kinetics curves—i.e. from 30 to 300 seconds only. It is apparent form the absorbance curves that there is some variation in results from one experiment to the next. This variation may be due to small differences between batches of purified enzymes, peptides, or compounds, as well as to human error. Additionally, comparison of the curves for Aldolase alone with those for DMSO suggested that even at the low concentrations used, DMSO appeared to have a small, but reproducible, effect on the TRAP-Aldolase interaction and/or on the assay reaction.
Figure 25B:
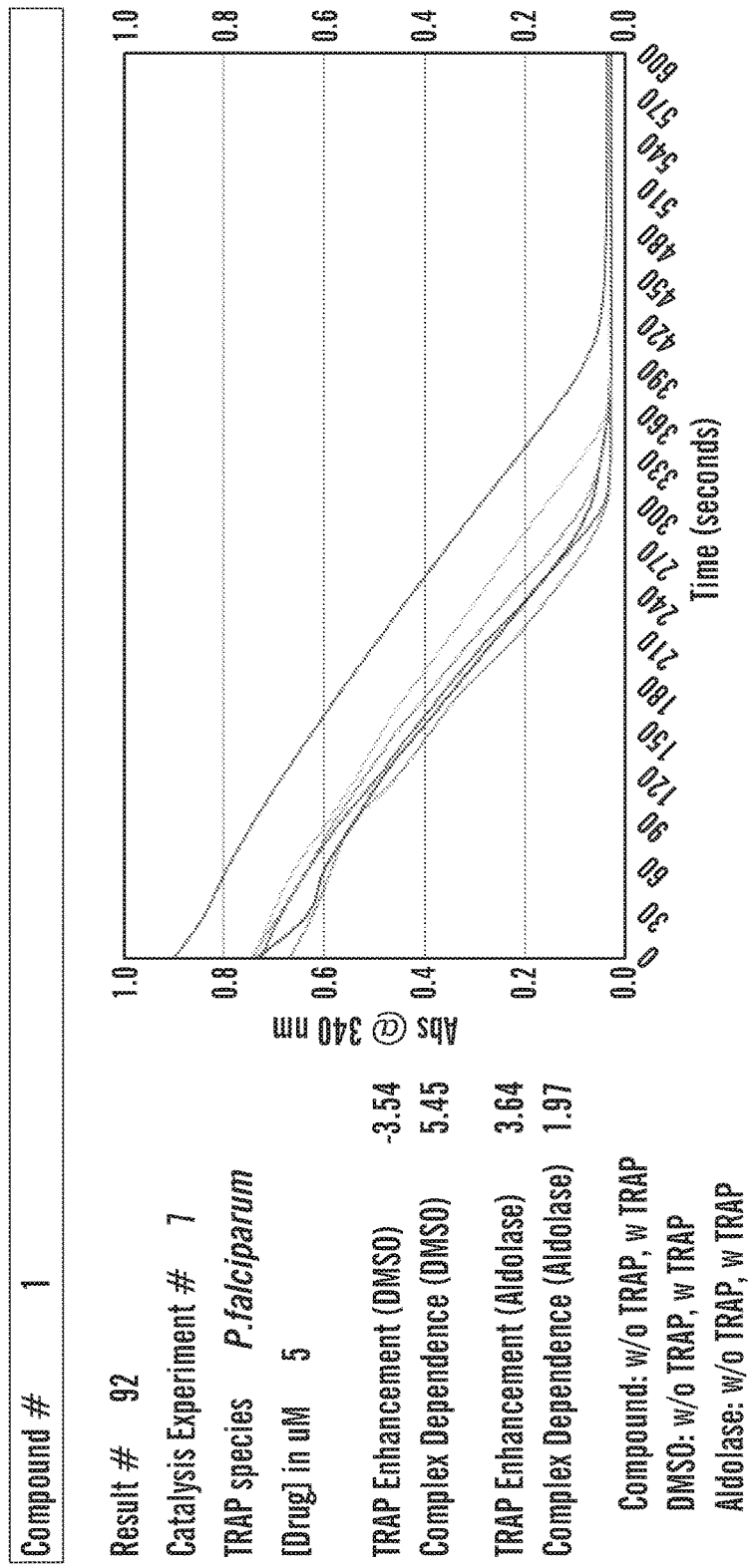
Figure 25C:
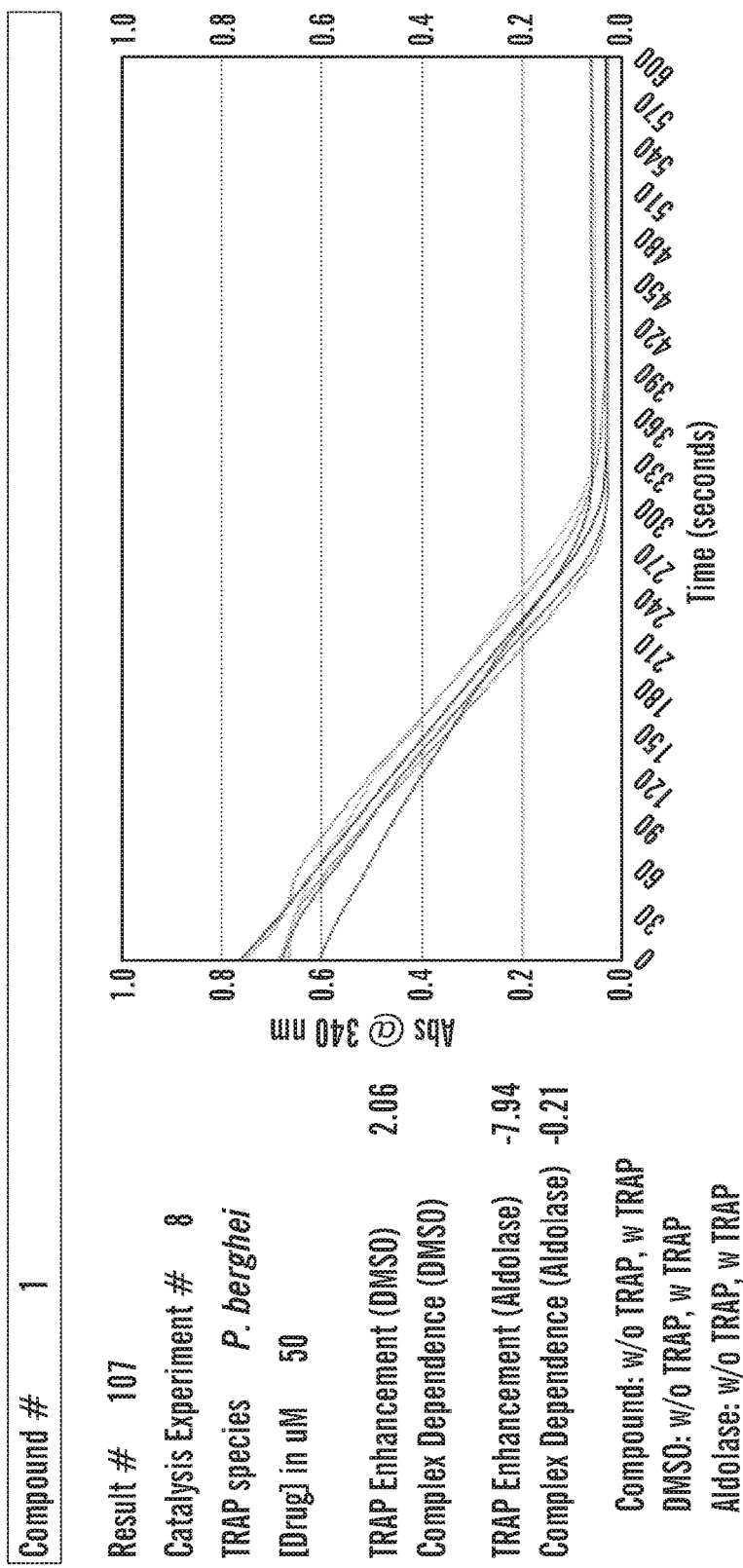
Figure 25D:
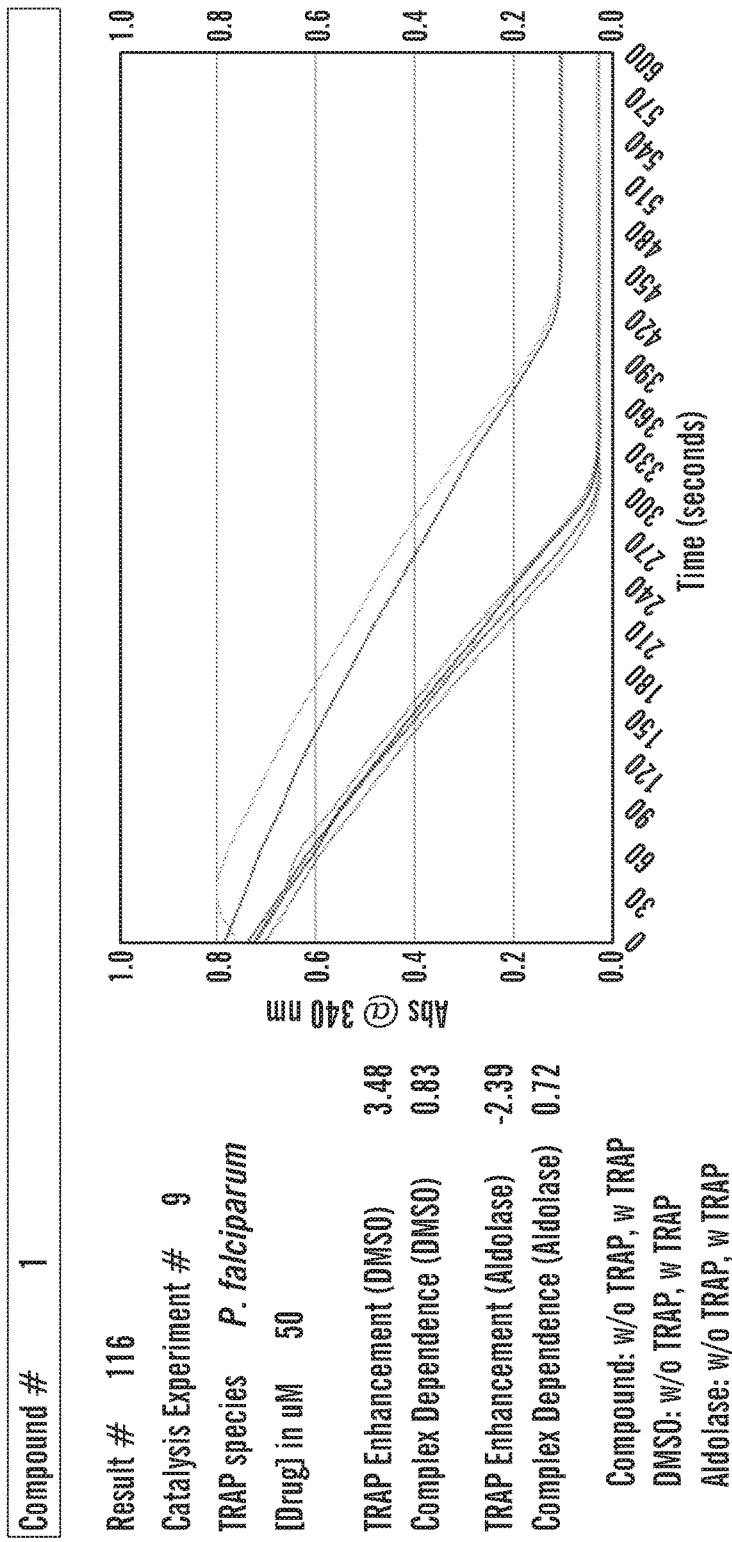
Figure 25E:
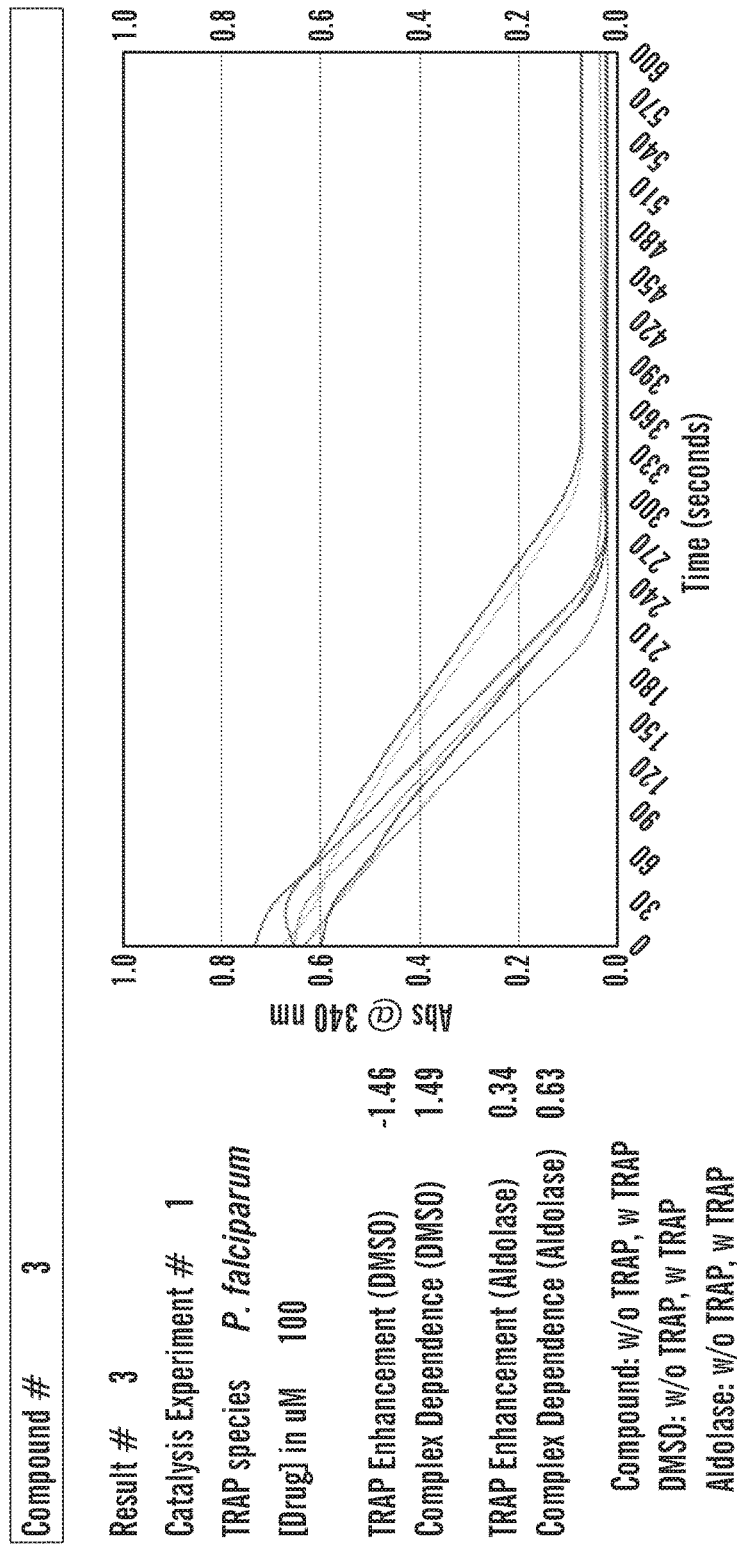
Figure 25F:
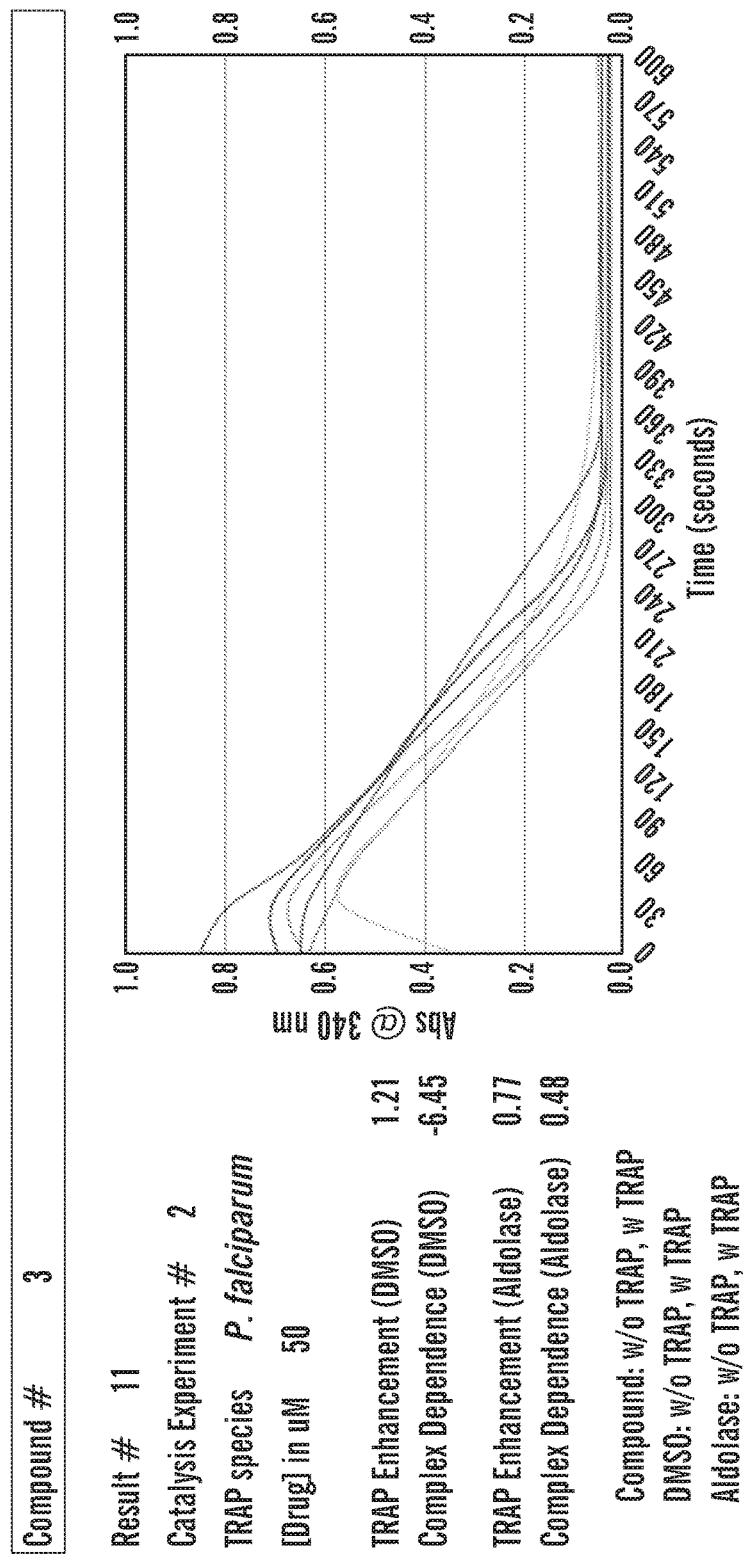
Figure 25G:
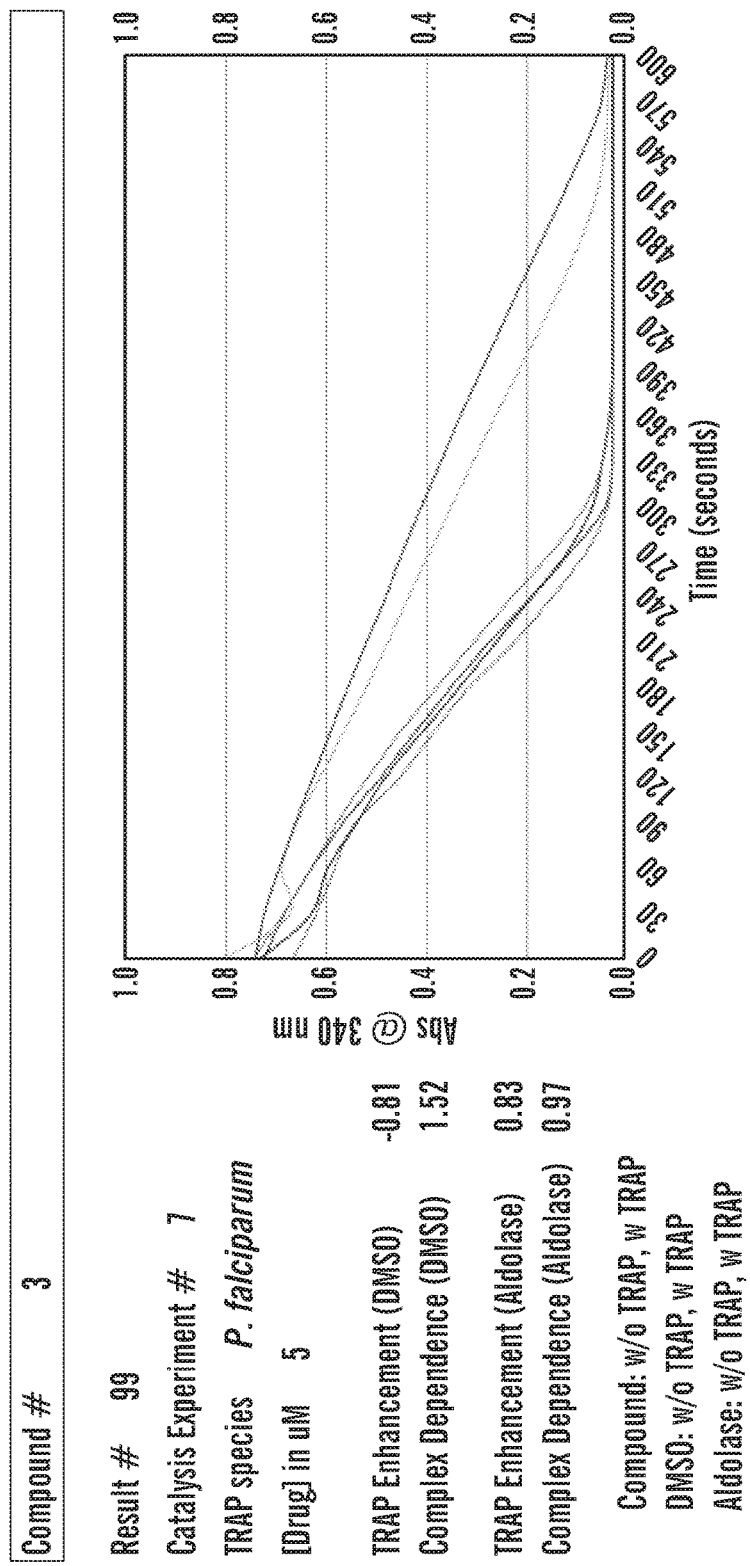
Figure 25H:
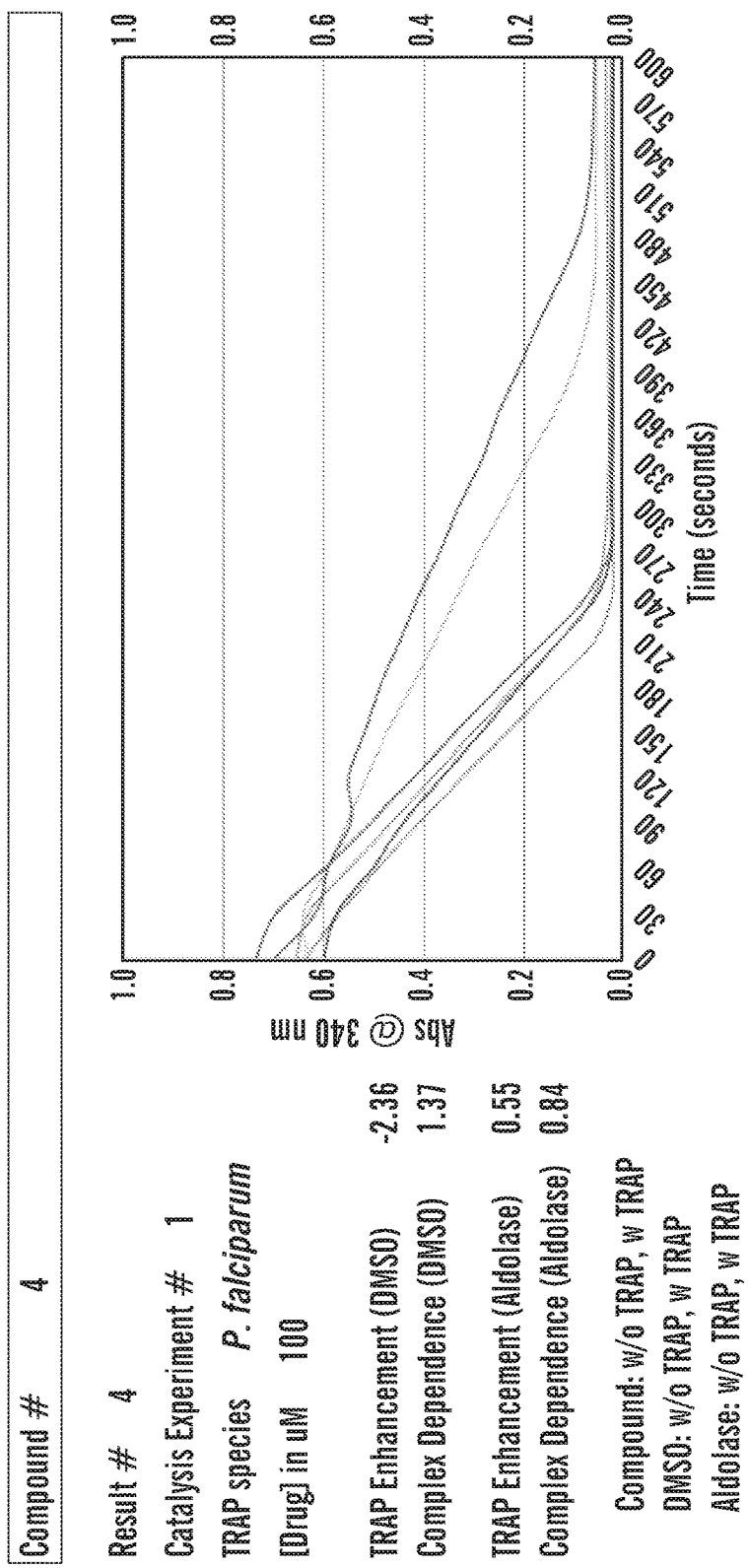
Figure 25I:
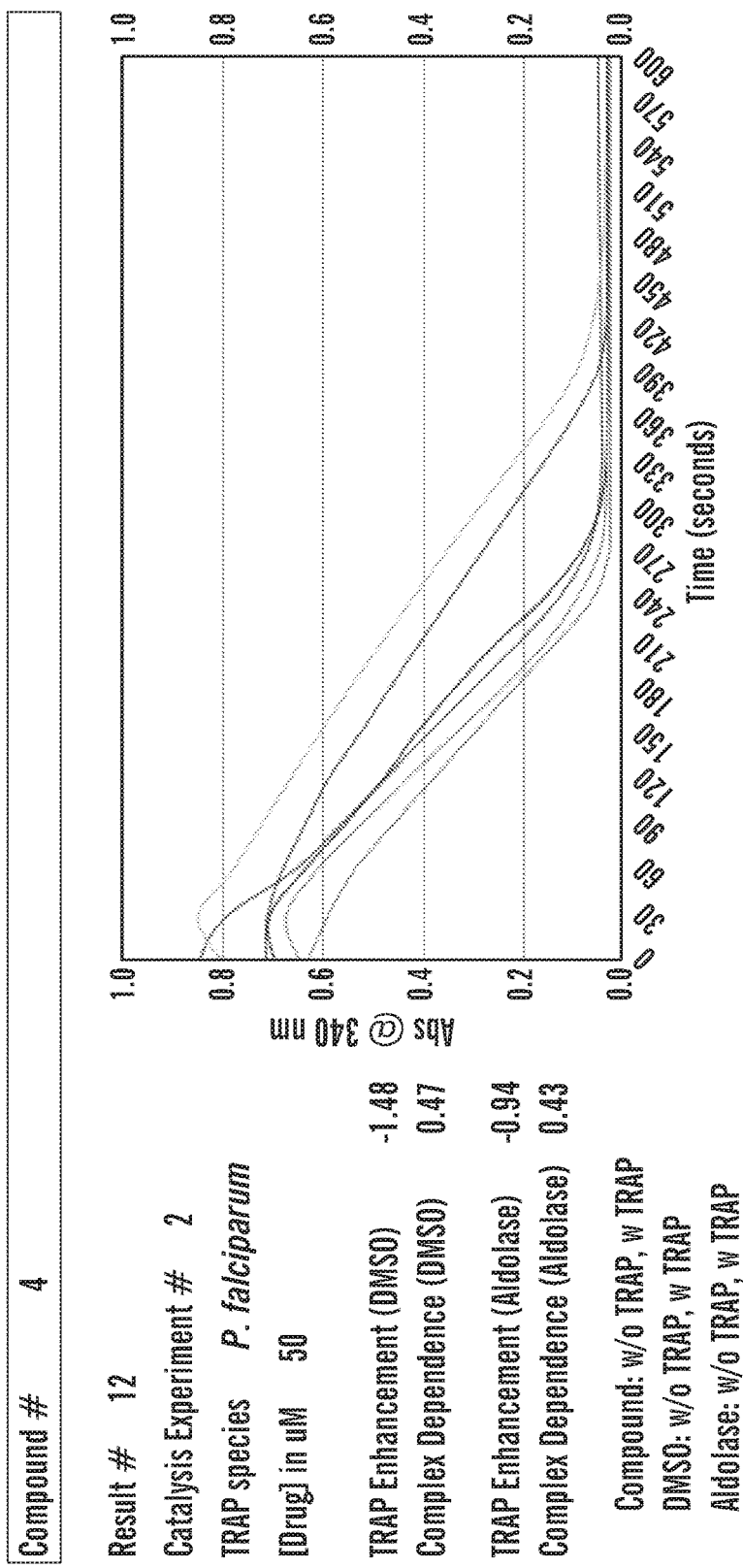
Figure 25J:
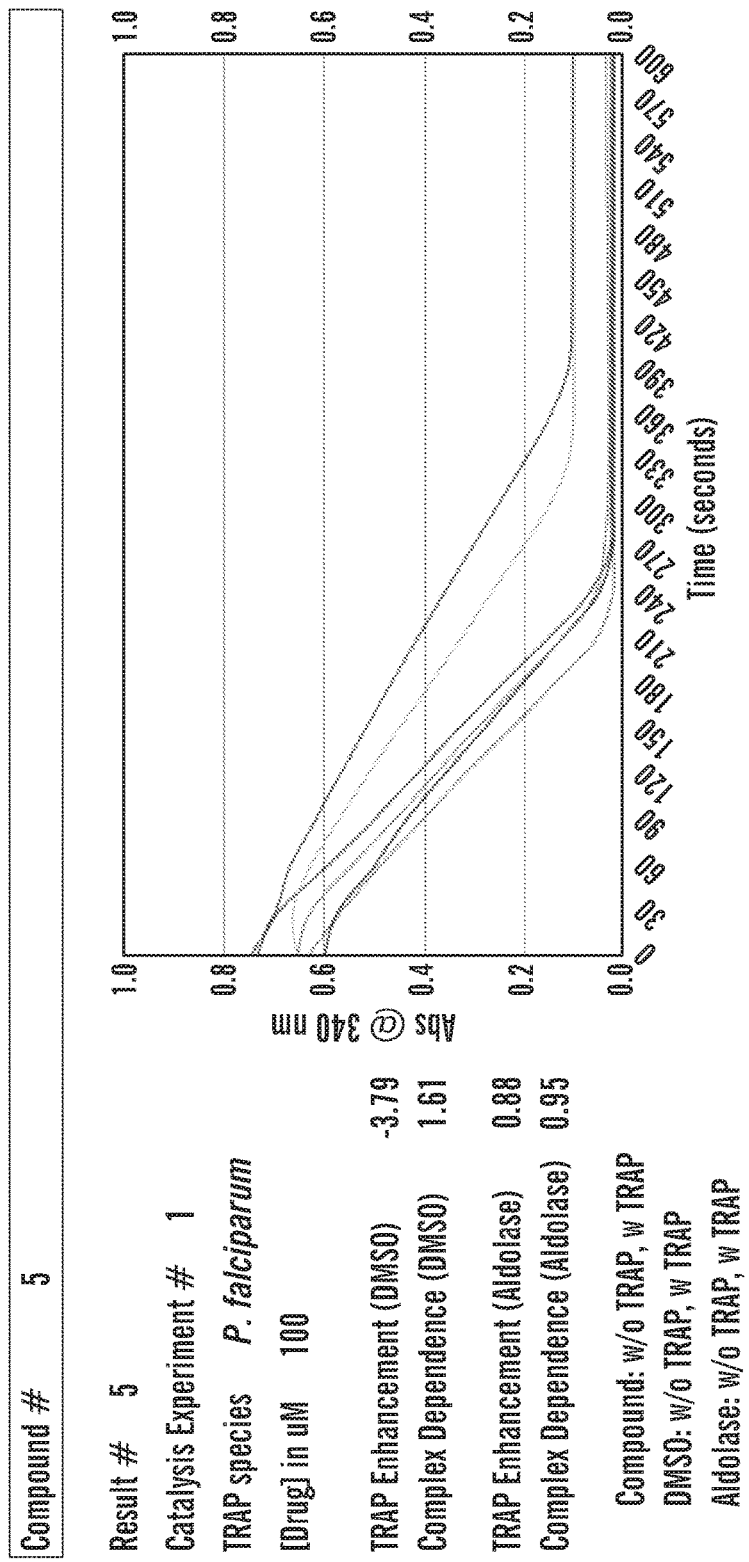
Figure 25K:
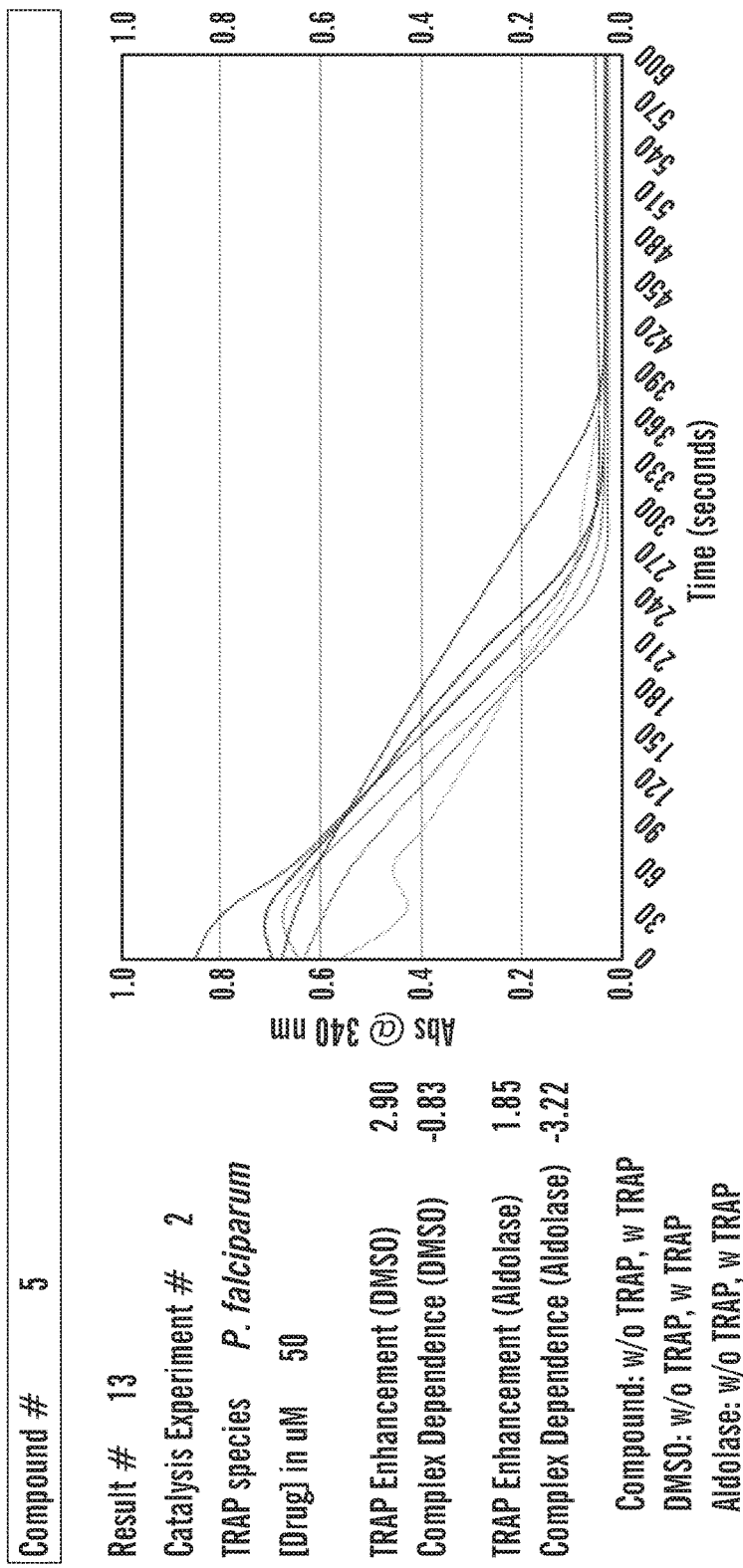
Figure 25L:
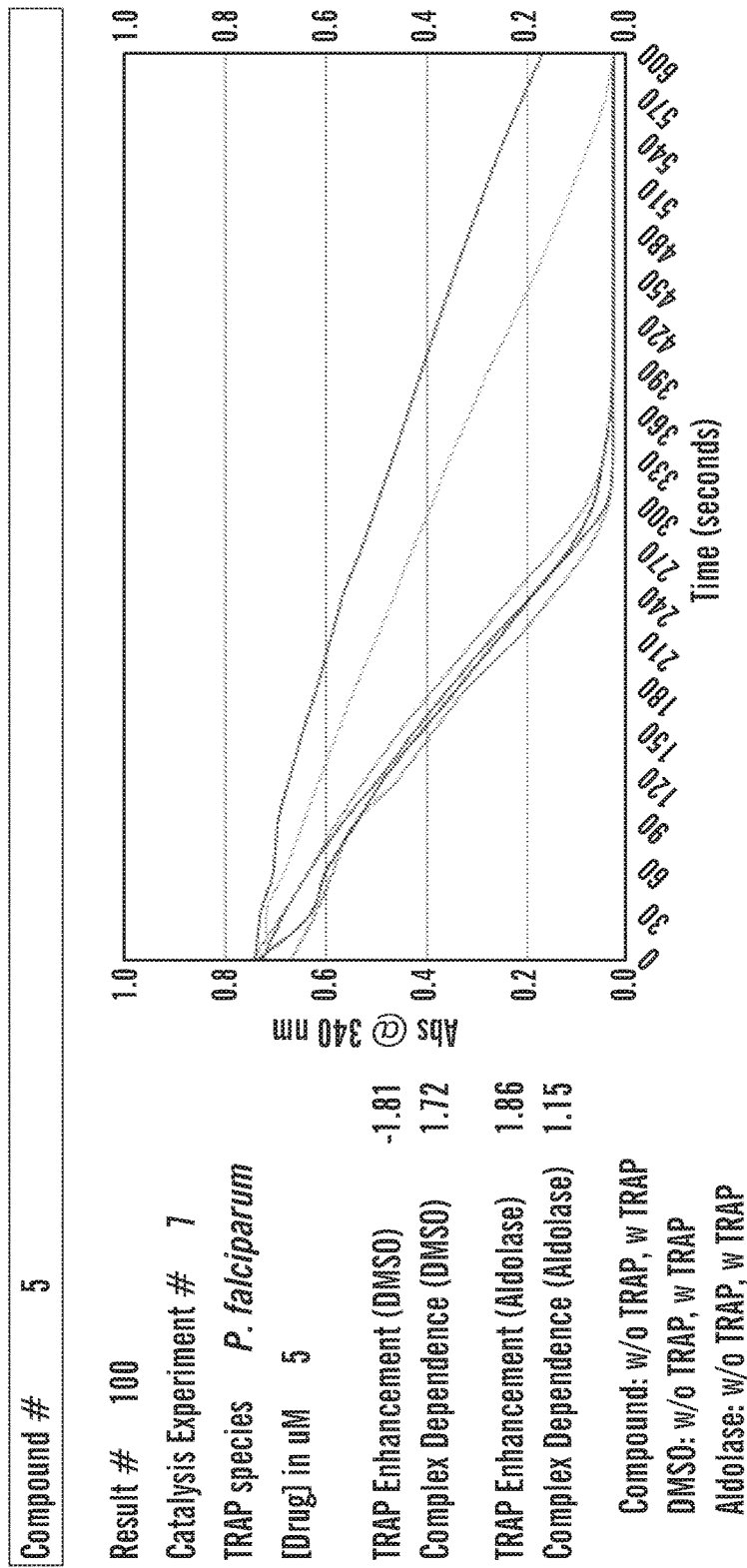
Figure 25M:
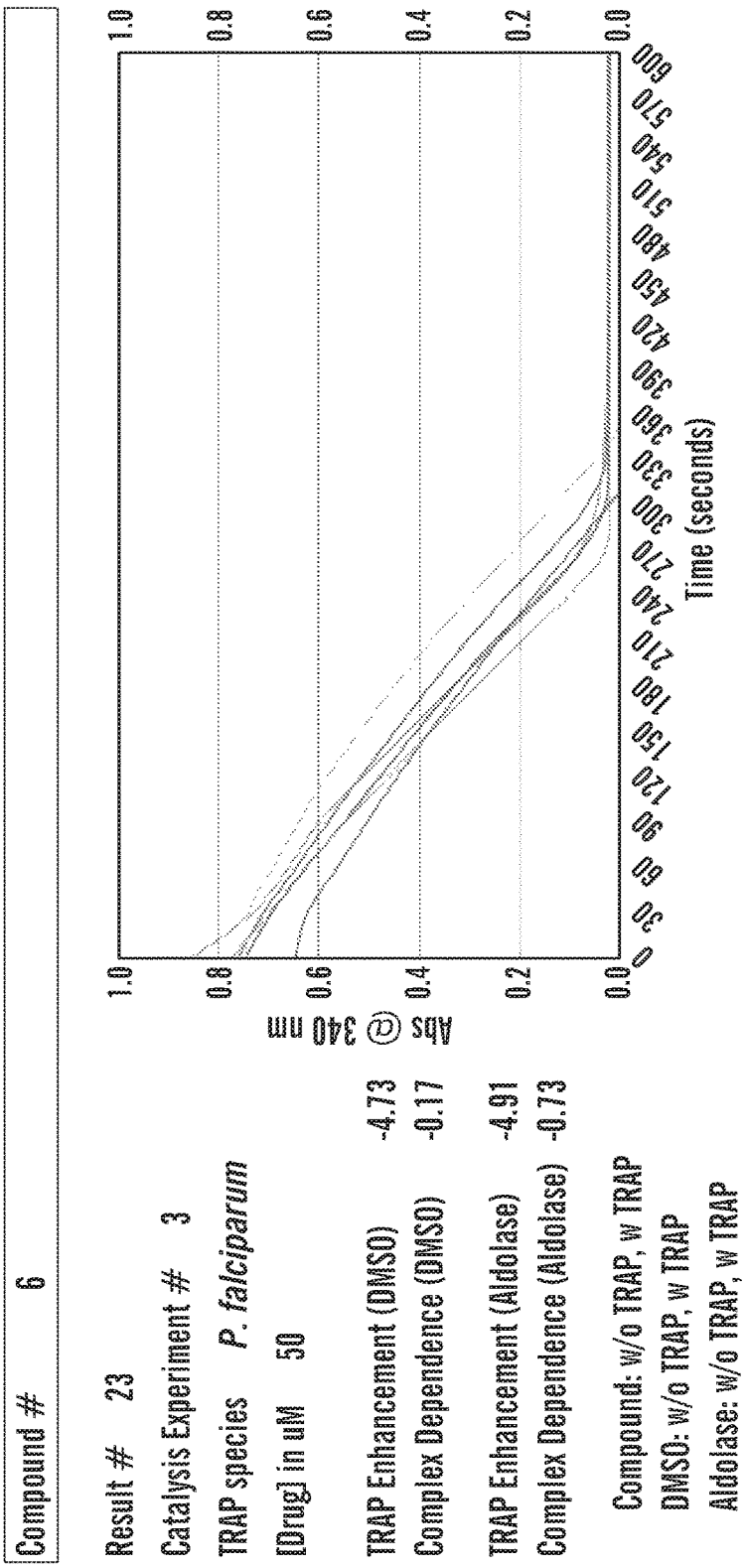
Figure 25N:
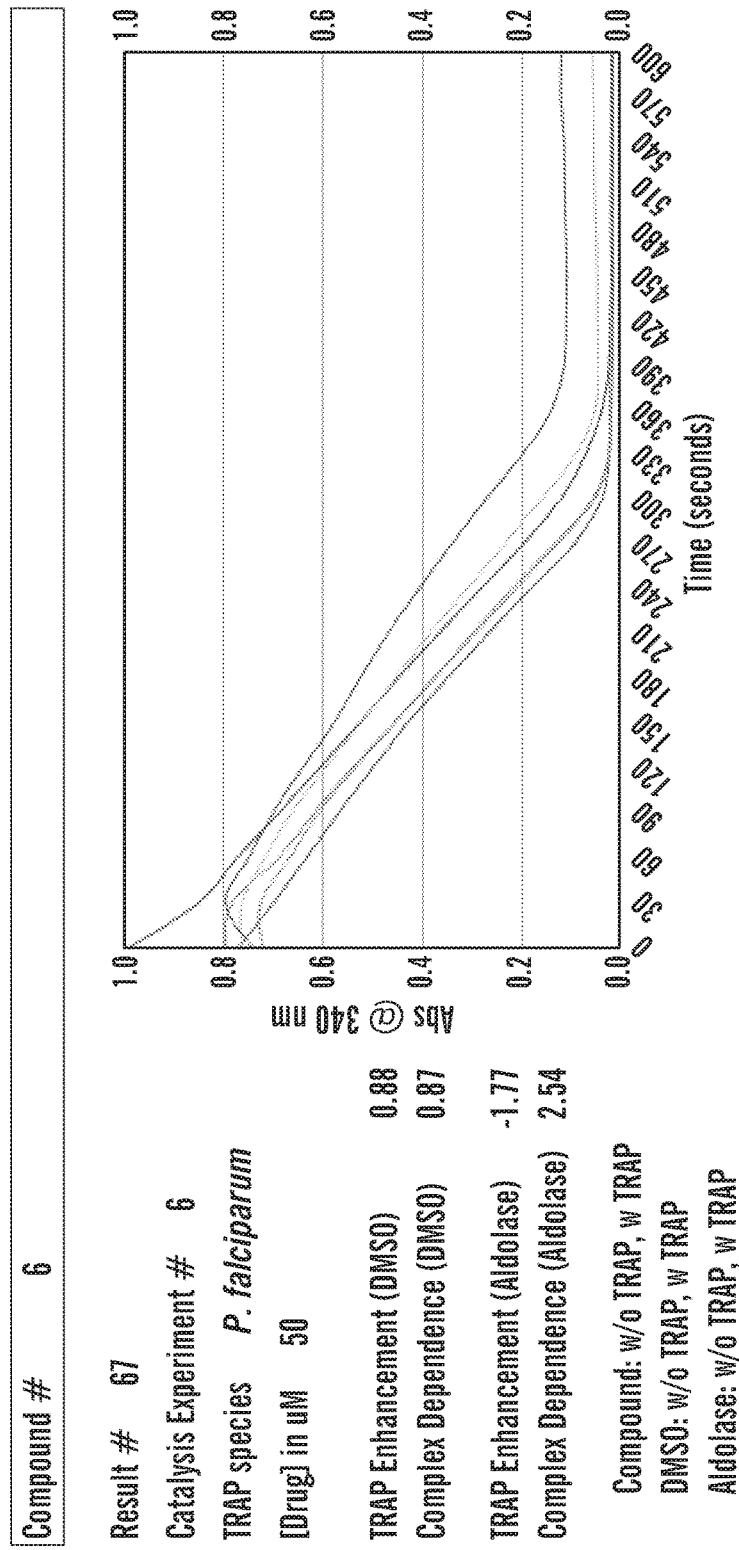
Figure 25O:
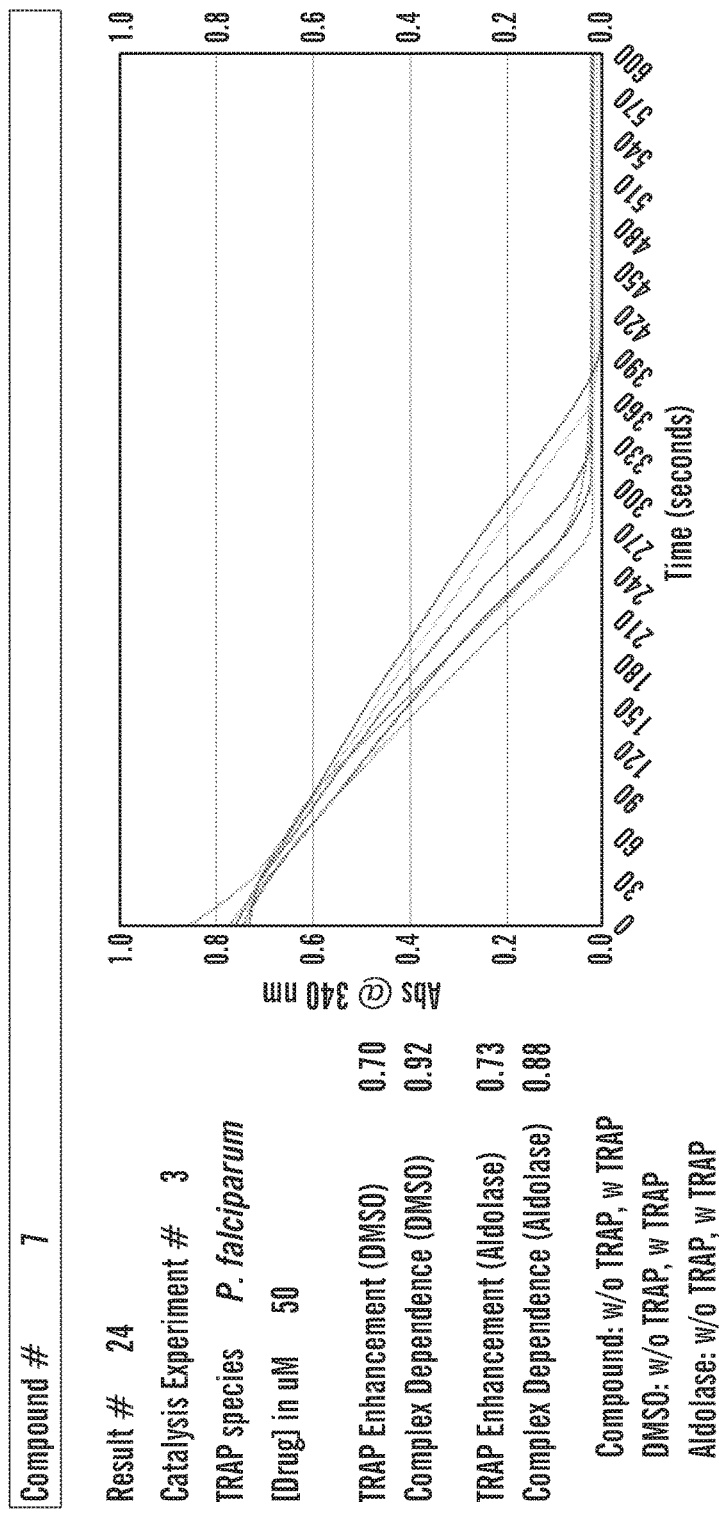
Figure 25P:
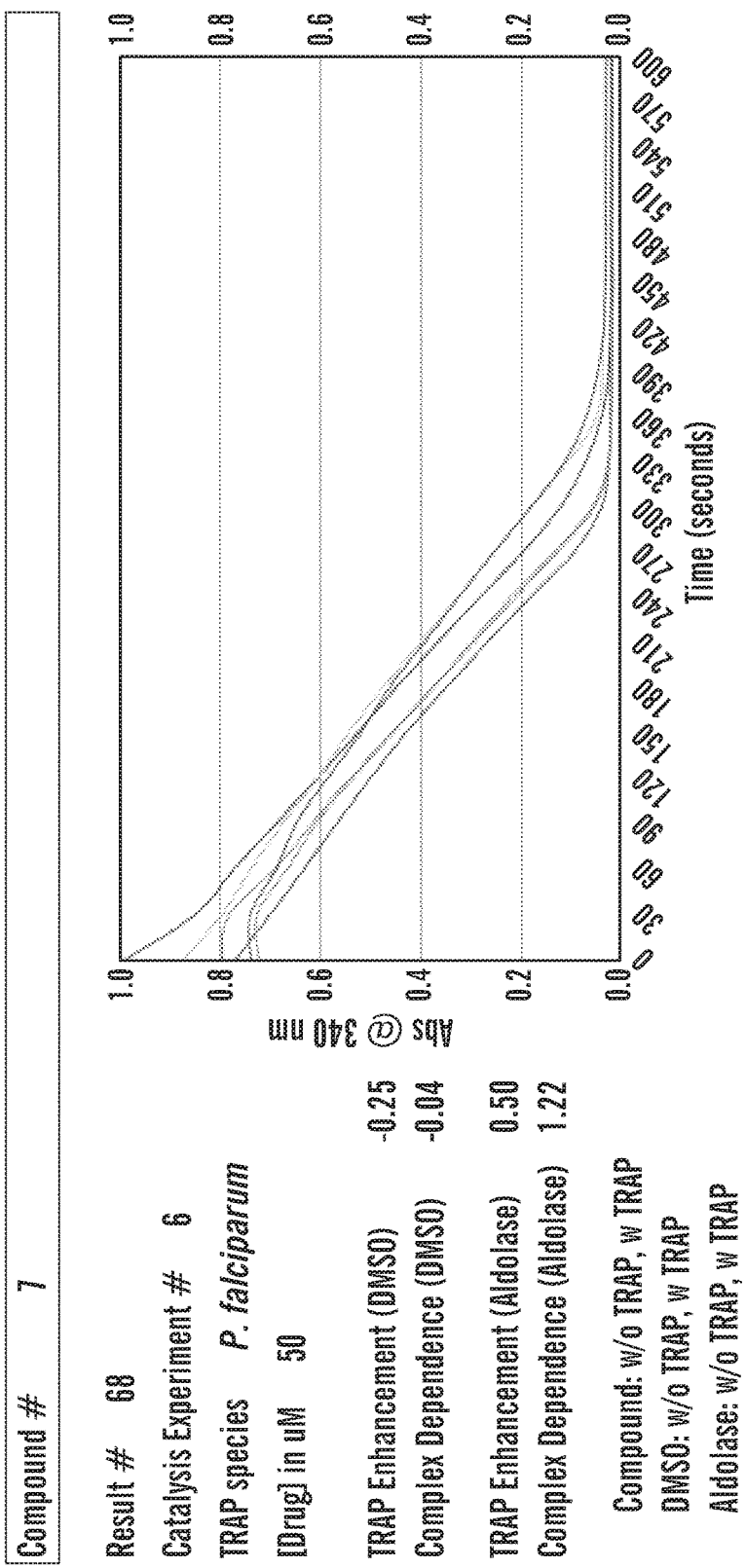
Figure 25Q:
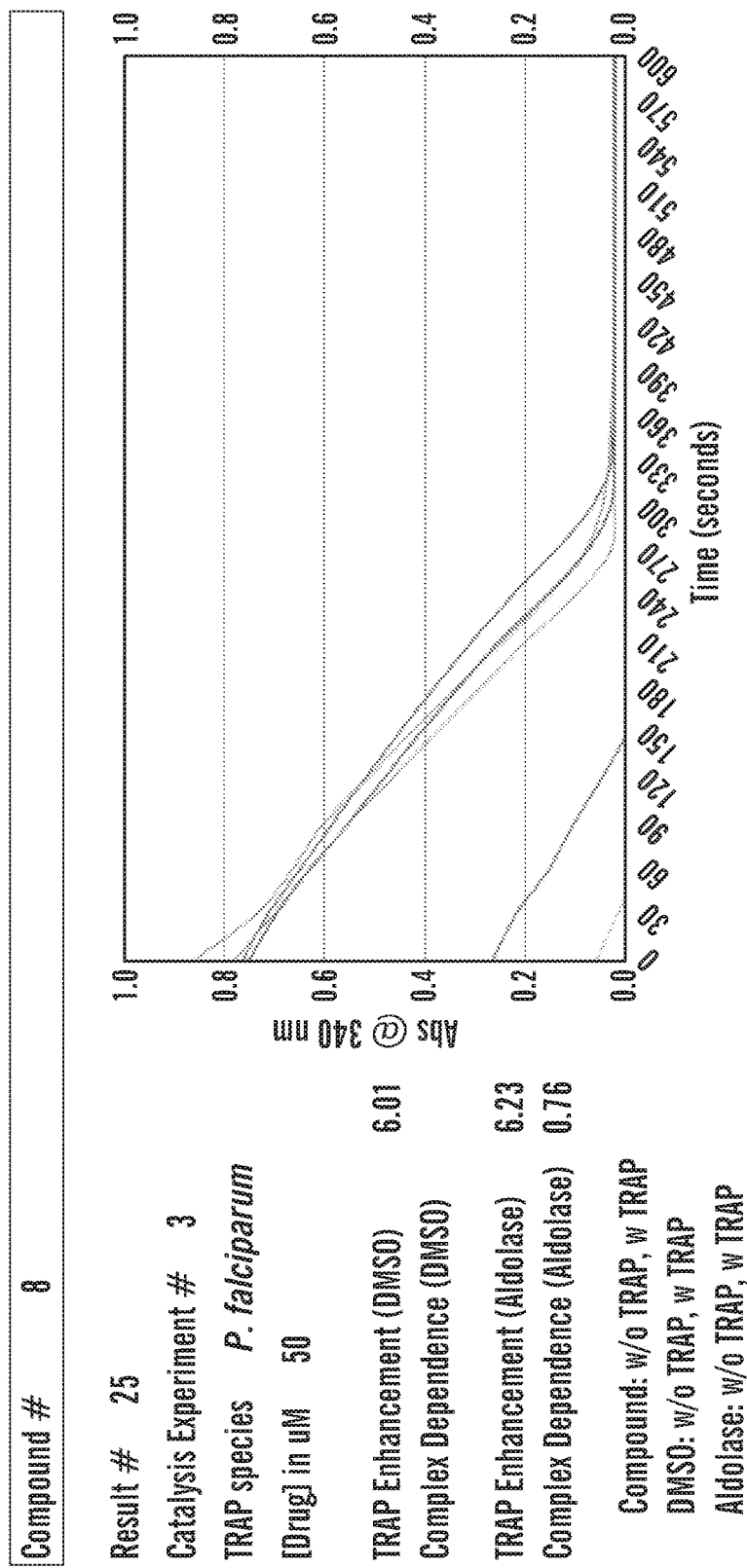
Figure 25R:
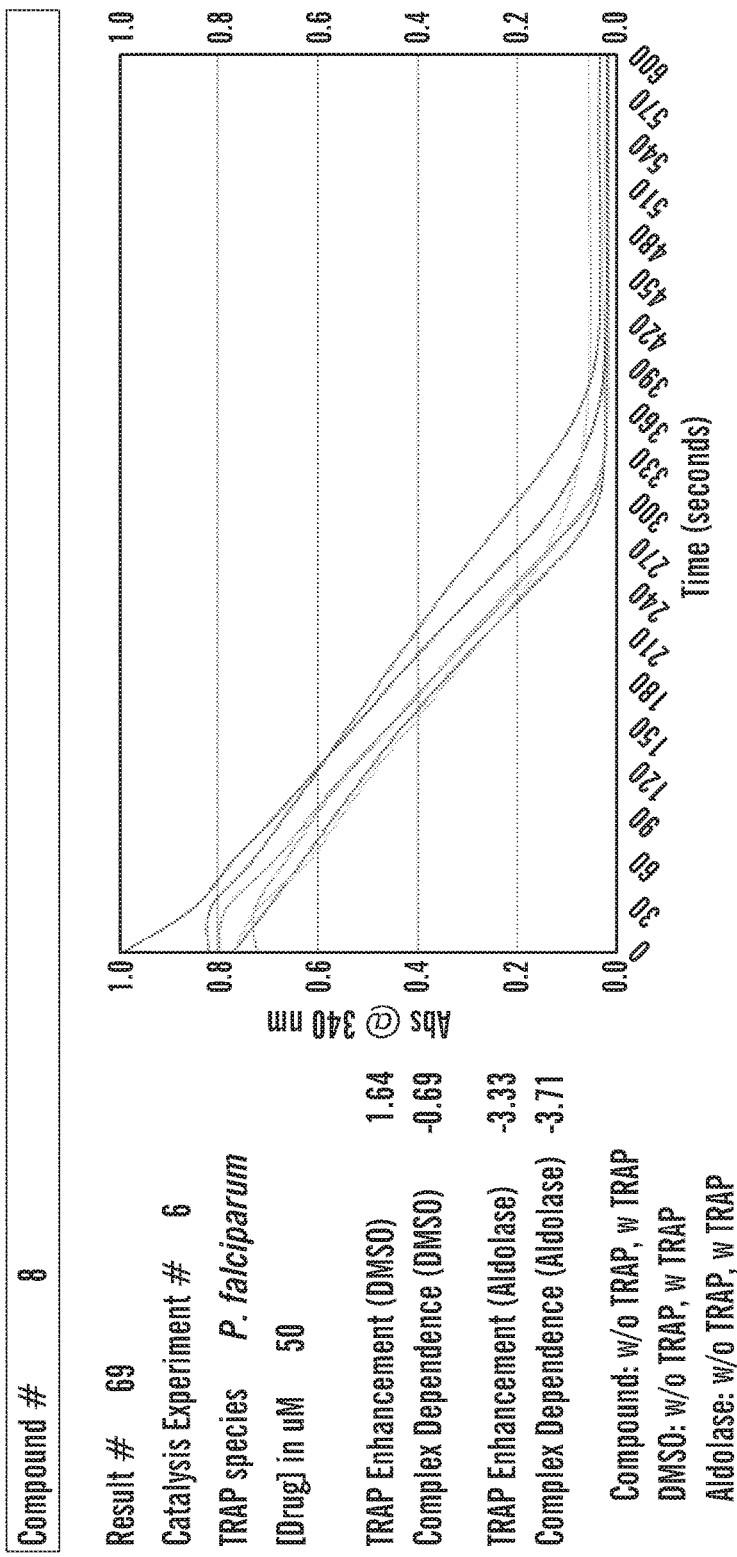
Figure 25S:
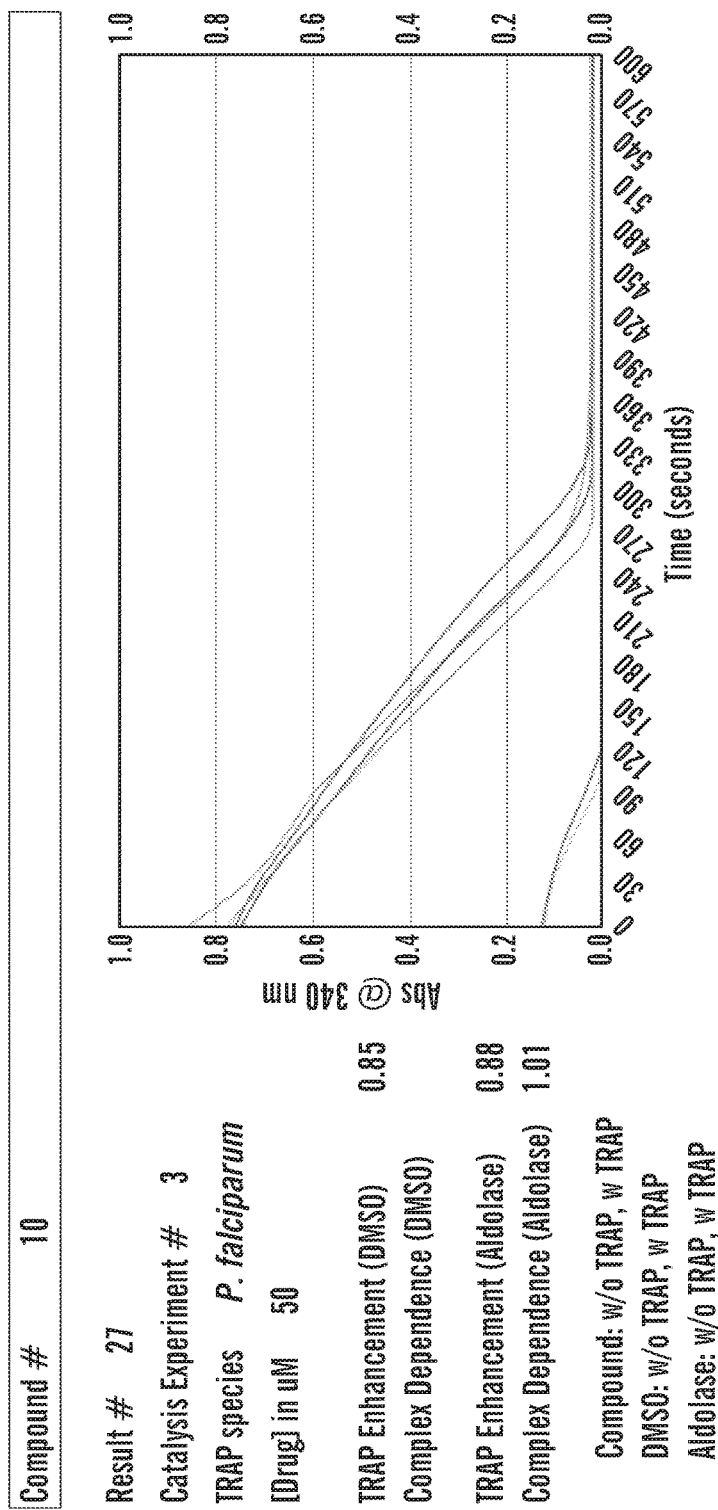
Figure 25T:
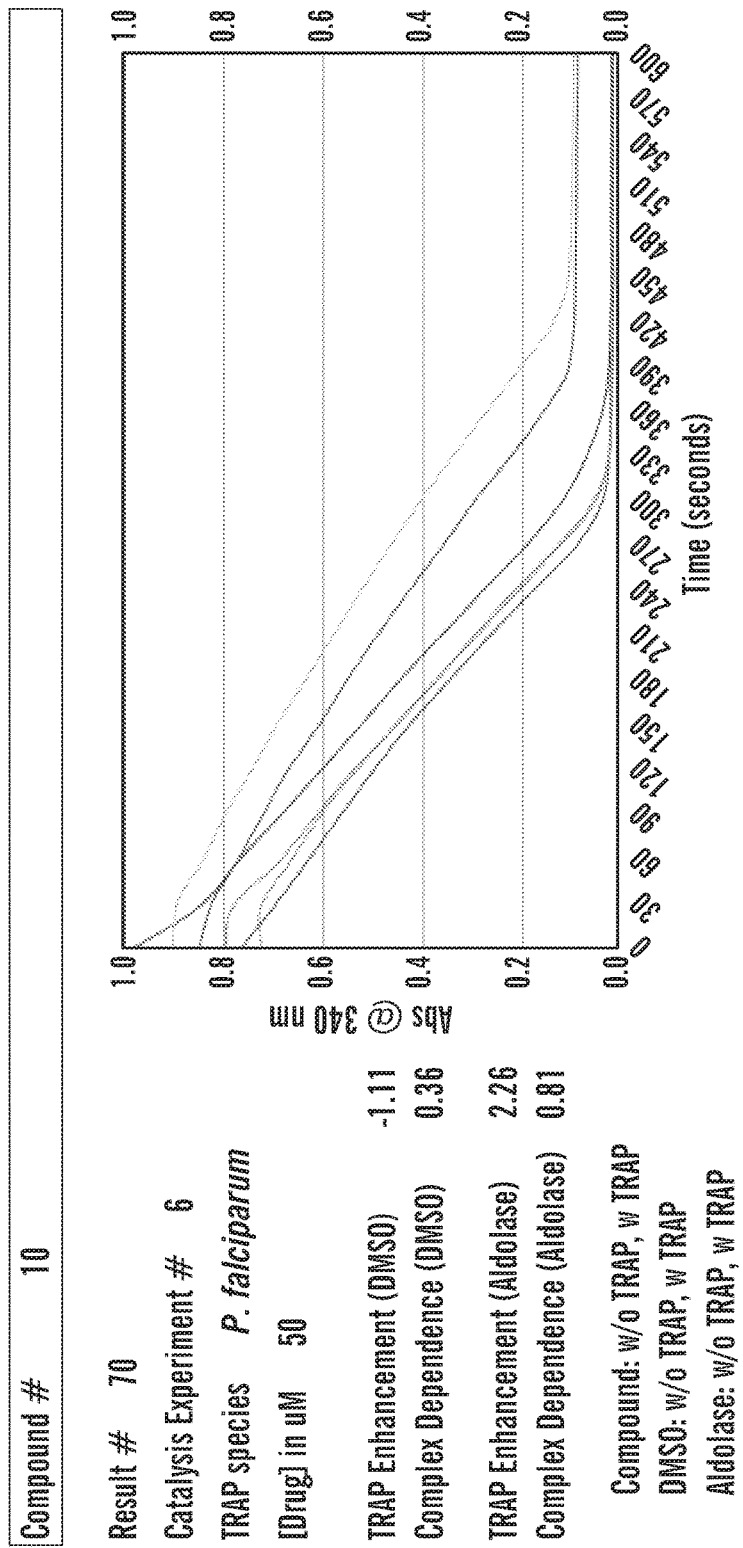
Figure 25U:
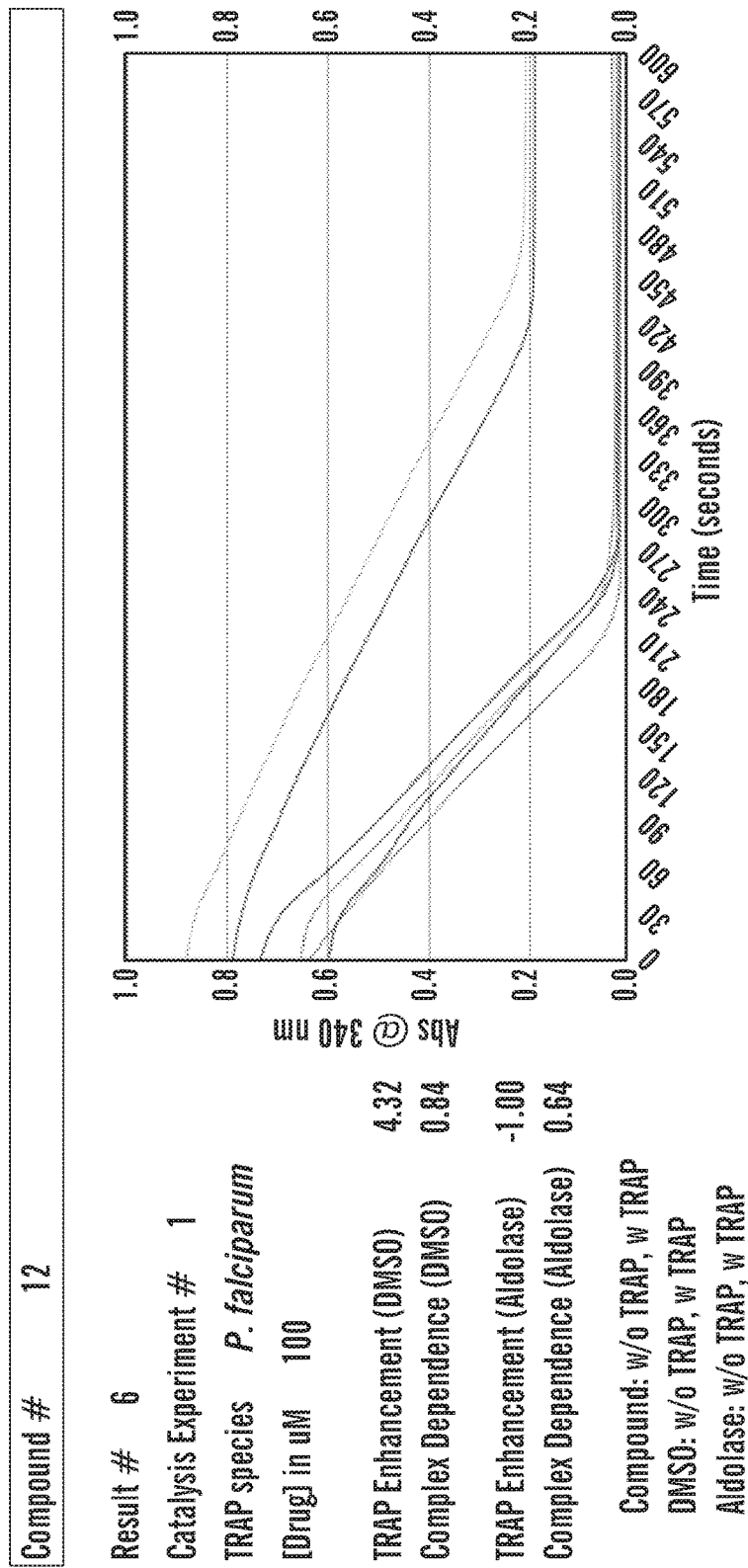
Figure 25V:
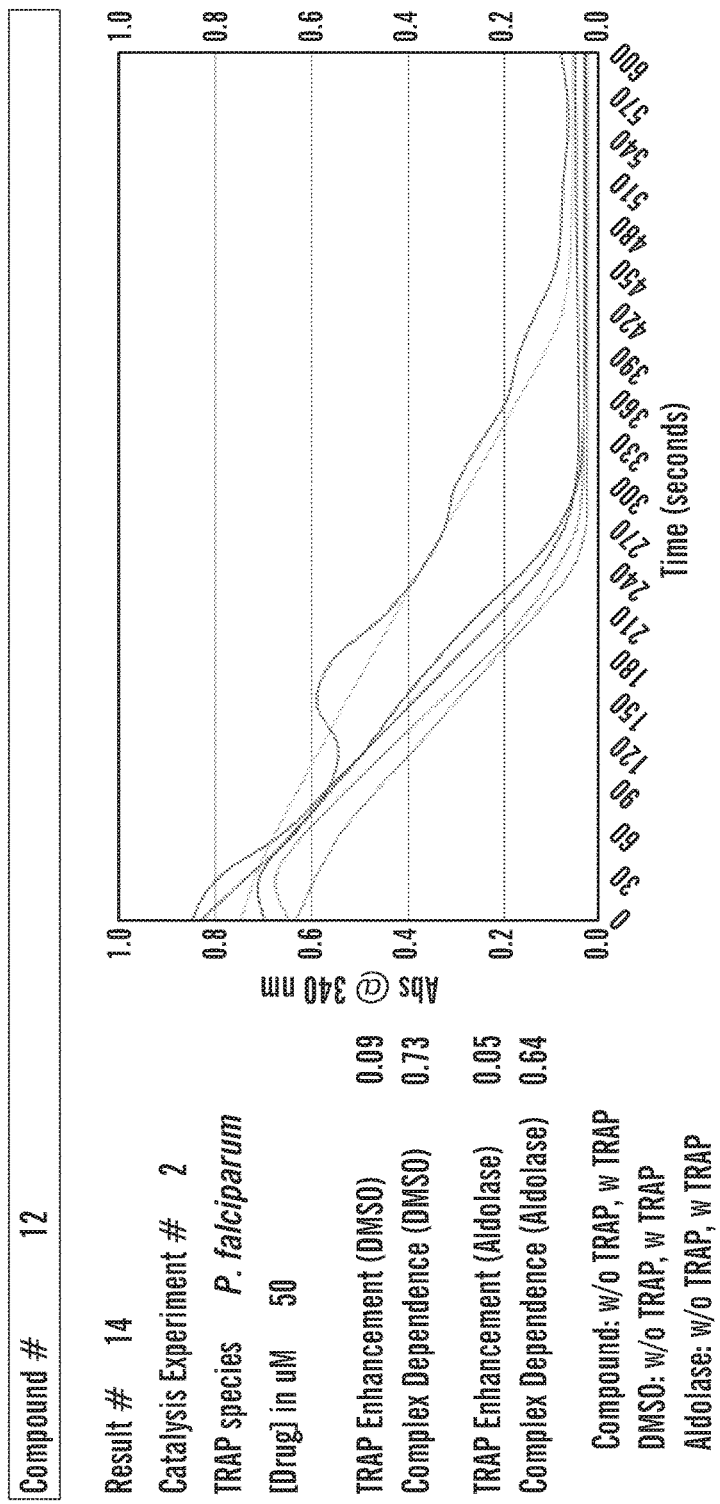
Figure 25W:
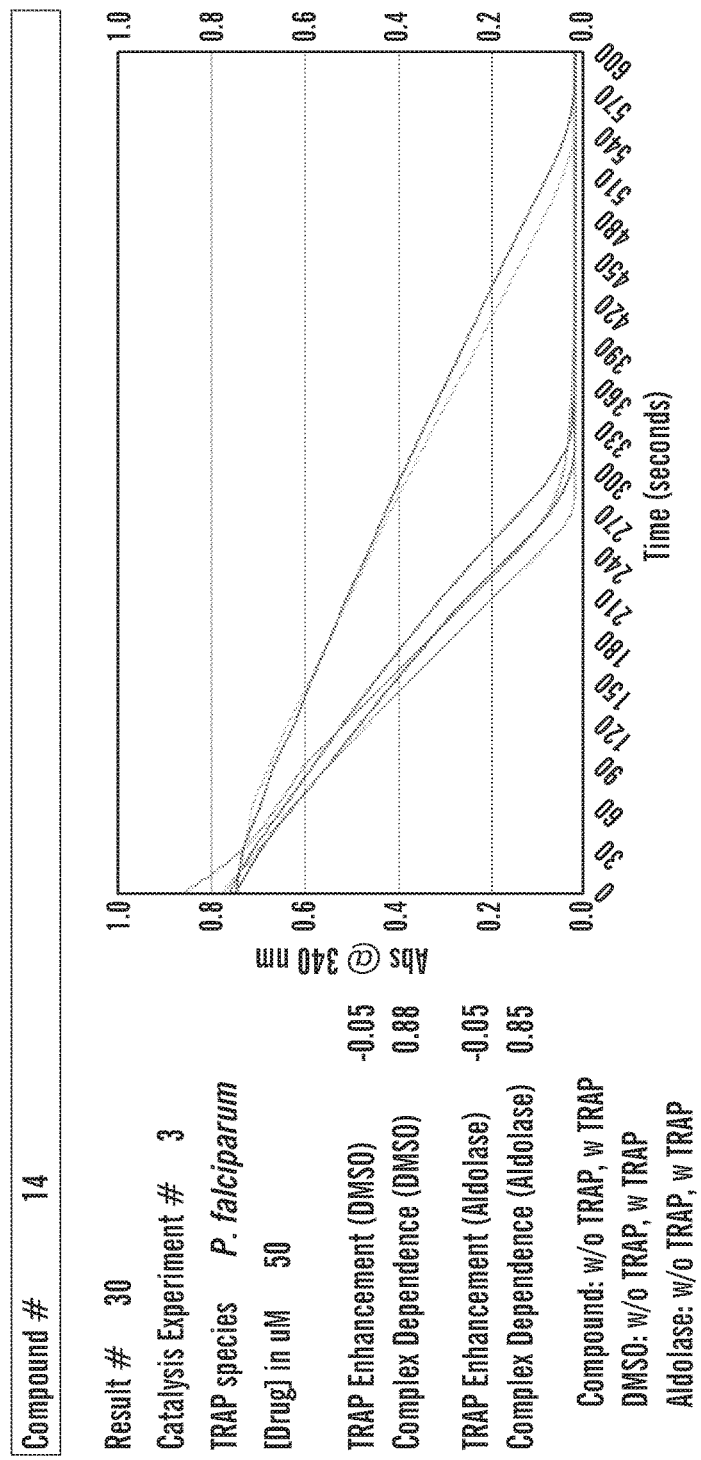
Figure 25X:
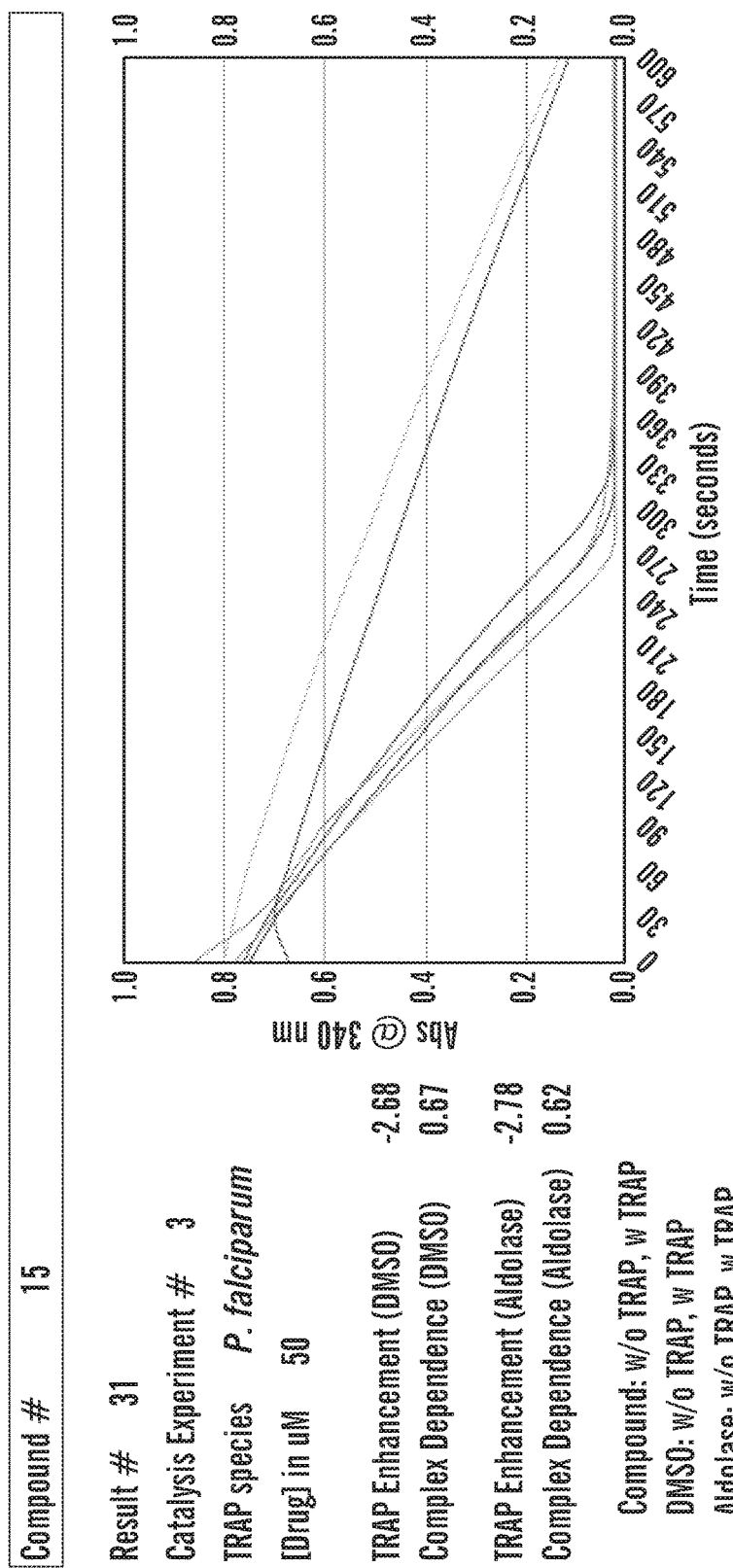
Figure 25Y:
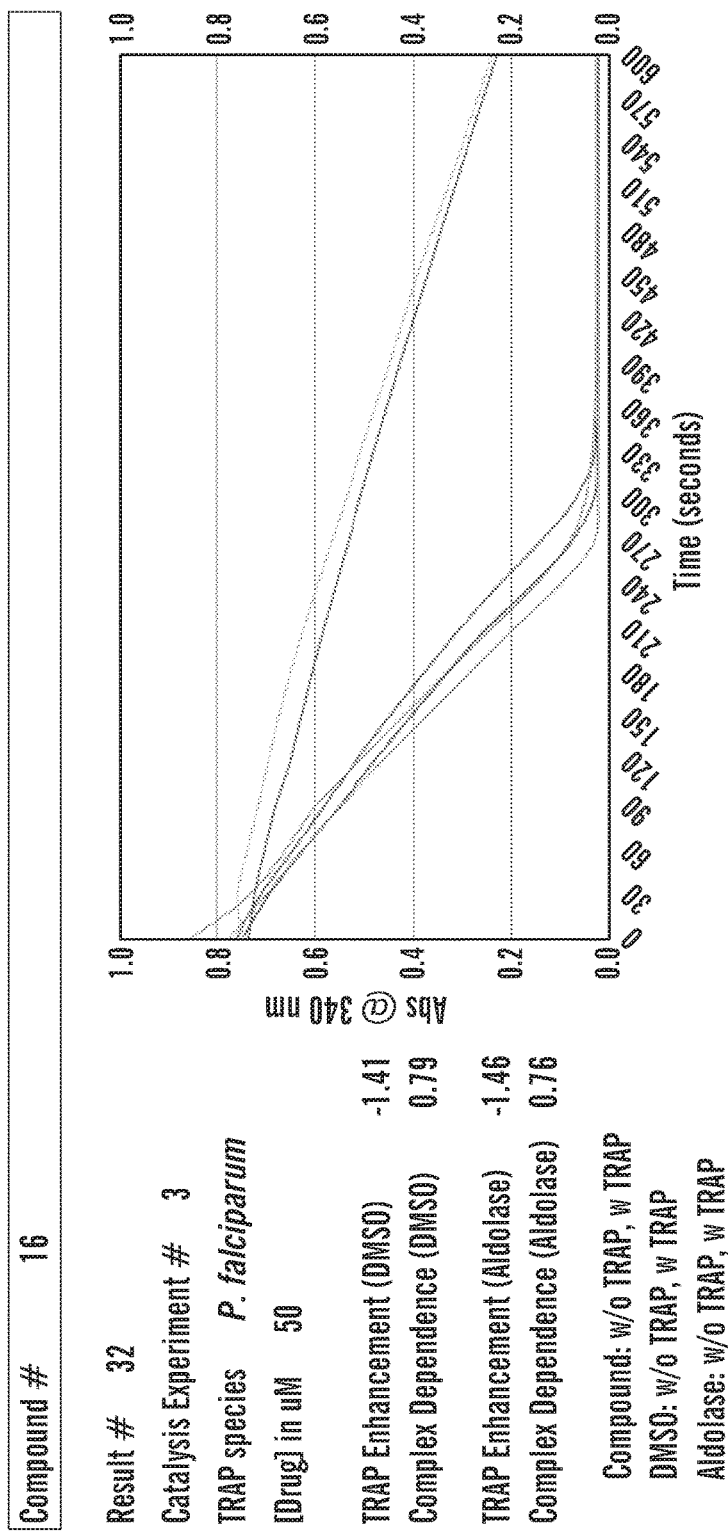
Figure 25Z:
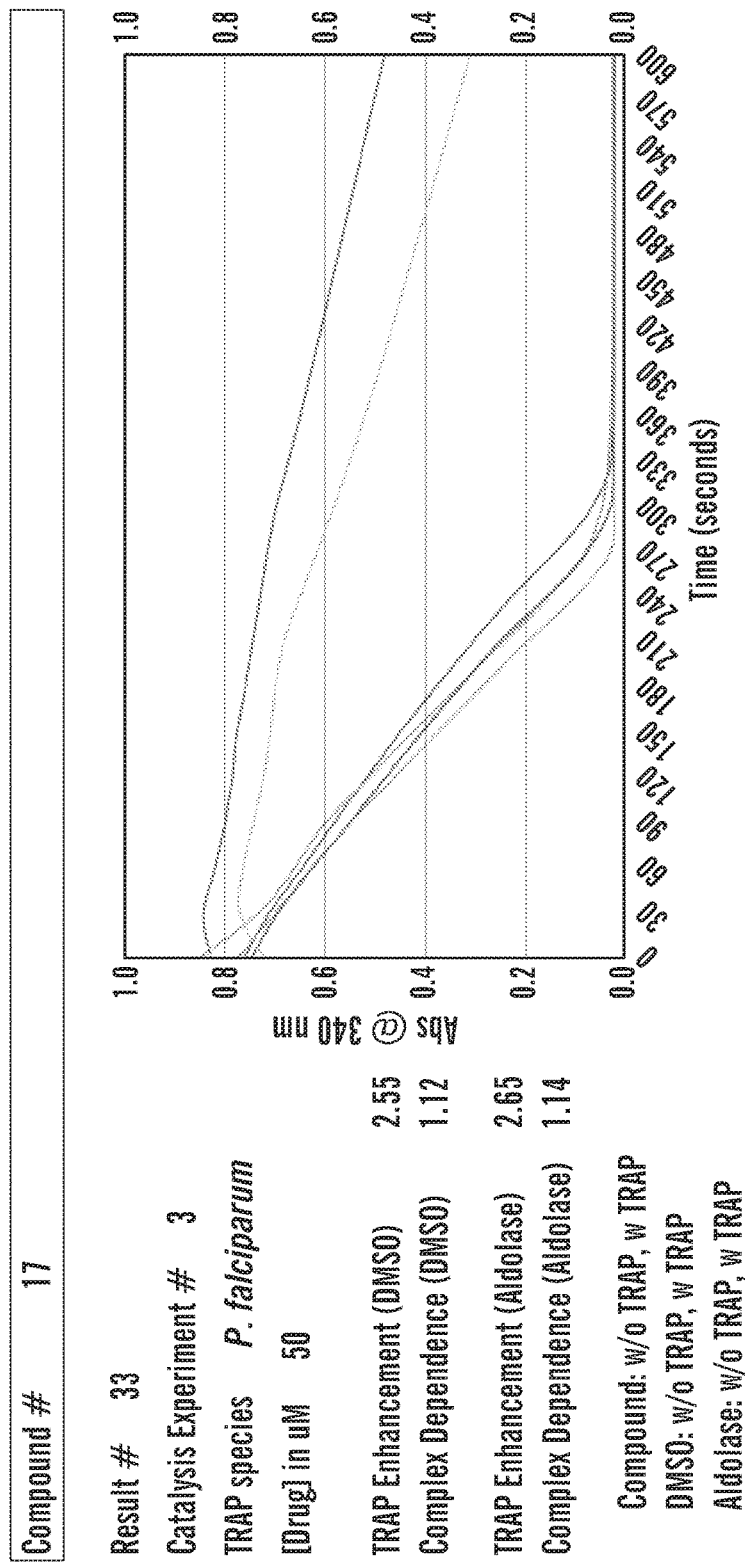
Figure 25A:
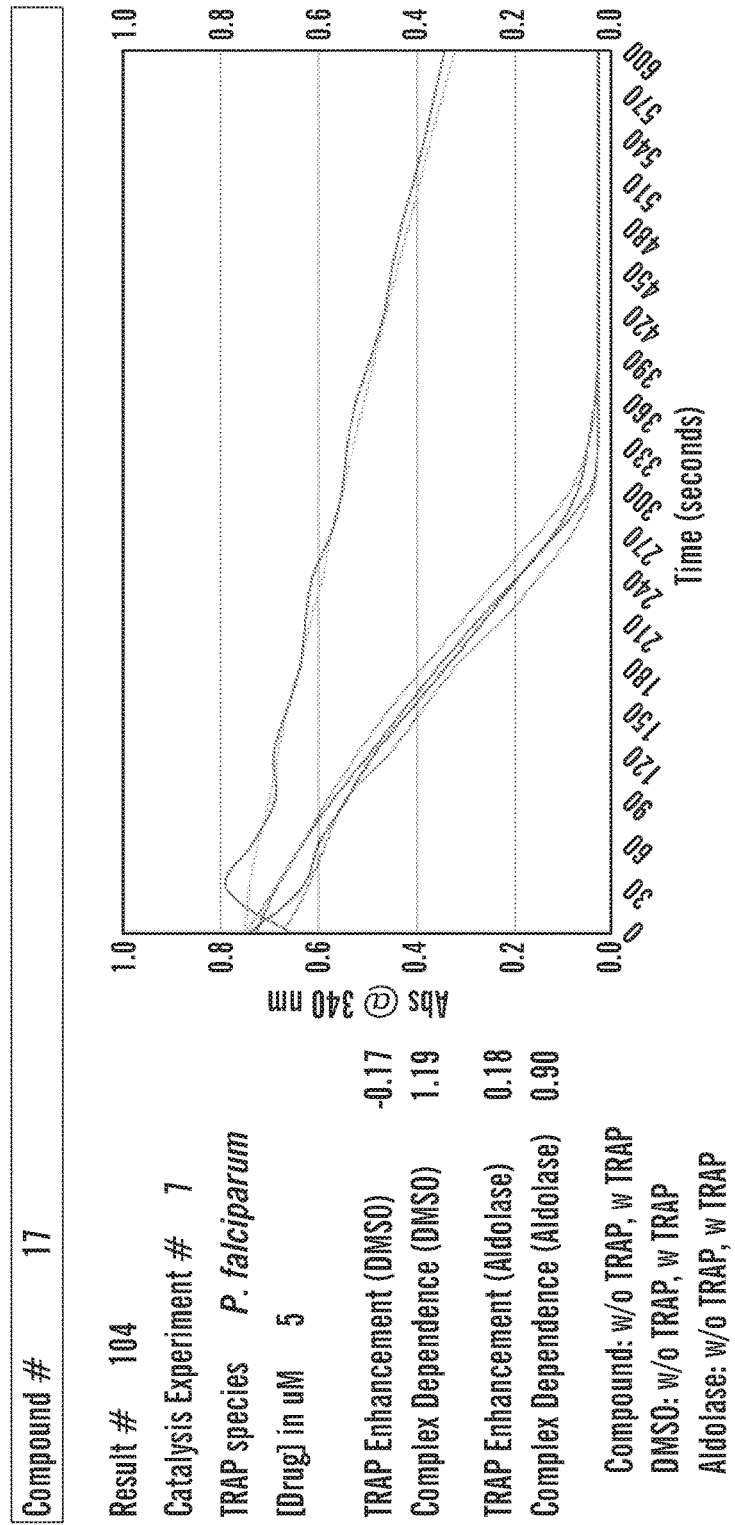
Figure 25B:
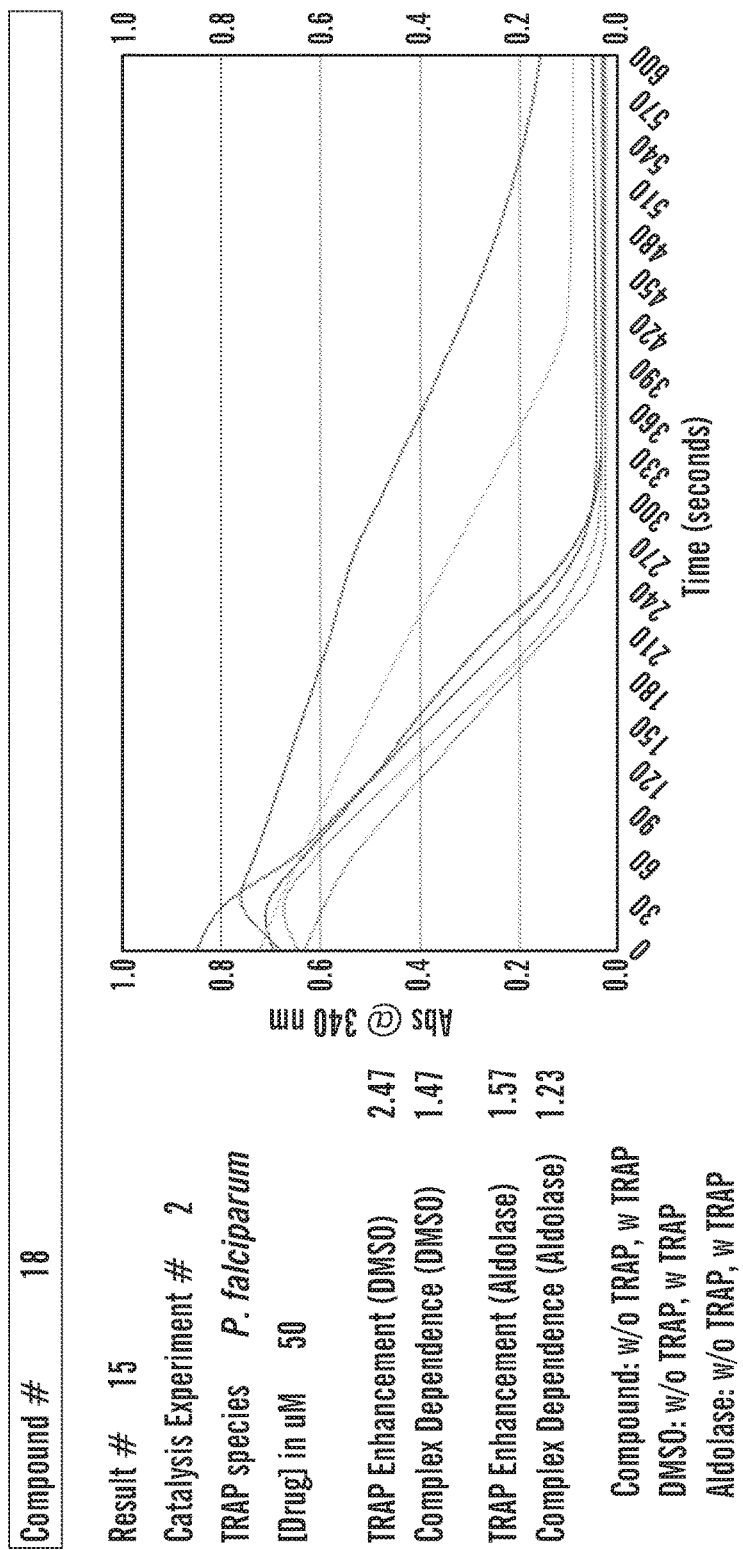
Figure 25C:
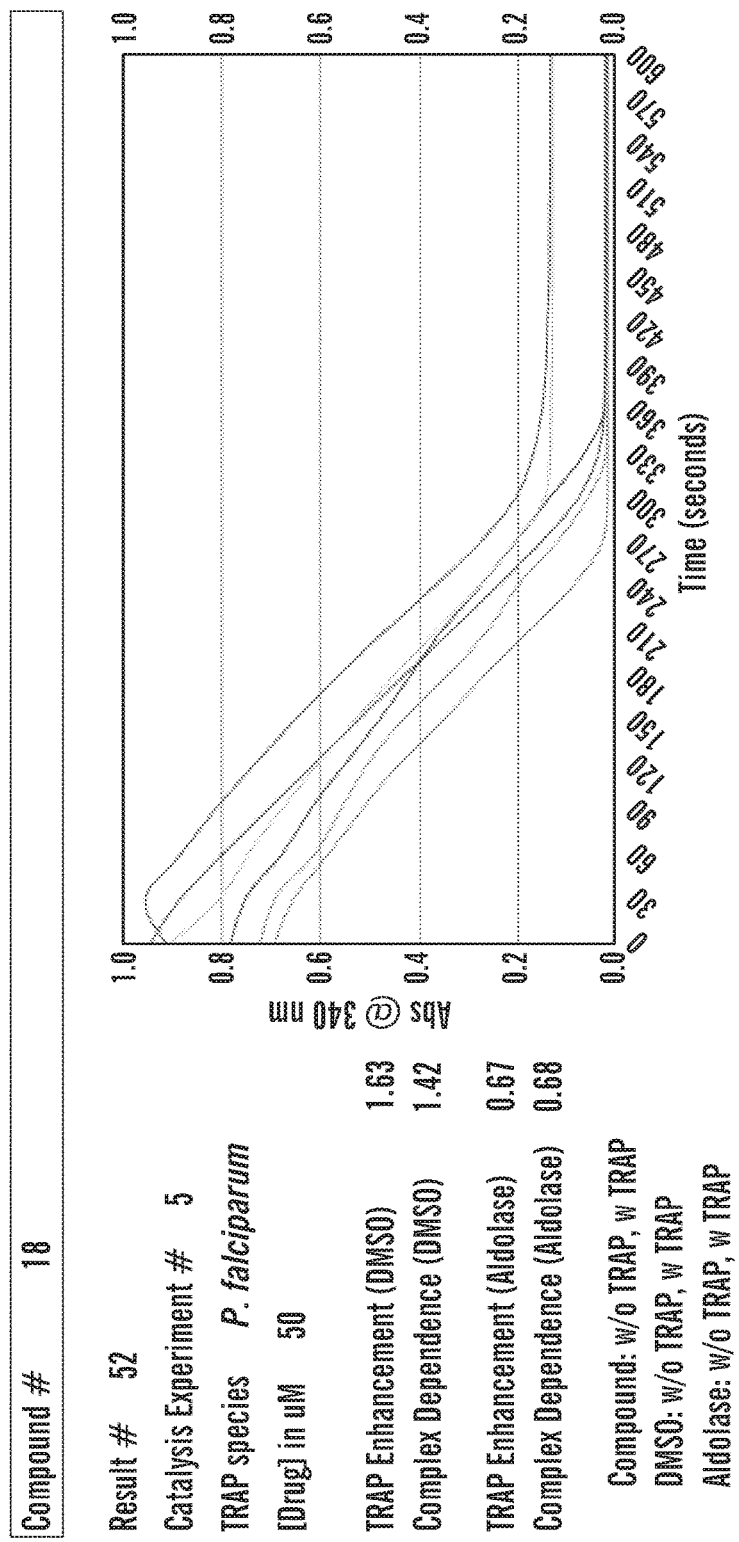
Figure 25D:
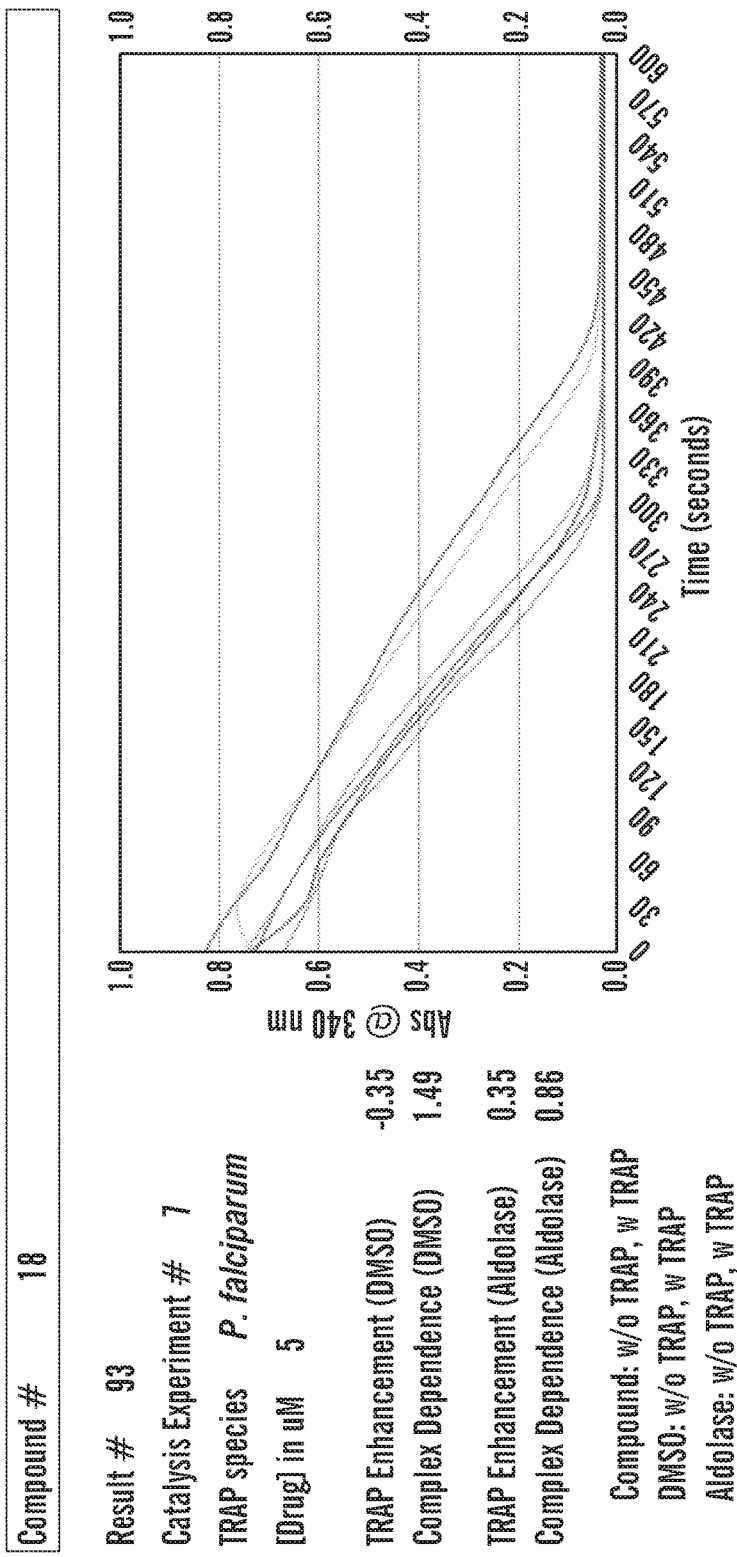
Figure 25E:
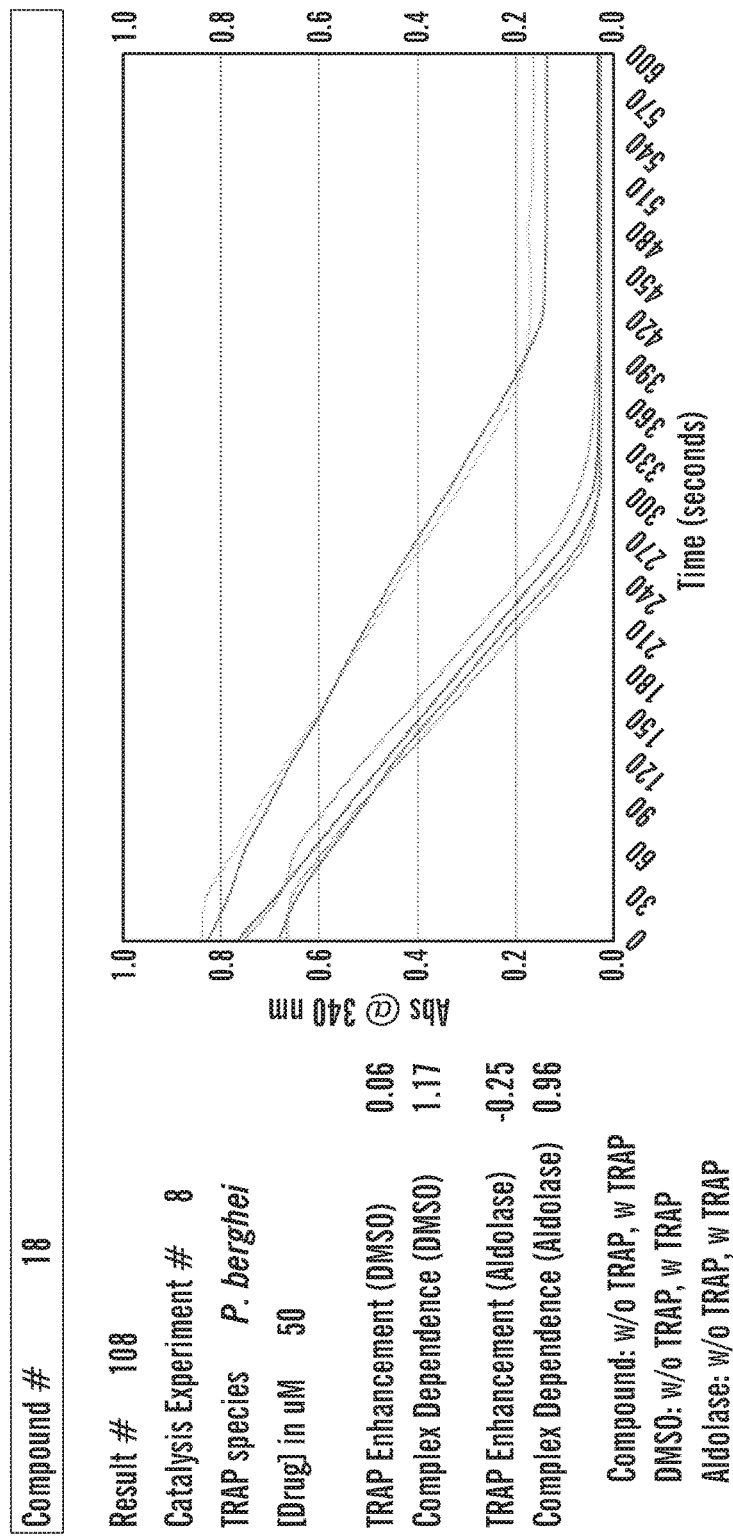
Figure 25F:
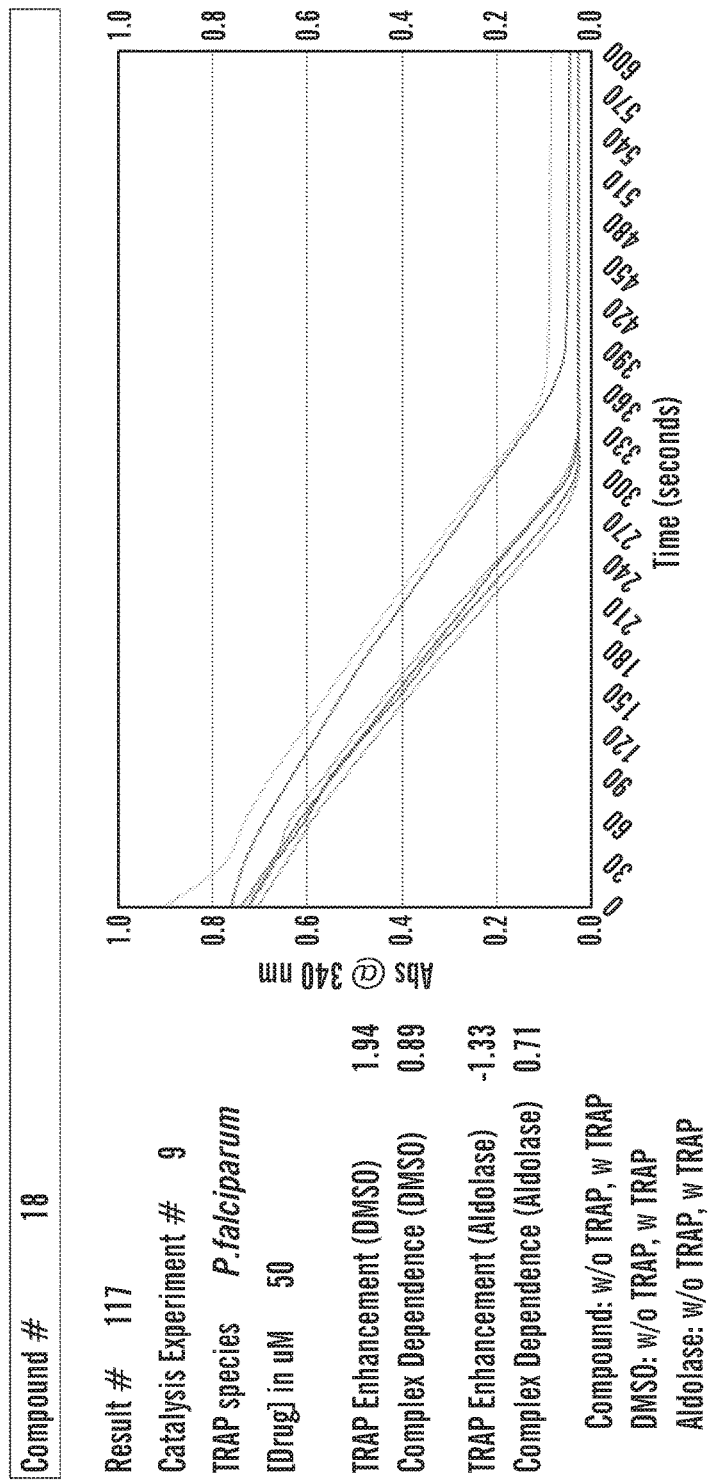
Figure 25G:
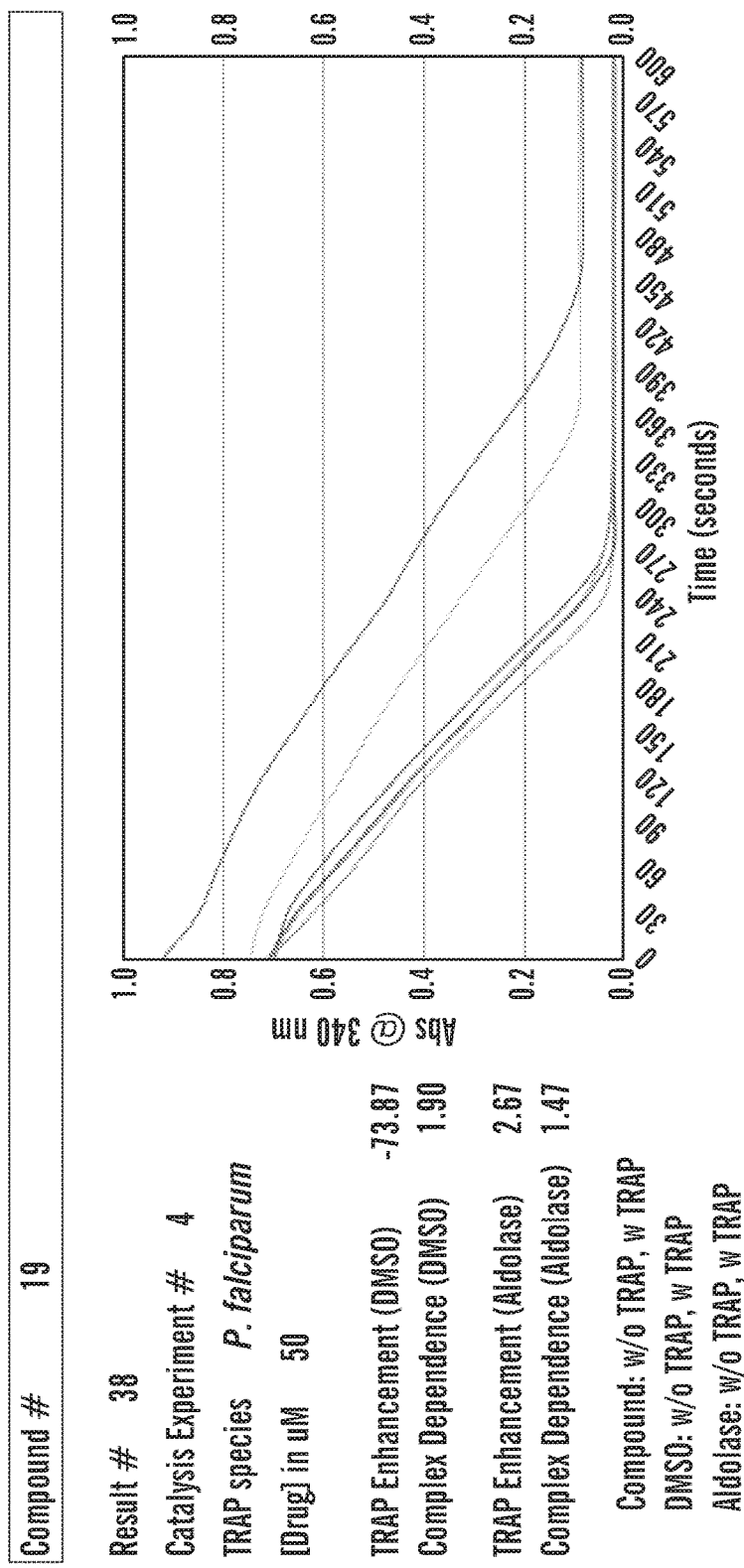
Figure 25H:
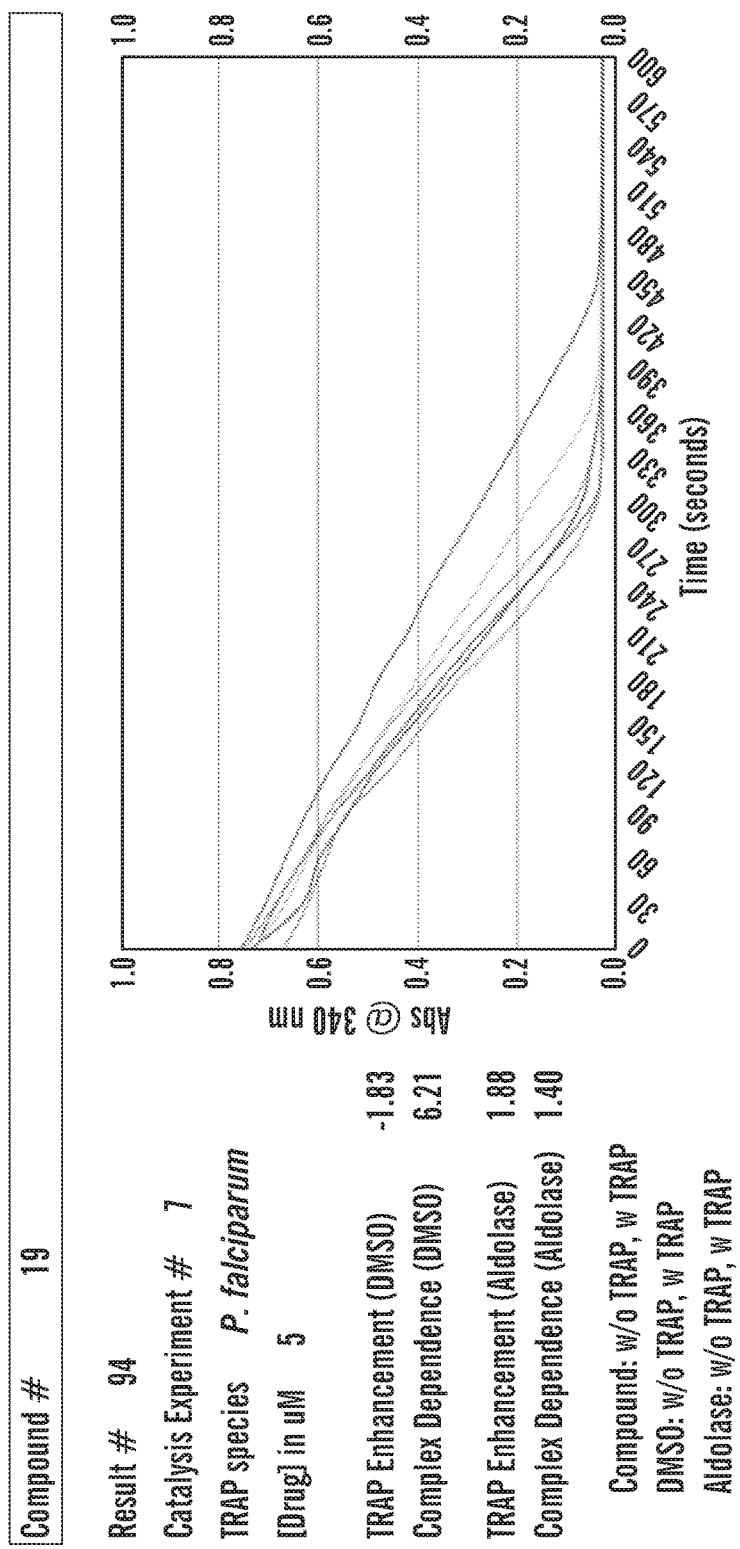
Figure 25I:
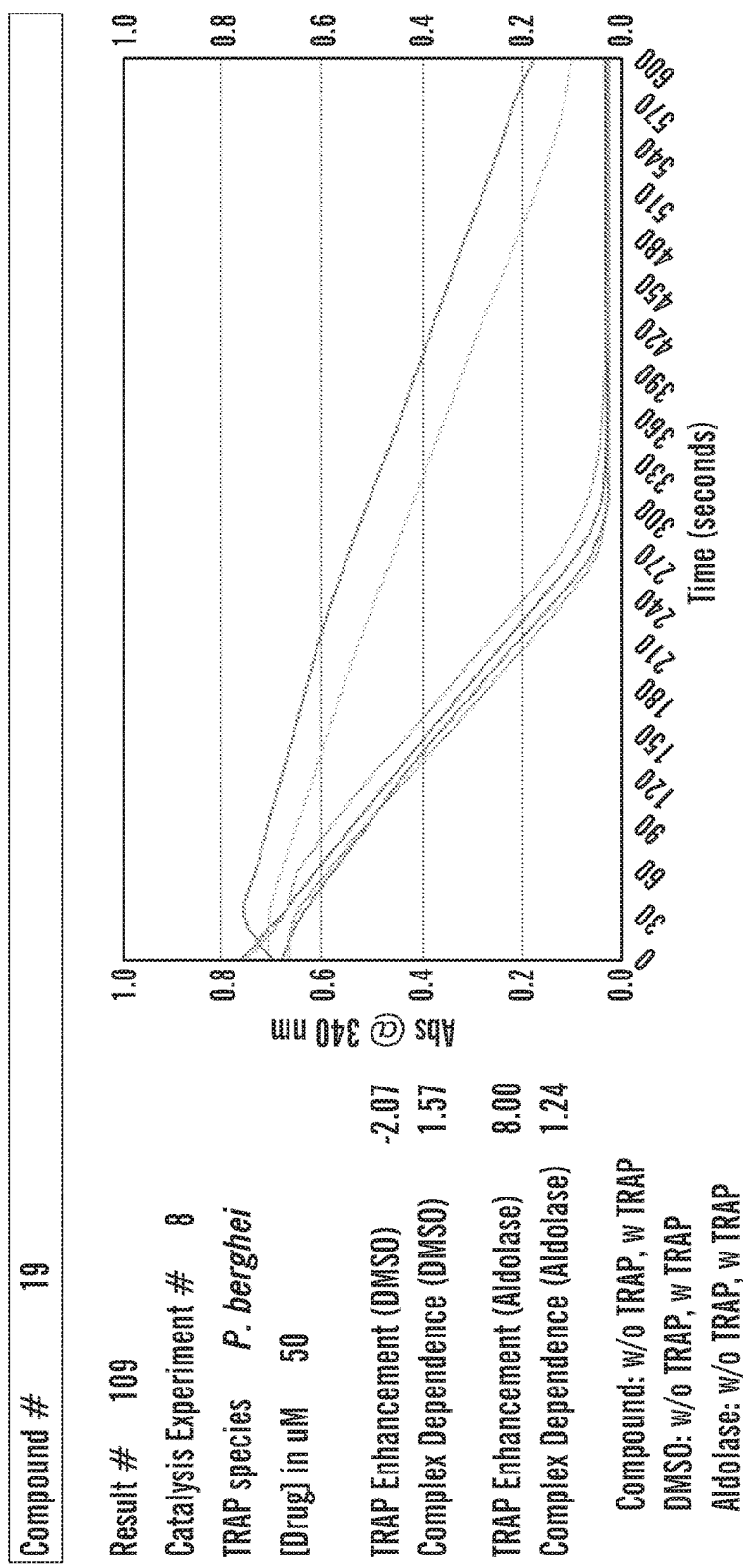
Figure 25J:
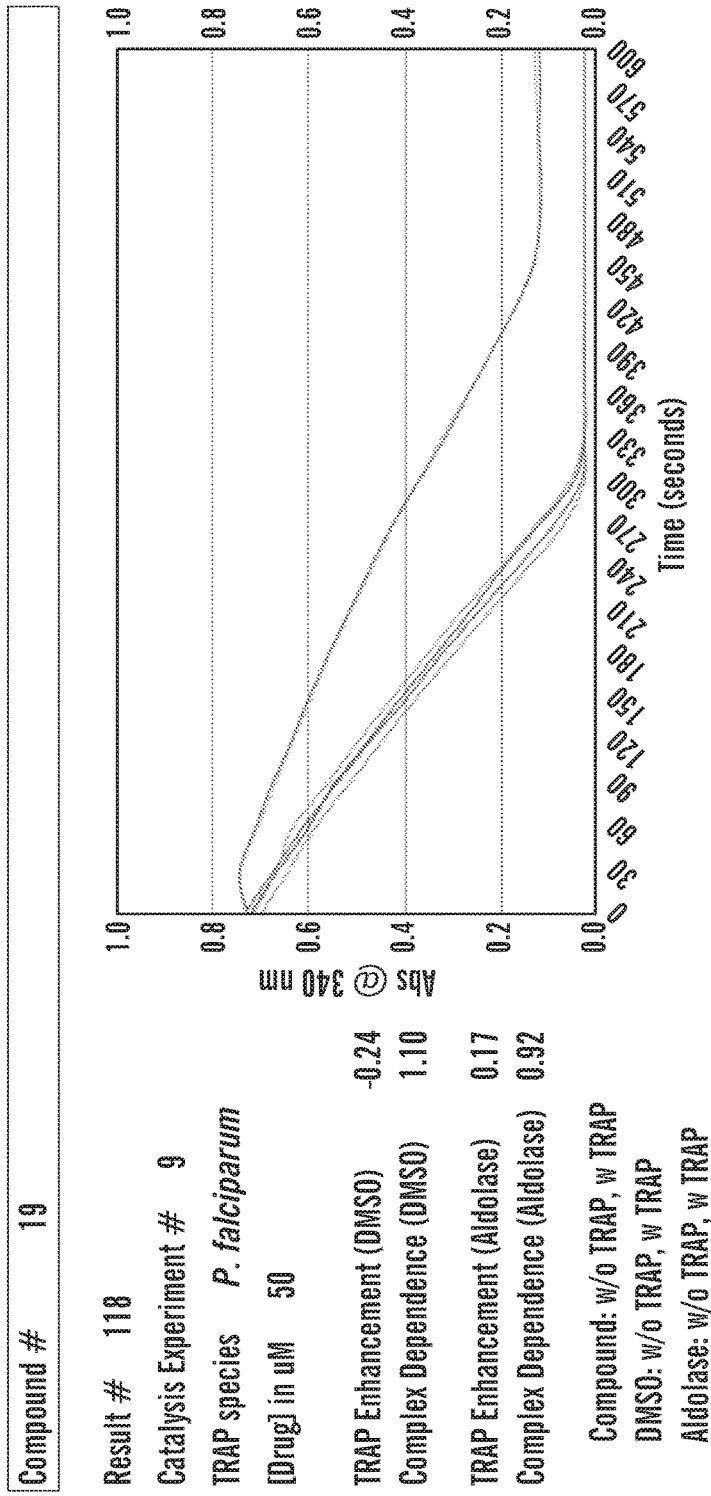
Figure 25K:
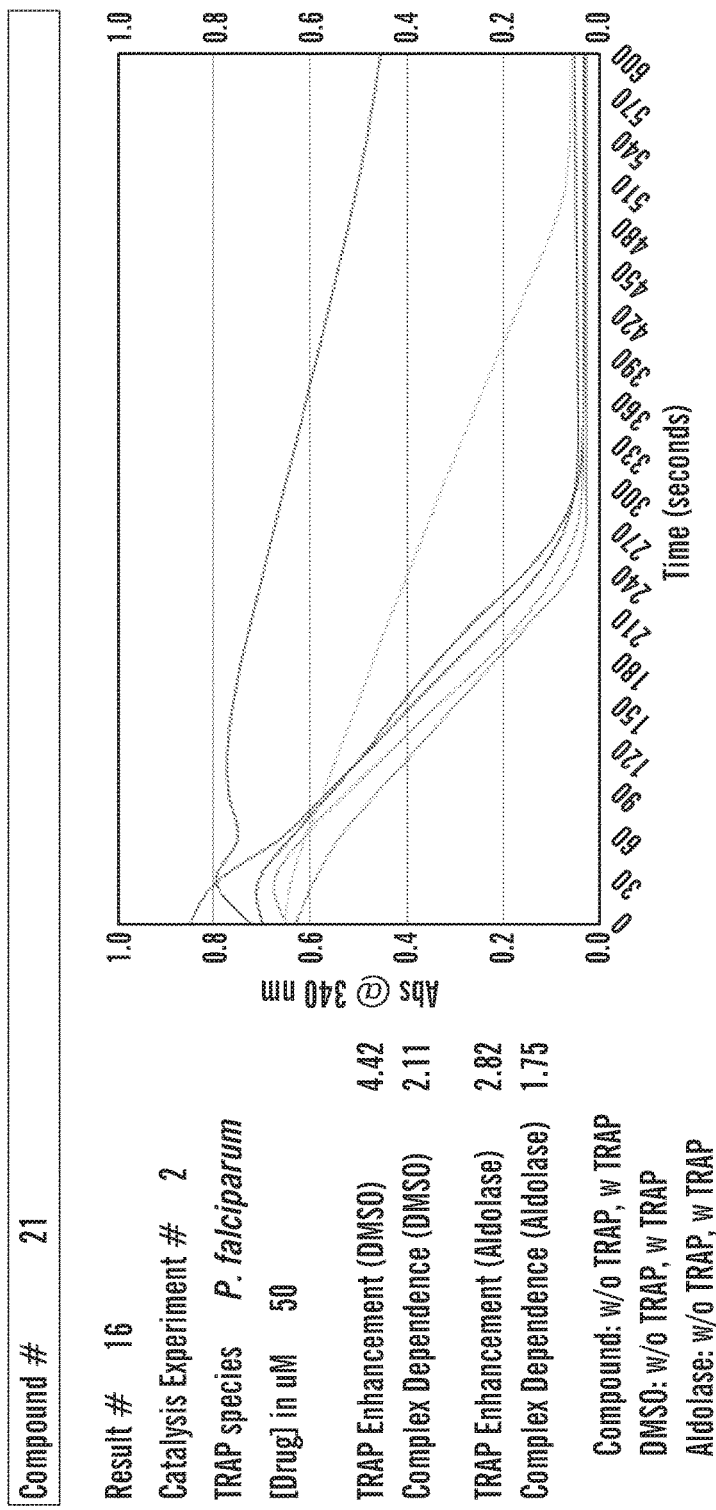
Figure 25L:
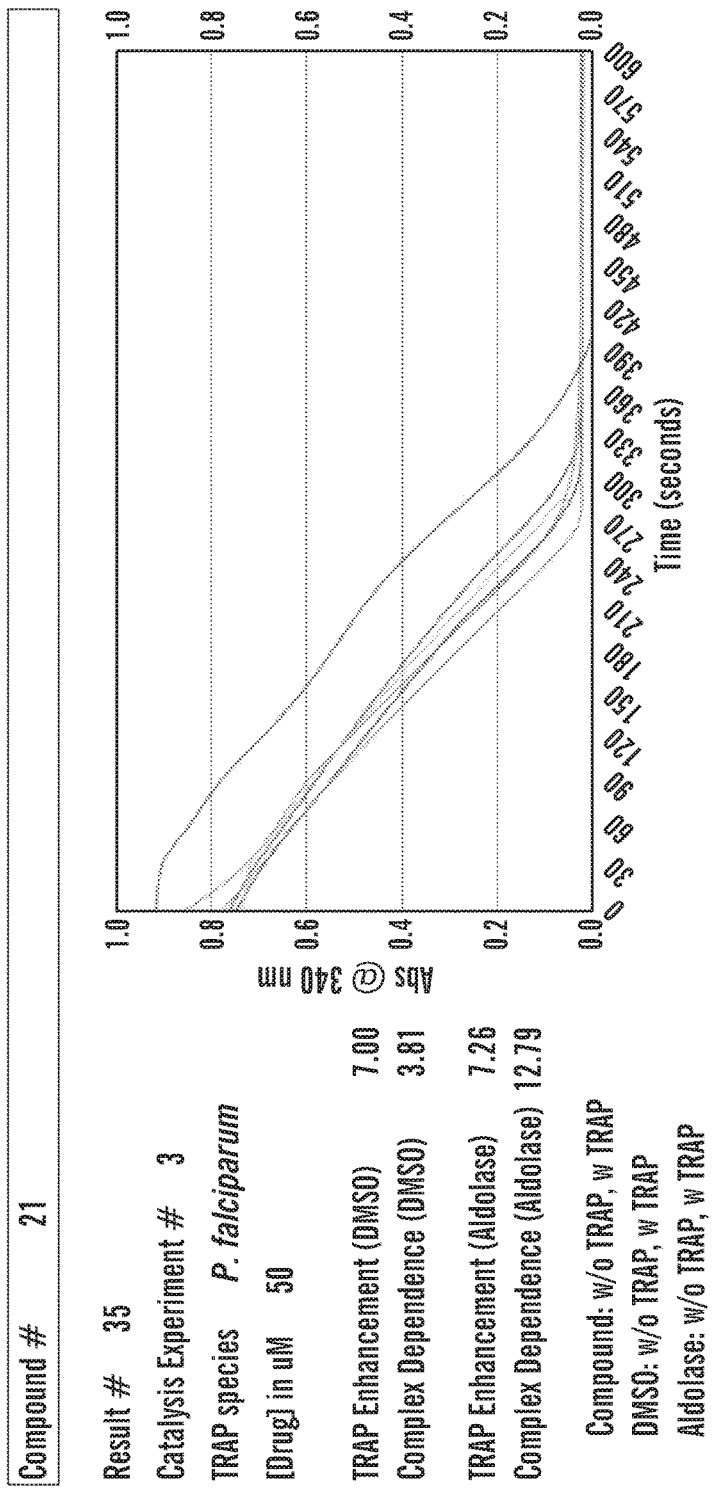
Figure 25M:
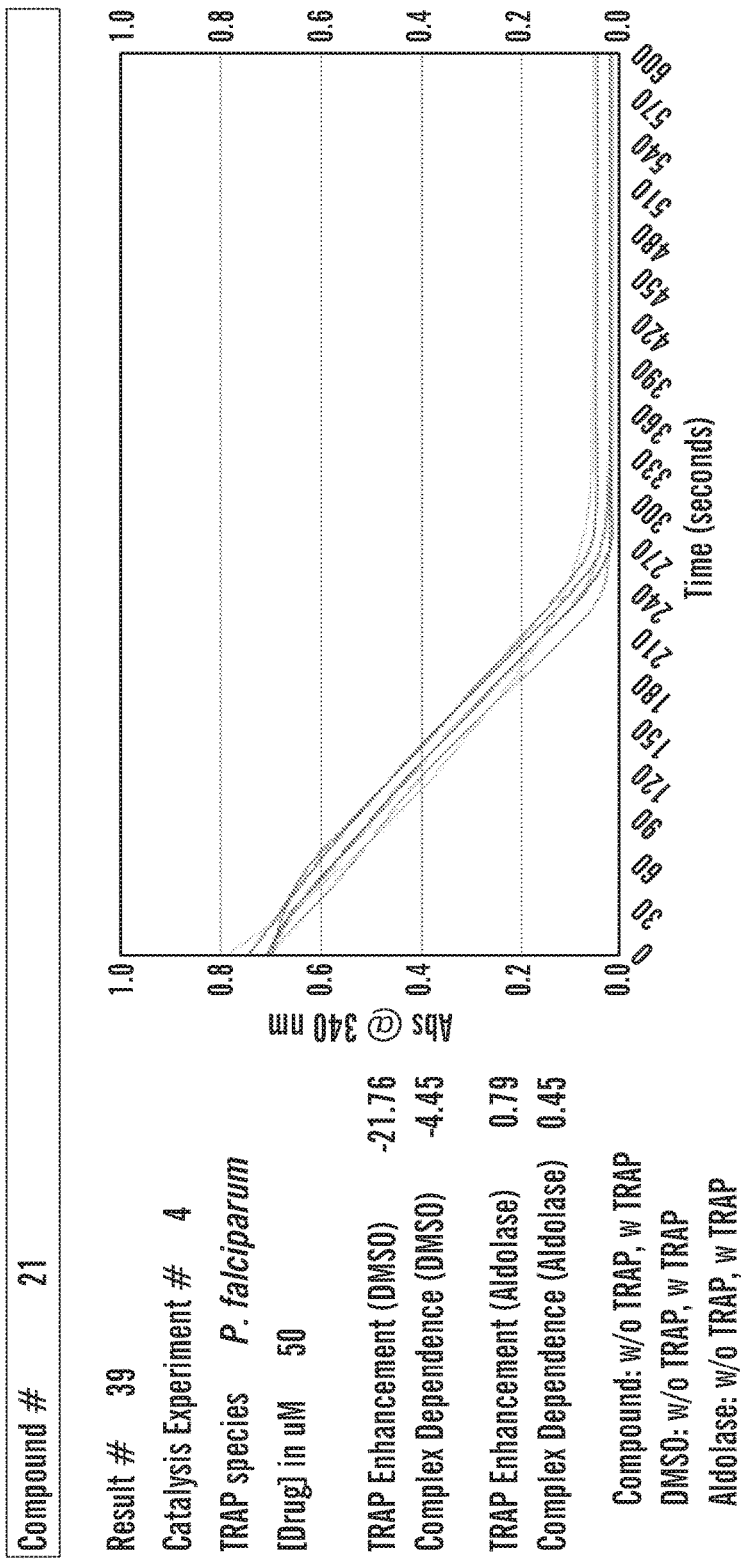
Figure 25N:
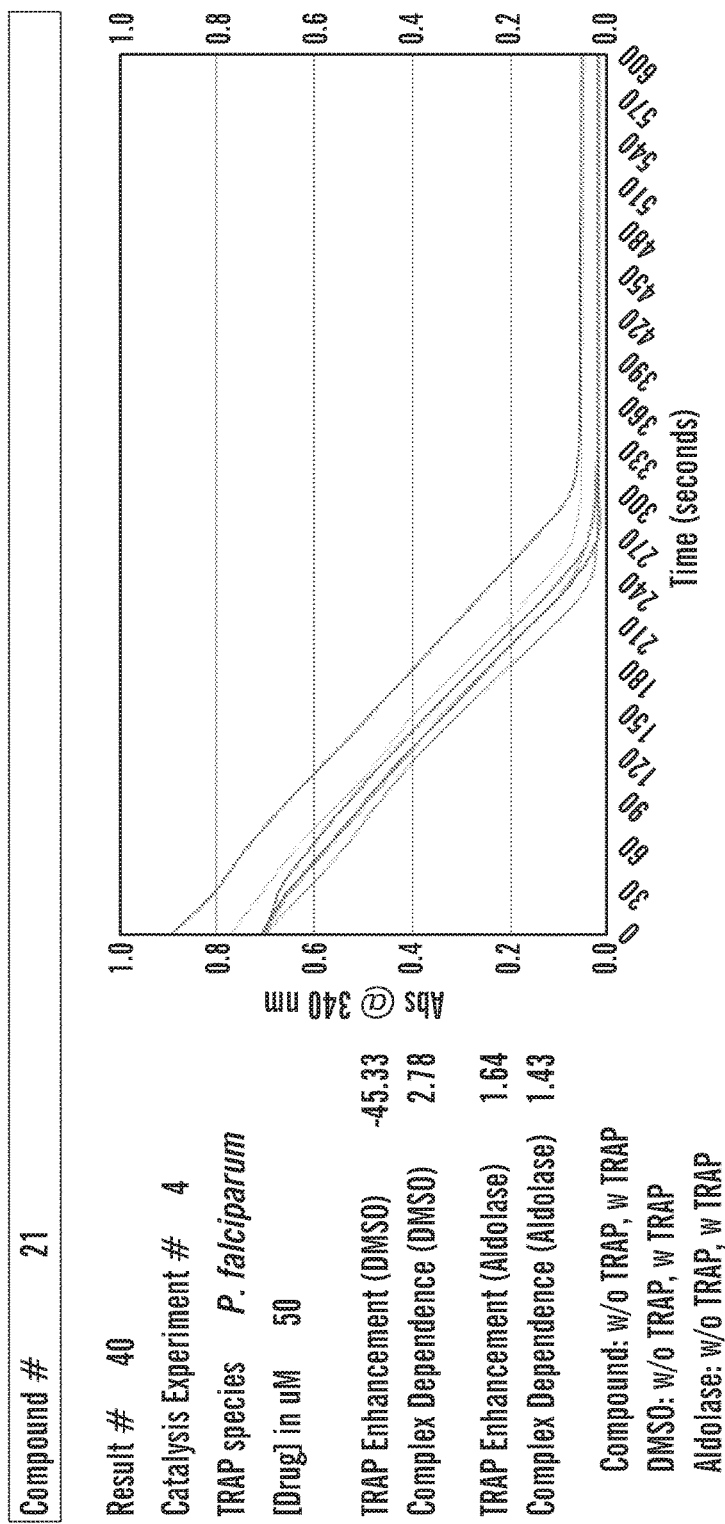
Figure 25P:
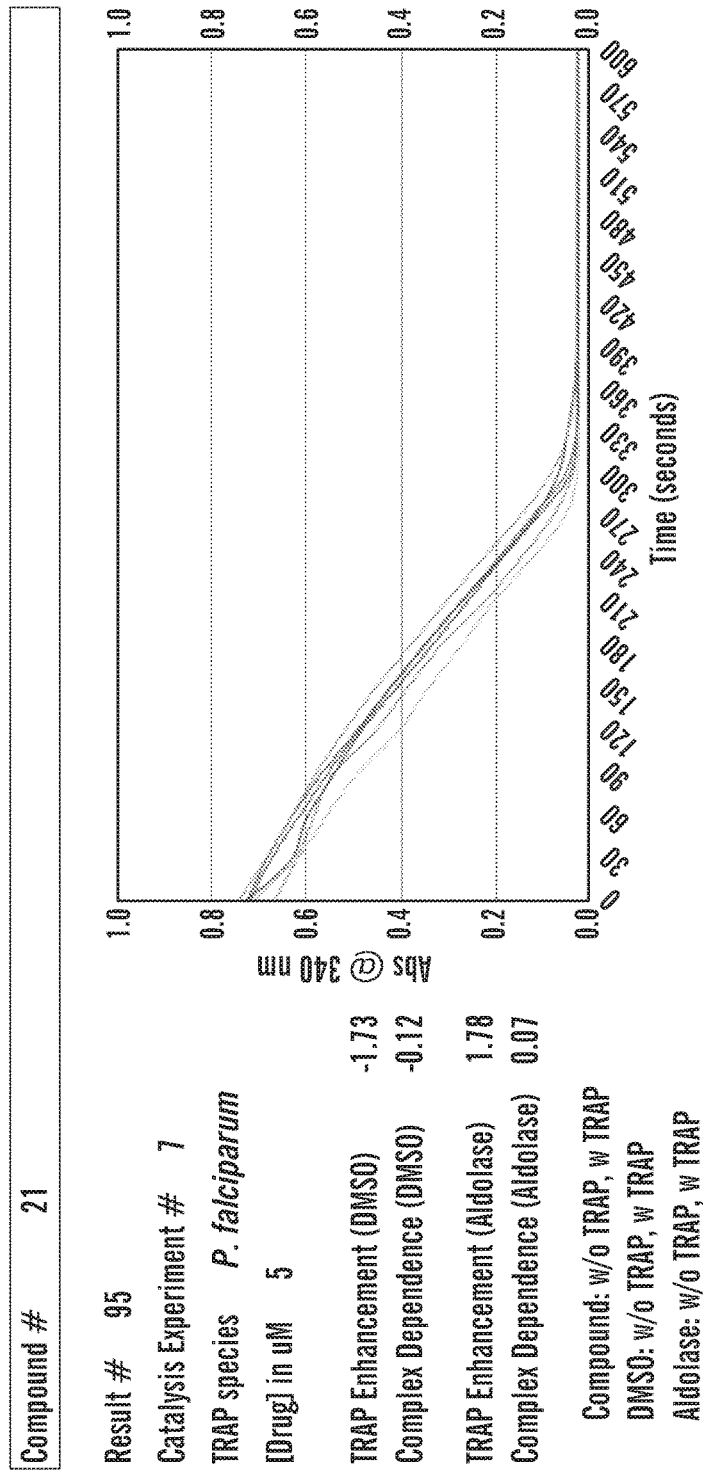
Figure 25Q:
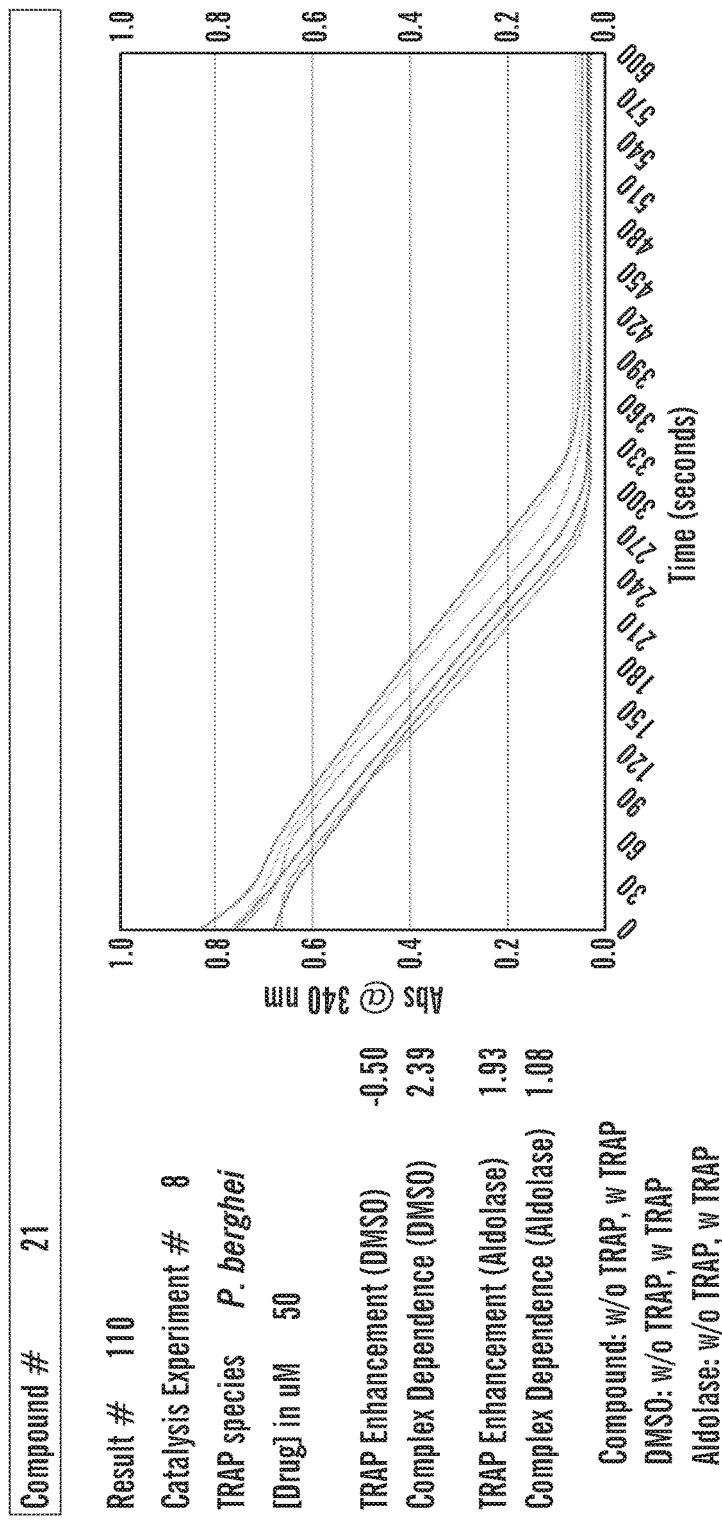
Figure 25R:
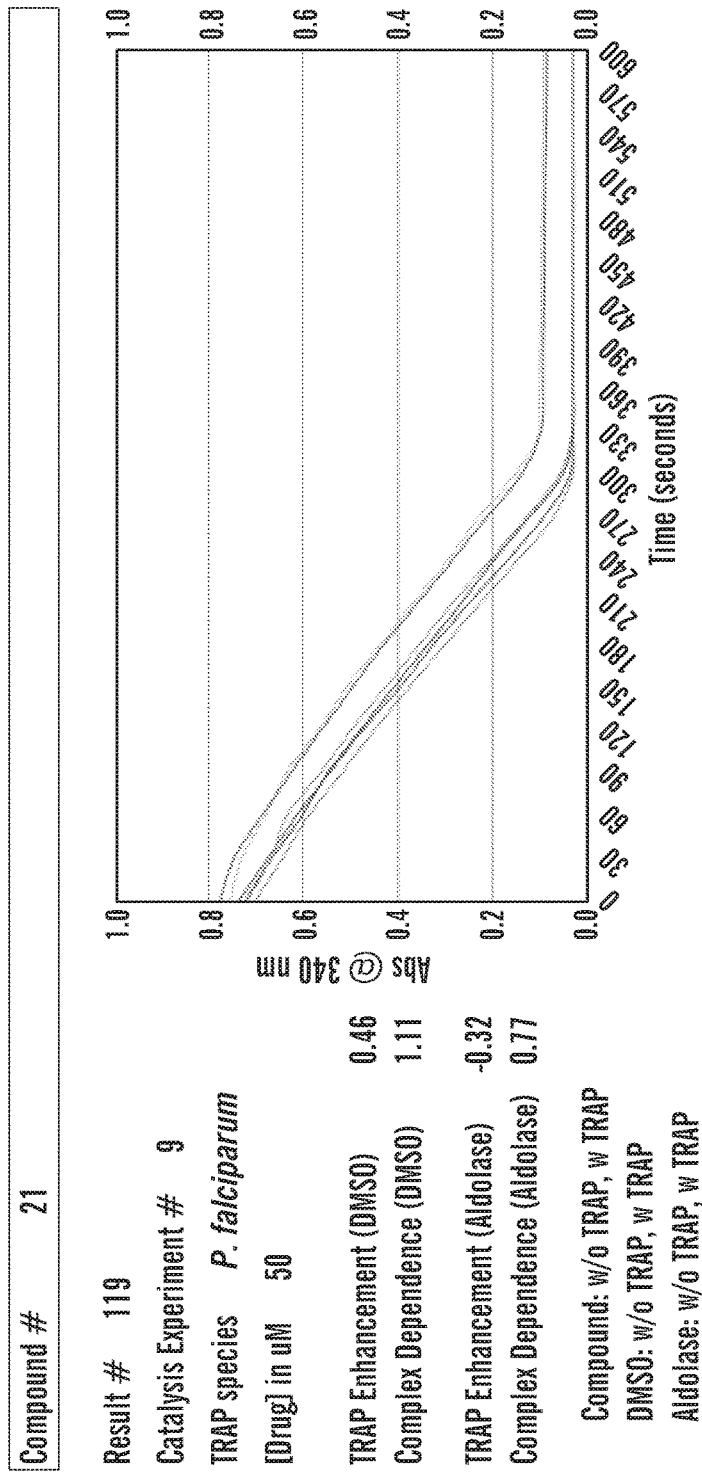
Figure 25S:
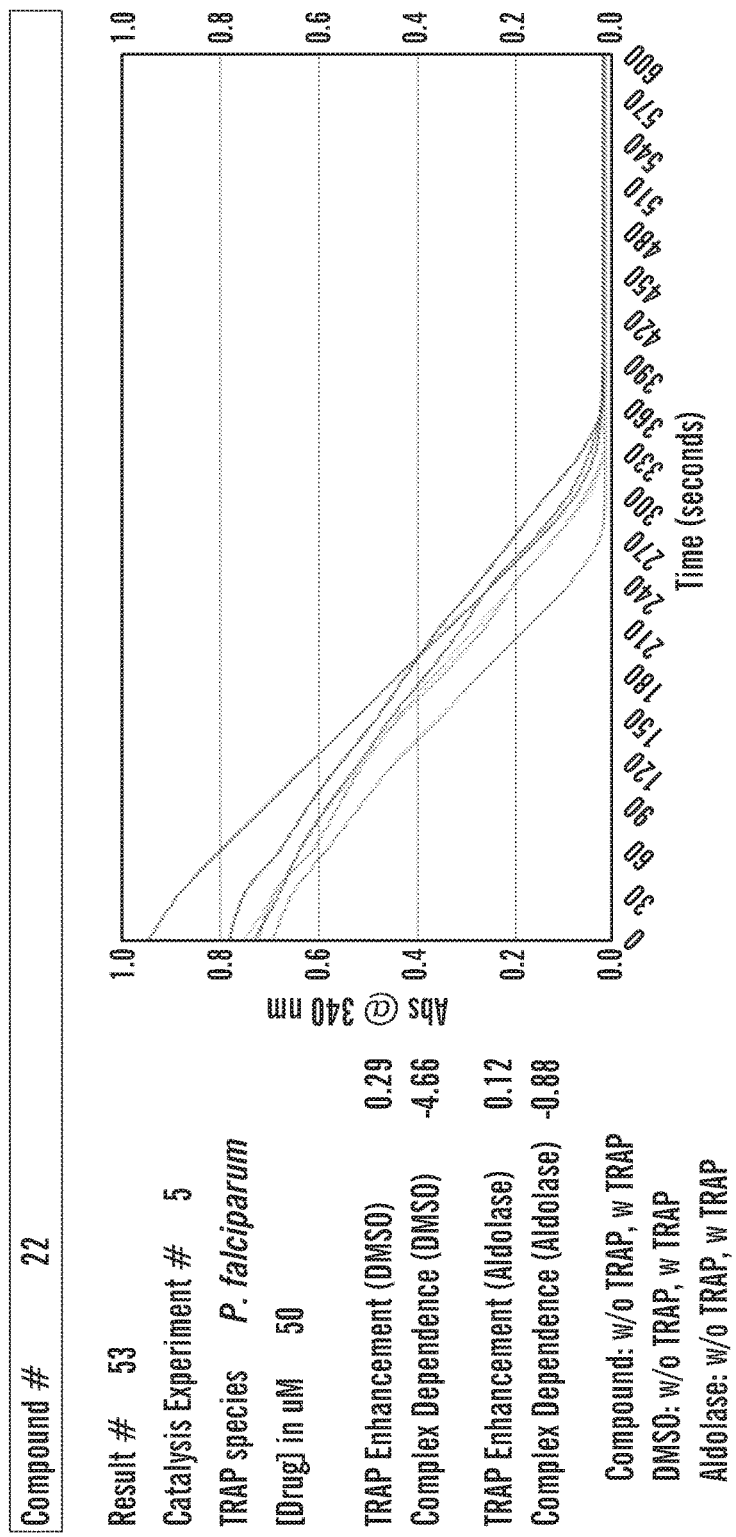
Figure 25T:
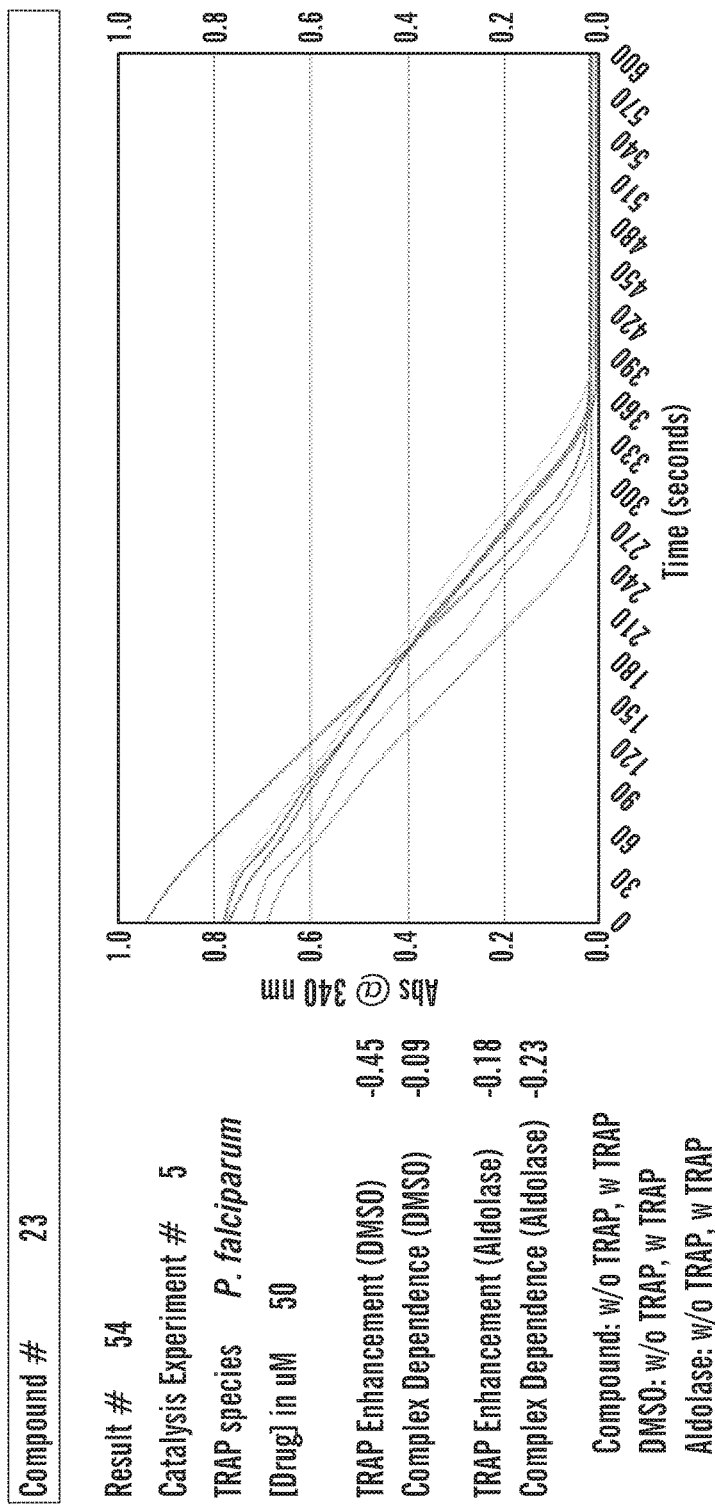
Figure 25U:
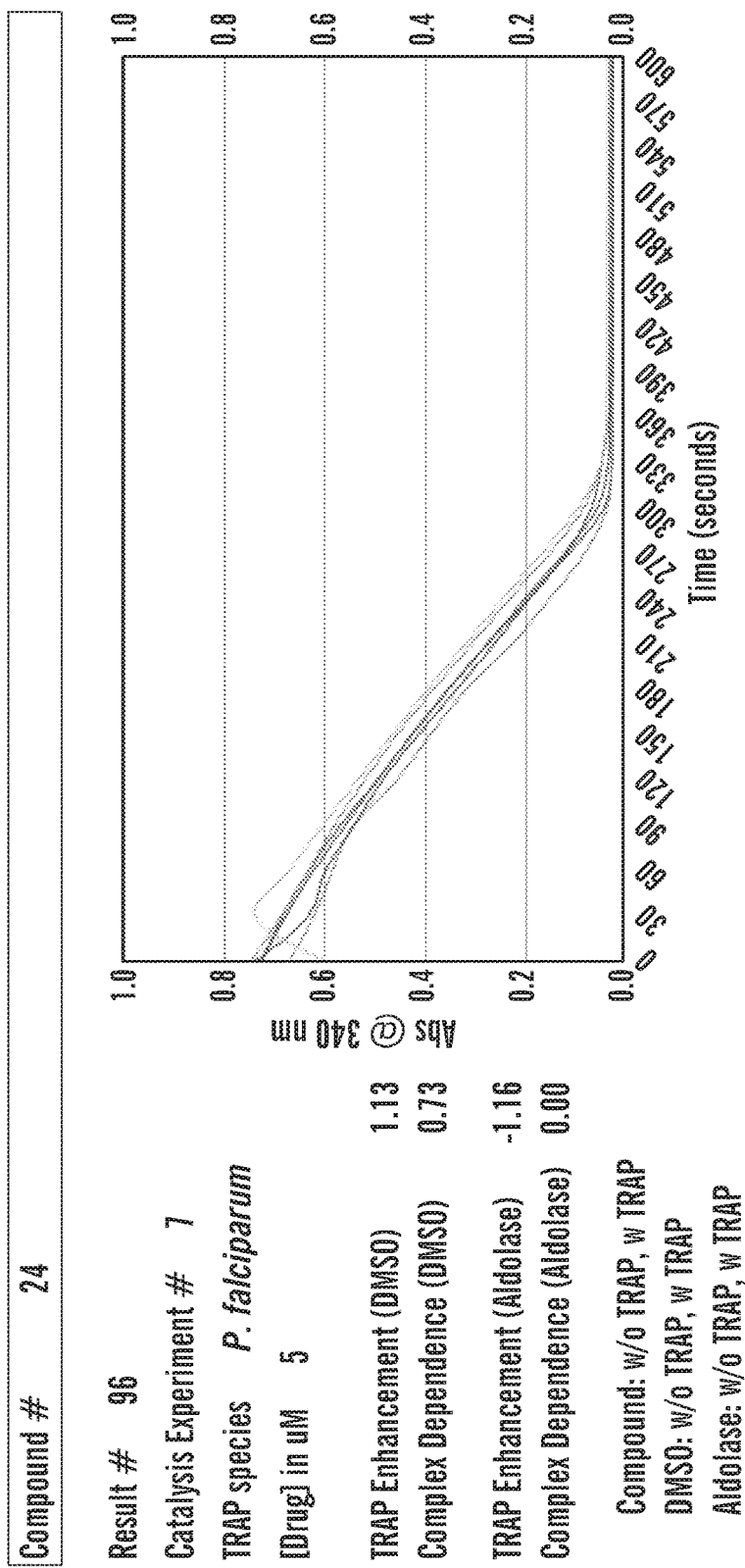
Figure 25V:
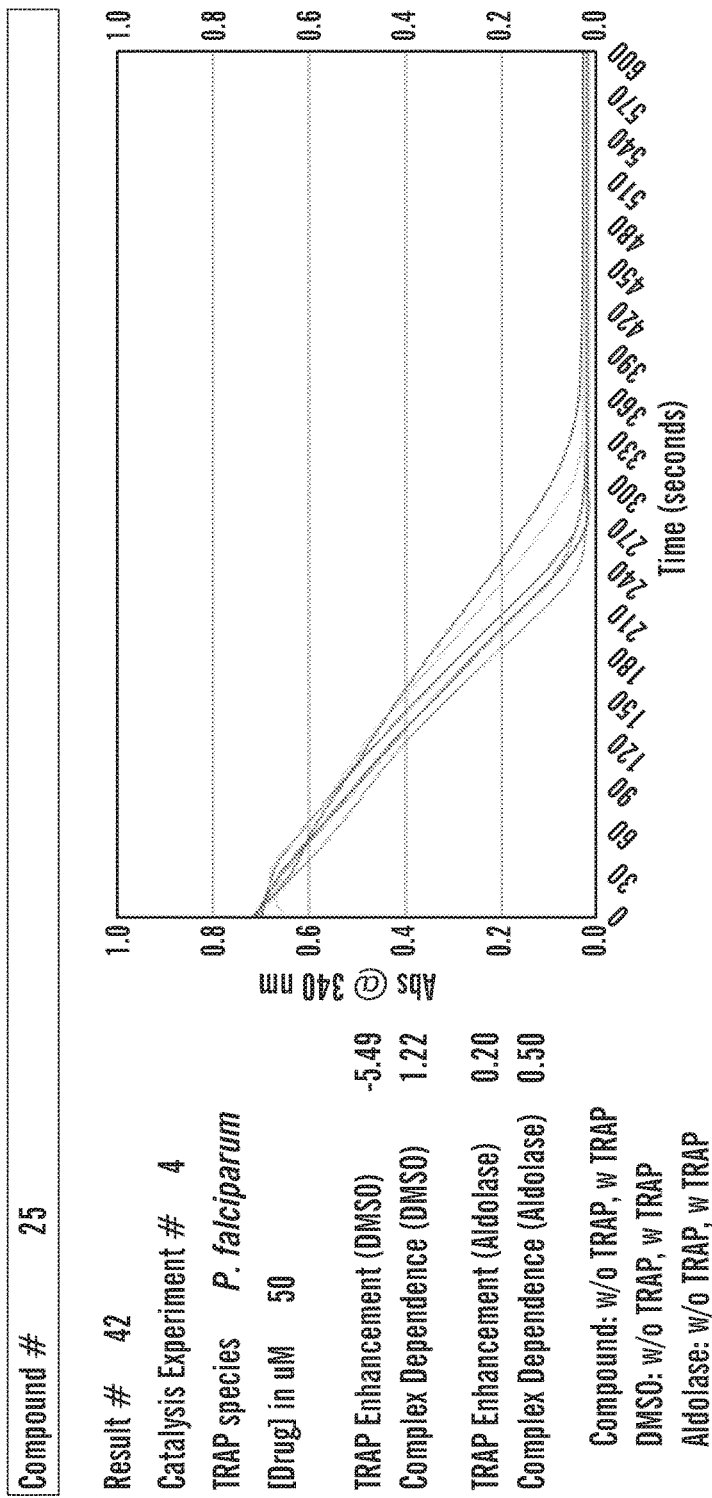
Figure 25W:
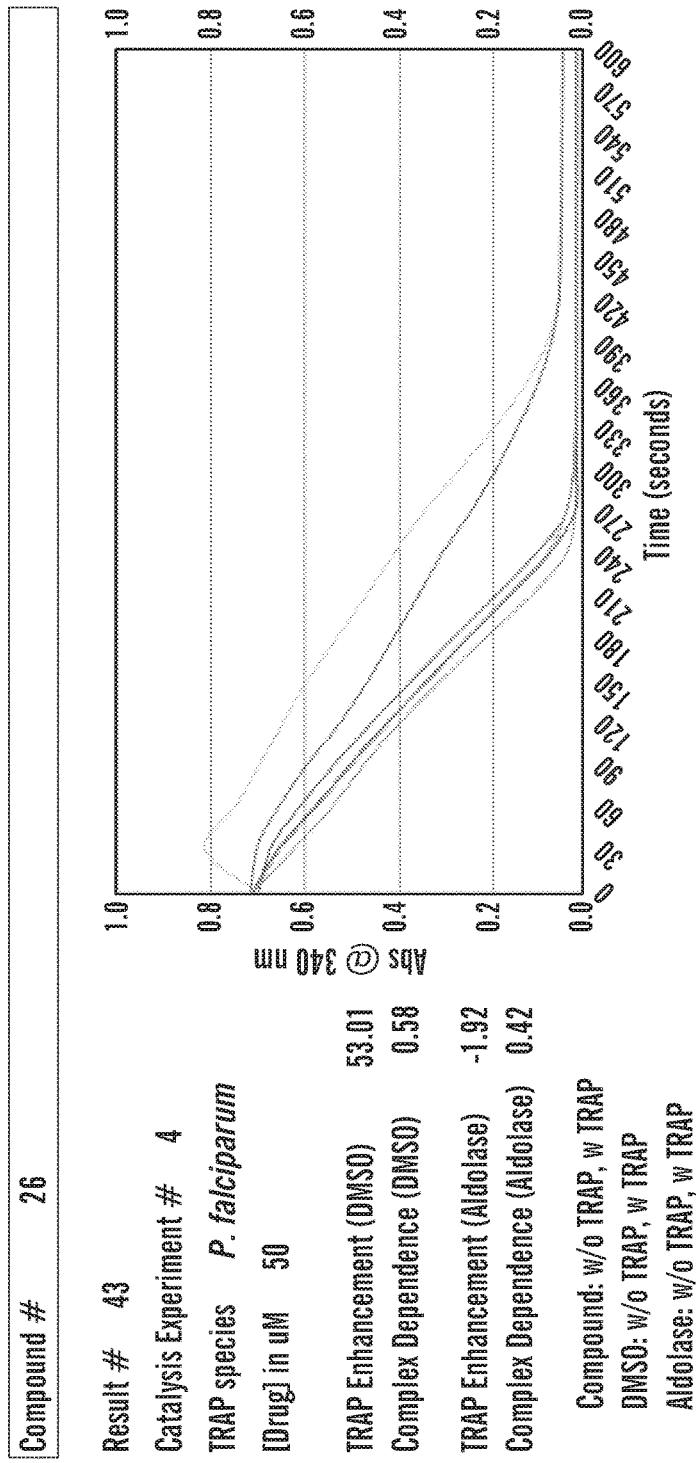
Figure 25X:
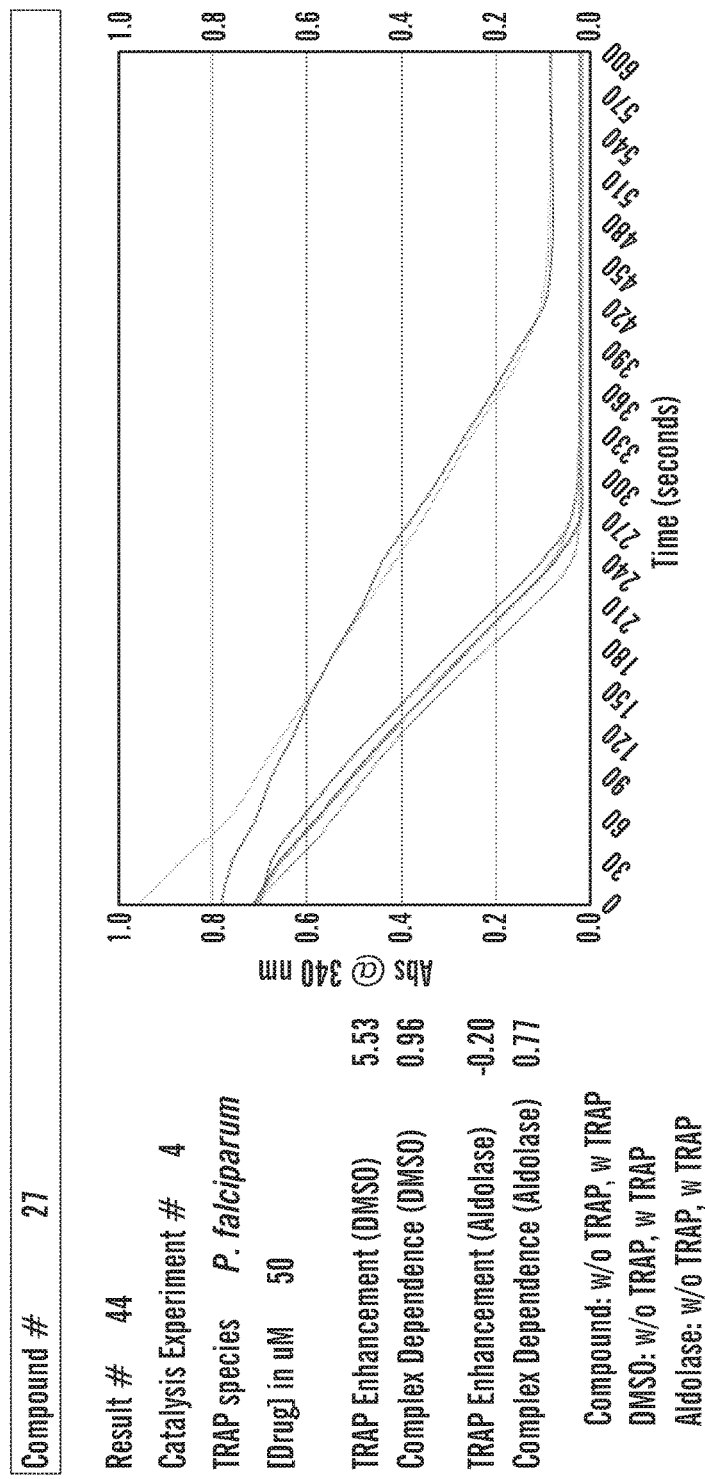
Figure 25Y:
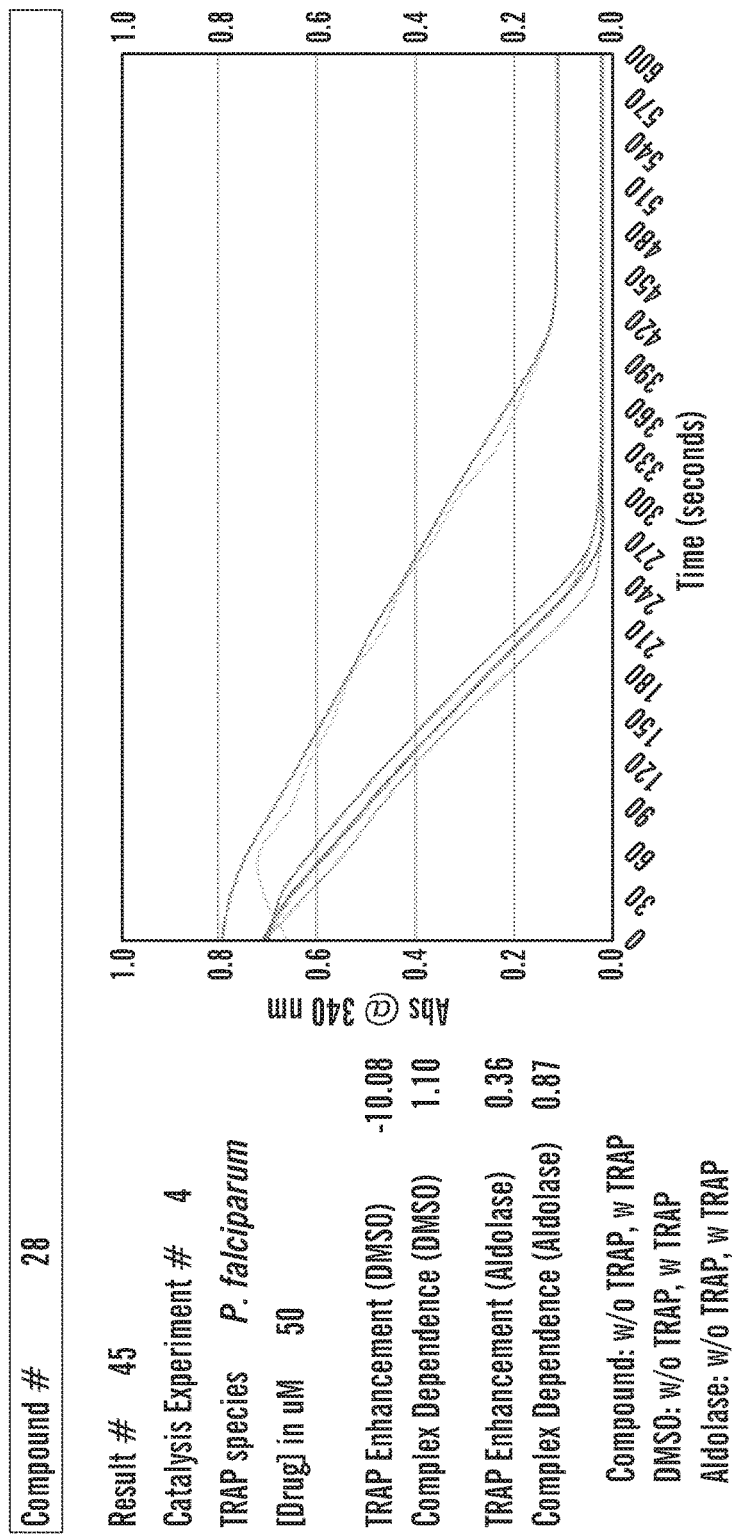
Figure 25Z:
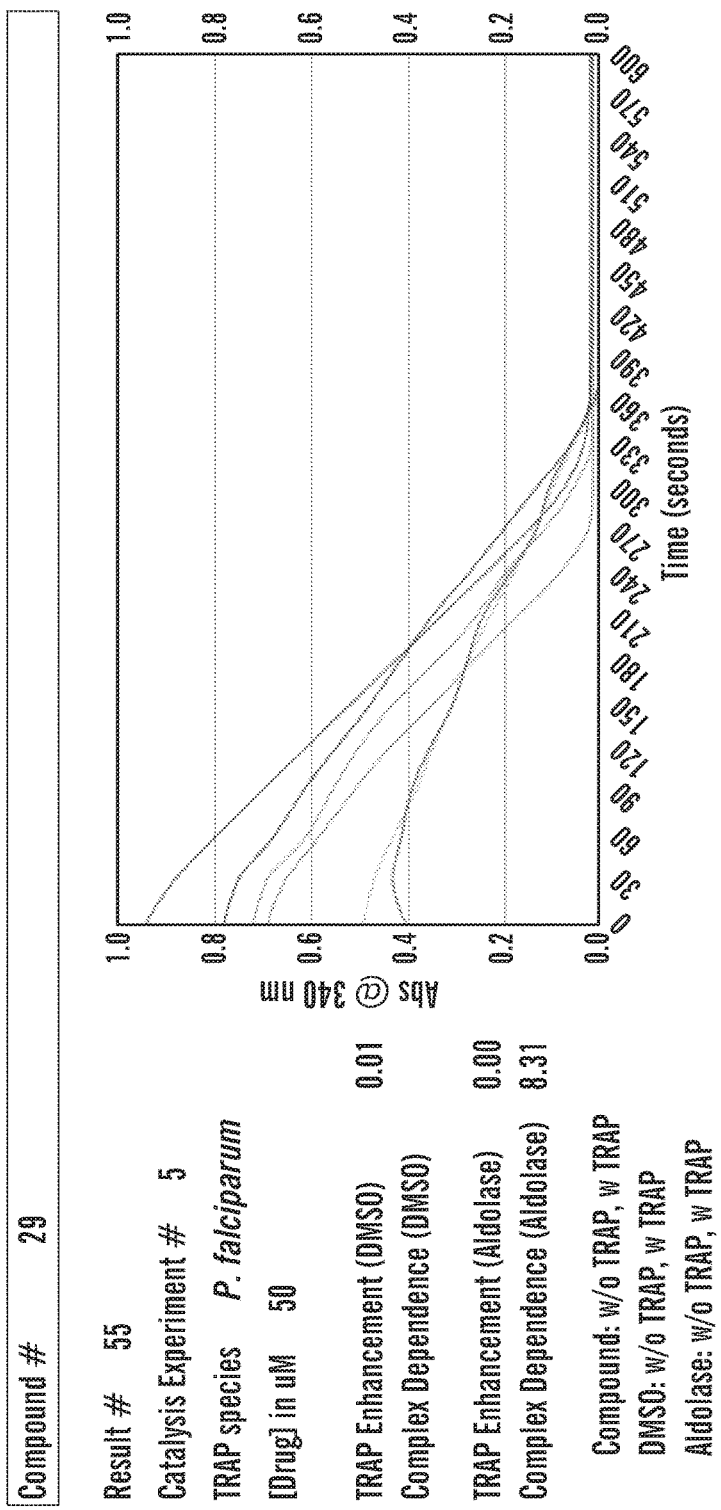

In an idealized workflow, a multitude of approaches would be used in concert (FIG. 23): bioinformatics and genomics approaches would identify a potential target; biochemical assays, mutagenesis studies, and animal models would validate it; high-throughput crystallography efforts would yield multiple high-resolution structures with druggable pockets; computational modeling, docking, and VLS would rapidly pull a subset of likely binders from large electronic chemical databases; VLS hits validated in vitro and in vivo would be used as starting points for SAR and cheminformatics analyses that could generate a much larger set of chemicals enriched for the desired pharmacophore and physico-chemical properties; this library could then be rapidly screened in high-throughput whole-cell assays to identify the most promising leads to carry forth into animal and clinical studies.

This cross-platform interdisciplinary approach would allow different methodologies to be employed in parallel, with the results of each informing the others in an iterative process aimed at bringing a large and diverse portfolio of drug leads to pre-clinical and clinical testing as quickly as possible.

Example 40—Enhancing a Protein-Protein Interaction

While stabilizing the TRAP-Aldolase interaction may seem like an unusual approach for rational drug design, the scientific literature contains several examples of biologically active small molecules that function by stabilizing protein-protein interactions in a bipartite manner. The fungal phytotoxin, fusioccin, induces plant wilting by stabilizing an otherwise transient interaction between the plant plasma membrane $H^+$-ATPase (PMA) and it's activating protein, 14-3-3. Crystallographic studies and isothermal titration calorimetry indicated that fusioccin increases the binding affinity between PMA and 14-3-3 approximately 90-fold, by burying an additional ~50 $Å^2$ of solvent exposed surface area on 14-3-3. Especially important for the purposes of this study, this compound demonstrated very low affinity towards 14-3-3 alone, which increased significantly in the presence of PMA (Wurtele et al., "Structural View of a Fungal Toxin Acting on a 14-3-3 Regulatory Complex," Embo J. 22:987-994 (2003), which is hereby incorporated by reference in its entirety). Another fungal product, Brefeldin A, exerts its toxic effects on ER-golgi transport by stabilizing the interaction between an ARF-GDP protein and its guanine nucleotide exchange factor (GEF). The GEF is thereby rendered unavailable for the activation of any other ARF proteins (Peyroche et al., "Brefeldin A Acts to Stabilize an Abortive ARF-GDP-Sec7 Domain Protein Complex: Involvement of Specific Residues of the Sec7 Domain," Mol. Cell. 3:275-285 (1999); Chardin and McCormick, "Brefeldin A: The Advantage of Being Uncompetitive," Cell 97:153-155 (1999), which are hereby incorporated by reference in their entirety).

In addition to these fungal toxins, several drugs in clinical or laboratory use were unexpectedly found to act by stabilizing protein complexes. The chemotherapeutic agents, taxol and epothilone, prevent tumor growth by stabilizing microtubules (Manfredi et al., "Taxol Binds to Cellular Microtubules," J. Cell. Biol. 94:688-696 (1982); Schiff et al., "Promotion of Microtubule Assembly in Vitro by Taxol," Nature 277:665-667 (1979); Schiff and Horwitz, "Taxol Assembles Tubulin in the Absence of Exogenous Guanosine 5'-Triphosphate or Microtubule-Associated Proteins," Biochemistry 20: 3247-3252 (1981); Jennewein and Croteau, "Taxol: Biosynthesis, Molecular Genetics, and Biotechnological Applications," Appl. Microbiol. Biotechnol. 57:13-19 (2001); Bollag et al., "Epothilones, a New Class of Microtubule-Stabilizing Agents with a Taxol-Like Mechanism of Action," Cancer Res. 55:2325-2333 (1995), which are hereby incorporated by reference in their entirety). Kirromycin and fusidic acid, two bacteriostatic antibiotics, prevent bacterial protein synthesis by locking the exchange factor-aminoacyl tRNA-GTP ternary complex into the prokaryotic ribosome's A-site, thereby blocking further peptide elongation (Agrawal et al., "Visualization of Elongation Factor G on the Escherichia coli 70S Ribosome: The Mechanism of Translocation," Proc. Nat'l. Acad. Sci. U.S.A. 95:6134-6138 (1998); Stark et al., "Visualization of Elongation Factor Tu on the Escherichia coli Ribosome," Nature 389:403-406 (1997), which are hereby incorporated by reference in their entirety). Finally, Cyclosporin A (CsA), FK506 (Prograf®), and rapamycin all produce their immunosuppressive effects by inducing otherwise nonexistent interactions between an immunophilin and other proteins important for cell signaling. In the case of CsA, the complex consists of the drug, cyclophilin A (CyPA), and calcineurin. FK506 bridges FK506-binding protein (FKBP12) and calcineurin, while rapamycin mediates the interaction between FKBP12 and FKBP-rapamycin-associated protein/rapamycin and FKBP12 target 1 (FRAP/RAFT1) (Ivery, "Immunophilins: Switched on Protein Binding Domains?" Med. Res. Rev. 20:452-484 (2000), which is hereby incorporated by reference in its entirety). These examples indicated—and the results of the present invention ultimately taught—that it could be possible to develop a clinically useful small molecule anti-malarial agent that enhances a protein-protein interface.

The present invention suggests that the development of protein-protein enhancers may prove to be a generally applicable method of targeted drug design that is especially suited to structure-based approaches. In fact, it may be easier to develop stabilizers of protein-protein interactions than inhibitors. For a small molecule to inhibit a protein-protein interaction, it must bind to its receptor with a higher affinity than—and at least similar specificity as—the protein's native ligand. A vast collection of failed drug candidates demonstrate how difficult it is to compete with eons of evolutionary pressure that produced the biomolecular interaction in the first place (Cochran, "Antagonists of Protein-Protein Interactions," Chem. Biol. 7:R85-94 (2000), which is hereby incorporated by reference in its entirety). Stabilizing that interaction, however, does not require competing with nature. Rather, this approach tries to nudge the interaction's equilibrium in the direction that is thermodynamically favored to begin with. Thus a candidate enhancer does not need to bind either member of a protein complex with particularly high affinity—it is the aggregate of affinities of the proteins for each other and for the drug that matter (Wurtele et al., "Structural View of a Fungal Toxin Acting on a 14-3-3 Regulatory Complex," Embo J. 22:987-994 (2003), which is hereby incorporated by reference in its entirety). As demonstrated by the compounds discovered here, adding just one or two contact points to a protein complex can make a very big difference in its stability.

The enhancer approach works especially well for situations in which the conformational dynamics of a protein complex are key to its function. The ability of the glideosome to provide the motive force necessary to travel along and into host cells is dependent on the highly coordinated interactions of its members. Aldolase must tightly bind both actin and TRAP to allow motion to begin, but it must also rapidly release the TRAP tail after its cleavage to allow motion to continue. Similarly, the cleavage of F16P must be tightly coupled to the motor's activity to provide the ATP molecules necessary for both actin polymerization and the actin-myosin power stroke. The various conformations of Aldolase, TRAP, actin, and MyoA must exist in the ideal equilibriums to promote the proper bind-and-release sequences for each of the glideosome interactions. Shifting these equilibriums in either direction by inhibiting or enhancing any of the interactions involved should "stall" the motor, just as loosening or over-tightening the gears in a car engine would have catastrophic effects. Nature abounds with similar vulnerable systems of exquisitely regulated biological motors and complexes, many of which may be targeted by the enhancer method.

The enhancer approach is also attractive for its ability to both promote parasite specificity and prevent the emergence of resistance. The region of Aldolase targeted by the present study is highly conserved, and with good reason—the residues involved play key roles in the enzyme's catalytic activities. Resistance mutations in Aldolase's active site would be highly unfavored as they would likely interfere with glycolytic energy generation. The flipside of this is that it could be very difficult to find molecules that would not interfere with human Aldolase as well. Adding TRAP to the drug target surface revealed additional non-conserved residues to focus on. Drugs could then be designed to have low affinity for Aldolase alone, although the aggregate affinity of the entire Aldolase-TRAP-drug complex could be very high.

This strategy of targeting a hybrid surface composed of a conserved target and a non-conserved target may be broadly applicable to anti-microbial or anti-tumor drug design. This may be especially useful for developing agents to fight eukaryotic pathogens, as many of their essential proteins have highly conserved human homologs, and are otherwise difficult to target specifically. It may also be possible to use this type of approach to design therapeutics for rapidly mutating viruses by selectively modulating host-pathogen interactions—i.e. preventing the dissociation of a viral surface protein from its host receptor may increase the virus's vulnerability to other drugs or to the host's own immune system. In this case, the druggable surface encompassing the viral protein would provide specificity, while the unlikelihood of mutations in the host protein may protect against the development of drug resistance. Similarly, one can envision targeting a complex of a normal housekeeping protein and a mutant oncoprotein to selectively kill cancer cells.

The enhancer design of the present study also allowed realization of the full potential of computer-aided, structure-based approach to drug discovery. VLS allowed us to target specific structural differences between multiple conformations of the target proteins—i.e. the helix-loop-helix shift from apo-Aldolase to TRAP-bound Aldolase, and the differences between mammalian Aldolases and *Plasmodium* Aldolase—in order to shift the apo-Aldolase/Aldolase-F16P/Aldolase-TRAP equilibrium towards the Aldolase-TRAP complex in a parasite-selective fashion. Thus, detailed knowledge of the specific atomic contacts mediating biological interactions can promote rapid and efficient enhancer design.

In summary, this work presents a proof-of-principle that the structure-based selective enhancement of protein-protein interactions is a viable, efficient, and effective method of novel drug development. The methods described herein can serve as a blueprint for future enhancer designs.

The successful visualization of the actin-Aldolase interface and the success of drug-design effort underscore the value of model-guided crystallography and crystallographically-targeted drug discovery. These techniques permitted benefiting from innovations in disparate fields and finding novel and creative solutions to complex problems.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method comprising:
    providing a complex of Aldolase of an apicomplexan organism and thrombospondin-related anonymous protein (TRAP) of an apicomplexan organism;
    providing one or more candidate compounds;
    contacting the candidate compounds and the complex in vitro to determine which of the one or more candidate compounds stabilize the complex; and
    screening the compounds, determined to stabilize the complex, in vitro for their ability to kill and/or inhibit growth of an apicomplexan organism.

2. The method according to claim 1, wherein the apicomplexan organism is selected from the group consisting of *Plasmodium falciparum, Plasmodium yoelii, Plasmodium chabaudi, Plasmodium berghei, Plasmodium knowlesi, Plasmodium vivax, Theileria annulata, Theileria parva, Babesia bovis, Cryptosporidium parvum, Cryptosporidium hominis, Toxoplasma gondii, Cyclospora cayetanensis, Isospora belli, Sarcocystis* spp., and *Eimeria* spp.

* * * * *

SEQUENCE LISTING

```
<160> NUMBER OF SEQ ID NOS: 38

<210> SEQ ID NO 1
<211> LENGTH: 369
<212> TYPE: PRT
<213> ORGANISM: artificial
<220> FEATURE:
<223> OTHER INFORMATION: Adolase consensus sequence
<220> FEATURE:
<221> NAME/KEY: MISC_FEATURE
<222> LOCATION: (1)..(12)
<223> OTHER INFORMATION: X is any amino acid
<220> FEATURE:
<221> NAME/KEY: MISC_FEATURE
<222> LOCATION: (16)..(17)
<223> OTHER INFORMATION: X is any amino acid
<220> FEATURE:
<221> NAME/KEY: MISC_FEATURE
<222> LOCATION: (20)..(20)
<223> OTHER INFORMATION: X is any amino acid
<220> FEATURE:
<221> NAME/KEY: MISC_FEATURE
<222> LOCATION: (22)..(22)
<223> OTHER INFORMATION: X is any amino acid
<220> FEATURE:
<221> NAME/KEY: MISC_FEATURE
<222> LOCATION: (24)..(24)
<223> OTHER INFORMATION: X is any amino acid
<220> FEATURE:
<221> NAME/KEY: MISC_FEATURE
<222> LOCATION: (27)..(27)
<223> OTHER INFORMATION: X is any amino acid
<220> FEATURE:
```

```
<221> NAME/KEY: MISC_FEATURE
<222> LOCATION: (31)..(32)
<223> OTHER INFORMATION: X is any amino acid
<220> FEATURE:
<221> NAME/KEY: MISC_FEATURE
<222> LOCATION: (54)..(56)
<223> OTHER INFORMATION: X is any amino acid
<220> FEATURE:
<221> NAME/KEY: MISC_FEATURE
<222> LOCATION: (59)..(59)
<223> OTHER INFORMATION: X is any amino acid
<220> FEATURE:
<221> NAME/KEY: MISC_FEATURE
<222> LOCATION: (64)..(64)
<223> OTHER INFORMATION: X is any amino acid
<220> FEATURE:
<221> NAME/KEY: MISC_FEATURE
<222> LOCATION: (99)..(99)
<223> OTHER INFORMATION: X is any amino acid
<220> FEATURE:
<221> NAME/KEY: MISC_FEATURE
<222> LOCATION: (105)..(107)
<223> OTHER INFORMATION: X is any amino acid
<220> FEATURE:
<221> NAME/KEY: MISC_FEATURE
<222> LOCATION: (120)..(120)
<223> OTHER INFORMATION: X is any amino acid
<220> FEATURE:
<221> NAME/KEY: MISC_FEATURE
<222> LOCATION: (126)..(126)
<223> OTHER INFORMATION: X is any amino acid
<220> FEATURE:
<221> NAME/KEY: MISC_FEATURE
<222> LOCATION: (155)..(155)
<223> OTHER INFORMATION: X is any amino acid
<220> FEATURE:
<221> NAME/KEY: MISC_FEATURE
<222> LOCATION: (161)..(162)
<223> OTHER INFORMATION: X is any amino acid
<220> FEATURE:
<221> NAME/KEY: MISC_FEATURE
<222> LOCATION: (172)..(172)
<223> OTHER INFORMATION: X is any amino acid
<220> FEATURE:
<221> NAME/KEY: MISC_FEATURE
<222> LOCATION: (174)..(175)
<223> OTHER INFORMATION: X is any amino acid
<220> FEATURE:
<221> NAME/KEY: MISC_FEATURE
<222> LOCATION: (183)..(183)
<223> OTHER INFORMATION: X is any amino acid
<220> FEATURE:
<221> NAME/KEY: MISC_FEATURE
<222> LOCATION: (189)..(189)
<223> OTHER INFORMATION: X is any amino acid
<220> FEATURE:
<221> NAME/KEY: MISC_FEATURE
<222> LOCATION: (203)..(203)
<223> OTHER INFORMATION: X is any amino acid
<220> FEATURE:
<221> NAME/KEY: MISC_FEATURE
<222> LOCATION: (205)..(205)
<223> OTHER INFORMATION: X is any amino acid
<220> FEATURE:
<221> NAME/KEY: MISC_FEATURE
<222> LOCATION: (211)..(211)
<223> OTHER INFORMATION: X is any amino acid
<220> FEATURE:
<221> NAME/KEY: MISC_FEATURE
<222> LOCATION: (218)..(219)
<223> OTHER INFORMATION: X is any amino acid
<220> FEATURE:
<221> NAME/KEY: MISC_FEATURE
<222> LOCATION: (225)..(227)
<223> OTHER INFORMATION: X is any amino acid
<220> FEATURE:
<221> NAME/KEY: MISC_FEATURE
<222> LOCATION: (229)..(229)
<223> OTHER INFORMATION: X is any amino acid
```

```
<220> FEATURE:
<221> NAME/KEY: MISC_FEATURE
<222> LOCATION: (246)..(246)
<223> OTHER INFORMATION: X is any amino acid
<220> FEATURE:
<221> NAME/KEY: MISC_FEATURE
<222> LOCATION: (248)..(249)
<223> OTHER INFORMATION: X is any amino acid
<220> FEATURE:
<221> NAME/KEY: MISC_FEATURE
<222> LOCATION: (252)..(252)
<223> OTHER INFORMATION: X is any amino acid
<220> FEATURE:
<221> NAME/KEY: MISC_FEATURE
<222> LOCATION: (254)..(254)
<223> OTHER INFORMATION: X is any amino acid
<220> FEATURE:
<221> NAME/KEY: MISC_FEATURE
<222> LOCATION: (256)..(256)
<223> OTHER INFORMATION: X is any amino acid
<220> FEATURE:
<221> NAME/KEY: misc_feature
<222> LOCATION: (259)..(259)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: MISC_FEATURE
<222> LOCATION: (271)..(271)
<223> OTHER INFORMATION: X is any amino acid
<220> FEATURE:
<221> NAME/KEY: MISC_FEATURE
<222> LOCATION: (286)..(286)
<223> OTHER INFORMATION: X is any amino acid
<220> FEATURE:
<221> NAME/KEY: MISC_FEATURE
<222> LOCATION: (289)..(289)
<223> OTHER INFORMATION: X is any amino acid
<220> FEATURE:
<221> NAME/KEY: MISC_FEATURE
<222> LOCATION: (294)..(294)
<223> OTHER INFORMATION: X is any amino acid
<220> FEATURE:
<221> NAME/KEY: MISC_FEATURE
<222> LOCATION: (296)..(296)
<223> OTHER INFORMATION: X is any amino acid
<220> FEATURE:
<221> NAME/KEY: MISC_FEATURE
<222> LOCATION: (318)..(318)
<223> OTHER INFORMATION: X is any amino acid
<220> FEATURE:
<221> NAME/KEY: MISC_FEATURE
<222> LOCATION: (321)..(321)
<223> OTHER INFORMATION: X is any amino acid
<220> FEATURE:
<221> NAME/KEY: MISC_FEATURE
<222> LOCATION: (327)..(328)
<223> OTHER INFORMATION: X is any amino acid
<220> FEATURE:
<221> NAME/KEY: MISC_FEATURE
<222> LOCATION: (331)..(332)
<223> OTHER INFORMATION: X is any amino acid
<220> FEATURE:
<221> NAME/KEY: MISC_FEATURE
<222> LOCATION: (336)..(336)
<223> OTHER INFORMATION: X is any amino acid
<220> FEATURE:
<221> NAME/KEY: misc_feature
<222> LOCATION: (356)..(357)
<223> OTHER INFORMATION: Xaa can be any naturally occurring amino acid
<220> FEATURE:
<221> NAME/KEY: MISC_FEATURE
<222> LOCATION: (361)..(361)
<223> OTHER INFORMATION: X is any amino acid
<220> FEATURE:
<221> NAME/KEY: MISC_FEATURE
<222> LOCATION: (363)..(369)
```

<223> OTHER INFORMATION: X is any amino acid

<400> SEQUENCE: 1

```
Xaa Xaa Xaa Xaa Xaa Xaa Xaa Xaa Xaa Xaa Lys Leu Pro Xaa
  1               5                  10                  15
Xaa Val Ala Xaa Glu Xaa Ala Xaa Thr Ala Xaa Lys Leu Val Xaa Xaa
             20                  25                  30
Gly Lys Gly Ile Leu Ala Ala Asp Glu Ser Thr Gln Thr Ile Lys Lys
         35                  40                  45
Arg Phe Asp Asn Ile Xaa Xaa Xaa Asn Thr Xaa Glu Asn Arg Ala Xaa
 50                  55                  60
Tyr Arg Asp Leu Leu Phe Gly Thr Lys Gly Leu Gly Lys Phe Ile Ser
 65                  70                  75                  80
Gly Ala Ile Leu Phe Glu Glu Thr Leu Phe Gln Lys Asn Glu Ala Gly
                 85                  90                  95
Val Pro Xaa Val Asn Leu Leu His Xaa Xaa Xaa Ile Ile Pro Gly Ile
                100                 105                 110
Lys Val Asp Lys Gly Leu Val Xaa Ile Pro Cys Thr Asp Xaa Glu Lys
            115                 120                 125
Ser Thr Gln Gly Leu Asp Gly Leu Ala Glu Arg Cys Lys Glu Tyr Tyr
        130                 135                 140
Lys Ala Gly Ala Arg Phe Ala Lys Trp Arg Xaa Val Leu Val Ile Asp
145                 150                 155                 160
Xaa Xaa Lys Gly Lys Pro Thr Asp Leu Ser Ile Xaa Glu Xaa Xaa Trp
                165                 170                 175
Gly Leu Ala Arg Tyr Ala Xaa Ile Cys Gln Gln Asn Xaa Leu Val Pro
                180                 185                 190
Ile Val Glu Pro Glu Ile Leu Ala Asp Gly Xaa His Xaa Ile Glu Val
            195                 200                 205
Cys Ala Xaa Val Thr Gln Lys Val Leu Xaa Xaa Val Phe Lys Ala Leu
        210                 215                 220
Xaa Xaa Xaa Gly Xaa Leu Leu Glu Gly Ala Leu Leu Lys Pro Asn Met
225                 230                 235                 240
Val Thr Ala Gly Tyr Xaa Cys Xaa Xaa Lys Thr Xaa Thr Xaa Asp Xaa
                245                 250                 255
Gly Phe Xaa Thr Val Arg Thr Leu Xaa Arg Thr Val Pro Pro Xaa Leu
            260                 265                 270
Pro Gly Val Val Phe Leu Ser Gly Gly Gln Ser Glu Glu Xaa Ala Ser
        275                 280                 285
Xaa Asn Leu Asn Ser Xaa Asn Xaa Leu Gly Pro His Pro Trp Ala Leu
290                 295                 300
Thr Phe Ser Tyr Gly Arg Ala Leu Gln Ala Ser Val Leu Xaa Thr Trp
305                 310                 315                 320
Xaa Gly Lys Lys Glu Asn Xaa Xaa Lys Ala Xaa Xaa Val Leu Leu Xaa
                325                 330                 335
Arg Ala Glu Ala Asn Ser Leu Ala Thr Tyr Gly Lys Tyr Lys Gly Gly
            340                 345                 350
Ala Gly Gly Xaa Xaa Ala Gly Ala Xaa Leu Xaa Xaa Xaa Xaa Xaa Xaa
        355                 360                 365
Xaa
```

<210> SEQ ID NO 2
<211> LENGTH: 365
<212> TYPE: PRT

<213> ORGANISM: Plasmodium berghei

<400> SEQUENCE: 2

```
Cys Ala Glu Tyr Lys Asn Ala Pro Met Lys Leu Pro Lys Glu Val Ala
1               5                   10                  15

Gln Glu Leu Ala Glu Thr Ala Lys Lys Leu Val Ala Ala Gly Lys Gly
            20                  25                  30

Ile Leu Ala Ala Asp Glu Ser Thr Gln Thr Ile Lys Lys Arg Phe Asp
        35                  40                  45

Asn Ile Lys Ile Glu Asn Thr Val Glu Asn Arg Ala Ser Tyr Arg Asp
    50                  55                  60

Leu Leu Phe Gly Thr Lys Gly Leu Gly Lys Phe Ile Ser Gly Ala Ile
65                  70                  75                  80

Leu Phe Glu Glu Thr Leu Phe Gln Lys Asn Glu Ala Gly Val Pro Leu
                85                  90                  95

Val Asn Leu Leu His Asp Glu Gly Ile Ile Pro Gly Ile Lys Val Asp
            100                 105                 110

Lys Gly Leu Val Ser Ile Pro Cys Thr Asp Asp Glu Lys Ser Thr Gln
        115                 120                 125

Gly Leu Asp Gly Leu Ala Glu Arg Cys Lys Glu Tyr Tyr Lys Ala Gly
    130                 135                 140

Ala Arg Phe Ala Lys Trp Arg Ala Val Leu Val Ile Asp Pro Ala Lys
145                 150                 155                 160

Gly Lys Pro Thr Asp Leu Ser Ile Gln Glu Val Ser Trp Gly Leu Ala
                165                 170                 175

Arg Tyr Ala Ser Ile Cys Gln Gln Asn Lys Leu Val Pro Ile Val Glu
            180                 185                 190

Pro Glu Ile Leu Ala Asp Gly Ala His Thr Ile Glu Val Cys Ala Thr
        195                 200                 205

Val Thr Gln Lys Val Leu Ala Ser Val Phe Lys Ala Leu His Asp Asn
    210                 215                 220

Gly Val Leu Leu Glu Gly Ala Leu Leu Lys Pro Asn Met Val Thr Ala
225                 230                 235                 240

Gly Tyr Asp Cys Thr Glu Lys Thr Lys Thr Asp Ile Gly Phe Phe
                245                 250                 255

Thr Val Arg Thr Leu Arg Arg Thr Val Pro Pro Ala Leu Pro Gly Val
            260                 265                 270

Val Phe Leu Ser Gly Gly Gln Ser Glu Glu Asp Ala Ser Ile Asn Leu
        275                 280                 285

Asn Ser Ile Asn Val Leu Gly Pro His Pro Trp Ala Leu Thr Phe Ser
    290                 295                 300

Tyr Gly Arg Ala Leu Gln Ala Ser Val Leu Asn Thr Trp Gln Gly Lys
305                 310                 315                 320

Lys Glu Asn Val Ala Lys Ala Arg Ala Val Leu Leu Gln Arg Ala Glu
                325                 330                 335

Ala Asn Ser Leu Ala Thr Tyr Gly Lys Tyr Lys Gly Ala Gly Gly
            340                 345                 350

Ser Thr Ala Gly Ala Leu Tyr Glu Lys Lys Tyr Val Tyr
        355                 360                 365
```

<210> SEQ ID NO 3
<211> LENGTH: 366
<212> TYPE: PRT
<213> ORGANISM: Plasmodium chabaudi

<400> SEQUENCE: 3

```
Cys Val Glu Tyr Lys Asn Ala Pro Met Lys Leu Pro Lys Glu Val Ala
1               5                   10                  15

His Glu Leu Ala Glu Thr Ala Lys Lys Leu Val Ala Pro Gly Lys Gly
            20                  25                  30

Ile Leu Ala Ala Asp Glu Ser Thr Gln Thr Ile Lys Lys Arg Phe Asp
        35                  40                  45

Asn Ile Lys Ile Glu Asn Thr Val Glu Asn Arg Ala Asn Tyr Arg Asp
    50                  55                  60

Leu Leu Phe Gly Thr Lys Gly Leu Gly Lys Phe Ile Ser Gly Ala Ile
65                  70                  75                  80

Leu Phe Glu Glu Thr Leu Phe Gln Lys Asn Glu Ala Gly Val Pro Leu
                85                  90                  95

Val Asn Leu Leu His Asp Glu Asp Ile Ile Pro Gly Ile Lys Val Asp
            100                 105                 110

Lys Gly Leu Val Ser Ile Pro Cys Thr Asp Asp Glu Lys Ser Thr Gln
        115                 120                 125

Gly Leu Asp Gly Leu Ala Glu Arg Cys Lys Glu Tyr Tyr Lys Ala Gly
    130                 135                 140

Ala Arg Phe Ala Lys Trp Arg Ala Val Leu Val Ile Asp Pro Val Lys
145                 150                 155                 160

Gly Lys Pro Thr Asp Leu Ser Ile His Glu Val Ser Trp Gly Leu Ala
                165                 170                 175

Arg Tyr Ala Ala Ile Cys Gln Gln Asn Lys Leu Val Pro Ile Val Glu
            180                 185                 190

Pro Glu Ile Leu Ala Asp Gly His Thr Ile Glu Val Cys Ala Thr
        195                 200                 205

Val Thr Gln Lys Val Leu Ala Ser Val Phe Lys Ala Leu His Asp Asn
    210                 215                 220

Gly Val Leu Leu Glu Gly Ala Leu Leu Lys Pro Asn Met Val Thr Ala
225                 230                 235                 240

Gly Tyr Asp Cys Thr Glu Lys Thr Lys Thr Asp Asp Ile Gly Phe Phe
                245                 250                 255

Thr Val Arg Thr Leu Arg Arg Thr Val Pro Pro Ala Leu Pro Gly Val
            260                 265                 270

Val Phe Leu Ser Gly Gly Gln Ser Glu Glu Asp Ala Ser Val Asn Leu
        275                 280                 285

Asn Ser Ile Asn Val Leu Gly Pro His Pro Trp Ala Leu Thr Phe Ser
    290                 295                 300

Tyr Gly Arg Ala Leu Gln Ala Ser Val Leu Ser Thr Trp Gln Gly Lys
305                 310                 315                 320

Lys Glu Asn Val Ala Lys Ala Arg Glu Val Leu Leu Gln Arg Ala Glu
                325                 330                 335

Ala Asn Ser Leu Ala Thr Tyr Gly Lys Tyr Lys Gly Ala Gly Gly
            340                 345                 350

Ser Thr Ala Gly Ala Ser Leu Tyr Glu Lys Lys Tyr Val Tyr
        355                 360                 365
```

<210> SEQ ID NO 4
<211> LENGTH: 369
<212> TYPE: PRT
<213> ORGANISM: Plasmodium falciparum

<400> SEQUENCE: 4

Met Ala His Cys Thr Glu Tyr Met Asn Ala Pro Lys Lys Leu Pro Ala
1               5                   10                  15

Asp Val Ala Glu Glu Leu Ala Thr Thr Ala Gln Lys Leu Val Gln Ala
            20                  25                  30

Gly Lys Gly Ile Leu Ala Ala Asp Glu Ser Thr Gln Thr Ile Lys Lys
            35                  40                  45

Arg Phe Asp Asn Ile Lys Leu Glu Asn Thr Ile Glu Asn Arg Ala Ser
        50                  55                  60

Tyr Arg Asp Leu Leu Phe Gly Thr Lys Gly Leu Gly Lys Phe Ile Ser
65                  70                  75                  80

Gly Ala Ile Leu Phe Glu Glu Thr Leu Phe Gln Lys Asn Glu Ala Gly
                85                  90                  95

Val Pro Met Val Asn Leu Leu His Asn Glu Asn Ile Ile Pro Gly Ile
                100                 105                 110

Lys Val Asp Lys Gly Leu Val Asn Ile Pro Cys Thr Asp Glu Glu Lys
            115                 120                 125

Ser Thr Gln Gly Leu Asp Gly Leu Ala Glu Arg Cys Lys Glu Tyr Tyr
            130                 135                 140

Lys Ala Gly Ala Arg Phe Ala Lys Trp Arg Thr Val Leu Val Ile Asp
145                 150                 155                 160

Thr Ala Lys Gly Lys Pro Thr Asp Leu Ser Ile His Glu Thr Ala Trp
                165                 170                 175

Gly Leu Ala Arg Tyr Ala Ser Ile Cys Gln Gln Asn Arg Leu Val Pro
                180                 185                 190

Ile Val Glu Pro Glu Ile Leu Ala Asp Gly Pro His Ser Ile Glu Val
            195                 200                 205

Cys Ala Val Val Thr Gln Lys Val Leu Ser Cys Val Phe Lys Ala Leu
210                 215                 220

Gln Glu Asn Gly Val Leu Leu Glu Gly Ala Leu Leu Lys Pro Asn Met
225                 230                 235                 240

Val Thr Ala Gly Tyr Glu Cys Thr Ala Lys Thr Thr Thr Gln Asp Val
                245                 250                 255

Gly Phe Leu Thr Val Arg Thr Leu Arg Arg Thr Val Pro Pro Ala Leu
            260                 265                 270

Pro Gly Val Val Phe Leu Ser Gly Gly Gln Ser Glu Glu Glu Ala Ser
            275                 280                 285

Val Asn Leu Asn Ser Ile Asn Ala Leu Gly Pro His Pro Trp Ala Leu
            290                 295                 300

Thr Phe Ser Tyr Gly Arg Ala Leu Gln Ala Ser Val Leu Asn Thr Trp
305                 310                 315                 320

Gln Gly Lys Lys Glu Asn Val Ala Lys Ala Arg Glu Val Leu Leu Gln
                325                 330                 335

Arg Ala Glu Ala Asn Ser Leu Ala Thr Tyr Gly Lys Tyr Lys Gly Gly
            340                 345                 350

Ala Gly Gly Glu Asn Ala Gly Ala Ser Leu Tyr Glu Lys Lys Tyr Val
            355                 360                 365

Tyr

<210> SEQ ID NO 5
<211> LENGTH: 389
<212> TYPE: PRT
<213> ORGANISM: Plasmodium knowlesi

<400> SEQUENCE: 5

```
Met Ser Ala Pro Tyr Pro Arg Met Val Ile Pro Phe Ser Cys Gln Asn
  1               5                  10                  15

Ser Cys Asp Val Tyr Ala Thr Val Ser Glu Tyr Lys Asn Ala Pro Leu
             20                  25                  30

Lys Leu Pro Ala Asp Val Ala Glu Glu Ile Ala Thr Thr Ala Lys Lys
             35                  40                  45

Leu Val Gln Ala Gly Lys Gly Ile Leu Ala Ala Asp Glu Ser Thr Gln
 50                  55                  60

Thr Ile Lys Lys Arg Phe Asp Asn Ile Asn Val Glu Asn Thr Val Glu
 65                  70                  75                  80

Asn Arg Ala Ala Tyr Arg Asp Leu Leu Phe Gly Thr Lys Gly Leu Gly
                 85                  90                  95

Lys Phe Ile Ser Gly Ala Ile Leu Phe Glu Glu Thr Leu Phe Gln Lys
                100                 105                 110

Asn Glu Ala Gly Val Pro Leu Val Asn Leu Leu His Asp Glu Gly Ile
            115                 120                 125

Ile Pro Gly Ile Lys Val Asp Lys Gly Leu Val Thr Ile Pro Cys Thr
    130                 135                 140

Asp Asp Glu Lys Ser Thr Gln Gly Leu Asp Gly Leu Ala Glu Arg Cys
145                 150                 155                 160

Lys Glu Tyr Tyr Lys Ala Gly Ala Arg Phe Ala Lys Trp Arg Ala Val
                165                 170                 175

Leu Val Ile Asp Pro Val Lys Gly Lys Pro Thr Asp Leu Ser Ile Gln
                180                 185                 190

Glu Thr Ala Trp Gly Leu Ala Arg Tyr Ala Ser Ile Cys Gln Gln Asn
            195                 200                 205

Lys Leu Val Pro Ile Val Glu Pro Glu Ile Leu Ala Asp Gly Ser His
    210                 215                 220

Thr Ile Glu Val Cys Ala Thr Val Thr Gln Lys Val Leu Ala Cys Val
225                 230                 235                 240

Phe Lys Ala Leu His Asp Gln Gly Ile Leu Leu Glu Gly Ala Leu Leu
                245                 250                 255

Lys Pro Asn Met Val Thr Ala Gly Tyr Asp Cys Thr Val Lys Thr Lys
                260                 265                 270

Thr Gln Asp Ile Gly Phe Leu Thr Val Arg Thr Leu Ser Arg Thr Val
            275                 280                 285

Pro Pro Ala Leu Pro Gly Val Val Phe Leu Ser Gly Gly Gln Ser Glu
    290                 295                 300

Glu Glu Ala Ser Val Asn Leu Asn Ser Met Asn Val Leu Gly Pro His
305                 310                 315                 320

Pro Trp Ala Leu Thr Phe Ser Tyr Gly Arg Ala Leu Gln Ala Ser Val
                325                 330                 335

Leu Asn Thr Trp Lys Gly Lys Lys Glu Asn Val Ala Lys Ala Arg Glu
                340                 345                 350

Val Leu Leu Lys Arg Ala Glu Ala Asn Ser Leu Ala Thr Tyr Gly Lys
            355                 360                 365

Tyr Lys Gly Gly Ala Gly Gly Ala Asp Ala Gly Ala Ser Leu Tyr Glu
    370                 375                 380

Lys Lys Tyr Val Tyr
385

<210> SEQ ID NO 6
<211> LENGTH: 351
<212> TYPE: PRT
```

<213> ORGANISM: Plasmodium vinckei

<400> SEQUENCE: 6

Met Lys Leu Pro Lys Glu Val Ala Gln Glu Leu Ala Asp Thr Ala Lys
1               5                   10                  15

Lys Leu Val Ala Pro Gly Lys Gly Ile Leu Ala Ala Asp Glu Ser Thr
            20                  25                  30

Gln Thr Ile Lys Lys Arg Phe Asp Asn Ile Lys Ile Asp Asn Thr Val
        35                  40                  45

Glu Asn Arg Ala Ser Tyr Arg Asp Leu Leu Phe Gly Thr Lys Gly Leu
    50                  55                  60

Gly Lys Phe Ile Ser Gly Ala Ile Leu Phe Glu Glu Thr Leu Phe Gln
65                  70                  75                  80

Lys Asn Glu Ala Gly Val Pro Leu Val Asn Leu Leu His Asp Gln Asn
                85                  90                  95

Ile Ile Pro Gly Ile Lys Val Asp Lys Gly Leu Val Ala Ile Pro Cys
            100                 105                 110

Thr Asp Asp Glu Lys Ser Thr Gln Gly Leu Asp Gly Leu Ala Glu Arg
        115                 120                 125

Cys Lys Glu Tyr Tyr Lys Ala Gly Ala Arg Phe Ala Lys Trp Arg Ala
    130                 135                 140

Val Leu Val Ile Asp Pro Ala Lys Gly Lys Pro Thr Asp Leu Ser Ile
145                 150                 155                 160

Gln Glu Val Ser Trp Gly Leu Ala Arg Tyr Ala Ala Ile Cys Gln Gln
                165                 170                 175

Asn Lys Leu Val Pro Ile Val Glu Pro Glu Ile Leu Ala Asp Gly Ala
            180                 185                 190

His Thr Ile Glu Val Cys Ala Ala Val Thr Gln Lys Val Leu Ala Ser
        195                 200                 205

Val Phe Lys Ala Leu His Asp Asn Gly Val Leu Leu Glu Gly Ala Leu
    210                 215                 220

Leu Lys Pro Asn Met Val Thr Ala Gly Tyr Asp Cys Pro Glu Lys Thr
225                 230                 235                 240

Lys Thr Glu Asp Ile Gly Phe Phe Thr Val Arg Thr Leu Ser Arg Thr
                245                 250                 255

Val Pro Pro Ala Leu Pro Gly Val Val Phe Leu Ser Gly Gly Gln Ser
            260                 265                 270

Glu Glu Asp Ala Ser Val Asn Leu Asn Ser Met Asn Val Leu Gly Pro
        275                 280                 285

His Pro Trp Ala Leu Thr Phe Ser Tyr Gly Arg Ala Leu Gln Ala Ser
    290                 295                 300

Val Leu Ser Thr Trp Gln Gly Lys Lys Glu Asn Ala Ala Lys Ala Gln
305                 310                 315                 320

Glu Val Leu Leu Gln Arg Ala Glu Ala Asn Ser Leu Ala Thr Tyr Gly
                325                 330                 335

Lys Tyr Lys Gly Gly Ala Gly Gly Ser Thr Ala Gly Ala Ser Leu
            340                 345                 350

<210> SEQ ID NO 7
<211> LENGTH: 369
<212> TYPE: PRT
<213> ORGANISM: Plasmodium vivax

<400> SEQUENCE: 7

Met Ala Thr Gly Ser Glu Tyr Lys Asn Ala Pro Leu Lys Leu Pro Ala

```
1               5                   10                  15
Glu Val Ala Glu Glu Ile Ala Thr Thr Ala Lys Lys Leu Val Glu Ala
            20                  25                  30

Gly Lys Gly Ile Leu Ala Ala Asp Glu Ser Thr Gln Thr Ile Lys Lys
            35                  40                  45

Arg Phe Asp Asn Ile Asn Val Glu Asn Thr Ile Glu Asn Arg Ala Ser
        50                  55                  60

Tyr Arg Asp Leu Leu Phe Gly Thr Lys Gly Leu Gly Lys Phe Ile Ser
65                  70                  75                  80

Gly Ala Ile Leu Phe Glu Glu Thr Leu Phe Gln Lys Asn Glu Ala Gly
                85                  90                  95

Val Pro Leu Val Asn Leu Leu His Asp Glu Gly Ile Ile Pro Gly Ile
            100                 105                 110

Lys Val Asp Lys Gly Leu Val Thr Ile Pro Cys Thr Asp Asp Glu Lys
            115                 120                 125

Ser Thr Gln Gly Leu Asp Gly Leu Ala Glu Arg Cys Lys Glu Tyr Tyr
    130                 135                 140

Lys Ala Gly Ala Arg Phe Ala Lys Trp Arg Ala Val Leu Val Ile Asp
145                 150                 155                 160

Pro Val Lys Gly Lys Pro Thr Asp Leu Ser Ile Gln Glu Thr Ala Trp
                165                 170                 175

Gly Leu Ala Arg Tyr Ala Ser Ile Cys Gln Gln Asn Lys Leu Val Pro
            180                 185                 190

Ile Val Glu Pro Glu Ile Leu Ala Asp Gly Ser His Thr Ile Glu Val
            195                 200                 205

Cys Ala Thr Val Thr Gln Lys Val Leu Ala Ser Val Phe Lys Ala Leu
210                 215                 220

His Asp Gln Gly Val Leu Leu Glu Gly Ala Leu Leu Lys Pro Asn Met
225                 230                 235                 240

Val Thr Ala Gly Tyr Asp Cys Ala Val Lys Thr Asn Thr Gln Asp Ile
                245                 250                 255

Gly Phe Leu Thr Val Arg Thr Leu Ser Arg Thr Val Pro Pro Ser Leu
            260                 265                 270

Pro Gly Val Val Phe Leu Ser Gly Gly Gln Ser Glu Glu Glu Ala Ser
            275                 280                 285

Val Asn Leu Asn Ser Ile Asn Ala Leu Gly Pro His Pro Trp Ala Leu
290                 295                 300

Thr Phe Ser Tyr Gly Arg Ala Leu Gln Ala Ser Val Leu Asn Thr Trp
305                 310                 315                 320

Lys Gly Lys Lys Glu Asn Val Glu Lys Ala Arg Glu Val Leu Leu Lys
                325                 330                 335

Arg Ala Glu Ala Asn Ser Leu Ala Thr Tyr Gly Lys Tyr Lys Gly Gly
            340                 345                 350

Ala Gly Gly Ala Asp Ala Gly Ala Ser Leu Tyr Glu Lys Lys Tyr Val
            355                 360                 365

Tyr

<210> SEQ ID NO 8
<211> LENGTH: 409
<212> TYPE: PRT
<213> ORGANISM: Plasmodium yoelii

<400> SEQUENCE: 8

Met Tyr Arg Thr Cys Ser Leu Asn Glu Ser Lys Cys Asp Asp Lys Ile
```

```
1               5                   10                  15
Tyr Ile Asp Leu Tyr Phe Ala Asn Leu Tyr Ile Tyr Asn Arg Lys Phe
            20                  25                  30

Gln Arg Leu Leu Lys Cys Ile Leu Thr Val Gly Cys Val Glu Tyr Lys
            35                  40                  45

Asn Ala Pro Met Lys Leu Pro Lys Glu Val Ala Gln Glu Leu Ala Glu
        50                  55                  60

Thr Ala Lys Lys Leu Val Ala Gly Lys Gly Ile Leu Ala Ala Asp
65                  70                  75                  80

Glu Ser Thr Gln Thr Ile Lys Lys Arg Phe Asp Asn Ile Lys Ile Glu
                85                  90                  95

Asn Thr Val Glu Asn Arg Ala Ser Tyr Arg Asp Leu Leu Phe Gly Thr
            100                 105                 110

Lys Gly Leu Gly Lys Phe Ile Ser Gly Ala Ile Leu Phe Glu Glu Thr
            115                 120                 125

Leu Phe Gln Lys Asn Glu Ala Gly Val Pro Leu Val Asn Leu Leu His
        130                 135                 140

Asp Glu Gly Ile Ile Pro Gly Ile Lys Val Asp Lys Gly Leu Val Ser
145                 150                 155                 160

Ile Pro Cys Thr Asp Asp Glu Lys Ser Thr Gln Gly Leu Asp Gly Leu
                165                 170                 175

Ala Glu Arg Cys Lys Glu Tyr Tyr Lys Ala Gly Ala Arg Phe Ala Lys
            180                 185                 190

Trp Arg Ala Val Leu Val Ile Asp Pro Ala Lys Gly Lys Pro Thr Asp
        195                 200                 205

Leu Ser Ile Gln Glu Val Ser Trp Gly Leu Ala Arg Tyr Ala Ser Ile
    210                 215                 220

Cys Gln Gln Asn Lys Leu Val Pro Ile Val Glu Pro Glu Ile Leu Ala
225                 230                 235                 240

Asp Gly Ala His Thr Ile Glu Val Cys Ala Thr Val Thr Gln Lys Val
                245                 250                 255

Leu Ala Ser Val Phe Lys Ala Leu His Asp Asn Gly Val Leu Leu Glu
            260                 265                 270

Gly Ala Leu Leu Lys Pro Asn Met Val Thr Ala Gly Tyr Asp Cys Thr
        275                 280                 285

Glu Lys Thr Lys Thr Asp Asp Ile Gly Phe Phe Thr Val Arg Thr Leu
    290                 295                 300

Arg Arg Thr Val Pro Pro Ala Leu Pro Gly Val Val Phe Leu Ser Gly
305                 310                 315                 320

Gly Gln Ser Glu Glu Asp Ala Ser Ile Asn Leu Asn Ser Ile Asn Val
                325                 330                 335

Leu Gly Pro His Pro Trp Ala Leu Thr Phe Ser Tyr Gly Arg Ala Leu
            340                 345                 350

Gln Ala Ser Val Leu Asn Thr Trp Gln Gly Lys Lys Glu Asn Val Ala
        355                 360                 365

Lys Ala Arg Glu Val Leu Leu Gln Arg Ala Glu Ala Asn Ser Leu Ala
370                 375                 380

Thr Tyr Gly Lys Tyr Lys Gly Gly Ala Gly Gly Ser Thr Ala Gly Ala
385                 390                 395                 400

Ser Leu Tyr Glu Lys Lys Tyr Val Tyr
            405

<210> SEQ ID NO 9
```

```
<211> LENGTH: 15
<212> TYPE: PRT
<213> ORGANISM: artificial
<220> FEATURE:
<223> OTHER INFORMATION: Plasmodium falciparum derived actin peptide

<400> SEQUENCE: 9

Phe Gln Gln Met Trp Ile Thr Lys Glu Glu Tyr Asp Glu Ser Gly
1               5                   10                  15

<210> SEQ ID NO 10
<211> LENGTH: 58
<212> TYPE: DNA
<213> ORGANISM: artificial
<220> FEATURE:
<223> OTHER INFORMATION: primer

<400> SEQUENCE: 10
gatctttcaa caaatgtgga tcacaaaaga ggaatacgat gaatcaggat aagagctc      58

<210> SEQ ID NO 11
<211> LENGTH: 57
<212> TYPE: DNA
<213> ORGANISM: artificial
<220> FEATURE:
<223> OTHER INFORMATION: primer

<400> SEQUENCE: 11
attgagctct tatcctgatt catcgtattc ctcttttgtg attgccattt gttgaaa       57

<210> SEQ ID NO 12
<211> LENGTH: 15
<212> TYPE: PRT
<213> ORGANISM: artificial
<220> FEATURE:
<223> OTHER INFORMATION: Plasmodium falciparum derived actin peptide

<400> SEQUENCE: 12

Phe Gln Gln Met Trp Ile Thr Lys Glu Glu Ala Asp Glu Ser Gly
1               5                   10                  15

<210> SEQ ID NO 13
<211> LENGTH: 15
<212> TYPE: PRT
<213> ORGANISM: artificial
<220> FEATURE:
<223> OTHER INFORMATION: Plasmodium falciparum derived actin peptide

<400> SEQUENCE: 13

Phe Gln Gln Met Ala Ile Thr Lys Glu Glu Tyr Asp Glu Ser Gly
1               5                   10                  15

<210> SEQ ID NO 14
<211> LENGTH: 15
<212> TYPE: PRT
<213> ORGANISM: artificial
<220> FEATURE:
<223> OTHER INFORMATION: Plasmodium falciparum derived actin peptide

<400> SEQUENCE: 14

Phe Gln Gln Met Ala Ile Thr Lys Glu Glu Ala Asp Glu Ser Gly
1               5                   10                  15

<210> SEQ ID NO 15
<211> LENGTH: 12
<212> TYPE: PRT
<213> ORGANISM: artificial
```

```
<220> FEATURE:
<223> OTHER INFORMATION: Plasmodium falciparum derived actin peptide

<400> SEQUENCE: 15

Ala Ala Ala Trp Ile Thr Lys Glu Glu Tyr Asp Glu
1               5                   10

<210> SEQ ID NO 16
<211> LENGTH: 12
<212> TYPE: PRT
<213> ORGANISM: artificial
<220> FEATURE:
<223> OTHER INFORMATION: Plasmodium falciparum derived actin peptide

<400> SEQUENCE: 16

Ala Ala Ala Trp Ile Thr Lys Gln Gln Tyr Asp Glu
1               5                   10

<210> SEQ ID NO 17
<211> LENGTH: 9
<212> TYPE: PRT
<213> ORGANISM: artificial
<220> FEATURE:
<223> OTHER INFORMATION: Plasmodium falciparum derived actin peptide

<400> SEQUENCE: 17

Trp Ile Thr Lys Glu Glu Tyr Asn Gln
1               5

<210> SEQ ID NO 18
<211> LENGTH: 37
<212> TYPE: DNA
<213> ORGANISM: artificial
<220> FEATURE:
<223> OTHER INFORMATION: primer

<400> SEQUENCE: 18
atcgatggat ccggaggtaa ctactatgta tgaaggt                          37

<210> SEQ ID NO 19
<211> LENGTH: 45
<212> TYPE: DNA
<213> ORGANISM: artificial
<220> FEATURE:
<223> OTHER INFORMATION: primer

<400> SEQUENCE: 19
gctactcgag gcggccgctt atctgtggac aatacttggt cctga                 45

<210> SEQ ID NO 20
<211> LENGTH: 38
<212> TYPE: DNA
<213> ORGANISM: artificial
<220> FEATURE:
<223> OTHER INFORMATION: primer

<400> SEQUENCE: 20
atcgatctcg aggcatggga gaagaagatg ttcaagct                         38

<210> SEQ ID NO 21
<211> LENGTH: 38
<212> TYPE: DNA
<213> ORGANISM: artificial
<220> FEATURE:
<223> OTHER INFORMATION: primer

<400> SEQUENCE: 21
```
tcgatcgcgg ccgcttagaa gcattttctg tggacaat                                  38

<210> SEQ ID NO 22
<211> LENGTH: 9
<212> TYPE: PRT
<213> ORGANISM: artificial
<220> FEATURE:
<223> OTHER INFORMATION: Plasmodium falciparum derived actin peptide

<400> SEQUENCE: 22

Trp Ile Thr Lys Glu Glu Tyr Asp Glu
1               5

<210> SEQ ID NO 23
<211> LENGTH: 9
<212> TYPE: PRT
<213> ORGANISM: artificial
<220> FEATURE:
<223> OTHER INFORMATION: Plasmodium falciparum derived actin peptide

<400> SEQUENCE: 23

Glu Asp Trp Tyr Ile Lys Thr Glu Glu
1               5

<210> SEQ ID NO 24
<211> LENGTH: 9
<212> TYPE: PRT
<213> ORGANISM: artificial
<220> FEATURE:
<223> OTHER INFORMATION: Plasmodium falciparum derived actin peptide

<400> SEQUENCE: 24

Asn Ile Thr Lys Gln Gln Asn Asp Glu
1               5

<210> SEQ ID NO 25
<211> LENGTH: 25
<212> TYPE: PRT
<213> ORGANISM: artificial
<220> FEATURE:
<223> OTHER INFORMATION: Plasmodium falciparum TRAP peptide

<400> SEQUENCE: 25

Glu Thr Leu Gly Glu Glu Asp Lys Asp Leu Asp Glu Pro Glu Gln Phe
1               5                   10                  15

Arg Leu Pro Glu Glu Asn Glu Trp Asn
            20                  25

<210> SEQ ID NO 26
<211> LENGTH: 6
<212> TYPE: PRT
<213> ORGANISM: artificial
<220> FEATURE:
<223> OTHER INFORMATION: Plasmodium falciparum TRAP peptide

<400> SEQUENCE: 26

Glu Glu Asn Glu Trp Asn
1               5

<210> SEQ ID NO 27
<211> LENGTH: 24
<212> TYPE: PRT
<213> ORGANISM: artificial
<220> FEATURE:
<223> OTHER INFORMATION: Plasmodium berghei TRAP peptide

```
<400> SEQUENCE: 27

Val Met Ala Asp Asp Glu Lys Gly Ile Val Glu Asp Glu Gly Phe Lys
1               5                   10                  15

Leu Pro Glu Asp Asn Asp Trp Asn
            20

<210> SEQ ID NO 28
<211> LENGTH: 6
<212> TYPE: PRT
<213> ORGANISM: artificial
<220> FEATURE:
<223> OTHER INFORMATION: Plasmodium berghei TRAP peptide

<400> SEQUENCE: 28

Glu Asp Asn Asp Trp Asn
1               5

<210> SEQ ID NO 29
<211> LENGTH: 13
<212> TYPE: PRT
<213> ORGANISM: artificial
<220> FEATURE:
<223> OTHER INFORMATION: Plasmodium falciparum TRAP peptide

<400> SEQUENCE: 29

Pro Glu Gln Phe Arg Leu Pro Glu Glu Asn Glu Trp Asn
1               5                   10

<210> SEQ ID NO 30
<211> LENGTH: 13
<212> TYPE: PRT
<213> ORGANISM: artificial
<220> FEATURE:
<223> OTHER INFORMATION: Plasmodium vivax TRAP peptide

<400> SEQUENCE: 30

Ala Asp Gln Phe Lys Leu Pro Glu Asp Asn Asp Trp Asn
1               5                   10

<210> SEQ ID NO 31
<211> LENGTH: 13
<212> TYPE: PRT
<213> ORGANISM: artificial
<220> FEATURE:
<223> OTHER INFORMATION: Plasmodium falciparum MTRAP peptide

<400> SEQUENCE: 31

Lys Asp Asn Lys Ala Met Asp Glu Glu Glu Phe Trp Ala
1               5                   10

<210> SEQ ID NO 32
<211> LENGTH: 13
<212> TYPE: PRT
<213> ORGANISM: artificial
<220> FEATURE:
<223> OTHER INFORMATION: Plasmodium vivax MTRAP peptide

<400> SEQUENCE: 32

Glu Asn Ser Lys Ser Met Tyr Glu Asp Glu Phe Trp Ala
1               5                   10

<210> SEQ ID NO 33
<211> LENGTH: 13
<212> TYPE: PRT
<213> ORGANISM: artificial
<220> FEATURE:
```

<223> OTHER INFORMATION: Plasmodium falciparum CTRP peptide

<400> SEQUENCE: 33

Asp Phe Glu Val Val Asp Ala Asp Asp Pro Met Trp Asn
1               5                   10

<210> SEQ ID NO 34
<211> LENGTH: 13
<212> TYPE: PRT
<213> ORGANISM: artificial
<220> FEATURE:
<223> OTHER INFORMATION: Plasmodium vivax CTRP peptide

<400> SEQUENCE: 34

Asp Phe Glu Val Ile Asp Ala Asn Asp Pro Met Trp Asn
1               5                   10

<210> SEQ ID NO 35
<211> LENGTH: 13
<212> TYPE: PRT
<213> ORGANISM: artificial
<220> FEATURE:
<223> OTHER INFORMATION: Plasmodium falciparum TLP peptide

<400> SEQUENCE: 35

Glu Gln Asn Ile Glu Ile Met Asn Asp Thr Gln Trp Lys
1               5                   10

<210> SEQ ID NO 36
<211> LENGTH: 13
<212> TYPE: PRT
<213> ORGANISM: artificial
<220> FEATURE:
<223> OTHER INFORMATION: Plasmodium vivax TLP peptide

<400> SEQUENCE: 36

Gln Asn Ile Glu Val Lys Pro Asp Glu Thr Ser Trp Gln
1               5                   10

<210> SEQ ID NO 37
<211> LENGTH: 559
<212> TYPE: PRT
<213> ORGANISM: Plasmodium falciparum

<400> SEQUENCE: 37

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
                20                  25                  30

Val Asp Glu Ile Lys Tyr Ser Glu Glu Val Cys Asn Asp Gln Val Asp
            35                  40                  45

Leu Tyr Leu Leu Met Asp Cys Ser Gly Ser Ile Arg Arg His Asn Trp
        50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Val Asn Val Phe Ser Asn Asn
                85                  90                  95

Ala Lys Glu Ile Ile Arg Leu His Ser Asp Ala Ser Lys Asn Lys Glu
            100                 105                 110

Lys Ala Leu Ile Ile Ile Arg Ser Leu Leu Ser Thr Asn Leu Pro Tyr
        115                 120                 125

Gly Arg Thr Asn Leu Thr Asp Ala Leu Leu Gln Val Arg Lys His Leu

-continued

```
            130                 135                 140
Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Ser Asp Arg Gly Val Lys Ile Ala Val Phe Gly Ile Gly Gln
                180                 185                 190

Gly Ile Asn Val Ala Phe Asn Arg Phe Leu Val Gly Cys His Pro Ser
            195                 200                 205

Asp Gly Lys Cys Asn Leu Tyr Ala Asp Ser Ala Trp Glu Asn Val Lys
        210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
                260                 265                 270

Cys Thr Ser Glu Ile Gln Glu Gln Cys Glu Glu Arg Cys Pro Pro
        275                 280                 285

Lys Trp Glu Pro Leu Asp Val Pro Asp Glu Pro Glu Asp Asp Gln Pro
        290                 295                 300

Arg Pro Arg Gly Asp Asn Ser Ser Val Gln Lys Pro Glu Glu Asn Ile
305                 310                 315                 320

Ile Asp Asn Asn Pro Gln Glu Pro Ser Pro Asn Pro Glu Glu Gly Lys
                325                 330                 335

Asp Glu Asn Pro Asn Gly Phe Asp Leu Asp Glu Asn Pro Glu Asn Pro
                340                 345                 350

Pro Asn Pro Asp Ile Pro Glu Gln Lys Pro Asn Ile Pro Glu Asp Ser
                355                 360                 365

Glu Lys Glu Val Pro Ser Asp Val Pro Lys Asn Pro Glu Asp Asp Arg
        370                 375                 380

Glu Glu Asn Phe Asp Ile Pro Lys Lys Pro Glu Asn Lys His Asp Asn
385                 390                 395                 400

Gln Asn Asn Leu Pro Asn Asp Lys Ser Asp Arg Asn Ile Pro Tyr Ser
                405                 410                 415

Pro Leu Pro Pro Lys Val Leu Asp Asn Glu Arg Lys Gln Ser Asp Pro
                420                 425                 430

Gln Ser Gln Asp Asn Asn Gly Asn Arg His Val Pro Asn Ser Glu Asp
            435                 440                 445

Arg Glu Thr Arg Pro His Gly Arg Asn Asn Glu Asn Arg Ser Tyr Asn
        450                 455                 460

Arg Lys Tyr Asn Asp Thr Pro Lys His Pro Glu Arg Glu Glu His Glu
465                 470                 475                 480

Lys Pro Asp Asn Asn Lys Lys Lys Gly Glu Ser Asp Asn Lys Tyr Lys
                485                 490                 495

Ile Ala Gly Gly Ile Ala Gly Gly Leu Ala Leu Leu Ala Cys Ala Gly
                500                 505                 510

Leu Ala Tyr Lys Phe Val Val Pro Gly Ala Ala Thr Pro Tyr Ala Gly
            515                 520                 525

Glu Pro Ala Pro Phe Asp Glu Thr Leu Gly Glu Glu Asp Lys Asp Leu
        530                 535                 540

Asp Glu Pro Glu Gln Phe Arg Leu Pro Glu Glu Asn Glu Trp Asn
545                 550                 555
```

```
<210> SEQ ID NO 38
<211> LENGTH: 13
<212> TYPE: PRT
<213> ORGANISM: artificial
<220> FEATURE:
<223> OTHER INFORMATION: TRAP consensus sequence
<220> FEATURE:
<221> NAME/KEY: MISC_FEATURE
<222> LOCATION: (1)..(7)
<223> OTHER INFORMATION: X is any amino acid
<220> FEATURE:
<221> NAME/KEY: MISC_FEATURE
<222> LOCATION: (8)..(9)
<223> OTHER INFORMATION: X is D, E, or N
<220> FEATURE:
<221> NAME/KEY: MISC_FEATURE
<222> LOCATION: (10)..(11)
<223> OTHER INFORMATION: X is any amino acid
<220> FEATURE:
<221> NAME/KEY: MISC_FEATURE
<222> LOCATION: (13)..(13)
<223> OTHER INFORMATION: X is any amino acid

<400> SEQUENCE: 38

Xaa Xaa Xaa Xaa Xaa Xaa Xaa Xaa Xaa Xaa Xaa Trp Xaa
1               5                   10
```

UNITED STATES PATENT AND TRADEMARK OFFICE
CERTIFICATE OF CORRECTION

PATENT NO. : 9,873,661 B2
APPLICATION NO. : 14/353438
DATED : January 23, 2018
INVENTOR(S) : Cardozo et al.

It is certified that error appears in the above-identified patent and that said Letters Patent is hereby corrected as shown below:

Column 1 at Lines 11-15, delete "This invention was made with government support under grant number DP2 OD004631 and F30HL094052 awarded by National Institutes of Health (NIH) and National Heart, Lung, and Blood Institute (NHLBI), respectively. The government has certain rights in this invention." and insert --This invention was made with government support under OD004631 and F30 HL094052 awarded by National Institutes of Health. The government has certain rights in the invention.--

Signed and Sealed this
Fourth Day of September, 2018

Andrei Iancu
*Director of the United States Patent and Trademark Office*